United States Patent
Tata et al.

(10) Patent No.: US 6,642,237 B1
(45) Date of Patent: Nov. 4, 2003

(54) GAMMA-HYDROXY-2-(FLUOROALKYLAMINOCARBONYL)-1-PIPERAZINEPENTANAMIDES AND USES THEREOF

(75) Inventors: James R. Tata, Westfield, NJ (US); Kevin T. Chapman, Scotch Plains, NJ (US); Joseph Leslie Duffy, Cranford, NJ (US); Nancy J. Kevin, East Brunswick, NJ (US); Yuan Cheng, Edison, NJ (US); Thomas A. Rano, Somerville, NJ (US); Fengqi Zhang, Edison, NJ (US); Tracy Huening, Madison, NJ (US); Brian Anthony Kirk, Basking Ridge, NJ (US); Zhijian Lu, Clinton, NJ (US); Subharekha Raghavan, Teaneck, NJ (US); Fred J. Fleitz, Franklin Park, NJ (US); Daniel E. Petrillo, Hoboken, NJ (US); Joseph D. Armstrong, III, Westfield, NJ (US); Richard J. Varsolona, Scotch Plains, NJ (US); David Askin, Warren, NJ (US); R. Scott Hoerrner, Westfield, NJ (US); Robert Purick, Edison, NJ (US)

(73) Assignee: Merck & Co., Inc., Rahway, NJ (US)

(*) Notice: Subject to any disclaimer, the term of this patent is extended or adjusted under 35 U.S.C. 154(b) by 0 days.

(21) Appl. No.: 09/718,223

(22) Filed: Nov. 21, 2000

Related U.S. Application Data

(60) Provisional application No. 60/167,478, filed on Nov. 24, 1999, and provisional application No. 60/177,053, filed on Jan. 20, 2000.

(51) Int. Cl.$^7$ ............... C07D 491/048; C07D 405/14; C07D 495/04; A61P 31/18; A61K 31/495
(52) U.S. Cl. ............... 514/252.02; 544/362; 544/376; 544/364; 544/295; 514/253.04; 514/253.11; 514/253.01; 514/252
(58) Field of Search ................... 544/362, 376, 544/364, 295, 224; 514/253.04, 253.11, 253.01, 252.2, 252.02

(56) References Cited

U.S. PATENT DOCUMENTS

| | | |
|---|---|---|
| 5,196,438 A | 3/1993 | Martin et al. |
| 5,413,999 A | 5/1995 | Vacca et al. |
| 5,455,351 A | 10/1995 | Kempf et al. |
| 5,484,801 A | 1/1996 | Al-Razzak et al. |
| 5,484,926 A | 1/1996 | Dressman et al. |
| 5,618,939 A | 4/1997 | Askin et al. |
| 5,646,148 A | 7/1997 | Huff et al. |

FOREIGN PATENT DOCUMENTS

| | | |
|---|---|---|
| WO | WO 93/09096 | 5/1993 |
| WO | WO 94/26717 | 11/1994 |
| WO | WO 95/16688 | 6/1995 |
| WO | WO 98/54178 | 12/1998 |
| WO | WO 99/33795 | 7/1999 |

OTHER PUBLICATIONS

Kohl et al., "Active human immunodeficiency virus protease is required for viral infectivity", Proc. Natl. Acad. Sci. USA, vol. 85, pp. 4686–4690 (Jul. 1988).

Ratner et al., "Complete nucleotide sequence of the AIDS virus, HTLV–III", Nature, vol. 313, pp. 277–284 (Jan. 1985).

Toh et al., "Close structural resemblance between putative polymerase of a *Drosophila* transposable genetic element 17.6 and *pol* gene product of Moloney murine leukaemia virus", The EMBO Journal, vol. 4, No. 5, pp. 1267–1272 (1985).

Power et al., "Nucleotide Sequence of SRV–1, a Type D Simian Acquired Immune Deficiency Syndrome Retrovirus", Science, vol. 231, pp. 1567–1572 (1986).

Pearl et al., "A structural model for the retroviral proteases", Nature, vol. 329, pp. 351–354 (Sep. 1987).

Hammer et al., "A controlled trial of two nucleotide analogues plus indinavir in persons with human immunodeficiency virus infection and CD4 cell counts of 200 per cubic millimeter of less", The New England Journal of Medicine, vol. 337, No. 11, pp. 725–733 (Sep. 1997).

Gulick et al., "Treatment with indiavir, zidovudine, and lamivudine in adults with human immunodeficiency virus infection and prior antiretroviral therapy", The New England Journal of Medicine, vol. 337, No. 11, pp. 734–738 (Sep. 1997).

Condra et al., "In vivo emergence of HIV–1 variants resistant to multiple protease inhibitors", Nature, vol. 374, pp. 569–571 (Apr. 1995).

Condra et al., "Genetic Correlates of In Vivo Viral Resistance to Indinavir, a Human Immunodeficiency Virus Type 1 Protease Inhibitor", Journal of Virology, pp. 8270–8276 (Dec. 1996).

(List continued on next page.)

*Primary Examiner*—Richard L. Raymond
*Assistant Examiner*—Hong Liu
(74) *Attorney, Agent, or Firm*—Kenneth R. Walton; Melvin Winokur; Valerie J. Camara

(57) ABSTRACT

γ-Hydroxy-2-(fluoroalkylaminocarbonyl)-1-piperazinepentanamide compounds are inhibitors of HIV protease and inhibitors of HIV replication. These compounds are useful in the prevention or treatment of infection by HV and the treatment of AIDS, either as compounds, pharmaceutically acceptable salts, pharmaceutical composition ingredients, whether or not in combination with other antivirals, immunomodulators, antibiotics or vaccines. Methods of treating AIDS and methods of preventing or treating infection by HIV are also described. These compounds are effective against HIV viral mutants which are resistant to HIV protease inhibitors currently used for treating AIDS and HIV infection.

28 Claims, No Drawings

OTHER PUBLICATIONS

Tisdale et al., "Cross–Resistance Analysis of Human Immunodeficiency Virus Type 1 Variants Individually Selected for Resistance to Five Different Protease Inhibitors", Antimicrobial Agents and Chemotherapy, pp. 1704–1710 (Aug. 1995).

Condra et al., "Virological and clinical implications of resistance to HIV–1 protease inhibitors", Drug Resistance Updates, vol. 1, pp. 292–299 (1998).

Patrick et al., "Protease inhibitor resistance during therapy", Antiviral Therapy, vol. 1, Supp. 1, pp. 17–18 (1996).

GAMMA-HYDROXY-2-(FLUOROALKYLAMINOCARBONYL)-1-PIPERAZINEPENTANAMIDES AND USES THEREOF

This application claims the benefit of U.S. Provisional Application No. 60/167,478, filed Nov. 24, 1999, and U.S. Provisional Application No. 60/177,053, filed Jan. 20, 2000, the disclosures of which are hereby incorporated by reference in their entireties.

FIELD OF THE INVENTION

The present invention is directed to γ-hydroxy-2-(fluoroalkylaminocarbonyl)-1-piperazinepentanamide compounds, their pharmaceutically acceptable salts, their synthesis, and their use as inhibitors of HIV protease. The compounds of the present invention are useful for preventing or treating infection by HIV and for treating AIDS.

References are made throughout this application to various publications in order to more fully describe the state of the art to which this invention pertains. The disclosures of these references are hereby incorporated by reference in their entireties for all purposes.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl et al., Proc. Nat'l Acad. Sci. 1988, 85: 4686, demonstrated that genetic inactivation of the HIV encoded protease resulted in the production of immature, non-infectious virus particles. These results indicated that inhibition of the HIV protease represents a viable method for the treatment of AIDS and the prevention or treatment of infection by HIV.

Nucleotide sequencing of HIV shows the presence of a pol gene in one open reading frame [Ratner et al., Nature 1985, 313: 277]. Amino acid sequence homology provides evidence that the pol sequence encodes reverse transcriptase, an endonuclease and an HIV protease [Toh et al., EMBO J. 1985, 4: 1267; Power et al., Science 1986, 231: 1567; Pearl et al., Nature 1987, 329: 351].

Several HIV protease inhibitors are presently in clinical use for the treatment of AIDS and HIV infection, including indinavir (see U.S. Pat. No. 5,413,999), nelfinavir (U.S. Pat. No 5,484,926), saquinavir (U.S. Pat. No. 5,196,438), and ritonavir (U.S. Pat. No. 5,484,801). Each of these protease inhibitors is a peptidomimetic, competitive inhibitor of the viral protease which prevents cleavage of the HIV gag-pol polyprotein precursor. Indinavir, for example, has been found to be highly effective in reducing HIV viral loads and increasing CD4 cell counts in HIV-infected patients, when used in combination with nucleoside reverse transcriptase inhibitors. See, for example, Hammer et al., New England J. Med. 1997, 337: 725–733 and Gulick et al., New England J. Med. 1997, 337: 734–739.

A substantial and persistent problem in the treatment of AIDS has been the ability of the HIV virus to develop resistance to the therapeutic agents employed to treat the disease. Resistance to HIV-1 protease inhibitors has been associated with 25 or more amino acid substitutions in both the protease and the cleavage sites. Many of these viral variants are resistant to all of the HIV protease inhibitors currently in clinical use. See Condra et al., Drug Resistance Updates 1998, 1: 1–7; Condra et al., Nature 1995, 374: 569–571; Condra et al., J. Virol. 1996, 70: 8270–8276; Patrick et al., Antiviral Ther. 1996, Suppl. 1: 17–18; and Tisdale et al., Antimicrob. Agents Chemother. 1995, 39: 1704–1710.

Attempts to address the resistance issue with "salvage therapy" consisting of high doses of multiple protease inhibitors have only been moderately successful due to the high level of cross resistance and toxicities associated with these protease inhibitors. Accordingly, there remains a need for new protease inhibitors having improved effectiveness against the viral variants.

The present invention is directed to novel protease inhibitors which are much more potent against HIV viral mutants than the known protease inhibitors.

SUMMARY OF THE INVENTION

The present invention provides a novel group of γ-hydroxy-2-(fluoroalkylaminocarbonyl)-1-piperazinepentanamide compounds which are potent inhibitors of HIV protease including mutant forms thereof that are resistant to known protease inhibitors. These compounds are useful in the inhibition of HIV protease, the prevention of infection by HIV, the treatment of infection by HIV and in the treatment of AIDS and/or ARC, when employed as compounds or pharmaceutically acceptable salts or hydrates (when appropriate) thereof, optionally as pharmaceutical composition ingredients, and optionally in combination with other antivirals, anti-infectives, immunomodulators, antibiotics or vaccines. More particularly, the present invention includes a compound of Formula (I):

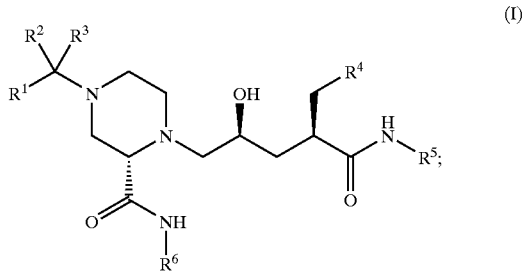

wherein

R$^1$ is C$_1$–C$_6$ alkyl, C$_2$–C$_6$ alkenyl, C$_2$–C$_6$ alkynyl, C$_3$–C$_6$ cycloalkyl, aryl, substituted aryl, heteroaryl, or substituted heteroaryl; wherein (i) each of the substituents on substituted aryl is independently
  (a) halogen,
  (b) cyano,
  (c) hydroxy,
  (d) C$_1$–C$_6$ alkyl,
  (e) C$_2$–C$_6$ alkenyl,
  (f) C$_2$–C$_6$ alkynyl,
  (g) fluorinated C$_1$–C$_6$ alkyl,
  (h) C$_1$–C$_6$ alkoxy,
  (i) fluorinated C$_1$–C$_6$ alkoxy,
  (j) S—(C$_1$–C$_6$ alkyl),
  (k) heterocycle, or (l) heterocycle substituted with one or more substituents independently selected from halogen, cyano, hydroxy, $C_1$–$C_6$ alkyl, $C_2$–$C_6$ alkenyl, $C_2$–$C_6$ alkynyl, fluorinated $C_1$–$C_6$ alkyl, $C_1$–$C_6$ alkoxy, fluorinated $C_1$–$C_6$ alkoxy, S—($C_1$–$C_6$ alkyl), and $NR^aR^b$;

(ii) each of the substituents on substituted heteroaryl is independently
  (a) halogen,
  (b) cyano,
  (c) hydroxy,
  (d) $NR^aR^b$,
  (e) $C_1$–$C_6$ alkyl,
  (f) $C_2$–$C_6$ alkenyl,
  (g) $C_2$–$C_6$ alkynyl,
  (h) fluorinated $C_1$–$C_6$ alkyl,
  (i) $C_1$–$C_6$ alkoxy,
  (j) fluorinated $C_1$–$C_6$ alkoxy,
  (k) S—($C_1$–$C_6$ alkyl),
  (l) phenyl,
  (m) phenyl substituted with one or more substituents independently selected from halogen, cyano, hydroxy, $C_1$–$C_6$ alkyl, $C_2$–$C_6$ alkenyl, $C_2$–$C_6$ alkynyl, fluorinated $C_1$–$C_6$ alkyl, $C_1$–$C_6$ alkoxy, fluorinated $C_1$–$C_6$ alkoxy, and S—($C_1$–$C_6$ alkyl),
  (l) heterocycle, or
  (m) heterocycle substituted with one or more substituents independently selected from halogen, cyano, hydroxy, $C_1$–$C_6$ alkyl, $C_2$–$C_6$ alkenyl, $C_2$–$C_6$ alkynyl, fluorinated $C_1$–$C_6$ alkyl, $C_1$–$C_6$ alkoxy, fluorinated $C_1$–$C_6$ alkoxy, S—($C_1$–$C_6$ alkyl), $NR^aR^b$, and a 5AAAAAAA- or 6-membered heteroaromatic ring consisting of carbon atoms and from 1 to 3 heteroatoms selected from N, O and S;

$R^2$ and $R^3$ are each independently hydrogen or $C_1$–$C_4$ alkyl; or $R^2$ and $R^3$ together with the carbon to which they are attached form $C_3$–$C_6$ cycloalkyl;

$R^4$ is $C_1$–$C_6$ alkyl, $C_3$–$C_6$ cycloalkyl, aryl, substituted aryl, heteroaryl, or substituted heteroaryl; wherein each of the substituents on substituted aryl is independently halogen, hydroxy, $C_1$–$C_6$ alkyl, $C_2$–$C_6$ alkenyl, $C_2$–$C_6$ alkynyl, fluorinated $C_1$–$C_6$ alkyl, $C_1$–$C_6$ alkoxy, or heteroaryl; and each of the substituents on substituted heteroaryl is independently halogen, hydroxy, $C_1$–$C_6$ alkyl, $C_2$–$C_6$ alkenyl, $C_2$–$C_6$ alkynyl, fluorinated $C_1$–$C_6$ alkyl, $C_1$–$C_6$ alkoxy, or aryl;

$R^5$ is carbocyclic, substituted carbocyclic, heterocyclic or substituted heterocyclic, wherein each of the substituents on substituted carbocyclic or substituted heterocyclic is independently halogen, hydroxy, $C_1$–$C_6$ alkyl, $C_2$–$C_6$ alkenyl, $C_2$–$C_6$ alkynyl, fluorinated $C_1$–$C_6$ alkyl, or $C_1$–$C_6$ alkoxy;

$R^6$ is fluorinated $C_1$–$C_6$ alkyl; and $R^a$ and $R^b$ are each independently hydrogen or $C_1$–$C_4$ alkyl; or $R^a$ and $R^b$ together with the nitrogen to which they are attached form $C_3$–$C_6$ azacycloalkyl;

or a pharmaceutically acceptable salt thereof.

The present invention also includes pharmaceutical compositions containing a compound of the present invention and methods of preparing such pharmaceutical compositions. The present invention further includes methods of treating AIDS, methods of preventing infection by HIV, and methods of treating infection by HIV. The present invention also includes methods for making compounds of the present invention and methods for making intermediates useful in the preparation of compounds of the present invention.

These and other embodiments, aspects and features of the present invention are either further described in or will be apparent from the ensuing description, examples, and appended claims.

DETAILED DESCRIPTION OF THE INVENTION

The present invention includes the compounds of Formula (I) above. These compounds and their pharmaceutically acceptable salts are HIV protease inhibitors.

A first embodiment of the present invention is a compound of Formula (I), wherein $R^1$ is $C_1$–$C_6$ alkyl, $C_2$–$C_6$ alkenyl, $C_2$–$C_6$ alkynyl, $C_3$–$C_6$ cycloalkyl, aryl, substituted aryl, heteroaryl, or substituted heteroaryl; wherein
  (i) each of the substituents on substituted aryl is independently
    (a) halogen,
    (b) cyano,
    (c) hydroxy,
    (d) $C_1$–$C_6$ alkyl,
    (e) $C_2$–$C_6$ alkenyl,
    (f) $C_2$–$C_6$ alkynyl,
    (g) fluorinated $C_1$–$C_6$ alkyl,
    (h) $C_1$–$C_6$ alkoxy,
    (i) heterocycle, or
    (j) heterocycle substituted with one or more substituents independently selected from halogen, cyano, hydroxy, $C_1$–$C_6$ alkyl, $C_2$–$C_6$ alkenyl, $C_2$–$C_6$ alkynyl, fluorinated $C_1$–$C_6$ alkyl, $C_1$–$C_6$ alkoxy, and $NR^aR^b$;
  (ii) each of the substituents on substituted heteroaryl is independently
    (a) halogen,
    (b) cyano,
    (c) hydroxy,
    (d) $NR^aR^b$,
    (e) $C_1$–$C_6$ alkyl,
    (f) $C_2$–$C_6$ alkenyl,
    (g) $C_2$–$C_6$ alkynyl,
    (h) fluorinated $C_1$–$C_6$ alkyl,
    (i) $C_1$–$C_6$ alkoxy,
    (j) phenyl,
    (k) phenyl substituted with one or more substituents independently selected from halogen, cyano, hydroxy, $C_1$–$C_6$ alkyl, $C_2$–$C_6$ alkenyl, $C_2$–$C_6$ alkynyl, fluorinated $C_1$–$C_6$ alkyl, and $C_1$–$C_6$ alkoxy,
    (l) heterocycle, or
    (m) heterocycle substituted with one or more substituents independently selected from halogen, cyano, hydroxy, $C_1$–$C_6$ alkyl, $C_2$–$C_6$ alkenyl, $C_2$–$C_6$ alkynyl, fluorinated $C_1$–$C_6$ alkyl, $C_1$–$C_6$ alkoxy, and $NR^aR^b$;

and all other variables are as originally defined above;
or a pharmaceutically acceptable salt thereof.

A second embodiment of the present invention is a compound of Formula (I), wherein $R^4$ is $C_1$–$C_6$ alkyl, $C_3$–$C_6$ cycloalkyl, phenyl, substituted phenyl, heteroaryl, or substituted heteroaryl, wherein heteroaryl is selected from pyridyl, pyrazinyl, pyrimidinyl, thiophenyl, thiazolyl, pyridofuranyl, pyrimidofuranyl, pyridothienyl, pyridazothienyl, pyridooxazolyl, pyridazooxazolyl, pyrimidooxazolyl, pyridothiazolyl, and pyridazothiazolyl; and wherein each of the substituents on substituted phenyl or substituted heteroaryl is independently halogen, hydroxy, $C_1$–$C_6$ alkyl, fluorinated $C_1$–$C_6$ alkyl, or $C_1$–$C_6$ alkoxy;

and all other variables are as originally defined above;

or a pharmaceutically acceptable salt thereof.

A third embodiment of the present invention is a compound of formula(I), wherein $R^4$ is $C_1$–$C_6$ alkyl, $C_3$–$C_6$ cycloalkyl, phenyl, substituted phenyl, heteroaryl, or substituted heteroaryl, wherein heteroaryl is selected from pyridyl, pyrazinyl, pyrimidinyl, and thiophenyl; and wherein each of the substituents on substituted phenyl or substituted heteroaryl is independently halogen, hydroxy, $C_1$–$C_6$ alkyl, fluorinated $C_1$–$C_6$ alkyl, or $C_1$–$C_6$ alkoxy;

and all other variables are as defined in the first embodiment;

or a pharmaceutically acceptable salt thereof.

A first class of the present invention is a compound of Formula (I), wherein $R^4$ is

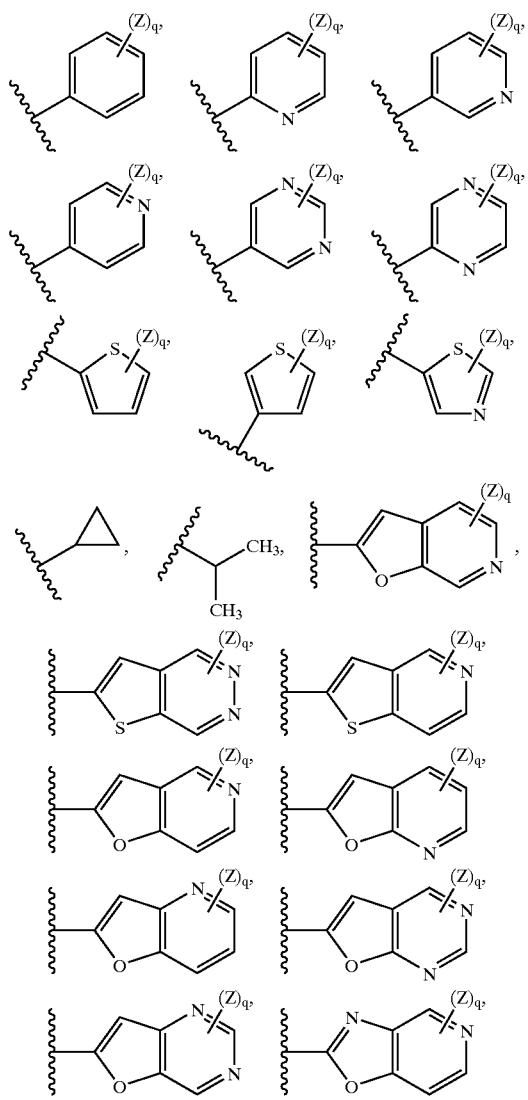

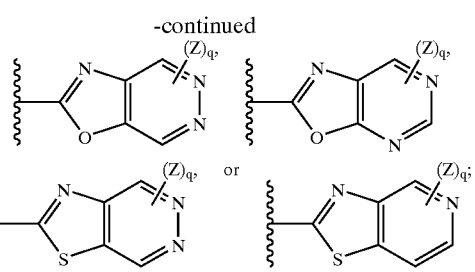

each

Z is independently hydrogen, halogen, cyano, $C_1$–$C_6$ alkyl, or $C_1$–$C_6$ alkoxy; and q is an integer from 0 to 2;

and all other variables are as defined in the second embodiment;

or a pharmaceutically acceptable salt thereof.

A second class of the present invention is a compound of Formula (I), wherein $R^4$ is

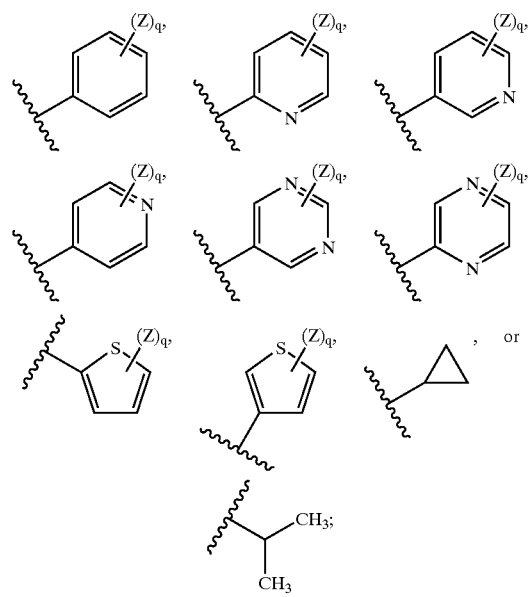

each

Z is independently hydrogen, halogen, cyano, $C_1$–$C_6$ alkyl, or $C_1$–$C_6$ alkoxy;

q is an integer from 0 to 2;

and all other variables are as defined in the third embodiment;

or a pharmaceutically acceptable salt thereof.

A fourth embodiment of the present invention is a compound of Formula (I), wherein $R^5$ is carbocyclic, substituted carbocyclic, heterocyclic or substituted heterocyclic, wherein carbocyclic is cyclopentyl, indanyl, or tetralin, and heterocyclic is chroman, thiochroman, or dioxoisothiochroman; wherein each of the substituents on substituted carbocyclic or substituted heterocyclic is independently halogen, hydroxy, $C_1$–$C_6$ alkyl, fluorinated $C_1$–$C_6$ alkyl, or $C_1$–$C_6$ alkoxy;

and all other variables are as originally defined or as defined in any one of the preceding embodiments or classes;

or a pharmaceutically acceptable salt thereof.

A third class of the present invention is a compound of Formula (I), wherein

R⁵ is

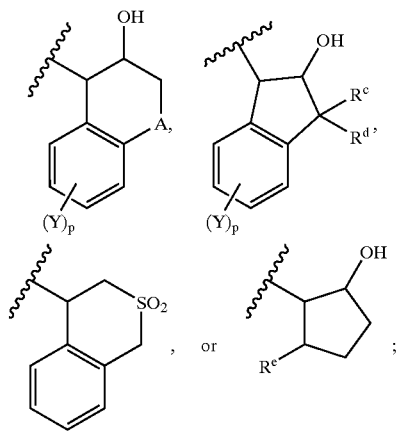

wherein
A is $CR^cR^d$, O, or S;
each Y is independently hydrogen, halogen, $C_1$-$C_6$ alkyl, fluorinated $C_1$-$C_6$ alkyl, or $C_1$-$C_6$ alkoxy;
$R^c$ and $R^d$ are each independently hydrogen or $C_1$-$C_4$ alkyl, or $R^c$ and $R^d$ together with the carbon to which they are attached from $C_3$-$C_6$ cycloalkyl;
$R^e$ is hydrogen, $C_1$-$C_4$ alkyl, fluorinated $C_1$-$C_4$ alkyl, or phenyl;
p is an integer from 0 to 2;
and all other variables are as defined in the fourth embodiment;

or a pharmaceutically acceptable salt thereof.

In a preferred aspect of the third class of the present invention, R⁵ is

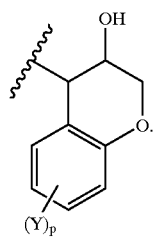

A fifth embodiment of the present invention is a compound of Formula (I), wherein, R⁶ is

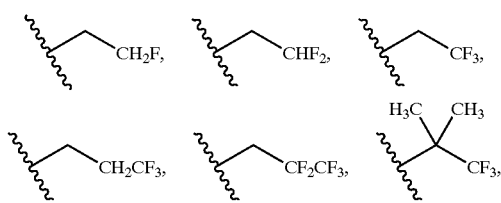

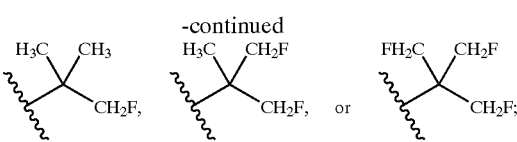

and all other variables are as originally defined or as defined in any of the preceding embodiments or classes;
or a pharmaceutically acceptable salt thereof.

In a preferred aspect of the fifth embodiment, R⁶ is

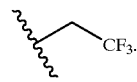

A sixth embodiment of the present invention is a compound of Formula (I), wherein R¹ is $C_1$-$C_6$ alkyl, $C_3$-$C_6$ cycloalkyl, aryl, substituted aryl, heteroaryl, or substituted heteroaryl, wherein heteroaryl is (i) a 5- or 6-membered aromatic ring consisting of carbon atoms and from 1 to 3 heteroatoms selected from N, S, and O or (ii) an 8- to 10-membered bicyclic ring system consisting of carbon atoms and from 1 to 3 heteroatoms selected from N, S, and O, wherein at least one of the rings in the bicyclic system is an aromatic ring; wherein
(i) each of the substituents on substituted aryl is independently
  (a) halogen,
  (b) cyano,
  (c) hydroxy,
  (d) $C_1$-$C_6$ alkyl,
  (e) $C_2$-$C_6$ alkenyl,
  (f) $C_2$-$C_6$ alkynyl,
  (g) fluorinated $C_1$-$C_6$ alkyl,
  (h) $C_1$-$C_6$ alkoxy,
  (i) fluorinated $C_1$-$C_6$ alkoxy,
  (j) S—($C_1$-$C_6$ alkyl),
  (k) heterocycle, or
  (l) heterocycle substituted with one or more substituents independently selected from halogen, cyano, hydroxy, $C_1$-$C_6$ alkyl, $C_2$-$C_6$ alkenyl, $C_2$-$C_6$ alkynyl, fluorinated $C_1$-$C_6$ alkyl, $C_1$-$C_6$ alkoxy, fluorinated $C_1$-$C_6$ alkoxy, S—($C_1$-$C_6$ alkyl), and $NR^aR^b$;
(ii) each of the substituents on substituted heteroaryl is independently
  (a) halogen,
  (b) cyano,
  (c) hydroxy,
  (d) $NR^aR^b$,
  (e) $C_1$-$C_6$ alkyl,
  (f) $C_2$-$C_6$ alkenyl,
  (g) $C_2$-$C_6$ alkynyl,
  (h) fluorinated $C_1$-$C_6$ alkyl,
  (i) $C_1$-$C_6$ alkoxy,
  (j) fluorinated $C_1$-$C_6$ alkoxy,
  (k) S—($C_1$-$C_6$ alkyl),
  (l) phenyl,
  (m) phenyl substituted with one or more substituents independently selected from halogen, cyano, hydroxy, $C_1$-$C_6$ alkyl, $C_2$-$C_6$ alkenyl, $C_2$-$C_6$ alkynyl, fluorinated $C_1$–$C_6$ alkyl, $C_1$–$C_6$ alkoxy, fluorinated $C_1$–$C_6$ alkoxy, and S—($C_1$–$C_6$ alkyl),
(l) heterocycle, or
(m) heterocycle substituted with one or more substituents independently selected from halogen, cyano, hydroxy, $C_1$–$C_6$ alkyl, $C_2$–$C_6$ alkenyl, $C_2$–$C_6$ alkynyl, fluorinated $C_1$–$C_6$ alkyl, $C_1$–$C_6$ alkoxy, fluorinated $C_1$–$C_6$ alkoxy, S—($C_1$–$C_6$ alkyl), $NR^aR^b$, and a 5- or 6-membered heteroaromatic ring consisting of carbon atoms and from 1 to 3 heteroatoms selected from N, O and S;
and all other variables are as originally defined or as defined in any of the preceding embodiments or classes;
or a pharmaceutically acceptable salt thereof.

A seventh embodiment of the present invention is a compound of Formula (I), wherein
$R^1$ is $C_1$–$C_6$ alkyl, $C_3$–$C_6$ cycloalkyl, aryl, substituted aryl, heteroaryl, or substituted heteroaryl, wherein heteroaryl is (i) a 5- or 6-membered aromatic ring consisting of carbon atoms and from 1 to 3 heteroatoms selected from N, S, and O or (ii) an 8- to 10-membered bicyclic ring system consisting of carbon atoms and from 1 to 3 heteroatoms selected from N, S, and O, wherein at least one of the rings in the bicyclic system is an aromatic ring; wherein
(i) each of the substituents on substituted aryl is independently
(a) halogen,
(b) cyano,
(c) hydroxy,
(d) $C_1$–$C_6$ alkyl,
(e) $C_2$–$C_6$ alkenyl,
(f) $C_2$–$C_6$ alkynyl,
(g) fluorinated $C_1$–$C_6$ alkyl,
(h) $C_1$–$C_6$ alkoxy,
(i) heterocycle, or
(j) heterocycle substituted with one or more substituents independently selected from halogen, cyano, hydroxy, $C_1$–$C_6$ alkyl, $C_2$–$C_6$ alkenyl, $C_2$–$C_6$ alkynyl, fluorinated $C_1$–$C_6$ alkyl, $C_1$–$C_6$ alkoxy, and $NR^aR^b$;
(ii) each of the substituents on substituted heteroaryl is independently
(a) halogen,
(b) cyano,
(c) hydroxy,
(d) $NR^aR^b$,
(e) $C_1$–$C_6$ alkyl,
(f) $C_2$–$C_6$ alkenyl,
(g) $C_2$–$C_6$ alkynyl,
(h) fluorinated $C_1$–$C_6$ alkyl,
(i) $C_1$–$C_6$ alkoxy,
(j) phenyl,
(k) phenyl substituted with one or more substituents independently selected from halogen, cyano, hydroxy, $C_1$–$C_6$ alkyl, $C_2$–$C_6$ alkenyl, $C_2$–$C_6$ alkynyl, fluorinated $C_1$–$C_6$ alkyl, and $C_1$–$C_6$ alkoxy
(l) heterocycle, or
(m) heterocycle substituted with one or more substituents independently selected from halogen, cyano, hydroxy, $C_1$–$C_6$ alkyl, $C_2$–$C_6$ alkenyl, $C_2$–$C_6$ alkynyl, fluorinated $C_1$–$C_6$ alkyl, $C_1$–$C_6$ alkoxy, and $NR^aR^b$;
and all other variables are as originally defined or as defined in any of the preceding embodiments or classes;
or a pharmaceutically acceptable salt thereof.

A fourth class of the present invention is a compound of Formula (I), wherein
$R^1$ is $C_1$–$C_6$ alkyl, $C_1$–$C_6$ cycloalkyl, phenyl, substituted phenyl, heteroaryl, or substituted heteroaryl, wherein heteroaryl is pyridyl, methylenedioxyphenyl, furanyl, benzofuranyl, benzothiofuranyl, benzoxazolyl, benzothiazolyl, azabenzothiazolyl, azabenzoxazolyl, azabenzofuranyl, azabenzothiofuranyl, oxazolyl, thiazolyl, isoxazolyl, triazolyl, thiadiazolyl, oxadiazolyl, indazolyl, pyrrolyl, pyrazolyl, thiophenyl, or thienothiophenyl; and wherein
(i) each of the substituents on substituted phenyl is independently
(a) halogen,
(b) cyano,
(c) hydroxy,
(d) $C_1$–$C_4$ alkyl,
(e) fluorinated $C_1$–$C_4$ alkyl,
(f) $C_1$–$C_4$ alkoxy,
(g) fluorinated $C_1$–$C_4$ alkoxy,
(h) S—($C_1$–$C_4$ alkyl),
(i) heterocycle which is a 5- or 6-membered unsaturated monocyclic ring consisting of carbon atoms and from 1 to 3 heteroatoms selected from N, O and S, or
(j) substituted heterocycle which is a 5- or 6-membered unsaturated monocyclic ring as defined in (i) substituted with one or more substituents independently selected from halogen, cyano, hydroxy, $C_1$–$C_4$ alkyl, fluorinated $C_1$–$C_4$ alkyl, $C_1$–$C_4$ alkoxy, fluorinated $C_1$–$C_4$ alkoxy, S—($C_1$–$C_4$ alkyl) and $NR^aR^b$; and
(ii) each of the substituents on substituted heteroaryl is independently
(a) halogen,
(b) cyano,
(c) hydroxy,
(d) $NR^aR^b$, if and only if the heteroaryl is pyridyl,
(e) $C_1$–$C_4$ alkyl,
(f) fluorinated $C_1$–$C_4$ alkyl,
(g) $C_1$–$C_4$ alkoxy,
(h) fluorinated $C_1$–$C_4$ alkoxy,
(i) S—($C_1$–$C_4$ alkyl),
(j) phenyl,
(k) phenyl substituted with one or more substituents independently selected from halogen, cyano, hydroxy, $C_1$–$C_4$ alkyl, fluorinated $C_1$–$C_4$ alkyl, $C_1$–$C_4$ alkoxy, fluorinated $C_1$–$C_4$ alkoxy, and S—($C_1$–$C_4$ alkyl),
(l) heterocycle which is a 5- or 6-membered unsaturated monocyclic ring consisting of carbon atoms and from 1 to 3 heteroatoms selected from N, O and S;
(m) substituted heterocycle which is a 5- or 6-membered unsaturated monocyclic ring as defined in (l) substituted with one or more substituents independently selected from halogen, cyano, hydroxy, $C_1$–$C_4$ alkyl, fluorinated $C_1$–$C_4$ alkyl, $C_1$–$C_4$ alkoxy, fluorinated $C_1$–$C_4$ alkoxy, S—($C_1$–$C_4$ alkyl), $NR^aR^b$, thiazolyl, oxazolyl, imidazolyl, pyrazolyl, triazolyl, pyrrolyl, furanyl, thienyl, isoxazolyl, and isothiazolyl;
and all other variables are as defined in the sixth embodiment;
or a pharmaceutically acceptable salt thereof.

A fifth class of the present invention is a compound of Formula (I), wherein

R¹ is $C_1$–$C_6$ alkyl, $C_1$–$C_6$ cycloalkyl, phenyl, substituted phenyl, heteroaryl, or substituted heteroaryl, wherein heteroaryl is pyridyl, methylenedioxyphenyl, furanyl, benzofuranyl, benzothiofuranyl, benzoxazolyl, benzothiazolyl, azabenzothiazolyl, azabenzoxazolyl, azabenzofuranyl, azabenzothiofuranyl, oxazolyl, thiazolyl, isoxazolyl, triazolyl, thiadiazolyl, oxadiazolyl, indazolyl, pyrrolyl, pyrazolyl, thiophenyl, or thienothiophenyl; and wherein
(i) each of the substituents on substituted phenyl is independently
  (a) halogen,
  (b) cyano,
  (c) hydroxy,
  (d) $C_1$–$C_4$ alkyl,
  (e) fluorinated $C_1$–$C_4$ alkyl,
  (f) $C_1$–$C_4$ alkoxy,
  (g) heterocycle which is a 5- or 6-membered unsaturated monocyclic ring consisting of carbon atoms and from 1 to 3 heteroatoms selected from N, O and S, or
  (h) substituted heterocycle which is a 5- or 6-membered unsaturated monocyclic ring as defined in (g) substituted with one or more substituents independently selected from halogen, cyano, hydroxy, $C_1$–$C_4$ alkyl, fluorinated $C_1$–$C_4$ alkyl, $C_1$–$C_4$ alkoxy and $NR^aR^b$; and
(ii) each of the substituents on substituted heteroaryl is independently
  (a) halogen,
  (b) cyano,
  (c) hydroxy,
  (d) $NR^aR^b$, if and only if the heteroaryl is pyridyl,
  (e) $C_1$–$C_4$ alkyl,
  (f) fluorinated $C_1$–$C_4$ alkyl,
  (g) $C_1$–$C_4$ alkoxy,
  (h) phenyl,
  (i) phenyl substituted with one or more substituents independently selected from halogen, cyano, hydroxy, $C_1$–$C_4$ alkyl, fluorinated $C_1$–$C_4$ alkyl, and $C_1$–$C_4$ alkoxy,
  (j) heterocycle which is a 5- or 6-membered unsaturated monocyclic ring consisting of carbon atoms and from 1 to 3 heteroatoms selected from N, O and S;
  (k) substituted heterocycle which is a 5- or 6-membered unsaturated monocyclic ring as defined in (j) substituted with one or more substituents independently selected from halogen, cyano, hydroxy, $C_1$–$C_4$ alkyl, fluorinated $C_1$–$C_4$ alkyl, $C_1$–$C_4$ alkoxy and $NR^aR^b$.
and all other variables are as defined in the seventh embodiment;
or a pharmaceutically acceptable salt thereof.

In a preferred aspect of the fourth class, heterocycle in (i)(i) and in (ii)(l) are each independently

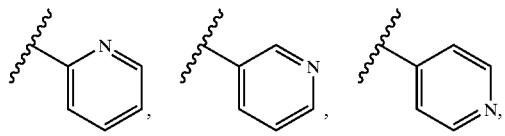

-continued

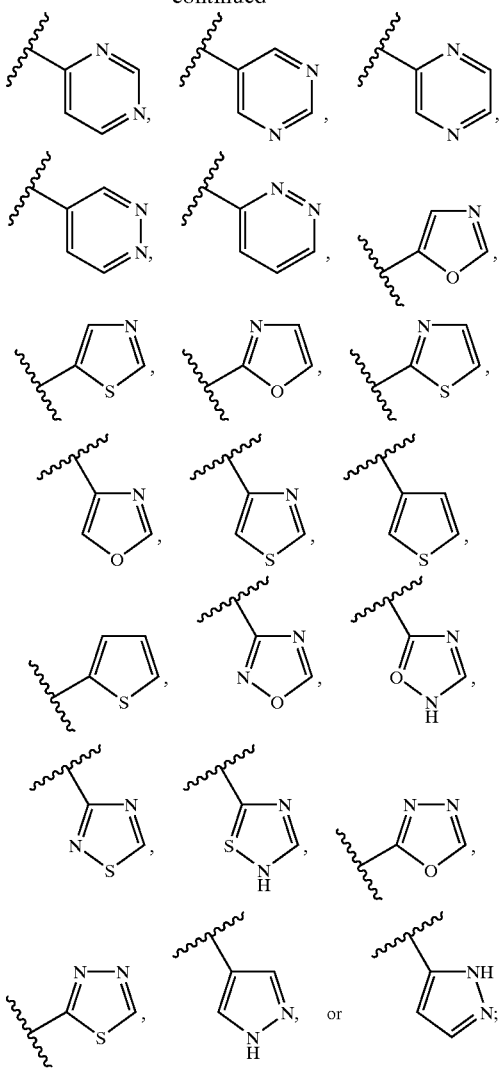

and wherein substituted heterocycle in (i)(j) is heterocycle as defined above with one or more substituents independently selected from halogen, cyano, $C_1$–$C_4$ alkyl, fluorinated $C_1$–$C_4$ alkyl, $C_1$–$C_4$ alkoxy, fluorinated $C_1$–$C_4$ alkoxy, and S—($C_1$–$C_4$ alkyl); and substituted heterocycle in (ii)(m) is heterocycle as defined above with one or more substituents independently selected from halogen, hydroxy, cyano, $C_1$–$C_4$ alkyl, fluorinated $C_1$–$C_4$ alkyl, $C_1$–$C_4$ alkoxy, fluorinated $C_1$–$C_4$ alkoxy, S—($C_1$–$C_4$ alkyl), $NR^aR^b$, thiazolyl, oxazolyl, imidazolyl, pyrazolyl, triazolyl, pyrrolyl, isoxazolyl, and isothiazolyl; or is

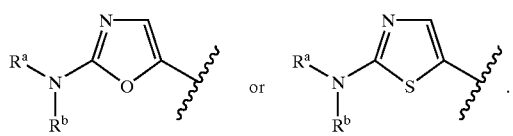

In a preferred aspect of the fifth class, heterocycle in (i)(g) and in (ii)(j) are each independently

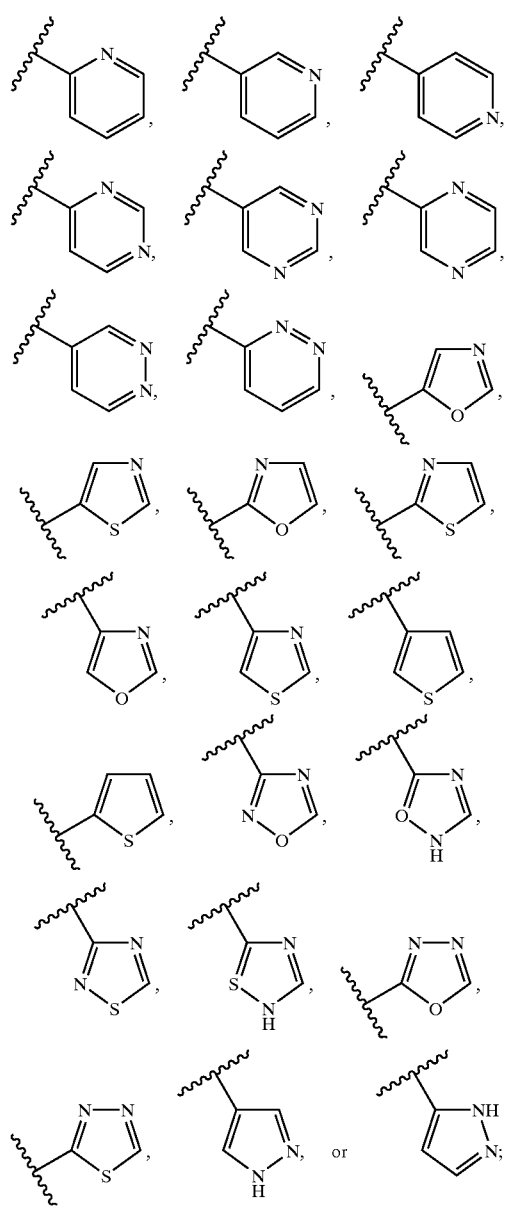

and wherein substituted heterocycle in (i)(h) is heterocycle as defined above with one or more substituents independently selected from halogen, cyano, $C_1$–$C_4$ alkyl, fluorinated $C_1$–$C_4$ alkyl, and $C_1$–$C_4$ alkoxy; and substituted heterocycle in (ii)(k) is heterocycle as defined above with one or more substituents independently selected from halogen, cyano, $C_1$–$C_4$ alkyl, fluorinated $C_1$–$C_4$ alkyl, and $C_1$–$C_4$ alkoxy; or is

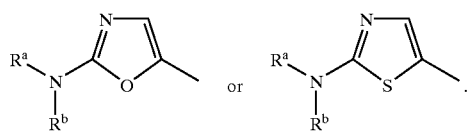

An eighth embodiment of the present invention is a compound of Formula (I), wherein $R^1$ is

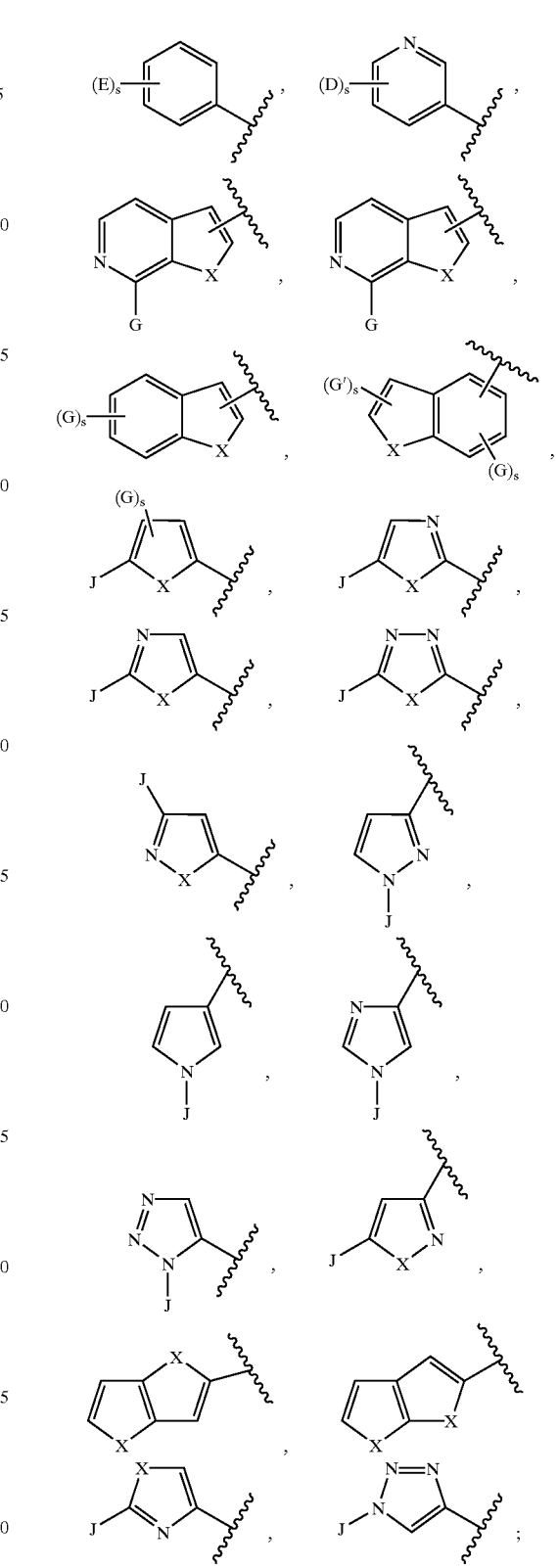

each D is independently hydrogen, halogen, cyano, hydroxy, $NR^aR^b$, $C_1$–$C_4$ alkyl, $C_1$–$C_4$ alkoxy, fluorinated $C_1$–$C_4$ alkoxy, S—($C_1$–$C_4$ alkyl), phenyl, substituted phenyl, heterocycle, or substituted heterocycle;

wherein substituted phenyl is phenyl with one or more subsituents independently selected from halogen, hydroxy, $C_1$–$C_4$ alkyl, and $C_1$–$C_4$ alkoxy; and wherein substituted heterocycle is heterocycle with one or more substituents independently selected from halogen, hydroxy, $C_1$–$C_4$ alkyl, $C_1$–$C_4$ alkoxy, fluorinated $C_1$–$C_4$ alkoxy, and S—($C_1$–$C_4$ alkyl);

each E is independently hydrogen, halogen, cyano, hydroxy, $C_1$–$C_4$ alkyl, $C_1$–$C_4$ alkoxy, heterocycle, or substituted heterocycle;

G and G' are each independently selected from hydrogen, halogen, cyano, hydroxy, $C_1$–$C_4$ alkyl, fluorinated $C_1$–$C_4$ alkyl, and $C_1$–$C_4$ alkoxy;

J is

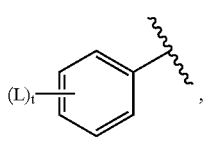, heterocycle, or substituted heterocycle;

each L is independently hydrogen, halogen, cyano, hydroxy, $C_1$–$C_4$ alkyl, fluorinated $C_1$–$C_4$ alkyl, or $C_1$–$C_4$ alkoxy;

X is O or S;

heterocycle in each of D, E and J is independently

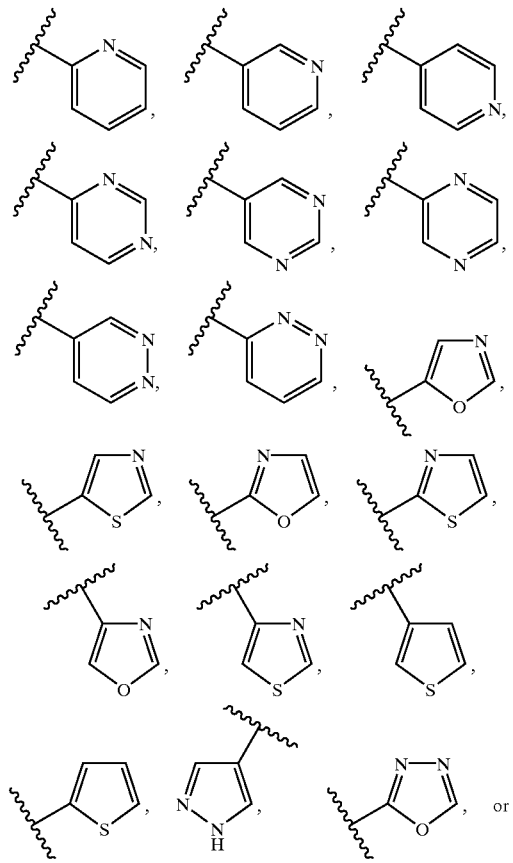

-continued

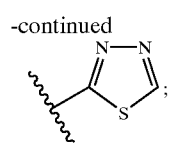;

substituted heterocycle in each of E and J is independently heterocycle as defined above with one or more substituents independently selected from halogen, hydroxy, cyano, $C_1$–$C_4$ alkyl, fluorinated $C_1$–$C_4$ alkyl, $C_1$–$C_4$ alkoxy, fluorinated $C_1$–$C_4$ alkoxy, S—($C_1$–$C_4$ alkyl), $NR^aR^b$, thiazolyl, oxazolyl, imidazolyl, pyrazolyl, triazolyl, pyrrolyl, isoxazolyl, and isothiazolyl; or is

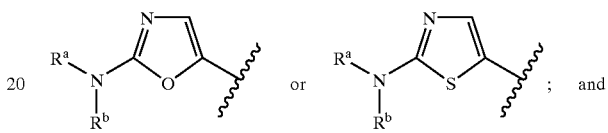

s, s', and t are each independently integers from 0 to 2;

and all other variables are as originally defined or as defined in any of the preceding embodiments or classes;

or a pharmaceutically acceptable salt thereof.

A ninth embodiment of the present invention is a compound of Formula (I), wherein $R^1$ is

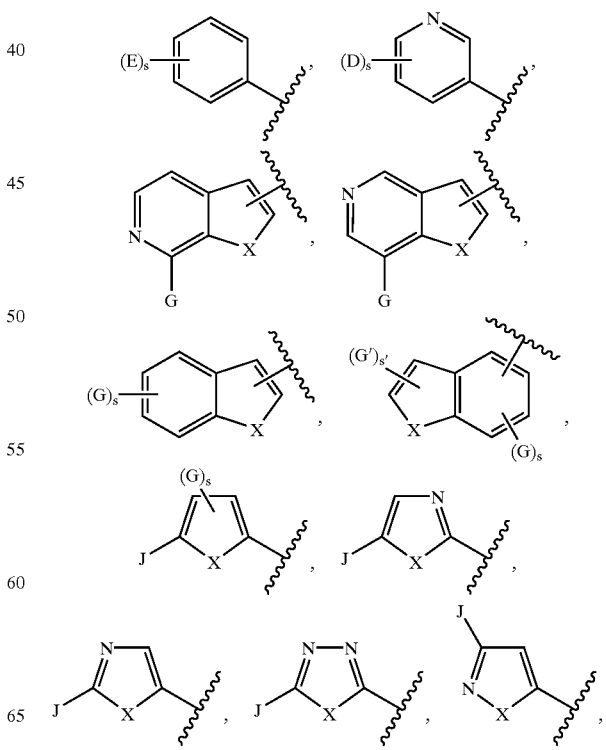

-continued

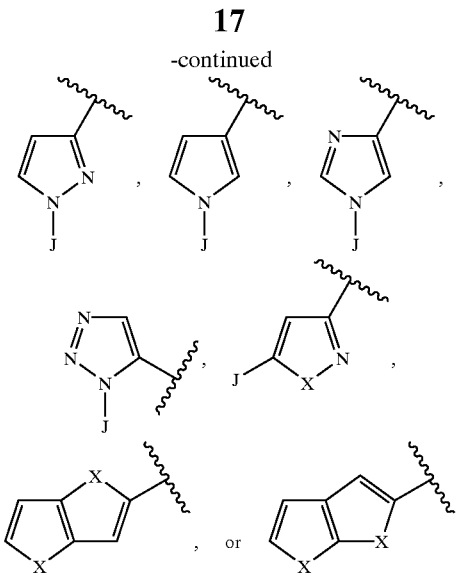

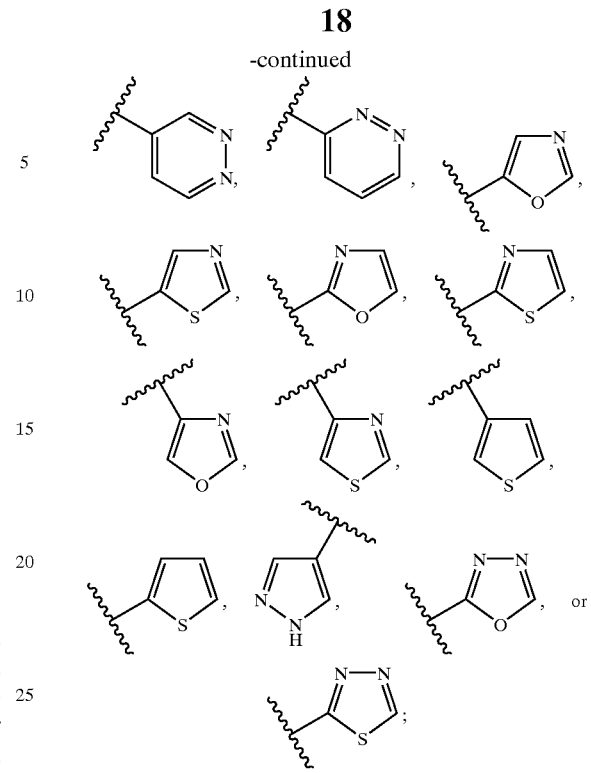

each D is independently hydrogen, halogen, cyano, hydroxy, $NR^aR^b$, $C_1$–$C_4$ alkyl, $C_1$–$C_4$ alkoxy, phenyl, substituted phenyl, heterocycle, or substituted heterocycle; wherein substituted phenyl is phenyl with one or more subsituents independently selected from halogen, hydroxy, $C_1$–$C_4$ alkyl, and $C_1$–$C_4$ alkoxy; and wherein substituted heterocycle is heterocycle with one or more substituents independently selected from halogen, hydroxy, $C_1$–$C_4$ alkyl, and $C_1$–$C_4$ alkoxy;

each E is independently hydrogen, halogen, cyano, hydroxy, $C_1$–$C_4$ alkyl, $C_1$–$C_4$ alkoxy, heterocycle, or substituted heterocycle;

G and G' are each independently selected from hydrogen, halogen, cyano, hydroxy, $C_1$–$C_4$ alkyl, fluorinated $C_1$–$C_4$ alkyl, and $C_1$–$C_4$ alkoxy;

J is

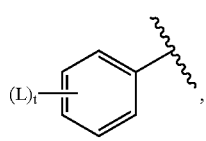

heterocycle, or substituted heterocycle;

each L is independently hydrogen, halogen, cyano, hydroxy, $C_1$–$C_4$ alkyl, fluorinated $C_1$–$C_4$ alkyl, or $C_1$–$C_4$ alkoxy;

X is O or S;

heterocycle in each of D, E and J is independently

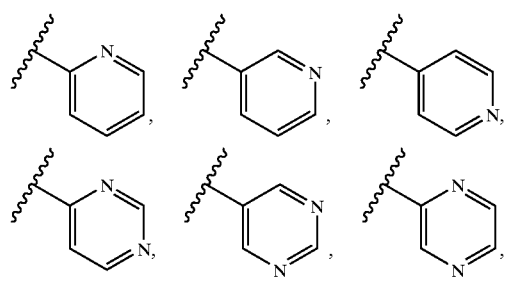

substituted heterocycle in each of E and J is independently heterocycle as defined above with one or more substituents independently selected from halogen, cyano, fluorinated $C_1$–$C_4$ alkyl and $C_1$–$C_4$ alkoxy; or is

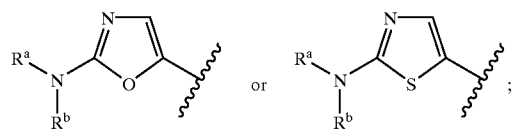

s, s', and t are each independently integers from 0 to 2;

and all other variables are as originally defined or as defined in any of the preceding embodiments or classes;

or a pharmaceutically acceptable salt thereof.

A sixth class of the present invention is a compound of Formula (I), wherein $R^6$ is

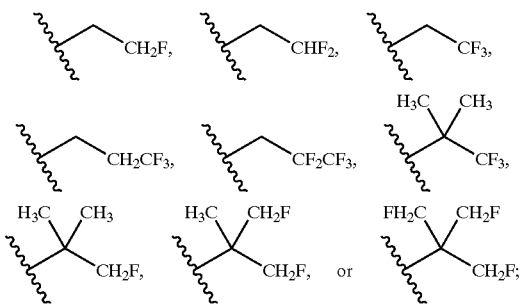

and all other variables are as defined in the eighth or the ninth embodiments.

A seventh class of the present invention is a compound of Formula (I), wherein

R⁴ is

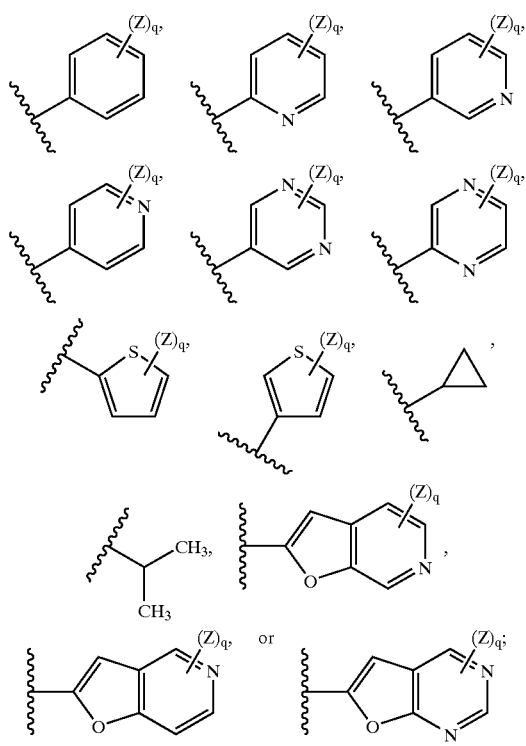

each Z is independently hydrogen, halogen, cyano, C₁–C₆ alkyl, or C₁–C₆ alkoxy;
q is an integer from 0 to 2;
and all other variables are as defined in the sixth class;
or a pharmaceutically acceptable salt thereof.

An eighth class of the present invention is a compound of Formula (I), wherein

R⁴ is

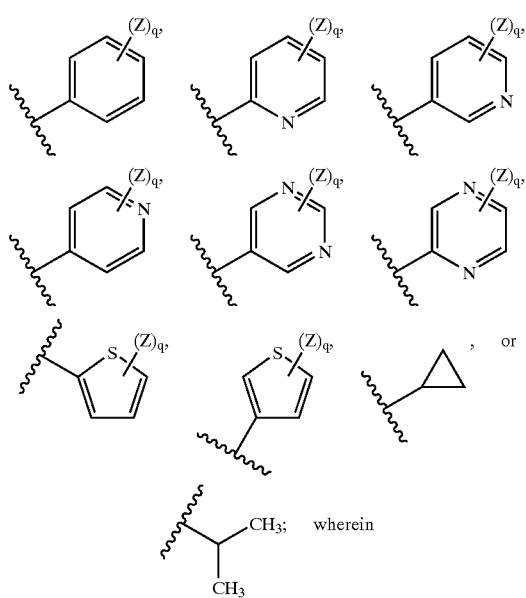

each Z is independently hydrogen, halogen, cyano, C₁–C₆ alkyl, or C₁–C₆ alkoxy;

q is an integer from 0 to 2;
and all other variables are as defined in the sixth class;
or a pharmaceutically acceptable salt thereof.

A ninth class of the present invention is a compound of Formula (I), wherein

R¹ is

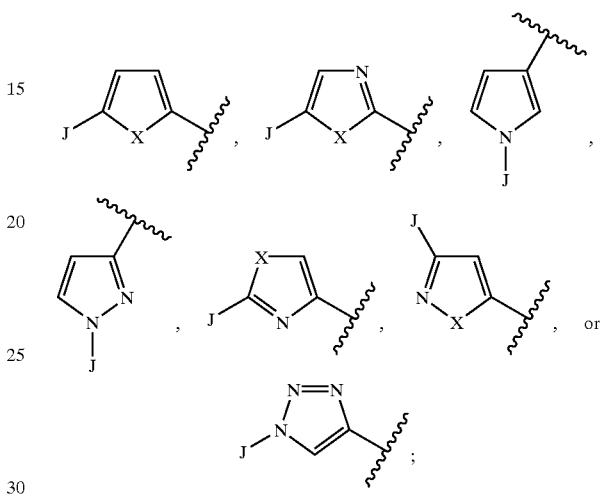

R² and R³ are each independently hydrogen or C₁–C₄ alkyl; or R² and R³ together with the carbon to which they are attached form C₃–C₆ cycloalkyl;

R⁴ is

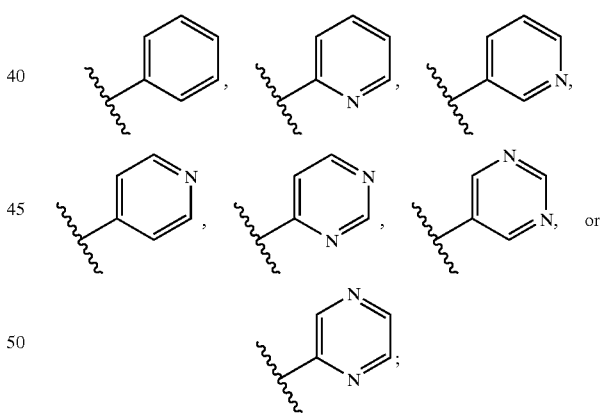

R⁵ is

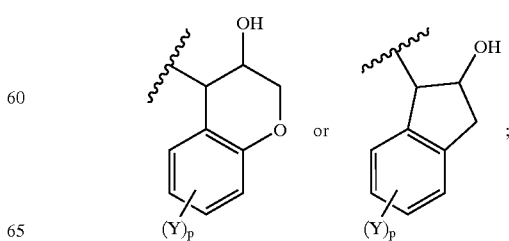

$R^6$ is

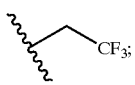

J is

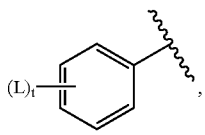

heterocycle, or substituted heterocycle;
heterocycle is

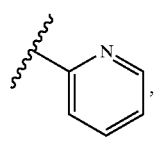 , 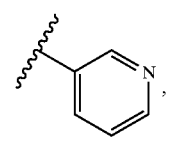 , 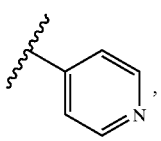 ,

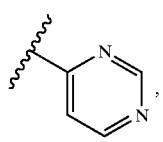 , 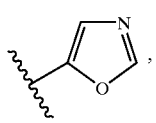 , 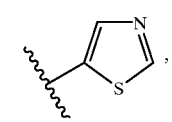 ,

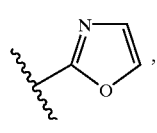 , 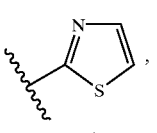 , 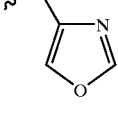 or

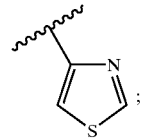 ;

- substituted heterocycle is heterocycle as defined above having one or more substituents independently selected from halogen, $C_1$–$C_4$ alkoxy, $C_1$–$C_4$ alkyl, fluorinated $C_1$–$C_4$ alkoxy, fluorinated $C_1$–$C_4$ alkyl, —S—$CH_3$, —N$(CH_3)_2$, thiazolyl, and oxazolyl;
- each L is independently hydrogen, halogen, cyano, hydroxy, $C_1$–$C_4$ alkyl, fluorinated $C_1$–$C_4$ alkyl, or $C_1$–$C_4$ alkoxy;
- X is O or S;
- each Y is independently hydrogen, halogen, $C_1$–$C_6$ alkyl, fluorinated $C_1$–$C_6$ alkyl, or $C_1$–$C_4$ alkoxy;
- p is an integer from 0 to 2; and
- t is an integer from 0 to 2;

or a pharmaceutically acceptable salt thereof.

In a preferred aspect of the ninth class, $R^2$ and $R^3$ are each independently hydrogen or methyl;
- each L is independently hydrogen, chlorine, or fluorine;
- each Y is independently hydrogen, chlorine, or fluorine; and
- each of the substituents on substituted heterocycle is independently chlorine, fluorine, methoxy, ethoxy, —$OCF_3$, —$OCHF_2$, methyl, ethyl, n-propyl, —S—$CH_3$, —N$(CH_3)_2$, and thiazolyl.

A tenth class of the present invention is a compound of Formula (I), wherein $R^1$ is

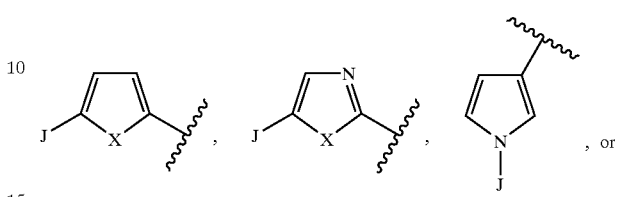

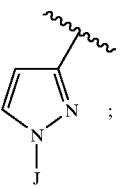 ;

$R^2$ and $R^3$ are each independently hydrogen or $C_1$–$C_4$ alkyl; or $R^2$ and $R^3$ together with the carbon to which they are attached form $C_3$–$C_6$ cycloalkyl;

$R^4$ is

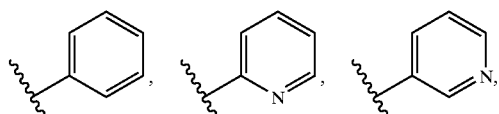

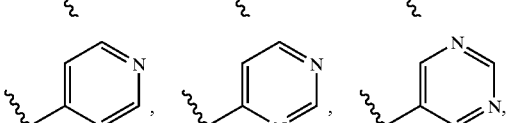

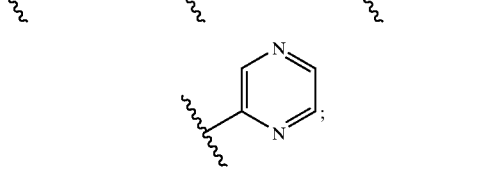

$R^5$ is

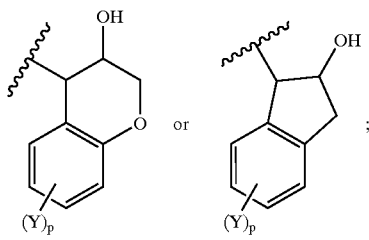

$R^6$ is

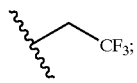

J is

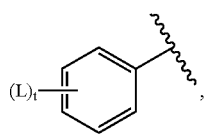

heterocycle, or substituted heterocycle;
heterocycle is

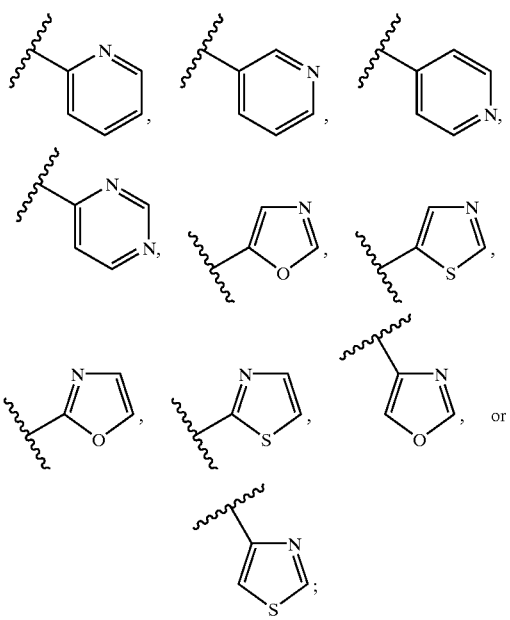

substituted heterocycle is heterocycle as defined above having one or more substituents independently selected from halogen and $C_1$–$C_4$ alkoxy;

each L is independently hydrogen, halogen, cyano, hydroxy, $C_1$–$C_4$ alkyl, fluorinated $C_1$–$C_4$ alkyl, or $C_1$–$C_4$ alkoxy;

X is O or S;

each Y is independently hydrogen, halogen, $C_1$–$C_6$ alkyl, fluorinated $C_1$–$C_6$ alkyl, or $C_1$–$C_4$ alkoxy;

p is an integer from 0 to 2; and t is an integer from 0 to 2;

or a pharmaceutically acceptable salt thereof.

In a preferred aspect of the tenth class, $R^2$ and $R^3$ are each independently hydrogen or methyl;

each L is independently hydrogen, chlorine, or fluorine;

each Y is independently hydrogen, chlorine, or fluorine; and each of the substituents on substituted heterocycle is independently chlorine, fluorine, or methoxy.

An eleventh class of the present invention is a compound of Formula (I), wherein $R^1$ is

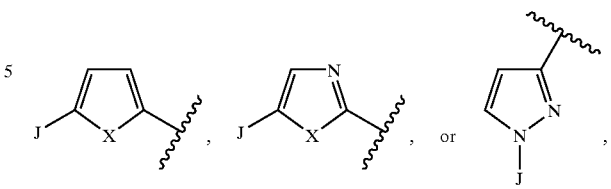

$R^2$ and $R^3$ are each independently hydrogen or $C_1$–$C_4$ alkyl; or $R^2$ and $R^3$ together with the carbon to which they are attached form $C_3$–$C_6$ cycloalkyl;

$R^4$ is

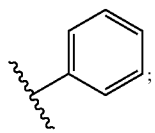

$R^5$ is

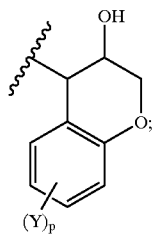

$R^6$ is

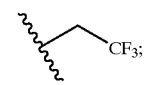

J is

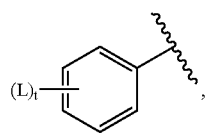

heterocycle, or substituted heterocycle;
heterocycle is

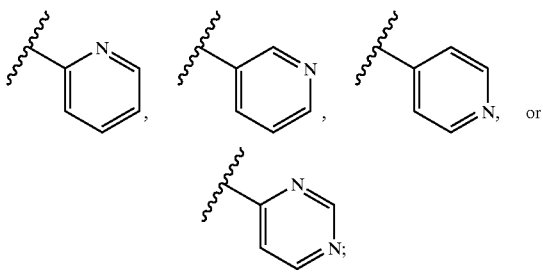

substituted heterocycle is heterocycle as defined above having one or more substituents independently selected from halogen, $C_1$–$C_4$ alkoxy, $C_1$–$C_4$ alkyl, fluorinated $C_1$–$C_4$ alkoxy, fluorinated $C_1$–$C_4$ alkyl, —S—$CH_3$, —N($CH_3$)$_2$, thiazolyl and oxazolyl;

each L is independently hydrogen, halogen, cyano, hydroxy, $C_1$–$C_4$ alkyl, fluorinated $C_1$–$C_4$ alkyl, or $C_1$–$C_4$ alkoxy;

X is O or S;

each Y is independently hydrogen, halogen, $C_1$–$C_6$ alkyl fluorinated $C_1$–$C_6$ alkyl, or $C_1$–$C_4$ alkoxy; and p is an integer from 0 to 2;

t is an integer from 0 to 2;

or a pharmaceutically acceptable salt thereof.

In a preferred aspect of the eleventh class, $R^2$ and $R^3$ are each independently hydrogen or methyl;

each L is independently hydrogen, chlorine, or fluorine;

each Y is independently hydrogen, chlorine, or fluorine; and each of the substituents on substituted heterocycle is independently chlorine, fluorine, methoxy, ethoxy, —$OCF_3$, —$OCHF_2$, methyl, ethyl, n-propyl, —S—$CH_3$, —N($CH_3$)$_2$, and thiazolyl.

Exemplifying the invention are compounds selected from the group consisting of (αR,γS,2S)-N-((3S,4S)-3,4-dihydro-3-hydroxy-2H-1-benzopyran-4-yl)-4-(1-furo[3,2-c]pyridin-2-yl-1-methylethyl)-γ-hydroxy-α-(phenylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-2-[[(2-fluoroethyl)amino]carbonyl]-4-(1-furo[3,2-c]pyridin-2-yl-1-methylethyl)-γ-hydroxy-α-(phenylmethyl)-1-piperazinepentanamide;

(αR,γS,2S)-N-((3S,4S)-3,4-dihydro-3-hydroxy-2H-1-benzofuran-4-yl)-2-[[[2-fluoro-1,1-bis(fluoromethyl)ethyl]amino]carbonyl]-4-(1-furo[3,2-c]pyridin-2-yl-1-methylethyl)-γ-hydroxy-α-(phenylmethyl)-1-piperazinepentanamide;

(αR,γS,2S)-2-[[[1,1-bis(fluoromethyl)ethyl]amino]carbonyl]-N-((3S,4S)-3,4-dihydro-3-hydroxy-2H-1-benzopyran-4-yl)-4-(1-furo[3,2-c]pyridin-2-yl-1-methylethyl)-γ-hydroxy-α-(phenylmethyl)-1-piperazinepentanamide;

(αR,γS,2S)-N-((3S,4S)-3,4-dihydro-3-hydroxy-2H-1-benzopyran-4-yl)-4-(1-furo[3,2-c]pyridin-2-yl-1-methylethyl)-γ-hydroxy-α-(phenylmethyl)-2-[[(3,3,3-trifluoropropyl)amino]carbonyl]-1-piperazinepentanamide;

(αR,γS,2S)-N-((3S,4S)-3,4-dihydro-3-hydroxy-2H-1-benzopyran-4-yl)-4-(1-furo[3,2-c]pyridin-2-yl-1-methylethyl)-γ-hydroxy-2-[[(2,2,3,3,3-pentafluoropropyl)-mino]carbonyl]-α-(phenylmethyl)-1-piperazinepentanamide;

(αR,γS,2S)-N-((3S,4S)-3,4-dihydro-3-hydroxy-2H-1-benzopyran-4-yl)-2-[[(2-fluoro-1,1-dimethylethyl)amino]carbonyl]-4-(1-furo[3,2-c]pyridin-2-yl-1-methylethyl)-γ-hydroxy-α-(phenylmethyl)-1-piperazinepentanamide;

(αR,γS,2S)-N-((1S,2R)-1,2-dihydro-2-hydroxy-1H-inden-1-yl)-4-(1-furo[3,2-c]pyridin-2-yl-1-methylethyl)-γ-hydroxy-α-(phenylmethyl)-2-[[(2,2,2-trifluoroethyl)amino]carbonyl]-1-piperazinepentanamide;

(αR,γS,2S)-N-((1S,2R)-1,2-dihydro-2-hydroxy-1H-inden-1-yl)-2-[[(2-fluoroethyl)amino]carbonyl]-4-[1-furo[3,2-c]pyridin-2-yl-1-methylethyl)-γ-hydroxy-α-(phenylmethyl)-1-piperazinepentanamide;

(αR,γS,2S)-N-((1S,2R)-1,2-dihydro-2-hydroxy-1H-inden-1-yl)-4-(1-furo[3,2-c]pyridin-2-yl-1-methylethyl)-γ-hydroxy-α-(phenylmethyl)-2-[[(3,3,3-trifluoropropyl)amino]carbonyl]-1-piperazinepentanamide;

(αR,γS,2S)-N-((1S,2R)-1,2-dihydro-2-hydroxy-1H-inden-1-yl)-4-(1-furo[3,2-c]pyridin-2-yl-1-methylethyl)-γ-hydroxy-2-[[(2,2,3,3,3-pentafluoropropyl)amino]carbonyl-α-(phenylmethyl)-1-piperazinepentanamide;

(αR,γS,2S)-4-(2-benzofuranylmethyl)-N-((3S,4S)-3,4-dihydro-3-hydroxy-2H-1-benzopyran-4-yl)-γ-hydroxy-α-(phenylmethyl)-2-[[(2,2,2-trifluoroethyl)amino]carbonyl-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[5-(3-pyridinyl)-1-furanyl]methyl]-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-(3-pyridinylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[5-(3-pyridinyl)-1-furanyl]methyl]-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[5-(5-pyrimidinyl)-1-furanyl]methyl]-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[(3-methyl-7-methoxy-4-benzofuranyl)methyl]-α-(3-phenylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[(7-methoxy-2-benzofuranyl)methyl]-α-(phenylmethyl)-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[(1-phenyl-1H-pyrrol-3-yl)methyl)-]-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[(1-phenyl-1H-imidazol-4-yl)methyl]-α-(phenylmethyl)-2-[[(2,2,2-trifluoroethyl)-amino]carbonyl]-1-piperazinepentanamide;

(αR,γS,2S)-4-(2-benzofuranylmethyl)-N-((1S,2R)-1,2-dihydro-2-hydroxy-1-inden-1-yl)-γ-hydroxy-α-(phenylmethyl)-2-[[(2,2,2-trifluoroethyl)amino]carbonyl]-1-piperazinepentanamide;

(αR,γS,2S)-N-((1S,2R)-1,2-dihydro-2-hydroxy-1H-inden-1-yl)-γ-hydroxy-α-(phenylmethyl)-4-(3-pyridinylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[(5-phenyl-2-furanyl)methyl]-α-(3-pyridinylmethyl)-2-[[(2,2,2-trifluoroethyl)-amino]carbonyl]-1-piperazinepentanamide;

(αR,γS,2S)-4-(2-benzopyranylmethyl)-N-((3S,4S)-3,4-dihydro-3-hydroxy-2H-1-benzopyran-4-yl)-γ-hydroxy-α-(3-pyridinylmethyl)-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(3-pyridinylmethyl)-4-(thieno[2,3-b]thien-2-ylmethyl)-2-[[(2,2,2-trifluoroethyl)amino]carbonyl]-1-piperazinepentanamide;

(αR,γS,2S)-4-[(2,6-difluorophenyl)methyl]-N-((3S,4S)-3,4-dihydro-3-hydroxy-2H-1-benzopyran-4-yl)-γ-hydroxy-α-(3-pyridinylmethyl)-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(3-pyridinylmethyl)-4-(thieno[3,2-b]thien-2-ylmethyl)-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[(7-methoxy-2-benzofuranyl)methyl]-α-(3-pyridinylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(3-pyridinylmethyl)-4-[[5-(2-thienyl)-2-furanyl]methyl]-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[(1-phenyl-1H-pyrrol-3-yl)methyl]-α-(3-pyridinylmethyl)-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-4-(1-phenyl-1H-imidazol-4-yl)methyl]-α-(3-pyridinylmethyl)-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[[5-(5-methyl-2-thienyl)-2-furanyl]methyl]-α-(3-pyridinylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[(5-phenyl-2-furanyl)methyl]-α-(4-pyridinylmethyl)-2-[[(2,2,2-trifluoroethyl)amino]carbonyl -1-piperazinepentanamide;

(αR,γS,2S)-4-(2-benzofuranylmethyl)-N-((3S,4S)-3,4-dihydro-3-hydroxy-2H-1-benzopyran-4-yl)-γ-hydroxy-α-(4-pyridinylmethyl)-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[1-methyl-1-[5-(4-pyridinyl)-2-furanyl]ethyl]-α-(phenylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[1-[5-(4-pyridinyl)-1-furanyl]ethyl]-2-[[(2,2,2-trifluoroethyl-amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[1-[5-(4-pyridinyl)-1-furanyl]ethyl]-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[1-methyl-1-(1-phenyl-1H-pyrazol-3-yl)ethyl]-α-(3-pyridinylmethyl)-2-[[(2,2,2-trifluoroethyl)amino]carbonyl]-1-piperazinepentanamide;

(α,γS,2S)-N-((3S,4S)-3,4-dihydro-3-hydroxy-2H-1-benzopyran-4-yl)-γ-hydroxy-4-[1-methyl-1-(3-phenyl-5-isoxazolyl)ethyl]-α-(3-pyridinylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[1-methyl-1-(3-phenyl-5-isoxazolyl)ethyl]]-α-(phenylmethyl)-2-[[(2,2,2-trifluoroethyl)amino]carbonyl]-1-piperazinepentanamide;

(αR,γS,2S)-4-[(7-chlorobenzofuran-2-yl)methyl]-N-((3S,4S)-3,4-dihydro-3-hydroxy-2H-1-benzopyran-4-yl)-γ-hydroxy-α-(3-pyridinylmethyl)-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-4-(1-furo[3,2-c]pyridin-2-yl-1-methylethyl)-γ-hydroxy-α-(phenylmethyl)-2-[[(2,2-difluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[5-(2-thiazolyl)-3-pyridinyl]methyl]-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[[5-(2-oxazolyl)-3-pyridinyl]methyl]-α-(phenylmethyl)-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[5-(4-thiazolyl)-3-pyridinyl]methyl]-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[5-(2-thiazolyl)-2-furanyl]methyl]-2-[[(2,2,2-trifluoroethyl)-amino]carbonyl]-1-piperazinepentanamide;

(αR,γS,2S)-4-[[5-(5-chloro-3-pyridinyl)-2-furanyl]methyl]-N-((3S,4S)-3,4-dihydro-3-hydroxy-2H-1-benzopyran-4-yl)-γ-hydroxy-α-(phenylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[(5-phenyl-2-furanyl)methyl]-α-(phenylmethyl)-2-[[(2,2,2-trifluoroethyl)amino]carbonyl]-1-piperazinepentanamide;

(αR,γS,2S)4-[(4-chloro-5-phenyl-2-furanyl)methyl]-N-((3S,4S)-3,4-dihydro-3-hydroxy-2H-1-benzopyran-4-yl)-γ-hydroxy-α-(phenylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[5-(2-pyridinyl)-2-furanyl]methyl]-2-[[(2,2,2-trifluoroethyl)-amino]carbonyl]-1-piperazinepentanamide;

(αR,γS,2S)-4-[[5-(5-chloro-2-pyridinyl)-2-furanyl]methyl]-N-((3S,4S)-3,4-dihydro-3-hydroxy-2H-1-benzopyran-4-yl)-γ-hydroxy-α-(phenylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[[5-(2-methyl-4-pyridinyl)-2-furanyl]methyl]-α-(phenylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-4-[[(5-(2-ethyl-4-pyridinyl)-2-furanyl]methyl]-γ-hydroxy-α-(phenylmethyl)-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[[5-(5-oxazolyl)-2-furanyl]methyl]-α-(phenylmethyl)-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[1-(4-pyridinyl)-1H-pyrrol-3-yl]methyl]-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[1-(3-pyridinyl)-1H-pyrrol-3-yl]methyl]-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[5-(4-pyridazinyl)-2-furanyl]methyl]-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[1-methyl-1-[3-methyl-5-(4-pyridinyl)-2-furanyl]ethyl]-α-(phenylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[5-(2-pyrazinyl)-2-furanyl]methyl]-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[[5-(1-methyl-1H-pyrazol-4-yl)-3-pyridinyl]methyl]-α-(phenylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[5-(2-thienyl)-3-pyridinyl]methyl]-2-[[(2,2,2-trifluoroethyl)amino]carbonyl-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[5-(3-thienyl)-3-pyridinyl]methyl]-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[5-(4-pyrimidinyl)-2-furanyl]methyl]-2-[[(2,2,2-trifluoroethyl)amino]carbonyl]-1-piperazinepentanamide;

(αR,γS,2S)-4-[(7-chlorofuro[3,2-c]pyridin-2-yl)methyl]-N-((3S,4S)-3,4-dihydro-3-hydroxy-2H-1-benzopyran-4-yl)-γ-hydroxy-α-(phenylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[5-(3-pyridinyl)-2-oxazolyl]methyl]-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[5-(2-pyridinyl)-2-oxazolyl]methyl]-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[1-methyl]-1-[5-(2-pyridinyl)-2-oxazolyl]ethyl]-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[1-methyl-1-[5-(3-pyridinyl)-2-oxazolyl]ethyl]-α-(phenylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[(5-phenyl-2-furanyl)methyl]-α-(5-pyrimidinylmethyl)-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[(5-phenyl-2-furanyl)methyl]-α-(2-pyrazinylmethyl)-2-[[(2,2,2-trifluoroethyl)amino]carbonyl]-1-piperazinepentanamide;

(αS,γS,2S)-N-((3S,4S)-3,4-dihydro-3-hydroxy-2H-1-benzopyran-4-yl)-γ-hydroxy-4-[[5-(2-pyridinyl)-2-furanyl]methyl]-α-(2-thienylmethyl)-2-[[(2,2,2-trifluoroethyl)-amino]carbonyl]-1-piperazinepentanamide;

(αS,γS,2S)-N-((3S,4S)-3,4-dihydro-3-hydroxy-2H-1-benzopyran-4-yl)-γ-hydroxy-4-[[5-(5-pyrimidinyl)-2-furanyl]methyl]-α-(5-thienylmethyl)-2-[[(2,2,2-trifluoroethyl)amino]carbonyl]-1-piperazinepentanamide;

(αS,γS,2S)-N-((3S,4S)-3,4-dihydro-3-hydroxy-2H-1-benzopyran-4-yl)-γ-hydroxy-4-[[5-(2-pyridinyl)-2-furanyl]methyl]-α-(3-thienylmethyl)-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[(5-phenyl-2-furanyl)methyl]-α-(2-pyridinylmethyl)-2-[[(2,2,2-trifluoroethyl)amino]carbonyl]-1-piperazinepentanamide;

(αR,γS,2S)-N-((1S,2R)-1,2-dihydro-2-hydroxy-1H-inden-1-yl)-γ-hydroxy-α-(phenylmethyl)-4-[[5-(2-pyridinyl)-2-furanyl]methyl]-2-[[(2,2,2-trifluoroethyl)-amino]carbonyl]-1-piperazinepentanamide;

(αR,γS,2S)-4-[[5-(5-chloro-2-pyridinyl)-2-furanyl]methyl]-N-((1S,2R)-1,2-dihydro-2-hydroxy-1H-inden-1-yl)-γ-hydroxy-α-(phenylmethyl)-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[1-methyl-1-[5-(5-chloro-3-pyridinyl)-2-oxazolyl]ethyl]-α-(phenylmethyl)-2-[[(2,2,2 trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[1-methyl-1-[5-(5-chloro-2-pyridinyl)-2-oxazolyl]ethyl]-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[(3-chloro-1-phenyl-1H-pyrrol-3-yl)methyl]-α-(3-pyridinylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[(4-chloro-1-phenyl-1H-pyrrol-3-yl)methyl]-α-(3-pyridinylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[1-methyl-1-(1-phenyl-1H-triazoyl-4-yl)ethyl]-α-(3-phenylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy4-[1-methyl-1-(1-phenyl-1H-triazoyl-4-yl)ethyl]-α-(3-pyridinylmethyl)-2-[[(2,2,2-trifluoroethyl)amino]carbonyl]-1-piperazinepentanamide;

(αR,γS,2S)-N-(4S-3,4-dihydro-1H-2,2-dioxobenzothiopyranyl)-γ-hydroxy-α-(phenylmethyl)-4-[[5-(5-pyrimidinyl)-1-furanyl]methyl]-2-[[(2,2,2-trifluoroethyl)amino]carbonyl]-1-piperazinepentanamide;

(αR,γS,2S)-N-(4S-3,4-dihydro-1H-2,2-dioxobenzothiopyranyl)-γ-hydroxy-α-(phenylmethyl)-4-[[5-(2-pyridinyl)-2-furanyl]methyl]-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[1-methyl-1-[5-(2-methyl-4-pyridinyl)-2-furanyl]ethyl]-α-(phenylmethyl)-2-[[(2,2,2-trifluoroethyl)amino]carbonyl]-1-piperazinepentanamide;

and pharmaceutically acceptable salts thereof.

Also exemplifying the invention are compounds selected from the group consisting of (αR,γS,2S)-N-[(3S,4S)-3,4-dihydro-3-hydroxy-2H-1-benzopyran-4-γ-hydroxy-4-[1-[5-(5-methoxy-3-pyridinyl)-2-oxazolyl]-1-methylethyl]-α-

(phenylmethyl)-2-[[(2,2,2-trifluoroethyl)amino]
carbonyl]-1-piperazinepentanamide;

(αR,γS,2S)-N-[(3S,4S)-3,4-dihydro-3-hydroxy-2H-1-
benzopyran-4-yl]-4-[5-(5-methyl-3-pyridinyl)-2-
oxazolyl]-1-methylethyl]-γ-hydroxy-α-(phenylmethyl)-
2-[[(2,2,2-trifluoroethyl)amino]carbonyl]-1-
piperazinepentanamide;

(αR,γS,2S)-N-[(3S,4S)-3,4-dihydro-3-hydroxy-2H-1-
benzopyran-4-yl]-4-[1-[5-(5-hydroxy-3-pyridinyl)-2-
oxazolyl]-1-methylethyl]-γ-hydroxy-α-(phenylmethyl)-
2-[[(2,2,2-trifluoroethyl)amino]carbonyl]-1-
piperazinepentanamide;

(αR,γS,2S)-4-[1-[5-[5-(difluoromethoxy)-3-pyridinyl]-2-
oxazolyl]-1-methylethyl]-N-[(3S,4S)-3,4-dihydro-3-
hydroxy-2H-1-benzopyran-4-yl]-γ-hydroxy-α-
(phenylmethylmethyl)-2-[[(2,2,2-trifluoroethyl)amino]
carbonyl]-1-piperazinepentanamide;

(αR,γS,2S)-4-[1-[5-[5-(difluoromethyl)-3-pyridinyl]-2-
oxazolyl]-1-methylethyl]-N-[(3S,4S)-3,4-dihydro-3-
hydroxy-2H-1-benzopyran-4-yl]-γ-hydroxy-α-
(phenylmethyl)-2-[[(2,2,2-trifluoroethyl)amino]
carbonyl]-1-piperazinepentanamide;

(αR,γS,2S)-N-[(3S,4S)-3,4-dihydro-3-hydroxy-2H-1-
benzopyran-4-yl]-4-[1-[5-(2-fluorophenyl)-2-oxazolyl]-
1-methylethyl]-γ-hydroxy-α-(phenylmethyl)-2-[[(2,2,2-
trifluoroethyl)amino]carbonyl]-1-piperazine-
pentanamide;

(αR,γS,2S)-N-[(3S,4S)-3,4-dihydro-3-hydroxy-2H-1-
benzopyran-4-yl]-4-[1-[5-(3-fluorophenyl)-2-oxazolyl]-
1-methylethyl]-γ-hydroxy-α-(phenylmethyl)-2-[[(2,2,2-
trifluoroethyl)amino]carbonyl]-1-piperazinepentanamide;

(αR,γγ,2S)-N-[(3S,4S)-3,4-dihydro-3-hydroxy-2H-1-
benzopyran-4-yl]-4-[1-[5-(4-fluorophenyl)-2-oxazolyl]-
1-methylethyl]-γ-hydroxy-α-(phenylmethyl)-2-[[(2,2,2-
trifluoroethyl)amino]carbonyl]-1-piperazinepentanamide;

(αR,γS,2S)-N-[(3S,4S)-3,4-dihydro-3-hydroxy-2H-1-
benzopyran-4-yl]-γ-hydroxy-4-[1-[5-(5-ethoxy-3-
pyridinyl)-2-oxazolyl]-1-methylethyl]-α-
(phenylmethyl)-2-[[(2,2,2-trifluoroethyl)amino]
carbonyl]-1-piperazinepentanamide;

(αR,γS,2S)-N-[(3S,4S)-3,4-dihydro-3-hydroxy-2H-1-
benzopyran-4-yl]-γ-hydroxy-4-[1-[5-(5-fluoro-3-
pyridinyl)-2-oxazolyl]-1-methylethyl]-α-
(phenylmethyl)-2-[[(2,2,2-trifluoroethyl)amino]
carbonyl]-1-piperazinepentanamide;

(αR,γS,2S)-N-[(3S,4S)-3,4-dihydro-3-hydroxy-2H-1-
benzopyran-4-yl]-γ-hydroxy-4-[1-[5-(5-ethyl-3-
pyridinyl)-2-oxazolyl]-1-methylethyl]-α-
(phenylmethyl)-2-[[(2,2,2-trifluoroethyl)amino]
carbonyl]-1-piperazinepentanamide;

(αR,γS,2S)-N-[(3S,4S)-3,4-dihydro-3-hydroxy-2H-1-
benzopyran-4-yl]-γ-hydroxy4-[1-methyl-1-[5-(5-propyl-
3-pyridinyl)-2-oxazolyl]ethyl]-α-(phenylmethyl)-2-[[(2,
2,2-trifluoroethyl)amino]carbonyl]-1-
piperazinepentanamide;

(αR,γS,2S)-N-[(3S,4S)-3,4-dihydro-3-hydroxy-2H-1-
benzopyran-4-yl]-γ-hydroxy-4-[1-methyl-1-[4-methyl-5-
(3-pyridinyl)-2-oxazolyl]ethyl]-α-(phenylmethyl)-2-[[(2,
2,2-trifluoroethyl)amino]carbonyl]-1-
piperazinepentanamide;

(αR,γS,2S)-N-[(3S,4S)-3,4-dihydro-3-hydroxy-2H-1-
benzopyran-4-yl]-γ-hydroxy-4-[1-[5-(5-methoxy-3-
pyridinyl)-4-methyl-2-oxazolyl]-1-methylethyl]-α-
(phenylmethyl)-2-[[(2,2,2-trifluoroethyl)amino]
carbonyl]-1-piperazinepentanamide;

(αR,γS,2S)-N-[(3S,4S)-3,4-dihydro-3-hydroxy-2H-1-
benzopyran-4-yl]-γ-hydroxy-4-[1-methyl-1-[5-[5-
(methylthio)-3-pyridinyl]-2-oxazolyl]ethyl]-α-
(phenylmethyl)-2-[[(2,2,2-trifluoroethyl)amino]
carbonyl]-1-piperazinepentanamide;

(αR,γS,2S)-N-[(3S,4S)-3,4-dihydro-3-hydroxy-2H-1-
benzopyran-4-yl]-γ-hydroxy-4-[1-[5-(5-dimethylamino-
3-pyridinyl)-2-oxazolyl]-1-methylethyl]-α-
(phenylmethyl)-2-[[(2,2,2-trifluoroethyl)amino]
carbonyl]-1-piperazinepentanamide;

(αR,γS,2S)-4-[1-[3-(5-methoxy-3-pyridinyl)-5-isoxazoly]-
1-methylethyl]-N-[(3S,4S)-3,4-dihydro-3-hydroxy-2H-1-
benzopyran-4-yl]-γ-hydroxy-α-(phenylmethyl)-2-[[(2,
2-trifluoroethyl)amino]carbonyl]-1-
piperazinepentanamide;

(αR,γS,2S)-4-[1-[2-(5-methoxy-3-pyridinyl)-4-thiazolyl]-1-
methylethyl]-N-[(3S,4S)-3,4-dihydro-3-hydroxy-2H-1-
benzopyran-4-yl]-γ-hydroxy-α-(phenylmethyl)-2-[[(2,2,
2-trifluoroethyl)amino]carbonyl]-1-
piperazinepentanamide;

(αR,γS,2S)-4-[1-[2-(5-chloro-3-pyridinyl)-4-thiazolyl]-1-
methylethyl]-N-[(3S,4)-3,4-dihydro-3-hydroxy-2H-1-
benzopyran-4-yl]-γ-hydroxy-α-(phenylmethyl)-2-[[(2,2,
2-trifluoroethyl)amino]carbonyl]-1-
piperazinepentanamide;

(αR,γS,2S)-4-[1-[2-(3-pyridinyl)-4-thiazolyl]-1-
methylethyl]-N-[(3S,4S)-3,4-dihydro-3-hydroxy-2H-1-
benzopyran-4-yl]-γ-hydroxy-α-(phenylmethyl)-2-[[(2,2,
2-trifluoroethyl)amino]carbonyl]-1-
piperazinepentanamide;

(αR,γS,2S)-N-[(3S,4S)-3,4-dihydro-3-hydroxy-2H-1-
benzopyran-4-yl]-γ-hydroxy-4-[1-[1-(5-methoxy-3-
pyridinyl)-1H-pyrazol-3-yl]-1-methylethyl]-α-
(phenylmethyl)-2-[[(2,2,2-trifluoroethyl)amino]
carbonyl]-1-piperazinepentanamide;

(αR,γS,2S)-N-[(3S,4S)-3,4-dihydro-3-hydroxy-2H-1-
benzopyran-4-yl]-γ-hydroxy-4-[1-[1-(5-chloro-3-
pyridinyl)-1H-pyrazol-3-yl]-1-methylethyl]-α-
(phenylmethyl)-2-[[(2,2,2-trifluoroethyl)amino]
carbonyl]-1-piperazinepentanamide;

(αR,γS,2S)-N-[(3S,4S)-3,4-dihydro-3-hydroxy-2H-1-
benzopyran-4-yl]-γ-hydroxy-4-[1-[1-(5-fluoro-3-
pyridinyl)-1H-pyrazol-3-yl]-1-methylethyl]-α-
(phenylmethyl)-2-[[(2,2,2-trifluoroethyl)amino]
carbonyl]-1-piperazinepentanamide;

(αR,γS,2S)-N-[(3S,4S)-3,4-dihydro-3-hydroxy-2H-1-
benzopyran-4-yl]-γ-hydroxy-4-[1-[1-(3-pyridinyl)-1H-
pyrazol-3-yl]-1-methylethyl]-α-(phenylmethyl)-2-[[(2,2,
2-trifluoroethyl)amino]carbonyl]-1-
piperazinepentanamide;

(αS,γS,2S)-4-[1-[5-phenyl-2-oxazolyl]-1-methylethyl]-N-
[(3S,4S)-3,4-dihydro-3-hydroxy-2H-1-benzopyran-4-yl]-
α-(furo[2,3-c]pyridin-2-ylmethyl)-γ-hydroxy-2-[[(2,2,2-
trifluoroethyl)amino]carbonyl]-1-piperazinepentanamide;

(αS,γS,2S)-4-[1-[5-(4-chlorophenyl)-2-oxazolyl]-1-
methylethyl]-N-[(3S,4)-3,4-dihydro-3-hydroxy-2H-1-
benzopyran-4-yl]-α-(furo[2,3-c]pyridin-2-ylmethyl)-γ-
hydroxy-2-[[2,2,2-trifluoroethyl)amino]carbonyl]-1-
piperazinepentanamide;

(αS,γS,2S)-4-[1-[5-(4-fluorophenyl)-2-oxazolyl]-1-
methylethyl]-N-[(3S,4S)-3,4-dihydro-3-hydroxy-2H-1-
benzopyran-4-yl]-α-(furo[2,3-c]pyridin-2-ylmethyl)-γ-
hydroxy-2-[[(2,2,2-trifluoroethyl)amino]carbonyl]-1-
piperazinepentanamide;

(αS,γS,2S)-4-[1-[5-(4-chlorophenyl)-2-oxazolyl]-1-
methylethyl]-N-[(3S,4S)-3,4-dihydro-3-hydroxy-2H-1-
benzopyran-4-yl]-α-(furo[2,3-c]pyridin-3-ylmethyl)-γ-
hydroxy-2-[[(2,2,2-trifluoroethyl)amino]carbonyl]-1-
piperazinepentanamide;

(αS,γS,2S)-4-[1-[5-(4-fluorophenyl)-2-oxazolyl]-1-methylethyl]-N-[(3S,4S)-3,4-dihydro-3-hydroxy-2H-1-benzopyran-4-yl]-α-(furo[2,3-c]pyridin-3-ylmethyl)-γ-hydroxy-2-[[(2,2,2-trifluoroethyl)amino]carbonyl]-1-piperazinepentanamide;

(αS,γS,2)-N-[(3S,4S)-3,4-dihydro-3-hydroxy-2H-1-benzopyran-4-yl]-4-[1-[5-(4-fluorophenyl)-2-oxazolyl]-1-methylethyl]-α-(furo[2,3-d]pyrimidin-6-ylmethyl)-γ-hydroxy-2-[[(2,2,2-trifluoroethyl)amino]carbonyl]-1-piperazinepentanamide;

and pharmaceutically acceptable salts thereof.

A preferred aspect of the present invention is a compound selected from the group consisting of (αR,γS,2S)-N-((3S,4S)-3,4-dihydro-3-hydroxy-2H-1-benzopyran-4-yl)-4-(1-furo[3,2-c]pyridin-2-yl-1-methylethyl)-γ-hydroxy-α-(phenylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[(5-phenyl-2-furanyl)methyl]-α-(4-pyridinylmethyl)-2-[[(2,2,2-trifluoroethyl)amino]carbonyl]-1-piperazinepentanamide;

(αR,γS, 2S)-N-((3S,4S)-3,4-dihydro-3-hydroxy-2H-1-benzopyran-4-yl)-γ-hydroxy-4-[1-methyl-1-(1-phenyl-1H-pyrazol-3-yl)ethyl]-α-(3-pyridinylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[5-(2-pyridinyl)-2-furanyl]methyl]-2-[[(2,2,2-trifluoroethyl)-amino]carbonyl]-1-piperazinepentanamide;

(αR,γS,2S)-4-[[5-(5-chloro-2-pyridinyl)-2-furanyl]methyl]-N-((3S,4S)-3,4dihydro-3-hydroxy-2H-1-benzopyran-4-yl)-γ-hydroxy-α-(phenylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[1-methyl-1-[5-(3-pyridinyl)-2-oxazolyl]ethyl]-α-(phenylmethyl)-2-[[(2,2,2-trifluoroethyl)amino]carbonyl]-1-piperazinepentanamide;

(αR,γS,2S)-N-[(3S,4S)-3,4-dihydro-3-hydroxy-2H-1-benzopyran-4-yl]-γ-hydroxy-4-[1-[5-(5-methoxy-3-pyridinyl)-2-oxazolyl]-1-methylethyl]-α-(phenylmethyl)-2-[[(2,2,2-trifluoroethyl)amino]carbonyl]-1-piperazinepentanamide;

(αR,γS,2S)-N-[(3S,4S)-3,4-dihydro-3-hydroxy-2H-1-benzopyran-4-yl]-γ-hydroxy4-[1-[5-(5-fluoro-3-pyridinyl)-2-oxazolyl]-1-methylethyl]-α-(phenylmethyl)-2-[[(2,2,2-trifluoroethyl)amino]carbonyl]-1-piperazinepentanamide;

(αR,γS,2S)-N-[(3S,4S)-3,4-dihydro-3-hydroxy-2H-1-benzopyran-4-yl]-γ-hydroxy-4-[1-[1-(5-fluoro-3-pyridinyl)-1H-pyrazol-3-yl]-1-methylethyl]-α-(phenylmethyl)-2[[(2,2,2-trifluoromethyl)amino]carbonyl]-1-piperazinepentanamide;

(αS,γS,2S)-4-[1-[5-(4-chlorophenyl)-2-oxazolyl]-1-methylethyl-N-[(3S,4S)-3,4-dihydro-3-hydroxy-2H-1-benzopyran-4-yl]-α-(furo[2,3-c]pyridin-2-ylmethyl)-γ-hydroxy-2-[[(2,2,2-trifluoroethyl)amino]carbonyl]-1-piperazinepentanamide;

(αS,γS,2S)-4-[1-[5-(4-fluorophenyl)-2-oxazolyl]-1-methylethyl]-N-[(3S,4S)-3,4-dihydro-3-hydroxy-2H-1-benzopyran-4-yl]-α-(furo[2,3-c]pyridin-2-ylmethyl)-γ-hydroxy-2-[[(2,2,2-trifluoroethyl)amino]carbonyl]-1-piperazinepentanamide;

(αS,γS,2S)-4-[1-[5-(4-chlorophenyl)-2-oxazolyl]-1-methylethyl]-N-(3S,4S)-3,4-dihydro-3-hydroxy-2H-1-benzopyran-4-yl]-α-(furo[2,3-c]pyridin-3-ylmethyl)-γ-hydroxy-2-[[(2,2,2-trifluoroethyl)amino]carbonyl]-1-piperazinepentanamide;

(αS,γS,2S)-4-[1-[5-(4-fluorophenyl)-2-oxazolyl]-1-methylethyl]-N-[(3S,4S)-3,4-dihydro-3-hydroxy-2H-1-benzopyran-4-yl]-α-(furo[2,3-c]pyridin-3-ylmethyl)-γ-hydroxy-2-[[(2,2,2-trifluoroethyl)amino]carbonyl]-1-piperazinepentanamide;

(αS,γS,2S)-N-[(3S,4S)-3,4-dihydro-3-hydroxy-2H-1-benzopyran-4-yl]-4-[1-[5-(4-fluorophenyl)-2-oxazolyl]-1-methylethyl]-α-(furo[2,3-d]pyrimidin-6-ylmethyl)-γ-hydroxy-2-[[(2,2,2-trifluoroethyl)amino]carbonyl]-1-piperazinepentanamide;

and pharmaceutically acceptable salts thereof.

Other embodiments of the present invention include the following:

(a) A pharmaceutical composition comprising a therapeutically effective amount of a compound of Formula (I) and a pharmaceutically acceptable carrier.

(b) A pharmaceutical composition made by combining a therapeutically effective amount of a compound of Formula (I) and a pharmaceutically acceptable carrier.

(c) The pharmaceutical composition of (a), wherein the composition further comprises a therapeutically effective amount of at least one AIDS treatment agent selected from the group consisting of AIDS antiviral agents, immunomodulators, and anti-infective agents.

(d) The pharmaceutical composition of (a), wherein the composition further comprises a therapeutically effective amount of at least one antiviral agent selected from the group consisting of non-nucleoside HIV reverse transcriptase inhibitors and nucleoside HIV reverse transcriptase inhibitors.

(e) The pharmaceutical composition of (d), further comprising a therapeutically effective amount of an additional HIV protease inhibitor.

(g) The pharmaceutical composition of (a), wherein the composition further comprises a therapeutically effective amount of at least one antiviral agent which is a CCR5 receptor antagonist.

(h) The pharmaceutical composition of (a), wherein the composition further comprises a therapeutically effective amount of at least one antiviral agent which is an HIV integrase inhibitor.

(i) The pharmaceutical composition of (a), further comprising a cytochrome P450 monooxygenase inhibitor (e.g., indinavir or ritonavir or a pharmaceutically acceptable salt thereof) in an amount effective to improve the pharmacokinetics of the compound.

(j) A method of inhibiting HIV protease in a subject in need thereof which comprises administering to the subject a therapeutically effective amount of a compound of Formula (I).

(k) A method of preventing or treating infection by HIV in a subject in need thereof which comprises administering to the subject a therapeutically effective amount of a compound of Formula (I).

(i) A method of treating AIDS in a subject in need thereof which comprises administering to the subject a therapeutically effective amount of a compound of Formula (I).

(m) The method of (j) or (k) or (l), wherein the compound of Formula (I) is administered in combination with a therapeutically effective amount of at least one AIDS treatment agent selected from the group consisting of AIDS antiviral agents, immunomodulators, and anti-infective agents.

(n) The method of (j) or (k) or (l), wherein the compound of Formula (I) is administered in combination with a therapeutically effective amount of at least one antiviral agent selected from the group consisting of non-nucleoside HIV reverse transcriptase inhibitors and nucleoside HIV reverse transcriptase inhibitors.

(o) The method of (j) or (k) or (l), wherein the compound is administered in combination with a cytochrome P450 monooxygenase inhibitor in an amount effective to improve the pharmacokinetics of the compound.

(p) A method of inhibiting HIV protease in a subject in need thereof which comprises administering to the subject a therapeutically effective amount of any one of the compositions set forth in (a) to (i).

(q) A method of preventing or treating infection by HIV in a subject in need thereof which comprises administering to the subject a therapeutically effective amount of any one of the compositions set forth in (a) to (i).

(r) A method of treating AIDS in a subject in need thereof which comprises administering to the subject a therapeutically effective amount of any one of the compositions set forth in (a) to (i).

Additional embodiments of the invention include the pharmaceutical compositions and methods set forth in (a)–(r) above, wherein the compound employed therein is a compound of one of the embodiments, classes, or subclasses of compounds described above.

The present invention also includes a process for preparing compounds of Formula (11):

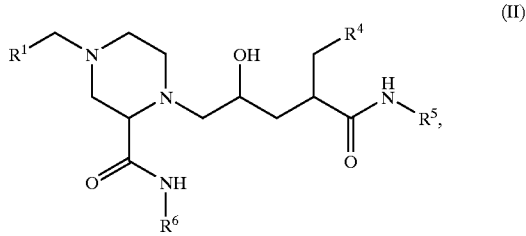

which comprises reacting a piperazine of Formula (III):

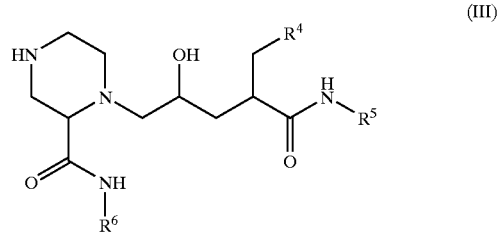

with an aldehyde of formula $R^1$—CHO in the presence of a reducing agent; wherein $R^1$, $R^4$, $R^5$ and $R^6$ are independently as defined above in Formula (I) or as defined in any embodiments, classes or aspects thereof. Suitable reducing agents include sodium cyanoborohydride, sodium triacetoxyborohydride, hydrogen plus a hydrogenation catalyst (e.g., a trasition metal catalyst—such as Ni, Pt or Pd—or a compound thereof—such as a halide, hydroxide, or oxide—), zinc with HCl, sodium borohydride, iron pentacarbonyl with alcoholic KOH, and selenophenol (PhSeH). In one embodiment, the reducing agent is sodium cyanoborohydride or sodium triacetoxyborohydride.

The reaction is typically conducted in a solvent, which can be any inorganic or organic substance which can dissolve, disperse, and/or suspend the reactants and is chemically inert under the reaction conditions employed. Suitable solvents include $C_2$–$C_4$ nitriles (e.g., acetonitrile and propionitrile), N,N-di-$C_1$–$C_6$ alkyl tertiary amides of $C_1$–$C_6$ alkylcarboxylic acids (e.g., DMF and N,N-dimethylacetamide), $C_5$–$C_6$ cyclic tertiary amides (e.g., N-methylpyrrolidone), aliphatic $C_2$–$C_6$ ethers and di-ethers (e.g., ethyl ether, MTBE and dimethoxyethane), $C_4$–$C_6$ cyclic ethers and di-ethers (e.g., THF and dioxane), and combinations of two or more of the foregoing. In one embodiment, the solvent is an N,N-di-$C_1$–$C_4$ alkyl tertiary amide of a $C_1$–$C_4$ alkylcarboxylic acid. In another embodiment, the solvent is DMF, N,N-dimethylacetamide, or N-methylpyrrolidone.

The reaction temperature is suitably in a range of from about –20 to about 100° C., and is typically in a range of from about –10 to about 80° C. In one embodiment, the temperature is in a range of from about 0 to about 50° C (e.g., from about 0 to about 30° C.).

The relative amounts of reactants and reagents are typically selected so as to maximize the conversion of Compound III and the yield of Compound II. Accordingly, at least about one equivalent of aldehyde is typically employed per equivalent of Compound III. In one embodiment, the aldehyde is employed in an amount in the range of from about 1 to about 5 equivalents (e.g., from about 1 to about 1.5 equivalents) per equivalent of Compound II. The reducing agent is typically also employed in an amount of at least about one equivalent per equivalent of Compound III. In one embodiment, an equal number of equivalents of reducing agent and aldehyde are employed in the reaction.

In a typical procedure, Compound III and the aldehyde are dissolved in the solvent at a relatively low temperature (e.g., below about 5° C.), followed by addition of the reducing agent, after which the reaction mixture is warmed to reaction temperature (e.g., from about 20 to about 25° C.) and maintained at that temperature until the reaction is complete, as determined by a standard method of monitoring the progress of the reaction (e.g., HPLC). Compound II can then be recovered from the reaction mixture using conventional procedures such as filtration and washing of the precipitate. Yields of at least about 70% can be achieved by the process.

One embodiment of this process is a process for preparing compounds of Formula (II-A):

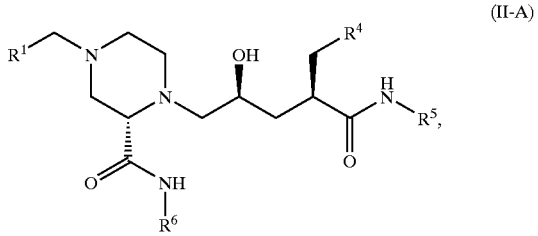

which comprises reacting a piperazine of Formula (III-A):

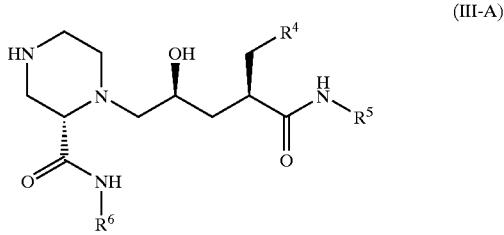
(III-A)

with an aldehyde of formula $R^1$—CHO in the presence of a reducing agent; wherein $R^1$, $R^4$, $R^5$ and $R^6$ are independently as defined above in Formula (I) or as defined in any embodiments, classes or aspects thereof.

Another embodiment of this process is a process as set forth in the preceding paragraph, wherein:

$R^1$ is 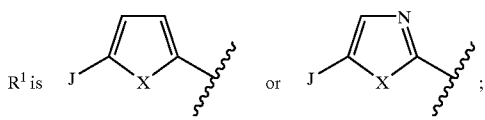

wherein X is O or S, and J is

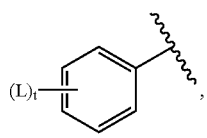

heterocycle, or substituted heterocycle; where
t is an integer from zero to 2;
each L is independently hydrogen, halogen, cyano, hydroxy, $C_1$–$C_4$ alkyl, fluorinated $C_1$–$C_4$ alkyl, or $C_1$–$C_4$ alkoxy;
heterocycle is

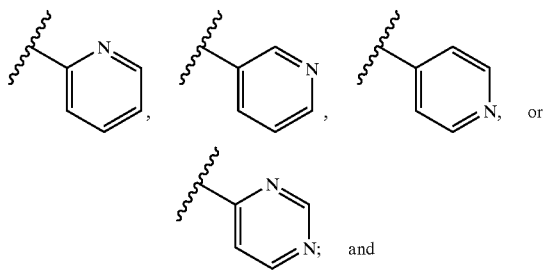

substituted heterocycle is heterocycle as defined above having one or more substituents independently selected from halogen, $C_1$–$C_4$ alkoxy, $C_1$–$C_4$ alkyl, fluorinated $C_1$–$C_4$ alkoxy, fluorinated $C_1$–$C_4$ alkyl, —S—$CH_3$, —N($CH_3$)$_2$, thiazolyl, and oxazolyl;
$R^4$ is

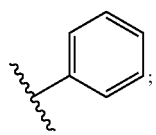

$R^5$ is

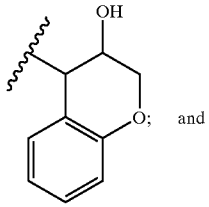
and $R_6$ is

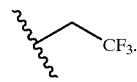

As used herein, the term "$C_1$–$C_6$ alkyl" refers to a linear or branched chain alkyl group having from 1 to 6 carbon atoms, and is selected from the hexyl alkyl and pentyl alkyl isomers, n-, iso-, sec- and t-butyl, n- and isopropyl, ethyl and methyl. "$C_1$–$C_4$ alkyl" refers to a linear or branched chain alkyl group having from 1 to 4 carbon atoms, and is selected from n-, iso-, sec- and t-butyl, n- and isopropyl, ethyl and methyl.

The term "$C_2$–$C_6$ alkenyl" refers to a linear or branched chain alkenyl group having from 2 to 6 carbon atoms, and is selected from the hexyl alkenyl and pentyl alkenyl isomers, 1-, 2- and 3-butenyl, 1- and 2-isobutenyl, 1- and 2-propenyl, and ethenyl. "$C_2$–$C_4$ alkenyl" has an analogous definition.

The term "$C_2$–$C_6$ alkynyl" refers to a linear or branched chain alkynyl group having from 2 to 6 carbon atoms, and is selected from the hexyl alkynyl and pentyl alkynyl isomers, 1-, 2- and 3-butynyl, 1- and 2-propynyl, and ethynyl. "$C_2$–$C_4$ alkynyl" has an analogous definition.

The term "$C_1$–$C_6$ alkoxy" means an —O—alkyl group wherein alkyl is $C_1$ to $C_6$ alkyl as defined above. "$C_1$–$C_4$ alkoxy" has an analogous meaning; i.e., it is an alkoxy group selected from methoxy, ethoxy, n-propoxy, isopropoxy, n-butoxy, isobutoxy, tert-butoxy, and sec-butoxy. Similarly, "$C_1$–$C_3$ alkoxy" is selected from methoxy, ethoxy, n-propoxy, and isopropoxy.

The term "$C_3$–$C_6$ cycloalkyl" refers to a cyclic ring selected from cyclopropyl, cyclobutyl, cyclopentyl, and cyclohexyl. "$C_3$–$C_5$ cycloalkyl" has an analogous meaning.

The term "$C_3$–$C_6$ azacycloalkyl" refers to a saturated monocyclic group consisting of one nitrogen and from 3 to 6 carbon atoms, selected from azetidinyl (i.e., azacyclobutyl), pyrrolidinyl (azacyclopentyl), piperidinyl (azacyclohexyl), and hexahydroazepinyl (azacycloheptyl). "$C_3$–$C_5$ azacycloalkyl" has an analogous meaning.

The term "halogen" (which may alternatively be referred to as "halo") refers to fluorine, chlorine, bromine and iodine (alternatively, fluoro, chloro, bromo, and iodo).

The term "fluorinated $C_1$–$C_6$ alkyl" (which may alternatively be referred to as "$C_1$–$C_6$ fluoroalkyl") means a $C_1$–$C_6$ alkyl group as defined above with one or more fluorine substituents. The term "fluorinated $C_1$–$C_4$ alkyl" has an analogous meaning. Representative examples of suitable fluoroalkyls include the series $(CH_2)_{0-3}CF_3$ (i.e., trifluoromethyl; 2,2,2-trifluoroethyl; 3,3,3-trifluoro-n-propyl, etc.), 1-fluoroethyl, 2-fluoroethyl, 2,2-difluoroethyl, 3,3,3-trifluoroisopropyl, 1,1,1,3,3,3-hexafluoroisopropyl, and perfluorohexyl.

The term "fluorinated $C_1$–$C_6$ alkoxy" (which may alternatively be referred to as "$C_1$–$C_6$ fluoroalkoxy") means a $C_1$–$C_6$ alkoxy group as defined above wherein the alkyl moiety has one or more fluorine substituents. The terms "fluorinated $C_1$–$C_4$ alkoxy" and "fluorinated $C_1$–$C_3$ alkoxy" have analogous meanings. Representative examples include the series $O(CH_2)_{0-3}CF_3$ (i.e., trifluoromethoxy, 2,2,2-trifluoroethoxy, 3,3,3-trifluoro-n-propoxy, etc.), 1,1,1,3,3,3-hexafluoroisopropoxy, and so forth.

The term "carbocyclic" (which may alternatively be referred to as "carbocycle") refers to a saturated or unsaturated monocyclic ring consisting of from 5 to 7 carbon atoms or a saturated or unsaturated bicyclic ring consisting of from 7 to 10 carbon atoms. It is understood that either or both rings of the bicyclic may be saturated or unsaturated. Exemplary carbocyclics include, but are not limited to, cyclopentyl, cyclohexyl, cylcoheptyl, cyclopentenyl, cyclohexenyl, cycloheptenyl, phenyl, naphthyl, tetrahydronaphthyl (tetralin), indenyl, and indanyl.

The term "aryl" refers to aromatic mono- and polycarbocyclic ring systems, wherein the carbocyclic rings in the polyring systems may be fused or attached to each other via a single ring carbon. Suitable aryl groups include, but are not limited to, phenyl, naphthyl, and biphenylenyl.

The term "substituted aryl" refers to an aryl group as defined above having one or more substituents independently selected from cyano, halo, hydroxy, $C_1$–$C_6$ alkyl, $C_2$–$C_6$ alkenyl, $C_2$–$C_6$ alkynyl, $C_1$–$C_6$ alkoxy, fluorinated $C_1$–$C_6$ alkyl, fluorinated $C_1$–$C_6$ alkoxy, heterocycle, substituted heterocycle, and the like.

The term "heterocyclic" (which may alternatively be referred to as "heterocycle") refers to (i) a 4- to 8-membered, saturated or unsaturated monocyclic ring consisting of carbon atoms and one or more heteroatoms selected from N, O and S or (ii) a 7- to 10-membered bicyclic ring system, either ring of which is saturated or unsaturated, consisting of carbon atoms and one or more heteroatoms selected from N, O and S; and wherein the nitrogen and sulfur heteroatoms in (i) or (ii) are optionally oxidized, and the nitrogen heteroatom is optionally quaternized. The heterocyclic ring may be attached at any heteroatom or carbon atom, provided that attachment results in the creation of a stable structure. Representative examples of heterocyclic groups include azetidinyl, piperidinyl, piperazinyl, azepinyl, pyrrolyl, indazolyl, pyrrolidinyl, pyrazolyl, pyrazolidinyl, imidazolyl, imidazolidinyl, imidazolinyl, pyridyl, pyrazinyl, pyrimidinyl, pyridazinyl, oxazolyl, oxazolidinyl, triazolyl, isoxazolyl, isoxazolidinyl, morpholinyl, thiazolyl, thiadiazolyl, thiazolidinyl, isothiazolyl, quinoxazolinyl, isothiazolidinyl, methylenedioxyphenyl, quinolinyl, isoquinolinyl, benzimidazolyl, thiadazolyl, benzopyranyl, benzothiazolyl, benzoazolyl, furyl, tetrahydrofuryl, benzofuranyl, benzothiofuranyl, azabenzofuranyl, benzothiazolyl, azabenzothiazolyl, azabenzoxazolyl, tetrahydropuranyl, thiophenyl (alternatively referred to herein as "thienyl"), thienothiophenyl, benzothiophenyl, and oxadiazolyl.

The term "substituted heterocyclic" (alternatively "substituted heterocycle") refers to a heterocyclic group as defined above having one or more substituents independently selected from cyano, halo, hydroxy, amino, $C_1$–$C_4$ alkylamino, di-($C_1$–$C_4$ alkyl)amino, $C_3$–$C_6$ azacycloalkyl, $C_1$–$C_6$ alkyl, $C_2$–$C_6$ alkenyl, $C_2$–$C_6$ alkynyl, $C_1$–$C_6$ alkoxy, fluorinated $C_1$–$C_6$ alkyl, fluorinated $C_1$–$C_6$ alkoxy, aryl (e.g., phenyl), and the like.

The term "heteroaryl" refers to a heterocyclic group as defined above, wherein the monocyclic ring (i) is an aromatic ring and in the bicyclic ring system (ii) at least one ring is an aromatic ring. In one aspect, heteroaryl refers to (i) a 5- or 6-membered aromatic ring consisting of carbon atoms and from 1 to 3 heteroatoms selected from N, S, and O or (ii) an 8- to 10-membered bicyclic ring system consisting of carbon atoms and from 1 to 3 heteroatoms selected from N, S, and O wherein at least one of the rings in the bicyclic system is an aromatic ring.

The term "substituted heteroaryl" refers to a heteroaryl group as defined above having one or more substituents independently selected from cyano, halo, hydroxy, amino, $C_1$–$C_4$ alkylamino, (di-($C_1$–$C_4$ alkyl)amino, $C_3$–$C_6$ azacycloalkyl, $C_1$–$C_6$ alkyl, $C_2$–$C_6$ alkenyl, $C_2$–$C_6$ alkynyl, $C_1$–$C_6$ alkoxy, fluorinated $C_1$–$C_6$ alkyl, fluorinated $C_1$–$C_6$ alkoxy, aryl (e.g., phenyl), substituted aryl, heterocycle, and substituted heterocycle.

The term "substituted" includes mono- and poly-substitution by a named substituent to the extent such single and multiple substitution is chemically allowed and results in a chemically stable compound.

The symbol "~~~" in front of an open bond in the structural formula of a group marks the point of attachment of the group to the rest of the molecule.

When any variable or term occurs more than one time in any constituent or formulas set forth herein (e.g., Formula (I)), its definition on each occurrence is independent of its definition at every other occurrence. Thus, for example, if $R^2$ and $R^3$ in Formula (I) are both designated as "$C_1$–$C_4$ alkyl", $R^2$ and $R^3$ can represent the same or different alkyl groups embraced by the term. As another example, in an embodiment of Formula (I) in which $R^1$ and $R^4$ are both heteroaryl, $R^1$ and $R^4$ can be the same or different heteroaryl groups.

Combinations of substituents and/or variables are permitted only to the extent such combinations result in stable compounds.

The present invention includes pharmaceutical compositions useful for inhibiting HIV protease, comprising an effective amount of a compound of this invention, and a pharmaceutically acceptable carrier. Pharmaceutical compositions useful for preventing or treating infection by HIV, or for treating AIDS or ARC, are also encompassed by the present invention, as well as a method of inhibiting HIV protease, and a method of preventing or treating infection by HIV, or of treating AIDS or ARC. An aspect of the present invention is a pharmaceutical composition comprising a therapeutically effective amount of a compound of the present invention in combination with a therapeutically effective amount of an agent useful for treating HIV infection and/or AIDS (alternatively referred to as an HIV/AIDS treatment agent) selected from:

(1) an HIV/AIDS antiviral agent, (2) an anti-infective agent, and (3) an immunomodulator.

The present invention also includes the use of a compound of the present invention as described above as a medicament for (a) inhibiting HIV protease, (b) preventing or treating infection by HIV, or (c) treating AIDS or ARC. The present invention further includes the use of a compound of the present invention as described above in the preparation of a medicament for (a) inhibiting HIV protease, (b) preventing or treating infection by HIV, or (c) treating AIDS or ARC.

The present invention also includes the use of any of the HIV protease inhibiting compounds of the present invention as described above in combination with one or more HIV/AIDS treatment agents selected from an HIV/AIDS antiviral agent, an anti-infective agent, and an immunomodulator for use as a medicament for (a) inhibiting HIV protease, (b) preventing or treating infection by HIV, or (c) treating AIDS or ARC, said medicament comprising an effective amount of the HIV protease inhibitor compound and an effective amount of the one or more treatment agents.

The present invention further includes the use of any of the HIV protease inhibiting compounds of the present invention as described above in combination with one or more HIV/AIDS treatment agents selected from an HIV/AIDS antiviral agent, an anti-infective agent, and an immunomodulator for the manufacture of a medicament for (a) inhibiting HIV protease, (b) preventing or treating infection by HIV, or (c) treating AIDS or ARC, said medicament comprising an effective amount of the HIV protease inhibitor compound and an effective amount of the one or more treatment agents.

The compounds of the present invention may have asymmetric centers and may occur, except when specifically noted, as mixtures of stereoisomers or as individual diastereomers, or enantiomers, with all isomeric forms being included in the present invention.

A therapeutically effective amount of the compounds of the present invention are useful in the inhibition of HIV protease, the prevention or treatment of infection by human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by e.g., blood transfusion, exchange of body fluids, bites, accidental needle stick, or exposure to patient blood during surgery. The compounds of the invention can also be used in "salvage" therapy; i.e., the compounds can be used to treat HIV infection, AIDS, or ARC in HIV-positive subjects whose viral load achieved undetectable levels via conventional therapies employing known protease inhibitors, and then rebounded due to the emergence of HIV mutants resistant to the known inhibitors.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV protease, e.g., by competitive inhibition. Thus the compounds of this invention are commercial products to be sold for these purposes.

The present invention also provides for the use of a compound of structural formula (I) to make a pharmaceutical composition useful for inhibiting HIV protease and in the treatment of AIDS or ARC.

The compounds of the present invention may be administered in the form of pharmaceutically acceptable salts. The term "pharmaceutically acceptable salt" refers to all acceptable salts of the compounds of Formula (I) (in the form of water- or oil-soluble or dispersible products) and includes the conventional non-toxic salts or the quaternary ammonium salts which are formed, e.g., from inorganic or organic acids or bases. Examples of acid addition salts include acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like. Base salts include ammonium salts, alkali metal salts such as sodium and potassium salts, alkaline earth metal salts such as calcium and magnesium salts, salts with organic bases such as ethylenediamine, N-methylglutamine, N,N'-dibenzylethylene-diamine, chloroprocaine, diethanolamine, procaine, choline, N-benzylphenethylamine, diethylamine, piperazine, tris(hydroxymethyl) aminomethane, tetramethylammonium hydroxide, and dicyclohexylamine, and salts with amino acids such as arginine, lysine, ornithine, and so forth. Also, the basic nitrogen-containing groups may be quaternized with such agents as lower alkyl halides, such as methyl, ethyl, propyl, and butyl chlorides, bromides, and iodides; dialkyl sulfates such as dimethyl, diethyl, dipropyl, dibutyl, and diamyl sulfates; long chain halides such as decyl, lauryl, myristyl and stearyl chlorides, bromides, and iodides; and aralkyl halides such as benzyl and phenethyl bromides and others. The salt can be used as a dosage form for modifying the solubility or hydrolysis characteristics of the compound or can be used in sustained release or pro-drug formulations.

Also, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

The term "administration" and variants thereof (e.g., "administering" a compound) in reference to a compound of the invention each mean providing the compound or a prodrug of the compound to the individual in need of treatment. When a compound of the invention or prodrug thereof is provided in combination with one or more other active agents (e.g., AIDS antivirals), "administration" and its variants are each understood to include concurrent and sequential provision of the compound or prodrug thereof and other agents.

Thus, in accordance with the present invention there is further provided a method of treating and a pharmaceutical composition for treating HIV infection and AIDS. The treatment involves administering to a subject in need of such treatment a pharmaceutical composition comprising a pharmaceutical carrier and a therapeutically effective amount of a compound of the present invention.

As used herein, the term "composition" is intended to encompass a product comprising the specified ingredients in the specified amounts, as well as any product which results, directly or indirectly, from combination of the specified ingredients in the specified amounts.

The expression "pharmaceutically acceptable" means that the carrier, diluent or excipient must be compatible with the other ingredients of the formulation and not deleterious to the recipient thereof.

The term "subject," (alternatively referred to herein as "patient") as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated.

These pharmaceutical compositions may be in the form of orally-administrable suspensions or tablets, nasal sprays, sterile injectible preparations, for example, as sterile injectible aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing-agents known in the art.

The injectible solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters of polyethylene glycols, which are solid at ordinary temperatures, but liquefy and/or dissolve in the rectal cavity to release the drug.

The compounds of this invention can be administered orally to humans in a dosage range of 0.01 to 1000 mg/kg body weight in divided doses. One preferred dosage range is 0.1 to 200 mg/kg body weight orally in divided doses. Another preferred dosage range is 0.5 to 100 mg/kg body weight orally in divided doses. For oral administration, the compositions are preferably provided in the form of tablets containing 1 to 1000 milligrams of the active ingredient, particularly 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention is also directed to combinations of the HIV protease inhibitor compounds with one or more agents useful in the treatment of HIV infection and/or AIDS. For example, the compounds of this invention may be effectively administered, whether at periods of pre-exposure and/or post-exposure, in combination with effective amounts of the HIV/AIDS antivirals, imunomodulators, antiinfectives, or vaccines, such as those in Table 1 as follows:

TABLE 1

HIV/AIDS ANTIVIRALS, IMUNOMODULATORS, ANTIINFECTIVES, AND OTHER TREATMENTS

| Drug Name | Manufacturer | Indication |
| --- | --- | --- |
| ANTIVIRALS | | |
| Amprenavir<br>141 W94<br>GW 141 | Glaxo Wellcome | HIV infection, AIDS, ARC<br>(protease inhibitor) |
| Abacavir<br>GW 1592<br>1592U89 | Glaxo Welcome | HIV infection, AIDS, ARC<br>(reverse transcriptase inhibitor) |
| Acemannan | Carrington Labs<br>(Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen<br>(Los Angeles, CA) | ARC, PGL, HIV positive, AIDS |
| Alpha Interferon | Glaxo Wellcome | Kaposi's sarcoma, HIV, in combination w/Retrovir |
| Ansamycin<br>LM 427 | Adria Laboratories<br>(Dublin, OH)<br>Erbamont<br>(Stamford, CT) | ARC |
| Antibody which | Advanced Biotherapy | AIDS, ARC |

TABLE 1-continued

HIV/AIDS ANTIVIRALS, IMUNOMODULATORS, ANTIINFECTIVES, AND OTHER TREATMENTS

| Drug Name | Manufacturer | Indication |
|---|---|---|
| neutralizes pH labile alpha aberrant Interferon | Concepts (Rockville, MD) | |
| AR177 | Aronex Pharm | HIV infection, AIDS, ARC |
| beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infections, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| Cytovene Ganciclovir | Syntex | sight threatening CMV peripheral CMV retinitis |
| Delaviridine | Pharmacia-Upjohn | HIV infection, AIDS, ARC (protease inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb combination with AZT/d4T | HIV infection, AIDS, ARC; |
| DMP-450 | AVID (Camden, NJ) | HIV infection, AIDS, ARC (protease inhibitor) |
| EL10 | Elan Corp, PLC (Gainesville, GA) | HIV infection |
| Efavirenz (DMP 266) (-)6-Chloro-4(S)-cyclopropylethynyl-4(S)-trifluoro-methyl-1,4-dihydro-2H-3,1-benzoxazin-2-one, | DuPont (SUSTIVA ®), Merck (STOCRIN ®) | HIV infection, AIDS, ARC (non-nucleoside RT inhibitor) |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| Compound A | Merck | HIV infection, AIDS, ARC, asymptomatic HIV positive |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (protease inhibitor) |

TABLE 1-continued

HIV/AIDS ANTIVIRALS, IMUNOMODULATORS, ANTIINFECTIVES, AND OTHER TREATMENTS

| Drug Name | Manufacturer | Indication |
|---|---|---|
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston TX) | HIV infection, AIDS, ARC |
| Ritonavir (ABT-538) | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | gential HSV & CMV infections |
| Virazole Ribavirin | Viratek/ICN (Costa Mesa, CA) | asymptomatic HIV positive, LAS, ARC |
| VX-478 | Vertex | HIV infections, AIDS, ARC |
| Zalcitabine | Hoffmann-La Roche | HIV infection, AIDS, ARC with AZT |
| Zidovudine; AZT | Glaxo Wellcome | HIV infections, AIDS, ARC, Kaposi's sarcoma in combination with other therapies (reverse transcriptase inhibitor) |
| ABT-378; Lopinavir | Abbott | HIV infection, AIDS, ARC (protease inhibitor) |
| ABT-378/r; Combination of lopinavir and ritonavir; Kaletra | Abbott | HIV infection, AIDS, ARC (protease inhibitor) |
| JE2147/AG1776 | Agouron | HIV infection, AIDS, ARC (protease inhibitor) |
| T-20 | Trimeris | HIV infection, AIDS, ARC (fusion inhibitor) |
| T-1249 | Trimeris | HIV infections, AIDS, ARC (fusion inhibitor) |
| BMS 232632 | Bristol-Myers-Squibb | HIV infection, AIDS, ARC (protease inhibitor) |
| PRO 542 | Progenics | HIV infection, AIDS, ARC (attachment inhibitor) |
| PRO 140 | Progenics | HIV infection, AIDS, ARC (CCR5 co-receptor inhibitor) |
| TAK-779 | Takeda | HIV infection, AIDS, ARC (injectable CCR5 receptor antagonist) |
| DPC 681 & DPC 684 | DuPont | HIV infection, AIDS, ARC (protease inhibitors) |
| DPC 961 & DPC 083 | DuPont | HIV infection, AIDS, ARC (nonnucleoside reverse) transcriptase inhibitors) |
| IMMUNO-MODULATORS | | |
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | blocks HIV fusion with CD4+ cells |
| Gamma Interferon | Genentech | ARC, in combination w/TNF (tumor necrosis factor) |
| Granulocyte Macrophage Colony Stimulating | Genetics Institute Sandoz | AIDS |

TABLE 1-continued

HIV/AIDS ANTIVIRALS, IMUNOMODULATORS, ANTIINFECTIVES, AND OTHER TREATMENTS

| Drug Name | Manufacturer | Indication |
|---|---|---|
| Factor Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma, AIDS, ARC, in combination w/AZT |
| SK&F106528 Soluble T4 | Smith Kline | HIV infection |
| Thymopentin | Immunobiology Research Institute | HIV infection |
| Tumor Necrosis Factor; TNF | Genentech | ARC, in combination w/gamma Interferon |
| etanercept | Immunex Corp (Enbrel ®) | rheumatoid arthritis |
| infliximab | Centocor (Remicade ®) | rheumatoid arthritis and Crohn's disease |
| ANTI-INFECTIVES | | |
| Clindamycin with Primaquine | Pharmacia Upjohn | PCP |
| Fluconazole | Pfizer | cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidia diarrhea |

TABLE 1-continued

HIV/AIDS ANTIVIRALS, IMUNOMODULATORS, ANTIINFECTIVES, AND OTHER TREATMENTS

| Drug Name | Manufacturer | Indication |
| --- | --- | --- |
| Intraconazole-R51211 | Janssen Pharm. | histoplasmosis; cryptococcal meningitis |
| Trimetrexate | Warner-Lambert | PCP |

OTHER

| | | |
| --- | --- | --- |
| Daunorubican | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Leukotriene B4 Receptor Antagonist | — | HIV infection |
| Megestrol Acetate | Bristol-Myers Squibb | treatment of anorexia assoc. w/AIDS |
| Soluble CD4 Protein and Derivatives | — | HIV infection |
| Testosterone | Alza, Smith Kline | AIDS-related wasting |
| Total Enteral Nutrition | Norwich Eaton Pharmaceuticals | diarrhea and malabsorption, related to AIDS |

It will be understood that the scope of combinations of the compounds of this invention with HIV/AIDS antivirals, immunomodulators, anti-infectives or vaccines is not limited to the list in Table 1 above, but includes in principle any combination with any pharmaceutical composition useful for the treatment of HIV infection and/or AIDS.

One suitable combination is a compound of the present invention and a nucleoside inhibitor of HIV reverse transcriptase such as AZT, 3TC, ddC, or ddI. Another suitable combination is a compound of the present invention and a non-nucleoside inhibitor of HIV reverse transcriptase, such as efavirenz, and optionally a nucleoside inhibitor of HIV reverse transcriptase, such as AZT, 3TC, ddC or ddI.

Still another suitable combination is any one of the combinations in the preceding paragraph, further comprising an additional HIV protease inhibitor such as indinavir, Compound A, nelfinavir, ritonavir, saquinavir, amprenavir, or abacavir. An aspect of this combination is the combination wherein the additional inhibitor of HIV protease is the sulfate salt of indinavir. Another aspect of this combination is the combination in which the additional protease inhibitor is selected from nelfinavir and ritonavir. Still another aspect of this combination is the combination in which the additional inhibitor of HIV protease is saquinavir, which is typically administered in a dosage of 600 or 1200 mg tid.

Other suitable combinations include a compound of the present invention with the following (1) efavirenz, optionally with AZT and/or 3TC and/or ddI and/or ddC, and optionally with indinavir; (2) any of AZT and/or ddI and/or ddC and/or 3TC, and optionally with indinavir; (3) d4T and 3TC and/or AZT; (4) AZT and 3TC; and (5) AZT and d4T.

Another aspect of the present invention is co-administration of a compound of the present invention with an inhibitor of cytochrome P450 monooxygenase in an amount effective to improve the pharmacokinetics of the compound. Compounds of the invention can be metabolized, at least in part, by cytochrome P450 (CYP3A4). Co-administration of compounds of the invention with a cytcochrome P450 inhibitor can improve the pharmacokinetic profile of the compound in subjects (e.g., humans); i.e., co-administration can increase $C_{max}$ (the maximum plasma concentration of the compound), AUC (area under the curve of plasma concentration of the compound versus time), and/or the half-life of the compound. Suitable P450 inhibitors include, but are not limited to, indinavir and ritonavir. It is to be understood that the primary role of indinavir and ritonavir in this circumstance is as a pharmacokinetic modulator and not as a protease inhibitor; i.e., an amount of indinavir or ritonavir which is effective for improving the pharmacokinetics of the compound can provide a secondary or even negligible contribution to the antiviral effect. Improvements in the pharmacokinetic profile have been observed for compounds of the present invention, when co-dosed with P450-inhibiting amounts of either ritonavir or indinavir.

A compound of the present invention can also be administered in combination with an HIV integrase inhibitor such as a compound described in WO 99/62520, WO 99/62513, or WO 99/62897. A compound of the present invention can also be administered in combination with a CCR5 receptor antagonist, such as a compound described in WO00/59502 or WO 00/59503.

In the above-described combinations, the compound of the present invention and other active agents may be administered together or separately. In addition, the administration of one agent may be prior to, concurrent with, or subsequent to the administration of other agent(s). These combinations may have unexpected or synergistic effects on limiting the spread and degree of infection of HIV.

Efavirenz is (-)-6-chloro-4-cyclopropylethynyl-4-trifluoromethyl-1,4-dihydro-2H-3,1-benzoxazin-2-one, also known as DMP-266 or SUSTIVA® (DuPont) or STO-CRIN® (Merck). Efavirenz and its utility as an HIV reverse transcriptase inhibitor is described in U.S. Pat. No. 5,519,021 and in the corresponding PCT published application, WO 95/20389. Efavirenz can be synthesized by the protocol of U.S. Pat. No. 5,633,405. Additionally, the asymmetric synthesis of an enantiomeric benzoxazinone by a highly enantioselective acetylide addition and cyclization sequence is described in Thompson et al., *Tetrahedron Letters* 1995, 36: 8937–40, as well as in the PCT publication, WO 96/37457.

AZT is 3'-azido-3'-deoxythymidine, is also known as zidovudine, and is available from Burroughs-Wellcome under the tradename RETROVIR®. Stavudine is 2',3'-didehydro-3'-deoxythymidine, is also known as 2',3'- dihydro-3'-deoxythymidine and d4T, and is available from Bristol-Myers Squibb under the tradename ZERIT®. 3TC is (2R-cis)-4-amino-1-[2-(hydroxymethyl)-1,3-oxathiolan-5-yl]-2(1H)-pyrimidinone, is also known as (−)-1-[(2R,5S)-2-(hydroxymethyl)-1,3-oxathiolan-5-yl]cytosine and lamivudine, and is available from Glaxo Wellcome under the tradename EPIVIR®. ddC is 2',3'-dideoxycytidine, is also known as zalcitabine, and is available from Hoffman LaRoche under the tradename HIVID®. ddI is 2',3'-dideoxyinosine, is also known as didanosine, and is available from Bristol-Myers-Squibb under the tradename VIDEX®. The preparation of ddC, ddI and AZT are also described in EPO 0,484,071.

Indinavir is N-(2(R)-hydroxy-1(S)-indanyl)-2(R)-phenylmethyl-4-(S)-hydroxy-5-(1-(4-(3-pyridyl-methyl)-2(S)-N'-(t-butylcarboxamido)-piperazinyl))pentaneamide, and can be prepared as described in U.S. Pat. No. 5,413,999. Indinavir is generally administered as the sulfate salt at a dosage of 800 mg three times a day. Indinavir sulfate is available from Merck under the tradename CRIXIVAN®.

Compound A is N-(2(R)-hydroxy-1(S)-indanyl)-2(R)-phenylmethyl-4(S)-hydroxy-5-(1-(4-(2-benzo[b]furanylmethyl)-2(S)-N'-(t-butylcarboxamido)piperazinyl)) pentaneamide, preferably administered as the sulfate salt. Compound A can be prepared as described in U.S. Pat. No. 5,646,148.

Ritonavir is [5S-(5R*,8R*,10R*, 11R*)]-10-hydroxy-2-methyl-5-(1-methylethyl)-1-[2-(1-methylethyl)-4-thiazolyl]-3,6-dioxo-8,11-bis(phenylmethyl)-2,4,7,12-tetraazatridecan-13-oic acid 5-thiazolylmethyl ester, also known as 5-thiazolylmethyl [(aS)-a-[(1S,3S)-1-hydroxy-3-[(2S)-2-[3-[(2-isopropyl-4-thiazolyl)methyl]-3-methylureido]-3-methylbutyramido]-4-phenylbutyl] phenethyl]carbamate. It is available from Abbott under the tradename NORVIR®. Ritonavir can be prepared as described in U.S. Pat. No. 5,484,801.

Nelfinavir is [3S-[2(2S*,3S*),3a,4ab,8ab]]-N-(1,1-dimethylethyl)decahydro-2-[2-hydroxy-3-[(3-hydroxy-2-methylbenzoyl)amino]-4-(phenylthio)butyl]-3-isoquinolinecarboxamide, also known as (3S,4aS,8aS)-N-tert-Butyl-2-[(2R,3R)-3-(3,2-crestoamido)-2-hydroxy-4-(phenylthio)butyl]decahydro-3-isoquinolinecarboxamide. VIRACEPT®, the monomethanesulfonate salt of nelfinavir (nelfinavir mesylate) is commerically available from Agouron. Nelfinavir can be prepared as described in U.S. Pat. No. 5,484,926.

Saquinavir is N-tert-butyl-decahydro-2-[2(R)-hydroxy-4-phenyl-3(S)-[[N-(2-quinolylcarbonyl)-L-asparaginyl] amino]butyl]-(4aS ,8aS)-isoquinoline-3(S)-carboxamide. Saquinavir can be prepared in accordance with procedures disclosed in U.S. Pat. No. 5,196,438. INVIRASE® (saquinavir mesylate) is available from Roche Laboratories.

Amprenavir is 4-amino-N-((2 syn,3S)-2-hydroxy-4-phenyl-3-((S)-tetrahydrofuran-3-yloxycarbonylamino)-butyl)-N-isobutyl-benzenesulfonamide, also known as Compound 168 and 141 W94. Amprenavir is an aspartyl protease inhibitor that can be prepared by following the procedures described in U.S. Pat. No. 5,585,397. Amprenavir is available under the tradename AGENERASE® from Glaxo Wellcome. Amprenavir can be prepared as described in U.S. Pat. No. 5,783,701.

Abacavir is (1S,4R)-cis-4-[2-amino-6-(cyclopropylamino)-9H-purin-9-yl]-2-cyclopentene-1-methanol, also known as 1592U89. Abacavir can be prepared by following the protocol of EP 0434450.

Abbreviations used in the instant specification, particularly the Schemes and Examples, are as follows:

Alloc=allyloxycarbonyl
AcOH=acetic acid
BOC or Boc=t-butyloxycarbonyl
BOC-ON=2-(tert-butoxycarbonylamino)-2-phenyl acetonitrile
Bu=butyl
CBZ=carbobenzoxy (alternatively, benzyloxycarbonyl)
CSA=camphorsulfonic acid
DCE=dichloroethane
DCM=dichloromethane
DMF=dimethylformamide
DMSO=dimethylsulfoxide
DIEA=diisopropylethylamine
EDC=1-ethyl-3-(3-dimethylaminopropyl) carbodiimide
ES=electron spray (ionization)
Et=ethyl
$Et_2O$=diethyl ether
EtOAc=ethyl acetate
EtOH=ethanol
HBTU=1-hydroxybenzotriazole
HOAT=1-hydroxy-7-azabensotriazole
HOBT=1-hydroxy benzotriazole hydrate
HPLC=high performance liquid chromatography
IPA=isopropyl alcohol
KF=Karl Fisher titration for water
LC=liquid chromatography
Me=methyl
MeOH=methanol
MS=mass spectrometry
NMP=N-methyl pyrrolidinone
NMR=nuclear magnetic resonance
$Pd(dppf)Cl_2$=1,1'-bis(diphenylphosphino)ferrocene palladium dichloride
Ph=phenyl
TBAF=tetrabutylammonium fluoride
TBSCl=t-butyldimethylsilyl chloride
TBSOTf=t-butyldimethylsilyl triflate
TEA=triethylamine
TFA=trifluoroacetic acid
TFEA=trifluoroethylamine
$Tf_2O$=triflic anhydride
THF=tetrahydrofuran
TLC=thin layer chromatgraphy
TMEDA=N,N,N',N'-tetramethylethylenediamine
TMSCN=trimethylsilyl cyanide
TsOH=p-toluenesulfonic acid The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

The preparation of the compounds of the present invention can be carried out in sequential or convergent synthetic routes, as shown in Schemes 1–8 below. A compound of Formula (I) can be prepared in accordance with Scheme 1, wherein Compound I is readily prepared via literature procedures described in Dorsey et al., *J. Med. Chem.* 1994, 37: 3443–3451, and also in U.S. Pat. No. 5,413,999. Treatment of the hydroxyl compound 1 with triflic anhydride and lutidine in an inert solvent such as dichloromethane provides triflate 2. Displacement of the triflate with piperazine 3 occurs on heating in an inert solvent such as isopropanol to give lactone 4. Hydrolysis of lactone 4 with an aqueous lithium hydroxide provides the hydroxy acid which is conveniently protected with a standard silyl protecting group such as t-butyldimethylsilyl by reaction with either t-butyldimethylsilyl chloride in the presence of imidazole in an inert solvent or the reaction with the silyl triflate and diisopropyl ethylamine in an inert solvent such as dichloromethane. Mild aqueous hydrolysis of the silyl ester provides the protected hydroxy-acid 5. Amide coupling of compound 5 with $NH_2R^5$ to obtain 6 is typically performed by the carbodiimide method with reagents such as 1-ethyl-3-(3-dimethylaminopropyl) carbodiimide (EDC) and HOBT in an inert solvent such as dichloromethane. Other methods of forming the amide or peptide bond include, but are not limited to, the synthetic routes via an acid chloride, azide, mixed anhydride or activated ester. The silyl protecting group is removed with fluoride to arrive at compound 7. The BOC protecting group on the amine is then removed with a strong acid such as trifluoroacetic acid or hydrochloric acid in an alcoholic solvent such as methanol to give the penultimate intermediate 8. Penultimate 8 is then reacted with the desired aldehyde 9 and a reducing agent such as sodium cyanoborohydride or sodium triacetoxyborohydride in an inert solvent such as dichloromethane to give compound 10.

SCHEME 1

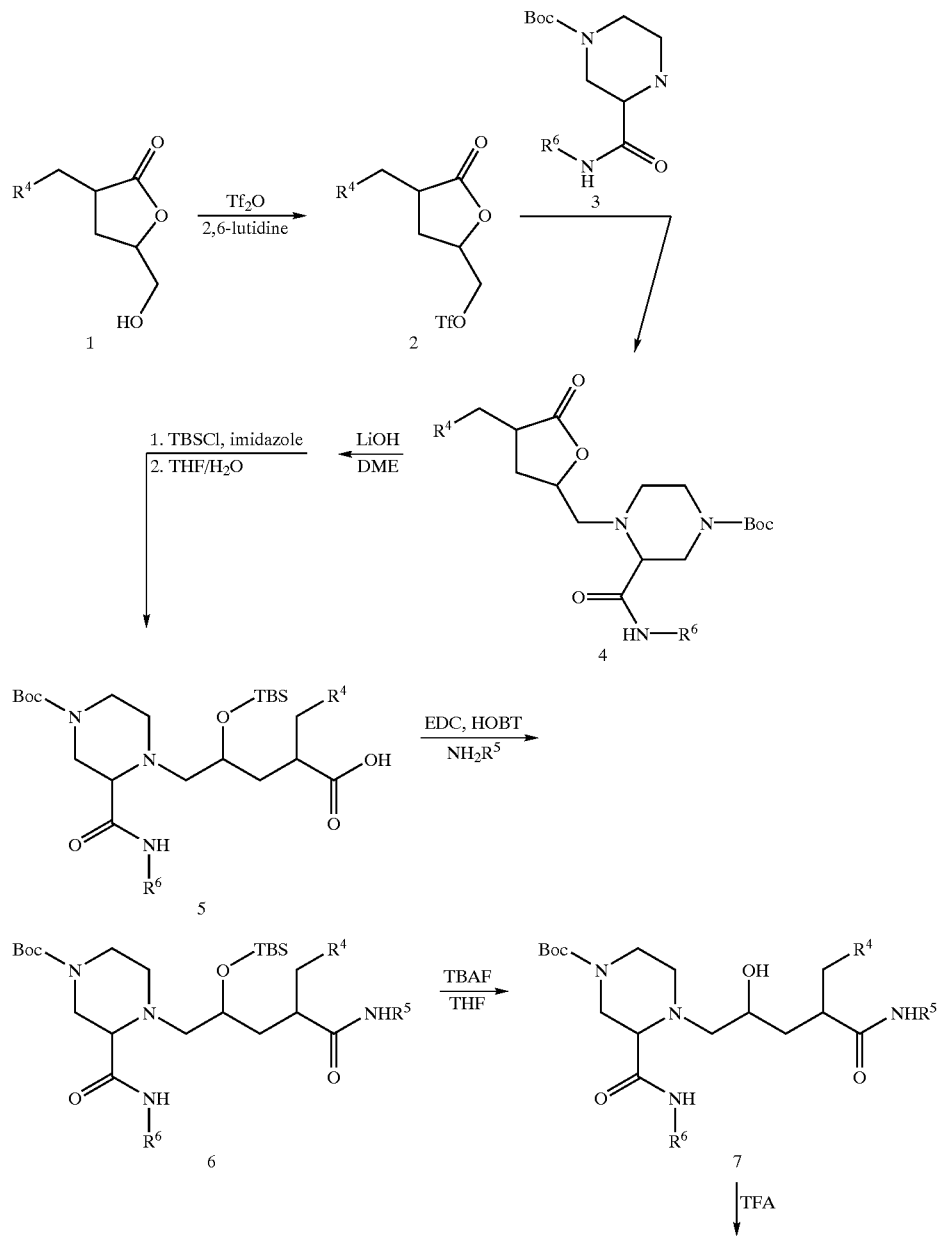

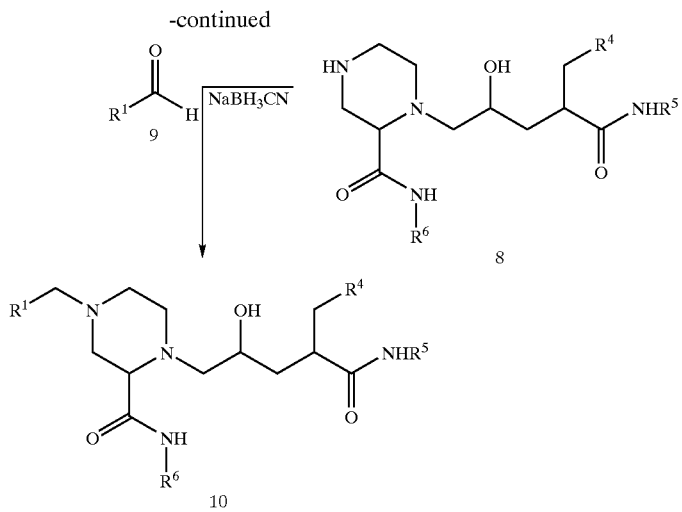

A more convergent route to compounds of the present invention is presented in Scheme 2, below. The orthogonally protected piperazine 11 can be selectively deprotected. The BOC protecting group can be removed by treatment with strong acids such as trifluoroacetic acid in dichloromethane or HCl in methanol. The resulting amine 12 can then be reacted with an aldehyde in the presence of a reducing agent such as sodium cyanoborohydride or sodium triacetoxyborohydride to give piperazine 13. Removal of the Alloc protecting group is readily accomplished with a palladium catalyst in the presence of a nucleophilic trapping agent such as 1,3-dimethylbarbituric acid or as in *J. Org. Chem.* 1993, 58, 6109–6113. Displacement of the triflate of 2 with piperazine 14, as in Scheme 1 gives lactone 15 which is then converted into compounds of the present invention following the route depicted in Scheme 1.

SCHEME 2

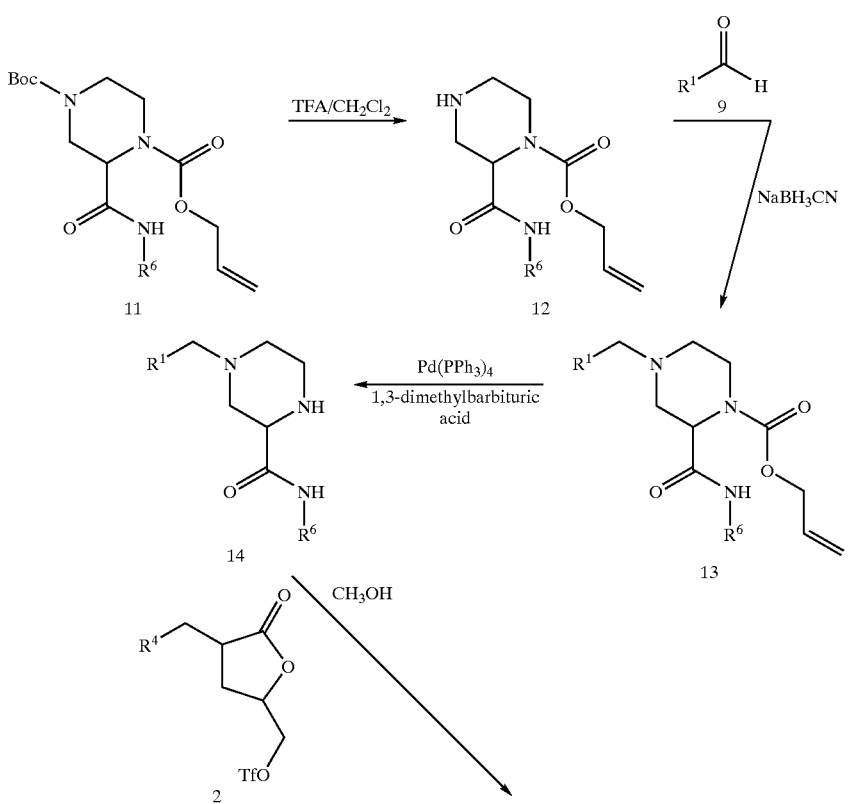

-continued

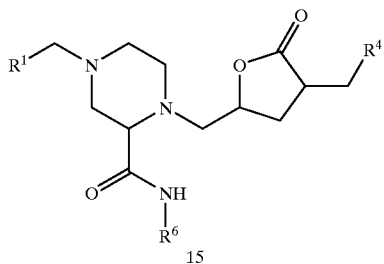
15

An alternative route to the instant compounds is presented in Scheme 3, as exemplified for $NH_2R^5$=aminoindanol. Compound 16 can be easily prepared according to the procedures described in the literature including, but not limited to, those described in *Tetrahedron Letters* 1995, 36: 2195–2198 and U.S. Pat. No. 5,646,148. As shown in Part A of Scheme 3, the epoxide opening can be carried out by heating piperazine 3 and the epoxide in an inert solvent. Acidic removal of the protecting groups can be accomplished by treatment with hydrochloric acid in an alcoholic solvent such as methanol, ethanol or isopropanol. The resulting intermediate 18 is then reductively aminated as in Scheme 1 to provide the compounds of the present invention. Alternatively, as shown in Part B of Scheme 3, the epoxide opening can be preformed with fully elaborated piperazine 14 to give 20. Once again the protecting group is removed with strong acid to give 19.

Scheme 3

Part A

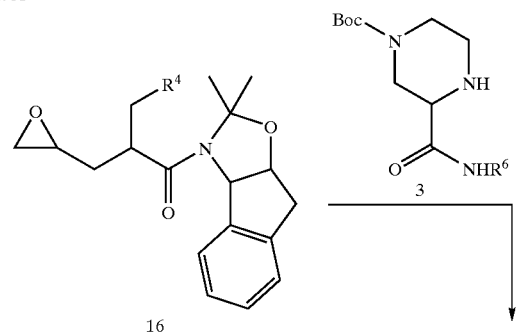
16

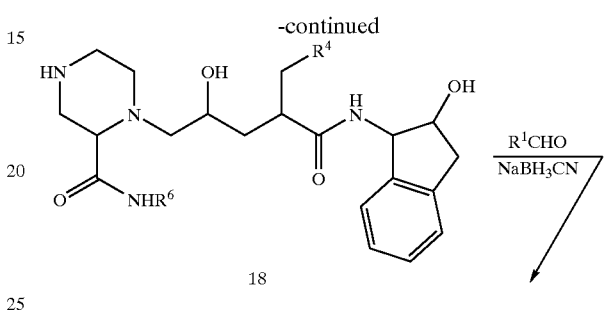
18

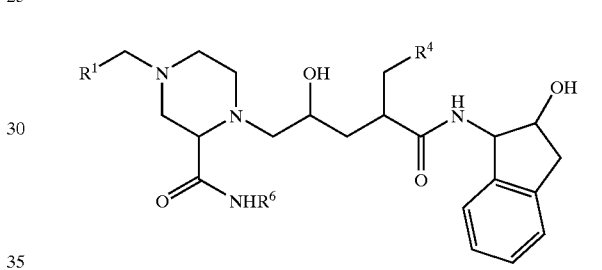
19

Part B

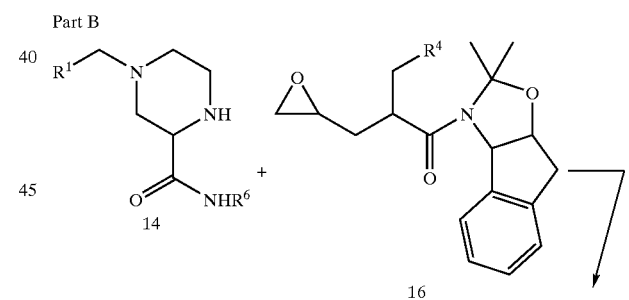
14 + 16

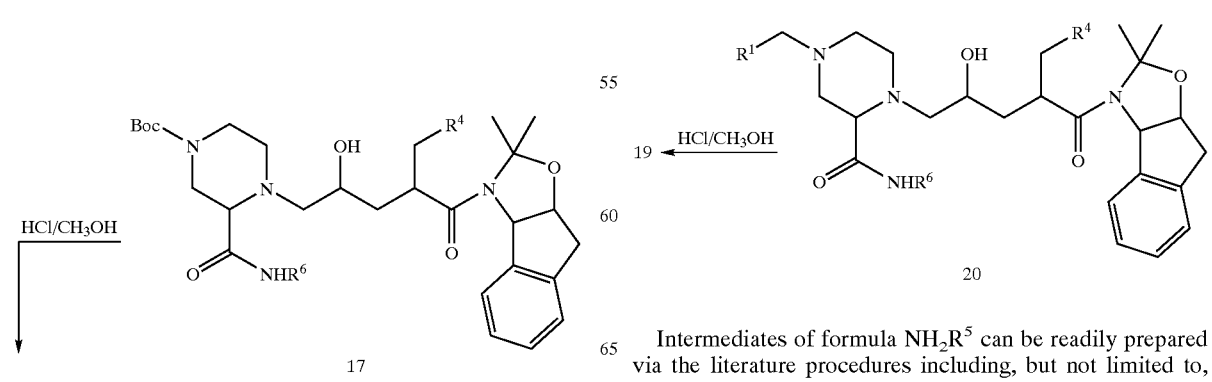
17 / 20

Intermediates of formula $NH_2R^5$ can be readily prepared via the literature procedures including, but not limited to, those found in *Tetrahedron Letters* 1991 32: 711–714, Tetrahedron Letters 1995, 36: 3993–3996 and Synthesis 1998, 938–961. A procedure for preparing cis-aminochromanols by the stereoselective hydroge bromide-promoted hydrogenation of an α-hydroxyoxime is described in Davies et al., Tetrahedron Letters 2000, 41: 8021–8025.

Piperazine intermediates are readily prepared from the known piperazine carboxylic acid 21, which can be prepared as described in Hel. Chem. Acta. 1960, 43: 888–896. Selective monoprotection of the piperazine is carried out using BOC anhydride as described in Tetrahedron Letters 1989, 30: 5193–5196. The remaining unprotected amine can then be protected with any number of chloroformates including allyl chloroformate or benzyl chloroformate to give 23. Amide couplings of 23 with $NH_2R^6$ to give 24 are performed using standard amide coupling reactions as described above. Many $NH_2R^6$ amines are commercially available and others can be prepared via literature methods including, but not limited to, those described in Tetrahedron Letters 1999, 40, 3831–3834. Acidic removal of the BOC protecting group as before gives 25. The Alloc group can be removed as before. The CBZ group is readily removed by hydrogenolysis with a palladium catalyst under a hydrogen atmosphere in an alcoholic solvent such as methanol or ethanol. Removal of the protecting groups can also be accomplished by a number of methods known in the art, such as those described in Greene, Protective Groups in Organic Synthesis, John Wiley and Sons, New York, 1991. These deprotected intermediates are then carried onto compounds of the instant invention via the synthetic routes shown in Schemes 1, 2 and 3.

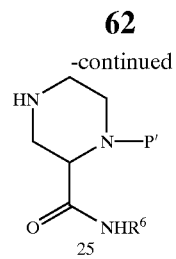
-continued

The desired aldehyde intermediates are, in many cases, commercially available (e.g., Aldrich Chemical). Other aldehydes of interest can be prepared by literature methods including classical methods familiar to those skilled in the art. Stille and Suzuki coupling of commercially and readily available aryl and heteroaryl halides, aryl trialkylstannanes, and arylboronic acids also provides the desired aldehydes as exemplified for bromofuran in Scheme 5 below. Aldehyde 27 can be reacted with trialkylarylstannane 26 in the presence of a palladium catalyst by the method of Gronowitz et al., J. Heterocyclic Chem. 1995, 35: 771, to give 28. Alternatively, trialkylstannane 30 can be coupled with arylhalides such as 29 to give 31 which can be deprotected under mild conditions with dilute hydrochloric acid to give aldehyde 28. Other aldehydes are available via metal halogen exchange followed by anion quenching with DMF as described by Vogel et al., J. Chem. Soc. Perkin Trans I, 1974, 37. Metalation of a biaryl or heterobiaryl compound such as 32 with a strong base such as n-butyllithium at low temperature in an inert solvent such as THF followed by anion trapping with DMF also provides aldehydes such as 28.

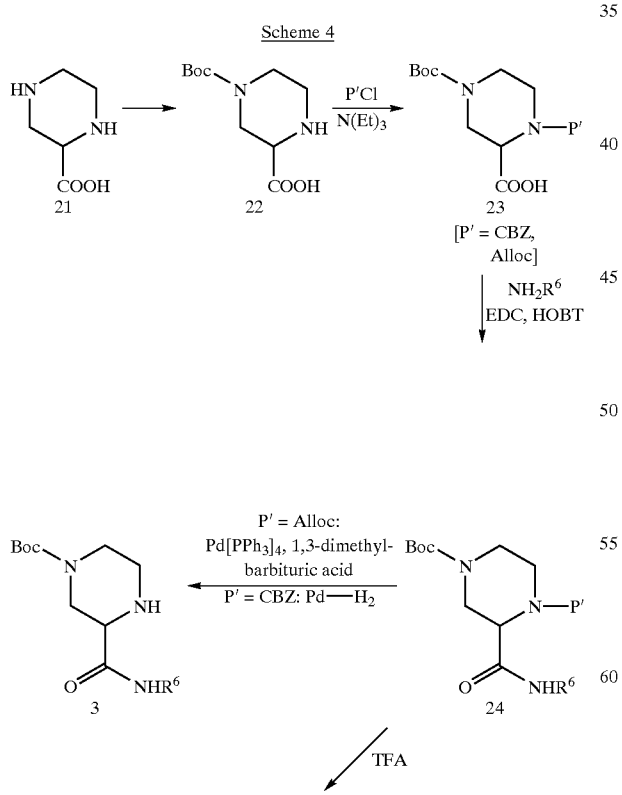

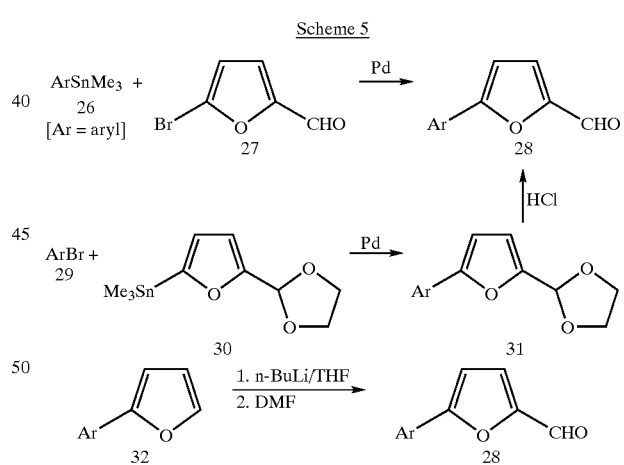

When $R^2$ and $R^3$ are alkyl, the necessary intermediates can be formed as shown in Scheme 6 below. Piperazine 12 can be treated with TMSCN and a ketone in acetic acid to give intermediate 34 according to the method described in J. Org. Chem. 1990, 55, 4207–4209. The Alloc protecting group is removed as described in Scheme 4 and the resulting intermediate, 35, is then treated with an excess of a Grignard to give the gem-dialkyl compound 14A. This intermediate is then converted to the compounds of the present invention via chemistry described in Schemes 2 and 3 above.

Scheme 6

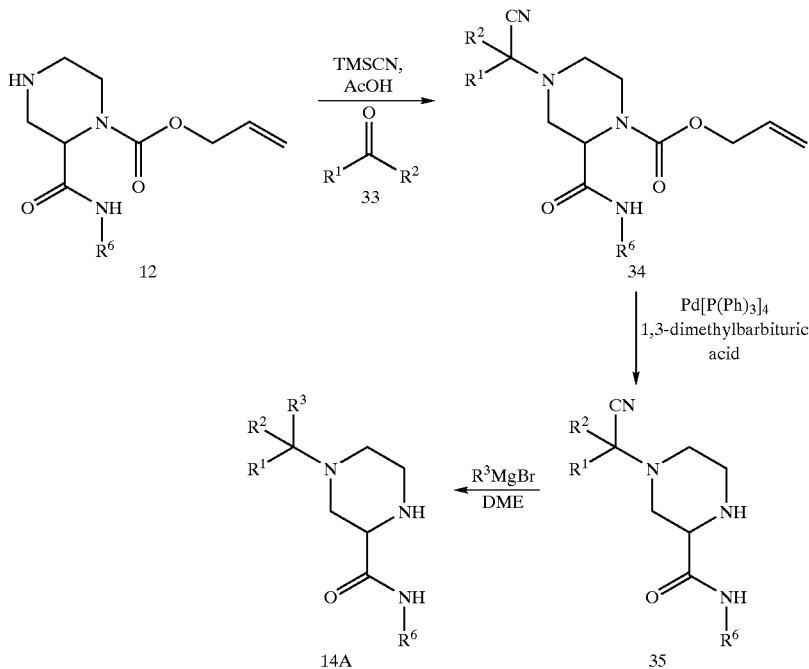

An additional route to intermediates such as 14A, where $R^2$ and $R^3$ are alkyl or cycloalkyl, is depicted in Scheme 7, below. Alkylation of piperazine 25, where P' is an appropriate protecting group such as those described above, with alkylating agent 36, is conveniently carried out in the presence of copper oxide, copper, and a tertiary amine base according to methods described in *J. Org. Chem* 1996, 61: 6517–6522, *J. Am. Chem. Soc.* 1960, 4908, and *J. Org. Chem.* 1994, 59: 2282–2284, where $R^2$ and $R^3$ are alkyl or cycloalkyl and X is a leaving group such as bromine, chlorine, mesylate, triflate, or phosphonate. Heterocycles of interest can be prepared from the acetylenic piperazine 37 using chemistry known to those skilled in the art. For example, intermediates such as 39 can be formed by the reaction of iodo or bromo phenols such as 38 with 37 according to the procedures of Castro et al., *J. Org. Chem.* 1966, 31: 4071–4078, Larock et al., *J. Org. Chem.* 1995, 60: 3270, or Arcadi et al., *Synthesis* 1986, 749. Triazole intermediates 41 are readily available from the reaction of 37 and aryl or heteroaryl azides as shown for phenylazide 40 in an inert high boiling solvent such as dichlorobenzene according to the method of Sakamoto et. al. as described in *Heterocycles* 1993, 35: 1273. Sydnones, such as 42, are available by procedures detailed in *J. Heterocycl. Chem.* 1992, 29: 1013–1015. They can be reacted with 37 to give pyrazoles such as 43 according to the procedure of Gotthardt et al. as described in *Chem. Ber.* 1968, 101: 536. Isoxazole intermediates such as 45 can be formed by treatment of the piperazine 37 with nitrones like 44 in a high boiling solvent such as nitrobenzene as described in *Liebigs Ann. Chem.* 1992, 947–952. Each of these piperazine intermediates can be converted to compounds of the instant invention via chemistry depicted in Schemes 1–3 above.

Scheme 7

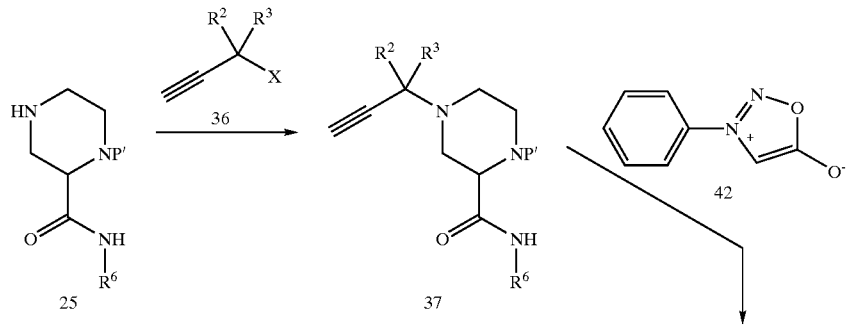

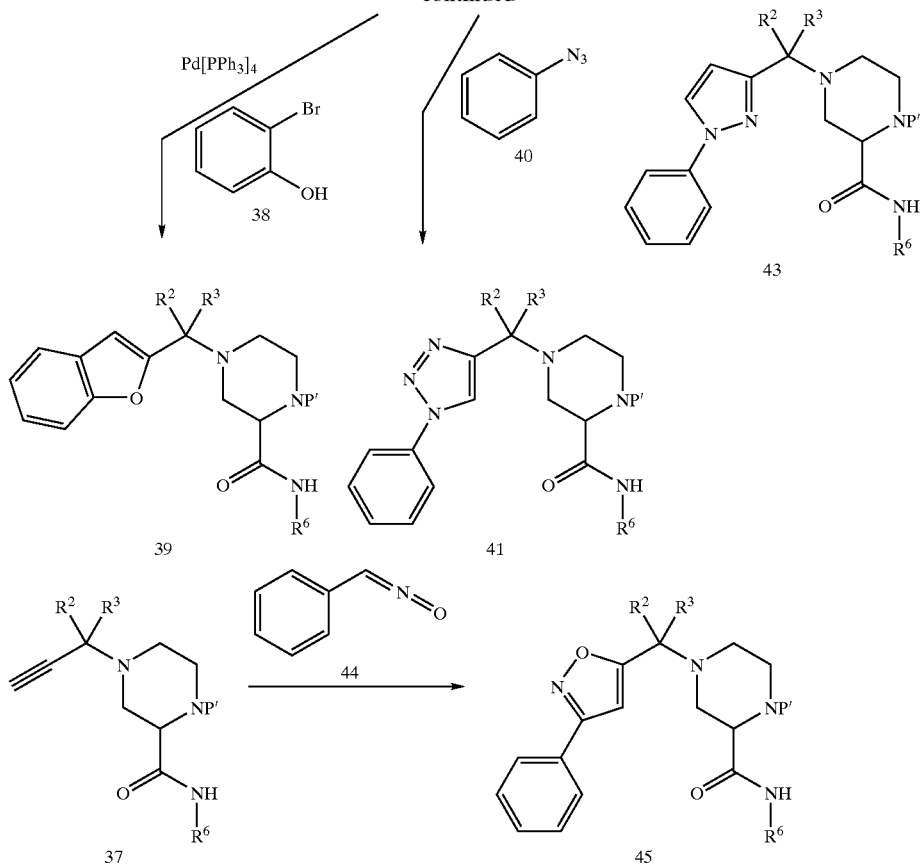

Oxazolyl piperazine intermediates such as 50 are available via the route shown in Scheme 8 below. Alkylation of piperazine 25 with bromo acid 46 in the presence of silver triflate in an inert solvent such as THF, according to methods detailed in *J. Org. Chem.* 1995, 60: 4013–4016, provides 47. Amide coupling of amine 48 to acid 47 to provide 49 can be carried out by any of the methods described above including the EDC/HOBT method. Amines such as 48 are prepared via chemistry described in *Org. Synth.* 1986, 64: 19–26 and *Tetrahedron Letters* 1999, 40: 6739–6743. Oxazole formation is accomplished by the action of a strong acid such as sulfuric acid on 49 in an inert solvent at elevated temperature, or as described in *J. Med. Chem.* 1996, 39: 2753–2763, to give intermediate 50. Again, intermediates such as these can be transformed into compounds of the instant invention via synthetic routes shown in Schemes 1,2, and 3.

Scheme 8

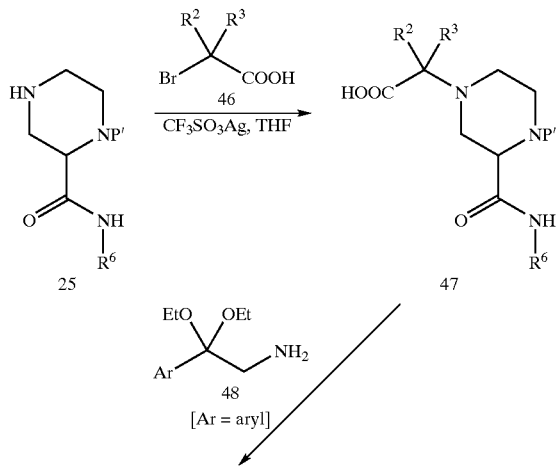

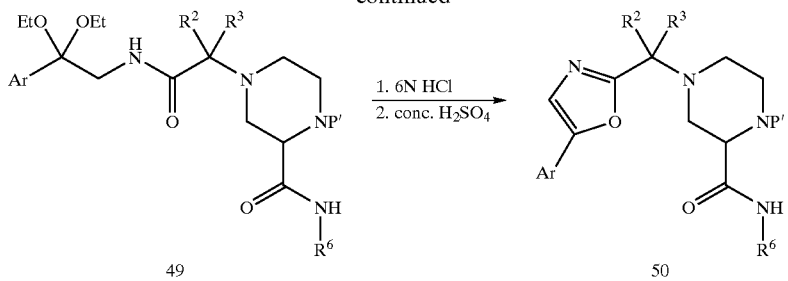

The present invention also includes a process for preparing a nitrogen-protected piperazine carboxamide of Formula (I*):

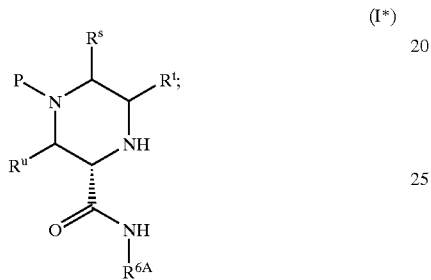

wherein the process comprises:
(A) hydrogenating a pyrazine carboxamide of Formula (II*):

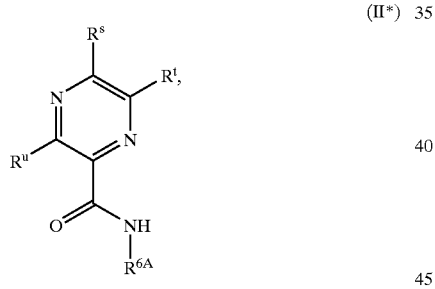

in a solvent to obtain the corresponding piperazine carboxamide of Formula (III*):

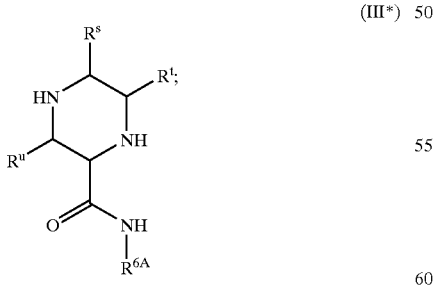

(B) resolving the S-carboxamide isomer of Compound III* by:
(b1) forming a solution comprising Compound III*, a chiral acid, and solvent;
(b2) crystallizing from the solution a salt which contains predominantly either the S- or R-isomer;
(b3) if the precipitated salt crystals consist predominantly of the desired isomer, separating the salt crystals from the mother liquor; and
(b4) if the mother liquor consists predominantly of the desired isomer, separating the salt crystals from the mother liquor and recovering the isomer from the mother liquor; and
(C) breaking the separated crystalline salt of the S-carboxamide isomer by treating the salt with base, and treating the free S-isomer with a nitrogen-protecting agent to obtain piperazine amide (I*); wherein
P is a nitrogen-protecting group;
$R^{6A}$ is hydrogen, $C_1$–$C_6$ alkyl or fluorinated $C_1$–$C_6$ alkyl; and
each of $R^s$, $R^t$ and $R^u$ is independently hydrogen, $C_1$–$C_4$ alkyl, —C(=O)$R^w$, —COO$R^w$, or —C(=O)N$R^w R^z$, where $R^w$ and $R^z$ are each independently hydrogen or $C_1$–$C_4$ alkyl.

The piperazine carboxamides of Formula I* are useful as intermediates in the preparation of compounds of the invention as described above. In this process, the group $R^{6A}$ in Compounds I*, II*, and III* is hydrogen, $C_1$–$C_6$ alkyl or fluorinated $C_1$–$C_6$ alkyl. In one embodiment, $R^{6A}$ is hydrogen, $C_1$–$C_4$ alkyl or fluorinated $C_1$–$C_4$ alkyl. In another embodiment, $R^{6A}$ is $C_1$–$C_4$ alkyl (e.g., methyl, ethyl, isopropyl, t-butyl, and so forth). In an aspect of the preceding embodiment, $R^{6A}$ is t-butyl.

In still another embodiment, $R^{6A}$ is fluorinated $C_1$–$C_6$ alkyl. In an aspect of the preceding embodiment, $R^{6A}$ is

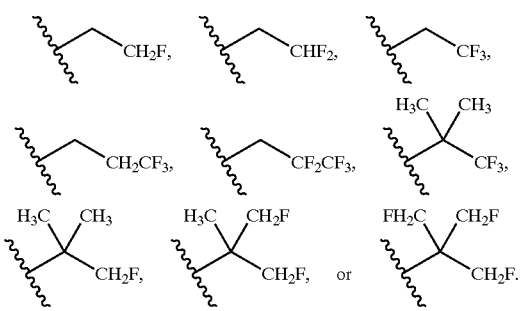

In another aspect of the preceding embodiment $R^{6A}$ is

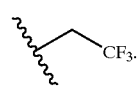

In the process, each of $R^s$, $R^t$ and $R^u$ is independently hydrogen, $C_1$–$C_4$ alkyl, —C(=O)$R^w$, —COO$R^w$, or —C(=O)N$R^w R^z$, where $R^w$ and $R^z$ are each independently hydrogen or $C_1$–$C_4$ alkyl. In one embodiment, one of $R^s$, $R^t$ and $R^u$ is hydrogen, $C_1$–$C_4$ alkyl, —C(=O)$R^w$, —COO$R^w$, or —C(=O)N$R^w R^z$, and the other two of $R^s$, $R^t$ and $R^u$ is hydrogen. In another embodiment, each of $R^s$, $R^t$ and $R^u$ is hydrogen.

P in Compound I* is a nitrogen-protecting group. Suitable protective groups and methods for protecting nitrogen via these groups include those described in *Protective Groups in Organic Chemistry*, J. F. W. McOmie, editor, Plenum Press, 1973; Theodora W. Greene, *Protective Groups in Organic Synthesis*, John Wiley & Sons, 1985; and W. Greene and P. G. M. Wuts, *Protective Groups in Organic Synthesis*, John Wiley & Sons, 1991.

In one embodiment, P is: (a) ($C_1$–$C_4$ alkyl)-oxycarbonyl, (b) ($C_3$–$C_8$ cycloalkyl)-oxycarbonyl, (c) benzyloxycarbonyl in which the benzyl is optionally substituted with 1 or 2 substituents independently selected from $C_1$–$C_4$ alkyl, —O—$C_1$–$C_4$ alkyl, and halo, (d) benzyl optionally substituted with 1 or 2 substituents independently selected from $C_1$–$C_4$ alkyl, —O—$C_1$–$C_4$ alkyl, and halo, (e) trihaloacetyl, or (f) tri-($C_1$–$C_4$ alkyl)silyl. Exemplary protecting groups include t-butyloxycarbonyl, benzyloxycarbonyl, benzyl, 4-methoxybenzyl, 2,4-dimethoxybenzyl, trifluoroacetyl, trimethylsilyl, or triethylsilyl. In an aspect of the process of the invention, P is t-butyloxycarbonyl.

In Step A of the process of the invention, the pyrazine carboxamide of Formula II* in a mixture with a solvent is hydrogenated, optionally in the presence of a hydrogenation catalyst, to form the corresponding piperazine carboxamide.

Suitable solvents include organic compounds, or mixtures thereof, which are chemically inert under the reaction conditions employed in Step A and which can also dissolve, suspend, and/or disperse Compound II* during the hydrogenation. Suitable solvents can be selected from the group consisting of $C_3$–$C_{12}$ linear and branched alkanes, $C_1$–$C_6$ linear and branched halogenated alkanes, $C_5$–$C_7$ cycloalkanes, $C_6$–$C_{10}$ aromatic hydrocarbons, dialkyl ethers wherein each alkyl is independently a $C_1$–$C_6$ alkyl, $C_4$–$C_8$ dialkoxyalkanes, $C_4$–$C_6$ cyclic ethers and diethers, $C_6$–$C_8$ aromatic ethers, and $C_1$–$C_6$ alkyl alcohols. Exemplary solvents include carbon tetrachloride, chloroform, methylene chloride, 1,2-dichloroethane (DCE), 1,1,2-trichloroethane (TCE), 1,1,2,2-tetrachloroethane, cyclohexane, toluene, o- and m- and p-xylene, ethylbenzene, ethyl ether, MTBE, THF, dioxane, 1,2-dimethoxyethane (DME), anisole, phenetole, methanol, ethanol, n- and iso-propanol, and tert-butyl alcohol.

In one embodiment, the solvent is selected from the group consisting of $C_2$–$C_6$ linear and branched halogenated alkanes, dialkyl ethers wherein each alkyl is independently a $C_1$–$C_4$ alkyl, $C_4$–$C_6$ cyclic ethers and diethers, and $C_1$–$C_4$ alkyl alcohols. In an aspect of the preceding embodiment, the solvent is a $C_1$–$C_4$ alkyl alcohol. In another aspect of the preceding embodiment, the solvent is methanol or ethanol.

The solvent can also be a mixture comprising water and one or more organic co-solvents. Suitable co-solvents include the organic solvents set forth in the preceding two paragraphs. In one embodiment, the co-solvent is a $C_1$–$C_6$ monohydric alcohol. In an aspect of this embodiment, the co-solvent is methanol or ethanol. The water can comprise from about 5 to about 95 volume percent based on the total volume of solvent.

The hydrogenation of pyrazine carboxamide II* can be conducted over a wide range of temperatures, although the temperature is typically in the range of from about −25 to about 200° C. (e.g., from about −20 to about 100° C.). In one embodiment, the temperature is in the range of from about 0 to about 80° C. In another embodiment, the temperature is from about 15 to about 60° C.

The pressure is not a critical aspect of the process of the invention, although atmospheric and superatmospheric pressures tend to be expedient. In one embodiment, the pressure is at least about 15 psia (103 kPa). In another embodiment, the pressure is in the range of from about 10 psia (68.9 kPa) to about 10,000 psia (68,950 kPa) (e.g., from about 50 psia (345 kPa) to about 1,000 psia (6,895 kPa)).

In one embodiment, the hydrogenation is conducted at a temperature in the range of from about 10 to about 100° C. and at a pressure of from about 2 psig (115 kPa) to about 1000 psig (6996 kPa). In another embodiment, the hydrogenation is conducted at a temperature in the range of from about 15 to about 60° C. and at a pressure in the range of from about 5 psig (135.8 kPa) to about 40 psig (377.1 kPa).

Any catalyst which is capable of expediting the hydrogenation of the pyrazine ring in Compound II* may be employed in the process of the invention. Typically, the catalyst comprises one or more transition metals, or compounds thereof, and especially comprises one or more of the Group VIII metals (or compounds thereof) as set forth in the Periodic Table of the Elements (see, e.g., the 78th edition of the *Handbook of Chemistry and Physics*, CRC Press (1997)). The metals can be employed in elemental form or as compounds (e.g., as oxides, hydroxides, or halides). Suitable hydrogenation catalysts include palladium, rhenium, rhodium, platinum, or nickel. The catalyst can be supported or unsupported. Suitable catalyst supports include carbon, silica, alumina, silicon carbide, aluminum fluoride, and calcium fluoride. Palladium is particularly suitable for use in the process of the invention. Exemplary palladium catalysts include Pd.black (i.e., fine metallic palladium particles), Pd/C (i.e., palladium on a carbon support), and Pd(OH)$_2$/C.

The hydrogen source is typically hydrogen gas, optionally in admixture with a carrier gas that is inert to the process of the invention (e.g., nitrogen or a noble gas such as helium or argon).

The hydrogenation can be carried out in batches or continuously in various types of reactors such as a fixed bed reactor or an agitated slurry reactor in which the slurry of gas, solvent, pyrazine carboxamide II*, and catalyst is continuously agitated by mechanical or gas means. A suitable reaction vessel for relatively small scale, batch-wise hydrogenations is an autoclave equipped with a stirrer or rocker to agitate the reaction mixture. In a batch process, the order of addition of pyrazine carboxamide II, solvent, and hydrogenation catalyst to the reaction vessel (also referred to herein as the reaction "pot") is not critical. The reaction components can, for example, be added concurrently, either together or separately, or they can be added sequentially in any order. In one embodiment, Compound II pre-mixed with the solvent is charged to the reaction vessel followed by addition of the catalyst. The hydrogenation can then be conducted by charging hydrogen gas, optionally in admixture with one or more inert gases, to the vessel containing the mixture comprising pyrazine carboxamide II*, solvent, and catalyst, and then agitating the mixture under reaction conditions.

Any amount of catalyst and hydrogen can be employed which results in the formation of at least some of Compound III*. Of course, the maximum conversion of Compound III* and maximum yield of Compound III* is normally desired, and relative proportions of reactants and reagents suitable for this purpose are typically employed.

The uptake of hydrogen is not a critical process parameter, although at least a stoichiometric amount of hydrogen gas is typically employed.

The amount of catalyst employed in Step A is suitably at least about 0.01 mole percent transition metal (e.g., Pd), and is typically in the range of from about 0.01 to about 5 (e.g., from about 0.1 to about 5) mole percent transition metal, based on the total moles of transition metal and Compound II*. In one embodiment, the amount of catalyst is in the range of from about 1 to about 5 (e.g., from about 2 to about 3) mole percent transition metal. In another embodiment, the catalyst comprises palladium (e.g., Pd/C or Pd(OH)$_2$/C), and the amount of palladium catalyst is in the range of from about 1 to about 5 mole percent.

The yield of piperazine carboxamide III* in Step A can be at least about 80% (e.g., from about 85% to about 99%), and are often at least about 85% (e.g., from about 90% to about 99%)

Step B of the process of the invention involves the resolution of the S-carboxamide isomer from the racemic piperazine carboxamide III* resulting from hydrogenation step A, via the formation and separation of diastereomeric salts. Suitable chiral acids for use in Step (b1) include optically active forms of tartaric acid, mandelic acid, camphoric acid, 10-camphorsulfonic acid, pyroglutamic acid, O,O-diacetyltartaric acid, O,O-dibenzoyltartaric acid, O,O-di-4-toluyltartaric acid, and N-acetyl derivatives of amino acids such as N-acetylleucine. A preferred chiral acid is (S)-camphorsulfonic acid or (R)-camphorsulfonic acid. The chiral acid is especially (S)-camphorsulfonic acid, and the crystallized (S)-camphorsulfonate salt resulting from crystallizing step (b2) is a mono- or bis-salt of the S-isomer. The amount of chiral acid employed in Step B is typically in the range of from about 0.5 to about 3 equivalents per equivalent of racemic piperazine carboxamide III.

The solvent can be any chemically inert organic or inorganic substance, or combinations thereof, which can dissolve Compound III* and the chiral acid. Suitable solvents include water, $C_1$–$C_6$ monohydric alcohols (e.g., methanol, ethanol, n-propanol, n-butanol, n-pentanol, isopropanol, and sec-butyl alcohol), $C_2$–$C_8$ polyhydric alcohols (e.g., ethylene glycol, propylene glycol, and glycerol), $C_2$–$C_4$ nitriles (e.g., acetonitrile and propionitrile), N,N-di-$C_1$–$C_6$ alkyl tertiary amides of $C_1$–$C_6$ alkylcarboxylic acids (e.g., DMF), aliphatic $C_2$–$C_6$ ethers and di-ethers (e.g., ethyl ether, MTBE and dimethoxyethane), $C_4$–$C_6$ cyclic ethers and di-ethers (e.g., THF and dioxane), and combinations of two or more of the foregoing. In one embodiment, the solvent is selected from the group consisting of $C_1$–$C_6$ monohydric alcohols, aliphatic $C_2$–$C_6$ ethers and di-ethers and $C_4$–$C_6$ cyclic ethers and di-ethers. In an aspect of the preceding embodiment, the solvent is an alcohol such as methanol or ethanol. In another embodiment, the solvent is the combination of a $C_1$–$C_6$ monohydric alcohol and a $C_1$–$C_4$ nitrile. In an aspect of the preceding embodiment, the solvent is a mixture of ethanol and acetonitrile.

In another embodiment, the solvent is a mixture comprising water and at least one organic co-solvent. In an aspect of this embodiment, water comprises at least about 2 volume percent of the solvent (e.g., from about 2 to about 95 volume percent) based on the total volume of solvent. In another aspect of this embodiment, the aqueous solvent comprises from about 2 to about 70 volume percent (e.g., from about 5 to about 50 volume percent) water, with the balance of the solvent being organic co-solvent. Suitable co-solvents include the organic solvents set forth in the preceding paragraph. In one embodiment, the co-solvent is a $C_1$–$C_6$ monohydric alcohol optionally in combination with a $C_1$–$C_4$ nitrile. In an aspect of this embodiment, the solvent is water, ethanol, and acetonitrile.

The crystallization of the S- or R-isomer as set forth in Step (b2) above can be accomplished using conventional techniques, such as by cooling the solution or by concentrating the solution via vacuum or evaporative removal of solvent, and optionally seeding the solution with the appropriate crystal salt. If the resulting crystals are predominantly the desired S-isomer, the crystals can then be separated by filtration and followed optionally by the washing and drying of the filter cake. If the precipiated crystals are predominantly the R-isomer, a salt which contains predominantly the S-isomer can be obtained from the mother liquor, such as by evaporative or vacuum removal of the solvent.

The yield of the S-carboxamide isomer in Step B can be in a range of from about 20% to about 40%, and is often from about 30% to about 40%, based upon the racemic piperazine carboxamide. (The yield based upon the desired S-enantiomer is twice these values; i.e., from about 40% to about 80%, and often from about 60% to about 80%.)

Step C of the process of the invention involves breaking the crystallized salt by treating the S-isomer-containing salt with base and sequentially or concurrently treating the S-isomer with a nitrogen-protecting agent to obtain piperazine carboxamide I*. Suitable bases for breaking the recovered S-isomer include bases selected from the group consisting of alkali metal hydroxides, alkali metal carbonates, alkali metal oxides, $C_1$–$C_6$ alkoxides of alkali metals, alkaline earth metal hydroxides, alkaline earth metal oxides, tetra ($C_1$–$C_4$ alkyl)ammonium hydroxides, and tri-($C_1$–$C_4$ alkyl)amines. Exemplary bases include hydroxides, carbonates, and oxides of lithium, sodium and potassium; methoxides, ethoxides, and n- and iso-propoxides of lithium, sodium, and potassium; tetramethyl- and tetraethyl-ammonium hydroxide; triethylamine; and diisopropylethylamine. In one embodiment, the base is selected from the group consisting of alkali metal hydroxides. In an aspect of the preceding embodiment, the base is NaOH or KOH.

The base can also be an alkanolamine (e.g., ethanolamine), a hydroxylamine (e.g., hydroxylamine per se, N-methylhydroxylamine, N,N-dimethylhydroxylamine, or N-ethylhydroxylamine), or a diamine (e.g., ethylenediamine, tetramethylenediamine, or hexamethylenediamine).

A typical procedure can employ an aqueous base (e.g., aqueous NaOH), wherein the crystallized salt is slurried in an organic solvent and the slurry is mixed with aqueous base resulting in a solution or a biphasic mixture, followed by addition of and reaction with the nitrogen-protecting agent (e.g., Boc$_2$O). The formation of the slurry and the biphasic mixture/solution is suitably conducted at temperatures in the range of from about 0 to about 100° C., and is typically conducted at a temperature of from about 10 to about 60° C. In one embodiment, the temperature is in the range of from about 15 to about 35° C. The organic solvent can suitably be selected from $C_1$–$C_{12}$ linear and branched alkanes, $C_1$–$C_{12}$ linear and branched halogenated alkanes, $C_5$–$C_{10}$ cycloalkanes, $C_6$–$C_{14}$ aromatic hydrocarbons, dialkyl ethers wherein each alkyl is independently a $C_1$–$C_{10}$ alkyl, $C_4$–$C_8$ dialkoxyalkanes, $C_4$–$C_8$ cyclic ethers and diethers, $C_6$–$C_8$ aromatic ethers, $C_2$–$C_{10}$ dialkyl ketones wherein each alkyl is independently $C_1$–$C_8$ alkyl, $C_1$–$C_6$ alkyl esters of $C_1$–$C_6$ alkylcarboxylic acids, primary $C_1$–$C_{10}$ alkyl alcohols, sec ondary C₃–C₁₀ alkyl alcohols, tertiary C₄–C₁₀ alkyl alcohols, primary amides of C₁–C₆ alkylcarboxylic acids, N—C₁–C₆ alkyl secondary amides or N,N-di-C₁–C₆ alkyl tertiary amides of C₁–C₆ alkylcarboxylic acids, C₂–C₆ aliphatic nitriles, C₇–C₁₀ aromatic nitriles, and mixtures thereof. Exemplary solvents include carbon tetrachloride, chloroform, methylene chloride, 1,2-dichloroethane (DCE), 1,1,2-trichloroethane (TCE), 1,1,2,2-tetrachloroethane, cyclohexane, toluene, o- and m- and p-xylene, ethylbenzene, ethyl ether, MTBE, THF, dioxane, 1,2-dimethoxyethane (DME), anisole, phenetole, acetone, methyl ethyl ketone (MEK), methyl acetate, ethyl acetate, IPAc, ethanol, n- and iso-propanol, tert-butyl alcohol, dimethylformamide (DMF), acetonitrile, propionitrile, benzonitrile, and p-tolunitrile.

Another typical procedure can employ a non-aqueous base, wherein the crystallized salt is suspended in organic solvent, optionally including a small amount of water (e.g., from about 0 to about 10 volume percent) as co-solvent, the suspension mixed with an organic base, and the mixture stirred until homogeneous, followed by addition of and reaction with the nitrogen-protecting agent. The formation of the suspension and the homogeneous mixture is suitably conducted at temperatures in the range of from about 0 to about 100° C., and is typically conducted at a temperature of from about 10 to about 60° C. (e.g., from about 15 to about 35° C.). Suitable organic solvents include those set forth in the preceding paragraph. In one embodiment, the solvent is a mixture of C₂–C₄ aliphatic nitrile and a C₁–C₄ alkyl ester of a C₁–C₄ alkylcarboxylic acid (e.g., a mixture of acetonitrile and isopropyl acetate).

It is normally desired to completely break the crystallized salt so as to obtain the free base (S)-piperazine carboxamide. Accordingly, the base is typically employed in an amount of at least about 2 equivalents per equivalent of crystallized salt.

Treating with base to break the salt in Step C also includes eluting a solution of the crystalline salt through a suitable ion exchange column, such that the chiral acid and the piperazine amide elute separately. The crystalline salt solution can be prepared by dissolving the salt crystals obtained in Step B in a suitable solvent (e.g., the solvents set forth above in the description of Step B). In the case where the desired salt crystals are present in the Step B mother liquor (i.e., Step (b4)), the mother liquor can be passed directly through the column and thereby avoiding isolation of the salt crystal. The eluted piperazine carboxamide can then be reacted with a suitable nitrogen protecting agent to afford Compound I*.

While any amount of nitrogen-protecting agent can be employed which results in the formation of at least some of Compound I*, the amount of agent typically employed is that which can maximize the conversion of the S-isomer of III* to I*. Accordingly, the amount of nitrogen-protecting agent is suitably at least about 1 equivalent per equivalent of III*. In one embodiment, the amount of nitrogen-protecting agent is in the range of from about 1 to about 1.5 equivalents per equivalent of III*.

Yields of at least about 85% (e.g., from about 90% to about 99%) for Compound I* can be obtained in Step C.

Another aspect of the invention is a process for racemizing an optically pure or enriched piperazine carboxamide selected from:

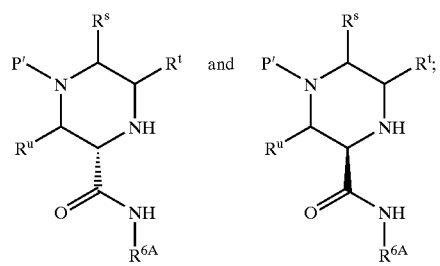

which comprises treating the piperazine carboxamide with a strong base in a solvent at a temperature in the range of from about 0 to about 250° C.; wherein P' is either hydrogen or a nitrogen-protecting group P as defined above; and R⁶ᴬ, Rˢ, Rᵗ and Rᵘ are each as defined above. Suitable strong bases include of alkali metal hydroxides and C₁–C₆ alkoxides of alkali metals. Exemplary strong bases include the methoxides, ethoxides, n- and iso-propoxides, and tert-butoxides of lithium, sodium, and potassium. Suitable solvents include the organic solvents set forth above as useful in Step C. The reaction temperature is more typically in the range of from about 40 to about 120° C.

In an embodiment of the racemization process, the starting piperazine carboxamide is the R-isomer:

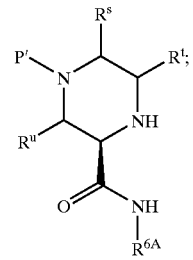

The mother liquor from Step (b3) or the salt crystals from Step (b4) can be a source of the R-isomer, wherein the diastereomeric salt containing the isomer can be broken by treating with base in the same manner as that described above in Step C for the S-isomer, to afford the R-isomer. Once racemized the piperazine carboxamide can be subjected to the resolution process as described in Step B above to obtain additional quantities of the desired S-isomer.

An embodiment of the invention is a process which comprises Steps A, B and C as set forth above, and which further comprises:

(Z) reacting a pyrazine carboxylic acid of Formula (IV*):

(IV*)

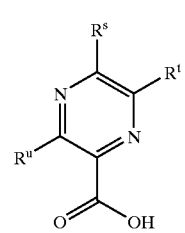

with R⁶ᴬNH₂, or an acid salt thereof, in the presence of a coupling agent to obtain pyrazine carboxamide II*; wherein R⁶ᴬ, Rˢ, Rᵗ and Rᵘ are each as defined above.

Acid salts of the amine, R⁶ᴬNH₂, suitable for use in Step Z include salts of inorganic acids (e.g., HCl, sulfuric acid, nitric acid, etc.) and of organic acids (e.g., acetic acid, trifluoroacetic acid, alkyl and aryl sulfonic acids, etc.)

While any amount of the Compound IV* can be employed which results in the formation of at least some of Compound II*, the maximum conversion of Compound IV* and maximum yield of Compound II* is normally desired. Accordingly, the-amount of Compound IV* typically employed in Step Z is at least about one equivalent per equivalent of the amine. In one embodiment, the amount of Compound IV* is in the range of from about 0.5 to about 5 equivalents per equivalent of amine. In another embodiment, the amount of Compound IV* is in the range of from about 0.9 to about 2 (e.g., from about 1 to about 1.5) equivalents per equivalent of amine.

The coupling agent in Step Z can be any organic compound which facilitates the amidation of the carboxylic acid group in IV* by $R^{64}NH_2$. Suitable coupling agents include carbodiimides (e.g., such as dicyclohexylcarbodiimide, diisopropylcarbodiimide, EDC, and the like), N,N'-carbonyldiimidazole, $POCl_3$, $TiCl_4$, $SO_2ClF$, and chlorosulfonyl isocyanate. In one embodiment, the coupling agent is EDC. In an aspect of the preceding embodiment, the coupling agent is EDC in combination with HOBT.

While any amount of coupling agent can be employed which results in the formation of at least some of Compound II*, the maximum conversion of Compound IV* and maximum yield of Compound II* is normally desired. Accordingly, the amount of coupling agent typically employed in Step Z is at least about one equivalent per equivalent of IV*. In one embodiment, the amount of coupling agent is in the range of from about 1 to about 5 equivalents per equivalent of IV*. In another embodiment, the amount of coupling agent is in the range of from about 1 to about 2 equivalents per equivalent of IV*.

The amidation of Compound IV* can be conducted over a wide range of temperatures, although the temperature is typically in the range of from about $-20$ to about $150°$ C. (e.g., from about $-15$ to about $120°$ C.). In one embodiment, the temperature is in the range of from about $-5$ to about $65°$ C. In another embodiment, the temperature is from about 0 to about $50°$ C. In still another embodiment, the temperature is from about 10 to about $35°$ C.

In a typical procedure, the pyrazine carboxylic acid IV* is dissolved, dispersed or suspended in an organic solvent, followed by the sequential addition of the amine and the coupling agent. The mixture is maintained at reaction temperature for a period sufficient to achieve maximum conversion, after which the amidated product is recovered from the reaction mixture by conventional separation and isolation procedures.

Organic solvents suitable for use in Step Z include the $C_1$–$C_{12}$ linear and branched alkanes, $C_1$–$C_{12}$ linear and branched halogenated alkanes, $C_5$–$C_{10}$ cycloalkanes, $C_6$–$C_{14}$ aromatic hydrocarbons, dialkyl ethers wherein each alkyl is independently a $C_1$–$C_{10}$ alkyl, $C_4$–$C_8$ dialkoxyalkanes, $C_4$–$C_8$ cyclic ethers and diethers, $C_6$–$C_8$ aromatic ethers, $C_2$–$C_{10}$ dialkyl ketones wherein each alkyl is independently $C_1$–$C_8$ alkyl, $C_1$–$C_6$ alkyl esters of $C_1$–$C_6$ alkylcarboxylic acids, primary $C_1$–$C_{10}$ alkyl alcohols, secondary $C_3$–$C_{10}$ alkyl alcohols, tertiary $C_4$–$C_{10}$ alkyl alcohols, primary-amides of $C_1$–$C_6$ alkylcarboxylic acids, N—$C_1$–$C_6$ alkyl secondary amides or N,N-di-$C_1$–$C_6$ alkyl tertiary amides of $C_1$–$C_6$ alkylcarboxylic acids, $C_2$–$C_6$ aliphatic nitriles, $C_7$–$C_{10}$ aromatic nitriles, and mixtures thereof.

If desired, the progress of the reaction in any one or all of Steps Z, A, B and C can be followed by monitoring the disappearance of a reactant (e.g., Compound II* or $H_2$ in Step A) and/or the appearance of the product (e.g., III* in step A) using such analytical techniques as TLC, HPLC, NMR or GC.

Yields of at least about 70% (e.g., from about 70% to about 90%) for pyrazine carboxamide II* can be obtained in Step Z, and yields of from about 85% to about 95% can often be achieved.

Another embodiment of the process of the invention is a process for preparing a nitrogen-protected piperazine carboxamide of formula A1:

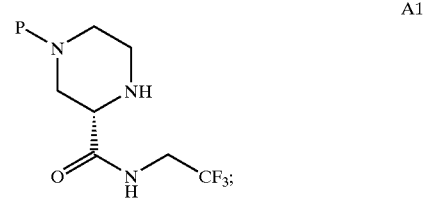

A1 wherein P is a nitrogen-protecting group and the process comprises:

(A) hydrogenating a pyrazine carboxamide of formula A2:

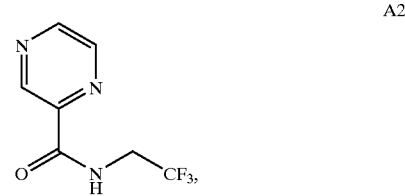

A2 in a solvent and in the presence of a transition metal catalyst to obtain a piperazine carboxamide of formula A3:

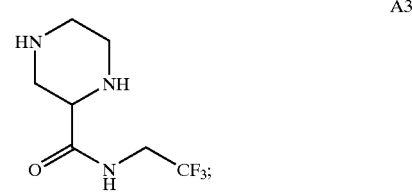

A3

(B) resolving the S-carboxamide isomer of Compound A3 by:
  (b1) forming a solution comprising Compound A3, (S)-camphorsulfonic acid, and solvent; and
  (b2) crystallizing from the solution a salt which contains predominantly the S-isomer; and
(C) breaking the separated crystal salt of the S-carboxamide isomer by treating the salt with base, and treating the resulting free base S-isomer with a nitrogen-protecting agent to obtain piperazine carboxamide A1.

The general reaction conditions and procedures, choice of solvents, choice and/or amounts of reactants and reagents described earlier for Steps A, B and C apply to Steps A, B and C of this embodiment as well. The crystallization in Step (b2) can optionally be assisted by seeding the solution with the (S)-camphorsulfonate salt of the (S)-isomer.

In an aspect of this embodiment, the resolution of the S-carboxamide isomer is conducted in a solvent consisting of acetonitrile, ethanol, and water with from about 1.2 to about 2.0 equivalents (e.g., from about 1.5 to about 1.9 equivalents) of (S)-CSA per equivalent of racemic A3. In a preferred aspect of this embodiment, the resolution of the S-carboxamide isomer is conducted in a solvent consisting of acetonitrile, ethanol, and water with from about 1.2 to about 2.0 equivalents (e.g., from about 1.6 to about 1.8 equivalents; or about 1.7 equivalents) of (S)-CSA per equivalent of racemic A3, wherein water constitutes from about 2 to about 7 weight percent (e.g., from about 4 to about 5 weight percent) of the solvent and the volume ratio of acetonitrile to ethanol is in the range of from about 9:1 to about 6:4.

The enantiomeric excess of the resulting salt can be upgraded by (i) forming a slurry of the salt in a solvent system comprising acetonitrile, ethanol and water (e.g., from about 50 to about 95 volume percent acetonitrile, from about 49 to about 4 volume percent ethanol, and from about 1 to about 5 volume percent water; another example: from about 1:1 to about 15:1 (v/v) acetonitrile:95% ethanol), (ii) aging the slurry by heating it for a period of time (e.g., at a temperature of from about 50 to about 90° C. for at least about one hour), and then (iii) cooling the slurry (e.g., to a temperature in the range of from about 0 to about 30° C.). The resulting crystals have an increased ee and can be recovered by conventional means (e.g., filtration, washing with the slurry solvent, and drying).

Another embodiment of the process is a process which comprises Steps A, B and C as set forth in the preceding embodiment, and which further comprises:

(Z) reacting a pyrazine carboxylic acid of Formula A4:

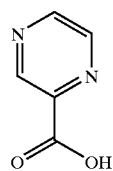

A4 with CF$_3$CH$_2$NH$_2$, or an acid salt thereof, in the presence of EDC and HOBT to obtain pyrazine carboxamide A2.

The general reaction conditions and procedures, choice of solvents, choice and/or amounts of reactants and reagents described earlier for Step Z apply to Step Z of this embodiment as well.

Another embodiment of the present invention is a compound of Formula (V*):

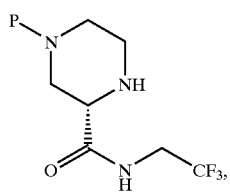

(V*)

wherein P is a nitrogen-protecting group. In an aspect of this embodiment, P is Boc.

The following examples serve only to illustrate the invention and its practice. The examples are not to be construed as limitations on the scope or spirit of the invention.

EXAMPLE 1

(αR,γS,2S)-N-((3S,4S)-3,4-dihydro-3-hydroxy-2H-1-benzopyran-4-yl)-4-(1-furo[3,2-c]pyridin-2-yl-1-methylethyl)-γ-hydroxy-α-(phenylmethyl)-2-[[(2,2,2-trifluoroethyl)amino]carbonyl]-1-piperazinepentanamide

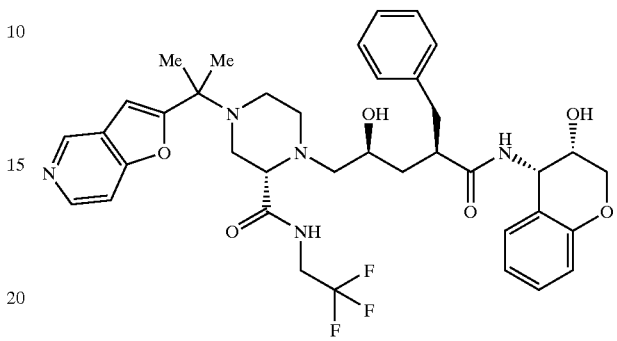

Step A

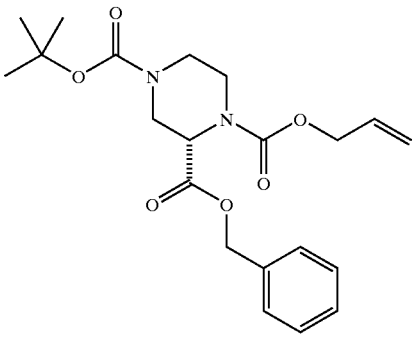

To a solution of 1,4-piperazine-2-(S)-carboxylic acid [bis (+)-CSA salt] (54.9 g, 92.2 mmol) in 1 L THF was added 1N aqueous NaOH until the resulting solution was pH 9 (250 mL). The solution was cooled to 0° C., and BOC-ON (22.7 g, 92.2 mmol, as a solution in 200 mL THF) was added via an addition funnel. The resulting solution was warmed to ambient temperature over 5 hours, then cooled again to 0° C. Allyl chloroformate (9.78 mL, 92.2 mmol) was added via syringe, followed by an additional 100 mL of 1N aqueous NaOH. The solution was warmed to ambient temperature overnight, then concentrated to minimum volume by rotary evaporator. The resulting mixture was acidified to pH 1 with 1N aqueous HCl, and extracted with ethyl acetate (400 mL×2). The organic layers were washed with brine (200 mL) dried (MgSO$_4$) and concentrated in vacuo, affording 44.9 g of a yellow oil. This material was dissolved in 400 mL DMF, followed by the addition of CsHCO$_3$ (14.8 g, 76.1 mmol) and Cs$_2$CO$_3$ (14.3 g, 44.2 mmol). To this mixture was added benzyl bromide (14.2 mL, 120 mmol). After 20 hours at ambient temperature, an additional aliquot of benzyl bromide (5.50 mL, 46.2 mmol) was added. After an additional 4 hours at ambient temperature, the reaction was quenched by the addition of 200 mL of saturated aqueous NaHCO$_3$. The mixture was extracted with ethyl acetate (400 mL×2). The organic layers were washed with H$_2$O (300 mL×2) and brine (300 mL), dried (MgSO$_4$), and concentrated in vacuo to afford 55.2 g of a yellow oil. Purification by flash chromatography (5% ethyl acetate in dichloromethane) afforded the title compound as a clear oil.

¹H NMR (CDCl₃, 300 MHz) 7.35 (s, 5H), 5.90 (m, 1H), 5.20 (m, 4H), 4.70 (m, 5H), 3.95 (m, 1H), 3.30 (m, 1H), 3.10 (dt, 1H), 2.85 (m, 1H), 1.45 (s, 9H).

Step B

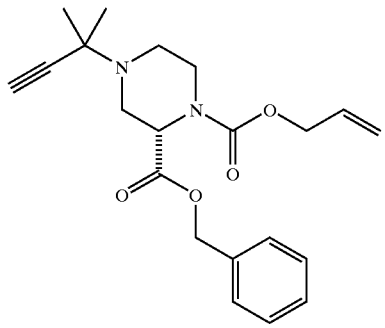

To the intermediate prepared in Step A (28.0 g, 69.9 mmol) in 400 mL of dichloromethane was added 200 mL trifluoroacetic acid at ambient temperature. After 5 hours, the solution was poured slowly onto 1 L of saturated aqueous NaHCO₃. To this mixture was added 2.5 N aqueous NaOH until the aqueous layer was pH 7. The organic layer was extracted, dried (Na₂SO₄), and concentrated in vacuo affording a clear oil. To 5.75 g (19.6 mmol) of this intermediate in 50 mL of THF was added 194 mg (2.00 mmol) CuCl. The mixture was cooled to 0° C., and 3-chloro-3-methyl-1-butyne (2.20 mL, 19.6 mmol) was added via syringe, followed by Cu powder (124 mg, 2.00 mmol) and triethylamine (6.00 mL, 43.0 mmol). The resulting mixture was warmed to ambient temperature overnight. The reaction mixture was then filtered through celite, and the solution diluted with ethyl acetate (300 mL), and washed with saturated aqueous NaHCO₃ (300 mL) and brine (300 mL). The organic layer was dried (MgSO₄) and concentrated in vacuo affording a yellow oil. Purification by flash chromatography (20% ethyl acetate in hexane) afforded the title compound as a clear oil. ¹H NMR (CDCl₃, 400 MHz) 7.39 (s, 5H), 5.92 (m, 1H), 5.20 (m, 4H), 4.80 (d, 1H), 4.62 (dd, 2H), 3.93 (dd, 1H), 3.58 (t, 1H), 3.28 (dt, 1H), 2.98 (dd, 1H), 2.40 (d, 1H), 2.22 (m, 1H), 1.76 (s, 1H), 1.36 (s, 3H), 1.32 (s, 3H).

Step C

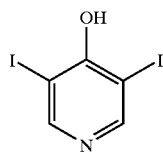

To a solution of 4-hydroxypyridine (10.0 g, 105 mmol) in 200 mL of methanol was added N-iodosuccinimide (47.1 g, 210 mmol). The solution was heated to reflux for 3 hours, and the resulting precipitate was filtered hot. The filtrate was dried in vacuo, affording the title compound as a white solid. ¹H NMR (DMSO-D₆, 300 MHz) 8.25 (s, 2H), 2.50 (s, 1H).

Step D

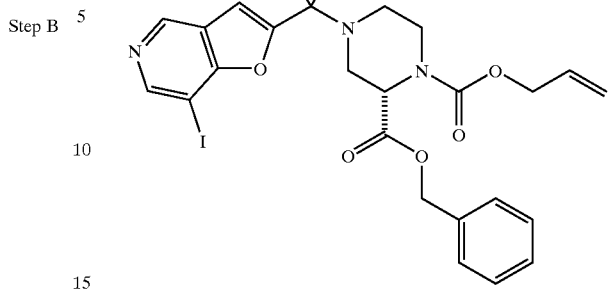

To a solution of the intermediate prepared in Step B (4.30 g, 11.6 mmol) in pyridine (150 mL) was added the intermediate prepared in Step C (4.03 g, 11.6 mmol). To this solution was added Cu₂O (2.50 g, 17.4 mmol). The resulting mixture was heated to reflux for 2 hours, then cooled to ambient temperature. The reaction was quenched by the addition of 200 mL of saturated aqueous NaHCO₃, and extracted with ethyl acetate (500 mL×2). The organic layers were washed with 10% aqueous NH₄OH (300 mL×3) and brine (300 mL), dried (MgSO₄), and concentrated in vacuo. Purification by flash chromatography (45% ethyl acetate in hexane) afforded the title compound as a yellow gum. ¹H NMR (CDCl₃, 400 MHz) 8.68 (s, 1H), 8.66 (s, 1H), 7.30 (s, 5H), 6.59 (s, 1H), 5.84 (m, 1H), 5.27 (m, 4H), 4.76 (d, 1H), 4.60 (m, 2H), 3.90 (dd, 1H), 3.63 (dd, 1H), 3.27 (dt, 1H), 2.99 (dd, 1H), 2.34 (dt, 1H), 2.23 (dq, 1H), 1.93 (s, 6H).

Step E

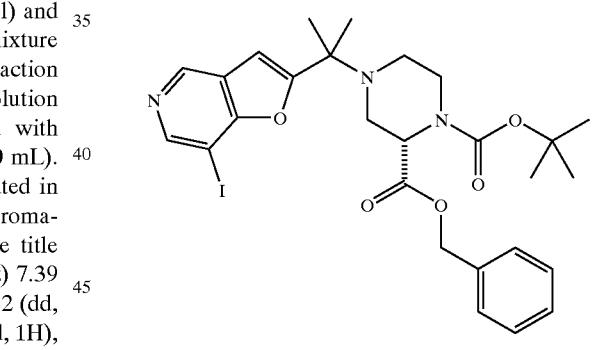

To a solution of tris(dibenzylidineacetone)dipalladium(0) (371 mg, 0.405 mmol) in 50 mL of THF was added 1,4-bis(diphenylphosphino)butane (466 mg, 0.810 mmol). After stirring 20 min at ambient temperature, this solution was added via cannula to a solution of the intermediate from Step D (4.77 g, 8.10 mmol) and thiosalicilic acid (1.87 g, 12.1 mmol) in 50 mL THF. After 1 hour at ambient temperature the reaction was diluted with 1 L diethyl ether and extracted with 1% aqueous HCl (250 mL×3). The combined aqueous layers were neutralized with excess saturated aqueous NaHCO₃, and the resulting suspension was extracted with ethyl acetate (500 mL×2). These organic layers were washed with brine (200 mL), dried (MgSO₄), and concentrated in vacuo affording 4.26 g of a yellow solid. This material was dissolved in 800 mL dichloromethane. To this solution was added triethyl amine (1.47 mL, 10.5 mmol), di-tert-butyldicarbonate (2.03 g, 9.29 mmol) and 4-dimethylaminopyridine (ca. 20 mg). After 1 hour at ambient temperature the reaction was quenched by the addition of 500 mL of saturated aqueous NaHCO₃. The mixture was extracted with dichloromethane (200 mL×3), the organic layers were dried (Na₂SO₄) and concentrated in vacuo, affording 5.109 g of a yellow solid. Purification by flash chromatography (20% ethyl acetate in dichloromethane) afforded the title compound as a white solid. ¹H NMR (CDCl₃, 400 MHz) 8.69 (m, 2H), 7.35 (s, 5H), 6.60 (s, 1H), 5.17 (m, 2H), 4.60 (d, 1H), 3.80 (dd, 1H), 3.62 (dd, 1H), 3.20 (dt, 1H), 3.01 (dd, 1H), 2.32 (dt, 1H), 2.14 (m, 1H), 1.45 (s, 9H), 1.44 (s, 3H), 1.37 (s, 3H).

Step F

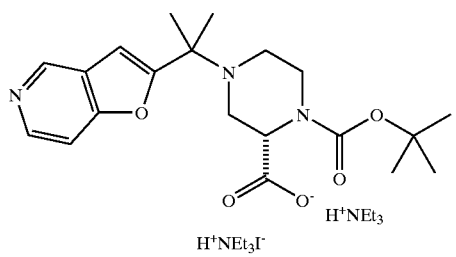

To a solution of the intermediate from Step E (3.41 g, 5.63 mmol) in methanol (100 mL) was added triethylamine (1.96 mL, 14.1 mmol) and 10% Pd(0) on carbon (200 mg). The reaction vessel was charged with 1 atmosphere of H₂ and stirred at ambient temperature. An additional 200 mg of 10% Pd(0) on carbon was added after 24, 48, 56 and 64 hours at ambient temperature. The reaction was then filtered through celite and concentrated in vacuo affording the title compound as a white solid. ¹H NMR (CDCl₃, 400 MHz) 9.65 (s, 2H), 8.79 (s, 1H), 8.40 (d, 1H), 7.35 (d, 1H), 6.59 (s, 1H), 4.43 (d, 1H), 3.75 (m, 2H), 3.30 (m, 1H) 3.08 (q, 12 H), 2.85 (m, 1H), 2.20 (m, 1H), 2.03 (m, 1H), 1.55 (t, 18 H), 1.40 (s, 15H).

Step G

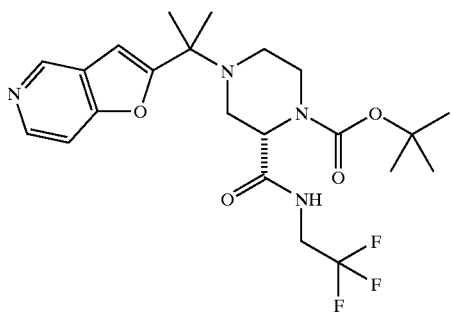

To a solution of the intermediate from Step F (200 mg, 0.278 mmol) in dichloromethane (3 mL) was added triethylamine (116 μL, 0.834 mmol), trifluoroethylamine (33.2 μL, 0.420 mmol), HOAT (41.6 mg, 0.306 mmol) and EDC (58.6 mg, 0.306 mmol). After 12 hours at ambient temperature the solution was concentrated by rotary evaporator and purified by flash chromatography (30% dichloromethane in ethyl acetate) to afford the title compound as a clear oil. ¹H NMR (CDCl₃, 400 MHz) 8.86 (s, 1H), 8.46 (d, 1H), 7.46 (s, 1H), 7.37 (d, 1H), 6.61 (s, 1H), 4.67 (s, 1H), 3.98 (m, 3H), 3.51 (d, 1H), 3.02 (m, 1H), 2.91 (d, 1H), 2.30 (dd, 1 H), 2.20 (t, 1H), 1.50 (s, 6H), 1.38 (s, 9H). HPLC-MS (ES) 471.4 (M+1).

Step H

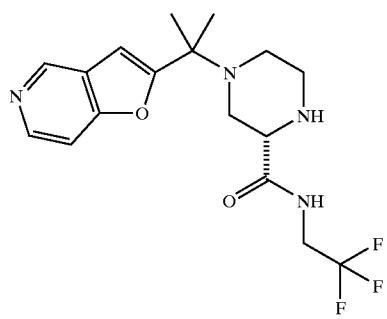

To a solution of the intermediate from Step G (135 mg, 0.278 mmol) in dichloromethane (5 mL) was added trifluoroacetic acid (2.5 mL). After 3 hours at ambient temperature, the reaction was quenched by the addition of saturated aqueous NaHCO₃ (20 mL). The mixture was extracted with dichloromethane (20 mL×2) and concentrated in vacuo, affording the title compound as a colorless oil. This was used without further purification.

Step I

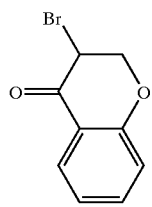

To a solution of 4-chromanone (10 g, 67.49 mmol) in 400 mL dichloromethane at 0° C. was added bromine (4.45 mL, 86.39 mmol) dropwise slowly. The reaction was monitored by TLC. After half an hour the reaction mixture was diluted with methylene chloride (100 mL) and was washed with water (300 mL). The organic layer was dried over anhydrous sodium sulfate and concentrated. The resulting product was dissolved in HOAc (100 mL) and sodium sulfite (8 g) was added. The reaction mixture was stirred at room temperature and reaction progress was monitored by TLC. After 48 hours the reaction mixture was poured into water and the product was extracted with methylene chloride. The organic layer was dried over anhydrous sodium sulfate and concentrated in vacuo to give the titled compound as a white solid. ¹H NMR (CDCl₃, 400 MHz): 7.93 (d, J=8.8 Hz, 1H), 7.54 (t, 1H), 7.08 (t, 1H), 7.02 (d, J=8.0 Hz, 1H), 4.63 (m, 4H)

Step J

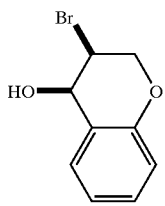

To a solution of 3-bromo-4-chromanone (2 g, 8.81 mmol) in methanol (20 mL) was added sodium borohydride (0.4 g, 10.57 mmol). The reaction was stirred at room temperature and monitored by TLC. After 2 hours the solvent was removed in vacuo and then diluted with ethyl acetate (50 mL). The resulting solution was washed with brine, dried over anhydrous sodium sulfate, filtered and concentrated in vacuo to give the titled compound as a white solid. $^1$H NMR (CDCl$_3$, 300 MHz): 7.32 (d, J=7.2 Hz, 1H), 7.23 (t, 1H), 6.96 (t, 1H), 6.84 (d, J=9.0 Hz, 1H), 4.82 (m, 1H), 4.54 (m, 1H), 4.38 (m, 2H).

Step K

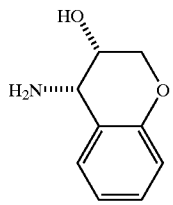

To a solution of 3-bromo-4-chromanol (2 g, 8.72 mmol) in acetonitrile (20 mL) was added concentrated sulfuric acid (1 mL, 17.47 mmol). The reaction mixture was stirred at 45° C.–50° C. for 18 hours. The solvent was removed in vacuo. Then water (10 mL) was added. The reaction mixture was heated to reflux. After 5 hours the reaction mixture was cooled to room temperature. The pH of the reaction mixture was adjusted to 12–13 by dropwise addition of aqueous 50% sodium hydroxide. The product was extracted with tetrahydrofuran three times. The organic layer were combined and dried over anhydrous sodium sulfate, filtered and concentrated in vacuo to give the title compound as a white solid. $^1$H NMR (CDCl$_3$, 300 MHz): 7.29 (d, J=7.8 Hz, 1H), 7.16 (t, 1H), 6.93, (t, 1H), 6.83 (d, J=8.4 Hz, 1H), 4.12 (m, 1H), 3.99 (m, 2H), 3.84 (m, 1H).

Step L

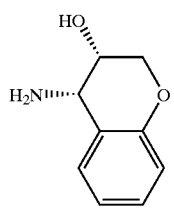

To a suspension of the racemic 4-amino-3-chromanol in ethanol (35 mL per gram of 4-amino-3-chromanol) was added 1.0 equivalent of (S)-(+) mandelic acid. The suspension was heated to 70° C. until forming a homogeneous solution. The solution was cooled to room temperature and white crystal was formed. After filtering the white crystal was dissolved in 3 N aqueous sodium hydroxide solution and the resolved product was extracted with ethyl acetate three times. The combined organic layer was dried over anhydrous sodium sulfate, filtered and concentrated in vacuo to give the titled compound as a white solid. The purity of the compound was verified by chiral HPLC with Crownpak CR+ column eluted with pH 1.0 perchloric acid solution. $^1$H NMR (CDCl$_3$, 300 MHz): 7.29 (d, J=7.8 Hz, 1H), 7.16 (t, 1H), 6.93, (t, 1H), 6.83 (d, J=8.4 Hz, 1H), 4.12 (m, 1H), 3.99 (m, 2H), 3.84 (m, 1H).

Step M

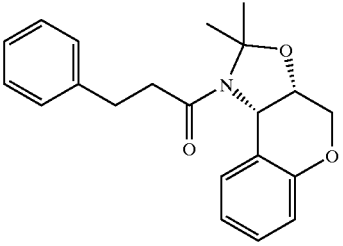

To a solution of the intermediate from Step L (5.97 g, 36.2 mmol) in THF (200 mL) was added hydrocinnamic acid (5.43 g, 36.2 mmol). The suspension was cooled to 0° C., and HOBT (5.23 g, 39.8 mmol) was added, followed by EDC (7.63 g, 39.8 mmol), and triethylamine (15.1 mL, 108 mmol). The mixture was warmed to ambient temperature and stirred 72 hours. The reaction mixture was poured onto 500 mL of 1.5 N aqueous HCl, and diluted with 200 mL of ethyl acetate. The organic layer was washed with an additional 200 mL of 1.5 N aqueous HCl, saturated aqueous NaHCO$_3$ (200 mL), and brine (200 mL), dried (MgSO$_4$), and concentrated in vacuo affording 16.0 g of a white solid. This material was dissolved in 400 mL of a 1:1 mixture of THF and 2,2-dimethoxypropane. To this solution was added 100 mg of p-toluenesulfonic acid, and the reaction was heated to reflux for 6 hours. The reaction was then cooled to ambient temperature and quenched by the addition of saturated aqueous NaHCO$_3$ (400 mL). The resulting mixture was extracted with ethyl acetate (400 mL×2). The organic layers were washed with brine (200 mL), dried (MgSO$_4$), and concentrated in vacuo, affording 12.3 g of a yellow oil. Purification by flash chromatography (30% ethyl acetate in hexane) afforded the title compound as a white solid. $^1$H NMR (CDCl$_3$, 300 MHz) 7.25 (m, 7H), 6.82 (m, 2H), 4.70 (d, 1H), 4.33 (m, 1H), 4.08 (d, 1H), 3.92 (s, 1H), 3.11 (m, 2H), 2.92 (m, 1H), 2.68 (m, 1H), 1.61 (s, 3H), 1.23 (s, 3H).

Step N

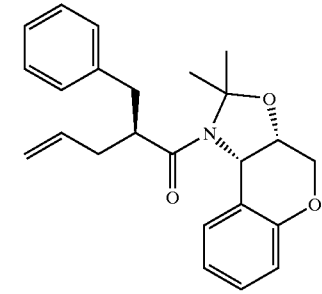

To a solution of the intermediate from Step N (6.36 g, 18.9 mmol) in THF (180 mL) was added allyl bromide (1.80 mL, 18.9 mmol). The solution was cooled to 22° C., and lithium hexamethyldisilylazide (20.8 mL of a 1.0 N solution in THF, 20.8 mmol) was added. After 10 min the reaction was quenched by the addition of saturated aqueous NH$_4$Cl (100 mL), and extracted with ethyl acetate (200 mL×2). The organic layers were washed with saturated aqueous NaHCO$_3$ (200 mL), brine (200 mL), dried (MgSO$_4$), and concentrated in vacuo. The resulting oil was purified by flash chromatography (25% ethyl acetate in hexane) affording the title compound as a white gum. $^1$H NMR (CDCl$_3$, 300 MHz) indicated a 5:1 mixture of rotamers: 7.30 (m, 5H), 7.05 (m, 1H), 6.80 (m, 1H), 6.4 (m, 1H), 5.85 (m, 1H), 5.15 (m, 1H), 4.98 (m, 1H), 4.40 (m, 1H), 4.25 (m, 2H), 3.38 (dd, 1H), 3.19 (m, 1H), 2.80 (m, 1H), 2.42 (m, 1H), 1.70 (s, 3H), 1.23 (s, 3H).

Step O

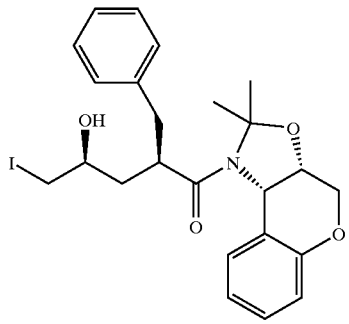

To a solution of the intermediate from Step N (6.10 g, 16.2 mmol) in 200 mL of ethyl acetate was added 200 mL of 0.5 aqueous NaHCO$_3$. The mixture was cooled to 0° C., and N-iodosuccinimide was added in a single portion. The reaction was warmed to ambient temperature and stirred 24 hr. The reaction was then diluted with ethyl acetate (500 mL). The organic layer was washed with 1N Na$_2$S$_2$O$_3$ (300 mL×2), and brine (300 mL), dried (MgSO$_4$), and concentrated in vacuo, affording a yellow oil. Purification by flash chromatography (30% ethyl acetate in hexane) afforded the title compound as a white solid. $^1$H NMR (CDCl$_3$, 300 MHz) indicated a 5:2 mixture of rotamers: 7.30 (m, 5H), 7.05 (m, 1H), 6.82 (m, 1H), 6.60 (m, 1H), 5.92 (d, 0.3H), 5.58 (d, 0.7H), 4.45 (m, 2H), 4.20 (m, 2H), 3.63 (m, 1H), 3.44 (m, 2H), 3.20 (m, 2H), 2.82 (m, 2H), 2.40 (d, 1H), 2.00 (m, 1H), 1.72 (s, 3H), 1.49 (d, 2H), 1.29 (s, 3H).

Step P

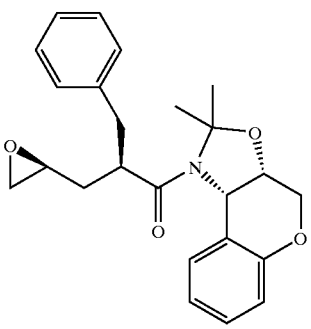

To a solution of the intermediate from Step O (7.71 g, 14.8 mmol) in ethyl acetate (300 mL) was added sodium methoxide (5.07 mL of a 25% solution in methanol, 22.2 mmol). After 10 minutes the reaction was quenched by the addition of saturated aqueous NaHCO$_3$ (300 mL). The organic layer was washed with brine (300 mL), dried (MgSO$_4$), and concentrated in vacuo affording the title compound as a white gum. This was used without further purification. $^1$H NMR (CDCl$_3$, 300 MHz) indicated a 5:2 mixture of rotamers: 7.30 (m, 5H), 7.10 (m, 1H), 6.82 (m, 1H), 6.50 (m, 1H), 5.89 (d, 0.3H), 5.40 (d, 0.7H), 4.40 (m, 2H), 4.15 (m, 2H), 3.40 (m, 2H), 3.00 (m, 1H), 2.85 (m, 2H), 2.50 (dd, 0.7H), 2.40 (dd, 0.3H), 2.20 (m, 1H), 1.72 (s, 3H), 1.49 (d, 1H), 1.29 (s, 3H).

Step Q

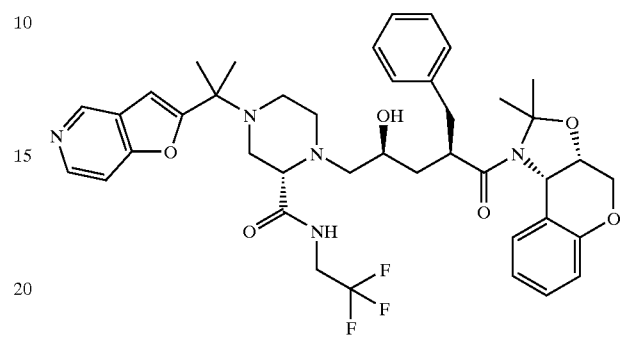

To a solution of the intermediate from Step P (1.34 g, 3.41 mmol) in 2-propanol (30 mL) was added the intermediate from Step H (1.15 g, 3.10 mmol). The solution was heated to reflux for 7 hr, then cooled to ambient temperature and concentrated in vacuo, affording 2.82 g of a black oil. Purification by flash chromatography (5% methanol in ethyl acetate) afforded the title compound as a yellow solid. $^1$H NMR (CDCl$_3$, 400 MHz) indicated a 4:1 mixture of rotamers: 9.40 (m, 1H), 8.90 (s, 1H), 8.55 (d, 1H), 7.30 (m, 6H), 7.10 (m, 1H), 6.81 (d, 1H), 6.68 (m, 4H), 5.90 (d, 0.3H), 5.69 (d, 0.7H), 4.43 (dd, 2H), 4.30 (m, 2H), 3.73 (m, 2H), 3.50 (m, 2H), 3.40 (m, 2H), 3.10 (m, 2H), 2.83 (m, 2H), 2.60 (m, 4H), 1.70 (s, 3H), 1.55 (s, 6H), 1.25 (s, 3H).

Step R (αR,γS,2S)-N-((3S,4S)-3,4-dihydro-3-hydroxy-2H-1-benzopyran-4-yl)-4-(1-furo[3,2-c]pyridin-2-yl-1-methylethyl)-γ-hydroxy-α-(phenylmethyl)-2-[[(2,2,2-trifluoroethyl)amino]carbonyl]-1-piperazinepentanamide piperazinepentanamide The intermediate from Step O (558 mg, 0.731 mmol) was dissolved in methanol saturated with gaseous HCl (40 mL). After stirring 12 hours at ambient temperature the reaction was quenched by the addition of saturated aqueous NaHCO$_3$ (200 mL). The resulting mixture was extracted with dichloromethane (50 mL×4). The organic layers were dried (Na$_2$SO$_4$) and concentrated in vacuo affording 518 mg of a yellow solid. Purification by flash chromatography afforded the title compound as a white solid. $^1$H NMR (CDCl$_3$, 400 MHz) 9.42 (t, J=4.8 Hz, 1H), 8.90 (s, 1H), 8.52 (d, J=6.0 Hz, 1H), 7.37 (d, J=5.6 Hz, 1H), 7.30 (m, 5H), 7.11 (t, J=8.4 Hz, 1H), 7.06 (d, J=7.6 Hz, 1H), 6.78 (m, 2H), 6.67 (s, 1H), 5.91 (d, J=8.4 Hz, 1H), 5.15 (dd, J=4.0 Hz, 1H), 4.27 (m, 1H), 4.06 (d, J=10.4 Hz, 1H), 4.00 (dd, J=4.8 Hz, J=11.6 Hz, 1H), 3.76 (m, 3H), 3.46 (s, 1H), 3.37 (s, 1H), 3.11 (d, J=11.6 Hz, 1H), 2.85 (m, 4H), 2.70 (m, 4H), 2.44 (m, 2H), 2.10 (d, J=5.2 Hz, 1H), 1.90 (t, J=11.2 Hz, 1H), 1.57 (s, 8H); HPLC-MS (ES) 724.6 (M+1).

EXAMPLE 2

(αR,γS,2S)-N-((3S,4S)-3,4-dihydro-3-hydroxy-2H-1-benzopyran-4-yl)-2-[[(2-fluoroethyl)amino] carbonyl]-4-(1-furo[3,2-c]pyridin-2-yl-1-methylethyl)-γ-hydroxy-α-(phenylmethyl)-1-piperazinepentanamide

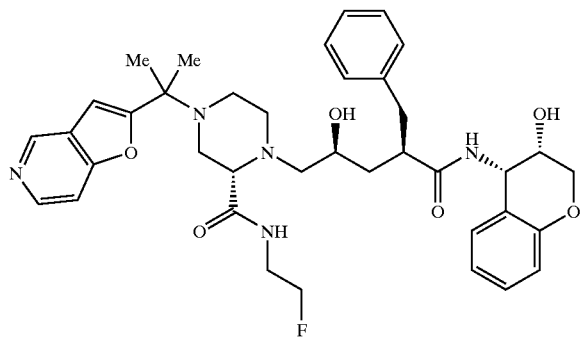

Step A

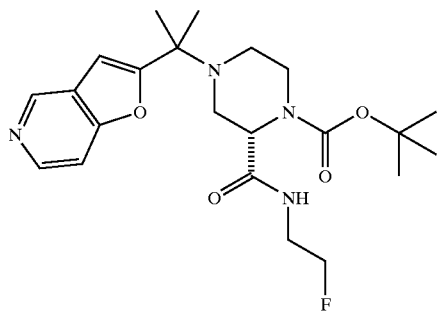

The title compound was obtained following the procedure described in Example 1, Step G, starting with the intermediate prepared as in Example 1, Step F (394 mg, 0.548 mmol) and 2-fluoroethylamine hydrochloride (70.9 mg, 0.712 mmol). Purification by flash chromatography (ethyl acetate) afforded the title compound as a clear oil. $^1$H NMR (CDCl$_3$, 400 MHz) 8.85 (s, 1H), 8.45 (d, 1H), 7.40 (d, 1H), 6.80 (s, 1H), 4.65 (m, 2H), 4.50 (m, 1H), 4.00 (s, 1H), 3.60 (m, 4H), 3.07 (m, 1H), 2.92 (d, 1H), 2.25 (dd, 1H), 2.20 (m, 1H), 1.55 (s, 6H), 1.43 (s, 9H); HPLC-MS (ES) 435.1 (M+1).

Step B

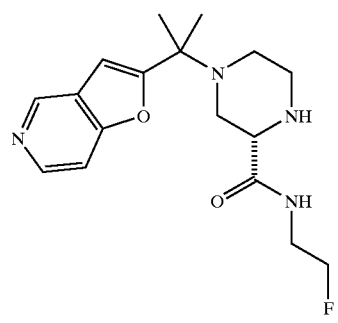

To a solution of the intermediate from Step A (220 mg, 0.507 mmol) in dichloromethane (5 mL) was added trifluoroacetic acid (2.5 mL). After 2 hours at ambient temperature the reaction was quenched by the addition of saturated aqueous NaHCO$_3$ (20 mL). The mixture was extracted with dichloromethane (20 mL×2) and concentrated in vacuo, affording the free piperazine as a white solid. This was used without further purification.

Step C

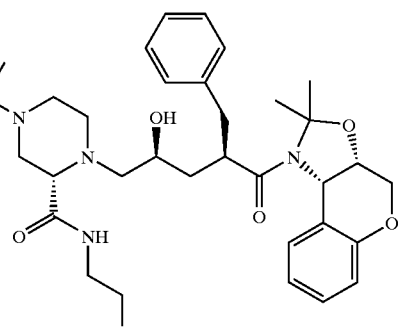

To a solution of the intermediate prepared in Step B (91.2 mg, 0.273 mmol) in 2-propanol was added the intermediate from Example 1, Step P (107 mg, 0.273 mg) as described in Example 1, Step Q. Purification by flash chromatography (2.5% methanol, 5% triethylamine in ethyl acetate) afforded the title compound. HPLC-MS (ES) 728.2 (M+1).

Step D (αR,γS,2S)-N-((3S,4S)-3,4-dihydro-3-hydroxy-2H-1-benzopyran-4-yl)-2-[[(2-fluoroethyl)amino] carbonyl]-4-(1-furo[3,2-c]pyridin-2-yl-1-methylethyl)-γ-hydroxy-α-(phenylmethyl)-1-piperazinepentanamide The title compound was obtained following the procedure described in Example 1, Step R, starting with the intermediate prepared in Example 2, Step C (52.2 mg, 71.8 μmol). Purification by preparative TLC (10% methanol in ethyl acetate) afforded the title compound as a white solid. $^1$H NMR (CDCl$_3$, 400 MHz) 9.04 (s, 1H), 8.89 (s, 1H), 8.50 (d, J=6.0 Hz, 1H), 7.42 (d, J=6.0 Hz, 1H), 7.72 (m, 5H), 7.10 (m, 2H), 6.78 (d, J=8.0 Hz, 1H), 6.66 (s, 1H), 6.01 (d, J=8.0 Hz, 1H), 5.15 (dd, J=11.6 Hz, J=7.2 Hz, 1H), 4.66 (m, 1H), 4.55 (m, 1H), 4.06 (d, J=10.8 Hz, 1H), 3.99 (dd, J=5.6 Hz, J=12.0 Hz, 1H), 3.77 (m, 2H), 3.55 (m, 1H), 3.34 (s, 1H), 3.06 (d, J=11.2 Hz, 1H), 2.90 (m, 4H), 2.70 (m, 2H), 2.47 (d, J=11.2 Hz, 2H), 1.90 (t, J=6.8 Hz, 1H), 1.72 (s, 3H), 1.57 (s, 3H); HPLC-MS (ES) 688.2 (M+1).

EXAMPLE 3

(αR,γS,2S)-N-((3S,4S)-3,4-dihydro-3-hydroxy-2H-1-benzofuran-4-yl)-2-[[[2-fluoro-1,1-bis(fluoromethyl)ethyl]amino]carbonyl]-4-(1-furo[3,2-c]pyridin-2-yl-1-methylethyl)-γ-hydroxy-α-(phenylmethyl)-1-piperazinepentanamide

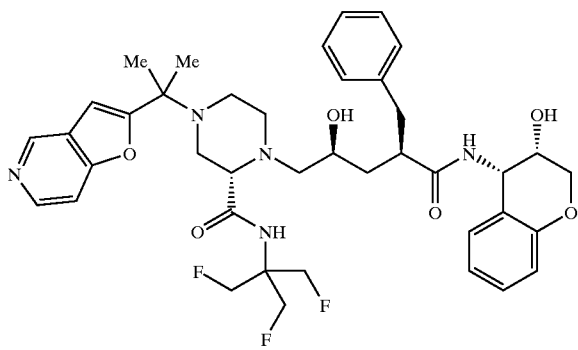

Step A

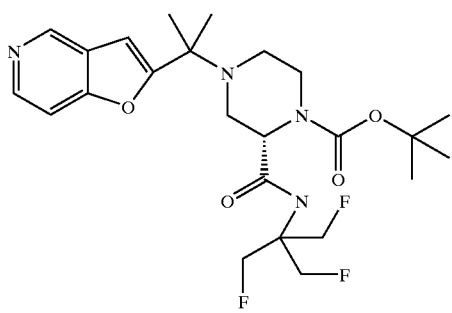

The title compound was obtained following the procedure described in Example 1, Step G, starting with the intermediate prepared in example 1, Step F (388 mg, 0.540 mmol) and 2-fluoro-1,1-bis-(fluoromethyl)-ethylamine hydrochloride (prepared as described in Ok, D.; Fisher, M. H.; Wyvratt, M. J.; Meinke, P. T.; *Tetrahedron Lett* 1999, 40, 3831–3834). (115 mg, 0.702 mmol). Purification by flash chromatography (ethyl acetate) afforded the title compound as a clear oil. $^1$H NMR (CDCl$_3$, 400 MHz) 8.88 (s, 1H), 8.50 (d, 1H), 7.40 (d, 1H), 6.60 (s, 1H), 4.85 (m, 6H), 4.60 (m, 1H), 4.00 (m, 1H), 3.45 (m, 1H), 3.10 (m, 1H), 2.90 (m, 1H), 2.37 (dd, 1H), 2.20 (m, 1H), 1.53 (s, 3H), 1.50 (s, 3H), 1.40 (s, 9H).

Step B

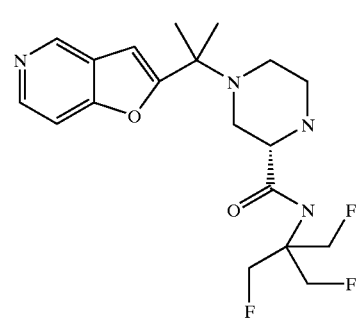

The title compound was obtained following the procedure described in Example 2, Step B, starting with the intermediate prepared in Example 3, Step A (209 mg, 0.419 mmol), affording the title compound as a clear oil. This was used without further purification.

Step C

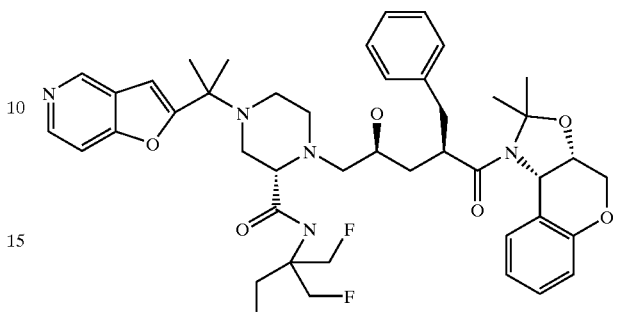

The title compound was obtained following the procedure described in Example 1, Step Q, starting with the intermediate prepared in Example 3, Step B (158 mg, 0.397 mmol) and the intermediate prepared in Example 1, Step P (156 mg, 0.397 mmol). Purification by flash chromatography (5% methanol in ethyl acetate) afforded the title compound. $^1$NMR (CDCl$_3$, 400 MHz) indicated a 4:1 mixture of rotamers: 9.20 (s, 1H), 8.90 (s, 1H), 8.53 (d, 1H), 7.43 (d, 1H), 7.39 (s, 1H), 7.30 (m, 5H), 7.22 (t, 1H), 7.13 (t, 1H), 6.82 (d, 1H), 6.68 (m, 3H), 5.90 (d, 0.2H), 5.70 (d, 0.8H), 4.93 (s, 3H), 4.80 (s, 3H), 4.42 (dd, 2H), 4.29 (d, 1H), 4.18 (d, 1H), 3.70 (t, 1H), 3.45 (m, 3H), 3.20 (m, 1H), 2.83 (m, 2H), 2.62 (m, 2H), 2.40 (m, 2H), 1.78 (t, 1H), 1.70 (s, 3H), 1.59 (s, 3H), 1.55 (s, 3H), 1.24 (s, 3H); HPLC-MS (ES) 792.2 (M+1).

Step D (αR,γS,2S)-N-((3S,4S)-3,4-dihydro-3-hydroxy-2H-1-benzofuran-4-yl)-2-[[[2-fluoro-1,1-bis(fluoromethyl)ethyl]amino]carbonyl]-4-(1-furo[3,2-c]pyridin-2-yl-1-methylethyl)-γ-hydroxy-α-(phenylmethyl)-1-piperazinepentanamide The title compound was obtained following the procedure described in Example 1, Step R, starting with the intermediate prepared in Example 3, Step C (31.6 mg, 40.0 μmol). Purification by preparative TLC (5% methanol in ethyl acetate) afforded the title compound as a white solid. $^1$H NMR (CDCl$_3$, 400 MHz) 9.17 (s, 1H), 8.90 (s, 1H), 8.52 (d, J=6.0 Hz, 1H), 7.43 (d, J=5.6 Hz, 1H), 7.22 (m, 5H), 7.10 (t, J=8.0Hz, 1H), 7.04 (d, J=7.6 Hz, 1H), 6.79 (d, J=8.4 Hz, 1H), 6.75 (d, J=8.0 Hz, 1H), 6.67 (s, 1H), 5.95 (m, 1H), 5.15 (dd, J=4.0 Hz, J=7.6 Hz, 1H), 4.95 (s, 3H), 4.83 (s, 3H), 4.01 (m, 2H), 3.76 (m, 1H), 3.26 (s, 1H), 3.18 (d, J=11.2 Hz, 1H), 2.94 (m, 4H), 2.63 (m, 2H), 2.42 (m, 2H), 1.90 (t, J=11.2 Hz, 1H), 1.59 (s, 3H), 1.57 (s, 3H); HPLC-MS (ES) 752.2 (M+1).

EXAMPLE 4

(αR,γS,2S)-2-[[[1,1-bis(fluoromethyl)ethyl]amino]
carbonyl]-N-((3S,4S)-3,4-dihydro-3-hydroxy-2H-1-
benzopyran-4-yl)-4-(1-furo[3,2-c]pyridin-2-yl-1-
methylethyl)-γ-hydroxy-α-(phenylmethyl)-1-
piperazinepentanamide

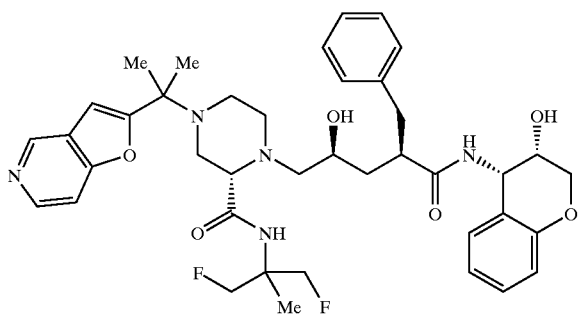

Step A

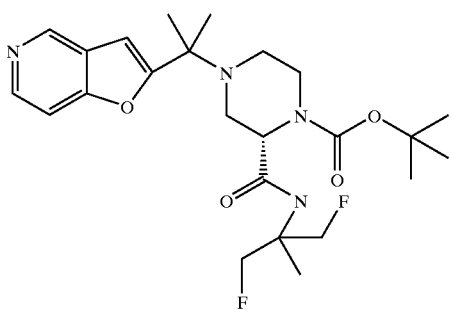

The title compound was obtained following the procedure described in Example 1, Step G, starting with the intermediate prepared in Example 1, Step F (394 mg, 0.548 mmol) and 2-fluoro-1-(fluoromethyl)-1-methyl-ethylamine hydrochloride (prepared as described in Ok, D.; Fisher, M. H.; Wyvratt, M. J.; Meinke, P. T.; *Tetrahedron Lett* 1999, 40, 3831–3834) (117 mg, 0.713 mmol). Purification by flash chromatography (ethyl acetate) afforded the title compound as a white solid. $^1$H NMR (CDCl$_3$, 400 MHz) 8.86 (s, 1H), 8.45 (d, 1H), 7.40 (d, 1H), 6.60 (s, 1H), 4.60 (m, 5H), 4.00 (s, 1H), 3.45 (s, 1H), 3.10 (t, 1H), 2.90 (s, 1H), 2.30 (dd, 1H), 2.18 (t, 1H), 1.81 (s, 1H), 1.55 (s, 3H), 1.50 (s, 3H), 1.48 (s, 3H), 1.40 (s, 9H).

Step B

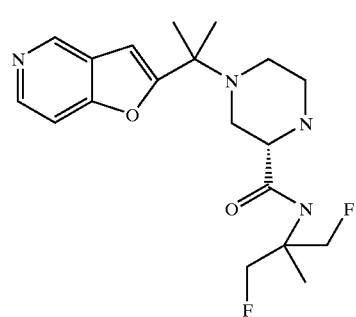

The title compound was obtained following the procedure described in Example 2, Step B, starting with the intermediate prepared in Example 4, Step A (190 mg, 0.396 mmol), affording the title compound as a colorless oil. This was used without further purification.

Step C

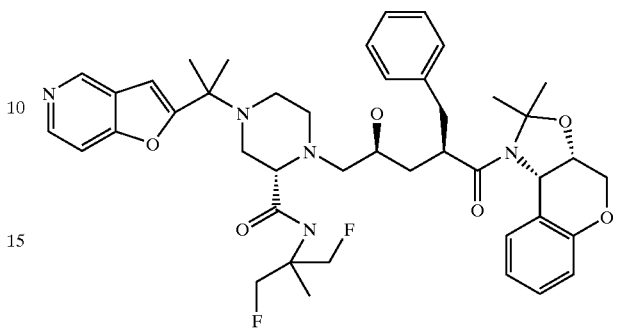

The title compound was obtained following the procedure described in Example 1, Step Q, starting with the intermediate prepared in Example 4, Step B (146 mg, 0.383 mmol), and the intermediate prepared in Example 1, Step P (151 mg, 0.383 mmol). Purification by flash chromatography (5% methanol in ethyl acetate) afforded the title compound as a clear oil. $^1$H NMR (CDCl$_3$, 400 MHz) indicated a 5:1 mixture of rotamers: 8.94 (s, 1H), 8.89 (s, 1H), 8.53 (d, 1H), 7.42 (d, 1H), 7.30 (m, 5H), 7.20 (t, 1H), 7.14 (t, 1H), 6.80 (d, 1H), 6.65 (m, 3H), 5.90 (d, 0.2H), 5.70 (d, 0.7H), 4.75 (m, 3H), 4.64 (m, 3H), 4.43 (dd, 1H), 4.30 (s, 1H), 4.20 (d, 1H), 3.70 (s, 1H), 3.45 (m, 4H), 3.20 (m, 2H), 2.80 (m, 2H), 2.60 (m, 2H), 2.40 (d, 1H), 1.68 (s, 3H), 1.58 (s, 3H), 1.55 (s, 3H), 1.53 (s, 3H), 1.24 (s, 3H); HPLC-MS (ES) 774.2 (M+1).

Step D (αR,γS,2S)-2-[[[1,1-bis(fluoromethyl)ethyl]amino]
carbonyl]-N-((3S,4S)-3,4-dihydro-3-hydroxy-2H-1-
benzopyran-4-yl)-4-(1-furo[3,2-c]pyridin-2-yl-1-
methylethyl)-γ-hydroxy-α-(phenylmethyl)-1-
piperazinepentanamide The title compound was obtained following the procedure described in Example 1, Step R, starting with the intermediate prepared in Example 4, Step C (82.4 mg, 107 μmol). Purification by preparative TLC (5% methanol in ethyl acetate) afforded the title compound as a white solid. $^1$H NMR (CDCl$_3$, 400 MHz) 8.91 (s, 2H), 8.52 (d, J=5.6 Hz, 1H), 7.42 (d, J=5.6 Hz, 1H), 7.24 (m, 5H), 7.11 (t, j=7.2 Hz, 1H), 7.06 (d, J=7.6 Hz, 1H), 6.77 (m, 1H), 6.67 (s, 1H), 5.93 (d, J=8.4 Hz, 1H), 5.14 (dd, J=7.2 Hz, 1H), 4.75 (quint, J=9.2 Hz, 2H), 4.63 (quint, J=10.8 Hz, 2H), 4.06 (d, J=11.6 Hz, 1H), 3.97 (dd, J=11.6 Hz, 1H), 3.81 (s, 1H), 3.75 (m, 1H), 3.24 (s, 1H), 3.12 (d, J=12.4 Hz, 1H), 2.89 (m, 6H), 2.67 (m, 2H), 2.42 (m, 1H), 1.90 (t, J=11.2 Hz, 1H), 1.59 (s, 3H), 1.57 (s, 3H); HPLC-MS (ES) 734.2 (M+1).

EXAMPLE 5

(αR,γS,2S)-N-((3S,4S)-3,4-dihydro-3-hydroxy-2H-1-benzopyran-4-yl)-4-(1-furo[3,2-c]pyridin-2-yl-1-methylethyl)-γ-hydroxy-α-(phenylmethyl)-2-[[(3,3,3-trifluoropropyl)amino]carbonyl]-1-piperazinepentanamide

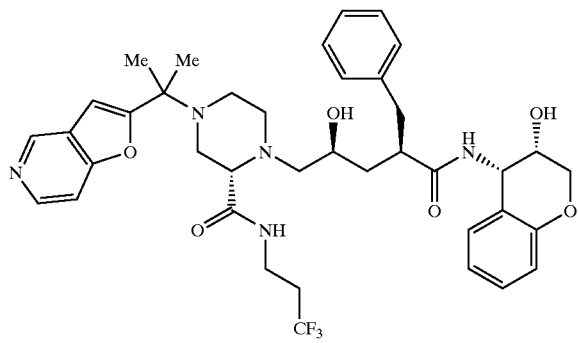

Step A

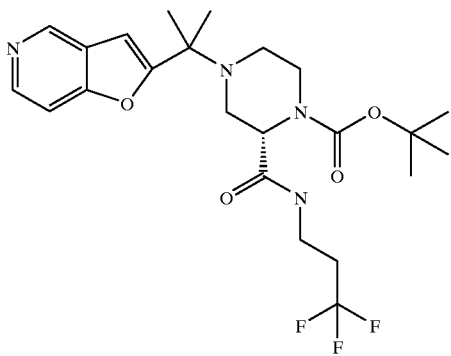

The title compound was obtained following the procedure described in Example 1, Step G, starting with the intermediate prepared in Example 1, Step F (400 mg, 0.556 mmol), and 3,3,3-trifluoropropylamine hydrochloride (109 mg, 0.729 mmol). Purification by flash chromatography (25% hexane in ethyl acetate) afforded the title compound as a colorless oil. $^1$H NMR (CDCl$_3$, 400 MHz) 8.85 (s, 1H), 8.46 (d, 1H), 7.37 (d, 1H), 6.60 (s, 1H), 4.59 (s, 1H), 3.99 (s, 1H), 3.59 (m, 3H), 2.90 (m, 2H, 2.41 (m, 2H), 2.22 (dd, 1H), 2.17 (m, 1H), 1.53 (s, 3H), 1.51 (s, 3H), 1.44 (s, 9H); HPLC-MS (ES) 485.2 (M+1).

Step B

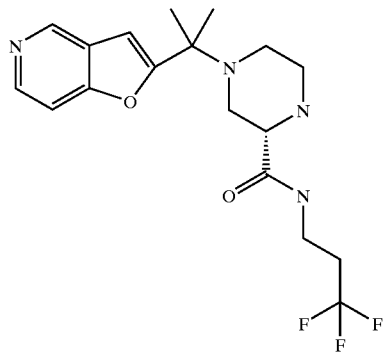

The title compound was obtained following the procedure described in Example 2, Step B, starting with the intermediate prepared in Example 5, Step A (266 mg, 0.550 mmol), affording the title compound as a colorless oil. This was used without further purification.

Step C

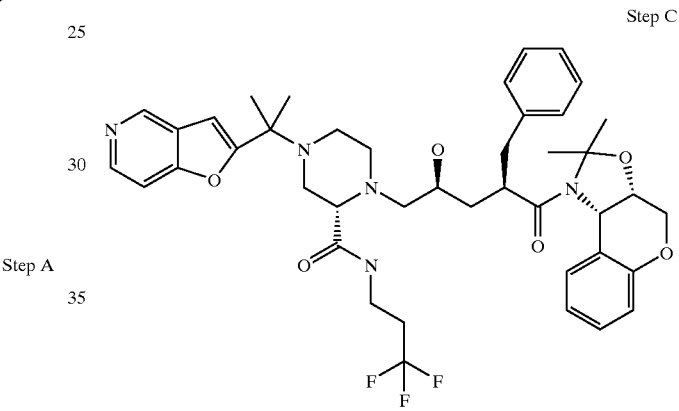

The title compound was obtained following the procedure described in Example 1, Step Q, starting with the intermediate prepared in Example 5, Step B (102 mg, 0.266 mmol) and the intermediate prepared in Example 1, Step P (106 mg, 0.271 mmol). Purification by flash chromatography afforded the title compound. HPLC-MS (ES) 778.3 (M+1).

Step D (αR,γS,2S)-N-((3S,4S)-3,4-dihydro-3-hydroxy-2H-1-benzopyran-4-yl)-4-(1-furo[3,2-c]pyridin-2-yl-1-methylethyl)-γ-hydroxy-α-(phenylmethyl)-2-[[(3,3,3-trifluoropropyl)amino]carbonyl]-1-piperazinepentanamide The title compound was obtained following the procedure described in Example 1, Step R, starting with the intermediate prepared in Example 5, Step C. Purification by flash chromatography (5% methanol in ethyl acetate) afforded the title compound as a white solid. $^1$H NMR (CDCl$_3$, 500 MHz) 8.99 (s, 1H), 8.88 (s, 1H), 8.50 (d, J=5.5 Hz, 1H), 7.37 (d, J=5.7 Hz, 1H), 7.28 (m, 2H), 7.21 (m, 2H), 7.08 (t, J=8.0 Hz, 2H), 6.78 (d, J=8.2 Hz, 2H), 6.65 (s, 1H), 6.15 (d, J=8.0 Hz, 1H), 5.16 (dd, J=3.9 Hz, J=7.8 Hz, 1H), 3.99 (m, 2H), 3.78 (m, 3H), 3.40 (m, 1H), 3.27 (t, J=2.9 Hz, 1H), 2.95 (t, J=10.3 Hz, 2H), 2.82 (m, 3H), 2.66 (m, 3H), 2.46 (m, 3H), 1.87 (t, J=11.0 Hz, 1H), 1.56 (s, 3H), 1.53 (s, 3H); HPLC-MS (ES) 738.3 (M+1).

EXAMPLE 6

(αR,γS,2S)-N-((3S,4S)-3,4-dihydro-3-hydroxy-2H-1-benzopyran-4-yl)-4-(1-furo[3,2-c]pyridin-2-yl-1-methylethyl)-γ-hydroxy-2-[[(2,2,3,3,3-pentafluoropropyl)amino]carbonyl]-α-(phenylmethyl)-1-piperazinepentanamide

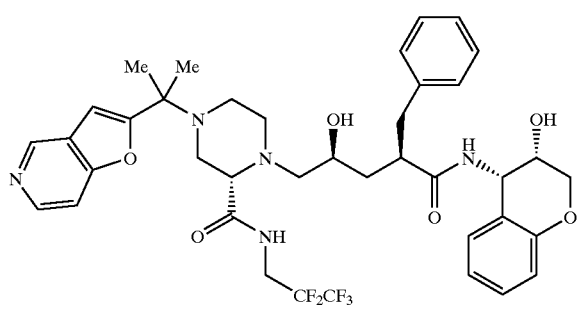

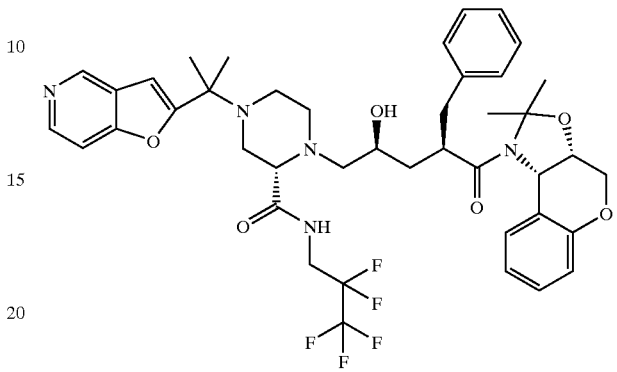

Step A

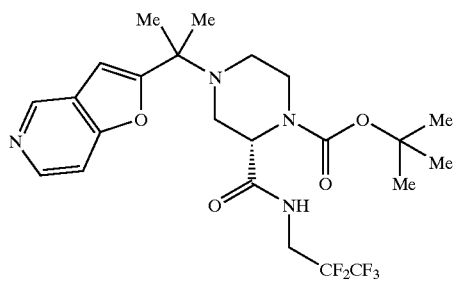

The title compound was obtained following the procedure described in Example 1, Step G, starting with the intermediate prepared in Example 1, Step F (400 mg, 0.556 mmol), and 2,2,3,3,3-pentafluoropropylamine (109 mg, 0.731 mmol). Purification by flash chromatography (25% hexane in ethyl acetate) afforded the title compound as a colorless oil. HPLC-MS (ES) 521.2 (M+1).

Step B

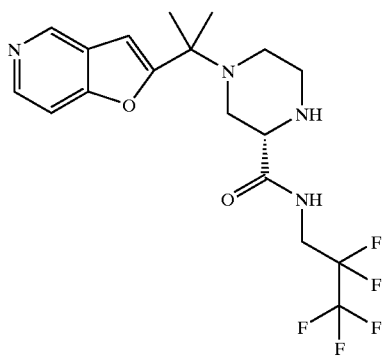

The title compound was obtained following the procedure described in Example 2, Step B, starting with the interme-diate prepared in Example 6, Step A (275 mg, 0.533 mmol), affording the title compound as a colorless oil. This was used without further purification. HPLC-MS (ES) 421.1 (M+1).

Step C

The title compound was obtained following the procedure described in Example 1, Step Q, starting with the intermediate prepared in Example 6, Step B (94.6 mg, 0.225 mmol) and the intermediate prepared in Example 1, Step P (91.0 mg, 0.231 mmol). Purification by flash chromatography (3% methanol in ethyl acetate) afforded the title compound. HPLC-MS (ES) 814.3 (M+1).

Step D (αR,γS,2S)-N-((3S,4S)-3,4-dihydro-3-hydroxy-2H-1-benzopyran-4-yl)-4-(1-furo[3,2-c]pyridin-2-yl-1-methylethyl)-γ-hydroxy-2-[[(2,2,3,3,3-pentafluoropropyl)amino]carbonyl]-α-(phenylmethyl)-1-piperazinepentanamide The title compound was obtained following the procedure described in Example 1, Step R, starting with the intermediate prepared in Example 6, Step C (37.9 mg, 46.6 μmol). Purification by flash chromatography (5% methanol in ethyl acetate) afforded 19.4 mg (54%) of the title compound as a white solid. $^1$H NMR (CDCl$_3$, 500 MHz) 9.28 (s, 1H), 8.94 (s, 1H), 8.53 (s, 1H), 7.41 (d, J=5.3 Hz, 1H), 7.28 (m, 2H), 7.23 (m, 2H), 7.10 (t, J=7.3 Hz, 1H), 7.06 (d, J=7.8 Hz, 1H), 6.78 (d, J=7.5 Hz, 2H), 6.71 (s, 1H), 6.10 (d, J=8.2 Hz, 1H), 5.15 (t, J=3.7 Hz, 1H), 4.38 (m, 1H), 4.04 (m, 2H), 3.80 (m, 3H), 3.42 (s, 1H), 3.07 (d, J=11.2 Hz, 1H), 2.79 (m, 13H), 2.46 (t, J=13.5 Hz, 2H), 1.91 (t, J=11.6 Hz, 1H), 1.58 (s, 3H), 1.57 (s, 3H); HPLC-MS (ES) 774.3 (M+1).

EXAMPLE 7

(αR,γS,2S)-N-((3S,4S)-3,4-dihydro-3-hydroxy-2H-1-benzopyran-4-yl)-2-[[(2-fluoro-1,1-dimethylethyl)amino]carbonyl]-4-(1-furo[3,2-c]pyridin-2-yl-1-methylethyl)-γ-hydroxy-α-(phenylmethyl)-1-piperazinepentanamide

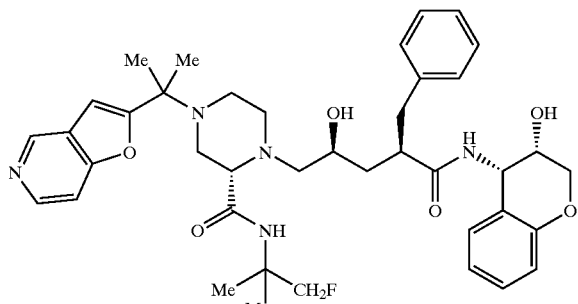

Step A

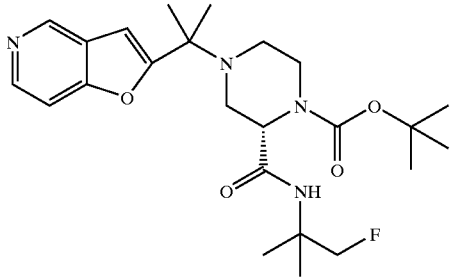

The title compound was obtained following the procedure described in Example 1, Step G, starting with the intermediate prepared in Example 1, Step F (400 mg, 0.556 mmol) and 1,1-dimethyl-2-fluoroethylamine hydrochloride (prepared as described in Ok, D.; Fisher, M. H.; Wyvratt, M. J.; Meinke, P. T.; *Tetrahedron Lett* 1999, 40, 3831–3834) (93.3 mg, 0.731 mmol). Purification by flash chromatography (25% hexane in ethyl acetate) afforded the title compound as a colorless oil. HPLC-MS (ES) 463.3 (M+1).

Step B

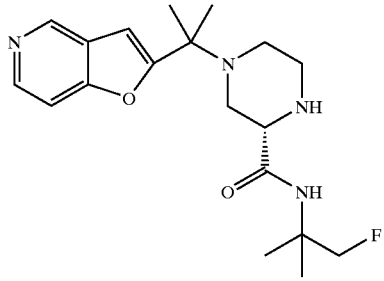

The title compound was obtained following the procedure described in Example 2, Step B, starting with the intermediate prepared in Example 7, Step A (245 mg, 0.530 mmol), affording the title compound as a clear oil. This was used without further purification. HPLC-MS (ES) 363.2 (M+1).

Step C

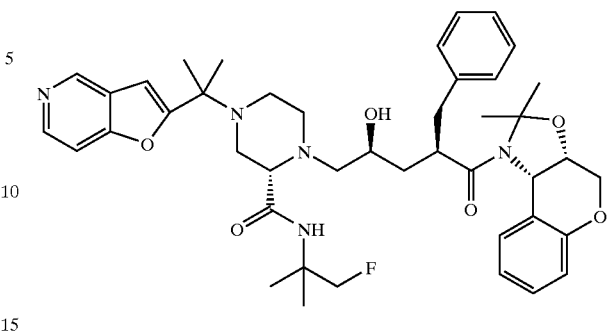

The title compound was obtained following the procedure described in Example 1, Step Q, starting with the intermediate prepared in Example 7, Step B (15.0 mg, 0.041 mmol) and the intermediate prepared in Example 1, Step P (24.3 mg, 0.062 mmol). Purification by preparative TLC (4% methanol in ethyl acetate) afforded the title compound as a white solid. HPLC-MS (ES) 756.4 (M+1).

Step D (αR,γS,2S)-N-((3S,4S)-3,4-dihydro-3-hydroxy-2H-1-benzopyran-4-yl)-2-[[(2-fluoro-1,1-dimethylethyl)amino]carbonyl]-4-(1-furo[3,2-c]pyridin-2-yl-1-methylethyl)-γ-hydroxy-α-(phenylmethyl)-1-piperazinepentanamide The title compound was obtained following the procedure described in Example 1, Step R, starting with the intermediate prepared in Example 7, Step C (17.0 mg, 0.022 mmol). Purification by preparative TLC (chromatotron, 5–10% methanol in ethyl acetate) afforded the title compound as a white solid. $^1$H NMR (CDCl$_3$, 500 MHz) 8.89 (s, 1H), 8.63 (s, 1H), 8.49 (d, J=5.7 Hz), 7.39 (d, J=5.7 Hz, 1H), 7.29 (m, 2H), 7.23 m (m, 2H), 7.07 (m, 2H), 6.78 (m, 2H), 6.66 (s, 1H), 6.07 (d, J=8.0 Hz, 1H), 5.18 (m, 1H), 4.64 (d, 1H), 4.54 (d, J=3.4 Hz, 1H), 4.45 (d, 1H), 4.04 (d, 1H), 3.99 (dd, J=5.0 Hz,1H), 3.82 (m, 1H), 3.75 (t, 1H), 3.21 (s, 1H, 3.08 (d, 1H), 2.95 (m, 2H), 2.80 m, 2H), 2.66 (m, 2H), 2.46 (m, 2H), 1.88 (t, 1H), 1.58 (s, 3H), 1.56 (s, 3H), 1.48 (s, 3H), 1.47 (s, 3H), 1.40 (t, 1H); HPLC-MS (ES) 716.3 (M+1).

EXAMPLE 8

(αR,γS,2S)-N-((1S,2R)-1,2-dihydro-2-hydroxy-1H-inden-1-yl)-4-(1-furo[3,2-c]pyridin-2-yl-1-methylethyl)-γ-hydroxy-α-(phenylmethyl)-2-[[(2,2,2-trifluoroethyl)amino]carbonyl]-1-piperazinepentanamide

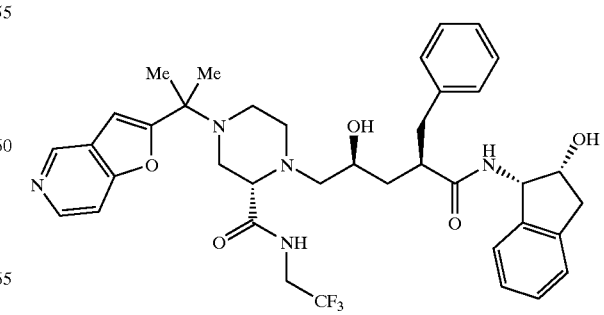

99

-continued

Step A

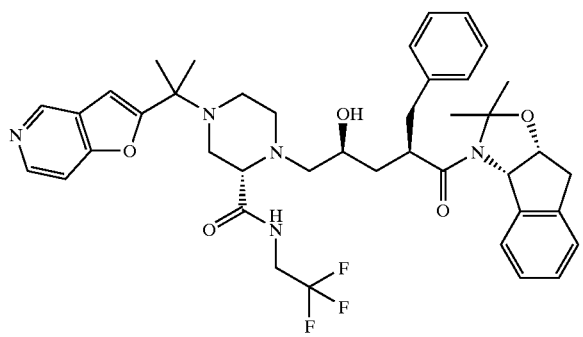

The title compound was obtained following the procedure described in Example 1, Step Q, starting with the intermediate prepared in Example 1, Step H (99.1 mg, 0.268 mmol) and the corresponding aminoindanyl epoxide (prepared as described in Maligres, P. E.; Weissman, S. A.; Upadhyaya, V.; Cianciosi, S. J.; Reamer, R. A.; Purick, R. M.; Sager, J.; Rossen, K.; Eng, K. K.; Askin, D.; Volante, R P.; Reider, P. J.; *Tetrahedron,* 1996, 52, 3327–3338) (50.0 mg, 0.132 mmol). Purification by flash chromatography (5% methanol in ethyl acetate) afforded the title compound as a clear oil. $^1$H NMR (CDCl$_3$, 400 MHz) 9.37 (t, 1H), 8.86 (s, 1H), 8.52 (d, 1H), 7.40 (d, 1H), 7.32 (m, 5H), 7.20 (m, 2H), 6.95 (t, 1H), 6.63 (s, 1H), 6.40 (d, 1H), 5.93 (d, 1H), 4.78 (s, 1H), 4.25 (m, 1H), 3.75 (m, 2H), 3.40 (m, 3H), 3.04 (s, 3H), 2.80 (m, 2H), 2.64 (m, 3H), 2.45 (m, 1H), 2.38 (m, 1H), 1.80 (m, 1H), 1.62 (s, 3H), 1.58 (s, 6H), 1.37 (s, 3H).

Step B (αR,γS,2S)-N-((1S,2R)-1,2-dihydro-2-hydroxy-1H-inden-1-yl)-4-(1-furo[3,2-c]pyridin-2-yl-1-methylethyl)-γ-hydroxy-α-(phenylmethyl)-2-[[(2,2,2-trifluoroethyl)amino]carbonyl]-1-piperazinepentanamide The title compound was obtained following the procedure described in Example 1, Step R, starting with the intermediate prepared in Example 8, Step A (50.5 mg, 67.6 μmol). Purification by flash chromatography (5% methanol in ethyl acetate) afforded the title compound as a white solid. $^1$H NMR (CDCl$_3$, 400 MHz) 9.34 (t, J=6.4 Hz, 1H), 8.87 (s, 1H), 8.48 (d, J=6.0 Hz, 1H), 7.36 (d, J=5.6 Hz, 1H), 7.30 (m, 2H), 7.23 (m, 2H), 7.16 (d, J=3.2 Hz, 1H), 7.07 (d, J=5.2 Hz, 1H), 6.65 (s, 1H), 6.13 (d, J=8.8 Hz, 1H), 5.27 (dd, J=4.4 Hz, J=8.4 Hz, 1H), 4.27 (m, 2H), 3.75 (m, 3H), 3.34 (s, 1H), 3.03 (m, 2H), 2.99 (m, 2H), 2.88 (m, 2H), 2.80 (m, 3H), 2.60 (m, 2H), 1.93 (t, J=11.2 Hz, 1H), 1.54 (s, 7H); HPLC-MS (ES) 708.4 (M+1).

100

EXAMPLE 9

(αR,γS,2S)-N-((1S,2R)-1,2-dihydro-2-hydroxy-1H-inden-1-yl)-2-[[(2-fluoroethyl)amino]carbonyl]-4-[1-furo[3,2-c]pyridin-2-yl-1-methylethyl)-γ-hydroxy-α-(phenylmethyl)-1-piperazinepentanamide

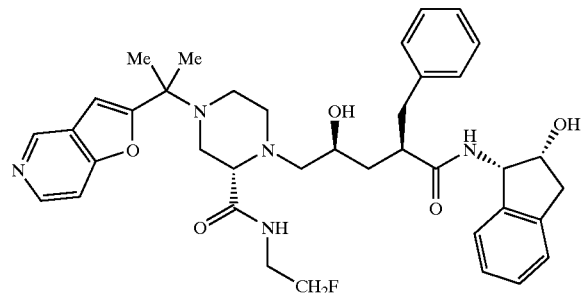

Step A

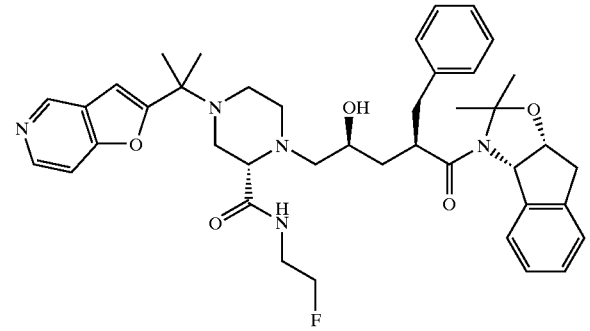

The title compound was obtained following the procedure described in Example 1, Step Q, starting with the intermediate prepared in Example 2, Step B (69.8 mg, 0.209 mmol) and the epoxide intermediate employed in Example 8, Step A (78.8 mg, 0.209 mmol). Purification by flash chromatography (2.5% methanol, 5% triethylamine in ethyl acetate) afforded the title compound as a colorless oil. $^1$H NMR (CDCl$_3$, 400 MHz) 9.0 (s, 1H), 8.86 (s, 1H), 8.50 (d, 1H), 7.42 (s, 1H), 7.30 (m, 5H), 7.20 (m, 2H), 6.95 (t, 1H), 6.62 (s, 1H), 6.40 (d, 1H), 5.93 (d, 1H), 4.78 (s, 1H), 4.68 (m, 1H), 4.50 (m, 1H), 3.80 (m, 2H), 3.60 (s, 1H), 3.43 (m, 2H), 3.30 (s, 1H), 3.05 (s, 2H), 2.80 (m, 1H), 2.62 (m, 3H), 2.40 (m, 2H), 1.76 (m, 1H), 1.64 (s, 3H), 1.57 (s, 7H), 1.32 (s, 3H); HPLC-MS (ES) 712.3 (M+1).

Step B (αR,γS,2S)-N-((1S,2R)-1,2-dihydro-2-hydroxy-1H-inden-1-yl)-2-[[(2-fluoroethyl)amino]carbonyl]-4-[1-furo[3,2-c]pyridin-2-yl-1-methylethyl)-γ-hydroxy-α-(phenylmethyl)-1-piperazinepentanamide The title compound was obtained following the procedure described in Example 1, Step R, starting with the intermediate prepared in Example 9, Step A (54.1 mg, 76.1 μmol). Purification by preparative TLC (10% methanol in ethyl acetate) afforded the title compound as a white solid. $^1$H NMR (CDCl$_3$, 400 MHz) 9.00 (s, 1H), 8.89 (s, 1H), 8.50 (d, J=5.6 Hz, 1H), 7.42 (d, J=5.6 Hz, 1H), 7.30 (m, 5H), 7.18 (s, 1H), 7.09 (s, 1H), 6.66 (s, 1H), 5.95 (d, J=8.4 Hz, 1H) 5.28 (dd, J=4.8 Hz, J=8.8 Hz, 1H), 4.66 (m, 1H), 4.54 (m, 1H), 4.28 (t, 1H), 3.80 (m, 2H), 3.71 (m, 1H), 3.61 (m, 1H), 3.56 (m, 1H), 3.36 (s, 1H, 3.04 (m, 2H), 2.84 (m, 4H), 2.71 (m, 2H), 2.48 (d, J=10.0 Hz, 1H) 1.94 (t, J=11.2 Hz, 1H), 1.57 (s, 8H); HPLC-MS (ES) 672.3 (M+1).

EXAMPLE 10

(αR,γS,2S)-N-((1S,2R)-1,2-dihydro-2-hydroxy-1H-inden-1-yl)-4-(1-furo[3,2-c]pyridin-2-yl-1-methylethyl)-γ-hydroxy-α-(phenylmethyl)-2-[[(3,3,3-trifluoropropyl)amino]carbonyl]-1-piperazinepentanamide

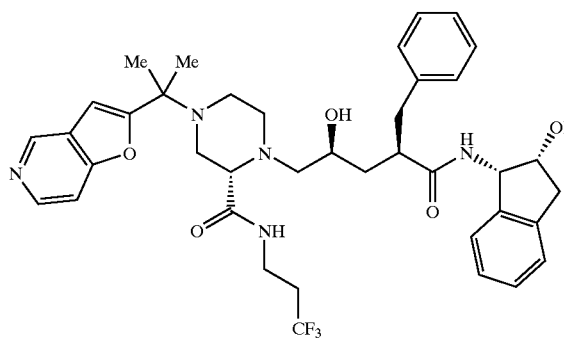

Step A

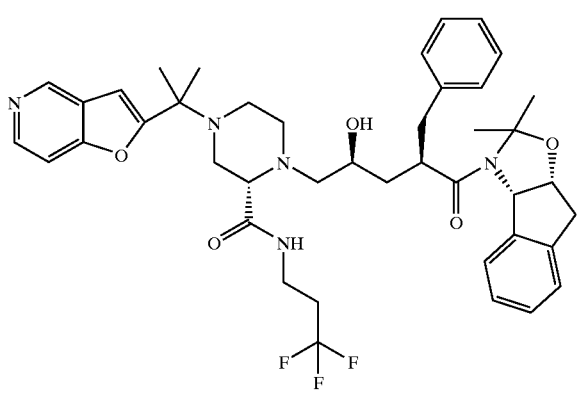

The title compound was obtained following the procedure described in Example 1, Step Q, starting with the intermediate prepared in Example 5, Step B (93.8 mg, 0.244 mmol) and the epoxide employed in Example 8, Step A (92.2 mg, 0.244 mmol). Purification by flash chromatography afforded the title compound. HPLC-MS (ES) 762.3 (M+1).

Step B (αR,γS,2S)-N-((1S,2R)-1,2-dihydro-2-hydroxy-1H-inden-1-yl)-4-(1-furo[3,2-c]pyridin-2-yl-1-methylethyl)-γ-hydroxy-α-(phenylmethyl)-2-[[(3,3,3-trifluoropropyl)amino]carbonyl]-1-piperazinepentanamide The title compound was obtained following the procedure described in Example 1, Step R, starting with the. intermediate prepared in Example 10, Step A. Purification by flash chromatography (5% methanol in ethyl acetate) afforded the title compound as a white solid. $^1$H NMR (CDCl$_3$, 500 MHz) 8.95 (s, 1H), 8.88 (s, 1H), 8.49 (d, J=5.7 Hz, 1H), 7.37 (d, J=5.7 Hz, 1H), 7.30 (m, 4H), 7.17 (d, J=2.3 Hz, 1H), 7.09 (d, J=2.6 Hz, 1H), 6.64 (s, 1H), 6.10 (d, J=8.5 Hz, 1H), 5.27 (dd, J=4.8 Hz, J=8.5 Hz, 1H), 4.28 (t, J=4.8 Hz, 1H), 3.76 (m, 2H), 3.41 (m, 1H), 3.28 (t, J=2.9 Hz, 1H), 3.04 (dd, J=5.3 Hz, J=16.7 Hz, 1H), 2.89 (m, 3H), 2.79 (m, 3H), 2.67 (m, 3H), 2.46 (m, 3H), 1.93 (t, 2H), 1.55 (s, 3H), 1.53 (s, 3H); HPLC-MS (ES) 722.2 (M+1).

EXAMPLE 11

(αR,γS,2S)-N-((1S,2R)-1,2-dihydro-2-hydroxy-1H-inden-1-yl)-4-(1-furo[3,2-c]pyridin-2-yl-1-methylethyl)-γ-hydroxy-2-[[(2,2,3,3,3-pentafluoropropyl)amino]carbonyl]-α-(phenylmethyl)-1-piperazinepentanamide

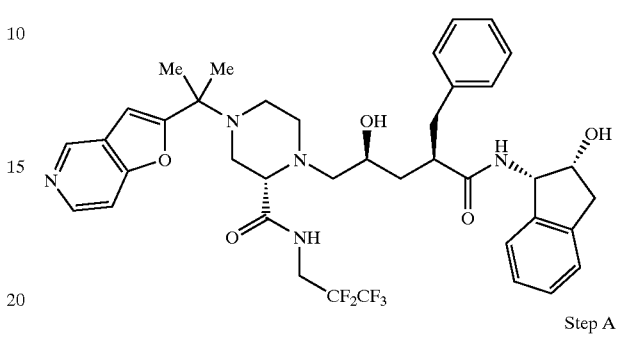

Step A

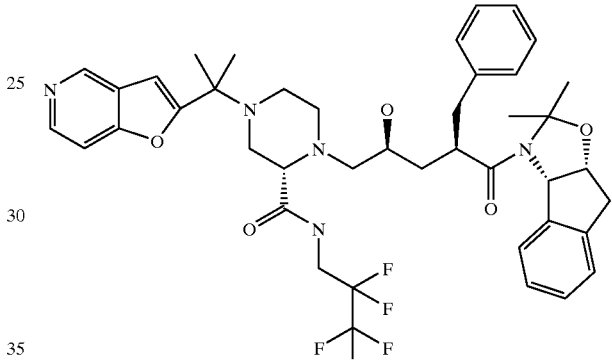

The title compound was obtained following the procedure described in Example 1, Step Q, starting with the intermediate prepared in Example 6, Step B (104 mg, 0.248 mmol) and the epoxide intermediate used in Example 8, Step A (94.0 mg, 0.249 mmol). Purification by flash chromatography (3% methanol in ethyl acetate) afforded the title compound as a white solid. HPLC-MS (ES) 798.4 (M+1).

Step B (αR,γS,2S)-N-((1S,2R)-1,2-dihydro-2-hydroxy-1H-inden-1-yl)-4-(1-furo[3,2-c]pyridin-2-yl-1-methylethyl)-γ-hydroxy-2-[[(2,2,3,3,3-pentafluoropropyl)amino]carbonyl]-α-(phenylmethyl)-1-piperazinepentanamide The title compound was obtained following the procedure described in Example 1, Step R, starting with the intermediate prepared in Example 11, Step A (42.8 mg, 0.0537 mmol). Purification by flash chromatography (3% methanol in ethyl acetate) afforded the title compound as a white solid. $^1$H NMR (CDCl$_3$, 500 MHz) 9.30 (s, 1H), 8.90 (s, 1H), 8.51 (d, J=4.5 Hz, 1H), 7.37 (d, J=5.0 Hz, 1H), 7.27 (m, 2H), 7.23 (m, 3H), 7.23 (s, 2H), 7.17 (s, 2H), 6.67 (s, 1H), 6.08 (d, J=8.2 Hz, 1H), 5.27 (m, 1H), 4.35 (m, 1H), 4.27 (s, 1H), 3.79 (m, 2H), 3.39 (s, 1H), 3.05 (m, 2H), 2.91 (m, 2H), 2.71 (m, 3H), 2.69 (m, 3H), 2.49 (m, 2H), 1.933 (t, 1H). HPLC-MS (ES) 758.4 (M+1).

EXAMPLE 12

(αR,γS,2S)-4-(2-benzofuranylmethyl)-N-((3S,4S)-3,
4-dihydro-3-hydroxy-2H-1-benzopyran-4-yl)-γ-
hydroxy-α-(phenylmethyl)-2-[[(2,2,2-trifluoroethyl)
amino]carbonyl]-1-piperazinepentanamide

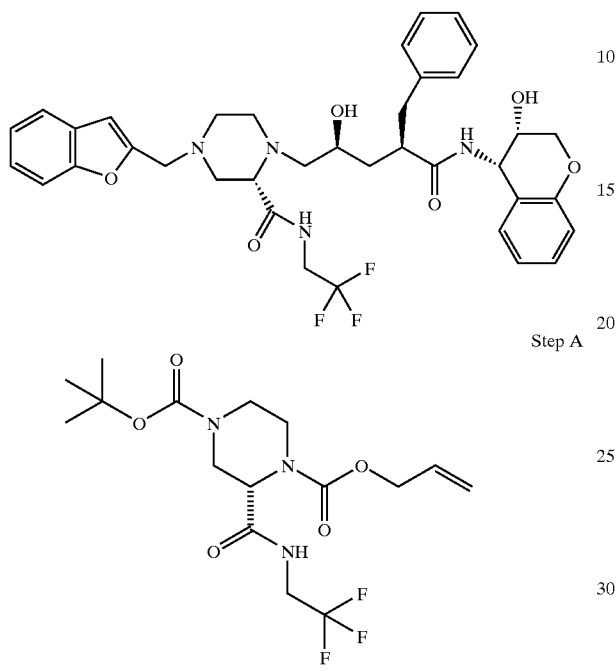

Step A

To a solution of 1,4-piperazine-2-(S)-carboxylic acid [bis (+)-CSA salt (30.0 g, 50.0 mmol) in 600 mL THF was added 1N aqueous NaOH until the resulting solution was pH 9 (150 mL). The solution was cooled to 0° C., and BOC-ON (12.3 g, 50.0) was added. The resulting solution was warmed to ambient temperature over 5 hours, then cooled again to 0° C. Allyl chloroformate (5.31 mL, 50.0 mmol) was added via syringe, followed by an additional 60 mL of 1N aqueous NaOH. The solution was warmed to ambient temperature overnight, then concentrated to minimum volume by rotary evaporator. The resulting mixture was acidified to pH 1 with 1N aqueous HCl, and extracted with ethyl acetate (400 mL×2). The organic layers were washed with brine (200 mL) dried (MgSO$_4$) and concentrated in vacuo, affording 23.7 g of a yellow oil. This material was dissolved in 750 mL of dichloromethane, followed by the addition of triethylamine (35.0 mL, 250 mmol), trifluoroethylamine (9.95 mL, 125 mmol), HOAT (10.2 g, 75.0 mmol), and EDC (14.4 g, 75.0 mmol). After 22 hours at ambient temperature the reaction mixture was quenched by the addition of saturated aqueous NaHCO$_3$ (500 mL). The organic layer was washed with an additional 500 mL of saturated aqueous NaHCO$_3$, then 1N aqueous NaHSO$_4$ (500 mL), and additional saturated aqueous NaHCO$_3$ (500 mL). The organic layer was dried (Na$_2$SO$_4$) and concentrated in vacuo. Purification by flash chromatography (40% ethyl acetate in hexane) afforded the title compound as a white solid. $^1$H NMR (CDCl$_3$, 400 MHz) 5.95 (m, 1H), 5.35 (d, 1H), 5.28 (d, 1H), 4.75 (s, 1H), 4.68 (d, 1H), 4.53 (d, 1H), 3.90 (m, 3H), 3.20 (dd, 1H), 3.00 (m, 1H), 1.45 (s, 9H).

Step B

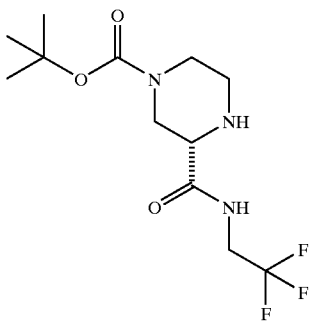

To a solution of tris (dibenzylidineacetone)dipalladium(0) (1.42 g, 1.55 mmol) in 150 mL of THF was added 1,4-bis (diphenylphosphino)butane (1.78 g, 3.10 mmol). After stirring 20 min at ambient temperature, this solution was added via cannula to a solution of the intermediate prepared in Step A (12.3 g, 31.0 mmol) and thiosalicilic acid (7.18 g, 46.6 mmol) in 150 mL of THF. After 1 hour at ambient temperature the reaction was diluted with 1 L of diethyl ether and extracted with 1% aqueous HCl (250 mL×3). The combined aqueous layers were neutralized with excess saturated NaHCO$_3$, and the resulting suspension was extracted with ethyl acetate (500 mL×2). These organic layers were washed with brine (200 mL), dried (MgSO$_4$), and concentrated in vacuo, affording the title compound as a clear oil. $^1$H NMR (CDCl$_3$, 400 MHz) 7.28 (s, 1H), 4.00 (dd, 1H), 3.97 (m, 2H), 4.70 (s, 1H), 3.40 (dd, 1H), 3.20 (dd, 1H), 3.05 (s, 1H), 2.93 (d, 1H), 2.81 (t, 1H), 1.80 (s, 1H), 1.43 (s, 9H).

Step C

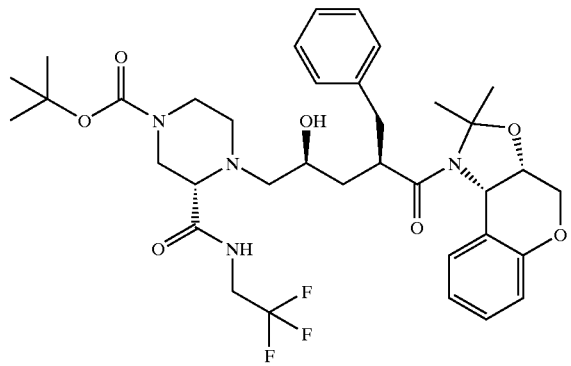

The title compound was obtained following the procedure described in Example 1, Step Q, starting with the intermediate prepared in Example 12, Step B (1.82 g, 5.86 mmol) and the intermediate prepared in example 1, Step P (2.53 g, 6.45 mmol). Purification by flash chromatography (65% ethyl acetate in hexane) afforded the title compound as a colorless oil. $^1$H NMR (CDCl$_3$, 400 MHz) 7.25 (m, 5H), 7.20 (t, 1H), 7.18 (t, 1H), 7.15 (t, 1H), 7.03 (t, 1H), 6.83 (m, 1H), 6.60 (m, 2H), 5.89 (d, 1H), 5.50 (s, 1H), 4.45 (dd, 1H), 3.97 (dd, 1H), 4.23 (d, 1H), 4.00 (m, 1H), 3.82 (m, 2H), 3.68 (m, 1H), 3.45 (m, 3H), 3.32 (m, 3H), 2.87 (m, 1H), 2.67 (d, 1H), 2.50 (m, 2H), 1.82 (t, 1H), 1.76 (s, 3H), 1.74 (s, 3H), 1.42 (s, 9H), 1.24 (s, 6H); HPLC-MS (ES) 705.3 (M+1).

Step D

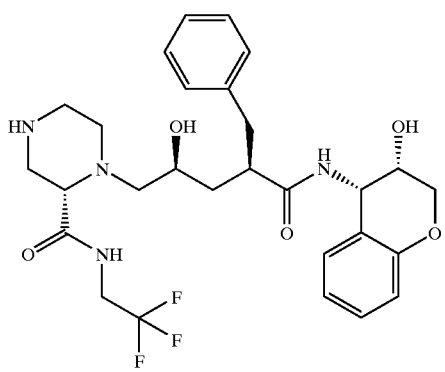

To a solution of the intermediate prepared in Step C (2.43 g, 3.45 mmol) in 2-propanol (20 mL) at 0° C. was added concentrated aqueous HCl (20 mL). After 16 hours at ambient temperature the, reaction was brought to pH 8 with 2N aqueous NaOH. The mixture was then extracted with ethyl acetate (200 mL×2). The organic layers were washed with brine (200 mL), dried (MgSO$_4$), and concentrated in vacuo affording the title compound as a white solid. $^1$H NMR (CDCl$_3$, 400 MHz) 9.05 (t, 1H), 7.28 (m, 5H), 7.13 (t, 1H), 7.10 (d, 1H), 6.80 (m, 2H), 6.20 (d, 1H), 5.20 (dd, 1H), 4.08 (m, 4H), 3.80 (m, 2H), 3.28 (s, 1H), 3.14 (m, 1H0, 2.98 (m, 4H), 2.65 (m, 2H), 2.48 (dd, 1H), 1.91 (t, 1H), 1.58 (t, 1H); HPLC-MS (ES) 565.2 (M+1).

Step E (αR,γS,2S)-4-(2-benzofuranylmethyl)-N-((3S,4S)-3,
4-dihydro-3-hydroxy-2H-1-benzopyran-4-yl)-γ-
hydroxy-α-(phenylmethyl)-2-[[(2,2,2-trifluoroethyl)
amino]carbonyl]-1-piperazinepentanamide To a solution of the intermediate prepared in Step D (86 mg, 0.15 mmol) in 3% acetic acid/DMF (1.5 mL) was added benzofuran-2-carboxaldehyde (26 μL, 0.18 mmol). After 10 min at ambient temperature, sodium triacetoxy borohydride (49 mg, 0.23 mmol) was added. After 4 hours at ambient temperature the reaction was diluted with ethyl acetate (30 mL) and washed with 5% aqueous NaHCO$_3$ (30 mL×4). The organic layer was washed with brine, dried (MgSO$_4$), and concentrated in vacuo. Purification by flash chromatography afforded the title compound as a white solid. $^1$H NMR (CD$_3$OD, 400 MHz) 7.53 (dd, J=0.8 Hz, J=7.6 Hz, 1H), 7.42 (d, J=8.0 Hz, 1H), 7.16 (m, 10H), 6.81 (dt, J=1.2 Hz, J=7.6 Hz, 1H), 6.72 (dd, J=1.2 Hz, J=8.4 Hz, 1H), 6.71 (s, 1H), 5.15 (d. J=4.4 Hz, 1H), 4.06 (m, 2H), 3.97 (m, 1H), 3.74 (m, 6H), 3.11 (dd, J=3.2 Hz, J=7.6 Hz, 1H), 3.00 (m, 4H), 2.75 (m, 4H), 2.62 (dd, J=8.0 Hz, J=11.6 Hz, 1H), 2.53 (t, J=8.4 Hz, 1H), 2.42 (m, 3H), 2.05 (t, J=11.2 Hz, 1H), 1.40 (dt, J=3.6 Hz, J=10.0 Hz, 1H); HPLC-MS (ES) 695.2 (M+1).

EXAMPLE 13

(αR,γS,2S)-N-((3S,4S)-3,4-dihydro-3-hydroxy-2H-
1-benzopyran-4-yl)-γ-hydroxy-α-(phenylmethyl)-4-
[[5-(3-pyridinyl)-1-furanyl]methyl]-2-[[(2,2,2-
trifluoroethyl)amino]carbonyl]-1-
piperazinepentanamide

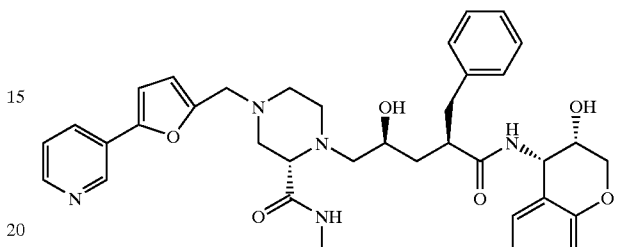

Step A

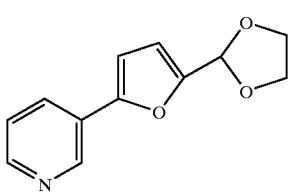

To a solution of 5-bromo-2-furaldehyde (20.0 g, 114 mmol) in 100 mL of benzene was added ethylene glycol (15.9 mL, 285 mmol) and p-toluenesulfonic acid monohydrate (282 mg, 1.48 mmol). The mixture was heated to reflux with azeotropic removal of water for 18 hours, then cooled to ambient temperature and concentrated in vacuo. The residue was dissolved in diethyl ether (1.5 L) and washed with saturated aqueous NaHCO$_3$ (150 mL), and brine (150 mL). The organic layer was dried (MgSO$_4$) and concentrated in vacuo affording an orange oil. This material was dissolved in THF (300 mL) and cooled to −78° C. To this solution was added sec-butyllithium (100 mL of a 1.3M solution in cyclohexane, 130 mmol) via cannula. After 1 hour at −78° C., a solution of trimethyltin chloride (12.6 g, 63 mmol, as a solution in 50 mL of THF) was added via cannula. After an additional 30 min at 78° C., the mixture was warmed to ambient temperature. After 2 hours the reaction was quenched by the addition of 100 mL of acetone, followed by 400 mL of water. The mixture was diluted with diethyl ether (500 mL). The organic layer was washed with saturated aqueous NaHCO$_3$ (150 mL×2), and brine, dried (MgSO$_4$), and concentrated in vacuo, affording an orange oil. This material was dissolved in DMF (320 mL), and 3-bromopyridine (5.5 mL, 57 mmol) was added, followed by tetrakis(triphenylphosphine)palladium(0) (2.0 g, 1.73 mmol). The solution was heated to 100° C. for 1 hour, then cooled to ambient temperature. The solution was poured onto diethyl ether (1 L) and washed with 5% aqueous NaHCO$_3$ (150 mL×3), and brine (150 mL). The organic-layer was dried (MgSO$_4$) and concentrated in vacuo. Purification by flash chromatography (50% ethyl acetate in hexane) afforded the title compound as an orange oil. $^1$H NMR (CDCl$_3$, 400 MHz) 8.87 (s, 1H), 8.44 (d, 1H), 7.89 (d, 1H), 7.24 (m, 1H), 6.65 (d, 1H), 6.49 (d, 1H), 5.94 (s, 1H), 4.11 (m, 2H), 3.98 (m, 2H).

Step B

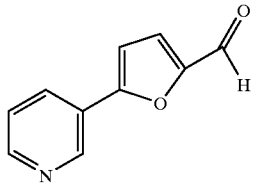

To a solution of the intermediate prepared in Step A (1.00 g, 4.60 mmol) in THF (100 mL) at 0° C. was added 1 N aqueous HCl (16.1 mL, 16.1 mmol). After warming to ambient temperature over 2 hours, the reaction was quenched by the addition of 1N NH$_4$OH until the reaction was pH 8. The reaction was diluted with 200 mL of ethyl acetate and washed with saturated aqueous NaHCO$_3$ (150 mL) brine (150 mL), dried (MgSO$_4$), and concentrated in vacuo, affording the title compound as a white solid. $^1$H NMR (CDCl$_3$, 400 MHz) 9.72 (s, 1H), 9.07 (s, 1H), 8.64 (d, 1H), 8.13 (d, 1H), 7.43 (m, 1H), 7.37 (d, 1H), 6.97 (d, 1H).

Step C (αR,γS,2S)-N-((3S,4S)-3,4-dihydro-3-hydroxy-2H-1-benzopyran-4-yl)-γ-hydroxy-α-(phenylmethyl)-4-[[5-(3-pyridinyl)-1-furanyl]methyl]-2-[[(2,2,2-trifluoroethyl)amino]carbonyl]-1-piperazinepentanamide The title compound was obtained following the procedure described in Example 12, Step E, starting with the intermediate prepared in Step B (307 mg, 1.77 mmol), and using the intermediate prepared in Example 12, Step D (500 mg, 0.886 mmol). Purification by recrystallization (dichloromethane/ethyl acetate) afforded the title compound as a white solid. $^1$H NMR (CDCl$_3$, 500 MHz) 9.04 (s, 1H), 8.90 (d, J=1.8 Hz, 1H), 8.52 (d, J=3.4 Hz, 1H), 7.90 (d, J=8.1 Hz, 1H), 7.29 (m, 7H), 7.12 (m, 1H), 7.09 (d, J=7.6 Hz, 1H), 6.81 (t, J=7.8 Hz, 2H), 6.72 (d, J=3.4 Hz, 1H), 6.37 (d, J=3.2 Hz, 1H), 6.02 (d, J=8.0 Hz, 1H), 5.19 (m, 1H), 4.14 (q, J=7.1 Hz, 2H), 4.06 (m, 2H), 3.82m, 2H), 3.72 (d, J=13.9 Hz, 1H), 3.62 (d, J=14.2 Hz, 1H), 3.51 (s, 1H), 3.36 (s, 1H), 2.98 (m, 3H), 2.94 (m, 1H), 2.82 (m, 1H), 2.74 (m, 2H), 2.61 (d, J=3.2 Hz, 1H), 2.48 (m, 2H), 2.21 (d, J=5.8 Hz, 1H), 1.91 (t, 1H), 1.69 (s, 1H), 1.57 (t, 1H); HPLC-MS (ES) 722.2 (M+1).

EXAMPLE 14

(αR,γS,2S)-N-((3S,4S)-3,4-dihydro-3-hydroxy-2H-1-benzopyran-4-yl)-γ-hydroxy-α-(phenylmethyl)-4-(3-pyridinylmethyl)-2-[[(2,2,2-trifluoroethyl)amino]carbonyl]-1-piperazinepentanamide

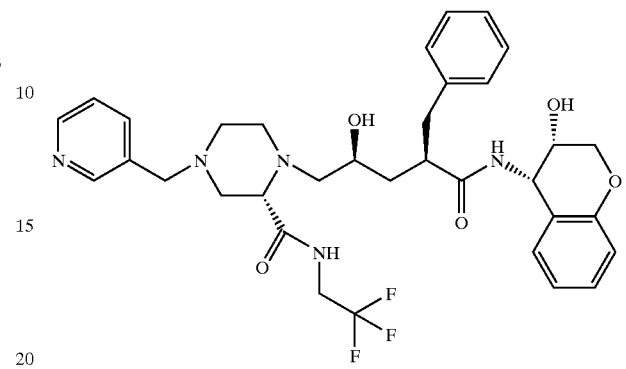

The title compound was obtained following the procedure described in Example 12, Step E, starting with 3-pyridine carboxaldehyde (32 μL, 0.30 mmol) and the intermediate prepared in Example 12, Step D (86 mg, 0.15 mmol). Purification by flash chromatography (10% methanol in dichloromethane) afforded the title compound as a white solid. $^1$H NMR (CD$_3$OD, 400 MHz) 8.47 (d, J=1.6 Hz, 1H), 8.43 (dd, J=1.6 Hz, J=4.8 Hz, 1H), 7.80 (d, J=6.0 Hz, 1H), 7.40 (dd, J=4.8 Hz, J=7.6 Hz, 1H), 7.22 (m, 5H), 7.11 (m, 2 H), 6.80 (dt, J=1.2 Hz, J=7.6 Hz, 1H), 6.73 (d, J=8.4 Hz, 1H), 5.16 (d, J=4.0 Hz, 1H), 4.08 (s, 2H), 3.94 (m, 1H), 3.80 (m, 4H), 3.57 (s, 3H), 3.11 (dd, J=3.2 Hz, J=7.2 Hz, 1 H), 2.98 (m, 3H), 2.76 (dd, J=6.4 Hz, J=13.2 Hz, 1 H), 2.67 (dd, J=2.4 Hz, J=10.8 Hz, 1H), 2.51 (m, 6H)2.05 (t, J=11.6 Hz, 1H), 1.41 (dt, J=3.6 Hz, J=10.0 Hz, 1H); HPLC-MS (ES) 656.3 (M+1).

EXAMPLE 15

(αR,γS,2S)-N-((3S,4S)-3,4-dihydro-3-hydroxy-2H-1-benzopyran-4-yl)-γ-hydroxy-α-(phenylmethyl)-4-[[5-(3-pyridinyl)-1-furanyl]methyl]-2-[[(2,2,2-trifluoroethyl)amino]carbonyl]-1-piperazinepentanamide

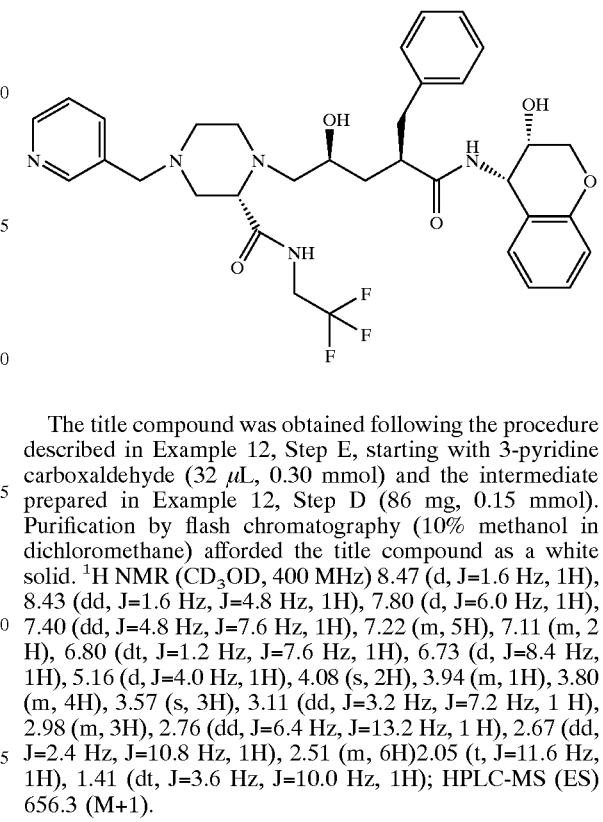

Step A

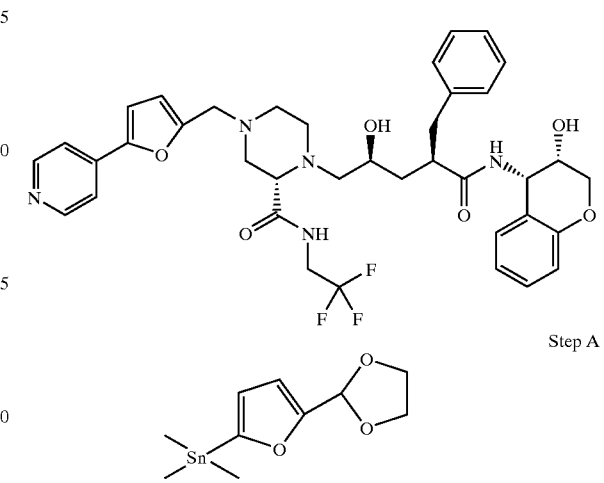

To a solution of 5-bromo-2-furaldehyde (20.0 g, 114 mmol) in 100 mL of benzene was added ethylene glycol (15.9 mL, 285 mmol) and p-toluenesulfonic acid monohydrate (282 mg, 1.48 mmol). The mixture was heated to reflux with azeotropic removal of water for 18 hours, then cooled to ambient temperature and concentrated in vacuo. The residue was dissolved in diethyl ether (1.5 L) and washed with saturated aqueous NaHCO$_3$ (150 mL), and brine (150 mL). The organic layer was dried (MgSO$_4$) and concentrated in vacuo affording an orange oil. This material was dissolved in THF (300 mL) and cooled to −78° C. To this solution was added sec-butyllithium (100 mL of a 1.3M solution in cyclohexane, 130 mmol) via cannula. After 1 hour at −78° C., a solution of trimethyltin chloride (12.6 g, 63 mmol, as a solution in 50 mL of THF) was added via cannula. After an additional 30 min at −78° C., the mixture was warmed to ambient temperature. After 2 hours the reaction was quenched by the addition of 100 mL of acetone, followed by 400 mL of water. The mixture was diluted with diethyl ether (500 mL). The organic layer was washed with saturated aqueous NaHCO$_3$ (150 mL×2), and brine, dried (MgSO$_4$), and concentrated in vacuo, affording the 5-trimethylstannylfuran-2-dioxolane as an orange oil.

Step B

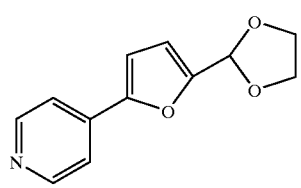

The intermediate prepared in Step A was dissolved in DMF (320 mL) and di-isopropylethylamine (11.9 mL, 68.0 mmol) was added, followed by 4-bromopyridine hydrochloride (11.8 g, 57.0 mmol). To this solution was then added tetrakis(triphenylphosphine)palladium(0) (2.0 g, 1.7 mmol), and the mixture was heated to 100° C. for 1 hour. The reaction was cooled to ambient temperature, and diluted with 1.5 L of diethyl ether. The organic layer was washed with 5% aqueous NaHCO$_3$ (300 mL×3), brine (300 mL), dried (MgSO$_4$) and concentrated in vacuo. Purification by flash chromatography (50% ethyl acetate in hexane) afforded the title compound as an orange solid. $^1$H NMR (CDCl$_3$, 400 MHz) 8.60 (d, 2H), 7.50 (d, 2H), 6.83 (d, 1H), 6.58 (d, 1H), 6.00 (s, 1H), 4.18 (m, 2H), 4.08 (m, 2H).

Step C

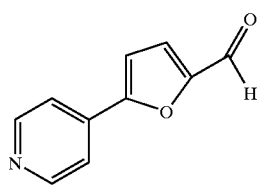

To a solution of the intermediate prepared in Step B (2.00 g, 9.20 mmol) in THF (200 mL) at 0° C. was added 1 N aqueous HCl (32.2 mL, 32.2 mmol). After warming to ambient temperature over 2 hours, the reaction was quenched by the addition of 1N NH$_4$OH until the reaction was pH 8. The reaction was diluted with 200 mL of ethyl acetate and washed with saturated aqueous NaHCO$_3$ (150 mL), brine (150 mL), dried (MgSO$_4$), and concentrated in vacuo, affording the title compound as an orange solid. $^1$H NMR (CDCl$_3$, 400 MHz) 9.87 (s, 1H), 8.62 (d, 2H), 7.61 (d, 2H), 7.32 (d, 1H), 7.01 (d, 1H).

Step D (αR,γS,2S)-N-((3S,4S)-3,4-dihydro-3-hydroxy-2H-1-benzopyran-4-yl)-γ-hydroxy-α-(phenylmethyl)-4-[[5-(3-pyridinyl)-1-furanyl]methyl]-2-[[(2,2,2-trifluoroethyl)amino]carbonyl]-1-piperazinepentanamide The title compound was obtained following the procedure described in Example 12, Step E, starting with the intermediate prepared in Step C (307 mg, 1.77 mmol), and using the intermediate prepared in Example 12, Step D (500 mg, 0.886 mmol). The material was obtained in >95% purity from the reaction mixture, as a white solid. $^1$H NMR (DMSO-D$_6$, 500 MHz) 8.55 (d, J=1.4 Hz, 1H), 8.41 (t, J=6.2 Hz, 1H), 7.79 (d, J=9.0 Hz, 1H), 7.58 (d, J=1.3 Hz, 1H), 7.20 (m, 3H), 7.06 (d, J=8.5 Hz, 1H), 6.76 (t, J=7.7 Hz, 1H), 6.69 (d, J=5.8 Hz, 1H), 6.49 (d, J=3.5 Hz, 1H), 5.09 (m, 2H), 4.58 (d, J=4.3 Hz, 1H), 4.12 (d, J=11.2 Hz, 1H), 4.05 (dd, J=4.1 Hz, J=11.5 Hz, 1H), 3.89 (m, 1H), 3.77 (m, 1H), 3.71 (d, J=2.5 Hz, 1H), 3.60 (s, 2H), 2.92 (m, 4H), 2.40 (t, J=9.4 Hz, 1H), 2.26 (m, 4H), 1.95 (t, J=11.6 Hz, 1H), 1.15 (t, J=8.4 Hz); HPLC-MS (ES) 722.2 (M+1).

EXAMPLE 16

(αR,γS,2S)-N-((3S,4S)-3,4-dihydro-3-hydroxy-2H-1-benzopyran-4-yl)-γ-hydroxy-α-(phenylmethyl)-4-[[5-(5-pyrimidinyl)-1-furanyl]methyl]-2-[[(2,2,2-trifluoroethyl)amino]carbonyl]-1-piperazinepentanamide

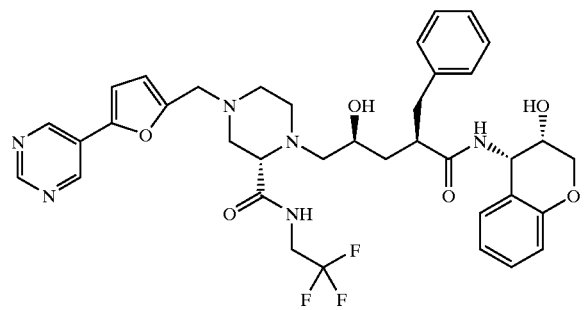

Step A

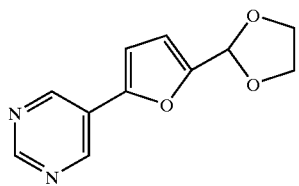

To a solution of the trimethylstannylfuran intermediate prepared in Example 15, Step A (5.00 g, 16.5 mmol) in DMF (100 mL) was added 5-bromopyrimidine (2.62 g, 16.5 mmol), followed by tetrakis(triphenylphosphine)palladium (0) (0.572 g, 0.49 mmol). The resulting mixture was heated to 100° C. for 1 hour, then cooled to ambient temperature and diluted with 1.2 L of diethyl ether. The organic layer was washed with saturated aqueous NaHCO$_3$ (500 mL×2), water (500 mL×2), and brine (500 mL), dried (MgSO$_4$), and concentrated in vacuo. Purification by recrystallization from diethyl ether/hexane afforded the furanylpyrimidine as an orange solid. $^1$H NMR (CDCl$_3$, 400 MHz) 9.11 (s, 1H), 9.01 (s, 2H), 6.80 (d, 1H), 6.59 (d, 1H), 6.00 (s, 1H), 4.18 (m, 2H), 4.07 (m, 2H).

Step B

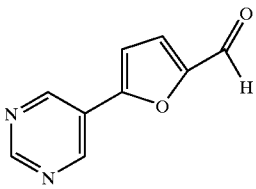

To a solution of the intermediate prepared in Step A (837 mg, 3.83 mmol) in THF (100 mL) and cooled to 0° C. To this solution was added 1 N aqueous HCl (10 mL, 10 mmol). After 1 hour at 0° C. the reaction was quenched by the addition of concentrated NH$_4$OH (50 mL). The mixture was diluted with ethyl acetate (200 mL), and the organic layer was washed with saturated aqueous NaHCO$_3$ (200 mL) and brine (200 mL), dried (MgSO$_4$), and concentrated in vacuo, affording the aldehyde as an orange solid. $^1$H NMR (CDCl$_3$, 400 MHz) 9.76 (s, 1H), 9.24 (s, 1H), 9.17 (s, 2H), 7.39 (d, 1H), 7.05 (d, 1H).

Step C (αR,γS,2S)-N-((3S,4S)-3,4-dihydro-3-hydroxy-2H-1-benzopyran-4-yl)-γ-hydroxy-α-(phenylmethyl)-4-[[5-(5-pyrimidinyl)-1-furanyl]methyl]-2-[[(2,2,2-trifluoroethyl)amino]carbonyl]-1-piperazinepentanamide The title compound was obtained following the procedure described in Example 12, Step E, starting with the aldehyde intermediate prepared in Step B (166 mg, 0.953 mmol), and using the intermediate prepared in Example 12, Step D (312 mg, 0.554 mmol). Purification by flash chromatography (3% methanol in ethyl acetate) afforded of the title compound as a white solid. $^1$H NMR (CDCl$_3$, 400 MHz) 9.11 (s, 1H), 8.97 (s, 1H), 8.89 (s, 1H), 7.28 (m, 5H), 7.12 (m, 2H), 6.80 (m, 3H), 6.42 (s, 1H), 6.08 (d, J=8.0 Hz, 1H), 5.18 (dd, J=4.1 Hz, 1H), 4.08 (m, 4H), 3.80 (s, 1H), 3.67 (m, 4H), 3.38 (s, 1H), 2.88 (m, 11H), 2.47 (d, J=10.4 Hz, 1H), 2.24 (s, 1H), 1.92 (t, J=11.2 Hz, 1H), 1.56 (t, J=10.8 Hz, 1H); HPLC-MS (ES) 723.5 (M+1).

EXAMPLE 17

(αR,γS,2)-N-((3S,4S)-3,4-dihydro-3-hydroxy-2H-1-benzopyran-4-yl)-γ-hydroxy-4-[(3-methyl-7-methoxy-4-benzofuranyl)methyl]-α-(3-phenylmethyl)-2-[[(2,2,2-trifluoroethyl)amino]carbonyl]-1-piperazinepentanamide

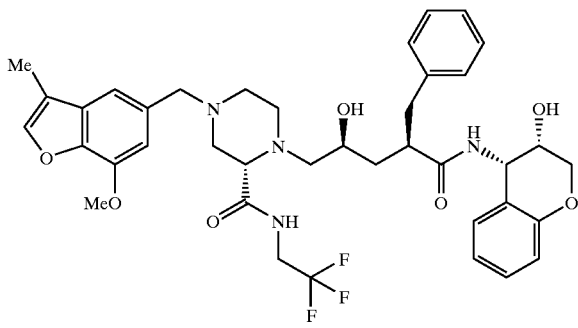

Step A

-continued

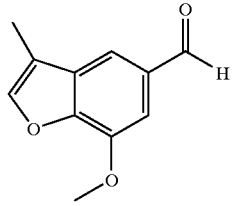

To a solution of 5-iodovanilin (3.00 g, 10.8 mmol) in DAF (10 mL) was added K$_2$CO$_3$ (3.72 g, 27.0 mmol), followed by allyl bromide (0.934 mL, 16.2 mmol). The reaction was heated to 50° C. for 1.5 hours, then cooled to ambient temperature and diluted with 300 mL of ethyl acetate. The organic layer was washed with 1 N aqueous NaHSO$_4$ (300 mL), 0.5 N NaHCO$_3$ (300 mL×3), and brine (300 mL). The organic layer was then dried (MgSO$_4$) and concentrated in vacuo, affording 3.38 g of the allyl ether as a yellow solid. This material was dissolved in DMF (20 mL), and to this solution was added Na$_2$CO$_3$ (853 mg, 8.05 mmol), sodium formate (1.37 g, 20.1 mmol), tetrabutylammonium chloride (2.46 g, 8.86 mmol), and palladium(II) acetate (90.4 mg, 0.403 mmol). The reaction was heated to 80° C. for 1 hour, then cooled to ambient temperature and diluted with 300 mL of ethyl acetate. The organic layer was washed with 1 N NaHSO$_4$ (300 mL), 0.5 N NaHCO$_3$ (300 mL×3), and brine (300 mL), dried (MgSO$_4$), and concentrated in vacuo, affording a brown oil. Purification by flash chromatography (25% ethyl acetate in hexane) afforded the aldehyde as a white solid. $^1$H NMR (CDCl$_3$, 400 MHz) 10.0 (s, 1H), 7.65 (s, 1H), 7.50 (s, 1H), 7.35 (s, 1H), 4.05 (s, 3H), 2.28 (s, 3H).

Step B (αR,γS,2S)-N-((3S,4S)-3,4-dihydro-3-hydroxy-2H-1-benzopyran-4-yl)-γ-hydroxy-4-[(3-methyl-7-methoxy-4-benzofuranyl)methyl]-α-(3-phenylmethyl)-2-[[(2,2,2-trifluoroethyl)amino]carbonyl]-1-piperazinepentanamide The title compound was obtained following the procedure described in Example 12, Step E, starting with the aldehyde prepared in Step A (22.3 mg, 0.118 mmol) and the intermediate prepared in Example 12, Step D (33.2 mg, 0.0589 mmol). Purification by flash chromatography (95% ethyl acetate in hexane) afforded the title compound as a white solid. $^1$H NMR (CDCl$_3$, 400 MHz) 9.19 (s, 1H), 7.44 (d, J=4.4 Hz, 1H), 7.27 (m, 5H), 7.14 (t, J=7.6 Hz, 1H), 7.09 (d, J=8.0 Hz, 1H), 7.01 (s, 1H), 6.82 (t, J=8.4 Hz, 1H), 6.69 (s, 1H), 5.94 (d, J=7.6 Hz, 1H), 4.20 (dd, J=4.4 Hz, J=8.8 Hz, 1H), 4.18 (m, 1H), 4.03 (m, 5H), 3.81 (m, 2H), 3.61 (m, 4H), 3.36 (s, 1H), 3.05 (d, J=12.0 Hz, 1H), 2.93 (m, 2H), 2.79 (m, 3H), 2.56 (d, J=9.2 Hz, 1H), 2.47 (d, J=10.8 Hz, 1H), 2.35 (t, J=8.0 Hz, 1H), 2.24 (s, 3H), 2.11 (d, J=6.4 Hz, 1H), 1.92 (t, J=11.2 Hz, 1H), 1.61 (m, 1H), 1.27 (s, 2H); HPLC-MS (ES) 739.4 (M+1).

EXAMPLE 18

(αR,γS,2S)-N-((3S,4S)-3,4-dihydro-3-hydroxy-2H-1-benzopyran-4-yl)-γ-hydroxy-4-[(7-methoxy-2-benzofuranyl)methyl]-α-(phenylmethyl)-2-[[(2,2,2-trifluoroethyl)amino]carbonyl]-1-piperazinepentanamide

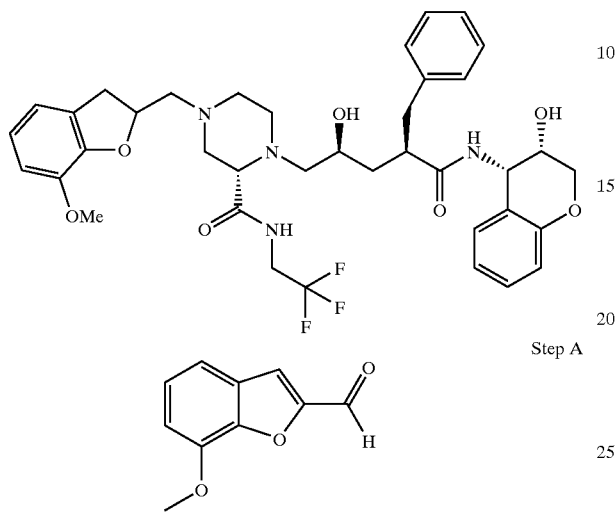

Step A

To a solution of 7-methoxy-2-benzofurancarboxylic acid (1.04 g, 5.42 mmol) in benzene (120 mL) was added methanol (40 mL), followed by trimethylsilyldiazomethane (2.72 mL of a 2.0 M solution in hexane, 5.42 mmol). After 30 min the reaction was diluted with dichloromethane (300 mL) and washed with saturated aqueous NaHCO₃ (300 mL). The organic layer was dried (Na₂SO₄) and concentrated in vacuo, affording 1.11 g of the carboxylic acid methyl ester as a white solid. This material was dissolved in THF (100 mL), and the resulting solution was cooled to 0° C. To this solution was added LiAlH₄ (13.5 mL of a 1.0 M solution in THF, 13.5 mmol). After 30 min the reaction was quenched by the slow addition of saturated aqueous NH₄Cl (100 mL). The mixture was diluted with ethyl acetate (300 mL), and the organic layer was washed with 1 N NaHSO₄ (300 mL), saturated aqueous NaHCO₃ (300 mL) and brine (300 mL), dried (MgSO₄) and concentrated in vacuo, affording 977 mg of the alcohol as a colorless oil. This material was dissolved in DMSO (20 mL), and to this solution was added triethylamine (4.52 mL, 32.5 mmol), followed by sulfur trioxide pyridine complex (2.58 g, 16.2 mmol). After 10 min the reaction was diluted with dichloromethane (200 mL) and washed with 1 N aqueous NaHSO₄ (200 mL), followed by 0.5 N aqueous NaHCO₃ (200 mL). The organic layer was dried (Na₂SO₄) and concentrated in vacuo, yielding the aldehyde as a yellow oil. ¹H NMR (CDCl₃, 400 MHz) 9.92 (s, 1H), 7.57 (s, 1H), 7.35 (d, 1H), 7.26 (t, 1H), 6.98 (d, 1H), 4.02 (s, 3H).

Step B (αR,γS,2S)-N-((3S,4S)-3,4-dihydro-3-hydroxy-2H-1-benzopyran-4-yl)-γ-hydroxy-4-[(7-methoxy-2-benzofuranyl)methyl]-α-(phenylmethyl)-2-[[(2,2,2-trifluoroethyl)amino]carbonyl]-1-piperazinepentanamide The title compound was obtained following the procedure described in Example 12, Step E, starting with the aldehyde prepared in Step A (25.6 mg, 0.145 mmol) and the intermediate prepared in Example 12, Step D (41.0 mg, 0.0727 mmol). Purification by flash chromatography (95% ethyl acetate in hexane) afforded the title compound as a white solid. ¹H NMR (CDCl₃, 400 MHz) 9.33 (s, 1H), 7.22 (m, 10H), 6.83 (m, 2H), 6.37 (s, 1H), 6.05 (d, J=8.0 Hz, 1H), 5.18 (dd, J=4.0 Hz, 1H), 4.27 (m, 1H), 4.07 (d, J=11.2 Hz, 1H), 4.01 (d, J=7.6 Hz, 1H), 4.00 (s, 3H), 3.87 (d, J=14.0 Hz, 1H), 3.78 (s, 1H), 3.75 (m, 1H, 1H), 3.63 (d, J=14.4 Hz, 1H), 3.34 (s, 1H), 3.00 (m, 2H), 2.92 (m, 2H), 2.75 (m, 3H), 2.56 (m, 2H), 2.23 (s, 1H), 1.91 (t, J=11.2 Hz, 1H), 1.57 (t, J=10.4 Hz, 1H). 1.27 (s, 1H); HPLC-MS (ES) 725.4 (M+1).

EXAMPLE 19

(αR,γS,2S)-N-((3S,4S)-3,4-dihydro-3-hydroxy-2H-1-benzopyran-4-yl)-γ-hydroxy-α-(phenylmethyl)-4-[(1-phenyl-1H-pyrrol-3-yl)methyl]-2-[[(2,2,2-trifluoroethyl)amino]carbonyl]-1-piperazinepentanamide

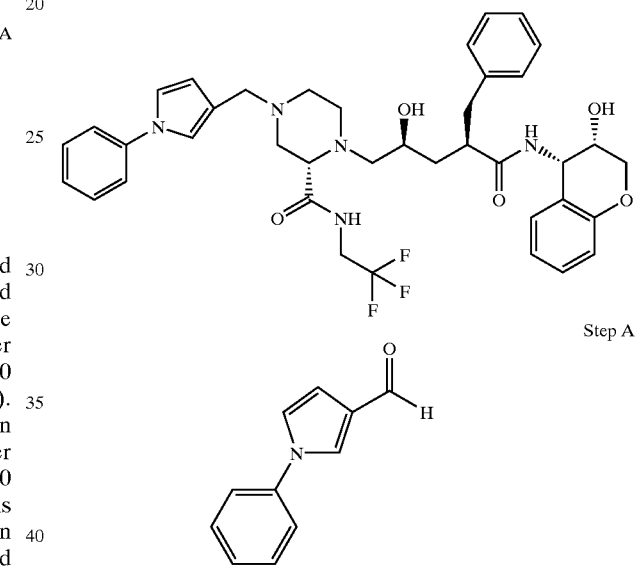

Step A

To a solution of aniline (1.68 mL, 18.4 mmol) in acetic acid (25 mL) was added 2,5-dimethoxy-3-tetrahydrofurancarboxaldehyde (2.95 g, 18.4 mmol). The resulting solution was heated to 90° C. for 30 min, then cooled to ambient temperature. The reaction was added slowly to saturated aqueous NaHCO₃ (500 mL), and the mixture was extracted with dichloromethane (200 mL). The organic layer was dried (Na₂SO₄) and concentrated in vacuo. Purification by flash chromatography (25% ethyl acetate in hexane) afforded the aldehyde as a yellow oil. ¹H NMR (CDCl₃, 400 MHz) 9.89 (s, 1H), 7.69 (s, 1H), 7.40 (m, 5H), 7.12 (d, 1H), 6.80 (d, 1H).

Step B (αR,γS,2S)-N-((3S,4S)-3,4-dihydro-3-hydroxy-2H-1-benzopyran-4-yl)-γ-hydroxy-α-(phenylmethyl)-4-[(1-phenyl-1H-pyrrol-3-yl)methyl]-2-[[(2,2,2-trifluoroethyl)amino]carbonyl]-1-piperazinepentanamide The title compound was obtained following the procedure described in Example 12, Step E, starting with the aldehyde prepared in Step A (19.7 mg, 0.115 mmol) and the intermediate prepared in Example 12, Step D (43.3 mg, 0.0767 mmol). Purification by flash chromatography (ethyl acetate)

afforded the title compound as a white solid. $^1$H NMR (CDCl$_3$, 400 MHz) 9.38 (s, 1H), 7.45 (t, J=6.4 Hz, 1H), 7.38 (d, J=8.4 Hz, 1H), 7.28 (m, 4H), 7.14 (t, J=7.2 Hz, 1H), 7.01 (s, 1H), 6.99 (s, 1H), 6.84 (d, J=7.6 Hz, 1H), 6.81 (d, J=8.0 Hz, 1H), 6.23 (t, J=2.0 Hz, 1H), 5.97 (d, J=8.0 Hz, 1H) 5.18 (dd, J=4.0 Hz, 1H), 4.17 (m, 1H), 4.07 (d, J=10.4 Hz, 1H), 4.01 (dd, J=5.2 Hz, J=11.6 Hz, 1H), 3.83 (s, 1H), 3.72 (m, 2H), 3.55 (d, J=13.2 Hz, 1H), 3.44 (d, J=13.2 Hz, 1H), 3.55 (s, 1H), 3.01 (d, J=11.6 Hz, 1H), 3.01 (d, J=15.2 Hz, 1H), 2.97(t, J=10.4 Hz, 1H), 2.89 (m, 1H), 2.81 (dd, J=4.4 Hz, J=12.0 Hz, 1H), 2.69 (m, 2H), 2.46 (d, J=10.8 Hz, 1H), 2.31 (t, J=10.4 Hz, 1H), 2.16 (s, 1H), 1.91 (t, J=10.8 Hz, 1H), 1.58 (m, 2H); HPLC-MS (ES) 720.5 (M+1).

EXAMPLE 20

(αR,γS,2S)-N-((3S,4S)-3,4-dihydro-3-hydroxy-2H-1-benzopyran-4-yl)-γ-hydroxy-4-[(1-phenyl-1H-imidazol-4-yl)methyl]-α-(phenylmethyl)-2-[[(2,2,2-trifluoroethyl)amino]carbonyl]-1-piperazinepentanamide

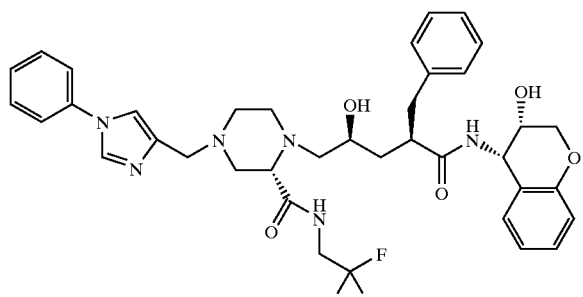

Step A

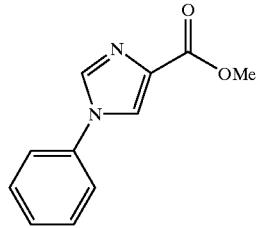

To a solution of aniline (3.16 mL, 34.7 mmol) in ethanol (66 mL) was added acetic acid (3.5 mL), followed by triethylorthoformate (5.77 mL, 34.7 mmol). The mixture was heated to reflux for 30 min, the cooled to ambient temperature. Methyl nitroacetate (6.38 mL, 69.4 mmol) was added, and the reaction was again heated to reflux for 3.5 hours. The mixture was then cooled to 0° C., and the precipitate that formed was collected by filtration and dried in vacuo, affording 5.16 g of the nitro enamine as a white solid. This material was dissolved in triethylorthoformate (60 mL). To the solution was added 10% Pd/C (1.70 g), and the reaction was placed under 2.5 atm of H$_2$ at 70° C. for 2 hours. The reaction was filtered through celite and concentrated in vacuo. The residue was dissolved in THF (300 mL) and cooled to 0° C., followed by addition of 1 N aqueous HCl until the solution was pH 1. After 30 min at 0° C. the solution was adjusted to pH 8 with saturated aqueous NaHCO$_3$ and extracted with ethyl acetate (300 mL). The organic layer was washed with brine (300 mL), dried (MgSO$_4$), and concentrated in vacuo. Purification by flash chromatography (65% ethyl acetate in hexane) afforded the title compound as a yellow solid: 1H NMR (CDCl$_3$, 400 MHz) 7.95 (s, 1H), 7.90 (s, 1H), 7.50 (m, 2H), 7.40 (m, 3H), 3.92 (s, 3H).

Step B

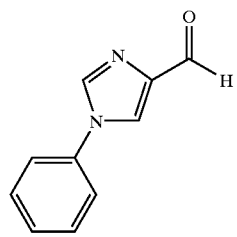

To a solution of the methyl ester prepared in Step A (200 mg, 0.990 mmol) in THF (4 mL) at 0° C. was added LiAlH$_4$ (1.98 mL of a 1.0 M solution in THF, 1.98 mmol). After 30 min the reaction was quenched by the addition of 20% aqueous NaOH (2 mL). The mixture was diluted with ethyl acetate (100 mL) and the organic layer was washed with brine (100 mL), dried (MgSO$_4$) and concentrated in vacuo, affording 166 mg of the alcohol as a colorless oil. This material was dissolved in 1:1 pentane:dichloromethane (10 mL). To this solution was added 1.10 g of celite, followed by MnO$_2$ (1.10 g, 12.7 mmol). After 2 hours the mixture was filtered through celite and concentrated in vacuo, affording the aldehyde, which was used without further purification. $^1$H NMR (CDCl$_3$, 300 MHz) 9.97 (s, 1H), 7.96 (s, 1H), 7.90 (s, 1H), 7.45 (m, 5H).

Step C (αR,γS,2S)-N-((3S,4S)-3,4-dihydro-3-hydroxy-2H-1-benzopyran-4-yl)-γ-hydroxy-4-[(1-phenyl-1H-imidazol-4-yl)methyl]-α-(phenylmethyl)-2-[[(2,2,2-trifluoroethyl)amino]carbonyl]-1-piperazinepentanamide The title compound was obtained following the procedure described in Example 12, Step E, starting with the aldehyde prepared in Step B (18 mg, 0.11 mmol) and the intermediate prepared in Example 12, Step D (50 mg, 0.089 mmol). Purification by flash chromatography (7% methanol in ethyl acetate) afforded the title compound as a white solid. $^1$H NMR (CD$_3$OD, 400 MHz) 8.10 (s, 1H), 7.81 (d, J=9.2 Hz, 1H) 7.53 (m, 6H), 7.40 (m, 1H), 7.23 (m, 5H), 7.18 (m, 1H), 7.10 (m, 2H), 6.82 (t, J=7.2 Hz, 1H), 6.72 (d, J=8.0 Hz, 1H), 5.16 (d, J=4.0 Hz, 1H), 4.08 (m, 2H), 3.98 (m, 1H), 3.76 (m, 4H), 3.62 (s, 2H), 3.15 (m, 1H), 3.03 (m, 3H), 2.75 (m, 6H), 2.59 (t, J=8.8 Hz, 1H), 2.41 (m, 2H), 2.05 (t, J=11.6 Hz, 1H), 1.41 (m, 2H); HPLC-MS (ES) 721.6 (M+1).

EXAMPLE 21

(αR,γS,2S)-4-(2-benzofuranylmethyl)-N-((1S,2R)-1,2-dihydro-2-hydroxy-1H-inden-1-yl)-γ-hydroxy-α-(phenylmethyl)-2-[[(2,2,2-trifluoroethyl)amino]carbonyl]-1-piperazinepentanamide

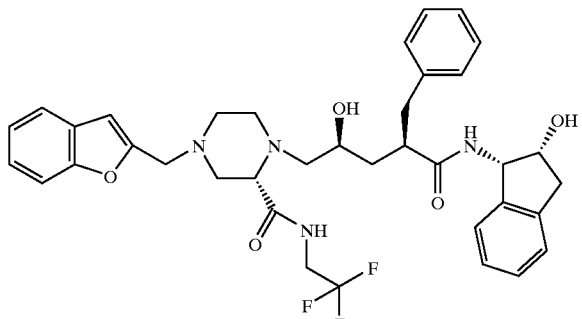

Step A

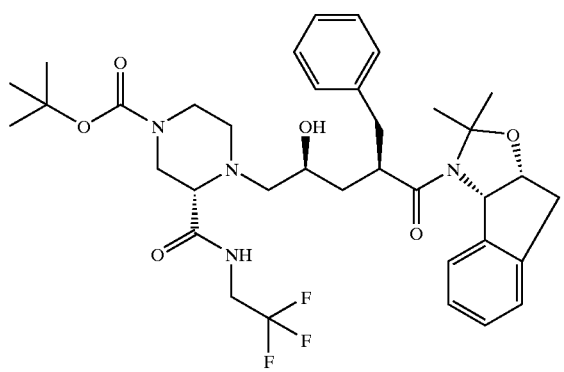

The title compound was obtained following the procedure described in Example 1, Step Q, starting with the intermediate prepared in Example 12, Step B (187 mg, 0.603 mmol) and the epoxide intermediate employed in Example 8, step A (250 mg, 0.663 mmol). Purification by flash chromatography (65% ethyl acetate in hexane) afforded the title compound as a colorless oil. $^1$H NMR (CDCl$_3$, 400 MHz) 7.25 (m, 8H), 6.92 (t, 1H), 6.40 (d, 1H), 5.63 (s, 1H), 4.83 (s, 1H), 3.90 (m, 3H), 3.78 (d, 1H), 3.51 (m, 4H), 3.30 (m, 1H, 3.19 (, 1H), 3.09 (s, 2H), 2.90 (d, 1H), 2.82 (dd, 1H), 2.66 (m, 1H), 2.52 (m, 2H), 1.88 (dd, 1H), 1.65 (s, 3H), 1.60 (t, 1H), 1.48 (s, 9H), 1.39 (s, 3H); HPLC-MS (ES) 689.2 (M+1).

Step B

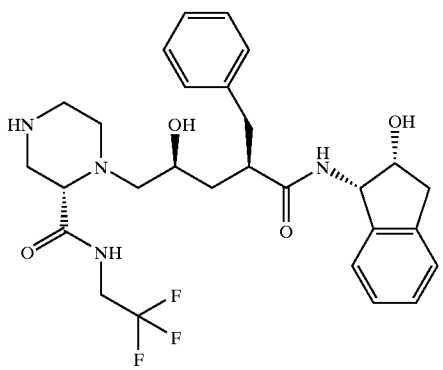

To a solution of the intermediate prepared in Step A (288 mg, 0.419 mmol) in 2-propanol (10 mL) at 0° C. was added concentrated aqueous HCl (10 mL). After 16 hours at ambient temperature the reaction was brought to pH 8 with 2N aqueous NaOH. The mixture was then extracted with ethyl acetate (200 mL×2). The organic layers were washed with brine (200 mL), dried (MgSO$_4$), and concentrated in vacuo affording the title compound as a white solid. $^1$H NMR (CDCl$_3$, 400 MHz) 9.00 (t, 1H), 7.22 (m, 9H), 6.17 (d, 1H), 5.28 (dd, 1H), 4.28 (t, 1H), 4.10 (m, 1H), 3.81 (m, 2H), 3.24 (m, 1H), 3.11 (m, 1H), 3.10 (dd, 1H), 3.00 (m, 2H), 2.90 (dd, 1H), 2.85 (m, 3H), 2.75 (m, 1H), 2.67 (m, 1H), 2.50 (dd, 1H), 1.98 (t, 1H), 1.58 (t, 1H); HPLC-MS (ES) 549.2 (M+1).

Step C (αR,γS, 2S)-4-(2-benzofuranylmethyl)-N-((1S,2R)-1,2-dihydro-2-hydroxy-1H-inden-1-yl)-γ-hydroxy-α-(phenylmethyl)-2-[[(2,2,2-trifluoroethyl)amino]carbonyl]-1-piperazinepentanamide The title compound was obtained following the procedure described in Example 12, Step E, starting with benzofuran-2-carboxaldehyde (22 mg, 0.15 mmol) and the intermediate prepared in Example 21, Step B (70 mg, 0.13 mmol). Purification by flash chromatography (1% methanol in ethyl acetate) afforded the title compound as a white solid $^1$H NMR (CD$_3$OD, 400 MHz) 7.52 (d, J=6.8 Hz, 1H), 7.42 (d, J=8 Hz, 1H), 7.18 (m, 5H), 6.70 (s, 1H), 5.19 (d, J=5.2 Hz, 1H), 4.31 (dt, J=2.4 Hz, J=5.2 Hz, 1H), 3.96 (m, 1H), 3.73 (m, 4 H), 3.10 (m, 2H), 3.03 (d, 5.2 Hz, 1H), 2.96 (m, 3H), 2.75 (m, 7H), 2.61 (dd, J=8.0 Hz, J=11.2 Hz, 1H), 2.54 (dd, J=2.8 Hz, J=8.4 Hz, 1H), 2.39 (m, 4H), 2.02 (dt, J=2.0 Hz, J=13.6 Hz, 1H), 1.40 (dt, J=2.8 Hz, J=10.0 Hz, 1H); HPLC-MS (ES) 679.2 (M+1).

EXAMPLE 22

(αR,γS,2S)-N-((1S,2R)-1,2-dihydro-2-hydroxy-1H-inden-1-yl)-γ-hydroxy-α-(phenylmethyl)-4-(3-pyridinylmethyl)-2-[[(2,2,2-trifluoroethyl)amino]carbonyl]-1-piperazinepentanamide

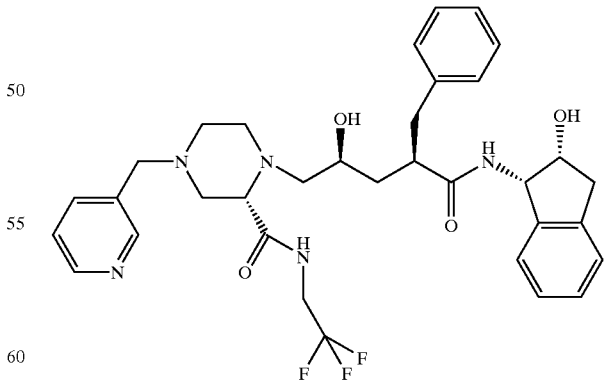

The title compound was obtained following the procedure described in Example 12, Step E, starting with pyridine-3 carboxaldehyde (28 mg, 0.26 mmol) and the intermediate prepared in Example 21, Step B (70 mg, 0.13 mmol). Purification by flash chromatography (10% methanol in ethyl acetate) afforded the title compound as a white solid $^1$H NMR (CD$_3$OD, 400 MHz) 8.47 (d. J=1.6 Hz, 1H), 8.43 (dd, J=1.6Hz, J=4.8 Hz, 1H), 7.81 (dt, J=1.6 Hz, J=8.0 Hz, 1H), 7.40 (dd, J=5.2 Hz, J=8.0 Hz, 1H), 7.19 (m, 9H), 5.20 (d, J=4.8 Hz, 1H), 4.32 (t, J=5.2 Hz, 1H), 3.83 (m, 3H), 3.56 (s, 2H), 3.04 (m, 4H), 2.85 (d, J=16.4 Hz, 1H), 2.77 (m, 1H), 2.66 (d, J=8.0 Hz, 1H), 2.47 (m, 7H), 2.02 (m, 1H), 1.34 (m, 1H); HPLC-MS (ES) 640.3 (M+1).

EXAMPLE 23

(αR,γS,2S)-N-((3S,4S)-3,4-dihydro-3-hydroxy-2H-1-benzopyran-4-yl)-γ-hydroxy-4-[(5-phenyl-2-furanyl)methyl]-α-(3-pyridinylmethyl)-2-[[(2,2,2-trifluoroethyl)amino]carbonyl]-1-piperazinepentanamide

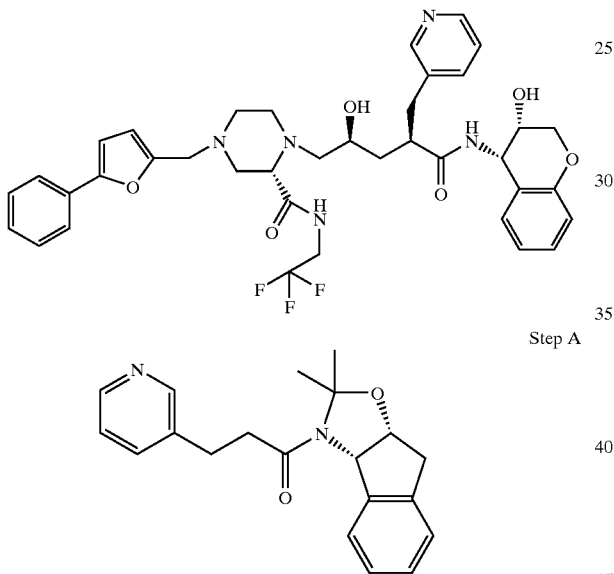

Step A

To a solution of 2(R)-hydroxy-1(S)-aminoindane (98.7 g, 660 mmol) in DMF (400 mL) was added dichloromethane (2.2 L), followed by 3-pyridine propionic acid (100 g, 660 mmol), HOBT (134 g, 990 mmol), and EDC (189 g, 990 mmol). After 2 hours the thick slurry was filtered and the filtrate was dried in vacuo. This material was dissolved in dichloromethane (1.5 L), and cooled to 0° C. To the solution was added 2-methoxypropene (259 mL, 2.69 mol), followed by camphorsulfonic acid (150 g, 697 mmol). The mixture was warmed to ambient temperature over 1 hour, then brought to pH 10 with 1 N aqueous NaOH. The organic layer was dried (Na$_2$SO$_4$) and concentrated in vacuo. The resulting yellow solid was tritrated with hexane to afford a beige solid. $^1$H NMR (CDCl$_3$, 400 MHz) 8.55 (s, 1H), 8.47 (d, 1H), 7.60 (d, 1H), 7.20 (m, 5H), 5.14 (d, 1H), 4.70 (m, 1H), 3.12 (m, 2H), 3.05 (s, 2H), 2.93 (m, 2H), 1.60 (s, 3H0, 1.34 (s, 3H).

Step B

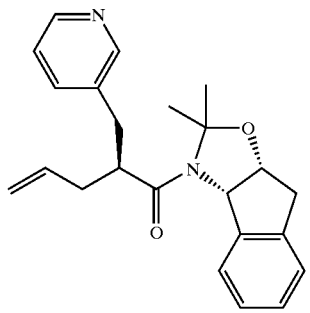

The title compound was obtained following the procedure described in Example 1, Step N, using the intermediate from Step A (30.0 g, 93.1 mmol). Tritration of the crude material with hexane afforded the title compound as a beige solid. $^1$H NMR (CDCl$_3$, 400 MHz) 8.60 (s, 1H), 8.50 (d, 1H), 7.61 (dt, 1H), 7.20 (m, 4H), 6.82 (t, 1H), 6.12 (d, 1H), 5.85 (m, 1H), 5.20 (d, 1H), 5.08 (d, 1H), 5.06 (s, 1H), 4.74 (s, 1H), 3.38 (dd, 1H), 3.10 (m, 1H), 3.00 (s, 2H), 2.78 (dd, 1H), 2.45 (m, 1H), 2.35 (m, 1H), 1.60 (s, 3H), 1.27 (s, 3H).

Step C

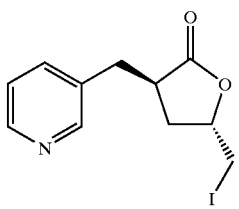

To a solution of the intermediate from Step B (29.8 g, 82.2 mmol) in THF (250 mL) was added water (250 mL). The mixture was cooled to 0° C., and I$_2$ (83.5 g, 329 mmol) was added, followed by methanesulfonic acid (10.7 mL, 164 mmol). The mixture was warmed to ambient temperature and stirred for 16 hours. The reaction was then diluted with ethyl acetate (1 L) and washed with 1 N NaHSO$_4$ (300 mL×3). The aqueous layer was brought to pH 8 with saturated aqueous NaHCO$_3$, and extracted with dichloromethane (500 mL×2). These organic layers were dried (Na$_2$SO$_4$) and concentrated in vacuo. Purification by flash chromatography (ethyl acetate) afforded the title compound as a beige solid. $^1$H NMR (CDCl$_3$, 400 MHz) 8.51 (d, 1H), 8.46 (s, 1H) 7.55 (d, 1H), 7.21 (s, 1H), 4.20 (m, 1H), 3.35 (dd, 1H), 3.20 (m, 2H), 3.18 (dd, 1H), 3.08 (m, 1H), 2.82 (dd, 1H), 2.20 (m, 2H); HPLC-MS (ES) 318.0 (M+1).

Step D

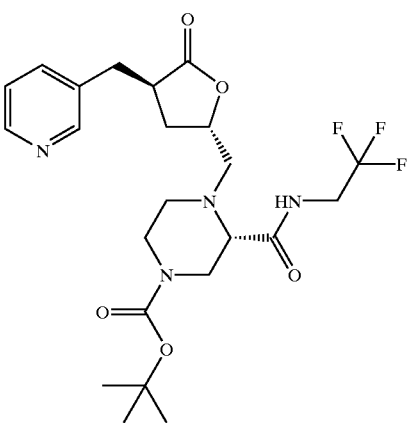

To a solution of the intermediate from Step C (6.90 g, 21.8 mmol) in DMF (15 mL) was added the intermediate from Example 12, Step B (5.83 g, 18.7 mmol), and di-iso-propylethylamine (3.92 mL, 22.5 mmol). The mixture was heated to 100° C. for 16 hours, then cooled to ambient temperature and diluted with ethyl acetate (1 L) and washed with 0.5 N aqueous NaHCO$_3$ (300 mL×3), and brine (300 mL), dried (MgSO$_4$) and concentrated in vacuo. Purification by flash chromatography afforded the title compound as a white solid. $^1$H NMR (CDCl$_3$, 400 MHz) 8.55 (d, 1H), 8.48 (s, 1H), 7.58 (dd, 1H), 7.26 (d, 1H), 7.00 (t, 1H), 4.46 (m, 1H), 4.05 (m, 1H0, 3.90 (m, 1H, 3.72 (m, 2H), 3.10 (m, 3H), 2.90 (m, 2H), 2.85 (dd, 1H), 2.60 (m, 2H), 2.40 (t, 1H), 2.05 (m, 1H), 1.95 (m, 1H), 1.42 (s, 9H).

Step E

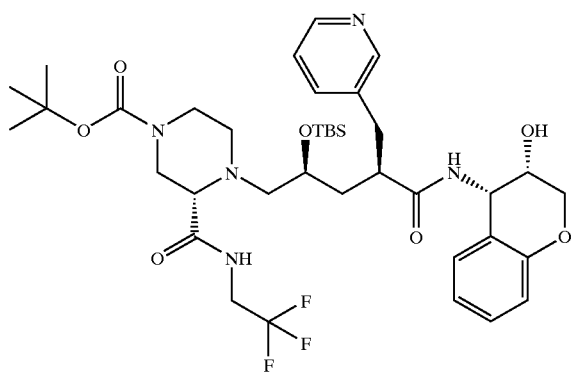

To a solution of the intermediate from Step D (3.35 g, 6.70 mmol) in 1,2-dimethoxyethane (30 mL) at 0° C. was added 1 N aqueous LiOH (7.36 mL, 7.36 mmol). After 30 min the reaction was concentrated in vacuo, and the carboxylic acid (lithium salt) product was dried to a white powder by repeated azeotropic drying with benzene in vacuo. This material was dissolved in DMF (50 mL), and to this solution was added-tert-butyldimethylsilyl chloride (10.1 g, 67.0 mmol), and imidazole (9.12 g, 134 mmol). After 2 hours at ambient temperature the reaction was quenched with 0.05 N aqueous pH 7 phosphate buffer (100 mL) and extracted with ethyl acetate (300 mL). The organic layer was washed with brine (300 mL), dried (MgSO$_4$) and concentrated in vacuo. The resulting silyl ester was dissolved in THF (20 mL) and water (10 mL) was added. The mixture was concentrated in vacuo, with the residual water removed by repeated azeotropic drying with benzene in vacuo. The resulting free acid was dissolved in DMF (100 mL), and to this solution was added the chiral aminochromanol intermediate from Example 1, Step L (1.11 g, 6.70 mmol), followed by HOBT (2.26 g, 16.7 mmol), di-iso-propylethamine (4.61 mL, 26.8 mmol), and HBTU (3.81 g, 10.0 mmol). After 16 hours at ambient temperature the reaction was diluted with ethyl acetate (300 mL) and washed with 0.5 N NaHO$_3$ (300 mL×3), and brine (300 mL). The organic layer was dried (MgSO$_4$) and concentrated in vacuo. Purification by flash chromatography afforded the title compound as a white solid. $^1$H NMR (CDCl$_3$, 400 MHz) 8.48 (s, 1H), 8.46 (d, 1H), 7.95 (d, 1H), 7.55 (d, 1H), 7.22 (dd, 1H), 7.16 (t, 1H), 7.14 (d, 1H), 6.84 (t, 1H), 6.79 (d, 1H), 5.20 (dd, 1H), 4.08 (s, 1H), 4.00 (dd, 1H), 3.80 (m, 4H), 3.64 (d, 1H), 3.62 (m, 1H), 3.00 (m, 4H), 2.80 (m, 2H), 2.42 (m, 2H), 2.23 (m, 2H), 1.42 (s, 9H), 0.89 (s, 9H), 0.02 (s, 3H), 0.02 (s, 3H).

Step F

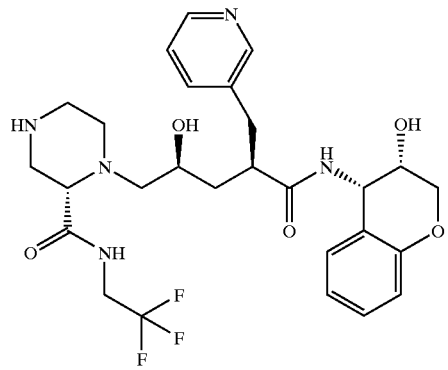

To a solution of the intermediate from Step E (5.32 g, 6.83 mmol) in 2-propanol (20 mL) at 0° C. was added concentrated aqueous HCl (20 mL). After 1 hour the reaction was added to saturated aqueous NaHCO$_3$ (400 mL) and extracted with dichloromethane until there was no product remaining in the aqueous layer by HPLC analysis (200 mL×20). The combined organic layers were concentrated in vacuo, affording the title compound as a white solid. $^1$H NMR (CDCl$_3$, 400 MHz) 8.41 (s, 1H), 8.39 (d, 1H), 7.76 (d, 1H), 7.34 (m, 1H), 7.10 (m 2H), 6.83 (t, 1H), 6.77 (d, 1H), 5.20 (d, 1H), 4.80 (s, 2H), 4.08 (m, 3H), 3.75 (m, 3H), 3.28 (t, 2H), 3.00 (m, 4H), 2.85 (m, 3H), 2.50 (dd, 1 H), 2.40 (dd, 1H), 2.10 (m, 1H), 1.40 (m, 1H).

Step G

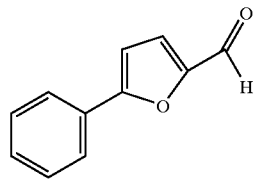

To a solution of 4-bromofuran carboxaldehyde (2.00 g, 11.4 mmol) in deoxygenated DMF (50 mL) was added tetrakis(triphenylphosphine)palladium(0) (660 mg, 0.570 mmol), followed by phenylboronic acid (1.39 g, 11.4 mmol), and 2 N aqueous Na$_2$CO$_3$ (11.4 mL of a 2.0 M solution, 22.9 mmol). The mixture was heated to 100° C. for 16 hours, the cooled to ambient temperature and diluted with ethyl acetate (500 mL). The mixture was washed with 0.5 N NaHCO$_3$ (300 mL×3) and brine (300 mL). The organic layer was dried (MgSO$_4$), and concentrated in vacuo. Purification by flash chromatography (35% ethyl acetate in hexane) afforded the title compound as a yellow oil. $^1$H NMR (CDCl$_3$, 300 MHz) 9.62 (s, 1H), 7.82 (d, 2H), 7.40.(m, 3H), 7.31 (d, 1H), 6.80 (d, 1H).

Step H (αR,γS,2S)-N-((3S,4S)-3,4-dihydro-3-hydroxy-2H-1-benzopyran-4-yl)-γ-hydroxy-4-[(5-phenyl-2-furanyl)methyl]-α-(3-pyridinylmethyl)-2-[[(2,2,2-trifluoroethyl)amino]carbonyl]-1-piperazinepentanamide The title compound was obtained following the procedure described in Example 12, Step E, starting with the intermediate prepared in Step F (368 mg, 0.652 mmol) and the aldehyde prepared in Step G (168 mg, 0.978 mmol). Purification by flash chromatography (10% methanol in ethyl acetate) afforded 348 mg (74%) of the title compound as a white solid. $^1$H NMR (CDCl$_3$, 400 MHz) 9.16 (s, 1H), 8.42 (d, J=3.6 Hz, 1H) 8.39 (d, 1H), 7.64 (d, J=7.6 Hz, 1H), 7.55 (d, J=8.0 Hz, 1H), 7.40 (t, J=7.2 Hz, 1H), 7.30 (d, J=7.6 Hz, 1H), 7.22 (dd, J=4.4 Hz, J=7.2 Hz, 1H), 7.11 (d, J=6.0 Hz, 1H), 6.82 (d, J=6.4 Hz, 1H), 6.61 (d, J=2.8 Hz, 1H), 6.50 (d, J=8.4 Hz, 1H), 6.33 (d, J=3.2 Hz, 1H), 5.22 (dd, J=4.0 Hz, J=8.0 Hz, 1H), 4.12 (m, 2H), 4.01 (dd, J=5.2 Hz, J=11.2 Hz, 1H), 3.84 (m, 1H), 3.78 (t, J=9.6 Hz, 1H), 3.72 (d, J=14.0 Hz, 1H), 3.56 (d, J=14.0 Hz, 1H), 3.49 (m, 1H), 3.34 (s, 1H), 3.00 (m, 2H), 2.88 (m, 1H)2.71 (m, 2H), 2.54 (dd, J=2.8 Hz, J=11.6 Hz, 1H), 2.45 (d, J=10.0 Hz, 1H), 1.87 (t, J=11.2 Hz, 1H), 1.51 (t, J=10.8 Hz, 1H); HPLC-MS (ES) 722.4 (M+1).

EXAMPLE 24

(αR,γS,2S)-4-(2-benzopyranylmethyl)-N-(3S,4S)-3,4-dihydro-3-hydroxy-2H-1-benzopyran-4-yl)-γ-hydroxy-α-(3-pyridinylmethyl)-2-[[(2,2,2-trifluoroethyl)amino]carbonyl]-1-piperazinepentanamide

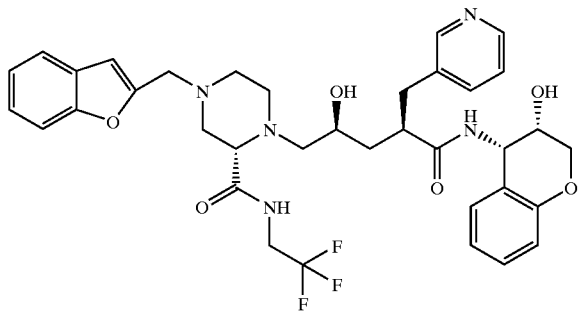

The title compound was obtained following the procedure described in Example 12, Step E, starting with the intermediate prepared in Example 23, Step F (357 mg, 0.632 mmol) and benzofuran-2-carboxaldehyde (185 mg, 1.26 mmol). Purification by flash chromatography (10% methanol in ethyl acetate) afforded the title compound as a white solid. $^1$H NMR (CDCl$_3$, 400 MHz) 9.19 (s, 1H), 8.45 (s, 2H), 7.56 (d, J=8.0 Hz, 2H), 7.44 (d, J=8.0 Hz, 1H), 7.29 (m, 6H), 7.12 (m, 2H), 6.82 (d, J=7.2 Hz, 2H), 6.65 (s, 1H), 6.33 (s, 1H), 5.22 (dd, J=4.4 Hz, 1H), 4.21 (m, 1H), 4.11 (d, J=10.8 Hz, 1H), 4.02 (dd, J=5.2 Hz, J=11.6 Hz, 1H), 3.88 (s, 1H), 3.78 (m, 2H), 3.68 (m, 2H), 3.35 (t, J=2.4 Hz, 1H), 2.99 (m, 3H), 2.87 (m, 1H), 2.76 (m, 3H), 2.61 (dd, J=3.2 Hz, J=11.6 Hz, 1H), 2.48 (m, 2H), 1.89 (t, J=11.2 Hz, 1H), 1.55 (t, J=10.4 Hz, 1H); HPLC-MS (ES) 696.3 (M+1).

EXAMPLE 25

(αR,γS,2S)-N-((3S,4S)-3,4-dihydro-3-hydroxy-2H-1benzopyran-4-yl)-γ-hydroxy-α-(3-pyridinylmethyl)-4-(thieno[2,3-b]thien-2-ylmethyl)-2-[[(2,2,2-trifluoroethyl)amino]carbonyl]-1-piperazinepentanamide

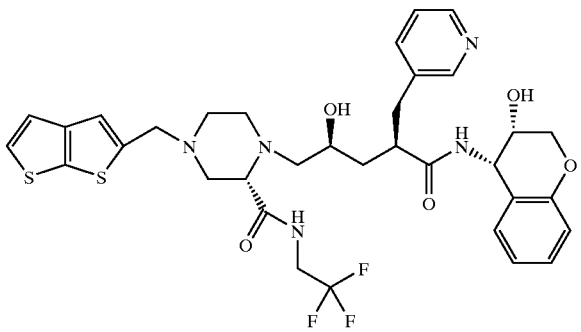

Step A

To a solution of 2-thieno-[2,3-b]thiophenecarboxylic acid (prepared as described in Gronowitz, S.; Persson, B. *Acta Chem. Scand.*, 1967, 21, 812–813) (0.981 g, 5.32 mmol) in benzene (38 mL) was added methanol (13 mL), followed by trimethylsilyldiazomethane (3.99 mL of a 1.5 M solution in hexane, 7.99 mmol). After 20 min at ambient temperature the reaction was quenched by the addition of acetic acid (5 mL), and the solution was concentrated in vacuo. This methyl ester was dissolved in THF (15 mL) and cooled to 0° C. To this solution was added lithium aluminum hydride (10.6 mL of a 1.0 M solution in THF, 10.6 mmol). After 20 min the reaction was quenched by the addition of 20% aqueous NaOH (20 mL). The mixture was diluted with ethyl acetate (100 mL) and washed with brine (100 mL). The organic layer was dried (MgSO$_4$) and concentrated in vacuo. The resulting alcohol was dissolved in dichloromethane (25 mL), and celite (100 mg) was added to the reaction, followed by pyridinium chlorochromate (1.57 g, 7.28 mmol). After 90 min the reaction was diluted with diethyl ether (200 mL) and filtered through celite. The liquid was concentrated in vacuo. Purification by flash chromatography (11% ethyl acetate in hexane) afforded the aldehyde. $^1$H NMR (CDCl$_3$, 400 MHz) 9.94 (s, 1H), 7.93 (s, 1H), 7.44 (d, 1H), 7.33 (d, 1H).

Step B (αR,γS,2S)-N-((3S,4S)-3,4-dihydro-3-hydroxy-2H-1-benzopyran-4-yl)-γ-hydroxy-α-(3-pyridinylmethyl)-4-(thieno[2,3-b]thien-2-ylmethyl)-2-[[(2,2,2-trifluoroethyl)amino]carbonyl]-1-piperazinepentanamide The title compound was obtained following the procedure described in Example 12, Step E, starting with the intermediate prepared in Example 23, Step F (357 mg, 0.632 mmol) and the aldehyde prepared in Step A (220 mg, 1.32 mmol). Purification by flash chromatography (7.5% methanol in ethyl acetate) afforded the title compound as a white solid.

¹H NMR (CD₃OD, 400 MHz) 8.40 (d, J=2 Hz, 1H), 8.35 (dd, J=1.6 Hz, J=4.8 Hz, 1H), 7.74 (dt, J=1.6 Hz, J=8.0 Hz, 1H), 7.39 (d, J=5.2 Hz, 1H), 7.33 (dd, J=4.8 Hz, J=3.2 Hz, 1H), 7.16 (d, J=5.2 Hz, 1H), 7.12 (m, 3H), 6.80 (dt, J=0.8 Hz, J=6.8 Hz, 1H), 6.73 (d, J=8 Hz, 1H), 5.81 (d, J=4 Hz, 1H), 4.03 (m, 3H), 3.78 (m, 3H), 3.04 (m, 4H), 2.79 (m, 2H), 2.67 (m, 1H), 2.56 (dd, J=7.6 Hz, J=3.2 Hz, 1H), 2.45 (m, 4H), 2.08 (dt, J=2.4 Hz, J=10.4 Hz, 1H); HPLC-MS (ES) 718.4 (M+1).

EXAMPLE 26

(αR,γS,2S)-4-[(2,6-difluorophenyl)methyl]-N-((3S,4S)-3,4-dihydro-3-hydroxy-2H-1-benzopyran-4-yl)-γ-hydroxy-α-(3-pyridinylmethyl)-2-[[(2,2,2trifluoroethyl)amino]carbonyl]-1-piperazinepentanamide

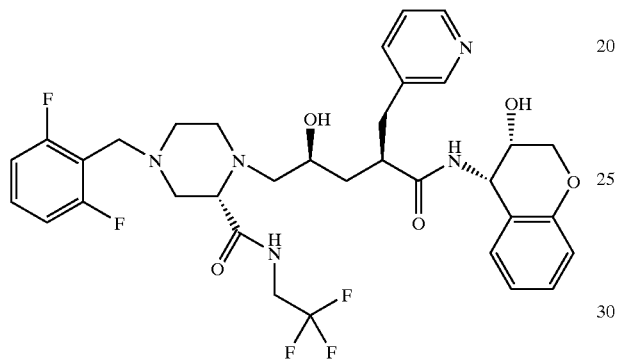

The title compound was obtained following the procedure described in Example 12, Step E, starting with the intermediate prepared in Example 23, Step F (50 mg, 0.089 mmol) and 2,6-difluorobenzaldehyde (25 mg, 0.178 mmol). Purification by flash chromatography (10% methanol in ethyl acetate) afforded the title compound as a white solid. ¹H NMR (CD₃OD, 400 MHz) 8.40 (s, 1H), 8.36 (dd, J=3.6 Hz, J=1.2 Hz, 1H), 7.74 (d, J=8.0 Hz, 1H), 7.35 (m, 2H), 7.10 (m, 2H), 7.01 (q, J=7.6 Hz, 2H), 6.82 (t, J=7.6 Hz, 1H), 6.74 (d, J=8.4 Hz, 1H), 5.18 (d, J=4.0 Hz, 1H), 4.03 (m, 3H), 3.77 (m, 2H), 3.70 (m, 3H), 3.0 (m, 4H), 2.9 (m, 2H), 2.78 (m, 2H), 2.60 (m, 2H), 2.53 (m, 1H), 2.38 (m, 4H), 2.06 (m, 1H), 1.40 (m, 1H); HPLC-MS (ES) 692.2 (M+1).

EXAMPLE 27

(αR,γS,2S)-N-((3S,4S)-3,4-dihydro-3-hydroxy-2H-1-benzopyran-4-yl)-γ-hydroxy-α-(3-pyridinylmethyl)-4-(thieno[3,2-b]thien-2-ylmethyl)-2-[[(2,2,2-trifluoroethyl)amino]carbonyl]-1-piperazinepentanamide

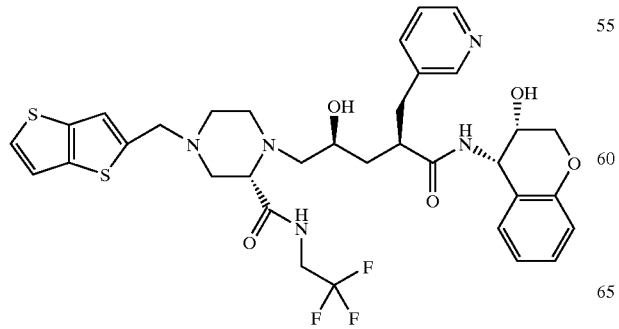

Step A

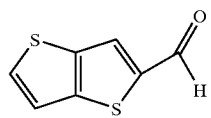

To a solution of thieno[3,2-B]thiophene (100 mg, 0.700 mmol) in DMF (5 mL) at 0° C. was added POCl₃ (110 mg, 0.700 mmol). The mixture was slowly heated to 100° C. over 1 hour and stirred at that temperature for 3 hours. The mixture was then cooled to ambient temperature and poured onto cold water (100 mL). The pH was adjusted to 6 with solid sodium acetate, and the mixture was extracted with diethyl ether (100 mL). The organic layer was washed with saturated aqueous NaHCO₃ (100 mL) and brine (100 mL), dried (MgSO₄) and concentrated in vacuo. Purification by flash chromatography (10% ethyl acetate in hexane) afforded the title compound as a yellow solid. ¹H NMR (CDCl₃, 400 MHz) 9.98 (s, 1H), 7.97 (s, 1H), 7.70 (d, 1H), 7.35 (d, 1H).

Step B (αR,γS,2S)-N-((3S,4S)-3,4-dihydro-3-hydroxy-2H-1-benzopyran-4-yl)-γ-hydroxy-α-(3-pyridinylmethyl)-4-(thieno[3,2-b]thien-2-ylmethyl)-2-[[(2,2,2-trifluoroethyl)amino]carbonyl]-1-piperazinepentanamide The title compound was obtained following the procedure described in Example 12, Step E, starting with the intermediate prepared in Example 23, Step F (50 mg, 0.089 mmol) and the aldehyde prepared in Step A (22.6 mg, 0.13 mmol). Purification by flash chromatography (13% methanol in ethyl acetate) afforded the title compound as a white solid. ¹H NMR (CD₃OD, 400 MHz) 8.40 (s, 1H), 8.36 (d, J=3.6 Hz, 1H), 7.75 (d, J=7.6 Hz, 1H), 7.44 (d, J=5.2 Hz, 1H), 7.33 (dd, J=4.8 Hz, J=8.0 Hz, 1H), 7.24 (d, J=5.2 Hz, 1H), 7.20 (s, 1H), 7.13 (d, J=7.6 Hz, 1H), 7.09 (t, J=7.6 Hz, 1H), 6.82 (t, J=7.2 Hz, 1H), 6.73 (d, J=8.0 Hz, 1H), 5.18 (d, J=4.0 Hz, 1H), 4.02 (m, 3H), 3.83 (m, 4H), 3.16 (dd, J=3.2 Hz, J=7.2 Hz, 1H) 3.03 (m, 4H), 2.83 (m, 3H), 2.70 (m, 1H), 2.62 (t, J=8.4 Hz, 1H), 2.42 (m, 5H), 2.08 (t, J=11.6 Hz, 1H), 1.43 (m, 1H); HPLC-MS (ES) 718.1 (M+1).

EXAMPLE 28

(αR,γS,2S)-N-((3S,4S)-3,4-dihydro-3-hydroxy-2H-1-benzopyran-4-yl)-γ-hydroxy-4-[(7-methoxy-2-benzofuranyl)methyl]-α-(3-pyridinylmethyl)-2-[[(2,2,2-trifluoroethyl)amino]carbonyl]-1-piperazinepentanamide

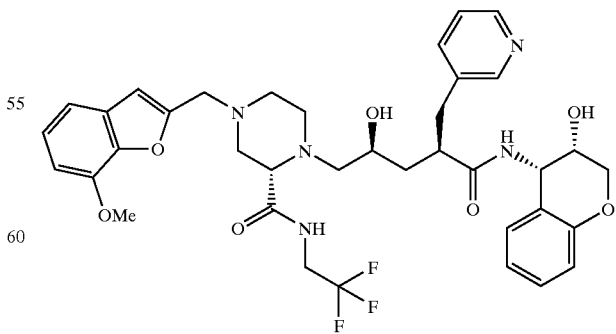

The title compound was obtained following the procedure described in Example 12, Step E, starting with the intermediate prepared in Example 23, Step F (53.1 mg, 0.094 mmol) and the aldehyde prepared in Example 18, Step A (33.1 mg, 0.188 mmol). Purification by flash chromatography (10% methanol in ethyl acetate) afforded the title compound as a white solid. $^1$H NMR (CD$_3$OD, 400 MHz) 8.34 (s, 1H), 8.28 (d, J=4.8 Hz, 1H), 7.67 (d, J=8.0 Hz, 1H), 7.26 (dd, J=4.8 Hz, J=8.0 Hz, 1H), 7.05 (m, 3H), 6.77 (m, 2H), 6.67 (d, J=8.0 Hz, 1H), 6.63 (s, 1H), 5.11 (d, J=4.0 Hz, 1H), 3.98 (m, 3H), 3.89 (s, 3H), 3.67 (m, 3H), 3.06 (dd, J=3.2 Hz, J=7.2 Hz, 1H), 2.91 (m, 1H), 2.74 (m, 2H), 2.65 (m, 1H), 2.54 (m, 1H), 2.43 (m, 1H), 2.35 (d, J=6.8 Hz, 1H), 2.00 (t, J=11.6 Hz, 1H), 1.36 (t, 1H); HPLC-MS (ES) 726.3 (M+1).

EXAMPLE 29

(αR,γS,2S)-N-((3S,4S)-3,4-dihydro-3-hydroxy-2H-1-benzopyran-4-yl)-γ-hydroxy-α-(3-pyridinylmethyl)-4-[[5-(2-thienyl)-2-furanyl] methyl]-2-[[(2,2,2-trifluoroethyl)amino]carbonyl]-1-piperazinepentanamide

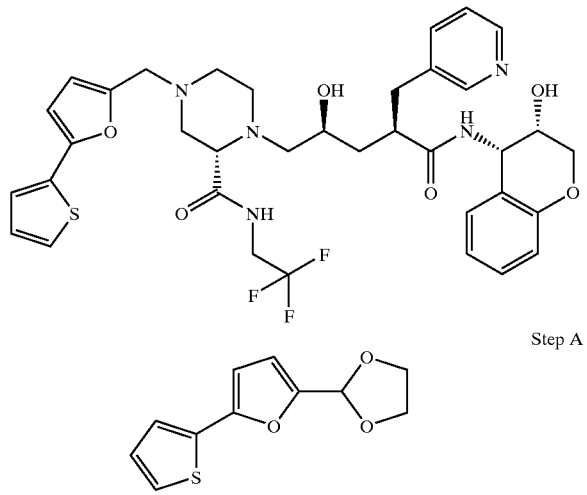

Step A

To a solution of 5-bromo-2-furaldehyde (20 g, 0.11 mol) in benzene (100 mL) was added ethylene glycol (16 mL, 0.28 mol) and p-toluenesulfonic acid (290 mg, 1.5 mmol). The reaction was heated to reflux for 16 hours with azeotropic removal of water, then cooled to ambient temperature and diluted with diethyl ether (1.5 L). The solution was washed with saturated aqueous NaHCO$_3$ (150 mL) and brine (200 mL), dried (MgSO$_4$), and concentrated in vacuo, affording 23 g of a colorless oil. A portion of this material (3.0 g, 14 mmol) was dissolved in DMF (8 mL). To this solution was added 2-(tributylstannyl)thiophene (5.2 mL, 16 mmol) and tetrakis(triphenylphosphine)-palladium(0) (560 mg, 0.48 mmol). The mixture was heated to 100° C. for 3 hours, then cooled to ambient temperature. The reaction was diluted with ethyl acetate (300 mL) and washed with 0.5 N aqueous NaHCO$_3$ (125 mL×3) and brine (125 mL), dried (MgSO$_4$) and concentrated in vacuo. Purification by flash chromatography (10% ethyl acetate in hexane) afforded the title compound. $^1$H NMR (CDCl$_3$, 400 MHz) 7.30 (m, 2H), 7.25 (d, 1H), 7.05 (t, 1H), 6.50 (d, 1H), 6.46 (d, 1H), 5.99 (s, 1H), 4.18 (m, 2H), 4.05 (m, 2H).

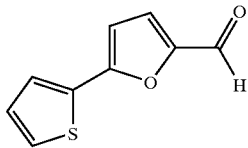

Step B

To a solution of the intermediate prepared in Step A (1,28 g, 5.75 mmol) in THF (35 mL) was added 1 N aqueous HCl (25 mL, 25 mmol). After 16 hours at ambient temperature the reaction was poured onto saturated aqueous NaHCO$_3$ (500 mL) and extracted with ethyl acetate (1 L). The organic layer was dried (MgSO$_4$) and concentrated in vacuo, affording the title compound as an orange oil. $^1$H NMR (CDCl$_3$, 400 MHz) 9.63 (s, 1H), 7.53 (d, 1H), 7.41 (d, 1H), 7.31 (d, 1H), 7.28 (d, 1H), 7.14 (t, 1H), 6.69 (d, 1H).

Step C (αR,γS,2S)-N-((3S,4S)-3,4-dihydro-3-hydroxy-2H-1-benzopyran-4-yl)-γ-hydroxy-α-(3pyridinylmethyl)-4-[[5-(2-thienyl)-2-furanyl] methyl]-2-[[(2,2,2-trifluoroethyl)amino]carbonyl]-1-piperazinepentanamide The title compound was obtained following the procedure described in Example 12, Step E, starting with the intermediate prepared in Example 23, Step F (43.3 mg, 0.0766 mmol) and the aldehyde prepared in Step B (29.4 mg, 0.165 mmol). Purification by flash chromatography (7% methanol in dichloromethane) afforded the title compound as a white solid. $^1$H NMR (CDCl$_3$, 500 MHz) 9.14 (s, 1H) 8.39 (d, J=4.1 Hz, 1H), 8.37 (s, 1H), 7.56 (d, J=7.8 Hz, 1H), 7.28 (m, 3H), 7.10 (m, 3H), 6.80 (t, J=8.0 Hz, 2H), 6.60 (d, J=8.3 Hz, 1H), 6.46 (d, J=3.4 Hz, 1H), 6.30 (d, J=Hz, 1H), 5.22 (dd, J=4.1 Hz, J=8.0 Hz, 1H), 4.10 Hz, (m, 3H), 3.82 (m, 2H), 3.69 (d, J=14.0 Hz, 2H), 3.55 (m, 3H), 3.34 (s, 1H), 2.97 (m, 4H), 2.70 (m, 3H), 2.53 (dd, J=3.0 Hz, J=11.7 Hz, 1H), 2.43 (m, 2H), 1.86 (t, 1H), 1.50 (t, 1H); HPLC-MS (ES) 728.3 (M+1).

EXAMPLE 30

(αR,γS,2S)-N-((3S,4S)-3,4-dihydro-3-hydroxy-2H-1-benzopyran-4-yl)-γ-hydroxy-4-[(1-phenyl-1H-pyrrol-3-yl)methyl]-α-(3-pyridinylmethyl)-2-[[(2,2,2-trifluoroethyl)amino]carbonyl]-1-piperazinepentanamide

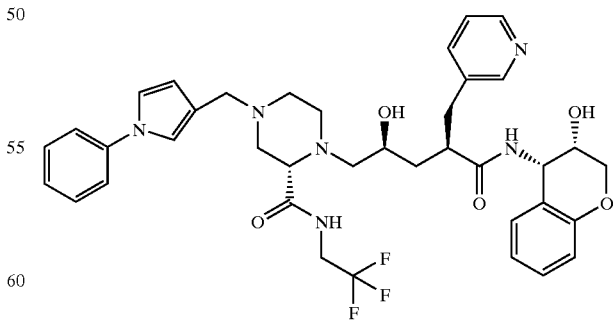

The title compound was obtained following the procedure described in Example 12, Step E, starting with the intermediate prepared in Example 23, Step F (52.7 mg, 0.0934 mmol) and the aldehyde prepared in Example 19, Step A (47.9 mg, 0.280 mmol). Purification by flash chromatography (10% methanol in ethyl acetate) afforded the title compound as a white solid. $^1$H NMR (CDCl$_3$, 400 MHz) 9.38 (s, 1H), 8.44 (s, 2H), 7.56 (d, J=7.6 Hz, 1H), 7.45 (t, J=8.4 Hz, 1H), 7.37 (d, J=7.6 Hz, 1H), 7.24 (d, J=12.8 Hz, 1H), 7.12 (m, 3H), 6.99 (s, 1H), 6.83 (t, J=9.6 Hz, 1H), 6.42 (s, 1H), 6.22 (s, 1H), 5.22 (dd, J=7.6 Hz, 1H), 4.15 (m, 1H), 4.11 (d, J=10.4 Hz, 1H), 4.00 (dd, J=11.6 Hz, 1H), 3.88 (s, 1H), 3.78 (t, J=10.0 Hz, 1H), 3.69 (m, 1H), 3.55 (d, J=13.2 Hz, 1H), 3.44 (d, J=13.2 Hz, 1H), 3.34 (s, 1H), 3.09 (d, J=12.0Hz, 1H), 3.00 (d, J=10.0 Hz, 1H), 2.46(d, J=10.8 Hz, 1H), 2.31 (t, J=7.6 Hz, 1H), 1.88 (t, J=11.2 Hz, 1H), 1.55 (t, J=10.4 Hz, 1H); HPLC-MS (ES) 721.4 (M+1).

EXAMPLE 31

(αR,γS,2S)-N-((3S,4S)-3,4-dihydro-3-hydroxy-2H-1-benzopyran-4-yl)-γ-hydroxy-4-(1-phenyl-1H-imidazol-4-yl)methyl]-α-(3-pyridinylmethyl)-2-[[(2,2,2-trifluoroethyl)amino]carbonyl]-1-piperazinepentanamide

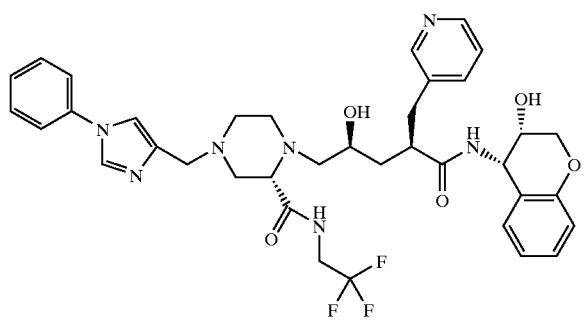

The title compound was obtained following the procedure described in Example 12, Step E, starting with the intermediate prepared in Example 23, Step F (90 mg, 0.160 mmol) and the aldehyde prepared in Example 20, Step B (14 mg, 0.081 mmol). Purification by flash chromatography (15% methanol in ethyl acetate) afforded the title compound as a white solid. $^1$H NMR (CD$_3$OD, 400 MHz) 8.41 (s, 1H), 8.36 (dd, J=1.2 Hz, J=4.8 Hz, 1H) 8.09 (d, J=1.2 Hz, 1H), 7.74 (d, J=7.6 Hz, 1H), 7.54 (m, 5H), 7.36 (m, 2H), 7.12 (m, 2H), 6.83 (dt, J=1.2 Hz, J=7.6 Hz, 1H), 6.73 (d, J=7.2 Hz, 1H), 5.18 (d, J=4.0 Hz, 1H), 4.00 (m, 3H), 3.77 (m, 3H), 3.59 (s, 2H), 3.12 (dd, J=3.2 Hz, J=7.6 Hz, 1H), 3.01 (m, 3H), 2.79 (m, 2H), 2.70 (m, 1H), 2.62 (m, 1H), 2.54 (m, 1H), 2.42 (m, 3H), 2.09 (t, J=11.2 Hz, 1H), 1.41 (m, 2H), 1.28 (s. 1H); HPLC-MS (ES) 722.4 (M+1).

EXAMPLE 32

(αR,γS,2S)-N-((3S,4S)-3,4-dihydro-3-hydroxy-2H-1-benzopyran-4-yl)-γ-hydroxy-4-[[5-(5-methyl-2-thienyl)-2-furanyl]methyl]-α-(3-pyridinylmethyl)-2-[[(2,2,2-trifluoroethyl)amino]carbonyl]-1-piperazinepentanamide

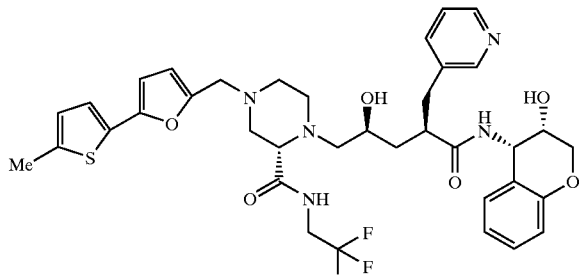

Step A

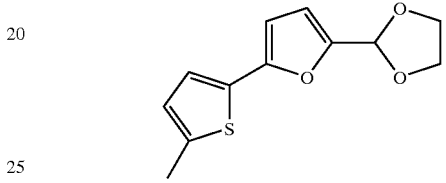

To a solution of the intermediate prepared in Example 29, Step A (1.00 g, 4.50 mmol) in THF (25 mL) at −78° C. was added sec-butyllithium (4.15 mL of a 1.3 M solution in cyclohexane, 5.40 mmol). After 30 min the reaction was warmed to −50° C. for 1 hour, then re-cooled to −78° C. Iodomethane (0.309 mL, 4.95 mmol) was added, and the reaction was warmed to 0° C. and stirred for 1 hour. The reaction was quenched by the slow addition of saturated aqueous NH$_4$Cl (20 mL) and diluted with ethyl acetate (200 mL). The organic layer was washed with saturated aqueous NaHCO$_3$ (100 mL), brine (100 mL), dried (MgSO$_4$), and concentrated in vacuo. Purification by flash chromatography (10% ethyl acetate in hexane) afforded the title compound. $^1$H NMR (CDCl$_3$, 400 MHz) 7.08 (d, 1H), 6.69 (d, 1H), 6.48 (d, 1H), 6.36 (d, 1H), 5.98 (s, 1H), 2.53 (s, 3H).

Step B

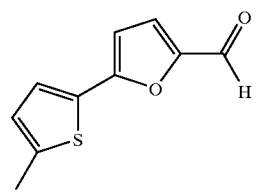

To a solution of the intermediate prepared in Step A (912 mg, 3.86 mmol) in THF (20 mL) at 0° C. was added 1 N aqueous HCl (10 mL, 10 mmol). After 1 hour the reaction was quenched by the slow addition of saturated aqueous NaHCO$_3$ (50 mL), and diluted with ethyl acetate (200 mL). The organic layer was washed with brine (200 mL), dried (MgSO$_4$), and concentrated in vacuo, affording the title compound, which was used without further purification. $^1$H NMR (CDCl$_3$, 400 MHz) 9.60 (s, 1H), 7.37 (d, 1H), 7.28 (d, 1H), 6.79 (d, 1H), 6.59 (d, 1H), 2.57 (s, 3H).

Step C (αR,γS,2S)-N-((3S,4S)-3,4-dihydro-3-hydroxy-2H-1-benzopyran-4-yl)-γ-hydroxy-4-[[5-(5-methyl-2-thienyl)-2-furanyl]methyl]-α-(3-pyridinylmethyl)-2-[[(2,2,2-trifluoroethyl)amino]carbonyl]-1-piperazinepentanamide The title compound was obtained following the procedure described in Example 12, Step E, starting with the intermediate prepared in Example 23, Step F (404 mg, 0.716 mmol)

and the aldehyde prepared in Step B (291 mg, 1.51 mmol). Purification by flash chromatography (5% methanol in ethyl acetate) afforded the title compound as a white solid. ¹H NMR (CDCl₃, 500 MHz) 9.18 (s, 1H), 8.35 (d, J=4.6 Hz, 1H), 8.30 (s, 1H), 7.53 (d, J=7.5 Hz, 1H) 7.20 (t, J=5.0 Hz, 1H), 7.10 (m, 2H), 7.02 (d, J=3.4 Hz, 1H), 6.77 (m, 4H), 6.35 (d, J=3.2 Hz, 1H), 6.26 (d, J=3.0 Hz, 1H), 5.21 (m, 1H), 4.08 (m, 4H), 3.79 (m, 2H), 3.68 (d, J=14.0 Hz, 2H), 3.52 (m, 3H), 3.32 (s, 1H), 2.93 (m, 4H), 2.67 (m, 4H), 2.50 (s, 3H), 2.44 (m, 4H), 1.85 (t, 1H), 1.47 (t, 1H); HPLC-MS (ES) 742.3 (M+1).

EXAMPLE 33

(αR,γS,2S)-N-((3S,4S)-3,4-dihydro-3-hydroxy-2H-1-benzopyran-4-yl)-γ-hydroxy4-[(5-phenyl-2-furanyl)methyl]-α-(4-pyridinylmethyl)-2-[[(2,2,2-trifluoroethyl)amino]carbonyl]-1-piperazinepentanamide

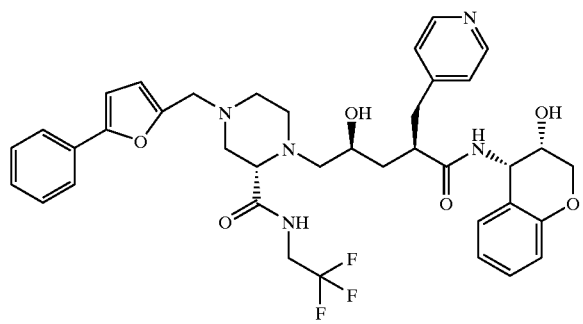

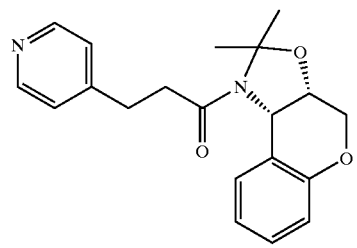

Step A

To a solution of 3-(4-pyridyl)-acrylic acid (25.0 g, 168 mmol) in 1:1 ethanol:THF (250 mL) was added 10% Pd(0)/C (2.50 g). The reaction vessel was placed under 110 psi of H₂ until 1.0 equivalent of H₂ had been consumed as indicated by a pressure drop in the reaction vessel. The mixture was then diluted with 1 L of hot methanol and filtered through celite, rinsing with hot methanol. The liquid obtained was concentrated in vacuo, affording 11.0 g (43% of 3-(4-pyridyl)-propionic acid. This material was dissolved in DMF (300 mL), and to this solution was added the aminochromanol intermediate from Example 1, Step L (12.0 g, 72.5 mmol), HOBT (11.7 g, 87.0 mmol), di-iso-propylethylamine (27.8 mL, 159 mmol) and HBTU (27.5 g, 72.5 mmol). After 2 hours at ambient temperature, the reaction was quenched with 0.5 N aqueous NaHCO₃ (500 mL) and diluted with ethyl acetate (1 L). The organic layer was washed with 0.5 N NaHCO₃ (300 mL×3), brine (300 mL), dried (MgSO₄), and concentrated in vacuo, affording 13.2 g (61%) of the amide as a white solid. A portion of this material (2.27 g, 7.61 mmol) was dissolved in dichlo romethane (100 mL), and 2-methoxypropene (3.64 mL, 38 mmol) was added, followed by camphorsulfonic acid (1.20 g, 5.17 mmol). After 3 hours at ambient temperature the reaction was quenched by the addition of 1.4 mL of triethylamine, and concentrated in vacuo. Purification by flash chromatography (3% methanol in ethyl acetate) afforded the title compound as a clear oil. ¹H NMR (CDCl₃, 400 MHz) 8.55 (d, 2H), 7.58 (s, 1H), 7.26 (m, 3H), 7.00 (d, 1H), 6.84 (t, 1H), 5.81 (s, 1h), 4.88 (s, 1H), 4.40 (d, 2H), 4.18 (m, 3H), 3.02 (m, 3H), 2.70 (m, 1H), 1.62 (s, 3H), 1.30 (s, 1H).

Step B

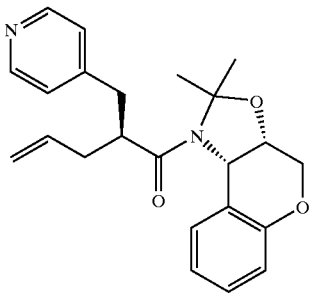

The title compound was obtained following the procedure described in Example 1, Step N, using the intermediate prepared in Step A (3.89 g, 11.5 mmol). Purification by flash chromatography (80% ethyl acetate in hexane) afforded the title compound as a colorless oil. ¹H NMR revealed a 3:1 mixture of rotamers. ¹H NMR of the major rotamer: (CDCl₃, 400 MHz) 8.60 (d, 1H), 7.26 (d, 1H), 7.20 (d, 1H), 7.10 (t, 1H), 6.80 (d, 1H), 6.50 (t, 1H), 6.23 (d, 1H), 5.85 (m, 1H), 5.20 (d, 2H), 4.99 (d, 1H), 4.40 (dd, 1H), 4.20 (dd, 1H), 3.40 (dd, 1H), 3.20 (m, 1H), 2.80 (m, 1H), 2.42 (m, 2H), 1.70 (s, 3H), 1.44 (s, 3H).

Step C

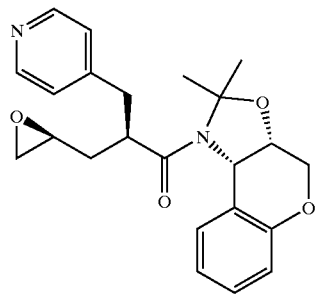

The title compound was obtained following the two step procedure described in Example 1, Steps O and P, using the intermediate prepared in Step B (3.32 g, 8.78 mmol). Purification by flash chromatography (2% methanol in ethyl acetate) afforded the title compound as a colorless oil. ¹H NMR revealed a 3:1 mixture of rotamers. ¹H NMR of the major rotamer (CDCl₃, 400 MHz) 8.60 (d, 2H), 7.26 (d, 2H), 7.17 (d, 1H), 7.13 (t, 1H), 6.63 (d, 1H), 6.58 (t, 1H), 6.38 (d, 1H), 5.39 (d, 1H), 4.43 (dd, 1H), 4.40 (d, 1H), 4.25 (d, 1H), 3.40 (m, 2H), 3.00 (m, 1H), 2.80 (m, 2H), 2.57 (t, 1H), 1.78 (s, 3H), 1.30 (s, 3H)

Step D

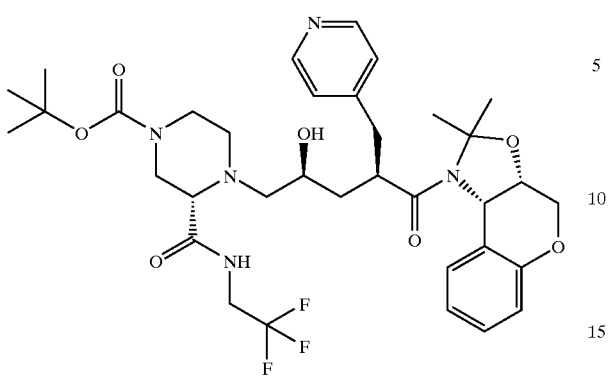

The title compound was obtained following the procedure described in Example 1, Step Q, using the intermediate prepared in Step C (1.89 g, 4.80 mmol) and the piperazine intermediate prepared in Example 12, Step B (1.50 g, 4.80 mmol). Purification by flash chromatography (4% methanol in ethyl acetate) provided the title compound as a yellow gum. $^1$H NMR (CDCl$_3$, 400 MHz) 8.60 (d, 2H), 7.35 (s, 1H, 7.22 (d, 2H), 7.10 (m, 2H), 6.81 (d, 1H), 6.63 (t, 1H), 6.50 (d, 1H), 5.60 (s, 1H). 4.40 (m, 2H), 4.20 (d, 1H), 3.95 (dd, 1H), 3.90 (t, 1H), 3.70 (m, 2H), 3.40 (m, 2H), 3.20 (, 2H), 3.08 (m, 1H), 2.93 (m, 1H), 2.80 (m, 1H), 2.42 (m, 1H), 1.80 (s, 3H), 1.45 (s, 9H), 1.28 (s, 3H).

Step E

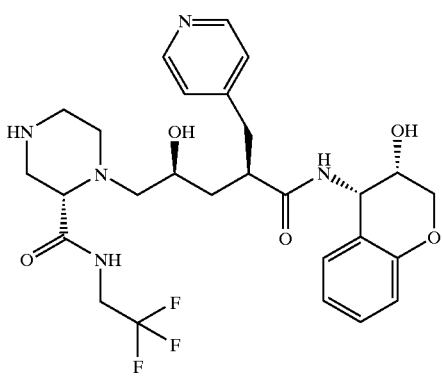

The title compound was obtained as a white solid following the procedure described in Example 12, Step D, using the intermediate prepared in Step D (2.13 g, 3.02 mmol). $^1$H NMR (CD$_3$OD, 400 MHz) 8.40 (d, 2H), 7.38 (m, 3H), 7.16 (m, 2H), 6.86 (t, 1H), 6.77 (d, 1H), 5.20 (d, 1H), 4.10 (m, 2H), 4.00 (m, 1H), 3.80 (m, 3H), 3.18 (m, 1H), 2.90 (m, 4H), 2.45 (dd, 1H), 2.35 (dd, 1H), 2.26 (m, 1H), 1.07 (m, 1H), 1.40 (m, 1H), 1.08 (d, 1H).

Step F (αR,γS,2S)-N-((3S,4S)-3,4-dihydro-3-hydroxy-2H-1-benzopyran-4-yl)-γ-hydroxy-4-[(5-phenyl-2-furanyl)methyl]-α-(4-pyridinylmethyl)-2-[[(2,2,2-trifluoroethyl)amino]carbonyl]-1-piperazinepentanamide The title compound was obtained following the procedure described in Example 12, Step E, starting with the intermediate prepared in Example 33, Step E (104 mg, 0.184 mmol) and the aldehyde prepared in Example 23, Step G (74 mg, 0.431 mmol). Purification by tritration of the crude material with diethyl ether afforded the title compound as a white solid. $^1$H NM (CD$_3$OD, 400 MHz) 8.39 (dd, J=1.6 Hz, J=4.7 Hz, 2H), 7.66 (d, J=8.4 Hz, 2H), 7.36 (t, J=7.4 Hz, 1H), 7.32 (d, J=6.1 Hz, 2H), 7.24 (t, J=7.4 Hz, 1H), 7.10 (m, 2H),6.83 (dt, J=1.1 Hz, J=7.7 Hz, 1H), 6.74 (d, J=8.2 Hz, 1H), 6.70 (d, J=3.3 Hz, 1H), 6.39 (d, J=3.3 Hz, 1H), 5.18 (d, J=4.1 Hz, 1H), 4.07 (m, 3H), 3.80 (m, 3H), 3.67 (s, 2H), 3.09 (dd, J=3.2 Hz, J=8.0 Hz, 2H), 3.00 (m, 2H), 2.81 (m, 3H), 2.57 (m, 2H), 2.42 (m, 3H), 2.08 (t, 1H), 1.39 (t, 1H); HPLC-MS (ES) 722.5 (M+1).

EXAMPLE 34

(αR,γS,2S)-4-(2-benzofuranylmethyl)-N-((3S,4S)-3,4-dihydro-3-hydroxy-2H-1-benzopyran-4-yl)-γ-hydroxy-α-(4-pyridinylmethyl)-2-[[(2,2,2-trifluoroethyl)amino]carbonyl]-1-piperazinepentanamide

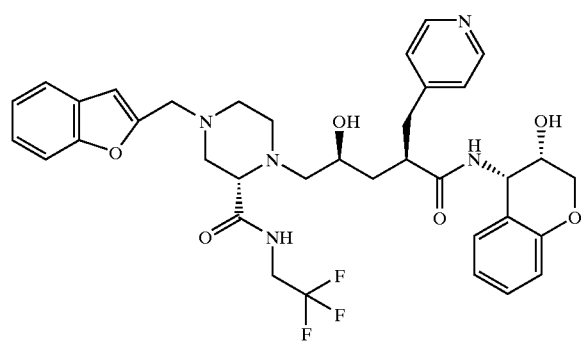

The title compound was obtained following the procedure described in Example 12, Step E, starting with the intermediate prepared in Example 33, Step E (50 mg, 0.088 mmol) and benzofuran-2-carboxaldehyde (30 mg, 0.20 mmol). Purification by flash chromatography (4% methanol in ethyl acetate) afforded the title compound as a white solid. $^1$H NMR (CDCl$_3$, 400 MHz) 9.22 (s, 1H), 8.49 (d, J=5.3 Hz, 2H), 7.56 (d, J=7.4 Hz, 1H), 7.43 (d, J=8.0 Hz, 1H), 7.32 (dt, J=1.3 Hz, J=8.0 Hz, 1H), 7.27 (d, J=0.6 Hz, 2H), 7.17 (m, 3H), 6.82 (d, J=8.2 Hz, 2H), 6.65 (s, 1H), 6.39 (d, 1H), 5.20 (dd, 1H), 4.09 (m, 2H), 4.01 (m, 1H), 3.82 (m, 1H), 3.79 (m, 2H), 3.66 (m, 3H), 3.35 (s, 1H), 3.03 (m, 4H), 2.70 (m, 5H), 2.46 (d, J=10.6 Hz, 2H), 1.87 (t, 1H), 1.58 (t, 1H); HPLC-MS (ES) 696.4 (M+1).

EXAMPLE 35

(αR,γS,2S)-N-((3S,4S)-3,4-dihydro-3-hydroxy-2H-1-benzopyran-4-yl)-γ-hydroxy-4-[1-methyl-1-[5-(4-pyridinyl)-2-furanyl]ethyl]-α-(phenylmethyl)-2-[[(2,2,2-trifluoroethyl)amino]carbonyl]-1-piperazinepentanamide

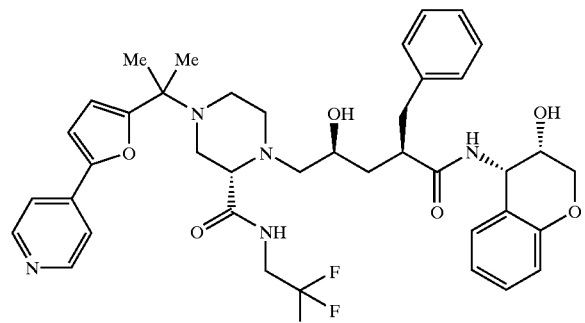

Step A

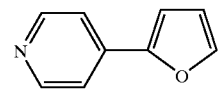

To a solution of 2-(tributylstannyl)-furan (52.1 mL, 165 mmol) in DMF (1.6 L) was added di-iso-propylethylamine (43.0 mL, 248 mmol), and 4-bromopyridine hydrochloride (35.4 g, 182 mmol), followed by tetrakis (triphenylphosphine)-palladium(0) (5.74 g, 49.7 mmol). The solution was heated to 100° C. for 4 hours, then cooled to ambient temperature and diluted with 2 L of diethyl ether. The organic layer was washed with 50% saturated aqueous KF (1 L×2), followed by saturated aqueous NaHCO$_3$ (1 L), and brine (1 L). The organic layer was dried (MgSO$_4$) and concentrated in vacuo. Purification by flash chromatography (35% ethyl acetate in hexane) afforded the title compound as a white solid. $^1$H NMR (CDCl$_3$, 400 MHz) 8.61 (d, 2H), 7.58 (d, 1H), 7.54 (d, 2H), 6.86 (d, 1H), 6.50 (t, 1H).

Step B

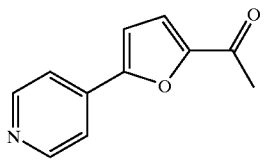

To a solution of the intermediate prepared in Step A (11.3 g, 78.3 mmol) in THF (300 mL) at −78° C. was added sec-butyllithium (66.3 mL of a 1.3 M solution in cyclohexane, 86.1 mmol). After 1 hour at −78° C., N-methoxy-N-methylacetamide (9.69 g, 94.0 mmol) was added. After 5 hours at −78° C. the reaction was quenched by the addition of saturated aqueous NH$_4$Cl (500 mL), warmed to ambient temperature, and diluted with ethyl acetate (500 mL). The organic layer was washed with saturated aqueous NaHCO$_3$ (500 mL), brine (500 mL), dried (MgSO$_4$), and concentrated in vacuo. Purification by flash chromatography (80% ethyl acetate in hexane) afforded the title compound as a yellow solid. $^1$H NMR (CDCl$_3$, 400 MHz) 8.70 (d, 2H), 7.63 (d, 2H), 7.30 (d, 1H), 6.99 (d, 1H), 2.56 (s, 3H)

Step C

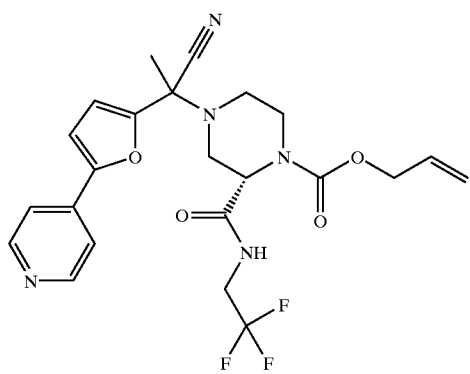

To a solution of the piperazine intermediate prepared in Example 12, Step A (18.2 g, 46.1 mmol) in dichloromethane (200 mL) was added trifluoroacetic acid (100 mL). After 1 hour the reaction was concentrated to a minimum mass under high vacuum, affording a colorless oil. To this material was slowly added trimethylsilyl cyanide (50 mL) via cannula under a vented atmosphere of nitrogen (Caution-HCN evolution). To this solution was then added the ketone intermediate prepared in Step B (6.63 g, 35.4 mmol). The resulting mixture was heated to 60° C. for 3 hours, then cooled to ambient temperature. The reaction was added slowly to a well stirred mixture of ice and 50% aqueous NH$_4$OH via cannula. This solution was extracted with ethyl acetate (500 mL×2), and the organic layers were washed with brine (500 mL), dried (MgSO$_4$), and concentrated in vacuo. Purification by flash chromatography (80% ethyl acetate in hexane) afforded the title compound (1:1 mixture of diastereomers) as a yellow solid.

Step D

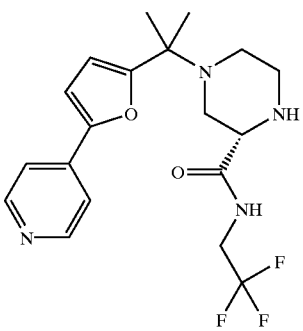

To a solution of the intermediate prepared in Step C (8.62 g, 17.6 mmol) in THF (90 mL) was added thiosalicilic acid (4.06 g, 23.3 mmol). In a separate flask was prepared a solution of dipalladium(0)tris(dibenzylidineacetone) (804 mg, 0.877 mmol) and 1,4-bis(diphenylphosphino)butane (1.01 g, 1.76 mmol) in THF (90 mL). The palladium(0) solution was added to the reaction mixture via cannula. After 2 hours, the reaction was quenched by the addition of 1% aqueous HCl (100 mL). The mixture was diluted with diethyl ether (300 mL) was washed with 1% aqueous HCl (100 mL×3). The combine aqueous layers were brought to pH 8 with saturated aqueous NaHCO$_3$, and extracted with ethyl acetate (300 mL). This organic layer was washed with brine, dried (MgSO$_4$) and concentrated in vacuo. The resulting oil was dissolved in 1,2-dimethoxyethane (200 mL) and cooled to −20° C. To this solution was added methylmagnesium chloride (50 mL of a 3.0 M solution in THF, 150 mmol), and the suspension was stirred at 20° C. for 20 hours. The reaction was quenched by the slow addition of saturated aqueous NH$_4$Cl (100 mL) and warmed to ambient temperature. The mixture was diluted with ethyl acetate (400 mL). The organic layer was washed with saturated aqueous NaHCO$_3$ (200 mL) and brine (200 mL), dried (MgSO$_4$), and concentrated in vacuo. Purification by flash chromatography (5% methanol in acetone) afforded the title compound as a beige solid. $^1$H NMR (CDCl$_3$, 400 MHz) 8.60 (d, 2H), 7.95 (t, 1H), 7.63 (d, 2H), 6.80 (d, 1H), 6.23 (d, 1H), 3.90 (m, 2H), 3.43 (dd, 1H), 2.95 (m, 1H), 3.82 (m, 2H), 2.60 (m, 2H), 2.46 (m, 1H), 1.49 (s, 3H), 1.47 (s, 3H).

Step E

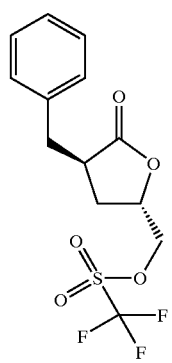

To a solution of dihydro-5(S)-(hydroxymethyl)-3(R)-(phenylmethyl)-3(2H)-furanone (prepared as described in Dorsey et al., *J. Med. Chem.* 1994, 37, 3443–3451) (4.04 g, 19.6 mmol) in dichloromethane (50 mL) at 0° C. was added 2,6-lutidine (3.42 mL, 29.4 mmol) followed by trifluoromethanesulfonic acid anhydride (4.28 mL, 25.5 mmol). After 1 hour the reaction was quenched by the addition of water (20 mL) and diluted with dichloromethane. The organic layer was washed with saturated aqueous NaHCO₃ (100 mL), dried (Na₂SO₄) and concentrated in vacuo. Purification by flash chromatography (5% methanol in acetone) afforded the title compound as a white solid. ¹H NMR (CDCl₃, 400 MHz) 7.32 (m, 3H), 7.20 (d, 2H), 4.60 (dd, 1H), 4.50 (m, 2H), 3.20 (dd, 1H), 3.08(m, 1H), 2.89 (dd, 1H), 2.20 (m, 2H).

Step F

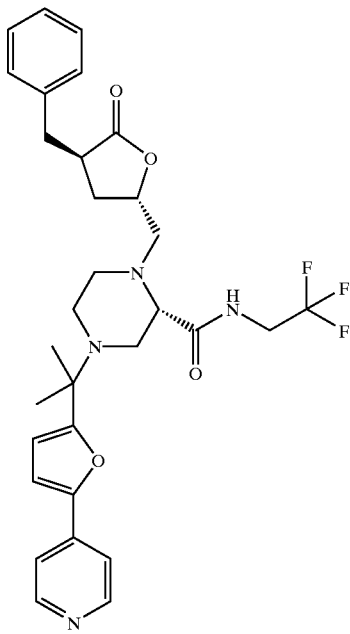

To a solution of the piperazine intermediate prepared in Step D (4.55 g, 11.5 mmol) in 2-propanol (11.5 mL) at 0° C. was added di-iso-propylethylamine (4.00 mL, 23.0 mmol), followed by the lactone intermediate prepared in Step E (4.27 g, 12.6 mmol). After 1 hour at 0° C. the reaction was quenched by the addition of saturated aqueous NaHCO₃ (100 mL) and diluted with ethyl acetate (200 mL). The organic layer was washed with brine (100 mL), dried (MgSO₄), and concentrated in vacuo. Purification by flash chromatography (ethyl acetate) afforded the title compound as a beige solid. ¹H NMR (CDCl₃, 400 MHz) 8.60 (d, 2H), 8.54 (s, 1h), 7.43 (d, 2H), 7.27 (m, 3H), 7.18 (d, 2H), 6.80 (d, 1H), 6.28 (d, 1H), 4.40 (m, 1H), 4.20 (m, 1H), 3.60 (m, 1H), 3.20 (m, 2H), 2.95 (m, 1H), 2.80 (m, 3H), 2.50 (m, 2H), 2.00 (m, 2H), 1.50 (s, 3H), 1.47 (s, 3H).

Step G

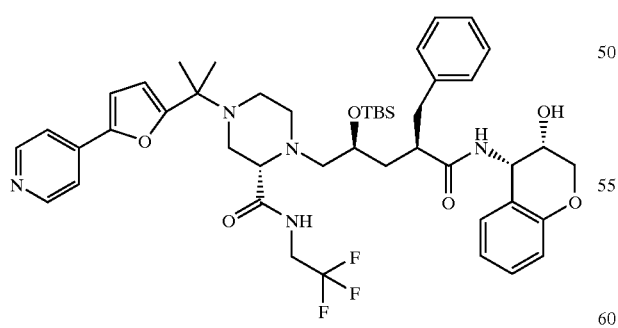

The title compound was obtained following the procedure described in Example 23, Step E, using the lactone intermediate prepared in Step F (3.16 g, 5.41 mmol), and the aminochromanol intermediate prepared in Example 1, Step L (1.16 g, 7.03 mmol). Purification by flash chromatography (75% ethyl acetate in hexane) afforded the title compound as a white solid. ¹H NMR (CDCl₃, 400 MHz) 8.60 (d, 2H), 8.42 (s, 1H), 7.46 (d, 2H), 7.30 (m, 3H), 7.20 (d, 2H), 7.15 (m, 1H), 6.85 (t, 1H), 6.80 (d, 1H), 6.28 (d, 1H), 5.62 (d, 1H), 5.19 (dd, 1H), 4.05 (m, 2H), 3.90 (m, 2H), 3.70 (m, 2H), 3.20 (t, 1H), 2.80 (m, 4H), 2.60 (m, 3H), 2.34 (m, 2H), 1.50 (s, 3H), 1.48 (s, 3H), 0.82 (s, 9H), 0.07 (s, 3H), 0.00 (s, 3H).

Step H (αR,γS, 2S)-N-((3S,4S)-3,4-dihydro-3-hydroxy-2H-1-benzopyran-4-yl)-γ-hydroxy-4-[1-methyl-1-[5-(4-pyridinyl)-2-furanyl]ethyl]-α-(phenylmethyl)-2-[[(2,2,2-trifluoroethyl)amino]carbonyl]-1-piperazinepentanamide To a solution of the intermediate prepared in Step G (4.12 g, 4.78 mmol) in THF (50 mL) was added tetrabutylammonium fluoride (47.8 mL of a 1.0 M solution in THF, 47.8 mmol). After 9 hours at ambient temperature the reaction was diluted with dichloromethane (300 mL) and washed with saturated aqueous NaHCO₃ (200 mL). The organic layer was dried (Na₂SO₄) and concentrated in vacuo. Purification by flash chromatography afforded the title compound as a white solid. ¹H NMR (CDCl₃, 400 MHz) 9.29 (t, J=6.4 Hz, 1H), 8.62 (dd, J=1.6 Hz, J=4.8 Hz, 1H), 7.47 (dd, J=1.6 Hz, J=4.4 Hz, 1H), 7.29 (m, 5H), 7.10 (t, J=8.8 Hz, 1H), 7.06 (d, J=7.6 Hz, 1H), 6.34 (d, J=3.2 Hz, 1H), 5.95 (d, J=8.0Hz, 1H), 5.16 (dd, J=4.4Hz, 1H), 4.13 (m, 1H), 4.07 (d, J=12.4Hz, 1H), 4.00 (dd, J=5.2Hz, J=12.0 Hz, 1H), 3.81 (m, 1H), 3.75 (t, J=10.0 Hz, 1H), 3.65 (m, 1H), 3.35 (s, 1H), 3.10 (d, J=11.6 Hz, 1H), 2.86 (m, 4H), 2.64 (m, 2H), 2.39 (m, 2H), 1.89 (t, J=10.8 Hz, 1H), 1.65 (t, 1H), 1.56 (s, 3H), 1.53 (s, 3H); HPLC-MS (ES) 750.4 (M+1).

EXAMPLE 36

(αR,γS,2S)-N-((3S,4S)-3,4-dihydro-3-hydroxy-2H-1-benzopyran-4-yl)-γ-hydroxy-α-(phenylmethyl)-4-[1-[5-(4-pyridinyl)-1-furanyl]ethyl]-2-[[(2,2,2-trifluoroethyl)amino]carbonyl]-1-piperazinepentanamide (αR,γS,2S)-N-((3S,4S)-3,4-dihydro-3-hydroxy-2H-1-benzopyran-4-yl)-γ-hydroxy-α-(phenylmethyl)-4-[1-[5-(4-pyridinyl)-1-furanyl]ethyl]-2-[[(2,2,2-trifluoroethyl)amino]carbonyl]-1-piperazinepentanamide

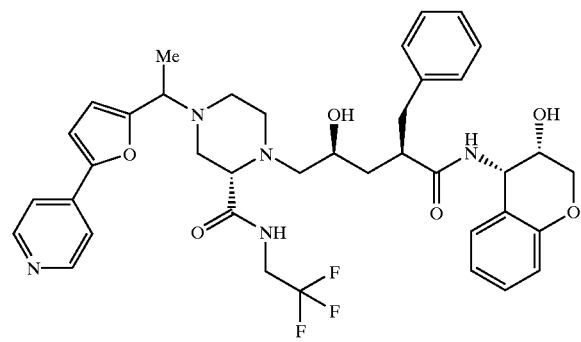

Step A

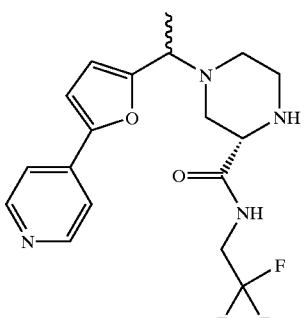

To a solution of the intermediate prepared in Example 35, Step C (740 mg, 1.56 mmol) in THF (5 mL) was added thiosalicilic acid (360 mg, 2.33 mmol). In a separate flask was prepared a solution of dipalladium(0)tris (dibenzylidineacetone) (72.5 mg, 0.079 mmol) and 1,4-bis (diphenylphosphino)butane (67.4 mg, 0.158 mmol) in THF (5 mL). The palladium(0) solution was added to the reaction mixture via cannula. After 2 hours, the reaction was quenched by the addition of 1% aqueous HCl (100 mL). The mixture was diluted with diethyl ether (300 mL) was washed with 1% aqueous HCl (50 mL×3). The combine aqueous layers were brought to pH 8 with saturated aqueous NaHCO$_3$, and extracted with ethyl acetate (100 mL). This organic layer was washed with brine, dried (MgSO$_4$) and concentrated in vacuo. Purification by flash chromatography (7% methanol in ethyl acetate) afforded the free piperazine as a white solid. To a solution of this intermediate (313 mg, 0.770 mmol) in ethanol (5 mL) was added NaBH$_4$ (582 mg, 15.4 mmol). The mixture was heated to 83° C. and stirred for 2.5 hours, then cooled to ambient temperature and diluted with dichloromethane (50 mL). The organic layer was washed with saturated aqueous NaHCO$_3$ (50 mL), dried (NaHCO$_3$) and concentrated in vacuo. Purification by flash chromatography (10% methanol in dichloromethane) afforded the title compound as a 1:1 mixture of diastereomers. $^1$H NMR (CDCl$_3$, 400 MHz) 8.60 (d, 2H), 7.73 (m, 1H), 7.48 (d, 2H), 6.83 (d, 1H), 6.30 (m, 1H), 3.90 (m, 4H), 3.49 (m, 1H) 3.00 (m, 2H), 2.90 (m, 1H), 2.80 (dd, 2H), 2.64 (m, 1H), 2.55 (m, 1H), 2.49 (m, 1H), 2.39 (m, 1H), 1.48 (d, 3H); HPLC-MS (ES) 383.3 (M+1) in two peaks, 1:1 ratio.

Step B

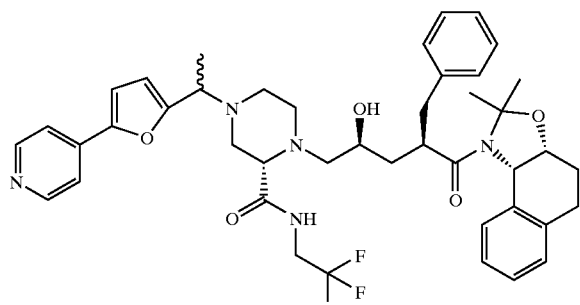

The title compound was obtained following the procedure described in Example 1, Step Q, starting with the intermediate prepared in Example 36, Step A (163 mg, 0.425 mmol) and the epoxide intermediate prepared in Example 1, Step P (235 mg, 0.597 mmol). Purification by flash chromatography (100:10:0.5 dichloromethane:methanol:NH$_4$OH) afforded 220 mg (67%) of a 1:1 mixture of diastereomers. HPLC-MS (ES) 776.6 (M+1) as 2 peaks, 1:1 ratio. This material was further purified by chromatotron, (0–3% methanol in ethyl acetate) affording material enriched in the faster eluting diastereomer. (Diastereomer A) and then material enriched in the slower eluting diastereomer (Diastereomer B).

Step C (αR,γS,2S)-N-((3S,4S)-3,4-dihydro-3-hydroxy-2H-1-benzopyran-4-yl)-γ-hydroxy-α-(phenylmethyl)-4-[1-[5-(4-pyridinyl)-1-furanyl]ethyl]-2-[[(2,2,2-trifluoroethyl)amino]carbonyl]-1-piperazinepentanamide The material enriched in Diastereomer A from Step B (32 mg, 41 μmol) was dissolved in 10 mL of a saturated solution of HCl (g) in methanol at 0° C. The reaction was warmed to ambient temperature over 18 hours, then quenched with saturated aqueous NaHCO$_3$ (15 mL). The mixture was extracted with dichloromethane, and the organic layer was dried (Na$_2$SO$_4$) and concentrated in vacuo. Purification by chromatotron (50% acetone in hexane) afforded the title compound as a white solid. (Diastereomer A, >95% diastereomerically pure) $^1$H NMR (CDCl$_3$, 500 MHz) 9.09 (s, 1H), 8.61 (d, J=4.5 Hz, 2H), 7.49 (d, J=6.0 Hz, 2H), 7.28 (m, 3H), 7.23 (m, 2H), 7.08 (m, 2H), 6.87 (d, J=3.4 Hz, 1H), 6.78 (m, 2H), 6.35 (d, J=3.6 Hz, 1H), 6.03 (d, J=8.0 Hz, 1H), 5.18 (m, 1H), 4.05 (m, 3H), 3.91 (d, J=6.9 Hz, 1H), 3,80 (m, 3H), 3.35 (s, 1H), 3.02 (d, 1H), 2.89 (m, 4H), 2.73 (m, 5H), 2.55 (m, 2H), 2.45 (dd, J=3.0 Hz, J=13.0 Hz, 1H), 1.89 (t, 1H), 1.55 (t, 1H), 1.51 (d, J=6.9 Hz, 3H); HPLC-MS (ES) 736.6 (M+1). Chiral HPLC (Chiralpak AD column, 20% 2-propanol in hexane) indicated>95% diastereomerically pure (t$_r$=14.80 min)

Step D (αR,γS,2S)-N-((3S,4S)-3,4-dihydro-3-hydroxy-2H-1-benzopyran-4-yl)-γ-hydroxy-α-(phenylmethyl)-4-[1-[5-(4-pyridinyl)-1-furanyl]ethyl]-2-[[(2,2,2-trifluoroethyl)amino]carbonyl]-1-piperazinepentanamide The title compound was obtained using the procedure described in Step C using the material enriched in Diastereomer B from Step B (23 mg, 30 ,mol). Purification by chromatotron (150:10:1 dichloromethane:methanol:NH$_4$OH) afforded 10 mg (46%) of a mixture of diastereomers with no appreciable diastereomeric enrichment over the starting material. A saturated solution of this material in 2-propanol was prepared, and 1 mL of this solution was injected on a chiral preparative HPLC (Chiralpak AD, 20% 2-propanol in hexane). The fractions enriched in diastereomer B were collected and concentrated in vacuo, affording of a white solid. Chiral HPLC (Chiralpak AD, 20% 2-propanol in hexane) indicated an 82:18 mixture of Diastereomer B (t$_r$=16.16 min) and Diastereomer A (t$_r$=14.80 min). $^1$H NMR of major diastereomer (CDCl$_3$, 500 MHz) 9.12 (s, 1H), 8.63 (d, J=5.5 Hz, 2H), 7.50 (d, J=4.6 Hz, 2H), 7.31 (m, 4H), 7.09 (d, J=7.6 Hz, 1H), 7.06 (d, J=7.5 Hz, 1H), 6.87 (d, J=3.4 Hz, 1H), 6.79 (t, J=7.8 Hz, 2H), 6.36 (d, J=3.4 Hz, 1H), 6.00 (d, J=8.0 Hz, 1H), 5.16 (dd, J=3.9 Hz, J=7.7 Hz, 1H), 4.06 (d, J=11.5 Hz, 1H), 3.96 (m, 4H), 3.80 (s, 2H), 3.34 (s, 1H), 2.96 (m, 4H), 2.78 (m, 4H), 2.68 (m, 4H), 2.45 (d, J=13.0 Hz, 2H), 2.19 (s, 1H), 1.90 (t, 1H), 1.55 (t, 1H), 1.49 (d, J=Hz, 3H); HPLC-MS (ES) 736.5 (M+1).

EXAMPLE 37

(αR,γS, 2S)-N-((3S,4S)-3,4-dihydro-3-hydroxy-2H-1-benzopyran-4-yl)-γ-hydroxy-4-[1-methyl-1-(1-phenyl-1H-pyrazol-3-yl)ethyl]-α-(3-pyridinylmethyl)-2-[[(2,2,2-trifluoroethyl)amino]carbonyl]-1-piperazinepentanamide

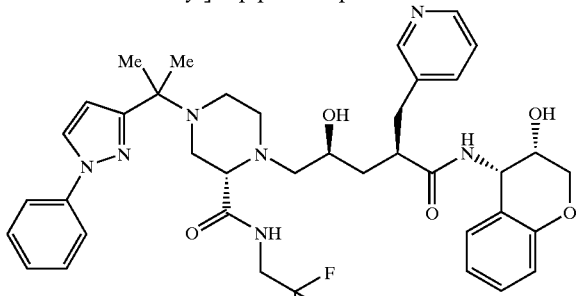

Step A

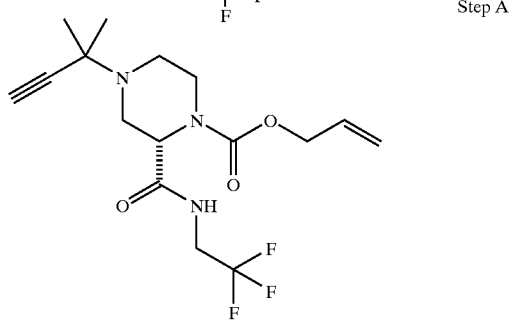

To a solution of the piperazine intermediate prepared in Example 12, Step A (15.3 g, 38.7 mmol) in dichloromethane (50 mL) was added trifluoroacetic acid (25 mL). After 70 min the reaction was concentrated in vacuo to a colorless oil. This material was dissolved in THF (200 mL) and cooled to 0° C. To this solution was added CuCl (380 mg, 3.87 mmol), followed by 3-Chloro-3-methyl-1-butyne (5.22 mL, 46.5 mmol), copper powder (250 mg, 3.87 mmol), and triethylamine (12 mL, 85.2 mmol). After warming to ambient temperature and stirring 16 hours, the reaction was filtered through celite. The liquor was diluted with ethyl acetate (500 mL) washed with saturated aqueous NaHCO₃ (500 mL), and brine (500 mL), dried (MgSO₄) and concentrated in vacuo. Purification by flash chromatography (10% methanol in dichloromethane) afforded the title compound as a colorless oil. $^1$H NMR (CDCl₃, 400 MHz) 7.50 (s, 1H), 5.91 (m, 1H), 5.33 (d, 1H), 5.20 (d, 1H), 4.80 (s, 1H, 4.60 (m, 2H), 3.93 (m, 3H), 3.52 (d, 1H), 3.14 (s, 1H), 2.96 (s, 1H), 2.43 (d, 1H), 2.28 (m, 2H), 1.42 (s, 3H), 1.38 (s, 3H); HPLC-MS (ES) 362.3 (M+1).

Step B

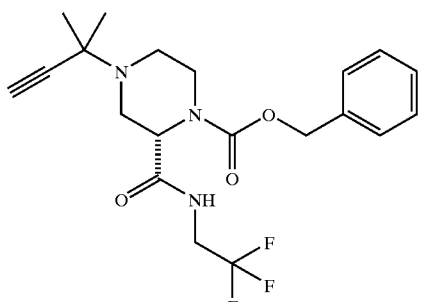

To a solution of the intermediate prepared in Step A (10.9 g, 30.1 mmol) in THF (150 mL) was added thiosalicilic acid (6.97 g, 45.2 mmol). In a separate flask was prepared a solution of dipalladium(0)tris(dibenzylidineacetone) (1.38 g, 1.51 mmol) and 1,4-bis(diphenylphosphino)butane (1.73 g, 3.01 mmol) in THF (150 mL). The palladium(0) solution was added to the reaction mixture via cannula. After 2 hours the reaction was quenched by the addition of 1% aqueous HCl (300 mL). The mixture was diluted with diethyl ether (600 mL) was washed with 1% aqueous HCl (100 mL×3). The combine aqueous layers were brought to pH 8 with saturated aqueous NaHCO₃, and extracted with ethyl acetate (500 mL). This organic layer was washed with brine, dried (MgSO₄) and concentrated in vacuo, affording a colorless oil. This material was dissolved in dichloromethane (250 mL) and cooled to 0° C. To this solution was added triethylamine (4.49 mL, 32.2 mmol) and benzoylchloride (4.60 mL, 32.2 mmol). The solution was warmed to ambient temperature and stirred for 18 hours, then quenched by the addition of saturated aqueous NaHCO₃ (200 mL). The organic layer was extracted and dried (Na₂SO₄) and concentrated in vacuo. Purification by flash chromatography (5% methanol in ethyl acetate) afforded the title compound as a colorless oil. $^1$H NMR (CDCl₃, 400 MHz) 7.27 (m, 5H), 5.18 (dd, 2H), 4.80 (s, 1H), 3.90 (m, 2H), 3.55 (d, 1H), 3.17 (s, 1H), 2.92 (s, 1H), 2.40 (dd, 1H), 2.24 (m, 2H), 1.41 (s, 3H), 1.39 (s, 3H); HPLC-MS (ES) 412.3 (M+1).

Step C

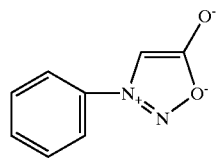

To a suspension of N-phenylglycine (10.0 g, 66.2 mmol) in acetic acid (70 mL) was added water (70 mL). The suspension was cooled to 0° C., and NaNO₂ (5.02 g, 72.8 mmol) was added slowly. After 90 min the reaction was extracted with benzene (200 mL×2). The organic layers were dried (MgSO₄) and to the resulting solution was added acetic anhydride (18.7 mL, 198 mmol). The reaction was heated to reflux for 18 hours; then cooled to ambient temperature and washed with saturated aqueous NaHCO₃ (300 mL), and brine. The organic layer was dried (MgSO₄) and concentrated in vacuo. Purification by flash chromatography (65% ethyl acetate in hexane) afforded of the title compound as a yellow solid. $^1$H NMR (CDCl₃, 400 MHz) 7.74 (d, 2H), 7.68 (m, 3H), 6.70 (s, 1H).

Step D

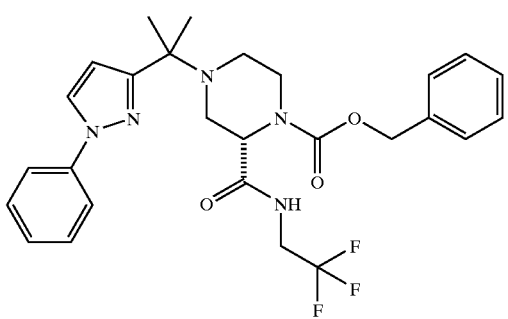

To a solution of the intermediate from Step B (6.95 g, 16.9 mmol) in m-dichlorobenzene (13 mL) was added the intermediate from Step C (2.74 g, 16.9 mmol). The resulting suspension was heated to 180° C. for 22 hours. The solvent was removed in vacuo. Purification by flash chromatography (30% ethyl acetate in hexane) afforded the title compound. $^1$H NMR (CDCl₃, 400 MHz) 8.17 (s, 1H), 7.78 (d, 2H), 7.52 (t, 2H), 7.30 (m, 5H), 6.40 (d, 1H), 5.17 (m, 2H), 4.70 (d, 1h), 3.94 (m, 4H), 3.60 (m, 1H), 3.37 (m, 3H), 3.00 (m, 2H), 2.44 (dt, 1H), 2.22 (m, 1H), 1.51 (s, 6H).

Step E

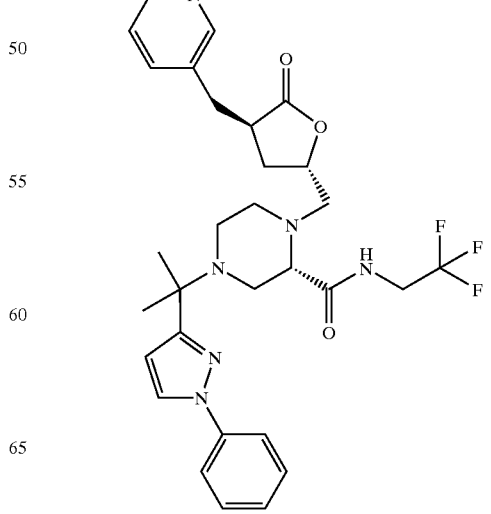

To a solution of the intermediate from Step D (5.66 g, 10.7 mmol) in methanol (50 mL) was added triethylamine (2.24 mL, 16.1 mmol), and 10% Pd(0) on carbon (1.13 g). The reaction mixture was placed under 1 atm of H₂ gas for 3 hours, then the reaction was filtered through celite. The solution was concentrated in vacuo, and the resulting oil was dissolved in DMF (8 mL). To this solution was added di-iso-propylethylamine (2.05 mL, 11.8 mL), followed by the intermediate from Example 23 Step C (3.39 g, 10.7 mmol). The solution was heated to 90° C. for 17 hours, then cooled to ambient temperature, diluted with ethyl acetate (300 mL) and washed with 0.5 N aqueous NaHCO₃ (200 mL×3). The organic layer was then washed with brine (200 mL), dried (MgSO₄) and concentrated in vacuo. Purification by flash chromatography (7% methanol in ethyl acetate) afforded the title compound. ¹H NMR (CD₃OD, 400 MHz) 8.48 (s, 1H), 8.43 (d, 1H), 8.16 (d, 1H), 8.04 (s, 1H), 7.78 (m, 2H), 7.52 (t, 2H), 7.41 (t, 1H), 7.36 (t, 1H), 6.50 (d, 1H), 4.67 (m, 1H), 4.00 (m, 1H), 3.76 (m, 1H), 3.27 (m, 1H), 3.18 (m, 2H), 3.04 (m, 2H), 2.80 (m, 1H), 2.58 (m, 4H), 2.17 (m, 2H), 1.53 (s, 6H); HPLC-MS (ES) 585.4 (M+1).

Step F

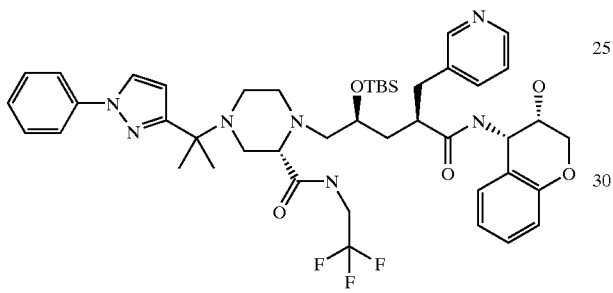

The title compound was obtained following the procedure described in Example 23, Step E, using the lactone intermediate prepared in Step E (1.94 g, 3.32 mmol), and the aminochromanol intermediate prepared in Example 1, Step L (0.80.g, 3.92 mmol). Purification by flash chromatography (15% ethyl acetate in hexane) afforded the title compound as a white solid. HPLC-MS (ES) 864.5 (M+1).

Step G (αR,γS,2S)-N-((3S,4S)-3,4-dihydro-3-hydroxy-2H-1-benzopyran-4-yl)-γ-hydroxy-4-[1-methyl-1-(1-phenyl-1H-pyrazol-3-yl)ethyl]-α-(3-pyridinylmethyl)-2-[[(2,2,2-trifluoroethyl)amino] carbonyl]-1-piperazinepentanamide To a solution of the intermediate prepared in Step F (1.70 g, 1.97 mmol) in THF (50 mL) was added tetrabutylammonium fluoride (19.7 mL of a 1.0 M solution in THF, 19.7 mmol). After 9 hours at ambient temperature the reaction was diluted with dichloromethane (300 mL) and washed with saturated aqueous NaHCO₃ (200 mL). The organic layer was dried (Na₂SO₄) and concentrated in vacuo. Purification by flash chromatography (10% methanol in dichloromethane) afforded the title compound as a white solid. ¹H NMR (CD₃OD, 400 MHz) 8.38 (d, J=2.0 Hz, 1H), 8.34 (dd, J=1.6 Hz, J=5.2 Hz, 1H), 8.10 (d, J=2.4 Hz, 1H), 7.72 (dd. J=1.2 Hz, J=7.6 Hz, 3H), 7.44 (t, J=8.0 Hz, 2H), 7.29 (m, 2H), 7.09 (m, 2H), 6.80 (dt, J=1.2 Hz, J=7.6 Hz, 1H), 6.72 (dd, J=0.8 Hz, J=8.4 Hz, 1H), 6.44 (d, J=2.4 Hz, 1H), 5.16 (d, J=4.0 Hz, 1H), 4.01 (m, 3H), 3.73 (m, 3H), 3.00 (m, 4H), 2.70 (m, 5H), 2.55 (t, J=8.0 Hz, 1H), 2.39 (m, 3H), 2.06 (t, J=11.6 Hz, 1H), 1.51 (s, 3H), 1.50 (s, 3H), 1.39 (dt, J 2.8 Hz, J=9.2 Hz, 1H); HPLC-MS (ES) 750.4 (M+1).

EXAMPLE 38

(αR,γS,2S)-N-((3S,4S)-3,4-dihydro-3-hydroxy-2H-1-benzopyran-4-yl)-γ-hydroxy-4-[1-methyl-1-(3-phenyl-5-isoxazolyl)ethyl]-α-(3-pyridinylmethyl)-2-[[(2,2,2-trifluoroethyl)amino]carbonyl]-1-piperazinepentanamide

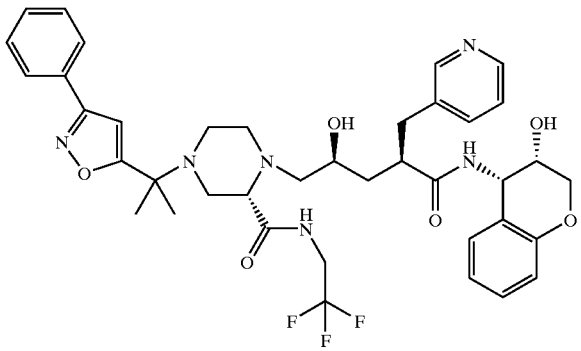

Step A

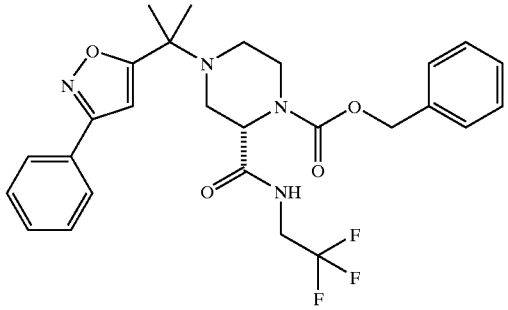

To a solution of bezaldehyde oxime (6.06 g, 50.0 mmol) in DMF (42 mL) at 0° C. was added N-chlorosuccinimide (6.68 g, 50.0 mmol) over 1 hour. The reaction was warmed to ambient temperature over 1 hour, then quenched by the addition of water (200 mL). The mixture was extracted with diethyl ether (200 mL×2), and the organic layers were washed with saturated aqueous NaHCO₃ (100 mL), brine (100 mL), and concentrated in vacuo, affording 6.4 g (82%) of the hydroxamic acid chloride as a white solid. This material (6.24 g, 40.2 mmol) was added to a solution containing the intermediate from Example 37, Step B (6,68 g, 16.25 mmol) and triethylamine (6.73 mL, 48.3 mmol) in THF (80 mL) over 3 hours. After 5 hours at ambient temperature the reaction was diluted with diethyl ether (300 mL) and washed with saturated aqueous NaHCO₃ (200 mL), brine (200 mL), dried (MgSO₄), and concentrated in vacuo. Purification by flash chromatography (35% ethyl acetate in hexane) afforded the title compound. ¹H NMR (CDCl₃, 400 MHz) 7.79 (d, 1H), 7.42 (m, 3H), 7.32 (m, 5H), 6.37 (s, 1H), 5.16 (s, 2H), 4.76 (m, 1H), 4.00 (m, 1H), 3.95 (m, 1H), 3.50 (m, 1H), 3.10 (m, 1H), 2.92 (m, 1H), 2.32 (dd, 1H), 2.20 (m, 1H), 1.51 (s, 3H), 1.49 (s, 3H); HPLC-MS (ES) 531.4 (M+1).

Step B

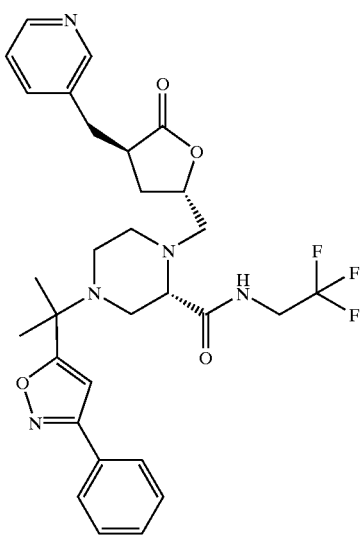

The title compound was obtained using the procedure described in Example 37, Step E, using the intermediate prepared in Step A (6.82 g, 12.9 mmol), and the lactone intermediate prepared in Example 23, Step C (710 mg, 2.46 mmol). Purification by flash chromatography (5% methanol in ethyl acetate) afforded the title compound as a colorless oil. HPLC-MS (ES) 586.4 (M+1).

Step C

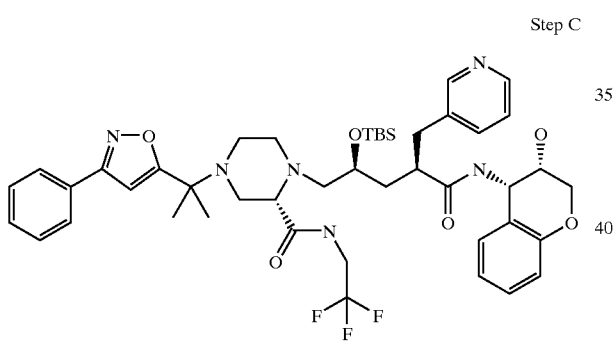

The title compound was obtained following the procedure described in Example 23, Step E, using the lactone intermediate prepared in Step B (560 mg, 0.96 mmol), and the aminochromanol intermediate prepared in Example 1, Step L (0.170 g, 1.13 mmol). Purification by flash chromatography (ethyl acetate) afforded the title compound as a white solid. HPLC-MS (ES) 865.5 (M+1).

Step D (αR,γS,2S)-N-((3S,4S)-3,4-dihydro-3-hydroxy-2H-1-benzopyran-4-yl)-γ-hydroxy-4-[1-methyl-1-(3-phenyl-5-isoxazolyl)ethyl]-α-(3-pyridinylmethyl)-2-[[(2,2,2-trifluoroethyl)amino]carbonyl)-1-piperazinepentanamide The title compound was prepared as described in Example 37, Step G, using the intermediate prepared in Step C (310 mg, 0.36 mmol). Purification by flash chromatography (6% methanol in dichloromethane) afforded the title compound as a white solid. $^1$H NMR (CD$_3$OD, 400 MHz) 8.38 (d, J=1.6 Hz, 1H), 8.34 (dd, J=1.6 Hz, J=4.8 Hz, 1H), 7.82 (m, 2H), 7.72 (d, J=8.0 Hz, 1H), 7.47 (m, 3H), 7.32 (dd, J=4.8 Hz, J=7.6 Hz, 1H), 7.10 (m, 2H), 6.82 (t, J=6.4 Hz, 1H), 6.75 (m, 3H), 5.16 (d, J=3.6 Hz, 1H), 4.03 (m, 3H), 3.76 (m, 3H), 3.01 (m, 4H), 2.80 (m, 3H), 2.64 (dd, J=6.8 Hz, J=10.4 Hz, 1H), 2.51 (t, J=8.4 Hz, 1H), 2.41 (m, 3H), 2.05 (t, J=11.2 Hz, 1H), 1.55 (s, 6H), 1.39 (m, 2H); HPLC-MS (ES) 751.5 (M+1).

EXAMPLE 39

(αR,γS,2S)-N-((3S,4S)-3,4-dihydro-3-hydroxy-2H-1-benzopyran-4-yl)-γ-hydroxy-4-[1-methyl-1-(3-phenyl-5-isoxazolyl)ethyl]]-α-(phenylmethyl)-2-[[(2,2,2-trifluoroethyl)amino]carbonyl]-1-piperazinepentanamide

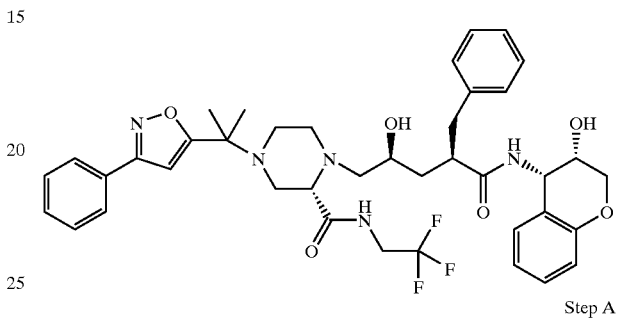

Step A

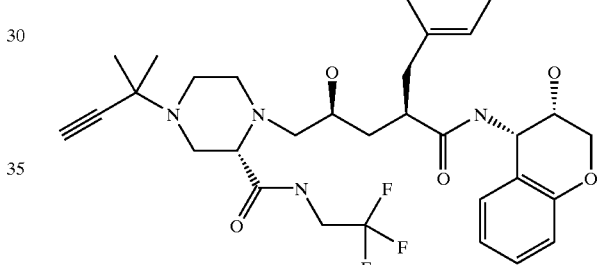

To a solution of the intermediate prepared in Example 12, Step D (1.01 g, 1.78 mmol) in THF (20 mL) at 0° C. was added triethylamine (0.546 mL, 3.92 mmol), followed by CuCl (17.6 mg, 1.78 mmol), 3-chloro-3-methylbutene (0.200 mL, 1.78 mmol), and copper powder (11.3 mg, 1.78 mmol). The mixture was warmed to ambient temperature and stirred 18 hours, then quenched by the addition of saturated aqueous NaHCO$_3$ (100 mL) and extracted with dichloromethane (100 mL×2). The organic layers were dried (Na$_2$SO$_4$) and concentrated in vacuo, yielding the title compound as a yellow solid. $^1$H NMR (CDCl$_3$, 400 MHz) 9.14 (m, 1H), 7.25 (m, 5H), 7.18 (t, 1H), 7.12 (d, 1H), 6.83 (t, 1H), 6.81 (d, 1H), 6.05 (d, 1H), 5.20 (dd, 1H), 4.06 (m, 3H), 3.90 (m, 1H), 3.60 (d, 1H), 3.40 (s, 1H), 3.21 (d, 1H), 2.94 (m, 2H), 2.80 (m, 2H), 2.65 (m, 3H), 2.47 (m, 3H), 2.23 (s, 1H), 1.93 (t, 1H), 1.60 (t, 1H), 1.40 (s, 6H).

Step B (αR,γS,2S)-N-((3S,4S)-3,4-dihydro-3-hydroxy-2H-1-benzopyran-4-yl)-γ-hydroxy-4-[1-methyl-1-(3-phenyl-5-isoxazolyl)ethyl]]-α-(phenylmethyl)-2-[[(2,2,2-trifluoroethyl)amino]carbonyl]-1-piperazinepentanamide To a solution of the intermediate prepared in Step A (500 mg, 0.794 mmol) in THF (1 mL) was added triethylamine (1.10 mL, 7.94 mmol). The solution was heated to 50° C., and a solution of the hydroxamic acid chloride prepared in Example 38, Step A (1.00 g, 6.43 mmol) in 2.2 mL THF was added via syringe pump over 5 hours. After 36 hours at 50° C. the reaction was cooled to ambient temperature and diluted with ethyl acetate (100 mL). The organic layer was washed with 0.5 N NaHCO₃ (100 mL), brine (100 mL), dried (MgSO₄) and concentrated in vacuo. Purification by flash chromatography (4% methanol in dichloromethane) afforded the title compound as a white solid. ¹H NMR (CDCl₃, 500 MHz) 9.16 (s, 1H), 7.80 (d, J=3.4 Hz, 1H), 7.47 (s, 2H), 7.28 (d, J=7.1 Hz, 2H), 7.22 (s, 2H), 7.08 (t, J=7.3 Hz, 2H), 6.79 (t, J=7.6 Hz, 2H), 6.43 (s, 1H0, 6.15 (d, J=8.0 Hz, 1H), 5.15 (m, 1H), 4.20 (m, 1H), 4.03 (m, 2H), 3.79 (m, 3H), 3.56 (s, 1H), 3.50 (q, J=6.8 Hz, 1H), 3.33 (s, 1H), 2.92 (m, 4H), 2.80 (d, 11.6 Hz, 1H), 2.71 (m, 4H), 2.45 (s, 2H), 2.32 (s, 1H), 1.90 (t, J=12.1 Hz, 2H), 1.57 (s, 3H), 1.55 (s, 3H), 1.22 (t, J=6.7 Hz, 1H); HPLC-MS (ES) 750.5 (M+1).

EXAMPLE 40

(αR,γS,2S)-4-[(7-chlorobenzofuran-2-yl)methyl]-N-((3S,4S)-3,4-dihydro-3-hydroxy-2H-1-benzopyran-4-yl)-γ-hydroxy-(α-(3-pyridinylmethyl)-2-[[(2,2,2-trifluoroethyl)amino]carbonyl]-1-piperazinepentanamide

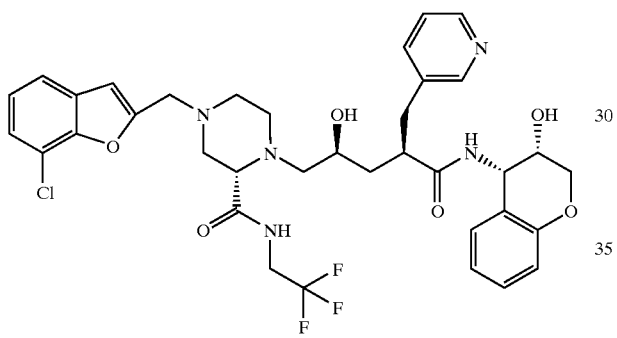

Step A

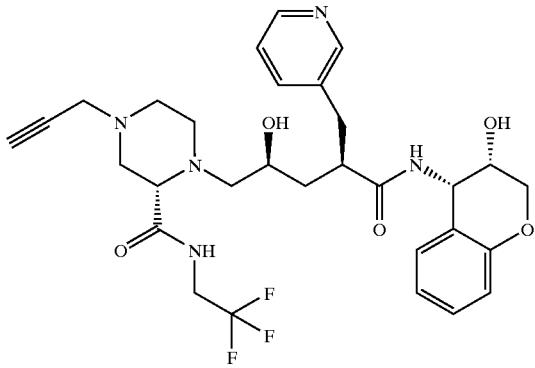

To a solution of the intermediate obtained in Example 23, Step F (57.7 mg, 0.102 mmol) in DMF (2 mL) at 0° C. was added di-iso-ppropylethyamine (44.5 μL, 0.255 mmol), followed by propargyl bromide (12.5 ul of an 80% solution in toluene, 0.1 12 mmol). The reaction was warmed to ambient temperature and stirred for 18 hours. The reaction was then quenched by the addition of 0.5 N aqueous NaHCO₃ (30 mL) and extracted with ethyl acetate (50 mL). The organic layer was washed with brine (20 mL), dried (MgSO₄) and concentrated in vacuo, affording the title compound as a beige solid. ¹H NMR (CDCl₃, 400 Mhz) 8.76 (t, 1H), 8.40 (d, 1H), 8.37 (s, 1H), 7.56 (d, 1H), 7.20 (m, 1H), 7.13 (dd, 1H), 6.80 (m, 2H), 6.60 (d, 1H), 5.20 (dd, 1H), 4.10 (m, 3H), 3.80 (m, 3H), 3.37 (m, 3H), 3.04 (m, 1H), 2.91 (m, 1H), 2.80 (m, 1H), 2.72 (m, 2H), 2.54 (m, 1H), 2.47 (dd, 1H), 1.87 (d, 1H), 154 (t, 1H);

Step B

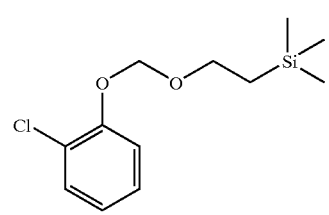

To a solution of 2-chlorophenol (0.500 mL, 4.83 mmol) in THF (10 mL) at 0° C. was added sodium hexamethyldisilylazide (5.30 mL of a 1.0 M solution in THF, 5.30 mmol). After 30 min at 0° C., 2-(trimethylsilyloxy)ethoxymethyl chloride (0.940 mL, 5.30 mmol) was added, and the solution was warmed to ambient temperature and stirred an additional 2 hours. The reaction was diluted with diethyl ether (100 mL) and washed with saturated aqueous NaHCO₃ (100 mL), and brine (100 mL), dried (MgSO₄), and concentrated in vacuo. Purification by flash chromatography (1% ethyl acetate in hexane) afforded the title compound. ¹H NMR (CDCl₃, 300 MHz) 7.36 (d, 1H), 7.21 (d, 2H), 6.96 (m, 1H), 5.30 (s, 2H), 3.80 (dd, 2H), 0.97 (dd, 1H), 0.00 (s, 9H).

Step C

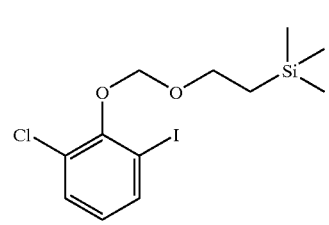

To a solution of the intermediate prepared in Step B (304 mg, 1.17 mmol) in THF (6 mL) at -78° C. was added t-butyllithium (0.760 mL of a 1.7 M solution in hexanes, 1.29 mmol). The solution was warmed to 0° C. for 45 min, then recooled to -78° C. A solution of 12 (327 mg, 1.29 mmol) in THF (3 mL) was added dropwise, and the reaction was slowly warmed to ambient temperature for 30 min. The reaction was quenched by the addition of saturated aqueous NaHCO₃ (30 mL) and diluted with diethyl ether (100 mL). The organic layer was washed with 1 N aqueous Na₂S₂O₃ (50 mL) and brine (50 mL), dried (MgSO₄), and concentrated in vacuo. Purification by flash chromatography (1% ethyl acetate in hexane) afforded the title compound. ¹H NMR (CDCl₃, 300 MHz) 7.68 (d, 1H), 7.35 (d, 1H), 6.77 (t, 1H), 5.19 (s, 2H), 4.02 (dd, 2H), 1.04 (dd, 1H), 0.02 (s, 9H).

Step D

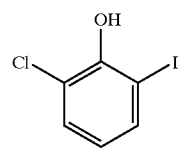

To a solution of the intermediate prepared in Step C (2.60 g, 6.76 mmol) in THF (20 mL) was added tetrabutylammonium fluoride (13.5 mL of a 1.0 M solution in THF, 13.5 mmol). The reaction was heated to reflux for 2 hours, then cooled to ambient temperature and poured onto ethyl acetate (100 mL). The resulting suspension was filtered through celite. The liquid was then washed with water (100 mL×2) and brine, dried (MgSO$_4$), and concentrated in vacuo. Purification by flash chromatography (2% ethyl acetate in hexane) afforded the title compound. $^1$H NMR (CDCl$_3$, 300 MHz) 7.62 (dd, 1H), 7.32 (dd, 1H), 6.63 (d, 1H), 5.93 (s, 1H).

Step E (αR,γS,2S)-4-[(7-chlorobenzofuran-2-yl)methyl]-N-((3S,4S)-3,4-dihydro-3-hydroxy-2H-1-benzopyran-4-yl)-γ-hydroxy-α-(3-pyridinylmethyl)-2-[[(2,2,2-trifluoroethyl)amino]carbonyl]-1-piperazinepentanamide To a solution of the intermediate prepared in Step A (37.4 mg, 0.0620 mmol) in pyridine (1 mL) was added the intermediate prepared in Step D (18.3 mg, 0.0744 mmol), followed by Cu$_2$O (13.3 mg, 0.093 mmol). The mixture was heated to reflux for 1.5 hours, then cooled to ambient temperature and diluted with dichloromethane (30 mL). The organic layer was washed with saturated aqueous NaHCO$_3$ (30 mL), dried (Na$_2$SO$_4$), and concentrated in vacuo. Purification by flash chromatography (10% methanol in ethyl acetate) afforded the title compound as a white solid. $^1$H NMR (CDCl$_3$, 400 MHz) 9.16 (s, 1H), 8.46 (s, 1H), 7.57 (d, 1H), 7.46 (d, J=7.6 Hz, 1H), 7.20 (m, 6H), 6.81 (d, J=6.8 Hz, 1H), 6.70 (s, 1H), 6.42 (d, J=8.0 Hz, 1H), 5.23 (d, 1H), 4.24 (m, 1H), 4.12 (d, J=10.8 Hz, 1H), 4.02 (m, 1H), 3.84 (m, 4H), 3.36 (s, 1H), 3.02 (m, 2H), 2.89 (m, 1H), 2.74 (m, 2H), 2.60 (d, J=11.2 Hz, 1H), 2.47 (d, J=12.0 Hz, 1H), 1.89 (t, J=12.4 Hz, 1H) 1.54 (t, 1H); HPLC-MS (ES) 730.4 (M+1).

EXAMPLE 41

(αR,γS,2S)-N-((3S,4S)-3,4-dihydro-3-hydroxy-2H-1-benzopyran-4-yl)-4-(1-furo[3,2-c]pyridin-2-yl-1-methylethyl)-γ-hydroxy-α-(phenylmethyl)-2-[[(2,2-difluoroethyl)amino]carbonyl]-1-piperazinepentanamide

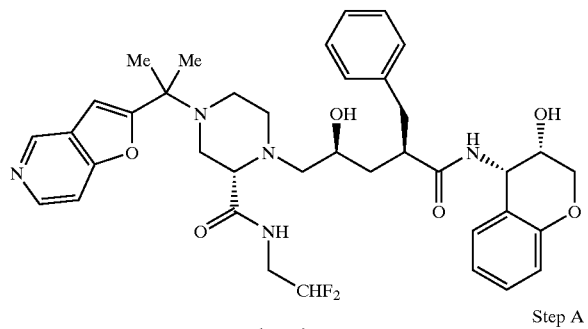

Step A

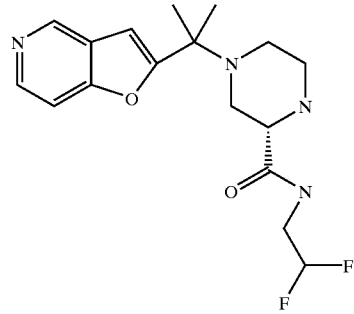

The title compound was obtained following the procedure described in Example 1, Step G, starting with the intermediate prepared in Example 1, Step F (200 mg, 0.278 mmol) and 2,2-difluoroethyllamine (33.8 mg, 4.20 mmol). Purification by flash chromatography (70% ethyl acetate in dichloromethane) afforded the title compound as a colorless oil. $^1$H NMR (CDCl$_3$, 400 MHz) 8.68 (s, 1H), 8.47 (d, 1H), 7.49 (d, 1H), 6.62 (s, 1H), 6.06 (t, 1H), 5.92 (t, 1H), 5.79 (t, 1H), 4.64 (s, 1H), 4.01 (s, 1H), 3.71 (m, 2H), 3.52 (d, 1H), 3.03 (m, 1H), 2.92 (d, 1H), 2.29 (dd, 1H), 2.20 (t, 1H), 1.93 (s, 1H), 1.54 (s, 3H), 1.45 (s, 3H).

Step B

The title compound was obtained following the procedure described in Example 2, Step B, starting with the intermediate prepared in Step A (127 mg, 0.278 mmol), affording the title compound as a colorless oil. This was used without further purification.

Step C (αR,γS,2S)-N-((3S,4S)-3,4-dihydro-3-hydroxy-2H-1-benzopyran-4-yl)-4-(1-furo[3,2-c]pyridin-2-yl-1-methylethyl)-γ-hydroxy-α-(phenylmethyl)-2-[[(2,2-difluoroethyl)amino]carbonyl]-1-piperazinepentanamide The title compound was obtained following the procedure described in Example 1, Steps Q, starting with the intermediate prepared in Step B (75.0 mg, 0.213 mmol) and the intermediate prepared in Example 1, Step P (50.0 mg, 0.133 mmol). Purification by flash chromatography (5% methanol in ethyl acetate) afforded 58.8 mg (62%) of the alcohol intermediate. This material was treated with acid as described in Example 1, Step R. Purification by preparative TLC (5% methanol in ethyl acetate) afforded the title compound as a white solid. $^1$H NMR (CDCl$_3$, 400 MHz) 9.16 (t, J=5.2 Hz, 1H), 8.88 (s, 1H), 8.50 (d, J=5.6 Hz, 1H), 7.40 (d, J=6.0 Hz, 1H), 7.29 (m, 2H), 7.23 (m, 3H), 7.10 (t, J=7.2 Hz, 1H), 7.06 (d, J=7.6 Hz, 1H), 6.79 (m, (m, 2H), 6.65 (s, 1H), 6.10 (t, 1H), 6.06 (d, J=8.0 Hz, 1H), 5.96 (t, J=3.6 Hz, 1H), 5.82 (t, 1H), 5.15 (dd, J=4.0 Hz, J=8.0 Hz, 1H), 4.06 (d, J=10.4 Hz, 1H), 4.00 (dd, J=5.2 Hz, J=11.6 Hz, 1H), 3.93 (m, 1H), 3.80 (m, 1H), 3.75 (m, 1H), 3.56 (m, 2H), 3.33 (s, 1H), 3.06 (d, J=11.6 Hz, 1H), 2.85 (m, 4H), 2.68 (m, 3H), 2.43 (dt, J=4.4 Hz, J=10.8 Hz, 2H), 1.90 (t, J=10.8 Hz, 1H), 1.58 (m, 1H), 1.56 (s, 6H); HPLC-MS (ES) 706.3 (M+1).

EXAMPLE 42

(αR,γS,2S)-N-((3S,4S)-3,4-dihydro-3-hydroxy-2H-1-benzopyran-4-yl)-γ-hydroxy-α-(phenylmethyl)4-[[5-(2-thiazolyl)-3-pyridinyl]methyl]-2-[[(2,2,2-trifluoroethyl)amino]carbonyl]-1-piperazinepentanamide

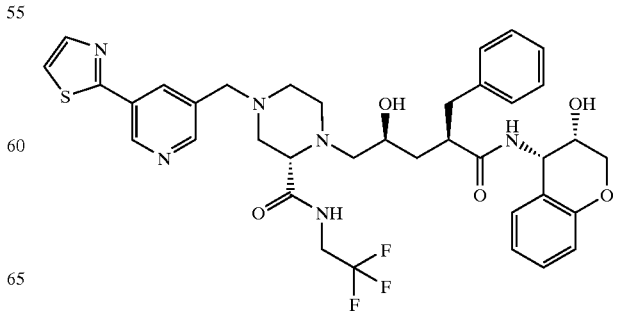

151

-continued

Step A

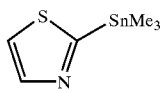

To stirred anhydrous diethyl ether (20 mL) cooled to −78° C. under $N_2$ was added nBuLi (2.1 mL, 5.46 mmol). Thiazole (425.0 mg; 4.99 mmol) in diethyl ether (12 mL) was then added dropwise. After 1 hour at −78° C. was added $Me_3SnCl$ (1.1 g, 5.5 mmol) in diethyl ether (7.5 mL) over a 10 minute period. The reaction was stirred at −78° C. for one hour before being allowed to reach ambient temperature. Filtration through celite followed by evaporation of the solvent in vacuo provided the desired stannane contaminated with approximately 15% of starting thiazole. $^1H$ NMR (400 MHz, $CDCl_3$) δ0.5 (s, 9H), 7.58 (d, J=3.6 Hz, 1H), 8.18 (d, J=3.6 Hz, $^1H$).

Step B

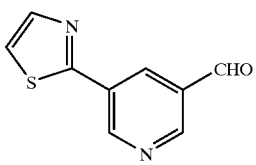

A mixture of bromide obtained from Example 59 Step D (200 mg; 1.08 mmol), AgO (250 mg; 1.08 mmol), and $Pd(PPh_3)_4$ (62 mg; 0.054 mmol) in dry DMF (4.3 mL) was stirred at 100° C. for 5 minutes after which time a solution of stannane obtained from Step A above (295 mg; 1.19 mmol) in dry DMF (2.0 mL) was added dropwise. After 18 hours, the mixture was filtered through celite; poured into EtOAc (100 mL); washed with $H_2O$, saturated $NaHCO_3$ solution, and brine; dried ($Na_2SO_4$), filtered, and concentrated in vacuo. Purification by flash column chromatography (25% EtOAc/hexane) provided the desired aldehyde as a pale yellow solid. $^1H$ NMR (400 MHz, $CDCl_3$): δ7.51 (d, J=3.3 Hz, 1H), 8.00 (d, J=3.3 Hz, 1H), 8.69 (apparent t, J=2.2 Hz, 1H), 9.13 (d, J=2.0 Hz, 1H), 9.45 (d, J=2.2 Hz, 1H), 10.22 (s, 1H).

Step C (αR,γS,2S)-N-((3S,4S)-3,4-dihydro-3-hydroxy-2H-1-benzopyran-4-yl)-γ-hydroxy-α-(phenylmethyl)-4-[[5-(2-thiazolyl)-3-pyridinyl]methyl]-2-[[(2,2,2-trifluoroethyl)amino]carbonyl]-1-piperazinepentanamide From a solution of the aldehyde obtained from Step B above (19 mg; 0.10 mmol), penultimate intermediate from Example 12 Step D (50 mg; 0.070 mmol), and $NaHB(OAc)_3$ (21 mg; 0.10 mmol) in anhydrous DMF (1.0 mL), using the procedure from Example 46 Step F, the titled compound was obtained as a white solid after purification by flash column chromatography (5% MeOH/$CH_2Cl_2$). $^1H$-NMR (400 MHz, $CD_3OD$): δ1.43 (m, 1H), 2.06 (m, 1H), 2.38–2.54 (complex m, 4H), 2.59–2.68 (complex m, 2H), 2.70–2.79 (complex m, 2H), 2.93–2.99 (m, 1H), 3.01–3.09 (complex m, 2H), 3.15 (dd, J=3.3, 7.1 Hz, 1H), 3.66 (s, 2H), 3.74–3.95 (complex m, 4H), 4.04–4.11 (complex m, 2H), 5.16 (d, J=4.1 Hz, 1H), 6.73 (dd, J=0.9, 8.2 Hz, 1H), 6.81 (apparent td, J=1.0, 7.5 Hz, 1H), 7.06–7.28 (complex m, 7H), 7.72 (d, J=3.3 Hz, 1H), 7.95 (d, J=3.2 Hz, 1H), 8.33 (apparent t, J=2.1 Hz, 1H), 8.56 (d, J=1.9 Hz, 1H), 9.03 (d, J=2.2 Hz, 1H); electrospray ionization mass spectrum: m/e 739.5 ($MH^+$ calcd for $C_{37}H_{41}F_3N_5O_6S$, 739.3).

152

EXAMPLE 43

(αR,γS,2S)-N-((3S,4S)-3,4-dihydro-3-hydroxy-2H-1-benzopyran-4-yl)-γ-hydroxy-4-[[5-(2-oxazolyl)-3-pyridinyl]methyl]-α-(phenylmethyl)-2-[[(2,2,2-trifluoroethyl)amino]carbonyl]-1-piperazinepentanamide

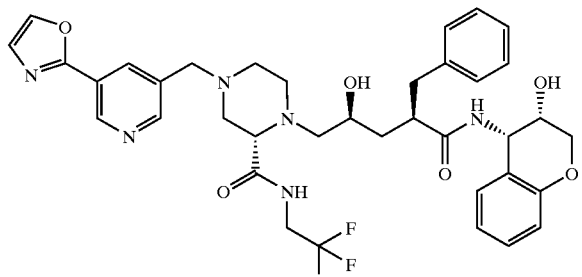

Step A

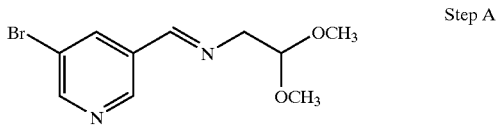

To a stirred solution of the aldehyde obtained from Example 59, Step D (225.0 mg; 1.20 mmol) in benzene (12 mL) was added aminoacetaldehyde dimethyl acetal (0.171 mL; 1.57 mmol). The reaction vessel was equipped with a Dean-Stark apparatus and heated to reflux for 1.5 hours. The reaction mixture was poured in EtOAc and washed with water and brine. Drying ($MgSO_4$), filtration and removal of the solvent in vacuo provided the desired acetal. $^1H$ NMR (400 MHz, $CDCl_3$) δ3.44 (s, 6H), 3.82 (d, J=7.2 Hz, 2H), 4.69 (dd, $J_1$=$J_2$=7.2 Hz, 1H), 8.38 (s, 1H), 8.43 (m, 1H), 8.72 (d, J=3.2 Hz, 1H), 8.75 (d, J=2.4 Hz, 1H).

Step B

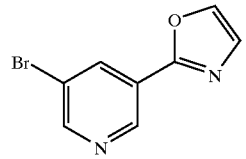

To the acetal obtained in Step A (361.0 mg; 1.32 mmol) was added with cooling to 0° C. concentrated $H_2SO_4$ (7 mL). Next, $P_2O_5$ (487.0 mg; 1.72 mmol) was added as a solid and the whole was heated to 100° C. for 30 minutes. The reaction mixture was allowed to reach ambient temperature and stirred overnight. The next day, the contents of the reaction were poured onto ice and concentrated $NH_4OH$ was added with cooling to 0° C. until the reaction mixture was approximately pH=8. The aqueous layer was extracted several times with $CHCl_3$. The organic layer was then washed with brine.

Drying (MgSO$_4$), filtration and removal of the solvent in vacuo provided quantitative yield of the desired oxazole. $^1$H NMR (400 MHz, CDCl$_3$) δ7.32 (s,1H), 7.81 (d, J=0.8 Hz, 1H), 8.49 (apparent t, J=2.0, 1H), 8.76 (d, J=2.2 Hz, 1H), 9.21 (d, J=2.0 Hz, 1H).

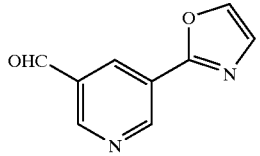

Step C

A nitrogen filled flask was charged with the oxazole obtained in Step B (98.0 mg; 0.44 mmol), NaOOCH (45.0 mg, 0.66 mmol) and Cl$_2$Pd(PPh$_3$)$_2$ (15.0 mg, 0.22 mmol). The atmosphere was replace with CO. DMF (4 mL) was then added. Carbon monoxide was then bubbled through the reaction mixture while the reaction was heated to 100° C. for approximately 2 hours. The reaction mixture was poured in EtOAc and washed with water and brine. After drying (MgSO$_4$), filtration and removal of the solvent in vacuo, purification employing Biotage flash chromatography (75% EtOAc/hex) provided the desired aldehyde. $^1$H NMR (400 MHz, CDCl$_3$) δ7.25 (d, J=3.7 Hz, 1H), 7.29 (m, 1H), 7.35 (d, J=3.6 Hz, 1H), 7.80 (m, 1H), 7.93 (m, 1H) 8.65 (m, 1H), 9.72 (s, 1H).

Step D (αR,γS,2S)-N-((3S,4S)-3,4-dihydro-3-hydroxy-2H-1-benzopyran-4-yl)-γ-hydroxy-4-[[5-(2-oxazolyl)-3-pyridinyl]methyl]-α-(phenylmethyl)-2-[[(2,2,2-trifluoroethyl)amino]carbonyl]-1-piperazinepentanamide From the aldehyde as obtained in Step C above (20.0 mg; 0.09 mmol), penultimate intermediate as obtained in Example 12, Step D (50.0 mg; 0.012 mmol) and NaBH(OAc)$_3$ (24.0 mg; 0.12 mmol) in anhydrous DMF (0.9 mL) following the general reductive amination procedure as described for Example 53, Step E was obtained the desired compound after Biotage flash chromatography (5% MeOH/DCM). $^1$H NMR (400 MHz, CD$_3$OD) δ1.41 (m, 1H), 2.06 (m, 1H), 2.36–2.54 (complex m, 5H), 2.56–2.67 (m, 2H), 2.68–2.80 (complex m, 2H), 2.91–3.09 (complex m, 4H), 3.14 (dd, J=3.3, 7.2 Hz, 1H), 3.66 (s, 2H), 3.73–3.98 (complex m, 6H), 4.01–4.12 (complex m, 2H), 5.15 (d, J=3.9 Hz, 1H), 6.72 (dd, J=1.0, 8.2 Hz, 1H), 6.81 (apparent td, J=1.1, 7.5 Hz, 1H), 7.05–7.14 (complex m, 2H), 7.18–7.30 (complex m, 5H), 7.37(d, J=0.7 Hz, 1H), 8.06 (d, J=0.7 Hz, 1H), 8.39 (m, 1H), 8.60 (d, J=1.9 Hz, 1H), 9.09 (d, J=2.0 Hz, 1H); electrospray ionization mass spectrum: m/e 723.4 (MH$^+$ calcd for C$_{37}$H$_{42}$F$_3$N$_6$O$_6$, 723.3).

EXAMPLE 44

(αR,γS,2S)-N-((3S,4S)-3,4-dihydro-3-hydroxy-2H-1-benzopyran-4-yl)-γ-hydroxy-α-(phenylmethyl)-4-[[5-(4-thiazolyl)-3-pyridinyl]methyl]-2-[[(2,2,2-trifluoroethyl)-amino]carbonyl]-1-piperazinepentanamide

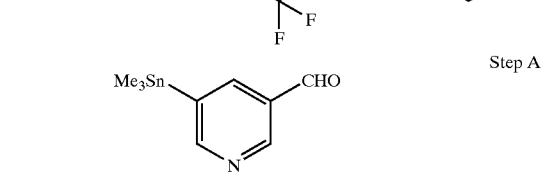

Step A

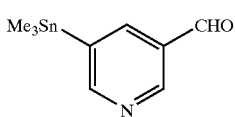

A stirred solution of the intermediate obtained from Example 59 Step D (483 mg; 2.60 mmol), (Me$_3$Sn)$_2$ (0.550 mL; 2.86 mmol), and PPh$_3$ (20 mg; 0.078 mmol) in dry toluene (10 mL) was degassed with nitrogen for 10 minutes after which Pd(PPh$_3$)$_4$ (150 mg; 0.13 mmol) was added and the solution heated to reflux. After 45 minutes, the reaction was poured into EtOAc (120 mL), washed successively with saturated NaHCO$_3$ solution and brine, dried (Na$_2$SO$_4$), filtered, and concentrated. Purification by Biotage column chromatography (40S; 15% EtOAc/hexane) provided the desired compound. $^1$H NMR (400 MHz, CDCl$_3$): δ0.41 (s, 9H), 8.27 (apparent t, J=1.9 Hz, 1H), 8.86 (d, J=1.5 Hz, 1H), 8.99 (d, J=2.1 Hz, 1H), 10.11 (s, 1H).

Step B

From a stirred solution of 4-bromothiazole (180 mg; 1.09 mmol), stannane intermediate from Step A above (147 mg; 0.545 mmol), and Pd(PPh$_3$)$_4$ (31 mg; 0.027 mmol) in DMF (5 mL), using the procedure from Example 49 Step A the desired compound was obtained after purification by Biotage column chromatography (35% EtOAc/hexane). $^1$H-NMR (400 MHz, CDCl$_3$): δ7.79 (d, J=1.9 Hz, 1H), 8.70 (apparent t, J=1.6 Hz, 1H), 8.98 (d, J=2.0 Hz, 1H), 9.07 (d, J=2.0 Hz, 1H), 9.44 (d, J=2.2 Hz, 1H), 10.22 (s, 1H).

Step C (αR,γS,2S)-N-((3S,4S)-3,4-dihydro-3-hydroxy-2H-1-benzopyran-4-yl)-γ-hydroxy-α-(phenylmethyl)-4-[[5-(4-thiazolyl)-3-pyridinyl]methyl]-2-[[(2,2,2-trifluoroethyl)amino]carbonyl]-1-piperazinepentanamide From a solution of the aldehyde obtained from Step B above (25 mg; 0.13 mmol), penultimate intermediate from Example 12 Step D (50 mg; 0.089 mmol), and NaHB(OAc)$_3$ (28 mg; 0.13 mmol) in anhydrous DMF (1.0 mL), using the procedure from Example 46 Step F, the titled compound was obtained as a white solid after purification by flash column chromatography (5% MeOH/CH$_2$Cl$_2$). $^1$H-NMR (400 MHz, CD$_3$OD): δ1.42 (m, 1H), 2.06 (m, 1H), 2.38–2.53 (complex m, 4H), 2.60–2.79 (complex m, 4H), 2.93–2.99 (m, 1H), 3.01–3.08 (complex m, 2H), 3.10 (dd, J=3.3, 7.0 Hz, 1H), 3.65 (s, 2H), 3.73–3.95 (complex m, 4H), 4.04–4.08 (complex m, 2H), 5.16 (d, J=3.9 Hz, 1H), 6.73 (d, J=8.2 Hz, 1H), 6.81 (apparent t, J=7.4 Hz, 1H), 7.06–7.28 (complex m, 7H), 8.12 (d, J=1.9 Hz, 1H), 8.36 (apparent t, J=2.1 Hz, 1H), 8.46 (d, J=1.9 Hz, 1H), 9.04 (d, J=2.2 Hz, 1H), 9.11 (d, J=1.9 Hz, 1H); electrospray ionization mass spectrum: m/e 739.5 (MH$^+$ calcd for C$_{37}$H$_{41}$F$_3$N$_5$O$_6$S, 739.3).

EXAMPLE 45

(αR,γS,2S)-N-((3S,4S)-3,4-dihydro-3-hydroxy-2H-1-benzopyran-4-yl)-γ-hydroxy-α-(phenylmethyl)-4-[[5-(2-thiazolyl)-2-furanyl]methyl]-2-[[(2,2,2-trifluoroethyl)amino]carbonyl]-1-piperazinepentanamide

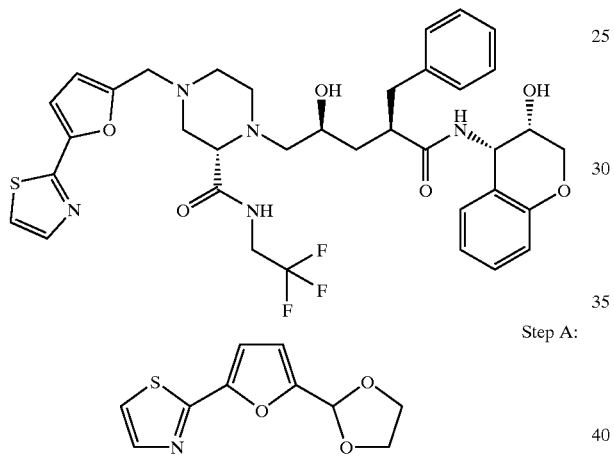

Step A:

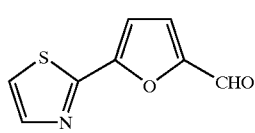

From a stirred solution of 2-bromothiazole (0.191 mL; 2.12 mmol), stannane intermediate from Example 46 Step B (321 mg; 1.06 mmol), and Pd(PPh$_3$)$_4$ (37 mg; 0.032 mmol) in DMF (10 mL), using the procedure from Example 46, Step B, the desired compound was obtained after purification by flash column chromatography (25% EtOAc/hexane). $^1$H-NMR (300 MHz, CDCl$_3$): δ4.02–4.19 (complex m, 4H), 6.01 (s, 1H), 6.57 (d, J=3.6 Hz, 1H), 6.97 (d, J=3.5 Hz, 1H), 7.31 (d, J=3.2 Hz, 1H), 7.83 (d, J=3.2 Hz, 1H).

Step B

From a stirred solution of intermediate from Step A above (133 mg; 0.60 mmol) and HCl solution (2.4 mL; 2.4 mmol) in THF (6.5 mL), following the procedure described in Example 46 Step E, the desired aldehyde was obtained after workup and was used without further purification. $^1$H-NMR (300 MHz, CDCl$_3$): δ7.16 (d, J=3.9 Hz, 1H), 7.35 (d, J=3.7 Hz, 1H), 7.48 (d, J=3.2 Hz, 1H), 7.93 (d, J=3.1 Hz, 1H), 9.72 (s, 1H).

Step C (αR,γS,2S)-N-((3S,4S)-3,4-dihydro-3-hydroxy-2H-1-benzopyran-4-yl)-γ-hydroxy-α-(phenylmethyl)-4-[[5-(2-thiazolyl)-2-furanyl]methyl]-2-[[(2,2,2-trifluoroethyl)amino]carbonyl]-1-piperazinepentanamide From a solution of the aldehyde obtained from Step D above (247 mg; 1.27 mmol), penultimate intermediate from Example 12 Step D (481 mg; 0.85 mmol), and NaHB(OAc)$_3$ (269 mg; 1.27 mmol) in anhydrous DMF (6 mL), using the procedure from Example 46 Step F was obtained after purification by Biotage column chromatography (40M; 5% MeOH/CH$_2$Cl$_2$) the titled compound as a white solid. $^1$H-NMR (400 MHz, CD$_3$OD): δ1.40 (m, 1H), 2.05 (m, 1H), 2.34–2.56 (complex m, 4H), 2.61 (m, 1H), 2.69–2.81 (complex m, 3H), 2.92–3.06 (complex m, 3H), 3.11 (dd, J=3.3, 7.7 Hz, 1H), 3.69 (s, 2H), 3.72–3.80 (complex m, 3H), 3.94–4.00 (complex m, 1H), 4.07–4.11 (complex m, 2H), 5.16 (d, J=4.1 Hz, 1H), 6.51 (d, J=3.3 Hz, 1H), 6.73 (d, J=8.2 Hz, 1H), 6.82 (apparent td, J=1.0, 7.5 Hz, 1H), 7.01 (d, J=3.5 Hz), 7.07–7.27 (complex m, 7H), 7.57 (d, J=3.3 Hz, 1H), 7.82 (d, J=3.3 Hz, 1H); electrospray ionization mass spectrum: m/e 728.4 (MH$^+$ calcd for C$_{36}$H$_{40}$F$_3$N$_5$O$_6$S, 728.3).

EXAMPLE 46

(αR,γS,2S)-4-[[5-(5-chloro-3-pyridinyl)-2-furanyl]methyl]-N-((3S,4S)-3,4-dihydro-3-hydroxy-2H-1-benzopyran-4-yl)-γ-hydroxy-α-(phenylmethyl)-2-[[(2,2,2-trifluoroethyl)amino]carbonyl]-1-piperazinepentanamide

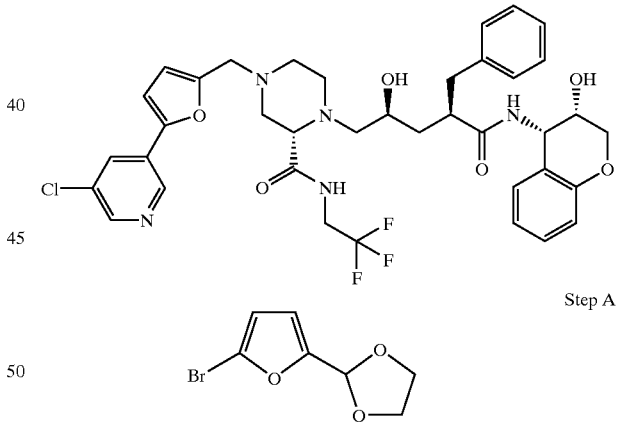

Step A

To a stirred solution of 5-bromo-2-furaldehyde (7.66 g; 43.8 mmol) in benzene (44 mL) was added ethylene glycol (6.02 mL; 109.5 mmol) and p-TsOH.H$_2$O (108 mg; 0.57 mmol). The reaction vessel was equipped with a Dean-Stark apparatus and heated to reflux for 75 minutes. The reaction mixture was poured in Et$_2$O (750 mL) and washed with saturated NaHCO$_3$ solution, water and brine. The organic layer was dried (MgSO$_4$), filtered, and concentrated in vacuo. The crude product was purified by flash column chromatography (gradient elution 4% to 5% EtOAc/hexane) to provide the desired compound as a pale yellow oil. $^1$H-NMR (300 MHz, CDCl$_3$): δ3.98–4.15 (complex m, 4H), 5.87 (s, 1H), 6.28 (d, J=3.2 Hz, 1H), 6.41 (d, J=3.6 Hz, 1H).

Step B

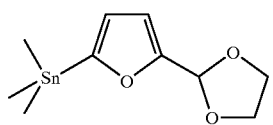

To a stirred solution of the intermediate from Step A (1.19 g; 5.43 mmol) in dry THF (29 mL) cooled to −78° C. was added dropwise t-BuLi (6.7 mL; 11.4 mmol). After 30 minutes a solution of trimethyltin chloride (1.19 g; 5.97 mmol) in dry THF (3 mL) was added dropwise. The reaction was allowed to warm to ambient temperature over 40 minutes. The volatiles were removed in vacuo and the residue was poured in Et$_2$O (200 mL), washed with saturated NaHCO$_3$, water, and brine, dried (Na$_2$SO$_4$), filtered, and concentrated in vacuo to provide the stannane which was used without further purification. $^1$H-NMR (300 MHz, CDCl$_3$): δ0.32 (s, 9H), 4.00–4.14 (complex m, 4H), 5.98 (s, 1H), 6.45 (d, J=3.0 Hz, 1H), 6.52 (d, J=3.2 Hz, 1H).

Step C

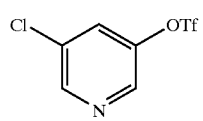

A suspension (60% wt) of NaH in mineral oil (1.36 g; 34.0 mmol) was charged to a flask under nitrogen atmosphere and washed two times with dry THF. It was then suspended in dry THF (100 mL) and cooled to 0° C. A solution of 5-chloro-3-pyridinol (4.0 g; 30.9 mmol) in dry THF (100 mL) was added dropwise and the ice bath was removed. After 30 minutes, the reaction mixture was recooled to 0° C., neat CF$_3$SO$_2$Cl was dripped in and again allowed to reach ambient temperature. Volatiles were removed in vacuo and the residue was poured into EtOAc/Et$_2$O (900 mL). The organic layer was washed with water and brine, dried (MgSO$_4$), filtered, and concentrated to provide the desired compound which was used without further purification. $^1$H-NMR (300 MHz, CDCl$_3$): δ7.68 (apparent t, J=2.2 Hz, 1H), 8.51 (d, J=2.4 Hz, 1H), 8.64 (d, J=2.0 Hz, 1H).

Step D

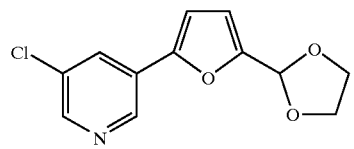

To a stirred solution of intermediate prepared in Step C (500 mg; 1.91 mmol) in dry DMF (19 mL) under nitrogen was added Pd(PPh$_3$)$_4$ (66 mg; 0.057 mmol) followed by AgO (237 mg; 1.91 mmol). After the mixture was stirred at 100° C. for 5 minutes, a solution of the stannane prepared in Step B in dry DMF (2 mL) was added. After an additional 10 minutes the mixture was cooled to room temperature, filtered through celite, and diluted with EtOAc (400 mL). After washing successively with saturated NaHCO$_3$ solution, water and brine, drying (Na$_2$SO$_4$), filtration, and removal of solvents in vacuo, the residue was purified by flash column chromatography (25% EtOAc/hexane) to provide the desired product. $^1$H-NMR (400 MHz, CDCl$_3$): δ4.00–4.19 (complex m, 4H), 5.98 (s, 1H), 6.54 (d, J=4.0 Hz, 1H), 6.73 (d, J=4.0 Hz, 1H), 7.93 (apparent t, J=2.0 Hz, 1H), 8.42 (m, 1H), 8.76 (m, 1H).

Step E

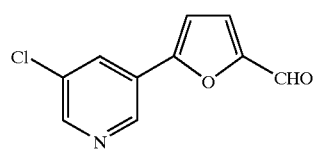

To a solution of intermediate prepared in Step D (430 mg; 1.71 mmol) dissolved in THF (20 mL) was added 1N HCl (6.84 mL; 6.84 mmol). After 75 minutes the solution was brought to basic pH by the addition of dilute NH$_4$OH. THF was removed in vacuo and the residue was poured into EtOAc/Et$_2$O (200 mL). After washing successively with saturated NaHCO$_3$ solution, water and brine, drying (Na$_2$SO$_4$), filtration, and removal of solvents in vacuo, the residue was purified by flash column chromatography (30% EtOAc/hexane) to provide the desired product. $^1$H-NMR (300 MHz, CDCl$_3$): δ6.97 (d, J=3.7 Hz, 1H), 7.35 (d, J=3.7 Hz, 1H), 8.11 (apparent t, J=2.1 Hz, 1H), 8.57 (s, 1H), 8.91 (s, 1H), 9.71 (s, 1H).

Step F (αR,γS,2S)-4-[[5-(5-chloro-3-pyridinyl)-2-furanyl]
methyl]-N-((3S,4S)-3,4-dihydro-3-hydroxy-2H-1-
benzopyran-4-yl)-γ-hydroxy-α-(phenylmethyl)-2-
[[(2,2,2-trifluoroethyl)amino]carbonyl]-1-
piperazinepentanamide To a solution of aldehyde obtained from Step E (277 mg; 1.34 mmol) above and penultimate obtained from Example 12 Step D (500 mg; 0.89 mmol) in anhydrous DMF (9 mL) was added NaHB(OAc)$_3$ (283 mg; 1.34 mmol). After 18 hours the solution was poured into EtOAc, washed with saturated NaHCO$_3$ solution, water and brine, dried (Na$_2$SO$_4$), filtered, and solvent removed in vacuo. Purification by Biotage column chromatography (40M, 5% MeOH/ CH$_2$Cl$_2$) provided the titled compound as a white solid. $^1$H-NMR (400 MHz, CD$_3$OD): δ1.40 (m, 1H), 2.06 (m, 1H), 2.37 (m, 1H), 2.42–2.53 (complex m, 3H), 2.57–2.62 (m, 1H), 2.70–2.82 (complex m, 3H), 2.92–3.05 (complex m, 3H), 3.12 (dd, J=3.4, 8.0 Hz, 1H), 3.69 (s, 2H), 3.74–3.80 (complex m, 3H), 3.91–4.00 (complex m, 1H), 4.04–4.11 (complex m, 2H), 5.16 (d, J=4.1 Hz, 1H), 6.48 (d, J=3.5 Hz, 1H), 6.73 (dd, J=0.9, 8.2 Hz, 1H), 6.82 (apparent td, J=1.1, 7.5 Hz, 1H), 7.00 (d, J=3.3 Hz, 1H), 7.07–7.27 (complex m, 7H), 8.13 (apparent t, J=2.1 Hz, 1H), 8.41 (d, J=2.2 Hz, 1H) 8.80 (d, J=1.8 Hz, 1H); electrospray ionization mass spectrum: m/e 756.4 (MH$^+$ calcd for $C_{38}H_{41}ClF_3N_5O_6$, 756.3).

EXAMPLE 47

(αR,γS,2S)-N-((3S,4S)-3,4-dihydro-3-hydroxy-2H-1-benzopyran-4-yl)-γ-hydroxy-4-[(5-phenyl-2-furanyl)methyl]-α-(phenylmethyl)-2-[[(2,2,2-trifluoroethyl)-amino]carbonyl]-1-piperazinepentanamide

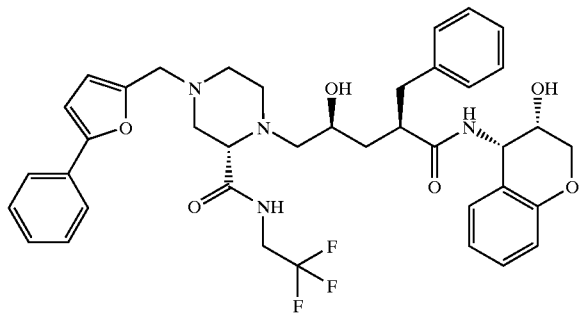

Step A (αR,γS,2S)-N-((3S,4S)-3,4-dihydro-3-hydroxy-2H-1-benzopyran-4-yl)-γ-hydroxy-4-[(5-phenyl-2-furanyl)methyl]-α-(phenylmethyl)-2-[[(2,2,2-trifluoroethyl)amino]carbonyl]-1-piperazinepentanamide To a solution of aldehyde obtained from Example 23 Step G (271 mg; 1.58 mmol) and penultimate intermediate obtained from Example 12 Step D (594 mg; 1.05 mmol) in anhydrous DMF (10 mL) was added NaHB(OAc)$_3$ (334 mg; 1.58 mmol). After 18 hours the solution was poured into EtOAc, washed with saturated NaHCO$_3$ solution, water and brine, dried (Na$_2$SO$_4$), filtered, and solvent removed in vacuo. Purification by Biotage column chromatography (40M; 4% MeOH/CH$_2$Cl$_2$) provided the titled compound as a white solid. $^1$H-NMR (400 MHz, CD$_3$OD): δ1.40 (m, 1H), 2.05 (m, 1H), 2.34–2.47 (complex m, 3H), 2.50–2.61 (complex m, 2H), 2.72–2.77 (complex m, 2H), 2.83 (m, 1H), 2.92–3.05 (complex m, 3H), 3.11 (dd, J=3.3, 8.0 Hz, 1H), 3.66 (s, 2H), 3.69–3.80 (complex m, 3H), 3.91–4.04 (complex m, 1H), 4.07–4.11 (complex m, 2H), 5.15 (d, J=3.9 Hz, 1H), 6.39 (d, J=3.3 Hz, 1H), 6.70 (d, J=3.1 Hz, 1H), 6.73 (apparent dd, J=1.0, 8.2 Hz, 1H), 6.82 (apparent td, J=1.1, 7.6 Hz, 1H), 7.06–7.27 (complex m, 8H), 7.37 (apparent t, J=7.7 Hz, 2H), 7.66 (apparent d, J=7.2 Hz, 2H); electrospray ionization mass spectrum: m/e 721.5 (MH$^+$ calcd for $C_{39}H_{43}F_3N_4O_6$, 721.3).

EXAMPLE 48

(αR,γS,2S)-4-[(4-chloro-5-phenyl-2-furanyl)methyl]-N-((3S,4S)-3,4-dihydro-3-hydroxy-2H-1-benzopyran-4-yl)-γ-hydroxy-α-(phenylmethyl)-2-[[(2,2,2-trifluoroethyl)amino]carbonyl]-1-piperazinepentanamide

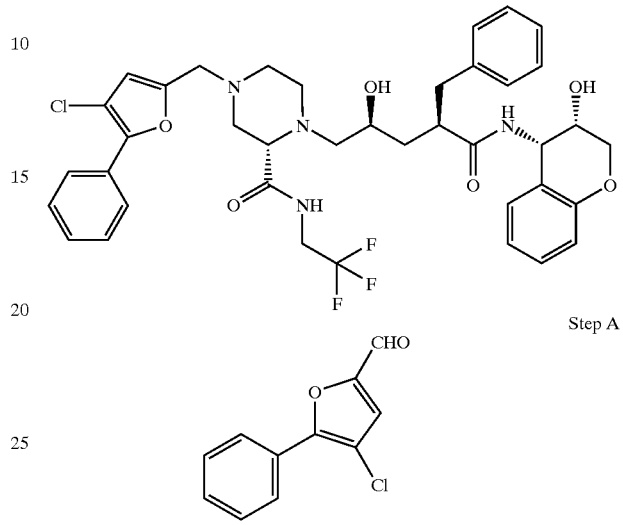

Step A

To a stirred solution of 3-chloro-2-phenyl-furan (200 mg; 1.12 mmol), (prepared as described in D. Obrecht, Helv. Chim. Acta 1989, 72, 447) in dry THF (10 mL) cooled to –78° C. was added dropwise n-BuLi (0.470 mL; 1.23 mmol). After 35 minutes, dry DMF (0.130 mL; 1.68 mmol) was added slowly. Fifteen minutes later the solution was allowed to stir at ambient temperature 2 hours. The reaction was quenched with saturated NaHCO$_3$ and poured in EtOAc/Et$_2$O (80 mL). After washing with water and brine, drying (MgSO$_4$), filtration, and removal of solvents in vacuo, the residue was purified by Biotage column chromatography (12M; 7% EtOAc/hexane) to provide the desired product. $^1$H-NMR (300 MHz, CDCl$_3$): δ7.28 (s, 1H), 7.43–7.51 (complex m, 3H), 8.06 (apparent d, J=7.8 Hz, 2H), 9.64 (s, 1H).

Step B (αR,γS,2S)-4-[(4-chloro-5-phenyl-2-furanyl)methyl]-N-((3S,4S)-3,4-dihydro-3-hydroxy-2H-1-benzopyran-4-yl)-γ-hydroxy-α-(phenylmethyl)-2-[[(2,2,2-trifluoroethyl)amino]carbonyl]-1-piperazinepentanamide From a solution of the aldehyde obtained from Step A above (41 mg; 0.200 mmol), penultimate intermediate from Example 12 Step D (75 mg; 0.133 mmol), and NaHB(OAc)$_3$ (43 mg; 0.200 mmol) in anhydrous DMF (1.2 mL) using the procedure from Example 46 Step F was obtained after purification by Biotage column chromatography (12M; 5% MeOH/CH$_2$Cl$_2$) the titled compound as a white solid. $^1$H-NMR (400 MHz, CDC$_3$OD): δ1.39 (m, 1H), 2.06 (m, 1H), 2.33–2.46 (complex m, 3H), 2.49–2.55 (m, 1H), 2.57–2.62 (m, 1H), 2.72–2.86 (complex m, 3H), 2.91–3.05 (complex m, 3H), 3.11 (dd, J=3.3, 8.0 Hz, 1H), 3.66 (s, 2H), 3.71–3.79 (complex m, 3H), 3.91–4.04 (complex m, 1H), 4.07–4.11 (complex m, 2H), 5.16 (d, J=4.1 Hz, 1H), 6.49 (s, 1H), 6.73 (apparent d, J=8.2 Hz, 1H), 6.82 (apparent td, J=1.1, 7.5 Hz, 1H), 7.07–7.27 (complex m, 7H), 7.33 (m, 1H), 7.43 (apparent t, J=7.6 Hz, 2H), 7.89 (apparent d, J=7.3 Hz, 2H); electrospray ionization mass spectrum: m/e 755.4 (MH⁺ calcd for $C_{39}H_{42}ClF_3N_4O_6$, 755.3).

EXAMPLE 49

(αR,γS,2S)-N-((3S,4S)-3,4-dihydro-3-hydroxy-2H-1-benzopyran-4-yl)-γ-hydroxy-α-(phenylmethyl)-4-[[5-(2-pyridinyl)-2-furanyl]methyl]-2-[[(2,2,2-trifluoroethyl)-amino]carbonyl]-1-piperazinepentanamide

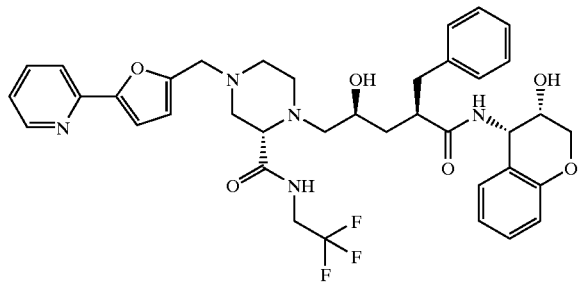

Step A

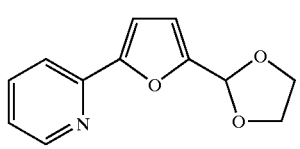

To a stirred solution of the stannane obtained from Example 46, Step B (630.0 mg; 2.08 mmol) in anhydrous DMF (20 mL) under $N_2$ was added 2-bromopyridine (0.397 mL; 4.16 mmol) and Pd(PPh₃)₄ (72 mg; 0.0624 mmol). The reaction vessel was heated to 100° C. for 40 minutes. The reaction mixture was poured in EtOAc and washed with water and brine. After drying (Na₂SO₄), filtration and removal of the solvent in vacuo, purification employing flash chromatography (30% EtOAc/hex) provided the desired acetal. ¹H NMR (300 MHz, CDCl₃) δ4.03–4.10 (complex m, 2H), 4.12–4.19 (complex m, 2H), 6.03 (s, 1H), 6.57 (d, J=3.4 Hz, 1H), 7.03 (d, J=3.4 Hz, 1H), 7.16 (m, 1H), 7.68–7.74 (complex m, 2H), 8.58 (m, 1H).

Step B

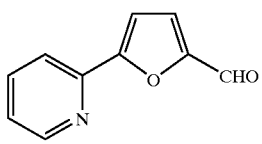

To a stirred solution of the acetal obtained in Step A (388.0 mg; 1.79 mmol) in THF (20 mL) was added 1N HCl (7.2 mL; 7.2 mmol). After approximately 1.25 hours, dilute NH₄OH was added until the pH of the reaction was basic. The mixture was then poured into EtOAc and washed with water and brine. Drying (Na₂SO₄), filtration and removal of the solvent in vacuo provided the desired aldehyde. ¹H NMR (300 MHz, CDCl₃) δ7.25 (d, J=3.7 Hz, 1H), 7.29 (m, 1H), 7.35 (d, J=3.6 Hz, 1H), 7.80 (m, 1H), 7.93 (m, 1H), 8.65 (m, 1H), 9.72 (s, 1H).

Step C (αR,γS,2S)-N-((3S,4S)-3,4-dihydro-3-hydroxy-2H-1-benzopyran-4-yl)-γ-hydroxy-α-(phenylmethyl)-4-[[5-(2-pyridinyl)-2-furanyl]methyl]-2-[[(2,2,2-trifluoroethyl)amino]carbonyl]-1-piperazinepentanamide From the aldehyde as obtained in Step C above (727.0 mg; 4.2 mmol), penultimate intermediate as obtained in Example 12, Step D (1.58 g; 2.79 mmol) and NaBH(OAc)₃ (890.0 mg; 4.2 mmol) in anhydrous DMF (20 mL) following the general reductive amination procedure as described for Example 53, Step E was obtained the desired compound after Biotage flash chromatography (5% MeOH/DCM) followed by recrystallization from hot EtOAc/hex. ¹H NMR (400 MHz, CD₃OD) δ1.41 (m, 1H), 2.05 (m, 1H), 2.33–2.49 (complex m, 4H), 2.50–2.57 (m, 1H), 2.58–2.65 (m, 1H), 2.69–2.85 (complex m, 4H), 2.91–3.08 (complex m, 4H), 3.12 (dd, J=3.3, 8.0 Hz, 1H), 3.70 (s, 2H), 3.73–3.81 (complex m, 4H), 3.91–4.01 (complex m, 2H), 4.02–4.12 (complex m, 2H), 5.15 (d, J=4.1 Hz, 1H), 6.48 (d, J=3.3 Hz, 1H), 6.72 (d, J=8.0 Hz, 1H), 6.82 (apparent td, J=1.0, 7.5 Hz, 1H), 7.05–7.40 (complex m, 9H), 7.77 (m, 1H), 7.84 (apparent td, J=1.6, 7.5 Hz, 1H), 8.49 (apparent d, J=4.8 Hz, 1H); electrospray ionization mass spectrum: m/e 722.5 (MH⁺ calcd for $C_{38}H_{43}F_3N_5O_6$, 722.3).

EXAMPLE 50

(αR,γS,2S)-4-[[5-(5-chloro-2-pyridinyl)-2-furanyl]methyl]-N-((3S,4S)-3,4-dihydro-3-hydroxy-2H-1-benzopyran-4-yl)-γ-hydroxy-α-(phenylmethyl)-2-[[(2,2,2-trifluoroethyl)amino]carbonyl]-1-piperazinepentanamide

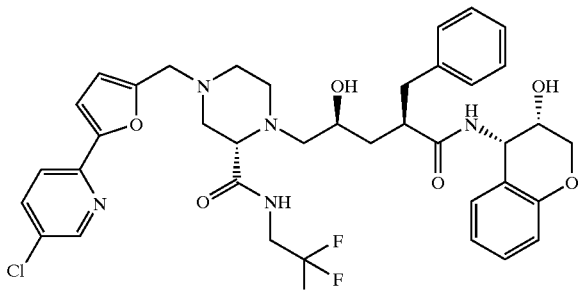

Step A

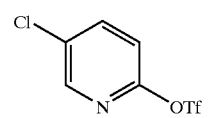

This intermediate was prepared in the same manner as Example 46 Step C, employing NaH suspension (340 mg; 8.47 mmol), 5-chloro-2-pyridinol (1.0 g; 7.7 mmol), and CF₃SO₂Cl (0.902 mL; 8.47 mmol). The crude product was purified by Biotage flash chromatography (40M; 7% EtOAc/hexane) to provide desired compound as a pale yellow oil. ¹H-NMR (300 MHz, CDCl₃): δ7.16 (d, J=8.0 Hz, 1H), 7.86 (dd, J=8.6, 2.7 Hz, 1H), 8.35 (d, J=2.2 Hz, 1H).

Step B

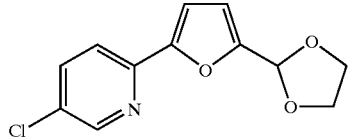

This intermediate was prepared in the same manner as Example 46 Step D, employing triflate obtained from Step A above (814 mg; 3.11 mmol), Pd(PPh₃)₄ (108 mg; 0.093 mmol), AgO (385 mg; 3.11 mmol), and intermediate obtained from Example 46 Step B (1.13 g; 3.73 mmol). Biotage column chromatography (40S, 15% EtOAc/hexane)

provided the bi-heteroaryl. ¹H-NMR (300 MHz, CDCl₃): δ4.04–4.16 (complex m, 4H), 6.00 (s, 1H), 6.57 (d, J=3.4 Hz, 1H), 7.01 (d, J=3.4 Hz, 1H), 7.66 (s, 1H), 8.51 (s, 1H).

Step C

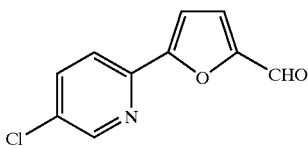

This aldehyde was prepared in the same manner as Example 46 Step E, employing the acetal obtained from Step B above (685 mg; 2.72 mmol). The desired aldehyde was obtained as a pale yellow solid and was used after workup without further purification. ¹H-NMR (400 MHz, CDCl₃): δ7.26 (d, J=3.7 Hz, 1H), 7.37 (d, J=3.7 Hz, 1H), 7.78 (dd, J=8.4, 2.3 Hz, 1H), 7.90 (d, J=8.4 Hz, 1H), 8.61 (d, J=2.5 Hz, 1H), 9.73 (s, 1H).

The aldehyde was also prepared as follows:

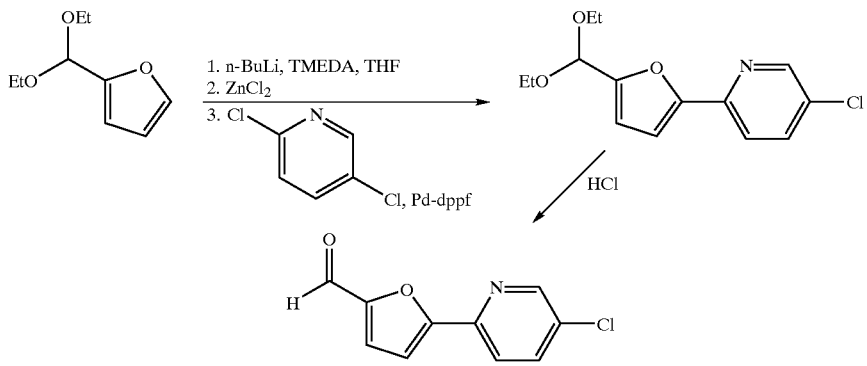

THF (125 mL; KF<200 ppm), TMEDA (24.40 mL; 1.1 eq.; KF<125 ppm) and 2-furaldehyde diethyl acetal (24.80 mL) were added at room temperature to a 1 L round bottomed flask equipped with a thermocouple, an overhead stirrer, N₂ inlet and an addition funnel. The solution was cooled to −40° C. over 15 min., and then n-BuLi (101 mL; 1.1 eq.) was added over 1 hour with the temperature maintained at less than −20° C. The mixture was stirred 15 min at −25° C., and then assayed via LC. The assay showed 96% deprotonation. The reaction mixture was then cooled to −35° C., and a slurry of 1.5M ZnCl₂/THF (68.5 mL; 0.7 eq.; KF=680 ppm—dried by soxhlet distillation through molecular sieves for 3 days) was added over 1 h while maintaining the temperature at less than <−20° C. throughout the addition. The mixture was then stirred for 30 min at −25° C. and warmed to 25° C. over 60 min. Solid Pd(dppf)Cl₂ (0.60 g; 0.5 mol %) was then added, followed by solid 2,5-dichloropyridine (23.91 g; 1.1 eq.), each in one portion. The mixture was then heated to 55° C. and aged for 3 h (95% conversion by NMR assay; ~85% assay yield by LC), after which the mixture was allowed to cool to room temperature and stirred overnight.

The reaction mixture was then cooled to 0° C. and quenched with 5° C. 5M AcOH (294 mL; 5 eq.) over 10 min with the temp. maintained less than 25° C. throughout. The mixture was agitated for 15 min at 23° C. and then allowed to settle for 2 h. The aqueous layer was removed and the organic layer was cooled to 0° C., followed by addition thereto of 5° C. 10% NaOH (250 mL; 5 mL/g) over 10 min with the temperature maintained <25° C. throughout. The mixture was agitated for 15 min at 23° C., allowed to settle for 2 h, the aqueous layer removed, followed by addition of sat'd brine (62.5 mL; 2.5 mL/g) over 2 min with the temp. maintained less than 25° C. The mixture was agitated for 15 min at 23° C., allowed to settle for 2 h, and the aqueous layer removed.

The organic soln. was concentrated down to 5 mL/g (125 mL) under vacuum with the soln.'s temperature maintained between 25–35° C. The concentrated solution was then diluted to 10 mL/g (250 mL) with heptane. This was repeated twice more to solvent switch completely to heptane (THF<1%). Darco G-60 (12.5 g) was added to the solution, and the mixture was heated to 50° C. for 2 h, cooled to 23° C. over 1 h and aged at 23° C. for 15 h. The mixture was then filtered through solka floc (25 g) and the filtercake was washed with heptane (250 mL).

The heptane solution of the acetal was then added to a 500 mL round bottomed flask equipped with a thermocouple, an overhead stirrer, an N₂ inlet and a distillation setup, concentrated down to 340 mL, and then diluted up with THF (25 mL). One quarter of an acid charge consisting of HCl (5M; 3 mL=10 mol % based on starting acetal) diluted in 12.5 mL of THF was added to the acetal soln. over 1 min and aged for 5 min at room temperature. The batch was then seeded with aldehyde 0.25 g and aged at room temperature for 15 min upon which some of the aldehyde began to crystallize out. The remaining acid charge was then added over 5 min and the slurry was aged at room temperature for 2 h. After such time, the deprotection was only 90% complete as determined by LC assay, so an additional 0.3 mL of acid was added to the slurry. The slurry was aged for an additional 30 min with little change in the percentage of deprotected aldehyde.

The slurry was constant volume batch concentrated at ~350 mL with 200 mL of heptane being flushed through to remove the THF and the EtOH which formed upon deprotection. (The temperature of the slurry was maintained <35° C.). The slurry was diluted to 375 mL with heptane and cooled to 23° C. The deprotection was complete at this time, with only about 1% acetal remaining. The solid aldehyde was filtered and displacement washed with 250 mL of r.t. heptane and dried overnight under a stream of nitrogen. The aldehyde was then dried for 2 days at 40° C. and 200 torr.

Step D (αR,γS,2S)-4-[[5-(5-chloro-2-pyridinyl)-2-furanyl]methyl]-N-((3S,4S)-3,4-dihydro-3-hydroxy-2H-1-benzopyran-4-yl)-γ-hydroxy-α-(phenylmethyl)-2-[[(2,2,2-trifluoroethyl)amino]carbonyl]-1-piperazinepentanamide From a solution of the aldehyde obtained from Step C above (42 mg; 0.200 mmol), penultimate intermediate from Example 12 Step D (75 mg; 0.133 mmol), and NaHB(OAc)$_3$ (43 mg; 0.200 mmol) in anhydrous DMF (1.2 mL) using the procedure from Example 46 Step F, the titled compound was obtained after purification by Biotage column chromatography (12M; 4% MeOH/CH$_2$Cl$_2$) as a white solid. $^1$H-NMR (400 MHz, CD$_3$OD): δ1.39 (m, 1H), 2.06 (m, 1H), 2.33–2.46 (complex m, 3H), 2.49–2.55 (m, 1H), 2.57–2.62 (m, 1H), 2.72–2.82 (complex m, 3H), 2.91–3.06 (complex m, 3H), 3.10 (dd, J=3.3, 8.0 Hz, 1H), 3.69 (s, 2H), 3.71–3.80 (complex m, 3H), 3.94–4.02 (complex m, 1H), 4.04–4.08 (complex m, 2H), 5.15 (d, J=4.1 Hz, 1H), 6.48 (d, J=3.3 Hz, 1H), 6.73 (dd, J=1.2, 8.2 Hz, 1H), 6.82 (apparent td, J=1.2, 7.5 Hz, 1H), 7.06 (d, J=3.3 Hz, 1H), 7.07–7.28 (complex m, 7H), 7.74 (dd, J=0.8, 8.6 Hz, 1H), 7.86 (dd, J=2.5, 8.6 Hz, 1H), 8.49 (m, 1H); electrospray ionization mass spectrum: m/e 756.4 (MH$^+$ calcd for C$_{38}$H$_{41}$ClF$_3$N$_5$O$_6$, 756.3).

Crystals of the title compound were obtained from n-propanol. m.p.=204–206° C.

EXAMPLE 51

(αR,γS,2S)-N-((3S,4S)-3,4-dihydro-3-hydroxy-2H-1-benzopyran-4-yl)-γ-hydroxy-4-[[5-(2-methyl-4-pyridinyl)-2-furanyl]methyl]-α-(phenylmethyl)-2-[[(2,2,2-trifluoroethyl)amino]carbonyl]-1-piperazinepentanamide

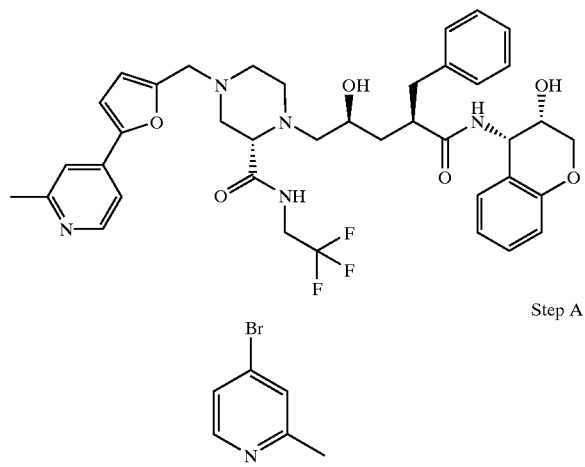

Step A

To a stirred suspension of 4-bromopyridine hydrochloride (20.7 g; 106.4 mmol) in dry THF (500 mL) cooled to −78° C. was added over 25 minutes MeMgBr (152 mL; 212.8 mmol). After 15 minutes, phenyl chloroformate (13.4 mL; 106.4 mmol) was added dropwise. After 20 minutes the reaction was allowed to warm to ambient temperature. The reaction was quenched with saturated NH$_4$Cl solution and poured into Et$_2$O (600 mL); washed with H$_2$O, 2N HCl, H$_2$O, and brine; dried (Na$_2$SO$_4$), filtered and concentrated. The residue was dissolved in dry toluene (450 mL) and a solution of o-chloranil (26.2 g; 106.4 mmol) in AcOH (220 mL) was added. After stirring 25 hours, the reaction was cooled to 0° C. and made basic with NaOH solution. The mixture was filtered through celite, the organic layer washed with H$_2$O and three times with 2N HCl. The acid extracts were combined, washed with Et$_2$O, and made basic with NaOH solution, then extracted three times with CH$_2$Cl$_2$. Drying (Na$_2$SO$_4$), filtration, and removal of volatiles in vacuo provided the desired compound as a yellow oil which was used without further purification. $^1$H NMR (300 MHz, CDCl$_3$): δ2.52 (s, 3H), 7.27 (m, 1H), 7.34 (d, J=1.4 Hz, 1H), 8.30 (d, J=5.3 Hz, 1H).

Step B

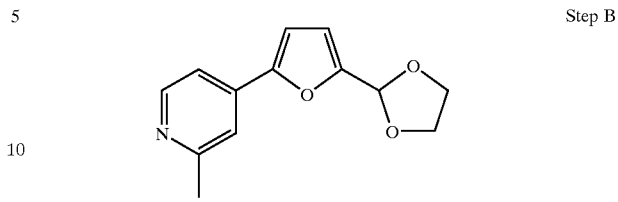

From a stirred solution of the intermediate from Step A above (800 mg; 4.65 mmol), stannane intermediate from Example 46 Step B (986 mg; 3.26 mmol), and Pd(PPh$_3$)$_4$ (161 mg; 0.140 mmol) in anhydrous DMF (23 mL), using the procedure from Example 49 Step A the desired compound was obtained after purification by flash column chromatography (50% EtOAc/hexane). $^1$H-NMR (400 MHz, CDCl$_3$): δ2.58 (s, 3H), 4.04–4.22 (complex m, 4H), 6.01 (s, 1H), 6.56 (d, J=3.0 Hz, 1H), 6.83 (d, J=3.2 Hz, 1H), 7.34 (m, 1H), 7.42 (s, 1H), 8.49 (d, J=5.0 Hz, 1H).

Step C

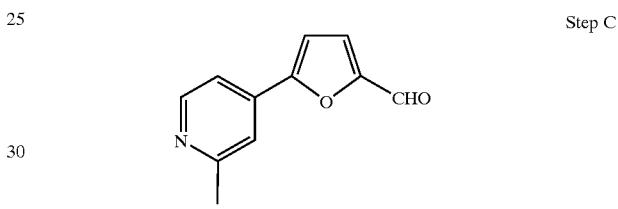

From a stirred solution of intermediate from Step B above (370 mg; 1.60 mmol) and HCl solution (6.4 mL; 6.4 mmol) in THF (16 mL), following the procedure described in Example 46 Step E, the desired aldehyde was obtained after workup and was used without further purification. $^1$H-NMR (300 MHz, CDCl$_3$): δ2.61 (s, 3H), 7.00 (d, J=3.7 Hz, 1H), 7.33 (d, J=3.6 Hz, 1H), 7.45 (dd, J=5.4, 1.3 Hz, 1H), 7.55 (s, 1H), 8.57 (d, J=4.2 Hz, 1H), 9.71 (s, 1H).

Step D (αR,γS,2S)-N-((3S,4S)-3,4-dihydro-3-hydroxy-2H-1-benzopyran-4-yl)-γ-hydroxy-4-[[5-(2-methyl-4-pyridinyl)-2-furanyl]methyl]-α-(phenylmethyl)-2-[[(2,2,2-trifluoroethyl)amino]carbonyl]-1-piperazinepentanamide From a solution of the aldehyde obtained from Step C above (297 mg; 1.59 mmol), penultimate intermediate from Example 12 Step D (628 mg; 1.11 mmol), and NaHB(OAc)$_3$ (337 mg; 1.59 mmol) in anhydrous DMF (12 mL), using the procedure from Example 46 Step F the titled compound was obtained after flash column chromatography (5% MeOH/CH$_2$Cl$_2$). $^1$H-NMR (400 MHz, CD$_3$OD): δ1.40 (m, 1H), 2.06 (m, 1H), 2.33–2.56 (complex m, 4H), 2.53 (s, 3H), 2.60 (m, 1H), 2.69–2.83 (complex m, 3H), 2.94 (m, 1H), 3.00–3.08 (complex m, 2H), 3.11 (dd, J=3.3, 8.0 Hz, 1H), 3.69 (s, 2H), 3.73–3.81 (complex m, 3H), 3.91–4.04 (complex m, 1H), 4.04–4.11 (complex m, 2H), 5.15 (d, J=4.1 Hz, 1H), 6.48 (d, J=3.4 Hz, 1H), 6.73 (d, J=8.2 Hz, 1H), 6.82 (apparent t, J=7.4 Hz, 1H), 7.06 (d, J=3.5 Hz, 1H), 7.11 (apparent t, J=8.5 Hz, 2H), 7.15–7.27 (complex m, 5H), 7.47 (dd, J=1.4, 5.5 Hz, 1H), 7.55 (s, 1H), 8.35 (d, J=5.5 Hz, 1H); electrospray ionization mass spectrum: m/e 736.5 (MH$^+$ calcd for C$_{39}$H$_{44}$F$_3$N$_5$O$_6$, 736.3).

EXAMPLE 52

(αR,γS,2S)-N-((3S,4S)-3,4-dihydro-3-hydroxy-2H-1-benzopyran-4-yl)-4-[[5-(2-ethyl-4-pyridinyl)-2-furanyl]methyl]-γ-hydroxy-α-(phenylmethyl)-2-[[(2,2,2-trifluoroethyl)amino]carbonyl]-1-piperazinepentanamide

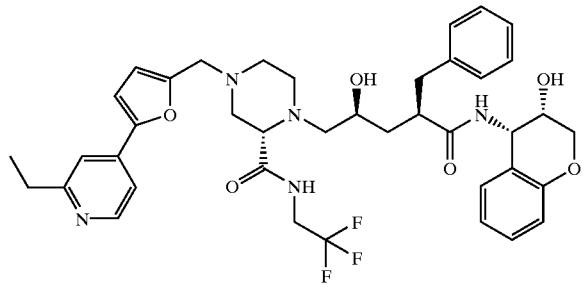

Step A

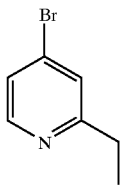

From 4-bromopyridine hydrochloride (5.0 g; 25.7 mmol) and EtMgBr (51.4 mL; 51.4 mmol) and using the procedure from Example 51 Step A, the desired intermediate was obtained and used without further purification. ¹H NMR (300 MHz, CDCl₃): δ1.29 (t, J=7.6 Hz, 3H), 2.80 (q, J=7.6 Hz, 2H), 7.28 (dd, J=5.3, 1.8 Hz, 1H), 7.34 (d, J=1.9 Hz, 1H), 8.33 (d, J=5.3 Hz, 1H).

Step B

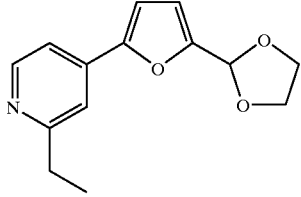

From a stirred solution of the intermediate from Step A above (1.10 g; 5.94 mmol), stannane intermediate from Example 46 Step B (1.50 g; 4.95 mmol), and Pd(PPh₃)₄ (172 mg; 0.149 mmol) in anhydrous DMF (30 mL), using the procedure from Example 49 Step A, the desired compound was obtained after purification by Biotage column chromatography (40% EtOAc/hexane). ¹H-NMR (300 MHz, CDCl₃): δ1.33 (t, J=7.6 Hz, 3H), 2.84 (q, J=7.6 Hz, 2H), 4.03–4.19 (complex m, 4H), 6.00 (s, 1H), 6.56 (d, J=3.5 Hz, 1H), 6.81 (d, J=3.4 Hz, 1H), 7.32 (dd, J=5.3, 1.6 Hz, 1H), 7.40 (s, 1H), 8.51 (d, J=5.2 Hz, 1H).

Step C

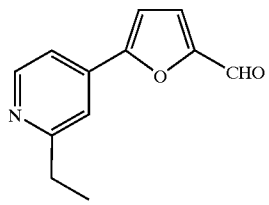

From a stirred solution of intermediate from Step B above (1.09 g; 4.44 mmol) and HCl solution (17.8 mL; 17.8 mmol) in THF (40 mL), following the procedure described in Example 46 Step E, the desired compound was obtained after workup and was used without further purification. ¹H-NMR (300 MHz, CDCl₃): δ1.35 (t, J=7.6 Hz, 3H), 2.89 (q, J=7.6 Hz, 2H), 7.02 (d, J=3.7 Hz, 1H), 7.34 (d, J=3.8 Hz, 1H), 7.46 (dd, J=5.2, 1.6 Hz, 1H), 7.55 (s, 1H), 8.60 (d, J=5.2 Hz, 1H), 9.72 (s, 1H).

Step D (αR,γS,2S)-N-((3S,4S)-3,4-dihydro-3-hydroxy-2H-1-benzopyran-4-yl)-4-[[5-(2-ethyl-4-pyridinyl)-2-furanyl]methyl]-γ-hydroxy-α-(phenylmethyl)-2-[[(2,2,2-trifluoroethyl)amino]carbonyl]-1-piperazinepentanamide From a solution of the aldehyde obtained from Step C above (29 mg; 0.146 mmol), penultimate intermediate from Example 12 Step D (55 mg; 0.097 mmol), and NaHB(OAc)₃ (31 mg; 0.146 mmol) in anhydrous DMF (1.0 mL), using the procedure from Example 46 Step F, the titled compound was obtained after workup as a white solid and was used without further purification. ¹H-NMR (400 MHz, CD₃OD): δ1.31 (t, J=7.6 Hz, 3H), 1.40 (m, 1H), 2.06 (m, 1H), 2.37 (m, 1H), 2.42–2.54 (complex m, 3H), 2.60 (m, 1H), 2.60 (m, 1H), 2.70–2.84 (complex m, 5H), 2.94 (m, 1H), 3.01–3.07 (complex m, 2H), 3.11 (dd, J=3.2, 8.1 Hz, 1H), 3.69 (s, 2H), 3.73–3.81 (complex m, 3H), 3.91–4.04 (complex m, 1H), 4.04–4.11 (complex m, 2H), 5.15 (d, J=3.9 Hz, 1H), 6.49 (d, J=3.3 Hz, 1H), 6.73 (d, J=8.2 Hz, 1H), 6.82 (apparent t, J=7.1 Hz, 1H), 7.06–7.27 (complex m, 8H), 7.48 (dd, J=1.6, 5.5 Hz, 1H), 7.56 (s, 1H), 8.38 (d, J=5.3 Hz, 1H); electrospray ionization mass spectrum: m/e 750.5 (MH⁺ calcd for C₄₀H₄₆F₃N₅O₆, 750.3).

EXAMPLE 53

(αR,γS,2S)-N-((3S,4S)-3,4-dihydro-3-hydroxy-2H-1-benzopyran-4-yl)-γ-hydroxy-4-[[5-(5-oxazolyl)-2-furanyl]methyl]-α-(phenylmethyl)-2-[[(2,2,2-trifluoroethyl)-amino]carbonyl]-1-piperazinepentanamide

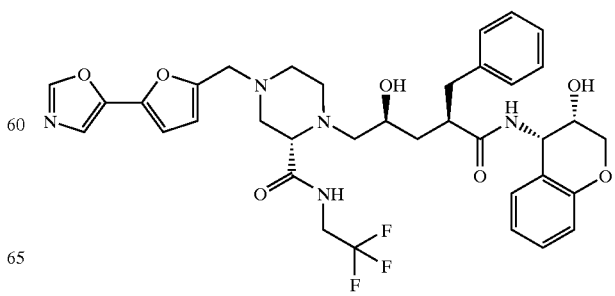

-continued

Step A

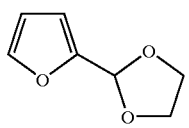

To a stirred solution of 2-furaldehyde (25.0 g; 260 mmol) in benzene (260 mL) was added ethylene glycol (37.0 mL; 650 mmol) and p-toluenesulfonic acid monohydrate (645 mg; 3.9 mmol). The reaction vessel was equipped with a Dean-Stark apparatus and heated to reflux for 5 hours. The reaction mixture was poured in diethyl ether (1.7 L) and washed with saturated $NaHCO_3$ solution, water and brine. After drying ($MgSO_4$), filtration and removal of the solvent in vacuo, purification employing flash chromatography (5% EtOAc/hexane) provided the desired acetal. $^1$H NMR (400 MHz, $CDCl_3$) δ3.99–4.08 (complex m, 2H), 4.11–4.18 (complex m, 2H), 5.93 (s, 1H), 6.37 (dd, J=1.8, 3.4 Hz, 1H), 6.46 (d, J=3.3 Hz, 1H), 7.44 (dd, $J_1=J_2=0.9$ Hz, 1H).

Step B

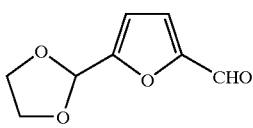

To a stirred solution of the acetal obtained in Step A (932 mg; 6.74 mmol) in anhydrous THF (20 mL) cooled to −78° C. was added tBuLi (4.36 mL; 7.4 mmol) dropwise. After one hour at −78° C., DMF (0.782 mL; 10.11 mmol) was added. The cooling bath was removed and the reaction vessel was allowed to reach ambient temperature at which time the contents of the reaction were poured into $Et_2O$. The combined organic layers were washed sequentially with dilute $NH_4Cl$ solution, water and brine. After drying ($MgSO_4$), filtration and removal of the solvent in vacuo, purification employing flash chromatography (15% EtOAc/hex) provided the desired aldehyde. $^1$H NM (300 MHz; $CDCl_3$) δ4.00–4.17 (complex m, 4H), 5.99 (s, 1H), 6.61 (d, J=3.5 Hz, 1H), 7.19 (d, J=3.4 Hz, 1H), 9.64 (s, 1H).

Step C

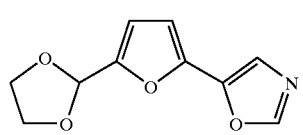

To a stirred solution of the aldehyde obtained in Step B (382 mg; 2.27 mmol) in anhydrous THF (20 mL) cooled to 0° C. was added sequentially 1 H-benzotriazol-1-ylmethyl isocyanide (359 mg; 2.27 mmol), EtOH (0.266 mL; 4.54 mmol) and potassium tert-butoxide (4.54 mL; 4.54 mmol). After approximately 30 minutes at 0° C., the cooling bath was removed and the reaction vessel was allowed to reach ambient temperature at which time the contents of the reaction were poured into EtOAc. The combined organic layers were washed with water and brine. After drying ($MgSO_4$), filtration and removal of the solvent in vacuo, purification employing flash chromatography (30% EtOAc/hexane) provided the desired oxazole. $^1$H NMR (400 MHz, $CDCl_3$) δ4.01–4.10 (m, 2H), 4.12–4.20 (m, 2H), 5.98 (s, 1H), 6.54 (d, J=3.6 Hz, 1H). 6.62 (d, J=3.6 Hz, 1H), 7.31 (s, 1H), 7.85 (s, 1H).

Step D

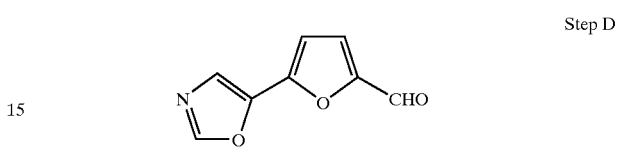

To a stirred solution of the oxazole obtained in Step C (225 mg; 1.08 mmol) in THF (6 mL) was added 1N HCl (4.32 mL; 4.32 mmol). After approximately 4 hours the contents of the reaction were poured into EtOAc. The combined organic layers were washed with dilute $NH_4OH$, water and brine. After drying ($MgSO_4$), filtration and removal of the solvent in vacuo, purification employing flash chromatography (30% EtOAc/hex) provided the desired aldehyde. $^1$H NMR (400 MHz, $CDCl_3$) δ6.8 (d, J=3.7 Hz, 1H), 7.34 (d, J=3.8 Hz, 1H), 7.59 (s, 1H), 7.98 (s, 1H). 9.70 (s, 1H).

Step E (αR,γS,2S)-N-((3S,4S)-3,4-dihydro-3-hydroxy-2H-1-benzopyran-4-yl)-γ-hydroxy-4-[[5-(5-oxazolyl)-2-furanyl]methyl]-α-(phenylmethyl)-2-[[(2,2,2-trifluoroethyl)amino]carbonyl]-1-piperazinepentanamide To a stirred solution of the penultimate intermediate obtained from Example 12 Step D (17 mg; 0.030 mmol) in anhydrous,DMF (0.5 mL) under $N_2$ was added the aldehyde obtained in Step D above (7.3 mg; 0.045 mmol) followed by $NaBH(OAc)_3$ (9.5 mg; 0.045 mmol). The reaction was stirred overnight. The following morning, the reaction solution was poured into EtOAc and washed with water and brine. After drying ($MgSO_4$), filtration and removal of the solvent in vacuo, purification employing flash chromatography (5% MeOH/DCM) provided the desired product after lyophilization from $MeCN/H_2O$ (1:1). $^1$H NMR (400 MHz, $CD_3OD$) δ1.40 (m, 1H), 2.06 (m, 1H), 2.34–2.52 (complex m, 4H), 2.54–2.61 (m, 1H), 2.68–2.79 (complex m, 4H), 2.92–3.06 (complex m, 4H), 3.10 (dd, J=3.4, 7.7 Hz, 1H), 3.65 (s, 2H), 3.73–3.79 (complex m, 4H), 3.94–4.01 (complex m, 2H), 4.05–4.12 (complex m, 2H), 5.15 (d, J=3.9 Hz, 1H), 6.45 (d, J=3.5 Hz, 1H), 6.71 (d, J=3.5 Hz, 1H), 6.73 (d, J=8.2 Hz, 1H), 6.82 (apparent td, J=1.2, 7.6 Hz, 1H), 7.08–7.15 (m, 2H), 7.18–7.22 (complex m, 6H), 8.20 (s, 1H); electrospray ionization mass spectrum: m/e 712.4 ($MH^+$ calcd for $C_{36}H_{41}F_3N_5O_7$, 712.3).

EXAMPLE 54

(αR,γS,2S)-N-((3S,4S)-3,4-dihydro-3-hydroxy-2H-1-benzopyran-4-yl)-γ-hydroxy-α-(phenylmethyl)-4-[[1-(4-pyridinyl)-1H-pyrrol-3-yl]methyl]-2-[[(2,2,2-trifluoroethyl)amino]carbonyl]-1-piperazinepentanamide

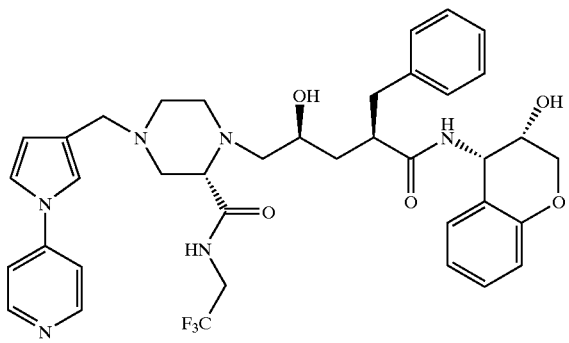

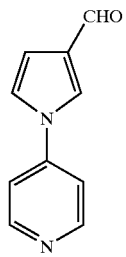

Step A

A solution of 4-aminopyridine (0.094 g, 1.0 mmol) and 2,5-dimethoxytetrahydrofurane (0.20 g, 1.25 mmol) in acetic acid (1 mL) was heated at 90° C. for 2 hours. The pH of the solution was adjusted to 10 with 1N NaOH. The aqueous layer was then extracted with dichloromethane (3×10 mL). The combined dichloromethane layers were washed with brine and dried over sodium sulfate. Removal of the solvent afforded the title compound as a light brown oil. The compound was pure enough for the next step. $^1$H NMR (300 MHz, CDCl$_3$): 9.88 (s, 1H), 8.70 (d, J=3 Hz, 2H), 7.80 (s, 1H), 7.36 (d, J=3 Hz, 2H), 7.22 (s, 1H), 6.85 (s, 1H).

Step B (αR,γS,2S)-N-((3S,4S)-3,4-dihydro-3-hydroxy-2H-1-benzopyran-4-yl)-γ-hydroxy-α-(phenylmethyl)-4-[[1-(4-pyridinyl)-1H-pyrrol-3-yl]methyl]-2-[[(2,2,2-trifluoroethyl)amino]carbonyl]-1-piperazinepentanamide A mixture of the aldehyde from Step A (18.9 mg, 0.11 mmol), penultimate from Example 12 Step D (40 mg, 0.073 mmol), and sodium triacetoxyborohydride (23 mg, 0.11 mmol) in anhydrous dichloroethane (2 mL) was stirred at room temperature overnight. After 18 hours, the solvent was removed via vacuum. Preparative TLC purification (EtOAc/hexane) gave the titled compound as a white solid. $^1$H NMR (400 MHz, CDCl$_3$) 1:1 rotamers: 9.20 (br s, 1H), 8.63 (dd, J=4.8, 1.6 Hz, 2H), 7.08–7.35 (m, 12H), 6.82 (m, 2H), 6.30 (s, 1H), 6.94 (d, J=8.4 Hz, 1H), 5.18 (m, 1H), 4.00–4.20 (m, 4H), 3.77 (m, 2H), 3.49 (AB q, J=36, 13.2 Hz, 2H), 3.37 (s, 1H), 2.41–3.05 (m, 11H), 2.37 (m, 1H), 1.92 (m, 1H), 1.59 (m, 1H). LC-MS (M$^+$+1)(EI) 721.

EXAMPLE 55

(αR,γS,2S)-N-((3S,4S)-3,4-dihydro-3-hydroxy-2H-1-benzopyran-4-yl)-γ-hydroxy-α-(phenylmethyl)-4-[[1-(3-pyridinyl)-1H-pyrrol-3-yl]methyl]-2-[[(2,2,2-trifluoroethyl)amino]carbonyl]-1-piperazinepentanamide

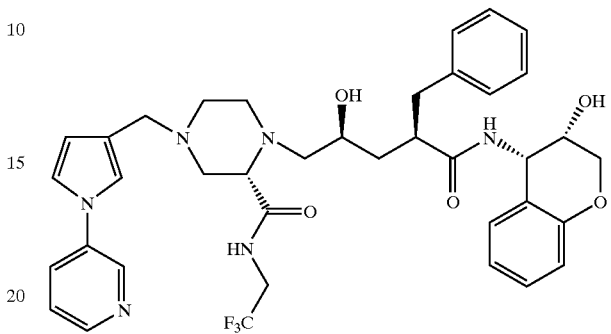

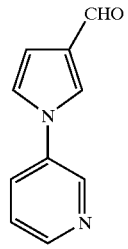

Step A

A solution of 3-aminopyridine (0.094 g, 1.1 mmol) and 2,5-dimethoxytetrahydrofuran (0.20 g, 1.25 mmol) in acetic acid (1 mL) was heated at 80° C. for 1 hour. The pH of the solution was adjusted to 10. The mixture was then extracted with dichloromethane (3×15 mL). The combined dichloromethane layers were washed with brine, and dried over sodium sulfate. The titled compound was obtained as a yellow solid. $^1$H NMR (CDCl$_3$, 400 MHz): 9.90 (s, 1H), 8.80 (d, J=2.8 Hz, 1H), 8.64 (dd, J=4.8, 1.6 Hz, 1H), 7.77 (m, 1H), 7.70 (d, J=1.6 Hz, 1H), 7.47 (m, 1H), 7.11 (d, J=2.4 Hz, 1H), 6.87 (dd, J=3.2, 2 Hz, 1H).

Step B (αR,γS,2S)-N-((3S,4S)-3,4-dihydro-3-hydroxy-2H-1-benzopyran-4-yl)-γ-hydroxy-α-(phenylmethyl)-4-[[1-(3-pyridinyl)-1H-pyrrol-3-yl]methyl]-2-[[(2,2,2-trifluoroethyl)amino]carbonyl]-1-piperazinepentanamide A mixture of the aldehyde from Step A (18.9 mg, 0.11 mmol), penultimate fro Example 12 Step D (40 mg, 0.073 mmol), and sodium triacetoxyborohydride (23 mg, 0.11 mmol) in anhydrous dichloroethane (2 mL) was stirred at room temperature overnight. After 18 hours, the solvent was removed via vacuum. The preparative TLC purification (EtOAc/Hexane) gave the titled compound as a white solid. $^1$H NMR (CDCl$_3$, 400 MHz): 9.30 (br s, 1H), 8.75 (s, 1H), 8.53 (d, J=4 Hz, 1H), 7.68 (m, 1H), 7.40 (dd, J=8.4, 5.2 Hz, 1H), 7.23 (m, 4H), 7.16 (m, 3H), 7.00(s, 1H), 6.82 (m, 2H), 6.30 (s, 1H), 6.02 (br s, 1H), 5.19 (m, 1H), 3.99–4.20. (m, 3H), 3.68–3.81 (m, 2H), 3.42–3.60 (m, 2H), 3.38 (s, 1H), 2.61–3.10 (m, 8H), 2.50 (m, 2H), 2.37 (m, 1H), 1.90 (m, 1H), 1.60 (m, 1H). LC-MS (M++1)(EI) 721.

EXAMPLE 56

(αR,γS,2S)-N-((3S,4S)-3,4-dihydro-3-hydroxy-2H-1-benzopyran-4-yl)-γ-hydroxy-α-(phenylmethyl)-4-[[5-(4-pyridazinyl)-2-furanyl]methyl]-2-[[(2,2,2-trifluoroethyl)-amino]carbonyl]-1-piperazinepentanamide

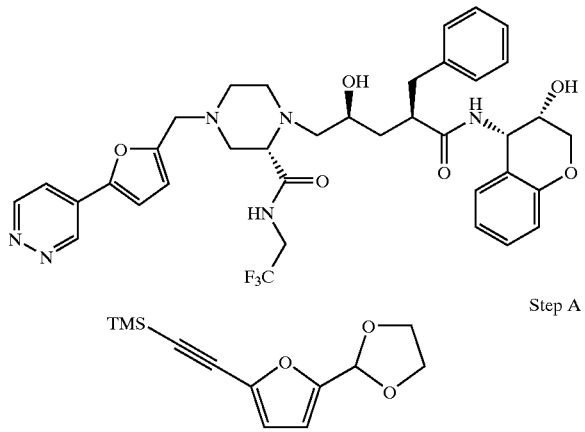

Step A

A mixture of 5-bromo-2-(1,3-dioxalane)furan (0.50 g, 2.4 mmol), (trimethylsilyl)acetylene (0.31 mL, 2.28 mmol), piperidine (1 mL, 10 mmol), and catalytic amount of tetrakis (triphenylphosphine)palladium, CuI and triphenylphosphine was heated to reflux for 30 min. Water (10 mL) was added. The mixture was extracted with ethyl acetate (3×20 mL). The combined ethyl acetate layers were washed with brine and dried over sodium sulfate. Flash chromatography using EtOAc/hexane 1:9 as the elute gave the titled compound as a colorless oil. $^1$H NMR (CDCl$_3$, 400 MHz): 6.90 (d, J=3.2 Hz, 1H), 6.67 (d, J=3.2 Hz, 1H), 5.91 (s, 1H), 4.00–4.20 (m, 4H), 0.22 (s, 9H).

Step B

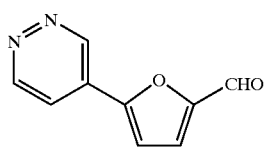

A solution of the titled compound from Step A (0.11 g, 0.47 mmol), 1,2,4,5-tetrazine in acetonitrile (5 mL) was refluxed for 2 days. No starting material was observed by TLC (EtOAc/hexane 2:8). The solvent was removed. The residue was stirred with 1M tetrabutylammonium fluoride (0.5 mL) in THF/water at room temperature for 2 days. Water (1 mL) was added and the mixture was extracted with ethyl acetate (3×15 mL). The combined ethyl acetate layers were washed with brine, and dried over sodium sulfate. Preparative TLC plate using 1:1 EtOAc/hexane as the elute afforded the pyridazine as a white solid (0.058 g, 58%). The pyridazine was then stirred with a mixture of 1N HCl (1 mL) and THF (5 mL) at room temperature for 4 hours. The mixture was basified with saturated sodium bicarbonate solution and extracted with dichloromethane (2×15 mL). The combined dichloromethane layers were dried over sodium sulfate. The titled compound was obtained as a yellow solid upon removal of the solvent. $^1$H NMR (CDCl$_3$, 400 MHz): 9.80 (s, 1H), 9.57 (m, 1H), 9.31 (dd, J=5.6, 1.2 Hz, 1H), 7.84 (dd, J=5.6, 2 Hz, 1H), 7.41 (d, J=4 Hz, 1H), 7.21 (d, J=4 Hz, 1H).

Step C (αR,γS,2S)-N-((3S,4S)-3,4-dihydro-3-hydroxy-2H-1-benzopyran-4-yl)-γ-hydroxy-α-(phenylmethyl)-4-[[5-(4-pyridazinyl)-2-furanyl]methyl]-2-[[(2,2,2-trifluoroethyl)-amino]carbonyl]-1-piperazinepentanamide A mixture of the aldehyde from Step B (22 mg, 0.12 mmol), penultimate prepared as in Example 12 Step D (65 mg, 0.12 mmol), and sodium triacetoxyborohydride (38 mg, 0.18 mmol) in anhydrous dichloroethane (2 mL) was stirred at room temperature overnight. After 18 hours, the solvent was removed via vacuum. Preparative TLC purification (EtOAc/MeOH 9:1) gave the titled compound as a yellow solid. $^1$H NMR (CDCl$_3$, 400 MHz): 9.41 (s, 1H), 9.16 (d, J=5.2 Hz, 1H), 8.79 (br s, 1H), 7.59 (dd, J=5.6, 2 Hz, 1H), 7.08–7.36 (m, 7H), 7.02 (d, J=3.6 Hz, 1H), 6.80 (m, 2H), 6.46 (d, J=3.2 Hz, 1H), 6.06 (d, J=8.4 Hz, 1H), 5.17 (dd, J=8, 4 Hz, 1H), 4.01–4.16 (m, 3H), 3.63–3.81 (m, 5H), 3.40 (s, 1H), 2.62–3.12 (m, 9H), 2.48 (m, 2H), 1.97 (m, 1H), 1.59 (m, 1H). LC-MS (M++1)(EI) 723.

EXAMPLE 57

(αR,γS,2S)-N-((3S,4S)-3,4-dihydro-3-hydroxy-2H-1-benzopyran-4-yl)-γ-hydroxy-4-[1-methyl-1-[3-methyl-5-(4-pyridinyl)-2-furanyl]ethyl]-α-(phenylmethyl)-2-[[(2,2,2-trifluoroethyl)amino]carbonyl]-1-piperazinepentanamide

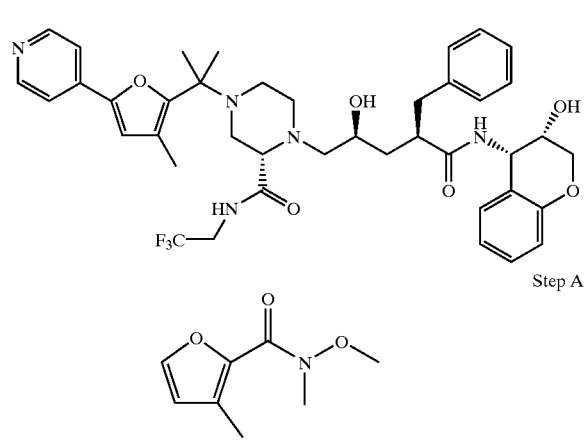

Step A

To a solution of commercially available methyl 3-methylfuroate (20.0 g, 140 mmol) in 100 mL of MeOH, NaOH (11.43 g, 280 mmol) in 20 mL of water was added. The yellowish solution was stirred at room temperature for 3 hours. TLC (1:9 EtOAc/hexane) showed no starting material. MeOH was removed and the pH of the aqueous solution was adjusted to 4 with 1N HCl. The slurry was extracted with ethyl acetate (5×100 mL). The combined ethyl acetate layers were washed brine, and dried over sodium sulfate. 3-methyl furoic acid was obtained as a white solid (13.2 g, 73%) after evaporation of the solvent. To a mixture of 3-methyl furoic acid (8.60 g, 68 mmol), N,O-dimethylhydroxylamine hydrochloride (8.0 g, 82 mmol), EDC (15.7 g, 82 mmol), and HOBT (11.07 g, 82 mmol) in dichloromethane (200 mL), triethylamine (14.4 mL, 100 mmol) was added. The solution was stirred at room temperature for 4 hours, and washed with 1N NaOH (50 mL), 1N HCl (50 mL), brine, and dried over sodium sulfate. The title compound was obtained as a colorless liquid upon removal of the solvent. ¹H NMR (CDCl₃, 400 MHz): 7.40 (s, 1H), 6.38 (s, 1H), 3.81 (s, 3H), 3.36 (s, 3H), 2.38 (s, 3H).

Step B

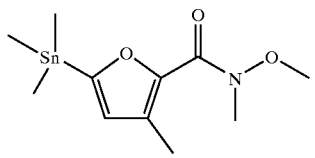

To a solution of the titled compound from Step A (6.0 g, 35.9 mmol) in dichloroethane (50 mL), a solution of bromine (2.22 mL, 43.1 mmol) in dichloroethane (5 mL) was added dropwise in about 30 min. The progress of the bromination was monitored by HPLC. The reaction was stirred at room temperature for 2 hours, until no starting material was seen by HPLC. The solution was diluted with dichloromethane (100 mL). The solution was then washed with saturated solution of sodium bicarbonate (50 mL), brine, and dried over sodium sulfate. The 5-brominated furan was obtained as a yellow oil (5.17 g, 58%) after chromatography (2:8 EtOAc/hexane). A mixture of the 5-bromofuran above (5.17 g, 20.8 mmol), hexamethylditin (7.5 g, 22.9 mmol), tetrakis(triphenylphosphine)palladium (1.2 g, 1 mmol), and triphenylphosphine (0.16 g, 0.62 mmol) in toluene (20 mL) was heated to reflux overnight. Water (100 mL) was added. The mixture was extracted with EtOAc (3×100 mL). The combined ethyl acetate layers were washed with brine, and dried over sodium sulfate. Flash chromatography using 1:9 EtOAc/hexane as the elute gave the titled compound as a colorless oil. ¹H NMR (CDCl₃, 300 MHz): 6.50 (s, 1H), 3.80 (s, 3H), 3.50 (s, 3H), 2.34 (s, 3H), 0.38 (s, 9H).

Step C

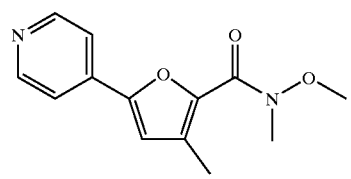

A mixture of the titled compound from Step B (1.40 g, 4.25 mmol), 4-bromopyridine hydrochloride (1.65 g, 8.5 mmol), diisopropylethylamine (DIEA) (1.63 mL, 9.36 mmol), and tetrakis(triphenylphosphine)palladium (0.15 g, 0.13 mmol) in DMF (10 mL) was heated to 100° C. overnight. Water (100 mL) was added and the mixture was extracted with ethyl acetate (3×100 mL). The combined ethyl acetate layers were washed with brine and dried over sodium sulfate. Flash chromatography using 1:1 EtOAc/hexane as the elute afforded the titled compound as a yellow solid. ¹H NMR (CDCl₃, 400 MHz): 8.66(d, J=6.4 Hz, 2H), 7.59 (d, J=6 Hz, 2H), 6.89 (s, 1H), 3.95 (s, 3H), 3.49 (s, 3H), 2.40 (s, 3H).

Step D

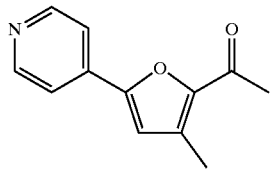

To a solution of the titled compound from Step C (0.77 g, 3.13 mmol) in THF (10 mL) at 0° C., 1.4 M solution of methyl magnesium bromide (11.2 mL, 15.65 mmol) in a mixture of toluene and THF was added slowly. The reaction was stirred at 0° C. for 2 hours. TLC (3:7 EtOAc/hexane) showed no starting material. Water (5 mL) was added. The mixture was extracted with ethyl acetate (3×15 mL). The combined ethyl acetate layers were washed with brine and dried over sodium sulfate. Flash chromatography using 3:7 EtOAc/hexane as the elute gave the titled compound as a colorless oil. ¹H NMR (CDCl₃, 400 MHz): 8.70 (d, J=6.4 Hz, 2H), 7.63 (d, J=6 Hz, 2H), 6.89 (s, 1H), 2.60 (s, 3H), 2.43 (s, 3H).

Step E

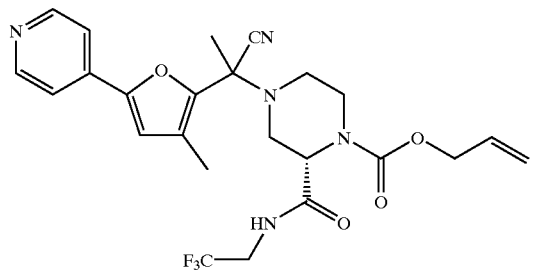

To a solution of Boc protected piperzine prepared as in Example 12 Step A (0.98 g, 2.48 mmol) in dichloromethane (10 mL), trifluoroacetic acid (5 mL) was added. The solution was stirred at room temperature for 3 hours. TLC (1:1 EtOAc/hexane) showed no starting material. The solvents were removed and dried under high vacuum for 2 hours. The residue was mixed with the titled compound from Step D (0.47 g, 2.34 mmol) and trimethylsilyl cyanide (3.11 mL, 23.4 mmol) and the mixture was heated at 60 C. overnight. LC-MS indicated that there was no starting ketone left. The mixture was poured into an icy ammonium hydroxide solution (10 mL). The aqueous solution was extracted with ethyl acetate (3×50 mL). The combined ethyl acetate layers were washed with brine and dried over sodium sulfate. Flash chromatography using 1:1 EtOAc/hexane as the elute gave the titled compound as a light yellow oil. ¹H NMR (CDCl₃, 400 MHz): a 4:6 mixture of diastereomers 8.61 (d, J=6.4 Hz, 2H), 7.62 (m, 0.8H), 7.60 (m, 1.2H), 6.89 (s, 0.4H), 6/82 (s, 0.6H), 6.50 (br s, 1H), 5.95 (m, 1H), 5.32 (m, 2H), 4.95 (m, 0.6H), 4.80 (m, 0.4H), 4.70 (m, 2H), 4.20 (m, 2H), 3.85 (m, 0.6H), 3.70 (m, 1H), 3.40 (m, 0.4H), 3.10 (m, 1H), 2.82 (m, 1H), 2.40 (m, 2H), 2.22 (s, 1.2H), 2.17 (s, 1.8H), 1.96 (s, 3H)

Step F

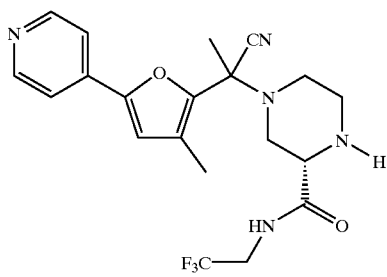

Step H

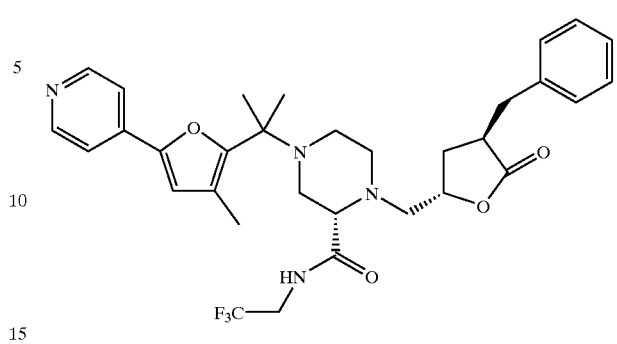

1,3-Dimethylbarbituric acid (1.45 g, 9.30 mmol) was added to a solution of the titled compound from Step E (0.94 g, 1.86 mmol) in THF at room temperature. The brown solution was stirred at room temperature for 20 min. Tetrakis(triphenylphosphine)palladium (0.21 g, 0.186 mmol) was added and the solution was stirred at room temperature for another 20 min. The color of the solution turned to redish. TLC (EtOAc) showed no starting material. 1N HCl (20 mL) was added. The mixture was extracted with ethyl acetate (2×30 mL). The aqueous was adjusted to pH=10 and extracted with chloroform (3×50 mL). The combined chloroform layers were dried over sodium sulfate. Flash chromatography (5:95 MeOH/CH$_2$Cl$_2$) afforded the titled compound as a yellow oil. $^1$H NMR: (CDCl$_3$, 400 MHz): a 4:6 mixture of diastereomers 8.70 (m, 1.2H), 8.61 (m, 0.8H), 7.64 (br s, 1H), 7.60 (m, 1.2H), 7.48 (m, 0.8H), 6.88 (s, 0.6H), 6.77 (s, 0.4H), 3.96 (m, 2H), 3.58 (m, 1H), 3.20 (m, 1H), 2.96 (m, 3H), 2.60 (s, 3H), 2.46 (s, 3H), 2.20 (m, 2H).

Step G

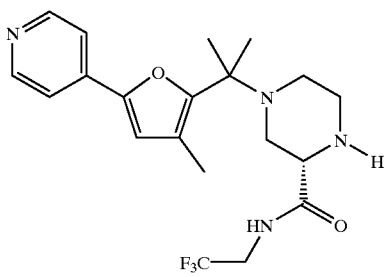

To a solution of the titled compound from Step F (0.716 g, 1.7 mmol) in DME (10 mL) at 0° C., methylmagnesium bromide (12 mL, 17 mmol, 1.4 M) was added. The mixture was stirred at 0° C. for 2 hours and room temperature for 30 min. TLC showed no starting material (5:95 MeOH/CH$_2$Cl$_2$). Water (10 mL) was added and the aqueous was extracted with ethyl acetate (3×20 mL). The combined ethyl acetate layers were washed with brine and dried over sodium sulfate. Flash chromatography using 5:95 MeOH/CH$_2$Cl$_2$ as the elute gave the titled compound as a gummy material. $^1$H NMR (CDCl$_3$, 400 MHz): 8.60 (d, J=6 Hz, 2H), 7.45 (d, J=6 Hz, 2H), 6.70 (s, 1H), 3.92 (m, 2H), 3.50 (m, 1H), 2.83 (m, 4H), 2.48 (m, 2H), 2.18 (s, 3H), 1.60 (s, 6H).

To a solution of the dihydro-5(S)-(hydroxymethyl)-3(R)-(phenylmethyl)-3(2H)-furanone (2.06 g, 10 mmol) in dichloromethane (50 mL) at 0° C., triflic anhydride and 2,6-lutidine were added. The solution was stirred at 0° C. for 1 hour. Water (10 mL) was added. The mixture was extracted with dichloromethane (2×50 mL). The combined dichloromethane layers were washed with brine (20 mL), and dried over sodium sulfate. The triflate was obtained as a white waxy material after flash chromatography using 2:8 EtOAc/hexane as the elute. A mixture of the triflate (0.33 g, 1.02 mmol), the titled compound from Step G (0.421 g, 1.02 mmol), and N,N-diisopropylethyl amine (0.21 mL, 1.23 mmol) in 2-propanol (10 mL) was stirred at room temperature overnight. After 20 hours, the solvent was removed. The residue was dissolved in dichloromethane (20 mL). The solution was washed with water, brine, and dried over sodium sulfate. The titled compound was obtained as a gummy material after flash chromatography using 7:3 EtOAc/hexane as the elute. $^1$H NMR (CDCl$_3$, 400 MHz): 8.60 (d, J=6 Hz, 2H); 8.05 (br s, 1H), 7.46 (d; J=6 Hz, 2H), 7.25 (m, 5H), 6.76 (s, 1H), 4.41 (m, 1H), 4.08 (m, 1H), 3.78 (m, 2H), 2.56–3.35 (m, 9H), 2.20 (s, 3H), 2.05 (m, 1H), 1.97 (m, 1H), 1.60 (s, 6H), 1.10 (m, 2H).

Step I

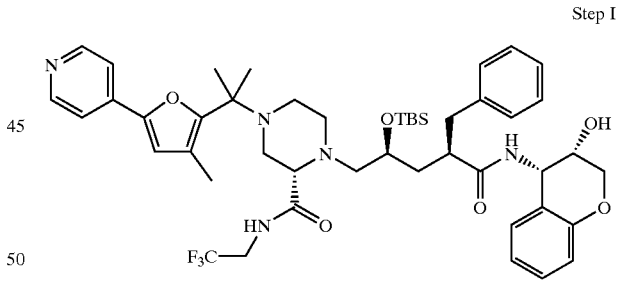

A mixture of the titled compound from Step H (0.452 g, 0.76 mmol) in dioxane (10 mL) and 1 mL of aqueous LiOH (38 mg, 0.90 mmol) was stirred at room temperature overnight. The solvent was removed azeotropically with toluene (3×10 mL). The residue was dissolved in 3:1 mixture of EtOAc/CH$_2$Cl$_2$ (10 mL). TBSOTf (0.38 mL, 1.66 mmol) and N,N-diisopropylethyl amine (0.31 mL, 1.81 mmol) were added. The mixture was stirred at room temperature and the reaction was monitored by LC/MS. More TBSOTf (up to 6 eq) and N,N-diisopropylethyl amine (up to 8 eq) were added. After 20 hours, water (10 mL) was added and the mixture was extracted with EtOAc (3×60 mL). The combined ethyl acetate layers were washed with brine, and dried over sodium sulfate. Evaporation of the solvent gave a colorless oil that was then mixed with 1:1 mixture of water and THF (5 mL). The solution was stirred at room temperature for 2 hours and LC/MS showed that there was no silyl ester left. The solvents were removed and dried under high vacuum. The residue was mixed with O-benzotriazol-1-yl-N,N,N',N'-tetramethyluronium hexafluorophosphate (0.80 g, 2.1 mmol), N,N-diisopropylethyl amine (0.66 mL, 3.78 mmol), aminochromanol (0.15 g, 0.90 mmol), and catalytic amount of 1-hydroxy-7-azabenzo-trazole in DMF (5 mL) at room temperature overnight. After 22 hours, water (10 mL) was added. The mixture was extracted with ethyl acetate (3×50 mL). The combined ethyl acetate layers were washed with brine, and dried over sodium sulfate. The titled compound was obtained as a white solid after flash chromatography using 1:1 EtOAc/hexane as the elute. $^1$H NMR (CDCl$_3$, 400 MHz): 8.58 (d, J=6 Hz, 2H), 8.18 (br s, 1H), 7.40 (d, J=6 Hz, 2H), 6.79–7.36 (m, 9H), 6.65 (s, 1H), 5.72 (br s, 1H), 5.17 (m, 1H), 4.00 (m, 4H), 3.82 (m, 1H); 3.70 (m, 2H), 3.18 (m, 1H), 2.81 (m, 7H), 2.30–3.10 (m, 6H), 2.08 (s, 3H), 1.50 (s, 6H), 0.82 (s, 9H), 0.02 (s, 3H), 0.01 (s, 3H).

Step J (αR,γS,2S)-N-((3S,4S)-3,4-dihydro-3-hydroxy-2H-1-benzopyran-4-yl)-γ-hydroxy-4-[1-methyl-1-[3-methyl-5-(4-pyridinyl)-2-furanyl]ethyl]-α-(phenylmethyl)-2-[[(2,2,2-trifluoroethyl)amino]carbonyl]-1-piperazinepentanamide To a solution of the titled compound from Step I (34 mg, 0.039 mmol) in THF (1 mL), 1 M solution of tetrabutylammonium fluoride (0.046 mL, 0.046 mmol) was added. The solution was stirred at room temperature for 1 hour. TLC (EtOAc/hexane=1:1) showed no reaction. Another 5 equivalents of tetrabutylammonium fluoride were added. The solution was stirred at 60° C. for 1 h and room temperature overnight. No starting material was seen by TLC. The solvent was removed. The titled compound was obtained as a white solid after preparative TLC using ethyl acetate as the elute. $^1$H NMR (CDCl$_3$, 400 MHz): 9.10 (br s, 1H), 8.60 (d, J=6 Hz, 2H), 7.43 (d, J=6 Hz, 2H), 7.28 (m, 5H), 7.10 (m, 2H), 6.80 (m, 2H), 6.71 (s, 1H), 5.99 (d, J=8 Hz, 1H), 5.18 (m, 1H), 4.00 (m, 3H), 3.80 (m, 2H), 3.60 (m, 1H), 3.38 (m, 1H), 2.40–3.10 (m, 11H), 2.20 (s, 3H), 1.90 (m, 1H), 1.60 (s, 3H), 1.58 (s, 3H), 1.40 (m, 1H). LC-MS (M++1)(EI) 764.

EXAMPLE 58

(αR,γS,2S)-N-((3S,4S)-3,4-dihydro-3-hydroxy-2H-1-benzopyran-4-yl)-γ-hydroxy-α-(phenylmethyl)-4-[[5-(2-pyrazinyl)-2-furanyl]methyl]-2-[[(2,2,2-trifluoroethyl)-amino]carbonyl]-1-piperazinepentanamide

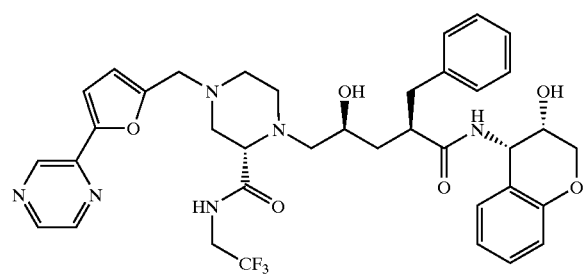

-continued

Step A

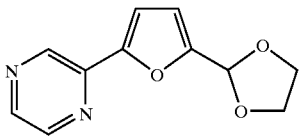

To a solution of the stannane from Example 46 Step B (2 g, 6.6 mmol) and chloropyrazine (756 mg, 6.6 mmol) in DMF (20 mL) was added dichlorobis(triphenylphosphine)palladium(II) (140 mg, 0.2 mmol). The reaction mixture was stirred at 100° C. for 20 hours to see the stannane was consumed (by TLC). It was cooled to room temperature and diluted with ethyl acetate (200 mL). The diluted solution was then washed with water (2×100 mL) and brine (100 mL). The organic layer was dried over anhydrous sodium sulfate and concentrated in vacuum to get a brown oil. The crude product was purified by flash column chromatography on silica gel with ethyl acetate as eluant to give the titled compound as a slightly yellow oil which solidified after standing. $^1$H NMR (CDCl$_3$, 300 MHz): δ8.99 (s,1H), 8.53 (d, J=2.4 Hz, 1H), 8.43 (d, J=2.4 Hz, 1H), 7.26 (s, 1H), 6.04 (s, 1H), 4.04–4.2 (m, 4H).

Step B

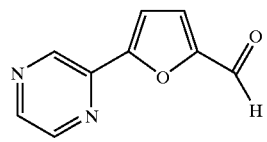

The intermediate from the previous step (1.1 g, 5.04 mmol) was dissolved in THF (25 mL). The solution was cooled to 0° C. and HCl (1 M, 25 mL) was added. The reaction solution was stirred at 0° C. for 10 minutes and slowly warmed to room temperature at which it was stirred for 10 hours. (The reaction was monitored by TLC). It was concentrated to about 30 mL. To the remaining mixture was added ethyl acetate (100 mL). Then 1 N NaOH was used to basicify the solution to pH=12. The organic layer was collected, dried over anhydrous sodium sulfate and concentrated in vacuum to give the titled compound as a pale solid. $^1$H NMR (CDCl$_3$, 300 MHz): δ9.77 (s, 1H), 9.18 (s, 1 H), 8.62 (d, J=2.4 Hz, 1 H), 8.59 (d, J=2.4, 1 H), 7.38 (d, J=3.9 Hz, 1 H), 7.33(d,J=3.9 Hz,1 H).

Step C (αR,γS,2S)-N-((3S,4S)-3,4-dihydro-3-hydroxy-2H-1-benzopyran-4-yl)-γ-hydroxy-α-(phenylmethyl)-4-[[5-(2-pyrazinyl)-2-furanyl]methyl]-2-[[(2,2,2-trifluoroethyl)amino]carbonyl]-1-piperazinepentanamide To a solution of the aldehyde from the previous step (21 mg, 0.11 mmol) and the penultimate (50 mg, 0.09 mmol) in DCE (5 mL) was added sodium triacetoxyborohydride (28 mg, 0.13 mmol). The reaction mixture was stirred at room temperature for 12 hours and purified on preparative TLC (2000 microns, CH$_2$Cl$_2$/acetone/2N NH$_3$ in methanol=47.5/47.5/5 as eluant) to give the titled compound as a white solid. $^1$H NMR (CD$_3$OD, 400 MHz): δ8.96 (s, 1H), 8.55 (d, J=2.1 Hz, 1b H), 8.43 (d, J=2.1 Hz, 1 H), 7.81 (d, J=6.6 Hz, 1 H), 7.07–7.27 (m, 7 H), 6.82 (dt, J=7.6, 1.2 Hz, 1 H), 6.72 (dd, J=1.2, 8.0 Hz, 1 H), 6.53 (d, J=2.1 Hz, 1 H), 5.16 (m, 1 H), 4.08–4.11 (m, 2 H), 3.94–4.00(m 1 H), 3.73–3.81 (m, 4 H), 3.13 (broad s, 1 H), 3.01–3.05 (m, 2 H), 2.92–2.97 (m, 2 H), 2.81 (broad d, J=11.2. 1 H), 2.73–2.77 (m, 2 H), 2.65 (t, J=11.2 Hz, 1 H), 2.52 (t, J=10 Hz, 1 H), 2.36–2.36 (m, 4 H), 2.02–2.14 (m, 1 H), 1.37–1.44 (m, 1 H). LC-MS (M$^+$+1) (EI) 723.4.

EXAMPLE 59

(αR,γS,2S)-N-((3S,4S)-3,4-dihydro-3-hydroxy-2H-1-benzopyran-4-yl)-γ-hydroxy-4-[[5-(1-methyl-1H-pyrazol-4-yl)-3-pyridinyl]methyl]-α-(phenylmethyl)-2-[[(2,2,2-trifluoroethyl)amino]carbonyl]-1-piperazinepentanamide

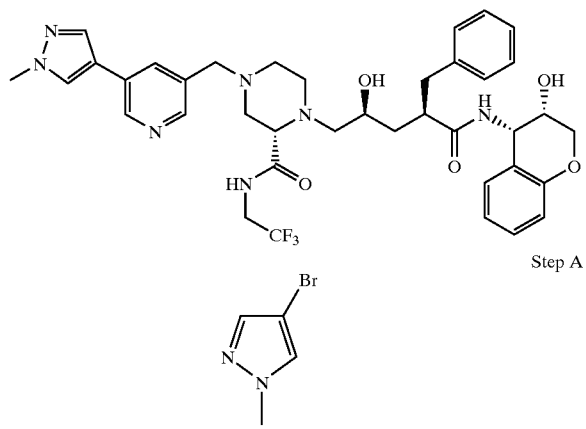

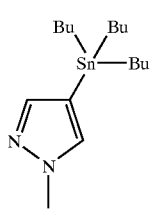

To a solution of 1-methyl pyrazole (10 g, 122 mmol) in chloroform (100 mL) was added a solution of bromine (78 g, 160 mmol in 50 mL chloroform) dropwise at room temperature. The reaction solution was refluxed for 8 hours. Then it was diluted with chloroform (200 mL) and 1 N NaOH was added until a clear solution was obtained. The organic layer was dried over anhydrous sodium sulfate and concentrated to give a slightly yellow oil. The crude product was purified by flash column chromatography on silica gel with hexanes/ethyl acetate=100/1.5 as eluant to get 4-bromo-1-methylpyrazole as a colorless oil. $^1$H NMR (CDCl$_3$, 300 MHz): δ7.44 (s, 1H), 7.38 (s, 1H), 3.89 (s, 3 H).

Step B

To a solution of 4-bromo-1-methylpyrazole (15 g, 38.5 mmol) in ether (150 mL) n-Butyllithium (2.5M in hexanes, 17 mL, 42.4 mmol) was added at −78° C. After the reaction solution was stirred at −78° C. for 30 minutes, tributyltin chloride (11.5 mL, 42.4 mmol) was added. It was stirred at −60° C. for 1 hour and warmed to room temperature, at which it was stirred for 1 more hour. Then, it was diluted with ethyl acetate (300 mL) and washed with water (200 mL) and brine. The organic layer was dried over anhydrous sodium sulfate and concentrated. The crude product was purified by flash column chromatography on silica gel with hexanes/ethyl acetate=10/1 as eluant to get 1-methyl-4-tributylstannylpyrazole as a white wax. $^1$H NMR (CDCl$_3$, 300 MHz): δ7.42 (s, 1H), 7.23 (s, 1H), 3.93 (s, 3 H). 1.28–1.55 (m, 18 H), 0.91 (t, J=15 Hz, 9 H).

Step C

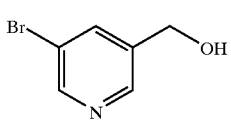

To a solution of borane-tetrahydrofuran complex (1 M in THF, 800 mL) in THF (250 mL) was added 5-bromonicotinic acid (40 g, 198 mmol) at small portions to keep the temperature of the reaction solution below 40° C. After the addition, the reaction solution was stirred at room temperature for 24 hours. It was quenched with sodium hydroxide solution (1 N, 1 L). The quenched mixture was heated to reflux for 12 hours. It was separated. The aqueous layer was extracted with ethyl acetate for 4 times (500 mL each time). The combined organic layer was dried over anhydrous sodium sulfate and concentrated to get the titled compound as a colorless oil. It was used in the next step without further purification. $^1$H NMR (CDCl$_3$, 300 MHz): δ8.59 (d, J=2.2 Hz, 1 H), 8.49 (d, J=1.4 Hz, 1 H), 7.90 (s, 1 H), 4.74 (s, 2 H).

Step D

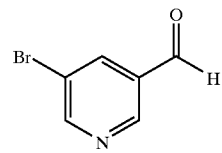

To a solution of the alcohol from the previous step (22.5 g, 120 mmol) in THF (1000 mL) was added manganese(IV) oxide (210 g, 2.4 mol). The reaction mixture was stirred at room temperature for 2 days. It was filtered and the solid was washed with ethyl acetate 3 times (200 mL each time). The combined filtrate and washes were concentrated and purified by flash column chromatography on silica gel with 1/1 ethyl acetate/hexanes as eluant to give the title compound as a white solid. $^1$H NMR (CDCl$_3$, 300 MHz): δ10.08 (s, 1 H), 8.99 (s, 1 H), 8.95 (d, J=0.6 Hz, 1 H), 8.30 (d, J=0.6 Hz, 1H).

Step E

To a solution of 1-methyl-4-tributylstannylpyrazole from Step B (519 mg, 1.4 mmol) and 3-bromo-5-pyridinecarboxaldehyde (200 mg, 1.08 mmol) in xylene (10 mL) was added tetrakis(triphenylphosphine)palladium(0) (37.5 mg, 0.03 mmol). After refluxing for 4 hours, the reaction mixture was cooled to room temperature. It was diluted with toluene (100 mL). Then, potassium fluoride(5 g) in water (10 mL) was added. The mixture was stirred at room temperature for 2 hours. It was filtered. The filtrate was washed with water (20 mL) and brine. The organic layer was dried over anhydrous sodium sulfate and concentrated. The crude product was purified on preparative TLC (2000 microns, CH$_2$Cl$_2$/acetone/2 N ammonia in methanol=10/10/1) to give the titled compound as a pale solid. $^1$H NMR (CDCl$_3$, 300 MHz): δ10.15 (s, 1 H), 8.97 (s, 1 H), 8.90 (s, 1 H), 8.20 (s, 1 H), 7.96 (s, 1 H), 7.76 (s, 1 H), 3.99 (s, 3 H).

Step F (αR,γS,2S)-N-((3S,4S)-3,4-dihydro-3-hydroxy-2H-1-benzopyran-4-yl)-γ-hydroxy-4-[[5-(1-methyl-1H-pyrazol-4-yl)-3-pyridinyl]methyl]-α-(phenylmethyl)-2-[[(2,2,2-trifluoroethyl)amino]carbonyl]-1-piperazinepentanamide To a solution of the aldehyde from the previous step (21 mg, 0.11 mmol) and the penultimate from Example 12 Step D (50 mg, 0.09 mmol) in DCE (5 mL) was added sodium triacetoxyborohydride (28 mg, 0.13 mmol). The reaction mixture was stirred at room temperature for 12 hours and purified on preparative TLC (2000 microns, CH$_2$Cl$_2$/acetone/2N NH$_3$ in methanol=47.5/47.5/5 as eluant) to give the titled compound as a white solid. $^1$H NMR (CD$_3$OD, 400 MHz): δ8.65 (d, J=2 Hz, 1 H), 8.30 (s, 1 H), 8.10 (s, 1 H), 7.98 (d, J=2 Hz, 1 H), 7.92 (d, J=0.4 Hz, 1 H), 7.18–7.28 (m, 5 H), 7.07–7.11 (m, 2 H), 6.80 (dt, J=7.6, 1.2 Hz, 1 H), 6.73 (d, J=8.0 Hz, 1 H), 5.16 (d, J=4 Hz, 1 H), 4.07–4.10 (m, 2 H), 3.94 (s, 3 H), 3.85–3.91 (m 1 H), 3.74–3.76 (m, 2 H), 3.60 (s, 2 H), 2.93–3.15 (m, 5 H), 2.74–2.79 (m, 2 H), 2.60–2.67 (m, 3 H), 2.40–2.55 (m, 4 H), 2.02–2.14 (m, 1 H), 1.37–1.44 (m, 1 H). LC-MS (M$^+$+1) (EI) 736.5.

EXAMPLE 60

(αR,γS,2S)-N-((3S,4S)-3,4-dihydro-3-hydroxy-2H-1-benzopyran-4-yl)-γ-hydroxy-α-(phenylmethyl)-4-[[5-(2-thienyl)-3-pyridinyl]methyl]-2-[[(2,2,2-trifluoroethyl)-amino]carbonyl]-1-piperazinepentanamide

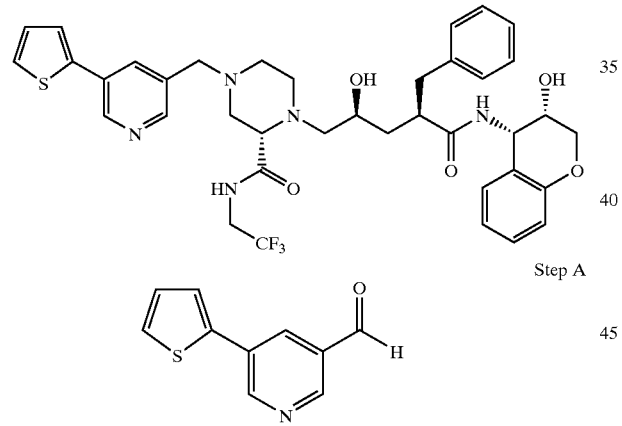

Step A

To a solution of 2-tributylstannylfurane (241 mg, 0.65 mmol) and 3-bromo-5-pyridinecarboxaldehyde from Example 59 Step D (100 mL, 0.54 mmol) in xylene (5 mL) was added tetrakis(triphenylphosphine)palladium(0) (19 mg, 0.02 mmol). After refluxing for 4 hours, the reaction mixture was cooled to room temperature. It was diluted with toluene (50 mL) and then potassium fluoride (2 g) in water (10 mL) was added. The mixture was stirred at room temperature for 2 hours. It was filtered. The filtrate was washed with water (20 mL) and brine. The organic layer was dried over anhydrous sodium sulfate and concentrated. The crude product was purified on preparative TLC (2000 microns, hexanes/ether=1/1) to give the titled compound as a pale solid. $^1$H NMR (CDCl$_3$, 300 MHz): δ10.17 (s, 1 H), 9.10 (d, J=2.1 Hz, 1 H), 8.96 (d, J=1.5 Hz, 1 H), 8.32 (t, J=2.1 Hz, 1 H), 7.43–7.48 (m, 1 H), 7.16–7.19 (m, 1 H).

Step B (αR,γS,2S)-N-((3S,4S)-3,4-dihydro-3-hydroxy-2H-1-benzopyran-4-yl)-γ-hydroxy-α-(phenylmethyl)-4-[[5-(2-thienyl)-3-pyridinyl]methyl]-2-[[(2,2,2-trifluoroethyl)-amino]carbonyl]-1-piperazinepentanamide To a solution of the aldehyde from the previous step (21 mg, 0.11 mmol) and the penultimate prepared as in Example 12 Step D (50 mg, 0.09 mmol) in DCE (5 mL) was added sodium triacetoxyborohydride (28 mg, 0.13 mmol). The reaction mixture was stirred at room temperature for 12 hours and purified on preparative TLC (2000 microns, CH$_2$Cl$_2$/acetone/2N NH$_3$ in methanol=47.5/4.75/5 as eluant) to give the titled compound as a white solid. $^1$H NMR (CD$_3$OD, 400 MHz): δ8.72 (d, J=2 Hz, 1 H), 8.38 (s, 1 H), 8.05 (s, 1 H), 7.50–7.55 (m, 2 H), 7.06–7.27 (m, 8 H), 6.8 (t, J=7.2, 1 H), 6.72 (d, J=8.0 Hz, 1 H), 5.16 (d, J=4 Hz, 1 H), 4.07–4.10 (m, 2 H), 3.74–3.91(m 3 H), 3.62 (s, 2 H), 2.93–3.15 (m, 5 H), 2.61–2.79 (m, 5 H), 2.38–2.54 (m, 5 H), 2.02–2.14 (m, 1 H), 1.37–1.44 (m, 1 H). LC-MS (M$^+$+1) (EI) 738.5.

EXAMPLE 61

(αR,γS,2S)-N-((3S,4S)-3,4-dihydro-3-hydroxy-2H-1-benzopyran-4-yl)-γ-hydroxy-α-(phenylmethyl)-4-[[5-(3-thienyl)-3-pyridinyl]methyl]-2-[[(2,2,2-trifluoroethyl)-amino]carbonyl]-1-piperazinepentanamide

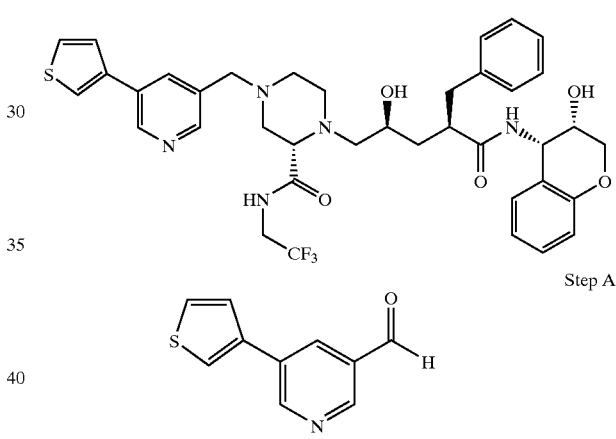

Step A

A solution of 3-Bromo-5-pyridinecarboxaldehyde from Example 59 Step D (200 mg, 1.08 mmol) and tetrakis(triphenylphosphine)palladium(0) (70 mg, 0.06 mmol) in DME (5 mL) was stirred at room temperature for 5 minutes. Thiophene-3-boronic acid (141 mg, 1.08 mmol) was added and the stirring was continued for 10 more minutes. Then, sodium carbonate solution (2 M, 5 mL) was added and the reaction mixture was heated to refluxed for 12 hours. After it was cooled to room temperature, the reaction mixture was distributed between ethyl acetate (50 mL) and water (50 mL). The organic layer was dried over anhydrous sodium sulfate, concentrated, and purified on preparative TLC (2000 microns, hexanes/ethyl acetate=1/1) to get 5-(3-furanyl)-3-pyridinecarboxaldehyde as a pale solid. $^1$H NMR (CDCl$_3$, 300 MHz): δ10.18 (s, 1 H), 9.11 (d, J=2.1 Hz, 1 H), 8.98 (d, J=1.8 Hz, 1 H), 8.33 (t, J=2.1 Hz, 1 H), 7.44 (dd, J=1.2, 1.5 Hz, 1 H), 7.44–7.52 (m, 2 H).

Step B (αR,γS,2S)-N-((3S,4S)-3,4-dihydro-3-hydroxy-2H-1-benzopyran-4-yl)-γ-hydroxy-α-(phenylmethyl)-4-[[5-(3-thienyl)-3-pyridinyl]methyl]-2-[[(2,2,2-trifluoroethyl)amino]carbonyl]-1-piperazinepentanamide To a solution of the aldehyde from the previous step (21 mg, 0.11 mmol) and the penultimate prepared as in Example 12 Step D (50 mg, 0.09 mmol) in DCE (5 mL) was added sodium triacetoxyborohydride (28 mg, 0.13 mmol). The reaction mixture was stirred at room temperature for 12 hours and purified on preparative TLC (2000 microns, CH$_2$Cl$_2$/acetone/2N NH$_3$ in methanol=47.5/47.5/5 as eluant) to give the titled compound as a white solid. $^1$H NMR (CD$_3$OD, 400 MHz): δ8.76 (s, 1 H), 8.38 (s, 1 H), 8.09 (s, 1 H), 7.82 (dd, J=1.2, 1.6 Hz, 1 H), 7.52–7.57 (m, 2 H), 7.18–7.28 (m, 5 H), 7.06–7.13 (m, 2 H), 6.81 (t, J=7.2, 1 H), 6.73 (d, J=8.0 Hz, 1 H), 5.16 (d, J=4 Hz, 1 H), 4.07–4.08 (m, 2 H), 3.74–3.91(m 3 H), 3.63 (s, 2 H), 2.93–3.15 (m, 5 H), 2.62–2.78 (m, 5 H), 2.38–2.54 (m, 5 H), 2.02–2.14 (m, 1 H), 1.37–1.44 (m, 1 H). LC-MS (M$^+$+1) (El) 738.5.

EXAMPLE 62

(αR,γS,2S)-N-((3S,4S)-3,4-dihydro-3-hydroxy-2H-1-benzopyran-4-yl)-γ-hydroxy-α-(phenylmethyl)-4-[[5-(4-pyrimidinyl)-2-furanyl]methyl]-2-[[(2,2,2-trifluoroethyl)amino]carbonyl]-1-piperazinepentanamide

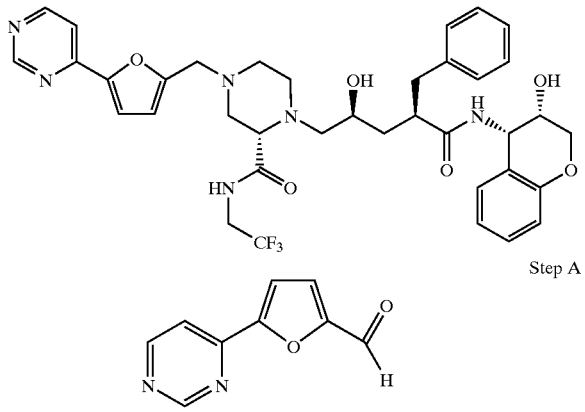

Step A

To a solution of the chloropyridyl intermediate (100 mg, 0.4 mmol) in methanol (5 mL) was added triethylamine (70 μl, 0.5 mmol) and palladium on carbon (10 mg). Hydrogen in balloon was applied and the reaction was monitored by HPLC. After stirring under the hydrogen atmosphere for 12 hours the reaction mixture was filtered. The filtrate was concentrated to get a pale solid. The solid obtained was stirred in a mixture of THF (10 mL) and HCl (1 N, 10 mL) for 10 hours. Ethyl acetate (100 mL) was added and it was washed with NaOH solution (1 N, 15 mL) and brine. The organic layer was concentrated and purified on preparative TLC (2000 microns, hexanes/ethyl acetate=1/1) to get the title compound as a pale solid. $^1$H NMR (CDCl$_3$, 300 MHz): δ9.77 (s, 1 H), 9.29 (d, J=1.2 Hz, 1 H), 8.85 (d, J=5.1 Hz, 1 H), 7.84 (dd, J=3.9, 1.2 Hz, 1 H), 7.46 (d, J=3.6 Hz, 1 H), 7.38 (d, J=3.9 Hz, 1 H),
Step B (αR,γS,2S)-N-((3S,4S)-3,4-dihydro-3-hydroxy-2H-1-benzopyran-4-yl)-γ-hydroxy-α-(phenylmethyl)-4-[[5-(4-pyrimidinyl)-2-furanyl]methyl]-2-[[(2,2,2-trifluoroethyl)amino]carbonyl]-1-piperazinepentanamide To a solution of the aldehyde from the previous step (21 mg, 0.11 mmol) and the penultimate prepared as in Example 12 Step D (50 mg, 0.09 mmol) in DCE (5 mL) was added sodium triacetoxyborohydride (28 mg, 0.13 mmol). The reaction mixture was stirred at room temperature for 10 hours and purified on preparative TLC (2000 microns, CH$_2$Cl$_2$/acetone/2N NH$_3$ in methanol=47.5/47.5/5 as eluant) to get the titled compound as a white solid. $^1$H NMR (CD$_3$OD, 400 MHz): δ9.04 (s, 1 H), 8.72 (d, J=5.2 Hz, 1 H), 7.75 (dd, J=1.2, 4.0 Hz, 1 H), 7.36 (d, J=3.6 Hz, 1 H), 7.20–7.27 (m, 4 H), 7.07–7.19 (m, 3 H), 6.82 (t, J=7.2, 1 H), 6.73 (d, J=8.0 Hz, 1 H), 6.57 (d, J=3.6 Hz, 1 H), 5.15 (d, J = 4 Hz, 1 H), 4.07–4.08 (m, 2 H), 3.74–3.91(m 3 H), 3.63 (s, 2 H), 2.93–3.15 (m, 5 H), 2.62–2.78 (m, 5 H), 2.38–2.54 (m, 5 H), 2.02–2.14 (m, 1 H), 1.37–1.44 (m, 1 H). LC-MS (M$^+$+1) (El) 723.5.

EXAMPLE 63

(αR,γS,2S)-4-[(7-chlorofuro[3,2-c]pyridin-2-yl)methyl]-N-((3S,4S)-3,4-dihydro-3-hydroxy-2H-1-benzopyran-4-yl)-γ-hydroxy-α-(phenylmethyl)-2-[[(2,2,2 trifluoroethyl)amino]carbonyl]-1-piperazinepentanamide

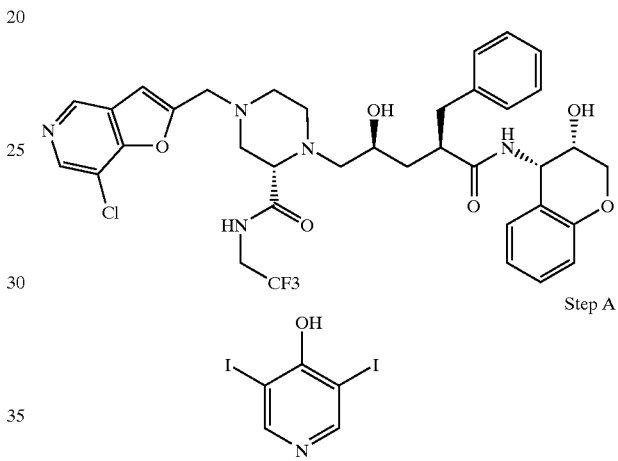

Step A

To a suspension of 4-hydroxypyridine (40 g, 421 mmol) in methanol (1 l) was added N-iodosuccinimide (189 g, 841 mmol). The reaction mixture was heated to reflux for 10 hours. After it was cooled to room temperature, it was filtered. The solid was washed with methanol (2×500 mL) and dried under high vacuum overnight to give the title compound as a pale powder. $^1$H NMR (DMSO, 300 MHz): δ8.25 (s).

Step B

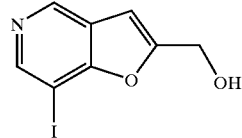

To a solution of 4-hydroxy-3,5-diiodopyridine (40 g, 115 mmol) in pyrrolidine (200 mL) was added tetrakis(triphenylphosphine)palladium(0) (3.4 g, 2.8 mmol) and copper(I) iodide (2.2 g, 11.5 mmol). It was stirred at room temperature for 20 minutes. Propargyl alcohol (3.3 g, 58 mmol) was introduced very slowly. After he reaction mixture was stirred at room temperature for 10 hours, the solvent was removed. The residue was dissolved in THF (200 mL) and the solution obtained was refluxed for 2 hours. The solvent was evaporated and the residue was distributed between ethyl acetate (500 mL) and saturated sodium bicarbonate (200 mL). The organic layer was dried over anhydrous sodium sulfate, concentrated and purified by flash column chromatography on silica gel with ethyl acetate as eluant to give the title compound as a white solid. ¹H NMR (CD₃OD, 300 MHz): δ8.75 (s, 1 H), 8.63 (s, 1 H), 6.99 (s, 1 H), 4.74 (s, 2 H).

Step C

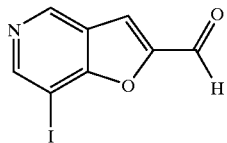

To a solution of the alcohol from the previous step (5.62 g, 20.4 mmol) in DMF (100 mL) was added manganese(IV) oxide (40 g, 409 mmol). The reaction mixture was stirred at room temperature for 2 days. Then, it was filtered. The solid was washed with boiling methanol for six times (100 mL each time). The combined filtrate and washes was concentrated to get the title compound as a white solid. ¹H NMR (DMSO, 400 MHz): δ9.91 (s, 1 H), 9.11 (s, 1 H), 8.90 (s, 1 H), 8.18 (s, 1 H).

Step D

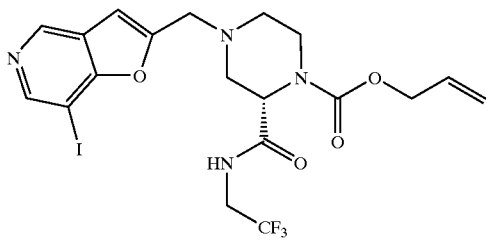

To a solution of the aldehyde from the previous step (3.14 g, 11.5 mmol) and the piperazine intermediate from Example 12 Step A (3.4 g following removal of the BOC with trifluroacetic acid, 11.5 mmol) in DCE (20 mL) was added sodium triacetoxyborohydride,(3.66 g, 17.3 mmol). The reaction mixture was stirred at room temperature for 12 hours. After most of the solvent was evaporated, the residue was distributed between ethyl acetate (200 mL) and saturated sodium bicarbonate (100 mL). The organic layer was dried over anhydrous sodium sulfate, concentrated and purified by flash column chromatography on silica gel with hexanes/ethyl acetate=1/1 as eluant to give the title compound as a white solid. ¹H NMR (CDCl₃, 400 MHz): δ8.77 (s, 1 H), 8.76 (s, 1 H), 6.88 (s, 1 H), 5.91–5.98 (m, 1 H), 5.25–5.36 (m, 2 H), 4.83–4.87 (m, 1 H), 4.66 (s, 1 H), 4.00 (broad s, 1 H), 3.84 (dd, J=15.2, 37.6 Hz, 2 H), 3.55 (d. J=10,8 Hz, 1 H), 3.20 (broad s, 1 H), 2.93 (d, J=10.8 Hz, 1 H), 2.32–2.41 (m, 2 H), 1.66 (broad s, 2 H).

Step E

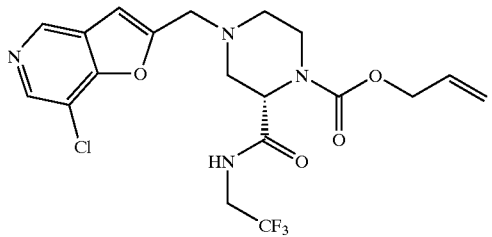

A solution of the intermediate from the previous step (2 g, 3.62 mmol) and copper(I) chloride (1.8 g, 18.1 mmol) in DMF (15 mL) was stirred at 110° C. for 6 hours. HPLC showed that the starting material was gone. It was distributed between ethyl acetate (500 mL) and concentrated ammonium hydroxide (300 mL). The organic layer was dried over anhydrous sodium sulfate, concentrated and purified by flash column chromatography on silica gel with hexanes/ethyl acetate=1/2 as eluant to get the title compound as a white solid. ¹H NMR (CDCl₃, 400 MHz): δ8.76 (s, 1 H), 8.39 (s, 1 H), 6.94 (s, 1 H), 5.90–5.97 (m, 1 H), 5.24–5.35 (m,2 H), 4.83–4.87 (m, 1 H), 4.66 (s, 1 H), 3.84 (dd, J=15.2, 37.6 Hz, 2 H), 3.60 (broad s, 1 H), 3.55 (d. J=10,8 Hz, 1 H), 2.99 (broad s, 1 H), 2.93 (d, J=10.8 Hz, 1 H), 2.32–2.41 (m, 2 H), 1.66 (broad s, 2 H).

Step F

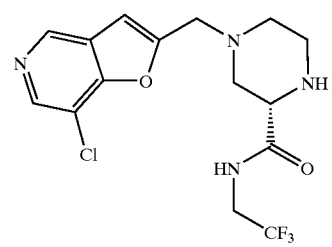

A suspension of tris(dibenzylideneacetone)dipalladium (0) (183 mg, 0.2 mmol) and 1,4-bis(diphenylphosphino) butane (85.3 mg, 0,2 mmol) in THF (20 mL) was stirred at room temperature for 20 minutes. Then, it was transferred to a solution of the intermediate from the previous step (910 mg, 1.97 mmol) and thiosalicylic acid (380 mg, 2.46 mmol) in THF (5 mL). After stirring at room temperature for 10 hours the reaction mixture was distributed between ethyl acetate (200 mL) and sodium hydroxide solution (1 N, 100 mL). The organic layer was dried over anhydrous sodium sulfate, concentrated and purified by flash column chromatography on silica gel with ethyl acetate/2 N ammonia in methanol=95/5 as eluant to give the title compound as a slightly yellow gum. ¹H NMR (CDCl₃, 400 MHz): δ8.76 (s, 1 H), 8.46 (s, 1 H), 7.76 (broad s, 1 H), 6.79 (s, 1 H), 3.84–4.02 (m, 2 H), 3.80 (d, J=3.2 Hz, 2 H), 3.56 (dd, J=3.6, 6.8 Hz, 1 H), 2.86–3.06(m, 3 H), 2.49–2.73 (m, 3 H), Step G (αR,γS,2S)-4-[(7-chlorofuro[3,2-c]pyridin-2-yl)
methyl]-N-((3S,4S)-3,4-dihydro-3-hydroxy-2H-1-
benzopyran-4-yl)-γ-hydroxy-α-(phenylmethyl)-2-
[[(2,2,2-trifluoroethyl)amino]carbonyl]-1-
piperazinepentanamide A solution of the piperazine intermediate from the previous step (378 mg, 1 mmol) and the epoxide from Example 1, Step P (394 mg, 1 mmol) in methanol (10 mL) was heated to reflux for 24 hours. After the solvent was evaporated, the residue was purified by flash column chromatography on silica gel with ethyl acetate/2 N ammonia in methanol=98/2 as eluant to get a white solid (485 mg). The solid obtained was dissolved in methanol (10 mL) and HCl (1 N in ether, 3 mL) was added. The solution obtained was stirred at room temperature for 8 hours. After the solvent was removed the residue was purified by flash column chromatography on silica gel with ethyl acetate/2 N ammonia in methanol=98/2 as eluant to give the title compound as a white solid. ¹H NMR (CDCl₃, 300 MHz): δ8.92–8.97 (m, 1 H), 8.77 (s, 1 H), 8.48 (s, 1 H), 7.20–7.32 (m, 5 H), 7.05–7.15 (m, 2 H), 6.77–6.82 (m, 2 H), 5.93 (d, J=8.4 Hz, 1 H), 5.14–5.18 (m, 1 H), 4.07–4.24 (m, 1 H), 3.96–4.04 (m, 2H), 3.67–3.87 (m, 5 H), 3.45–3.46 (m, 1 H), 3.37 (broad s, 1 H), 2.62–3.04 (m,

EXAMPLE 64

(αR,γS,2S)-N-((3S,4S)-3,4-dihydro-3-hydroxy-2H-1-benzopyran-4-yl)-γ-hydroxy-α-(phenylmethyl)4-[[5-(3-pyridinyl)-2-oxazolyl]methyl]-2-[[(2,2,2-trifluoroethyl)amino]carbonyl]-1-piperazinepentanamide

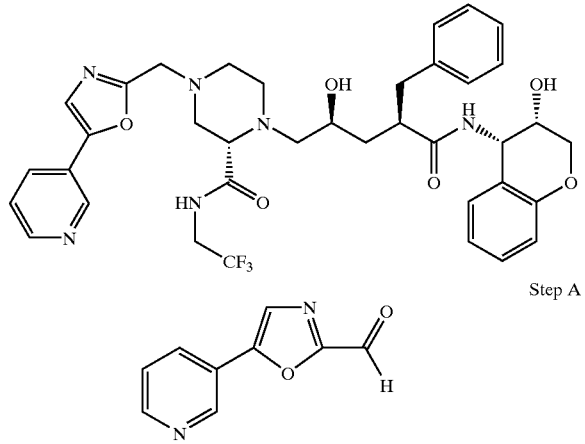

Step A

A solution of 5-(pyrid-3-yl)oxazole (4.0 g, 27.4 mmol) in THF (100 mL) was cooled to −78+ C. and butyllithium (2.5 M in hexanes, 13.1 mL, 32.8 mmol) was added. After it was stirred at −78° C. for 30 minutes, N-formylmorpholine (0.63 mL, 82.1 mmol) was added. The reaction solution was slowly warmed to room temperature at which it was stirred for 10 hours. Then, ethyl acetate (200 mL) was added and the diluted solution was washed with saturated sodium bicarbonate solution (200 mL). The organic layer was dried over anhydrous sodium sulfate, concentrated and purified by flash column chromatography on silica gel with 1/1 hexanes/ethyl acetate as eluant to give the title compound as a slightly yellow solid. $^1$H NMR (CDCl$_3$, 300 MHz): δ9.80 (s, 1 H), 9.04 (s, 1 H), 8.68 (d, J=1.5 Hz, 1 H), 8.07–8.10 (m, 1 H), 7.20 (d, J=1.5 Hz, 1 H), 7.41–7.45 (m, 1 H).

Step B (αR,γS,2S)-N-((3S,4S)-3,4-dihydro-3-hydroxy-2H-1-benzopyran-4-yl)-γ-hydroxy-α-(phenylmethyl)-4-[[5-(3-pyridinyl)-2-oxazolyl]methyl]-2-[[(2,2,2-trifluoroethyl)amino]carbonyl]-1-piperazinepentanamide To a solution of the aldehyde from the previous step (16 mg, 0.09 mmol) and the penultimate from Example 12 Step D (50 mg, 0.09 mmol) in DCE (3 mL) was added sodium triacetoxyborohydride (28 mg, 0.13 mmol). The reaction mixture was stirred at room temperature for 24 hours and purified on preparative TLC (2000 microns, CH$_2$Cl$_2$/acetone/2N NH$_3$ in methanol=47.5/47.5/5 as eluant) to give the titled compound as a white solid. $^1$H NMR (CD$_3$OD, 400 MHz): δ8.91 (d, J=1.6 Hz, 1 H), 8.52 (d, J=4.8 Hz, 1H), 8.14 (d, J=8.0 Hz, 1 H), 7.64 (s, 1H), 7.51–7.54 (m, 1 H), 7.07–7.26 (m, 7 H), 6.82 (t, J=7.2, 1 H), 6.73 (d, J=8.0 Hz, 1H), 5.16 (d, J=4 Hz, 1 H), 4.07–4.08 (m, 2 H), 3.80–3.96 (m, 1 H), 3.73–3.78 (m, 5 H), 3.13–3.16 (m, 1 H), 2.83–3.06 (m, 3 H), 2.57–2.78 (m, 4 H), 2.40–2.49 (m, 4 H), 2.02–2.14 (m, 1 H), 1.37–1.44 (m, 1 H). LC-MS (M$^+$+1) (EI) 723.7.

EXAMPLE 65

(αR,γS,2S)-N-((3S,4S)-3,4-dihydro-3-hydroxy-2H-1-benzopyran-4-yl)-γ-hydroxy-α-(phenylmethyl)-4-[[5-(2-pyridinyl)-2-oxazolyl]methyl]-2-[[(2,2,2-trifluoroethyl)amino]carbonyl]-1-piperazinepentanamide

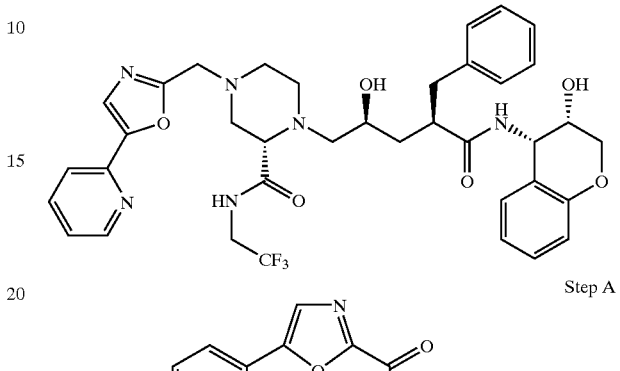

Step A

A solution of 5-(pyrid-2-yl)oxazole (4.0 g, 27.4 mmol) in THF (100 mL) was cooled to −78° C. and butyllithium (2.5 M in hexanes, 13.1 mL, 32.8 mmol) was added. After it was stirred at −78° C. for 30 minutes, N-formylmorpholine (0.63 mL, 82.1 mmol) was added. The reaction solution was slowly warmed to room temperature and then it was stirred for 10 hours. Ethyl acetate (200 mL) was added and the diluted solution was washed with saturated sodium bicarbonate solution (200 mL). The organic layer was dried over anhydrous sodium sulfate, concentrated and purified by flash column chromatography on silica gel with 1/1 hexanes/ethyl acetate as eluant to give the title compound as a slightly yellow solid. $^1$H NMR (CDCl$_3$, 300 MHz): δ8.69 (s, 1 H), 9.04 (s, 1 H), 7.98–8.00 (m, 1 H), 7.82–7.89 (m, 2 H), 7.36–7.25 (m, 1 H).

Step B (αR,γS,2S)-N-((3S,4S)-3,4-dihydro-3-hydroxy-2H-1-benzopyran-4-yl)-γ-hydroxy-α-(phenylmethyl)-4-[[5-(2-pyridinyl)-2-oxazolyl]methyl]-2-[[(2,2,2-trifluoroethyl)amino]carbonyl]-1-piperazinepentanamide To a solution of the aldehyde from the previous step (16 mg, 0.09 mmol) and the penultimate from Example 12 Step D (50 mg, 0.09 mmol) in DCE (3 mL) was added sodium triacetoxyborohydride (28 mg, 0.13 mmol). The reaction mixture was stirred at room temperature for 24 hours and purified on preparative TLC (2000 microns, CH$_2$Cl$_2$/acetone/2N NH$_3$ in methanol=47.5/47.5/5 as eluant) to give the titled compound as a white solid. $^1$H NMR (CD$_3$OD, 400 MHz): δ8.58 (d, J=1.6 Hz, 1 H), 7.90 (t, J=1.6 Hz, 1 H), 7.80 (t, J=1.6 Hz, 1 H), 7.68–7.69 (m, 1 H), 7.36–7.39 (m, 1 H), 7.09–7.25 (m,7 H), 6.83 (t, J=7.2, 1H), 6.73 (d, J=8.0 Hz, 1 H), 5.16 (d, J=4 Hz, 1 H), 4.07–4.08 (m, 2 H), 3.80–3.96 (m, 1 H), 3.73–3.78 (m, 5 H), 3.13–3.16 (m, 1 H), 2.83–3.06 (m, 3 H), 2.57–2.78 (m, 4 H), 2.40–2.49 (m, 4 H), 2.02–2.14 (m, 1 H), 1.37–1.44 (m, 1 H). LC-MS (M$^+$+1) (EI) 723.7.

EXAMPLE 66

(αR,γS,2S)-N-((3S,4S)-3,4-dihydro-3-hydroxy-2H-1-benzopyran-4-yl)-γ-hydroxy-α-(phenylmethyl)-4-[1-methyl-1-[5-(2-pyridinyl)-2-oxazolyl]ethyl]-2-[[(2,2,2-trifluoroethyl)amino]carbonyl]-1-piperazinepentanamide

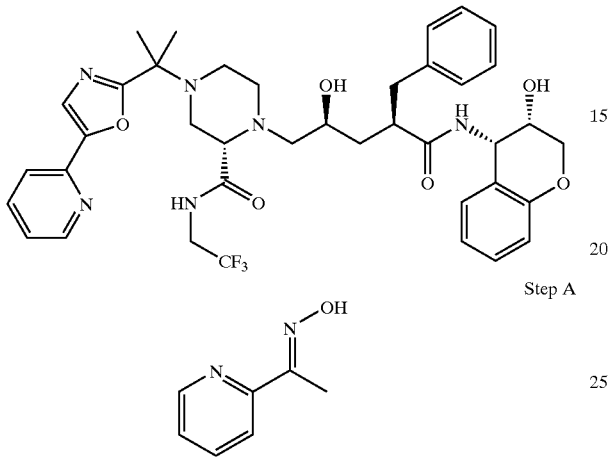

Step A

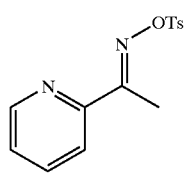

A solution of hydroxyamine hydrochloride (25 g, 360 mmol) in water (50 mL) was added to aqueous sodium hydroxide (20%, 70 mL). To this stirred solution was added 2-acetylpyridine (36.3 g, 300 mmol). The reaction mixture was cooled to 0° C. at which it was stirred for 3 hours to form a white precipitate. It was filtered. And the solid was washed with ice-cooled water (300 mL). The solid obtained was dissolved in 600 mL of boiling water. The hot water solution was slowly cooled to room temperature to form a white needle. It was filtered. The crystalline solid was washed with ice-cooled water (300 mL) and dried under high vacuum overnight to give the titled compound. $^1$H NMR (DMSO, 400 MHz): δ8.56 (d, J=0.8 Hz, 1 H), 7.80 (d, J=1.6 Hz, 1 H), 7.75 (dd, J=1.6, 6.0 Hz, 1 H), 7.32 (dd, J=6.0, 2.4 Hz, 1 H), 2.19 (s, 3 H).

Step B

A solution of the oxime form the previous step (31 g, 228 mmol) and p-toluenesulfonyl chloride (54.3 g, 285 mmol) in pyridine (100 mL) was stirred at room temperature for 24 hours to form a brown precipitate. 500 mL of ice-cooled water was added while stirring. The initially formed brown precipitate dissolved followed by the formation of a white precipitate. This precipitate was collected by filtration and washed with ice-cooled water (3×200 mL). It was dried under high vacuum to constant weight to give the titled compound. $^1$H NMR (CDCl$_3$, 400 MHz): δ8.61 (ddd, J=1.0, 1.8, 4.9 Hz, 1 H), 7.48 (d, J=8.4 Hz, 1 H), 7.82 (dt, J=0.9, 8.1 Hz, 1 H), 7.70 (dt, J=1.8, 7.7 Hz, 1 H), 7.32–7.39 (m, 3 H), 2.46 (s, 6 H).

Step C

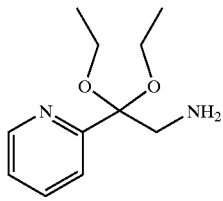

To a solution of the tosylate from the previous step (60 g, 205.2 mmol) in ethanol (1 L) was added potassium ethoxide (17.8 g, 211.4 mmol) at 0° C. It was slowly warmed to room temperature at which it was stirred for 1 hour. It was then diluted with 1 l of anhydrous ethanol and HCl gas was bubbled in for 1 hour to see some precipitate. It was concentrated. The residue was distributed between methylene chloride (500 mL) and saturated sodium carbonate (about 500 mL to get pH=10). The organic layer was concentrated and vacuum distilled to get the titled compound as a colorless oil. $^1$H NMR (CDCl$_3$, 400 MHz): δ8.67–8.70 (m, 1 H), 7.71–7.80.(m, 2H), 7.20–7.24 (m, 1 H), 3.35–3.49 (m, 4 H), 3.21 (s, 2 H), 1.21–1.28 (m, 6 H).

Step D

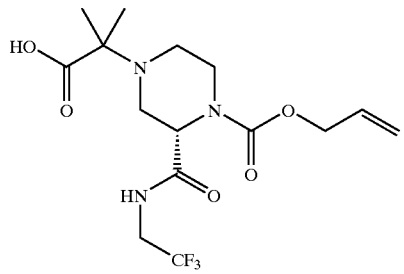

To a solution of the piperazine intermediate from Example 12, Step A (1 g, 3.39 mmol following removal of the BOC group with trifluoroacetic acid) and silver trifluoromethane sulfonate (725 mg, 2.82 mmol) in THF (5 mL) was added triethylamine. While stirring, a solution of 2-bromo-2-methylpropionic acid (472 mg, 2.82 mmol) in 5 mL of THF was introduced slowly (within 1.5 hours) through a syringe pump. The reaction mixture was stirred at room temperature for 2 hours after the additions. Then, it was filtered. The filtrate was concentrated and purified by flash column chromatography on silica gel with 10/1 ethyl acetate/methanol as eluant to give the title compound as a white solid. $^1$H NMR (CDCl$_3$, 400 MHz): δ9.02 (broad s, 1 H), 6.98 (broad s, 1 H), 5.90–6.00 (m, 1 H), 5.24–5.28 (m, 2 H), 5.65 (broad s, 1 H), 4.16 (broad s, 1 H), 2.90–2.93 (m, 1 H), 2.55–2.57 (m, 1 H), 2.40–2.41 (m, 1 H), 1.59–1.61 (m,1H).

Step E

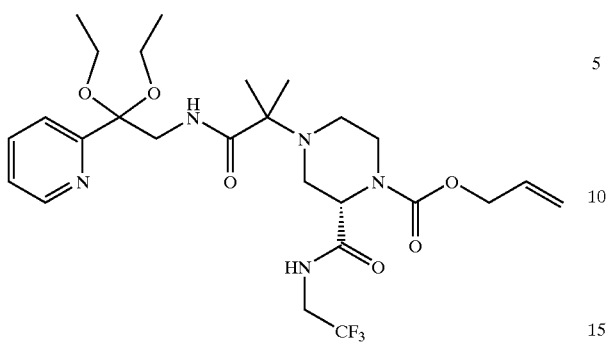

To a solution of the carboxylic acid from the previous step (2 g, 5.24 mmol) and the aminoacetal from Step C (1.33 g, 6.3 mmol) in DMF (20 mL) was added O-benzoltriazol-1-N,N,N',N'-tetramethyluronium hexafluorophosphate (4.77 g,12.6 mmol), 1-hydroxybenzotriazol hydrate (1.7 g, 12.6 mmol) and diisopropylethylamine (4.56 mL, 26.2 mmol). After stirring at room temperature for 10 hours, the reaction solution was distributed between ethyl acetate (300 mL) and water (300 mL). The organic layer was washed with water (200 mL) and brine. It was dried over anhydrous sodium sulfate, concentrated and purified by flash column chromatography on silica gel with 1/2 hexanes/ethyl acetate as eluant to get the title compound as a white solid. $^1$H NMR (CDCl$_3$, 400 MHz): δ8.66 (d, J=4.8 Hz, 1 H), 7.70 (d, J=3.6 Hz, 2 H), 7.27 (m, 1 H), 6.63 (t, J=6.1 Hz, 1 H), 5.89–5.99 (m, 1 H), 5.26–5.35 (m, 2 H), 4.65 (d, J=4.8 Hz, 3 H), 4.19 (dd, J=8.0, 13.6 Hz, 1 H), 3.92 (broad s, 2 H), 3.57–3.68 (m, 3 H), 3.27–3.40 (m, 3 H), 2.82 (s, 2 H), 2.79 (broad s, 1 H), 2.49 (d, J=5.6 Hz, 1 H), 2.29 (dd, J=4.0, 8.0 Hz, 1 H), 2.14 (dt, J=3.2, 11.6 Hz, 1 H), 1.20–1.25 (2t, J=7.2 Hz, 6 H), 1.11 (s, 3H), 1.03 (s, 3 H).

Step F

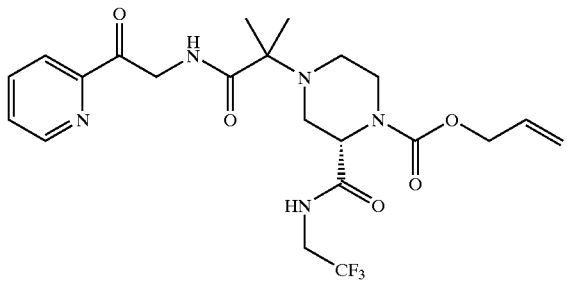

The acetal from the previous step (1.6 g, 2.79 mmol) was dissolved in THF (10 mL) and HCl (6 N, 10 mL) was added. The reaction solution was stirred at 70° C. for 12 hours until (by TLC) the acetal was consumed. It was diluted with 200 mL of ethyl acetate and 1 N sodium hydroxide solution was added until pH=10. The organic layer was dried over anhydrous sodium sulfate, concentrated and purified by flash column chromatography on silica gel with 10/1 ethyl acetate/methanol as eluant to give the title compound as a white solid. $^1$H NMR (CDCl$_3$, 400 MHz): δ8.70–8.1 (m, 1 H), 8.00 (dt, J=0.4, 6.8 Hz, 1 H), 7.86 (dt, J=1.6, 6.0 Hz, 1H), 7.51 (ddd, J=1.2, 4.8, 7.6 Hz, 1 H), 6.66 (broad s, 1 H), 5.89–5.99 (m, 1 H), 5.27–5.34 (m, 2 H), 5.11 (dd, J=6.8, 19.6 Hz, 1 H), 4.80–4.86 (m, 2 H), 4.68 (d, J=4.2 Hz, 2H), 4.00–4.09 (m, 1 H), 3.72 (d, J=12 Hz, 1 H), 3.45–3.50 (m, 1H), 3.27 (t, J=10.4 Hz, 1H), 2.91 (d, J=10.4 Hz, 1 H), 2.45 (dd, J=4.0, 12.0 Hz, 1 H), 2.35 (dt, J=2.8, 12 Hz, 1 H), 1.30 (s, 3 H), 1.27 (s, 3 H).

Step G

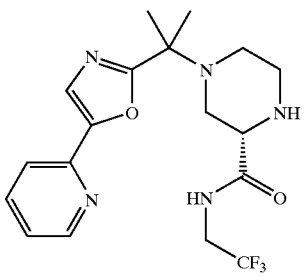

The ketoamide from the previous step (930 mg, 1.86 mmol) was dissolved in 6 mL of fuming sulfuric acid. It was stirred at 55–60° C. for 15 minutes. After cooled to room temperature it was carefully poured into ice-water (20 mL). While the aqueous solution was stirred, potassium hydroxide (solid) was added slowly until pH=12. It was extracted with ethyl acetate for 3 times (100 mL each time). The combined extractant was dried over anhydrous sodium sulfate, concentrated and purified by flash column chromatography on silica gel with 100/12 ethyl acetate/methanol as eluant to give the title compound as a colorless glass. $^1$H NMR (CDCl$_3$, 400 MHz): δ8.64 (t, J=4.8 Hz, 1 H), 8.19 (broad s, 1 H), 7.74–7.80 (m, 1 H), 7.59–7.65 (m, 2 H), 7.23–7.28 (m, 1 H), 3.92–4.03 (m, 2 H), 3.51 (dd, J=3.6, 5.6 Hz, 1 H), 2.84–2.99 (m, 2 H), 2.76–2.82 (m, 1 H), 2.56–2.64 (m, 3 H), 1.62 (s, 3 H), 1.61 (s, 3 H). LC-MS (M$^+$+1) (EI) 398.3, 399.3

Step H (αR,γS,2S)-N-((3S,4S)-3,4-dihydro-3-hydroxy-2H-1-benzopyran-4-yl)-γ-hydroxy-α-(phenylmethyl)-4-[1-methyl-1-[5-(2-pyridinyl)-2-oxazolyl]ethyl]-2-[[(2,2,2-trifluoroethyl)amino]carbonyl]-1-piperazinepentanamide A solution of the intermediate from the previous step (470 mg, 1.18 mmol) and the epoxide from Example 1, Step P (535.2 mg, 1.36 mmol) in ethanol (10 mL) was refluxed for 2 days. After the solvent was evaporated the residue was purified by flash column chromatography on silica gel with 10/1 ethyl acetate/methanol as eluant to get a white solid (580 mg) (LC-MS (M$^+$+1) (EI) 791.5). The solid obtained was dissolved in methanol (10 mL) and cooled to 0° C. HCl (1 N in ether, 10 mL) was added and the reaction solution was warmed to room temperature at which it was stirred for 10 hours. The solvent was evaporated. The residue was distributed between ethyl acetate (50 mL) and 1 N potassium hydroxide (10 mL). The organic layer was dried over anhydrous sodium sulfate, concentrated and purified by flash column chromatography on silica gel with 10/1 ethyl acetate/methanol as eluant to give the title compound as a white solid. $^1$H NMR (CD$_3$OD, 400 MHz): δ8.58 (dt, J=1.2, 4.8 Hz, 1 H), 7.91 (dt, J=1.6, 7.6 Hz, 1 H), 7.78 (d, J=8.0 Hz, 1 H), 7.67 (s, 1 H), 7.36–7.39 (m, 1 H), 7.05–7.22 (m, 7 H), 6.80 (t, J=7.2 Hz, 1 H), 6.72 (d, J=8.0 Hz, 1 H), 5.14 (d,J=4.1 Hz, 1H), 4.06 (s, 2 H), 3.91–4.01 (m,1 H), 3.70–3.87 (m, 3 H), 3.28–3.31 (m, 2 H), 3.08 (dd, J=3.3, 7.2 Hz, 1 H), 2.95–3.02 (m, 2 H), 2.87–2.94 (m, 2 H), 2.62–2.79 (m, 3 H), 2.49 (t, J=8.4 Hz, 1 H), 2.31–2.44 (m, 3 H), 1.98–2.05 (m, 1 H), 1.61 (s, 3 H), 1.60 (s, 3 H), 1.33–1.40 (m, 1 H). LC-MS (M$^+$+1) (EI) 751.5

EXAMPLE 67

(αR,γS,2S)-N-((3S,4S)-3,4-dihydro-3-hydroxy-2H-1-benzopyran-4-yl)-γ-hydroxy-4-[1-methyl-1-[5-(3-pyridinyl)-2-oxazolyl]ethyl]-α-(phenylmethyl)-2-[[(2,2,2-trifluoroethyl)amino]carbonyl]-1-piperazinepentanamide

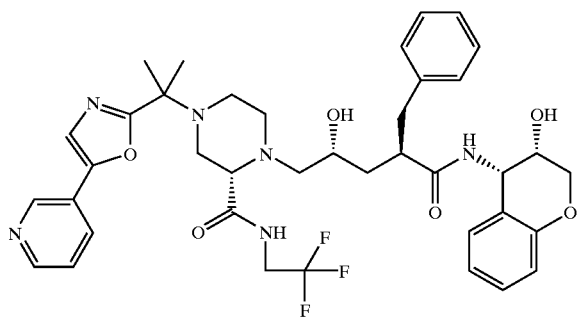

Step A

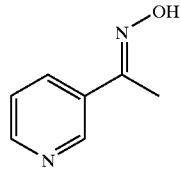

A solution of hydroxyamine hydrochloride (25 g, 360 mmol) in water (50 mL) was added to aqueous sodium hydroxide (20%, 70 mL). To this stirred solution was added 2-acetylpyridine (36.3 g, 300 mmol). The reaction mixture was cooled to 0° C. at which it was stirred for 3 hours to form a white precipitate. It was filtered. And the solid was washed with ice-cooled water (300 mL). The solid obtained was dissolved in 600 mL of boiling water. The hot water solution was slowly cooled to room temperature to form white needles. It was filtered. The crystalline solid was washed with ice-cooled water (300 mL) and dried under high vacuum over night to give the titled compound. $^1$H NMR (DMSO, 400 MHz): δ8.82 (d, J=1.8 Hz, 1 H), 8.54 (dd, J=1.6, 4.9 Hz, 1 H), 7.99(dt, J=4.0, 8.0 Hz, 1 H), 7.40 (dd, J=4.7, 8.0, Hz 1 H), 2.16 (s, 3 H).

Step B

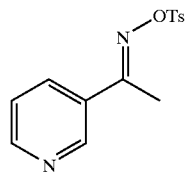

A solution of the oxime form the previous step (16.5 g, 121 mmol) and p-toluenesulfonyl chloride (29 g, 152 mmol) in pyridine (70 mL) was stirred at room temperature for 24 hours to form a brown precipitate. 300 mL of ice-cooled water added while stirring. The initially formed brown precipitate dissolved followed by the formation of a white precipitate. This precipitate was collected by filtration and washed with ice-cooled water for 3 times (100 mL each time). It was dried under high vacuum to constant weight to give the titled compound. $^1$H NMR (CDCl$_3$, 400 MHz): δ8.81 (d, J=1.7 Hz, 1 H), 8.67 (dd, J=2.0, 4.9 Hz, 1 H), 7.94 (dt, J=2.0, 8.3 Hz, 2 H), 7.90 (dt, J=1.6, 8.0 Hz, 1 H), 7.38 (d, J=8.0 Hz, 2 H), 7.32–7.36 (m, 1 H), 2.46 (s, 3 H), 2.39 (s, 3 H).

Step C

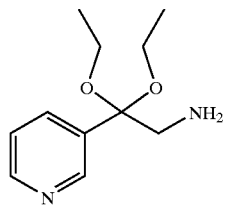

To a solution of 2-acetylpyridine tosylate from the previous step (30 g, 102.6 mmol) in ethanol (500 mL) was added potassium ethoxide (9.1 g, 105.7 mmol) at 0° C. It was slowly warmed to room temperature at which it was stirred for 1 hour. It was then diluted with 500 mL of anhydrous ethanol and HCl gas was bubbled in for 1 hour to see some precipitate. It was concentrated. The residue was distributed between methylene chloride (500 mL) and saturated sodium carbonate (about 500 mL to get pH=10). The organic layer was concentrated and vacuum distilled to get the titled compound as a colorless oil. $^1$H NMR (CDCl$_3$, 400 MHz): δ8.76–8.77 (m, 1 H), 8.58 (dd, J=1.8, 4.9 Hz, 1 H), 7.84 (dt, 1.8, 8.0 Hz, 1 Hz, 1H), 7.32 (ddd, J=0.8, 4.8, 8.0 Hz, 1 H), 3.37–3.53 (m, 4 H), 3.03 (s, 2 H), 1.25 (t, J=7.0 Hz, 6 H).

Step D

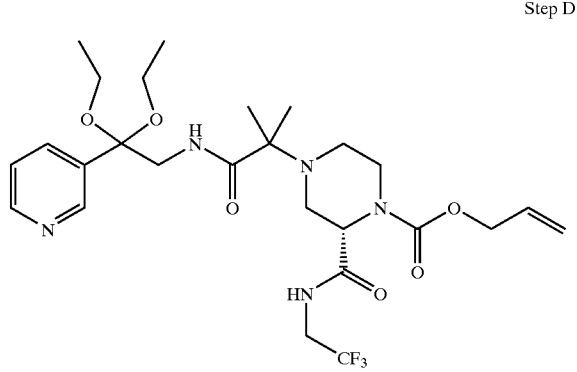

To a solution of the carboxylic acid from the Example 66, Step D (2 g, 5.24 mmol) and the aminoacetal from the previous step (1.33 g, 6.3 mmol) in DMF (20 mL) was added 0-benzoltriazol-1-N,N,N',N'-tetramethyluronium hexafluorophosphate (4.77 g,12.6 mmol), 1-hydroxybenzotriazol hydrate (1.7 g, 12.6 mmol) and diisipropylethylamine (4.56 mL, 26.2 mmol). After stirring at room temperature for 10 hours, the reaction solution was distributed between ethyl acetate (300 mL) and water (300 mL). The organic layer was washed with water (200 mL) and brine. It was dried over anhydrous sodium sulfate, concentrated and purified by flash column chromatography on silica gel with 1/2 hexanes/ethyl acetate as eluant to give the title compound as a white solid. $^1$H NMR (CDCl$_3$, 400 MHz): δ8.66 (d, J=4.8 Hz, 1 H), 7.70 (d, J=3.6 Hz, 2 H), 7.27 (m, 1 H), 6.63 (t, J=6.1 Hz, 1 H), 5.89–5.99 (m, 1 H), 5.26–5.35 (m, 2 H), 4.65 (d, J=4.8 Hz, 3 H), 4.19 (dd, J=8.0, 13.6 Hz, 1 H), 3.92 (broad s, 2 H), 3.57–3.68 (m, 3 H), 3.27–3.40 (m, 3 H), 2.82 (s, 2 H), 2.79 (broad s, 1 H), 2.49 (d, J=5.6 Hz, 1 H), 2.29 (dd, J=4.0, 8.0 Hz, 1 H), 2.14 (dt, J=3.2, 11.6 Hz, 1 H), 1.20–1.25 (2t, J=7.2 Hz, 6 H), 1.11 (s, 3H), 1.03 (s, 3 H).

Step E

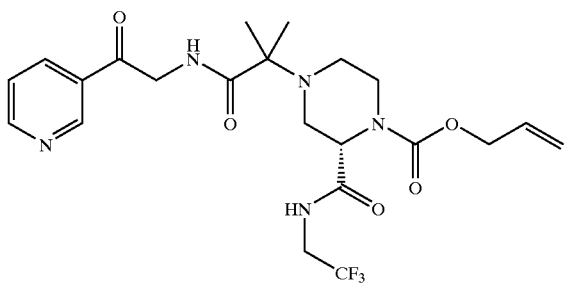

The acetal from the previous step (1.7 g, 2.96 mmol) was dissolved in THF (10 mL) and HCl (6 N, 10 mL) was added. The reaction solution was stirred at 70° C. for 12 hours, until the acetal was consumed. It was diluted with 200 mL of ethyl acetate and 1 N sodium hydroxide solution was added until pH=10. The organic layer was dried over anhydrous sodium sulfate, concentrated and purified by flash column chromatography on silica gel with 10/1 ethyl acetate/methanol as eluant to give the title compound as a white solid. $^1$H NMR (CDCl$_3$, 400 MHz): δ9.19 (s, 1 H), 8.82 (d, J=3.7 Hz, 1 H), 8.33 (broad s, 1 H), 8.23 (dt, J=2.0, 8.0 Hz, 1 H), 7.46 (dd, J=4.9, 7.8 Hz, 1 H), 6.76 (broad s, 1 H), 5.88–6.01 (m, 1 H), 5.27–5.36 (m, 2 H), 4.74–4.94 (m, 2 H), 4.68 (d, J=5.4 Hz, 2 H), 4.53 (dd, J=3.0, 15.6, 1 H), 4.00–4.26 (m, 2 H), 3.68–3.71 (m, 1 H), 3.64 (d, J=9.7 Hz, 1 H), 3.25 (t, J=9.3 Hz, 1 H), 2.87 (d, J=11.0 Hz, 1 H), 2.43 (dd, J=3.5, 11.5 Hz, 1 H), 2.33 (dt, J=3.3, 11.7 Hz, 1 H), 1.81 (broad s, 1 H), 1.68–1.71 (m, 1 H), 1.27 (s, 6 H).

Step F

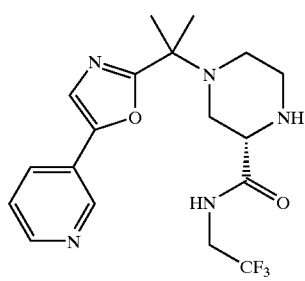

The ketoamide from the previous step (1.01 g mg, 2.02 mmol) was dissolved in 8 mL of fuming sulfuric acid. It was stirred at 55–60° C. for 20 minutes. After cooled to room temperature it was carefully poured into ice-water (20 mL). While the aqueous solution was stirred, potassium hydroxide (solid) was added slowly until pH=12. It was extracted with ethyl acetate for 3 times (100 mL each time). The combined extractant was dried over anhydrous sodium sulfate, concentrated and purified by flash column chromatography on silica gel with 100/12 ethyl acetate/methanol as eluant to give the title compound as a colorless glass. $^1$H NMR (CDCl$_3$, 400 MHz): δ8.91 (d, J=1.8 Hz, 1 H), 8.59 (dd, J=1.5, 4.9 Hz, 1 H), 8.08 (broad s, 1 H), 7.91 (dt, J=2.0, 8.0 Hz, 1 H), 7.38 (ddd, J=0.8, 4.9, 8.0 Hz, 1 H), 7.35 (s, 1 H), 3.91–4.00 (m, 2 H), 3.51 (dd, J=3.8, 5.6 Hz, 1 H), 2.84–2.99 (m, 3H), 2.76–2.82 (m, 1 H), 2.52–2.64 (m, 2 H), 1.61 (s, 3 H), 1.60 (s, 3 H). LC-MS (M$^+$+1) (EI) 398.3.

Step G (αR,γS,2S)-N-((3S,4S)-3,4-dihydro-3-hydroxy-2H-1-benzopyran-4-yl)-γ-hydroxy-4-[1-methyl-1-[5-(3-pyridinyl)-2-oxazolyl]ethyl]-α-(phenylmethyl)-2-[[(2,2,2-trifluoroethyl)amino]carbonyl]-1-piperazinepentanamide A solution of the intermediate from the previous step (608 mg, 1.53 mmol) and the epoxide from Example 1, Step P(6.93 mg, 1.76 mmol) in ethanol (15 mL) was refluxed for 12 hours. After the solvent was evaporated the residue was purified by flash column chromatography on silica gel with 10/1 ethyl acetate/methanol as eluant to get a white solid (620 mg) (LC-MS (M$^+$+1) (EI) 791.5). The solid obtained was dissolved in methanol (8 mL) and cooled to 0° C. HCl (1 N in ether, 10 mL) was added and the reaction solution was warmed to room temperature at which it was stirred for 10 hours. The solvent was evaporated. The residue was distributed between ethyl acetate (50 mL) and 1 N potassium hydroxide (10 mL). The organic layer was dried over anhydrous sodium sulfate, concentrated and purified by flash column chromatography on silica gel with 10/1 ethyl acetate/methanol as eluant to give the title compound as a white solid. $^1$H NMR (CD$_3$OD, 400 MHz): δ8.89 (d, J=1.8 Hz, 1 H), 8.51 (d, J=3.5 Hz, 1 H), 8.13 (dt, J=1.9, 8.0 Hz, 1 H), 7.81 (d, J=8.8 Hz, 1 H), 7.63 (s, 1 H), 7.51 (dd, J=4.9, 8.0 Hz, 1 H), 7.10–7.26 (m, 5 H), 7.05–7.09 (m, 2 H), 6.80 (t, J=7.2 Hz, 1 H), 6.72 (d, J=8.0 Hz, 1 H), 5.14 (d,J=3.9 Hz, 1 H), 4.06 (s, 2 H), 3.91–4.01 (m,1 H), 3.70–3.87 (m, 3 H), 3.28–3.31 (m, 1 H), 3.10–3.21 (m, 2 H), 2.89–3.04 (m, 4 H), 2.80 (broad s, 1 H), 2.63–2.75 (m, 3 H), 2.41–2.52 (m, 4 H), 1.98–2.05 (m, 1 H), 1.61 (s, 3 H), 1.60 (s, 3 H), 1.33–1.40 (m, 1 H). LC-MS (M$^+$+1) (EI) 751.5

EXAMPLE 68

(αR,γS,2S)-N-((3S,4S)-3,4-dihydro-3-hydroxy-2H-1-benzopyran-4-yl)-γ-hydroxy-4-[(5-phenyl-2-furanyl)methyl]-α-(5-pyrimidinylmethyl)-2-[[(2,2,2-trifluoroethyl)amino]carbonyl]-1-piperazinepentanamide

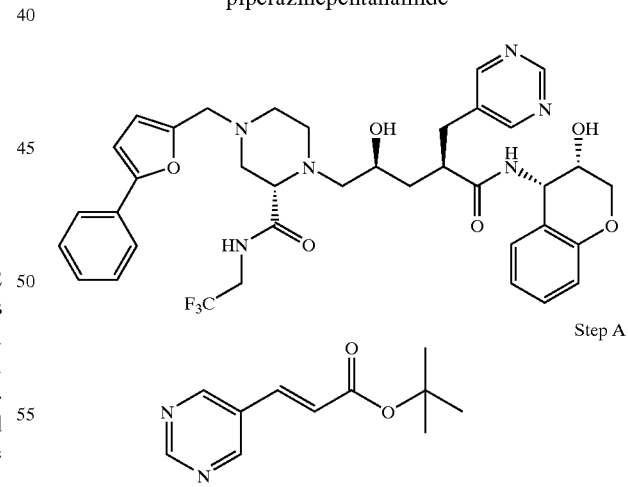

Step A

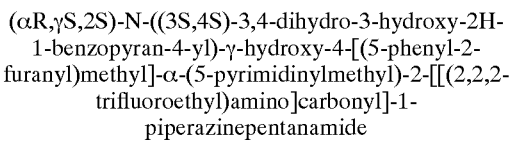

To a solution of 5-bromopyrimidine (2.4 g, 15.1 mmol) in t-butyl acrylate (30 mL) was added palladium acetate (169.4 mg, 0.755 mmol) and triethylamine (3 mL, 21.59 mmol). The flask was sealed and heated at 80° C. After 24 hours, another portion of palladium acetate (169.4 mg, 0.755 mmol) was added and the reaction mixture was heated at 80° C. for 24 hours. The solvent was removed in vacuo and the crude reaction mixture was purified by flash column chromatography on silica gel with 3:7 ethyl acetate/hexane as the eluant to give the titled compound. ¹H NMR (CDCl₃, 300 MHz): 9.18 (s, 1H), 8.86 (s, 2H), 7.52 (d, J=17.5 Hz, 1H), 6.50 (d, J=17.5 Hz, 1H), 1.55 (s, 9H).

Step B

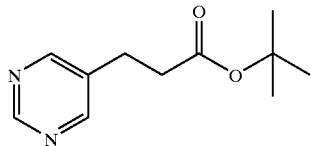

To the intermediate prepared in Step A (100 mg, 0.485 mmol) and triethylamine (0.135 mL, 0.97 mmol) in ethanol (5 mL) was added 10% palladium on carbon (18 mg). The reaction mixture was stirred under a hydrogen balloon and the progress of the reaction was monitored by TLC. After half an hour the reaction mixture was filtered through celite and the filtrate was concentrated in vacuo. The crude product was purified by flash column chromatography on silica gel with 3:7 ethyl acetate/hexane as the eluant to give the titled compound. ¹H NMR (CDCl₃, 300 MHz): 9.08 (s, 1H), 8.62 (s, 2H), 2.90 (t, 2H), 2.59 (t, 2H), 1.42 (s, 9H).

Step C

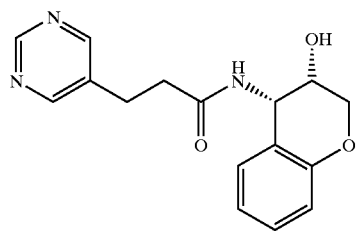

To the intermediate prepared in Step B (289 mg, 1.39 mmol) was added trifluoroacetic acid (10 mL) and stirred at room temperature for an hour. The solvent was removed in vacuo. The resulting product in methylene chloride (10 mL) was added aminochromanol (415 mg, 2.08 mmol;) prepared as in Example 1 Step L, EDC (531 mg, 2.78 mmol), HOBt (375 mg, 2.78 mmol) and N,N-diisopropylethylamine (1.2 mL, 6.95 mmol). The reaction mixture was stirred at room temperature overnight. A white precipitate of the titled compound was formed. The precipitated product was collected by filtration. The filtrate which also contained product was washed with water, dried over anhydrous sodium sulfate, filtered and concentrated in vacuo. ¹H NMR (CDCl₃, 300 MHz): 9.02 (s, 1H), 8.75 (s, 2H), 7.10 (m, 1H), 6.84 (m, 2H), 6.76 (m, 1H), 5.22 (m, 1H), 4.12 (m, 2H), 4.20 (m, 1H), 3.06 (t, 2H), 2.72 (t, 2H).

Step D

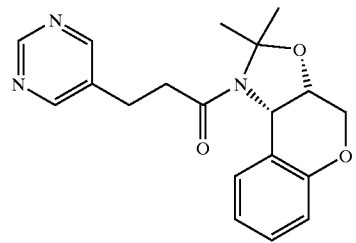

To the intermediate prepared in Step C (306 mg, 1.02 mmol) in methylene chloride (10 mL) was added 2-methoxypropene (0.491 mL, 5.11 mmol) and camphor-sulfonic acid (522 mg, 2.25 mmol). The reaction mixture was stirred at room temperature and the progress of the reaction was monitored by TLC. After 3 hours the crude reaction mixture was poured into 1 N aqueous sodium hydroxide solution and the product was extracted with ethyl acetate three times. The organic layers were combined, washed with brine, dried over anhydrous sodium sulfate, filtered and concentrated in vacuo. The crude product was purified by flash column chromatography on silica gel with ethyl acetate as the eluant to give the titled compound as a white solid. ¹H NMR (CDCl₃, 300 MHz): 9.10 (s, 1H), 8.68 (s, 2H), 7.12 (m, 1H), 6.98 (m, 1H), 6.86 (t, 2H), 4.92 (m, 1H), 4.39 (m, 1H), 4.28 (m, 1H), 4.18 (m, 1H), 3.10 (m, 2H), 3.00 (m, 2H), 1.60 (s, 3H), 1.25 (s, 3H).

Step E

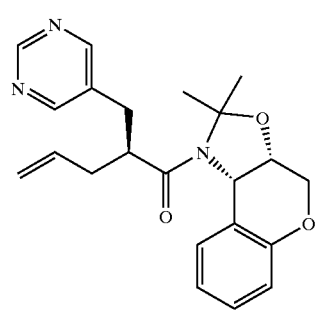

To a solution of intermediate prepared in Step D (122 mg, 0.3592 mmol) in anhydrous tetrahydrofuran (5 mL) at −25° C. was added allylbromide (0.034 mL, 0.395 mmol) followed by 1.0 M lithium bis(trimethylsilyl)amide in THF (0.395 mL, 0.395 mmol). The reaction mixture was stirred at −25° C. and progress of reaction was monitored by TLC. After 2 hours the reaction was quenched with water and warmed up to room temperature. The crude reaction mixture was extracted with ethyl acetate three times. The organic layers were combined, dried over anhydrous sodium sulfate, filtered and concentrated in vacuo. The crude product was purified by flash column chromatography on silica gel with 1:1 ethyl acetate/hexane as the eluant to give the titled compound as a white solid. ¹H NMR (CDCl₃, 300 MHz, mixture of rotamers R1 and R2 7:3 ratio): 9.16 (s, 0.7H, R1), 9.07 (s, 0.3H, R2), 8.74 (s, 1.4H, R1), 8.63 (s, 0.6H, R2), 7.66 (m, 0.3H), 7.18–7.04 (m, 1H), 6.90–6.78 (m, 1.4H), 6.55 (t, 0.7H), 6.22 (d, 0.7H), 5.94–5.68 (m, 1.3H), 5.22–4.94 (m, 2.7H), 4.42–4.02 (m, 3H), 3.37–3.12 (m, 2H), 2.84–2.77 (m, 1H), 2.50–2.26 (m, 2H), 1.35–1.07 (m, 6H).

Step F

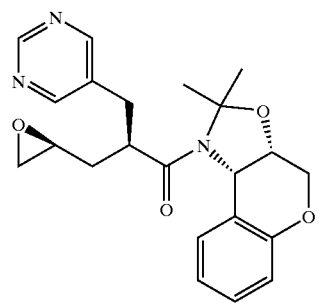

To the intermediate prepared in Step E (142 mg, 0.375 mmol) in ethyl acetate (6 mL) at 0° C. was added 0.5 M aqueous sodium bicarbonate solution (6 mL) and N-iodosuccinimide (177 mg, 0.788 mmol). The reaction mixture was allowed to warm to room temperature. After 14 hours the mixture was poured into aqueous sodium sulfite solution and extracted with ethyl acetate three times. The organic layers were combined, dried over anhydrous sodium sulfate, filtered and concentrated in vacuo. The resulting product was dissolved in ethyl acetate (5 mL) and sodium methoxide in methanol (25 wt. %, 0.136 mL, 0.596 mmol) was added. The reaction mixture was stirred at room temperature and progress of reaction was monitored by TLC. After an hour the mixture was poured into saturated sodium bicarbonate solution and the product was extracted with ethyl acetate three times. The combined organic layers were dried over anhydrous sodium sulfate, filtered and concentrated in vacuo. The crude titled product was purified by flash column chromatography on silica gel with ethyl acetate as the eluant. $^1$H NMR (CDCl$_3$, 300 MHz, mixture of rotamers R1 and R2 4:1 ratio): 9.17 (s, 0.8H, R1), 9.11 (s, 0.2H, R2), 8.72 (s, 1.6H, R1), 8.63 (s, 0.4H, R2), 7.69 (d, J=8.24 Hz, 0.2H, R2), 7.14–7.08 (m, 1H), 6.87–6.80 (m, 1.2H), 6.62–6.56 (m, 0.8H, R1), 6.36 (d, J=7.84, 0.8H, R1), 5.85 (d, J=5.55 Hz, 0.2H, R2), 5.34 (d, J=4.67 Hz, 0.8H, R1), 4.44–4.04 (m, 3H), 3.40–3.36 (m, 1.6H), 3.15–2.68 (m, 4H), 2.55–2.20 (m, 2.4H), 1.50–1.22 (m, 6H).

Step G

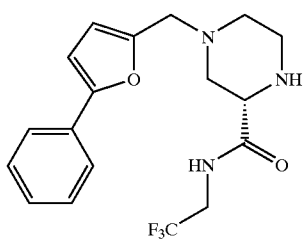

The intermediate prepared as in Example 12, Step A (500 mg, 1.32 mmol) was treated with 30% TFA/methylene chloride (20 mL). The reaction mixture was stirred at room temperature for an hour. Then solvents were removed in vacuo. The reaction mixture was diluted with chloroform. 1 N NaOH was added to adjust the pH to 14 followed by extraction with chloroform three times. The organic layers were combined, washed with brine, dried over anhydrous sodium sulfate, filtered and concentrated in vacuo. The resulting product (469 mg, 1.59 mmol) in dichloroethane (20 mL) was added the intermediate prepared in Example 23, Step G (273 mg, 1.59 mmol) followed by sodium triacetoxyborohydride (505 mg, 2.38 mmol). The reaction mixture was stirred at room temperature overnight. Then solvent was removed in vacuo. The crude product was purified by flash column chromatography on silica gel with 3:7 ethyl acetate/hexane as the eluant. The resulting intermediate (408 mg, 0.904 mmol) in methylene chloride (10 mL) was added 1,3-dimethylbarbituric acid (169 mg, 1.08 mmol). After stirring at room temperature for 5 min, Pd(PPh$_3$)$_4$ (52 mg, 0.045 mmol) was added. The reaction mixture was stirred at room temperature and progress of reaction was monitored by TLC. After an hour the mixture was poured into 1N NaOH and the product extracted with methylene chloride three times. The organic layers were combined, dried over anhydrous sodium sulfate, filtered and concentrated in vacuo. The crude reaction mixture was purified by flash column chromatography on silica gel with 8% methanol/ethyl acetate as the eluant to give the titled compound. $^1$H NMR (CDCl$_3$, 300 MHz): 7.77 (bs, 1H), 7.66–7.62 (m, 2H), 7.39–7.34 (m, 2H), 7.26–7.22 (m, 1H), 6.58 (d, J=3.24 Hz, 1H), 6.29 (d, J=3.02 Hz, 1H), 3.98–3.71 (m, 4H), 3.64 (d, J=9.68 Hz, 2H), 3.58–3.50 (m, 1H), 2.99–2.83 (m, 3H), 2.62–2.46 (m, 3H).

Step H

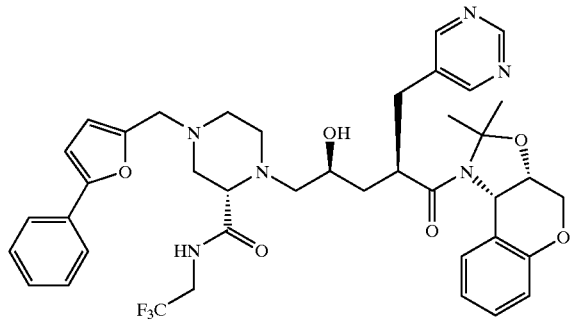

The intermediate prepared in Step G (98 mg, 0.266 mmol) and the intermediate prepared in Step F (105 mg, 0.266 mmol) in methanol (4 mL) was heated to reflux overnight. The solvent was removed in vacuo. The crude reaction mixture was purified by flash column chromatography on silica gel with 1:24 methanol/ethyl acetate as the eluant to give the titled compound as a white solid. $^1$H NMR (CDCl$_3$, 300 MHz, mixture of rotamers R1 and R2 4:1 ratio): 9.21 (bs, NH, 1H), 9.14 (s, 0.8H, R1), 9.09 (s, 0.2H, R2), 8.70 (s, 1.6H, R1), 8.61 (s, 0.4H, R2), 7.61 (d, J=7.36 Hz, 2H), 7.40–7.38 (m, 2H), 7.35–7.25 (m, 1H), 7.12–7.07 (m, 1H), 6.82–6.80 (m, 1.2H), 6.66–6.58 (m, 2H), 6.52–6.49 (m, 0.8H, R1), 6.31–6.28 (m, 1H), 5.88 (d, 0.2H, R2), 5.68 (d, J=4.61 Hz, 0.8H, R1), 4.44–4.07 (m, 5H), 3.78–2.40 (m, 21H), 1.81–1.71 (m, 1.6H, R1), 1.68 (s, 2.4H, R1), 1.60–1.55 (m, 0.4H, R2), 1.47 (s, 0.6H, R2), 1.34 (s, 0.6H, R2), 1.24 (s, 2.4H, R1).

Step I (αR,γS,2S)-N-((3S,4S)-3,4-dihydro-3-hydroxy-2H-1-benzopyran-4-yl)-γ-hydroxy4-[(5-phenyl-2-furanyl)methyl]-α-(5-pyrimidinylmethyl)-2-[[(2,2,2-trifluoroethyl)amino]carbonyl]-1-piperazinepentanamide To a solution of the intermediate obtained in Step H (92 mg, 0.123 mmol) in methanol (5 mL) was added 1 M HCl in ethyl ether (2.5 mL, 2.46 mmol). The reaction mixture was stirred at room temperature. After overnight the mixture was neutralized by 2 M ammonia in methanol. The solvent was removed in vacuo and the reaction mixture was diluted with chloroform and washed with 1 N NaOH. The aqueous layer was extracted with chloroform three times. The organic layers were combined, dried over anhydrous sodium sulfate, filtered and concentrated in vacuo. The crude product was purified by flash column chromatography with 4% 2M ammonia in methanol/ethyl acetate as the eluant. $^1$H NMR (CDCl$_3$, 300 MHz): 9.15 (bs, NH, 1H), 8.99 (s, 1H), 8.47 (s, 2H), 7.64–7.61 (m, 2H), 7.40–7.35 (m, 2H), 7.29–7.27 (m, 1H), 7.12–7.25 (m, 2H), 6.82–6.73 (m, 2H), 6.60 (d, J=3.27 Hz, 1H), 6.31 (d, J=3.30 Hz, 1H), 5.20–5.18 (m, 1H), 4.15–4.00 (m, 3H), 3.77–3.69 (m, 3H), 3.57–3.31 (m, 4H), 3.01–2.04 (m, 10H), 1.84–1.76 (m, 1H), 1.48–1.40 (m, 1H). LC-MS (M$^+$+1) (EI) 723.

EXAMPLE 69

(αR,γS,2S)-N-((3S,4S)-3,4-dihydro-3-hydroxy-2H-1-benzopyran-4-yl)-γ-hydroxy-4-[(5-phenyl-2-furanyl)methyl]-α-(2-pyrazinylmethyl)-2-[[[(2,2,2-trifluoroethyl)amino]carbonyl]-1-piperazinepentanamide

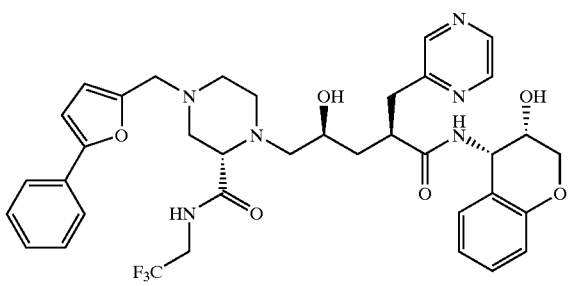

Step A

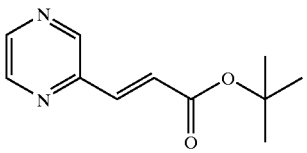

To a solution of chloropyrazine (0.78 mL, 8.73 mmol), t-butyl acrylate (6.4 mL, 43.6 mmol) and triethylamine (6.1 mL, 43.6 mmol) in anhydrous DMF (20 mL) was added palladium acetate (98 mg, 0.436 mmol) and 2-(di-t-butylphosphino)biphenyl (260 mg, 0.873 mmol). The flask was sealed and heated at 120° C. After 14 hours the reaction mixture was poured into water and the product was extracted with ethyl acetate. The organic layer was dried over sodium sulfate, filtered and concentrated in vacuo. The crude reaction mixture was purified by flash column chromatography on silica gel with 3:17 ethyl acetate/hexane as the eluant to give the titled compound. $^1$H NMR (CDCl$_3$, 300 MHz): 8.68 (s, 1H), 8.60 (m, 1H), 8.52 (m, 1H), 7.60 (d,J=15 Hz, 1H), 6.92 (d, J=15 Hz, 1H), 1.56 (s, 9H).

Step B

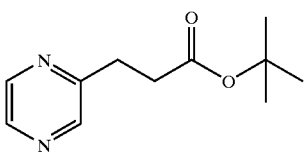

To the intermediate prepared in Step A (518 mg, 2.51 mmol) and triethylamine (0.71 mL, 5.10 mmol) in ethanol (20 mL) was added 10% palladium on carbon (95 mg). The reaction mixture was stirred under a hydrogen balloon and progress of reaction was monitored by HPLC. After 2 hours the reaction mixture was filtered through celite and the filtrate was concentrated in vacuo to give the titled compound. $^1$H NMR (CDCl$_3$, 400 MHz): 8.52 (s, 1H), 8.50 (m, 1H), 8.23 (m, 1H), 3.13 (t, 2H), 2.75 (t, 2H), 1.42 (s, 9H).

Step C

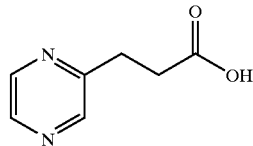

To the intermediate prepared in Step B (430 mg, 2.07 mmol) was added trifluoroacetic acid (20 mL) and stirred at room temperature for an hour. The solvent was removed in vacuo to give the titled compound. $^1$H NMR (CDCl$_3$, 400 MHz): 8.74 (m, 1H), 8.68 (s, 1H), 8.54 (m, 1H), 3.28 (t, 2H), 2.98 (t, 2H), 1.40 (s, 9H).

Step D

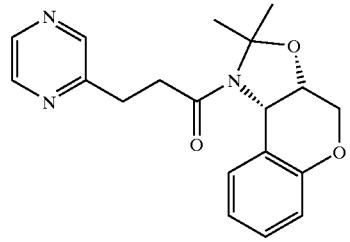

To the intermediate obtained in Step C (312 mg, 2.05 mmol) in methylene chloride (10 mL) was added aminochromanol (409 mg, 2.05 mmol) prepared as in Example 1 Step L, EDC (392 mg, 2.05 mmol), HOBt (277 mg, 2.05 mmol) and N,N-diisopropylethylamine (1.19 mL, 6.83 mmol). The reaction mixture was stirred at room temperature overnight. Then solvent was removed in vacuo. The reaction mixture was diluted with ethyl acetate and washed with brine. The aqueous layer was extracted with ethyl acetate three times. The organic layers were combined, dried over anhydrous sodium sulfate, filtered and concentrated in vacuo. The resulting product in methylene chloride (30 mL) was added 2-methoxypropene (0.8 mL, 8.33 mmol) and camphorsulfonic acid (350 mg, 1.51 mmol). The reaction mixture was stirred at room temperature and progress of reaction was monitored by TLC. After an hour the crude reaction mixture was poured into 1 N NaOH and the product was extracted with ethyl acetate three times. The organic layers were combined, washed with brine, dried over anhydrous sodium sulfate, filtered and concentrated in vacuo. The crude product was purified by flash column chromatography on silica gel with ethyl acetate as the eluant to give the titled compound. $^1$H NMR (CDCl$_3$, 300 MHz, mixture of rotamers R1 and R2 3:2 ratio): 8.59–8.39 (m, 3H), 7.40 (m, 0.4H, R2), 7.30 (m, 0.6H, R1), 7.20–7.10(m, 1H), 6.94–6.78 (m, 2H), 5.79 (m, 0.4H, R2), 5.18 (m, 0.6H, R1), 4.48–4.05 (m, 3H), 3.36–3.20 (m, 4H), 1.72 (s, 1.2H, R2), 1.56 (s, 1.8H, R1), 1.39 (s, 1.2H, R2), 1.28 (s, 1.8H, R1).

Step E

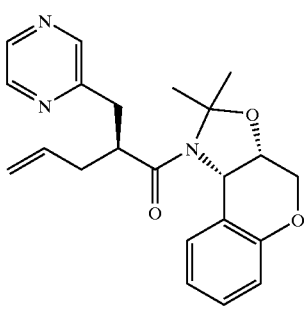

To a solution of intermediate prepared in Step D (622 mg, 1.83 mmol) in anhydrous tetrahydrofuran (20 mL) at −25° C. was added allylbromide (0.174 mL, 2.02 mmol) followed by 1.0 M lithium bis(trimethylsilyl)amide in THF (2.02 mL, 2.02 mmol). The reaction mixture was stirred at −25° C. and progress of reaction was monitored by TLC. After 2 hours the reaction was quenched with water and warmed up to room temperature. The crude reaction mixture was extracted with ethyl acetate three times. The organic layers were combined, dried over anhydrous sodium sulfate, filtered and concentrated in vacuo. The crude product was purified by flash column chromatography on silica gel with 1:1 ethyl acetate/hexane as the eluant to give the titled compound as a white solid. $^1$H NMR (CDCl$_3$, 300 MHz, mixture of rotamers R1 and R2 7:3 ratio): 8.60–8.42 (m, 3H), 7.16–7.10 (m, 1H), 6.98–6.68 (m, 3H), 5.95–5.62 (m, 1.3H), 5.20–4.99 (m, 2.7H), 4.48–4.06 (m, 3H), 3.75–3.64(m, 0.7H), 3.50–3.18 (m, 1.3H), 3.08–3.00 (m, 1H), 2.52–2.20 (m, 2H), 1.65–1.20 (m, 6H).

Step F

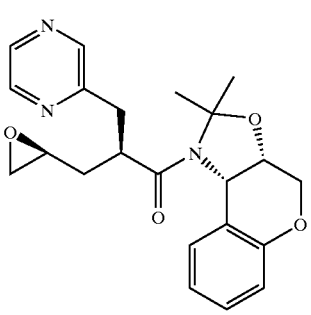

To the intermediate prepared in Step E (53 mg, 0.14 mmol) in ethyl acetate (2 mL) at 0° C. was added 0.5 M aqueous sodium bicarbonate solution (2 mL) and N-iodosuccinimide (95 mg, 0.421 mmol). The reaction mixture was allowed to gradually warm to room temperature and progress of reaction was monitored by HPLC. After 2.5 hours the reaction mixture was poured into aqueous sodium sulfite solution and the product was extracted with ethyl acetate three times. The organic layers were combined, dried over anhydrous sodium sulfate and concentrated in vacuo. The resulting product was dissolved in ethyl acetate (2.5 mL) and sodium methoxide in methanol (25 wt. %, 0.073 mL, 0.32 mmol) was added. The reaction mixture was stirred at room temperature and progress of reaction was monitored by TLC. After an hour the mixture was poured into saturated sodium bicarbonate solution and the product was extracted with ethyl acetate three times. The combined organic layers were dried over anhydrous sodium sulfate, filered and concentrated in vacuo. The crude product was purified by flash column chromatography on silica gel with ethyl acetate as the eluant to give the titled compound. $^1$H NMR (CDCl$_3$, 300 MHz, mixture of rotamers R1 and R2 2:1 ratio): 8.58–8.43 (m, 3H), 7.26 (m, 0.3H, R2), 7.16–7.11 (m, 0.7H, R1), 7.00–6.73 (m, 3H), 5.85 (d, J=5.50 Hz, 0.3H, R2), 5.40 (d, J=4.67 Hz, 0.7H, R1), 4.50–4.04 (m, 3H), 3.82–2.18 (m, 8H), 1.74 (s, 2H, R2), 1.60 (s, 1H, R2), 1.52 (s, 1H, R2), 1.30 (s, 2H, R1).

Step G

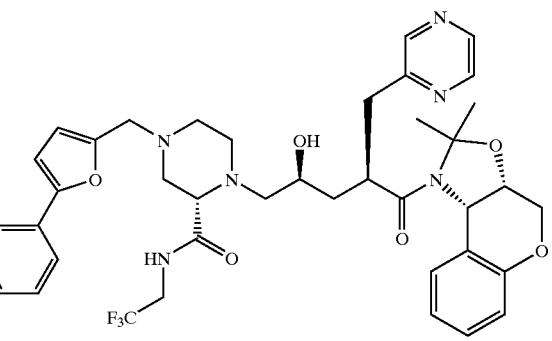

The intermediate prepared in Step F (90 mg, 0.244 mmol) and the intermediate prepared as in Example 68 Step G (150 mg, 0.38 mmol) in methanol (4 mL) were heated to reflux overnight. The solvent was removed in vacuo. The crude reaction mixture was purified by flash column chromatography on silica gel with 2% methanol/ethyl acetate as the eluant to give the titled compound as a white solid. $^1$H NMR (CDCl$_3$, 300 MHz, mixture of rotamers R1 and R2 3:1 ratio): 9.15 (bs, NH, 0.75H, R1), 9.08 (bs, NH, 0.25H, R2), 8.54 (s, 1.5H, R1) 8.52 (s, 0.5H, R2), 8.46 (s, 0.75H, R1), 8.41 (s, 0.25H, R2), 7.60 (m, 2H), 7.38 (m, 2H), 7.27 (m, 1H), 7.16–7.10 (m, 2H), 6.85–6.75 (m, 2H), 6.58 (m, 1H), 6.30 (m, 1H), 5.90 (d, 0.25H), 5.75 (d, 0.75H), 4.48–4.05 (m, 3H), 3.90–2.85 (m, 11H), 2.68–2.30 (m, 6H), 1.80–1.22 (m, 8H).

Step H (αR,γS,2S)-N-((3S,4S)-3,4-dihydro-3-hydroxy-2H-1-benzopyran-4-yl)-γ-hydroxy-4-[(5-phenyl-2-furanyl)methyl]-α-(2-pyrazinylmethyl)-2-[[(2,2,2-trifluoroethyl)amino]carbonyl]-1-piperazinepentanamide To a solution of the intermediate obtained in Step G (20 mg, 0.026 mmol) in methanol (1 mL) was added 1 M HCl in ethyl ether (0.52 mL, 0.52 mmol). The reaction mixture was stirred at room temperature and progress of reaction was monitored by HPLC. After 7 hours the mixture was neutralized by 2 M ammonia in methanol. The solvent was removed in vacuo. The mixture was diluted with chloroform and washed with 1 N NaOH. The aqueous layer was extracted with chloroform three times. The organic layers were combined, dried over anhydrous sodium sulfate, filtered and concentrated in vacuo. The crude product was purified by flash column chromatography with 6% methanol/chloroform as the eluant to give the title compound as a white solid. $^1$H NMR (CDCl$_3$, 300 MHz): 9.15 (bs, NH, 1H), 8.46 (s, 1H), 8.40 (m, 2H), 7.63 (m, 2H), 7.41–7.35 (m, 2H), 7.30–7.25 (m, 1H), 7.16–7.10 (m, 2H), 6.85–6.80 (m, 2H), 6.61 (m, 1H), 6.31 (m, 1H), 5.24 (m, 1H), 4.20–2.36 (m, 20H), 1.86 (m, 1H), 1.52 (m, 1H). LC-MS (M$^+$+1) (EI) 723.

EXAMPLE 70

(αS,γS,2S)-N-((3S,4S)-3,4-dihydro-3-hydroxy-2H-1-benzopyran-4-yl)-γ-hydroxy4-[[5-(2-pyridinyl)-2-furanyl]methyl]-α-(2-thienylmethyl)-2-[[(2,2,2-trifluoroethyl)amino]carbonyl]-1-piperazinepentanamide

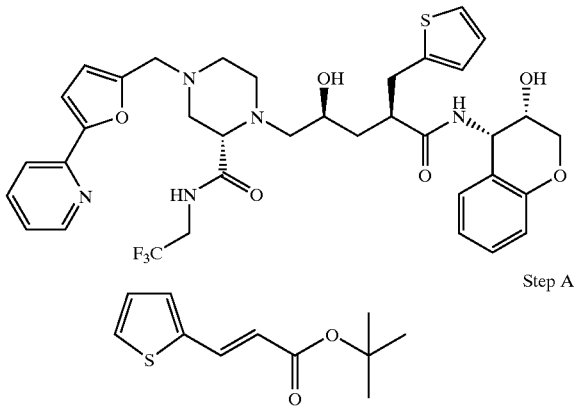

Step A

To a solution of 2-bromothiophene (0.59 mL, 6.13 mmol), t-butyl acrylate.(2.69 mL, 18.4 mmol) and triethylamine (4.27 mL, 30.7.mmol) in anhydrous acetonitrile (15 mL) was added palladium acetate (137.7 mg, 0.613 mmol) and tritolylphosphine (373.3 mg, 1.23 mmol). The flask was sealed and heated at 100° C. After 14 hours the reaction mixture was poured into brine and extracted with ethyl acetate three times. The organic layers were combined, dried over sodium sulfate, filtered and concentrated in vacuo. The crude product was purified by flash column chromatography on silica gel with 5% ethyl acetate/hexane as the eluant to give the titled compound. $^1$H NMR (CDCl$_3$, 300 MHz): 7.58 (d, J=16.3 Hz 1H), 7.45 (m, 1H), 7.36–7.27 (m, 2H), 6.20 (d, J=16 Hz, 1H), 1.56 (s, 9H).

Step B

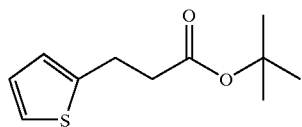

To the intermediate prepared in Step A (11.9 g, 56.1 mmol) in ethanol (400 mL) was added 10% palladium on carbon (2.5 g). The reaction mixture was stirred under a hydrogen balloon and progress of reaction was monitored by NMR after mini-workup. After 14 hours 40% conversion of starting material was observed. The reaction mixture was filtered through celite and concentrated in vacuo. The resulting material was retreated with Pd/C (2.5 g) in ethanol under a hydrogen balloon. After 5 hours, another portion of Pd/C (1 g) was added. The reaction mixture was stirred overnight and filtered through celite. The filtrate was concentrated in vacuo to give the titled compound. $^1$H NMR (CDCl$_3$, 300 MHz): 7.12 (m, 1H), 6.90 (m, 1H), 6.80 (m, 1H), 3.10 (t, 2H), 2.78 (t, 2H), 1.40 (s, 9H).

Step C

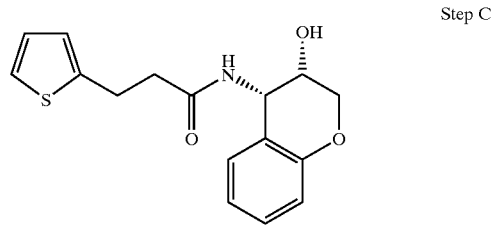

To the intermediate prepared in Step B (6 g, 38.3 mmol) was added trifluoroacetic acid (100 mL) and stirred at room temperature for 30 min. The solvent was then removed in vacuo. The resulting product in methylene chloride (100 mL) was added aminochromanol (6.77 g, 33.9 mmol) prepared as in Example 1 Step L, EDC (7.02 g, 36.7 mmol), HOBt (4.97 mg, 36.7 mmol) and N,N-diisopropylethylamine (19.7 mL, 113.0 mmol). After 14 hours the reaction mixture was poured into water and extracted with methylene chloride three times. The organic layers were combined, dried over anhydrous sodium sulfate, filtered and concentrated in vacuo. The crude product was purified with flash column chromatography on silica gel with 75% ethyl acetate/hexane as the eluant to give the titled compound. $^1$H NMR (CDCl$_3$, 300 MHz): 7.17 (m, 2H), 6.98–6.80 (m, 5H), 5.97 (bs, NH, 1H), 5.28 (m, 1H), 4.18–4.08 (m, 3H), 3.27 (m, 2H), 2.65 (m, 2H).

Step D

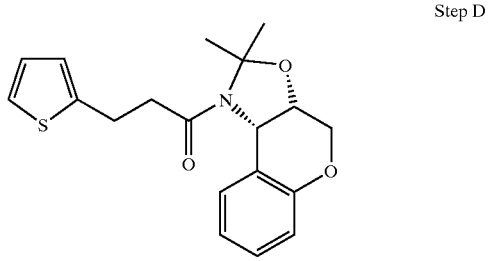

To the intermediate obtained in Step C (8.6 g, 28.4 mmol) in methylene chloride (400 mL) was added 2-methoxypropene (13.6 mL, 141.8 mmol) and camphorsulfonic acid (658 mg, 2.84 mmol). The reaction mixture was stirred at room temperature and progress of reaction was monitored by TLC. After half an hour the crude reaction mixture was poured into 1 N aqueous sodium hydroxide solution and the product was extracted with methylene chloride three times. The organic layers were combined, washed with brine, dried over anhydrous sodium sulfate, filtered and concentrated in vacuo. The crude product was purified by flash column chromatography on silica gel with 30% ethyl acetate/hexane as the eluant to give the titled compound. $^1$H NMR (CDCl$_3$, 300 MHz): 7.17–7.06 (m, 3H), 6.95–6.85 (m, 4H), 4.96 (m, 1H), 4.44–4.40 (m, 2H), 4.19 (m, 1H), 3.55 (m, 2H), 3.00 (m, 2H), 1.66 (s, 3H), 1.61 (s, 3H).

Step E

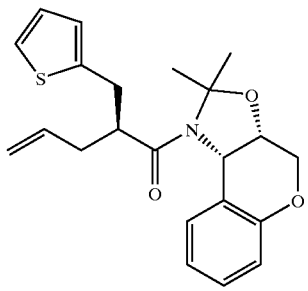

To a solution of intermediate prepared in Step D (4.09 g, 11.9 mmol) in anhydrous tetrahydrofuran (100 mL) at −25° C. was added allylbromide (1.24 mL, 14.3 mmol) followed by 1.0 M lithium bis(trimethylsilyl)amide in THF (14.3 mL, 14.3 mmol). The reaction mixture was stirred at −25° C. and progress of reaction was monitored by TLC. After 30 min the reaction was quenched with water and warmed up to room temperature. The crude reaction mixture was extracted with ethyl acetate three times. The organic layers were combined, dried over anhydrous sodium sulfate, filtered and concentrated in vacuo. The crude product was purified by flash column chromatography on silica gel with 1:4 ethyl acetate/hexane as the eluant to give the titled compound as a white solid. $^1$H NMR (CDCl$_3$, 300 MHz, mixture of rotamers R1 and R2 3:1 ratio): 7.70 (m, 0.25H, R2), 7.22–6.78 (m, 5.25H), 6.59 (t, 0.75H, R1), 6.38 (d, 0.75H, R1), 5.92–5.65 (m, 1.25H), 5.24–4.98 (m, 2.75H), 4.48–4.08 (m, 3H), 3.56–3.58 (m, 0.75H), 3.38–3.18 (m, 1H), 3.10–3.00 (m, 1H), 2.83 (m, 0.25H), 2.48–2.30 (m, 2H), 1.72 (s, 2.25H, R1), 1.38 (s, 0.75H, R2), 1.35 (s, 0.75H, R2), 1.30 (s, 2.25H, R1).

Step F

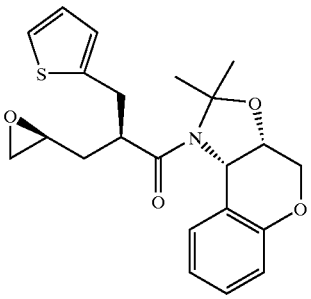

To the intermediate prepared in Step E (3.72 g, 9.72 mmol) in ethyl acetate (150 mL) at 0° C. was added 0.5 M aqueous sodium bicarbonate solution (150 mL) and N-iodosuccinimide (4.59 mg, 20.4 mmol). The reaction mixture was allowed to gradually warm to room temperature and progress of reaction was monitored by HPLC. After 6 hours the reaction mixture was poured into aqueous sodium sulfite solution and extracted with ethyl acetate three times. The organic layers were combined, dried over anhydrous sodium sulfate, filtered and concentrated in vacuo. The resulting product was dissolved in ethyl acetate (130 mL) and sodium methoxide in methanol (25 wt. %, 3.3 mL) was added. The reaction mixture was stirred at room temperature and progress of reaction was monitored by TLC. After an hour the mixture was poured into saturated sodium bicarbonate solution and extracted with ethyl acetate three times. The combined organic layers were dried over anhydrous sodium sulfate, filtered and concentrated in vacuo. The crude product was purified by column chromatography on silica gel with 50% ethyl acetate/hexane as the eluant to give the titled compound. $^1$H NMR (CDCl$_3$, 400 MHz, mixture of rotamers R1 and R2 3:1 ratio): 7.78 (m, 0.25H, R2), 7.21–6.81 (m, 5.25H), 6.65 (t, 0.75H, R1), 6.50 (d, 0.75H, R1), 5.90 (d, J=5.50 Hz, 0.25H, R2), 5.39 (d, J=4.5 Hz, 0.75H, R1), 4.47–4.09 (m, 3H), 3.622–3.56 (m, 0.75H, R1), 3.25–3.30 (m, 1H), 3.15–2.86 (m, 3H), 2.76–2.17 (m, 3H), 1.76–1.32 (m, 6H).

Step G

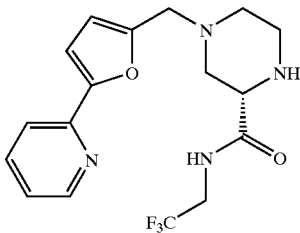

The intermediate prepared as in Example 68 Step H (4 g, 10.6 mmol) was treated with 30% TFA/methylene chloride (200 mL). The reaction mixture was stirred at room temperature for an hour. Then solvent was removed in vacuo. The reaction mixture was diluted with chloroform. Then 1 N NaOH was added to adjust the pH to 14 followed by extraction with chloroform three times. The organic layers were combined, washed with brine, dried over anhydrous sodium sulfate, filtered and concentrated in vacuo. To the resulting product (2.69 g, 9.12 mmol) in dichloroethane (50 mL) was added the intermediate prepared in Example 49, Step B (1.58 g, 9.12 mmol) followed by sodium triacetoxyborohydride (2.90 g, 13.7 mmol). The reaction mixture was stirred at room temperature overnight. Then solvent was removed in vacuo. The crude product was purified by column chromatography on silica gel with ethyl acetate as the eluant. The resulting intermediate (3.04 g, 6.71 mmol) in methylene chloride (100 mL) was added 1,3-dimethylbarbituric acid (1.26 g, 8.06 mmol). After stirring at room temperature for 5 min, Pd(PPh$_3$)$_4$ (388 mg, 0.336 mmol) was added. The reaction mixture was stirred at room temperature and progress of reaction was monitored by TLC. After an hour the mixture was poured into 1 N NaOH extracted with methylene chloride three times. The organic layers were combined, dried over anhydrous sodium sulfate, filtered and concentrated in vacuo. The crude reaction mixture was purified by flash column chromatography on silica gel with 10% methanol/ethyl acetate as the eluant to give the titled compound. $^1$H NMR (CDCl$_3$, 300 MHz): 8.58 (m, 1H), 7.69 (m, 2H), 7.16 (m, 1H), 6.98 (d, J=3.33 Hz, 1H), 6.36 (d, J=3.36 Hz, 1H), 4.05–3.64 (m, 5H), 3.52 (bs, NH, 1H), 3.04–2.87 (m, 3H), 2.66–2.44 (m, 3H).

Step H (αS,γS,2S)-N-((3S,4S)-3,4-dihydro-3-hydroxy-2H-1-benzopyran-4-yl)-γ-hydroxy-4-[[5-(2-pyridinyl)-2-furanyl]methyl]-α-(2-thienylmethyl)-2-[[(2,2,2-trifluoroethyl)amino]carbonyl]-1-piperazinepentanamide The intermediate prepared in Step F (867 mg, 2.17 mmol) and the intermediate prepared in Step G (800 mg, 2.17 mmol) in methanol (15 mL) was heated to reflux overnight. Then solvent was removed in vacuo. The crude reaction mixture was purified by flash column-chromatography on silica gel with ethyl acetate as the eluant. The resulting product (1.33 g, 1.77 mmol) in methanol (70 mL) was added 1N HCl in ethyl ether (26 mL, 26 mmol). The reaction mixture was stirred at room temperature and progress of reaction was monitored by HPLC. After 10 hours the mixture was neutralized by ammonium hydroxide in methanol. Then solvent was removed in vacuo. The mixture was diluted with chloroform and washed with 1 N NaOH. The aqueous layer was extracted with methylene chloride three times. The organic layers were combined, dried over anhydrous sodium sulfate, filtered and concentrated in vacuo. The crude product was purified by flash column chromatography with 4% methanol/ethyl acetate as the eluant to give the titled compound as a white solid. $^1$H NMR (CDCl$_3$, 300 MHz): 9.15 (bs, NH, 1H), 8.60 (m, 1H), 7.75–7.60 (m, 2H), 7.20–7.08 (m, 4H), 6.99–6.79 (m, 4H), 6.40 (m, 1H), 6.23 (m, 1H), 5.22 (m, 1H), 4.18–3.77 (m, 8H), 3.39–3.18 (m, 2H), 3.05–2.42 (m, 10H), 1.91–1.52 (m, 2H). LC-MS (M$^+$+1) (EI) 728.

EXAMPLE 71

(αS,γS,2S)-N-((3S,4S)-3,4-dihydro-3-hydroxy-2H-1-benzopyran-4-yl)-γ-hydroxy-4-[[5-(5-pyrimidinyl)-2-furanyl]methyl]-α-(5-thienylmethyl)-2-[[(2,2,2-trifluoroethyl)amino]carbonyl]-1-piperazinepentanamide

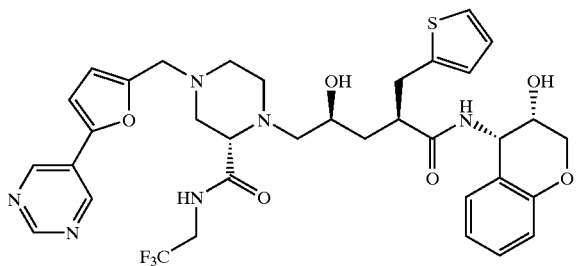

Step A

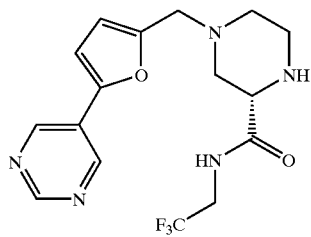

The intermediate prepared as in Example 68 Step (3 g, 7.95 mmol) was treated with 30% TFA/methylene chloride (150 mL). The reaction mixture was stirred at room temperature for an hour. Then solvents were removed in vacuo. The reaction mixture was diluted with chloroform. 1 N NaOH was added to adjust the pH to 14 followed by extraction with chloroform three times. The organic layers were combined, washed with brine, dried over anhydrous sodium sulfate, filtered and concentrated in vacuo. To the resulting product (1.95 g, 6.61 mmol) in dichloroethane (25 mL) was added the intermediate prepared as in Example 16 Step B (1.15 g, 6.61 mmol) followed by triethylamine (1.84 mL, 13.2 mmol) and sodium triacetoxyborohydride (2.10 g, 9.91 mmol). The reaction mixture was stirred at room temperature overnight. Then solvent was removed in vacuo. The crude product was purified by column chromatography on silica gel with 5% methanol/ethyl acetate as the eluant. The resulting intermediate (328 mg, 6.71 mmol) in methylene chloride (80 mL) was added 1,3-dimethylbarbituric acid (136 g, 0.87 mmol). After stirring at room temperature for 5 min, Pd(PPh$_3$)$_4$ (42 mg, 0.036 mmol) was added. The reaction mixture was stirred at room temperature and progress of reaction was monitored by TLC. After an hour the mixture was poured into 1N NaOH and extracted with methylene chloride three times. The organic layers were combined, dried over anhydrous sodium sulfate, filtered and concentrated in vacuo. The crude reaction mixture was purified by flash column chromatography on silica gel with 10% methanol/ethyl acetate with 0.1% ammonium hydroxide as the eluant to give the titled compound. $^1$H NMR (CDCl$_3$, 300 MHz): 9.08 (s, 1H), 8.98 (s, 2H), 7.62 (bs, NH, 1H), 6.79 (d, 1H), 6.38 (d, 1H), 4.00–3.80 (m, 2H), 3.67 (s, 2H), 3.52 (m, 1H), 3.02–2.84 (m, 3H), 2.68–2.38 (m, 3H).

Step B (αS,γS,2S)-N-((3S,4S)-3,4-dihydro-3-hydroxy-2H-1-benzopyran-4-yl)-γ-hydroxy-4-[[5-(5-pyrimidinyl)-2-furanyl]methyl]-α-(5-thienylmethyl)-2-[[(2,2,2-trifluoroethyl)amino]carbonyl]-1-piperazinepentanamide The intermediate prepared in Step A (187 mg, 0.51 mmol) and the intermediate prepared as in Example 70 Step G (202 mg, 0.51 mmol) in methanol (3.5 mL) were heated to reflux overnight. Then solvent was removed in vacuo. The crude reaction mixture was purified by flash column chromatography on silica gel with 3% methanol/ethyl acetate as the eluant. The resulting product (156 g, 0.20 mmol) in methanol (8 mL) at 0° C. was added 1 M HCl in ethyl ether (3.0 mL, 3.0 mmol). The reaction mixture was allowed to warm up to room temperature and progress of reaction was monitored by HPLC. After 14 hours the mixture was neutralized by ammonium hydroxide in methanol. Then solvent was removed in vacuo. The mixture was diluted with chloroform and washed with 1 N NaOH. The aqueous layer was extracted with chloroform three times. The organic layers were combined, dried over anhydrous sodium sulfate, filtered and concentrated in vacuo. The crude product was purified by flash column chromatography with 8% methanol/chloroform as the eluant to give the titled compound as a white solid. $^1$H NMR (CDCl$_3$, 300 MHz): 9.10 (s, 1H), 8.96 (s, 2H), 8.92 (bs, NH, 1H), 7.16–7.08 (m, 3H), 6.94–6.78 (m, 4H), 6.40 (d, J=3.36 Hz, 1H), 6.22 (d, J=8.02 Hz, 1H), 5.22 (m, 1H), 4.15–3.92 (m, 4H), 3.35–3.17 (m, 2H), 3.05–2.42 (m, 10H), 1.92–1.52 (m, 2H). LC-MS (M$^+$+1) (EI) 729.

EXAMPLE 72

(αS,γS,2S)-N-((3S,4S)-3,4-dihydro-3-hydroxy-2H-1-benzopyran4-yl)-γ-hydroxy-4-[[5-(2-pyridinyl)-2-furanyl]methyl]-α-(3-thienylmethyl)-2-[[(2,2,2-trifluoroethyl)amino]carbonyl]-1-piperazinepentanamide

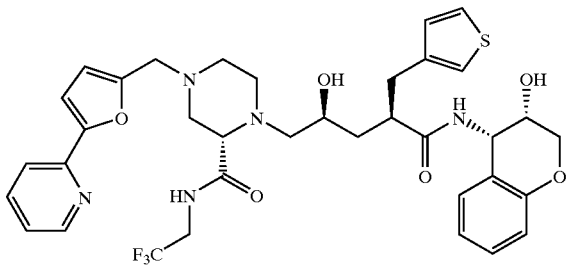

Step A

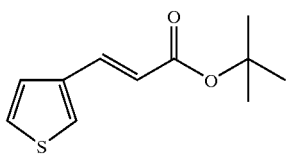

To a solution of 3-bromothiophene (0.58 mL, 6.13 mmol), t-butyl acrylate (2.70 mL, 18.4 mmol) and triethylamine (4.27 mL, 30.7 mmol) in anhydrous acetonitrile (15 mL) was added palladium acetate (137.7 mg, 0.613 mmol) and tri-tolylphosphine (373.3 mg, 1.23 mmol). The flask was sealed and heated at 100° C. After 14 hours the reaction mixture was poured into brine and extracted with ethyl acetate three times. The organic layers were combined, dried over sodium sulfate, filtered and concentrated in vacuo. The crude reaction mixture was purified by flash column chromatography on silica gel with 5% ethyl acetate/hexane as the eluant to give the titled compound. $^1$H NMR (CDCl$_3$, 300 MHz): 7.57 (d, J=15 Hz, 1H), 7.46 (m, 1H), 7.34–7.27 (m, 2H), 6.20 (d, J=16.3 Hz, 1H), 1.54 (s, 9H).

Step B

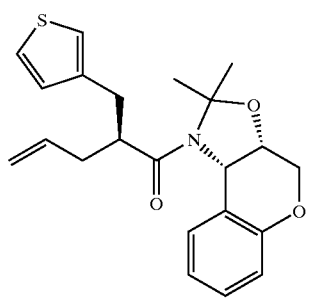

This intermediate was prepared by the same method described in Example 70. $^1$H NMR (CDCl$_3$, 300 MHz, mixture of rotamers R1 and R2 3:1 ratio): 7.72 (m, 0.25H, R2), 7.32–6.78 (m, 5.25H), 6.62 (t, 0.75H, R1), 6.36 (d, 0.75H, R1), 5.94–5.65 (m, 1.25H), 5.20–4.99 (m, 2.75 H), 4.45–4.06 (m, 3H), 3.38–3.12 (m, 2H), 2.90–2.72 (m, 1H), 2.45–2.25 (m, 2H), 1.72 (s, 2.25 H, R1), 1.36 (s, 0.75 H, R2), 1.27 (s, 2.25H, R1), 1.5 (s, 0.75H, R2).

Step C

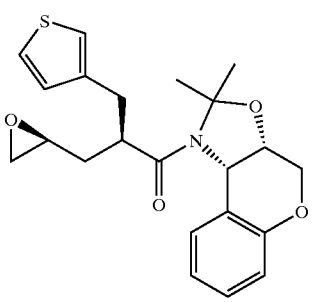

To the intermediate prepared in Step B (2.35 g, 6.12 mmol) in ethyl acetate (94 mL) at 0° C. was added 0.5 M aqueous sodium bicarbonate solution (94 mL) and N-iodosuccinimide (2.89 mg, 12.8 mmol). The reaction mixture was allowed to gradually warm to room temperature and progress of reaction was monitored by HPLC. After 6 hours the reaction mixture was poured into aqueous sodium sulfite solution and extracted with ethyl acetate three times. The organic layers were combined, dried over anhydrous sodium sulfate, filtered and concentrated in vacuo. The resulting product was dissolved in ethyl acetate (90 mL) and sodium methoxide in methanol (25 wt. %, 2 mL) was added. The reaction mixture was stirred at room temperature and progress of reaction was monitored by TLC. After an hour the mixture was poured into saturated sodium bicarbonate solution and extracted with ethyl acetate three times. The combined organic layers were dried over anhydrous sodium sulfate, filtered and concentrated in vacuo. The crude titled product was purified by column chromatography on silica gel with 50% ethyl acetate/hexane as the eluant to give the titled compound. $^1$H NMR (CDCl$_3$, 400 MHz, mixture of rotamers R1 and R2 3:1 ratio): 7.78 (m, 0.25H, R2), 7.34–6.80 (m, 5.25H), 6.67 (t, 0.75H, R1), 6.46 (d, 0.75H, R1), 5.88 (d, 0.25H, R2), 5.38 (d, 0.75H, R1), 4.48–4.09 (m, 3H), 3.46–3.34 (m, 2H), 3.19–2.46 (m, 5H), 2.30–2.18 (m, 1H), 2.76–2.17 (m, 3H), 1.77 (s, 2.25 H, R1), 1.46 (s, 0.75 H, R2), 1.39 (s, 0.75 H, R2), 1.32 (s, 2.25H, R1).

Step D (αS,γS,2S)-N-((3S,4S)-3,4-dihydro-3-hydroxy-2H-1-benzopyran-4-yl)-γ-hydroxy-4-[[5-(2-pyridinyl)-2-furanyl]methyl]-α-(3-thienylmethyl)-2-[[(2,2,2-trifluoroethyl)amino]carbonyl]-1-piperazinepentanamide The intermediate prepared in Step C (548 mg, 137 mmol) and the intermediate prepared as in Example 70 Step G (506 mg, 1.37 mmol) in methanol (8 mL) was heated to reflux overnight. Then solvent was removed in vacuo. The crude reaction mixture was purified by flash column chromatography on silica gel with ethyl acetate as the eluant. The resulting product (950 g, 1.26 mmol) in methanol (50 mL) was added 1 M HCl in ethyl ether (18.5 mL, 18.5 mmol). The reaction mixture was stirred at room temperature and progress of reaction was monitored by HPLC. After 9 hours the mixture was neutralized by ammonium hydroxide in methanol. Then solvent was removed in vacuo. The mixture was diluted with chloroform and washed with 1 N NaOH. The aqueous layer was extracted with methylene chloride three times. The organic layers were combined, dried over anhydrous sodium sulfate, filtered and concentrated in vacuo. The crude product was purified by flash column chromatography with 8% methanol/chloroform as the eluant to give the titled compound as a white solid. $^1$H NMR (CDCl$_3$, 400 MHz): 9.17 (bs, NH, 1H), 8.61 (m, 1H), 7.74 (m, 1H), 7.64 (d, J=7.8 Hz, 1H), 7.21–6.81 (m, 6H), 6.83 (m, 2H), 6.40 (d, J=3.3 Hz, 1H), 6.18 (d, J=8.8 Hz, 1H), 5.21 (m, 1H), 4.20–3.58 (m, 9H), 3.35 (m, 1H), 3.07–2.41 (m, 10H), 1.86 (m, 1H), 1.56 (m, 1H). LC-MS (M$^+$+1) (EI) 728.

EXAMPLE 73

(αR,γS,2S)-N-((3S,4S)-3,4-dihydro-3-hydroxy-2H-1-benzopyran-4-yl)-γ-hydroxy-4-[(5-phenyl-2-furanyl)methyl]-α-(2-pyridinylmethyl)-2-[[(2,2,2-trifluoroethyl)amino]carbonyl]-1-piperazinepentanamide

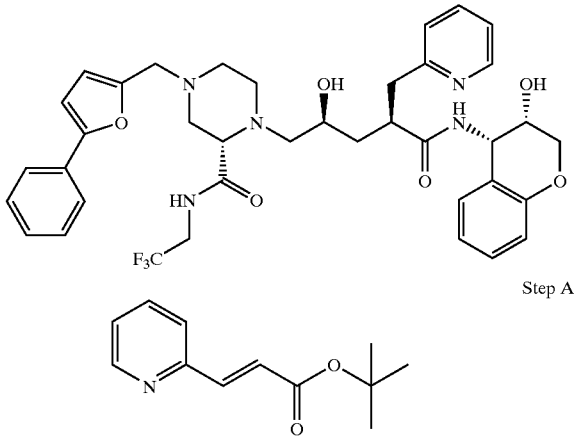

Step A

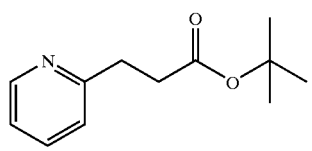

To a solution of 2-bromopyridine (0.60 mL, 6.33 mmol), t-butyl acrylate (4.6 mL, 31.6 mmol) and triethylamine (4.4 mL, 31.6 mmol) in anhydrous DMF (20 mL) was added palladium acetate (71 mg, 0.316 mmol) and 2-(di-t-butylphosphino)biphenyl (189 mg, 0.633 mmol). The flask was sealed and heated at 120° C. After 14 hours the reaction mixture was poured into water and extracted with ethyl acetate. The organic layer was dried over sodium sulfate, filtered and concentrated in vacuo. The crude reaction mixture was purified by flash column chromatography on silica gel with 15% ethyl acetate/hexane as the eluant to give the titled compound. $^1$H NMR (CDCl$_3$, 300 MHz): 8.62 (d, J=4.76 Hz, 1H),7.67 (m, 1H), 7.58 (d, J=15.81, 1H), 7.41 (d, J=7.82 Hz, 1H), 7.22 (m, 1H), 6.81 (d, J=15.72 Hz, 1H), 1.52 (s, 9H).

Step B

To the intermediate prepared in Step A (5.52 g, 26.6 mmol) and triethylamine (7 mL) in ethanol (250 mL) was added 10% palladium on carbon (1 g). The reaction mixture was stirred under a hydrogen balloon and progress of reaction was monitored by HPLC. After 4 hours the reaction mixture was filtered through celite and the filtrate was concentrated in vacuo to give the titled compound. $^1$H NMR (CDCl$_3$, 300 MHz): 8.72 (d, 1H), 7.60 (m, 1H), 7.18 (d, 1H), 7.10 (m, 1H), 3.08 (t, 2H), 2.70 (t, 2H), 1.42 (s, 9H).

Step C

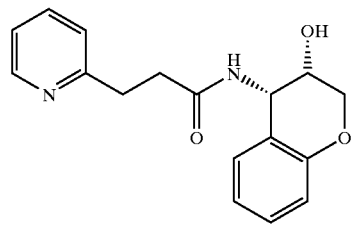

To the intermediate prepared in Step B (4.0 g, 26.6 mmol) was added trifluoroacetic acid (200 mL) and stirred at room temperature for an hour. Then solvent was removed in vacuo. The resulting product in methylene chloride (100 mL) was added aminochromanol (6.4 g, 26.7 mmol) prepared as in Example 1 Step L, EDC (6.63 g, 34.7 mmol), HOBt (4.68 g, 34.7 mmol) and N,N-diisopropylethylamine (18 mL, 106.7 mmol). The reaction mixture was stirred at room temperature overnight. A white precipitate of the titled compound was formed. The precipitated product was collected by filtration. The filtrate which also contained product was washed with water, dried over anhydrous sodium sulfate, filtered and concentrated in vacuo. $^1$H NMR (CDCl$_3$, 300 MHz): 8.20 (d, 1H), 7.64 (t, 1H), 7.25–7.06 (m, 3H), 6.90–6.80 (m, 3H), 5.26 (m, 1H), 4.20–4.16 (m, 3H), 3.19 (m, 2H), 2.78 (t, 2H).

Step D

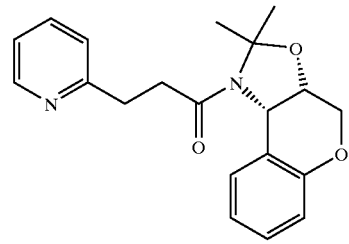

To the intermediate prepared in Step C (6.9 g, 23.1 mmol) in methylene chloride (400 mL) was added 2-methoxypropene (11.1 mL, 115.6 mmol) and camphorsulfonic acid (10.8 g, 46.3 mmol). The reaction mixture was stirred at room temperature and progress of reaction was monitored by TLC. After half an hour the crude reaction mixture was poured into 1 N NaOH and extracted with ethyl acetate three times. The organic layers were combined, washed with brine, dried over anhydrous sodium sulfate, filtered and concentrated in vacuo. The crude product was purified by flash column chromatography on silica gel with ethyl acetate as the eluant to give the titled compound as a white solid. $^1$H NMR (CDCl$_3$, 300 MHz, mixture of rotamers R1 and R2 2:1 ratio): 8.52 (m, 0.67 H, R1), 8.25 (m, 0.37 H, R2), 7.60 (m, 1H), 7.48 (m, 0.37 H, R2), 7.06 (m, 2H), 6.95–6.80 (m, 2H), 5.80 (m, 0.37H), 5.20 (m, 0.67H), 4.25–4.15 (m, 3H), 4.18 (m, 1H), 3.30–2.88 (m, 4H), 1.70 (s, 1H, R2), 1.52 (s, 2H, R1), 1.38 (m, 1H, R1), 1.26 (s, 2H, R2).

Step E

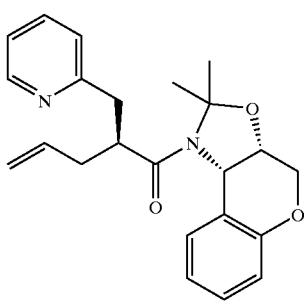

Step G

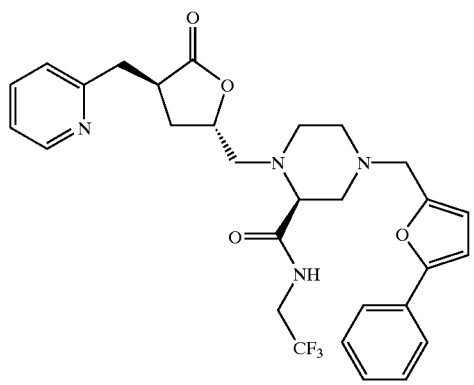

To a solution of intermediate prepared in Step D: (3.74 g, 11.1 mmol) in anhydrous tetrahydrofuran (100 mL) at −25° C. was added allylbromide (1.15 mL, 13.3 mmol) followed by 1.0 M lithium bis(trimethylsilyl)amide in THF (13.3 mL, 13.3 mmol). The reaction mixture was stirred at −25° C. and progress of reaction was monitored by TLC. After half an hour the reaction was quenched with water and warmed up to room temperature. The crude reaction mixture was extracted with ethyl acetate three times. The organic layers were combined, dried over anhydrous sodium sulfate and concentrated in vacuo. The crude product was purified by flash column chromatography on silica gel with 1:1 ethyl acetate/hexane as the eluant to give the titled compound as a white solid. $^1$H NMR (CDCl$_3$, 400 MHz, mixture of rotamers R1 and R2 2:1 ratio): 8.65 (d, 0.67H, R1), 8.53 (d, 0.37H), 7.73–7.59 (m, 1.37H), 7.25–7.08 (m, 3H), 6.92–6.60 (m, 2.67H), 5.97–5.70 (m, 1.37H), 5.23–5.00 (m, 2.67 H), 4.48–4.07 (m, 4H), 3.68(m, 0.67H), 3.50–3.20 (m, 1.3H), 3.02 (m, 1H), 2.52–2.23 (m, 2H), 1.70 (s, 2H, R1), 1.24 (s, 1H, R2), 1.22 (s, 1H, R2), 1.20 (s, 2H).

Step F

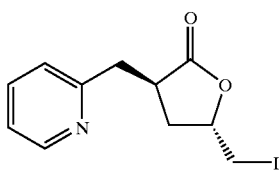

To the intermediate prepared in Step E (3.4 g, 9.0 mmol) in tetrahydrofuran (50 mL) and water (50 mL) at 0° C. was added iodine (9.1 g, 35.9 mmol) and methanesulfonic acid (1.16 mL, 17.9 mmol). The reaction mixture was allowed to gradually warm to room temperature. After 14 hours the reaction mixture was poured into aqueous sodium sulfite solution and extracted with methylene chloride three times. The organic layers were combined, dried over anhydrous sodium sulfate, filtered and concentrated in vacuo. The crude titled product was purified by flash column chromatography on silica gel with 60% ethyl acetate/hexane as the eluant. $^1$H NMR (CDCl$_3$, 400 MHz): 8.54 (m, 1H), 7.63 (m, 1H), 7.21–7.16 (m, 2H), 4.52 (m, 1H), 3.38–3.26 (m, 4H), 3.09–3.03 (m, 1H), 2.35–2.19 (m, 2H).

To the intermediate prepared in Step F (686 mg, 2.16 mmol) and the intermediate prepared as in Example 68 Step G (1.2 g, 3.25 mmol) in DMF (8 mL) was added N,N-diisopropylethylamine (0.57 mL, 3.25 mmol). The reaction mixture was heated to 75° C. for 36 hours. The reaction mixture was poured into water and extracted with ethyl acetate three times. The organic layers were combined, washed with water and brine, dried over anhydrous sodium sulfate, filtered and concentrated in vacuo. The crude reaction mixture was purified by flash column chromatography on silica gel with 2% methanol/ethyl acetate as the eluant to give the titled compound. $^1$H NMR (CDCl$_3$, 300 MHz): 8.51 (m, 1H), 7.64–7.58 (m, 3H), 7.40–7.34 (m, 2H), 7.27 (m, 1H), 7.18–7.14 (m, 2H), 6.57 (d, J=3.20 Hz, 1H), 6.28 (d, J=3.12 Hz, 1H), 4.49 (m, 1H), 3.68–3.21 (m, 7H), 3.00–2.51 (m, 9H), 2.12–2.04 (m, 2H).

Step H

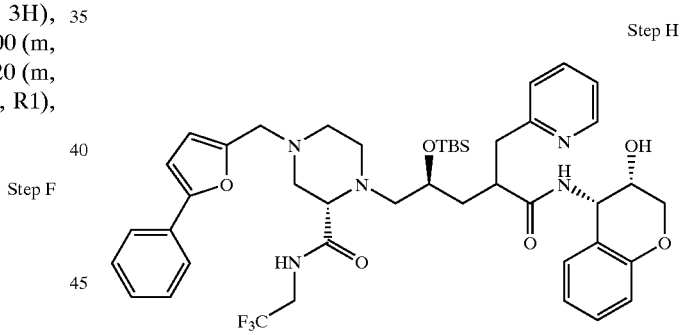

To a solution of the intermediate obtained in Step G (530 mg, 1.00 mmol) in DME (20 mL) was added 1 M LiOH aqueous solution (1.20 mL, 1.20 mmol). The reaction mixture was stirred at room temperature. After 14 hours solvent was removed by vacuo. The resulting intermediate in ethyl acetate (20 mL) was added N,N-diisopropylethylamine (0.868 mL, 4.99 mmol) followed by TBSOTf (0.802 mL, 3.50 mmol). The reaction mixture was stirred at room temperature and progress of reaction was monitored by TLC. After an hour the crude reaction mixture was concentrated with silica gel (2 g) in vacuo and passed through flash column chromatography with ethyl acetate as the eluant. Then the resulting product in 1:1 THF/H$_2$O solution was stirred at room temperature. After 14 hours the reaction mixture was extracted with ethyl acetate. The organic layer was dried over anhydrous sodium sulfate, filtered and concentrated in vacuo. To the resulting intermediate in DMF (8 mL) was added aminochromanol prepared as in Example 1 Step L (165 mg, 1.08 mmol), EDC (281 mg, 1.47 mmol) and HOBt (199 mg, 1.47 mmol). The reaction mixture was stirred at room temperature. After 14 hours the mixture was poured into water and extracted with ethyl acetate. The organic layer was dried over anhydrous sodium sulfate, filtered and concentrated in vacuo. The crude product was purified by flash column chromatography with ethyl acetate as the eluant to give the titled compound. $^1$H NMR (CDCl$_3$, 400 MHz): 8.41 (m, 1H), 7.66–7.61 (m, 3 H), 7.39 (m, 2H), 7.29–7.14 (m, 4H), 6.95–6.87 (m, 2H), 6.59 (m, 2H), 6.29 (d, 1H), 5.23 (m, 1H), 4.25–2.57 (m, 19H), 2.34–2.24 (m, 2H), 1.36 (m, 1H). LC-MS (M$^+$+1) (EI) 838.

Step I (αR,γS,2S)-N-((3S,4S)-3,4-dihydro-3-hydroxy-2H-1-benzopyran-4-yl)-γ-hydroxy-4-[(5-phenyl-2-furanyl)methyl]-α-(2-pyridinylmethyl)-2-[[(2,2,2-trifluoroethyl)amino]carbonyl]-1-piperazinepentanamide To the intermediate prepared in Step H (100 mg, 0.12 mmol) in THF (8 mL) was added HF/pyridine (0.36 mL). The reaction mixture was stirred at room temperature. After 14 hours the mixture was poured into 1N NaOH solution and extracted with ethyl acetate three times. The organic layers were combined, dried over anhydrous sodium sulfate, filtered and concentrated in vacuo. The crude product was purified by flash column chromatography with 5% methanol/ethyl acetate. 1H NMR (CDCl$_3$, 400 MHz, mixture of diastereomers D1 and D2 3:2 ratio): 9.21 (bs, NH, 0.4H, D2), 9.15 (bs, NH, 0.6H, D1), 8.53 (d, 0.4H, D2), 8.45 (d, 0.6H, D1), 7.65 (m, 3H), 7.40 (m, 2H), 7.30–7.12 (m, 4H), 6.88–6.78 (m, 2H), 6.60 (m, 2H), 6.34 (m, 1H), 5.25 (m, 0.6H, D1), 5.08.(m, 0.4H, D2), 4.30–4.10 (m, 4H), 3.84–2.40 (m, 17H), 1.90 (m, 1H), 1.50 (m, 1H). LC-MS (M$^+$+1) (EI) 722.

EXAMPLE 74

(αR,γS,2S)-N-((1S,2R)-1,2-dihydro-2-hydroxy-1H-inden-1-yl)-γ-hydroxy-α-(phenylmethyl)-4-[[5-(2-pyridinyl)-2-furanyl]methyl]-2-[[(2,2,2-trifluoroethyl)amino]carbonyl]-1-piperazinepentanamide

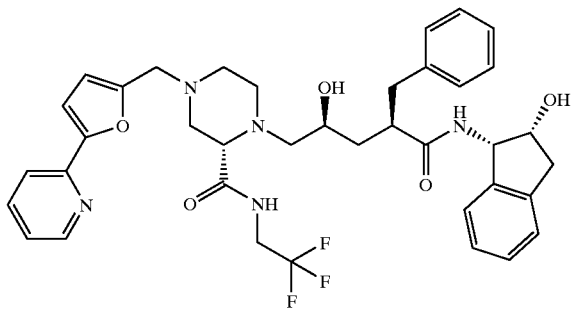

Step A

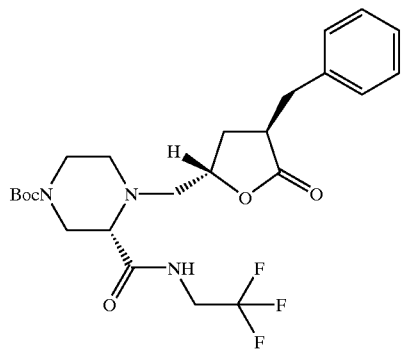

To a stirred solution of the piperazine prepared as in Example 12 Step B (11.3 g; 33.4 mmol) in EPA (54 mL) was added the triflate (6.95g; 22.3 mmol) prepared as in Example 35, Step E followed by DIEA (5.8 mL; 33.4 mmol). The reaction was aged approximately 4.5 hours, then the solvent was removed in vacuo. The remainder was poured in EtOAc and washed with water and brine. After drying (Na$_2$SO$_4$), filtration and removal of the solvent in vacuo, purification employing flash chromatography (50% EtOAc/hex) provided of the desired lactone. $^1$H NMR(400 MHz, CDCl$_3$) δ1.45 (s, 9H), 1.85–1.95 (m, 1H), 2.05–2.15 (m, 1H), 2.35–2.45 (m, 1H), 2.52–2.68 (complex m, 2H), 2.79–2.95 (complex m, 2H), 3.03–3.21 (complex m, 5H), 3.65–3.82 (complex m, 2H), 3.91–3.98 (m, 1H), 4.03–4.17 (m, 1H), 4.84–4.90 (m, 1H), 6.95 (broad s, 1H), 7.18–7.37 (complex m, 5H).

Step B

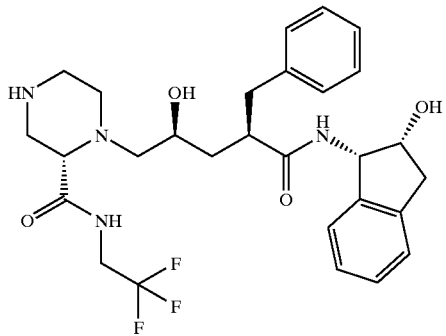

To a solution of the lactone from above (9.98 g; 20.0 mmol) in anhydrous DME (110 mL) cooled to 0° C. was added dropwise an aqueous solution of LiOH (23.0 mL; 22.0 mmol). The reaction was stirred 3 hours following the removal of the ice bath. The solvents were removed in vacuo at no greater than 35° C. and the residue azeotroped from benzene and MeCN until a foam was obtained. This solid was dissolved in dry DMF (55 mL). Imidazole was added (27.2g; 400 mmol), and the resulting solution cooled to 0° C. TBMSCl (30.1 g; 200 mmol) was then added to the reaction, the ice bath removed, and the mixture allowed to stir at ambient temperature. After 21 hours the mixture was poured into EtOAc (700 mL) and Et$_2$O (300 mL). After washing with dilute NaHCO$_3$, H$_2$O, and brine, drying (Na$_2$SO$_4$), filtration, removal of solvent in vacuo provided a mixture of mono- and bis-protected intermediate. This ester/acid mixture was dissolved in THF (200 mL)/H$_2$O (75 mL) and stirred 1.5 hours. Solvents were removed in vacuo and the residue azeotroped from toluene and MeCN. The residue was then taken up in DCM, dried (MgSO₄), filtered, and volatiles removed in vacuo to provide the acid, which was used without further purification. To a stirred solution of approximately 1.36 mmol of the acid intermediate in anhydrous NMP (25 mL) at 0° C. was added DIEA (0.711 mL; 4.08 mmol). The following solids were then added sequentially, waiting until complete dissolution of solid occurred before adding the next: HOBt (414 mg; 3.06 mmol); cis-aminoindanol (243 mg; 1.63 mmol); and HBTU (774 mg; 2.04 mmol). The solution was allowed to stir at ambient temperature 2.75 hours. The reaction was poured into EtOAc; washed with dilute NaHCO₃ solution, H₂O and brine; dried (MgSO₄), filtered, and concentrated in vacuo. Purification by Biotage column chromatography (40M; 40% EtOAc/hexane) provided the desired compound contaminated with ~10% of the undesired diastereomer, which was used without further purification.

The coupled intermediate was dissolved in anhydrous THF (4.6 mL), and TBAF (1.05 mL; 1.05 mmol) was added. The solution was heated to 50° C. After 16 hours, the reaction was poured into EtOAc/Et₂O and washed with dilute NaHCO₃, H₂O and brine. Drying (MgSO₄), filtration, and removal of solvent in vacuo was followed by Biotage column chromatography (40S; 85% EtOAc/hexane) and then by flash column chromatography (5% MeOH/DCM) to provide white solid.

To a stirred solution of this Boc-protected intermediate in anhydrous DCM (2.8 mL) cooled to 0° C. was added TFA (1.2 mL). The ice batch was removed and the solution stirred 1.75 hours. Volatiles were removed in vacuo and the residue azeotroped from DCM. This residue was dissolved in EtOAc and washed with 20% NH₄OH; 50% brine, brine, dried (MgSO₄), filtered, and solvents removed in vacuo to provide the desired amine as an off-white solid which was used without further purification.

Step C (αR,γS,2S)-N-((1S,2R)-1,2-dihydro-2-hydroxy-1H-inden-1-yl)-γ-hydroxy-α-(phenylmethyl)-4-[[5-(2-pyridinyl)-2-furanyl]methyl]-2-[[(2,2,2-trifluoroethyl)amino]carbonyl]-1-piperazinepentanamide From the aldehyde as obtained in Example 49, Step B (46.0 mg; 0.27 mmol), penultimate intermediate as obtained above (100.0 mg; 0.18 mmol) and NaBH(OAc)₃ (57.0 mg; 0.27 mmol) in anhydrous DMF (1.5 mL) following the general reductive amination procedure as described for Example 53, Step E was obtained the desired compound. ¹H NMR(400 MHz, CD₃OD) δ1.39 (m, 1H), 2.03 (m, 1H), 2.32–2.45 (complex m, 3H), 2.51 (m, 1H), 2.60 (m, 1H), 2.70–2.87 (complex m, 4H), 2.95–3.11 (complex m, 5H), 3.69 (s, 2H), 3.71–3.80 (complex m, 2H),3.90–3.99 (complex m, 1H), 4.32 (m, 1H), 5.19 (d, J=5.1 Hz, 1H), 6.48 (d, J=3.3 Hz, 1H), 7.06 (d, J=3.3 Hz, 1H), 7.11–7.28 (complex m, 9H), 7.77 (m, 1H), 7.84 (apparent td, J=1.6, 7.5 Hz, 1H), 8.49 (apparent d, J=4.8 Hz, 1H); electrospray ionization mass spectrum: m/e 706.5 (MH⁺ calcd for C₃₈H₄₃F₃N₅O₆, 706.3).

EXAMPLE 75

(αR,γS,2S)-4-[[5-(5-chloro-2-pyridinyl)-2-furanyl] methyl]-N-((1S,2R)-1,2-dihydro-2-hydroxy-1H-inden-1-yl)-γ-hydroxy-α-(phenylmethyl)-2-[[(2,2,2-trifluoroethyl)-amino]carbonyl]-1-piperazinepentanamide

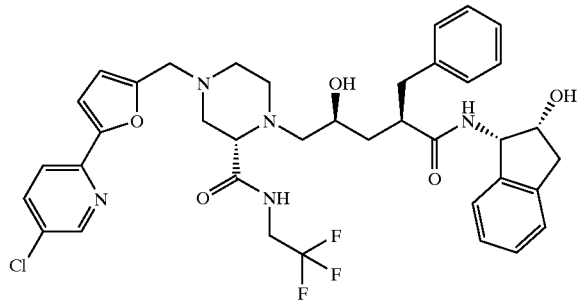

From a solution of the aldehyde obtained from Example 50, Step C (59 mg; 0.285 mmol), penultimate intermediate from Example 74 Step A (103 mg; 0.19 mmol), and NaHB (OAc)₃ (60 mg; 0.285 mmol) in anhydrous DMF (1.2 mL) using the procedure from Example 46, Step F, the titled compound was obtained as a white solid after purification by flash column chromatography (3% to 3.5% MeOH/CH₂Cl₂ gradient elution). ¹H-NMR (400 MHz, CD₃OD): δ1.39 (m, 1H), 2.03 (m, 1H), 2.32–2.45 (complex m, 3H), 2.51 (m, 1H), 2.60 (m, 1H), 2.70–2.87 (complex m, 4H), 2.95–3.11 (complex m, 5H), 3.69 (s, 2H), 3.71–3.80 (complex m, 2H), 3.90–3.99 (complex m, 1H), 4.32 (m, 1H), 5.19 (d, J=5.1 Hz, 1H), 6.48 (d, J=3.3 Hz, 1H), 7.06 (d, J=3.3 Hz, 1H), 7.11–7.28 (complex m, 9H), 7.74 (dd, J=0.6, 8.6 Hz, 1H), 7.85 (dd, J=2.4, 8.6 Hz, 1H), 8.49 (m, 1H); electrospray ionization mass spectrum:m/e 741.0 (MH⁺ calcd for C₃₈H₄₁ClF₃N₅O₅, 740.3).

EXAMPLE 76

(αR,γS,2S)-N-((3S,4S)-3,4-dihydro-3-hydroxy-2H-1-benzopyran-4-yl)-γ-hydroxy-4-[1-methyl-1-[5-(5-chloro-3-pyridinyl)-2-oxazolyl]ethyl]-α-(phenylmethyl)-2-[[(2,2,2 trifluoroethyl)amino] carbonyl]-1-piperazinepentanamide

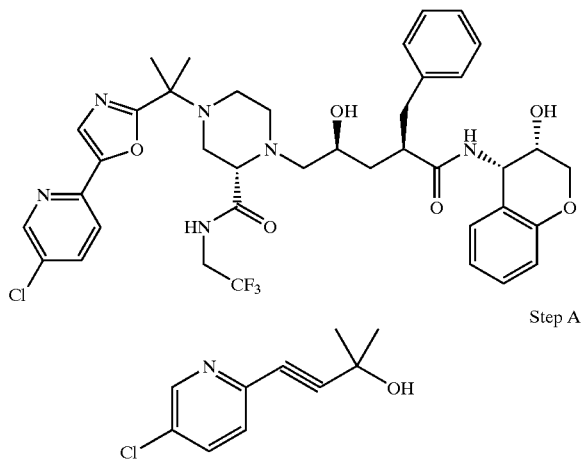

Step A

To a solution of 2,5-dichloropyridine (125 g, 845 mmol) and 2-methyl-3-butyn-2-ol (107 mL, 1.1 mol) in diethylamine (350 mmol, 3.4 mol) in a 3-neck 1 liter round bottom flask was added copper iodide (125 mg, 0.63 mmol) and dichlorobis(triphenylphosphine)palladium(II) (1.75 g, 2.5 mmol). The reaction mixture was refluxed for 24 hours. After it was cooled to room temperature, it was filtered. The solid was washed with diethylamine twice (100 mL each time) and discarded. The filtrate and washes were combined and concentrated to give a dark brown residue which solidified after standing. This crude product was dissolved in toluene (1 l) and washed with water for 3 times (500 mL each time). Then water (500 mL), tetrabutylammonium bromide (1.2 g) and sodium cyanide (12 g) was added. The mixture was stirred at room temperature for 24 hours. It was separated. The organic layer was dried over anhydrous sodium sulfate and concentrated to get the title compound as a brown oil, which was used in the next step without further purification. $^1$H NMR (CDCL$_3$, 400 Hz): δ8.54 (d, J=2.6 Hz, 1 H), 7.64 (dd, J=2.6, 8.6 Hz, 1 H), 7.37 (d, J=8.6 Hz, 1 H), 1.65 (s, 6 H). LC-MS (M$^+$+1) (EI) 196.1

Step B

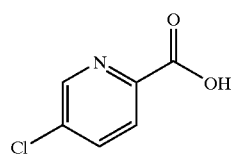

The acetylene form the previous step (150 g, 767 mmol) was dissolved in 2.5 mL of water in a 3-neck 4 liter round bottom flask with a mechanical stirrer. It was heated to 75° C., and a hot water bath was used to keep the reaction solution at 70–80° C. Potassium permanganate (400 g, 2.53 mol) was added in small portions to keep the reaction mixture below 80° C. The addition lasted 1.5 hours and HPLC showed that the acetylene was consumed after the addition. It was filtered. The solid was washed with boiling water twice (100 mL each time) and discarded. The combined aqueous layer and washes was concentrated at 80° C. to about 1 liter. It was filtered again to remove any remaining manganese dioxide. The filtrate was cooled to room temperature and concentrated HCl was added until pH=3. It was stirred at room temperature for 1 hour to form a yellow precipitate. It was cooled to 0° C. and filtered. The solid was washed with cooled water for several times and dried under high vacuum overnight to give the title compound as a pale powder. $^1$H NMR (CD$_3$OD, 400 Hz): δ8.66 (d, J=2.4 Hz, 1 H), 8.13 (d, J=8.4 Hz, 1 H), 8.03 (dd, J=2.4, 8.4 Hz, 1 H). LC-MS (M$^+$+1) (EI) 158.1

Step C

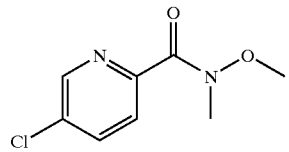

To a solution of the carboxylic acid from the previous step (60 g, 382 mmol) and 4-methylmorpholine (84 mL, 764 mmol) in methylene chloride (1 l), at −20° C., was added isobutylchloroformate (52 mL, 401 mmol). It was stirred at −20~−10° C. for 1 hour. Then, N,O-dimethylhydroxylamine hydrochloride (41 g, 420 mmol) was added. The reaction solution was slowly warmed to room temperature, at which it was stirred for 6 hours. It was poured into 1 liter of water. The organic layer was washed with water (500 mL) and brine (500 mL), dried over anhydrous sodium sulfate, concentrated, and purified by flash column chromatography on silica gel with hexanes/ethyl acetate=2/1 as eluant to give the title compound as a slightly yellow oil. $^1$H NMR (CDCl$_3$, 400 Hz): δ8.59 (s, 1H), 7.78 (dd, J=2.4, 8.4 Hz, 1H), 7.66 (broad s, 1 H), 3.77 (s, 3 H). 3.42 (s, 3H).

Step D

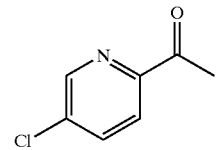

To a solution of the amide from the previous step (33.1 g, 165 mmol) in anhydrous THF (300 mL), at 0° C., was added methylmagnesium bromide (1.4M solution, 355 mL, 497 mmol). The reaction solution was stirred at 0° C. for 3 hours and poured into 800 mL of ice-water. Ethyl acetate was used to extract it (3 times, 500 mL each time). The combined organic layers was dried over anhydrous sodium sulfate, concentrated, and purified by flash column chromatography on silica gel with hexanes/ethyl acetate=3/1 as eluant to give the title compound as a white solid. $^1$H NMR (CDCl$_3$, 400 Hz): δ8.63 (d, J=2.1 Hz, 1H), 8.01 (d, J=8.2 Hz, 1H), 7.81 (dd, J=2.3, 8.4 Hz, 1 H), 2.72 (s, 3 H). LC-MS (M$^+$+1) (EI) 156.1

Step E

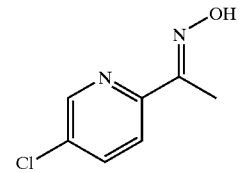

To a suspension of the acetylpyridine obtained as from the previous step (30 g, 193 mmol) and hydroxyamine hydrochloride (16.1 g, 231 mmol) in ethyl alcohol (200 mL) was added sodium hydroxide powder (10 g, 250 mmol). The reaction mixture was refluxed for 8 hours to see that the starting material was consumed by LCMS. The solvent was vacuum removed. The residue was washed with cooled water for several times to give the title compound as a white solid. $^1$H NMR (DMSO, 400 Hz): δ8.61–8.62 (m, 1 H), 7.84–7.91 (m, 2 H), 2.17 (s, 3 H).

Step F

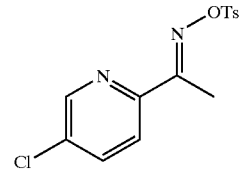

A solution of the oxime form the previous step (20 g, 117.2 mmol) and p-toluenesulfonyl chloride (28 g, 146.5 mmol) in pyridine (70 mL) was stirred at room temperature for 24 hours to form a brown precipitate. 500 mL of ice-cooled water added while stirring. The initially formed brown precipitate dissolved followed by the formation of a white precipitate. This precipitate was collected by filtration and washed with ice-cooled water for 4 times (200 mL each time). It was dried under high vacuum to constant weight to give the titled compound as a pale solid. $^1$H NMR (CDCl$_3$, 400 Hz): δ8.55 (dd, J=0.8, 2.5 Hz, 1 H), 7.93 (d, J=8.4 Hz, 2 H), 7.79 (dd, J=0.6, 8.0 Hz, 1 H), 7.67 (dd, J=2.4, 8.4 Hz, 1 H), 7.37 (d, J=8.0, 2 H), 2.46 (s, 3 H), 2.43 (s, 3 H). LC-MS (M⁺+1) (EI) 325.0, 152.7.

Step G

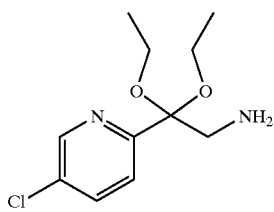

To a solution of potassium ethoxide (10.43 g, 121.1 mmol) in 30 mL anhydrous ethanol, at 0° C., was added a solution of the tosylamide from the previous step (38.16 g, 117.6 mmol) in ethanol (500 mL) dropwise through a dropping funnel. It was slowly warmed to room temperature at which it was stirred for 2 hours to form a white precipitate. It was diluted with 1 liter of anhydrous ether and filtered. The solid was washed with anhydrous ether (100 mL). To the combined filtrate and washes HCl gas was bubbled in for 1 hour to get a cloudy solution. It was concentrated. The residue was distributed between methylene chloride (500 mL) and saturated sodium carbonate (about 500 mL to get pH=12). The organic layer was concentrated to give the crude product as dark red gum, which was used in the next step without further purification. LC-MS (M⁺+1) (EI) 199.1.

Step I

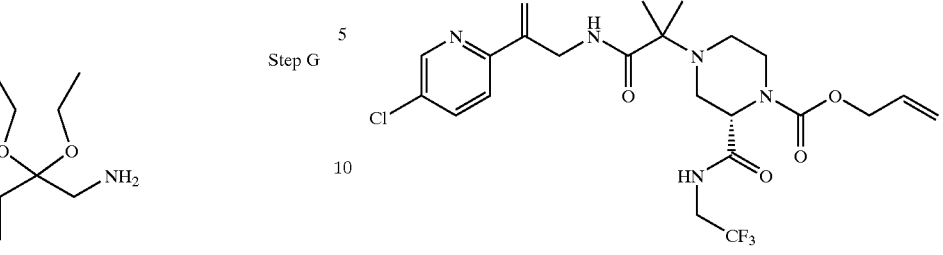

The acetal from the previous step (2.1 g, 3.45 mmol) was dissolved in THF (10 mL) and HCl (6 N, 10 mL) was added. The reaction solution was stirred at 50° C. for 8 hours to see the acetal was consumed by TLC. It was diluted with 200 mL of ethyl acetate and 1 N sodium hydroxide solution was added until pH=12. The organic layer was dried over anhydrous sodium sulfate, concentrated and purified by flash column chromatography on silica gel with 2/1 ethyl acetate/hexanes as eluant to give the title compound as a colorless glass. ¹H NMR (CDCl₃, 400 Hz): δ8.65 (d, J=2.2 Hz, 1 H), 8.16 (broad s, 1 H), 7.97 (d, J=8.4 Hz, 1 H), 7.83 (dd, J=2.1, 8.4 Hz, 1 H), 6.76 (broad s, 1 H), 5.88–6.01 (m, 1 H), 5.28–5.37 (m, 2 H), 5.05 (dd, J=6.9, 20 Hz, 1H), 4.82 (s, 2 H), 4.6 (d, J=5.3 Hz, 2 H), 4.00–4.26 (m, 3 H), 3.64–3.74 (m, 2 H), 3.25 (t, J=9.3 Hz, 1 H), 2.87 (d, J=11.0 Hz, 1 H), 2.43 (dd, J=3.5, 11.5 Hz, 1 H), 2.33 (dt, J=3.3, 11.7 Hz, 1 H), 1.81 (broad s, 1 H), 1.68–1.71 (m, 1 H), 1.29 (s, 3 H), 1.28 (s, 3 H).

Step H

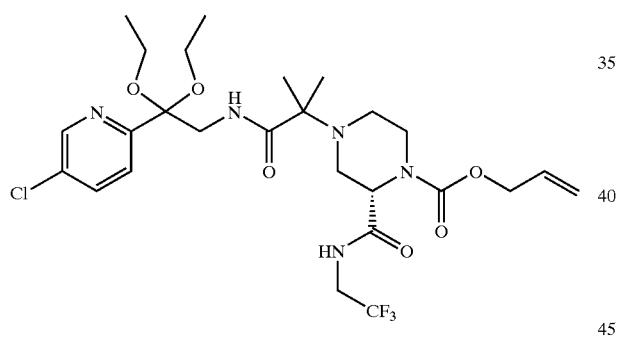

To a solution of the carboxylic acid from the Example 66 Step D (1.5 g, 3.93 mmol) in DMF (10 mL) was added O-benzoltriazol-1-N,N,N',N'-tetramethyluronium hexafluorophosphate (3.6 g, 9.44 mmol), 1-hydroxybenzotriazol hydrate (1.3 g, 9.44 mmol) and diisipropylethylamine (3.4 mL, 19.7 mmol). It was stirred at room temperature for 30 minutes, and the aminoacetal from the previous step (1.2 g, 4.72 mmol) was added. After stirring at room temperature for 10 hours, the reaction solution was distributed between ethyl acetate (400 mL) and water (400 mL). The organic layer was washed with brine. It was dried over anhydrous sodium sulfate, concentrated and purified by flash column chromatography on silica gel with 1/2 hexanes/ethyl acetate as eluant to give the title compound as a white solid. ¹H NMR (CDCl₃, 400 Hz): δ8.61 (t, J=1.6 Hz, 1 H), 7.66–7.71 (m, 2 H), 6.57 (broad s, 1 H), 5.89–5.99 (m, 1 H), 5.24–5.35 (m, 2 H), 4.65 (d, J=4.8 Hz, 3 H), 4.11–4.18 (m, 2 H), 3.80–3.98 (m, 3 H), 3.54–3.68 (m, 3 H), 3.24–3.40 (m, 3 H), 2.82 (t, J=11.5 Hz, 1 H), 2.52 (d, J=10.2 Hz, 1 H), 2.27 (dd, J=4.0, 11.7 Hz, 1 H), 2.16 (dt, J=4.0, 11.8 Hz, 1 H), 1.17–1.29 (m,4 H), 1.10 (s, 3H), 1.03 (s, 3 H).

Step J

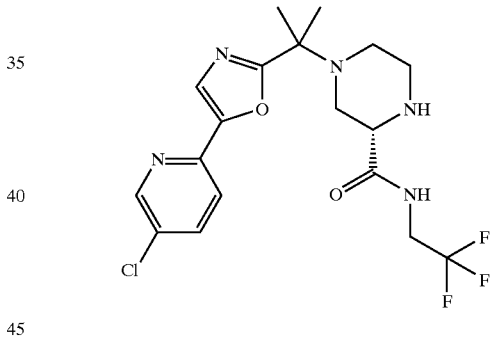

The ketoamide from the previous step (1.01 g, 1.89 mmol) was dissolved in 7 mL of fuming sulfuric acid. It was stirred at 55° C. for 15 minutes. After cooled to room temperature it was carefully poured into ice-water (250 mL). While the aqueous solution was stirred, potassium hydroxide (solid) was added slowly until pH=12. It was extracted with ethyl acetate for 3 times (200 mL each time). The combined extractant was dried over anhydrous sodium sulfate, and concentrated to give the title compound a pale solid. ¹H NMR (CDCl₃, 400 Hz): δ8.58 (d, J=2.3 Hz, 1 H), 8.21 (broad s, 1 H), 7.75 (dd, J=2.4, 8,4 Hz, 1 H), 7.57–7.61 (m, 2 H), 3.92–4.20 (m, 2 H), 3.56 (broad s, 1 H), 2.84–2.99 (m, 3 H), 2.76–2.82 (m, 1 H), 2.52–2.64 (m, 2 H), 1.61 (s, 3 H), 1.60 (s, 3 H). LC-MS (M⁺+1) (EI) 432.3.

Step K (αR,γS,2S)-N-((3S,4S)-3,4-dihydro-3-hydroxy-2H-1-benzopyran-4-yl)-γ-hydroxy-4-[1-methyl-1-[5-(5-chloro-3-pyridinyl)-2-oxazolyl]ethyl]-α-(phenylmethyl)-2-[[(2,2,2 trifluoroethyl)amino] carbonyl]-1-piperazinepentanamide A solution of the intermediate from the previous step (631 mg, 1.60 mmol) and the epoxide from Example 1, Step P (693 mg, 1.60 mmol) in ethanol (15 mL) was refluxed for 48 hours. After the solvent was evaporated the residue was purified by flash column chromatography on silica gel with 10/7 ethyl acetate/methanol as eluant to get a white solid (862 mg) (LC-MS (M$^+$+1) (EI) 825.6). The solid obtained was dissolved in methanol (20 mL) and cooled to 0° C. HCl (1 N in ether, 3.2 mL) was added and the reaction solution was warmed to room temperature at which it was stirred for 6 hours. The solvent was evaporated. The residue was distributed between ethyl acetate (200 mL) and 1 N potassium hydroxide (15 mL). The organic layer was dried over anhydrous sodium sulfate, concentrated and purified by flash column chromatography on silica gel with 10/7 ethyl acetate/methanol as eluant to give the title compound as a white solid. $^1$H NMR (CD$_3$OD, 400 Hz): δ8.58 (t, J=1.8 Hz, 1 H), 7.92 (dt, J=2.4, 8.6 Hz, 1 H), 7.75 (dd, J=1.5, 8.6 Hz, 1 H), 7.67 (d, J=1.9 Hz, 1 H), 7.12–7.26 (m, 6 H), 7.05–7.09 (m, 2 H), 6.80 (t, J=7.2 Hz, 1 H), 6.72 (d, J=8.0 Hz, 1 H), 5.13 (d, J=4.1 Hz, 1 H), 4.04–4.07 (m, 2 H), 3.91–4.01 (m,1 H), 3.77–3.83 (m, 1 H), 3.70–3.76 (m, 2 H), 3.07–3.09 (m, 1 H), 2.96–3.05 (m, 2 H), 2.84–2.94 (m, 2 H), 2.69–2.78 (m, 2 H), 2.62–2.66 (m, 1 H), 2.31–2.53 (m, 4 H), 1.98–2.05 (m, 1 H), 1.60 (s, 3 H), 1.59 (s, 3 H), 1.33–1.40 (m, 1 H). LC-MS (M$^+$+1) (EI) 785.5

EXAMPLE 77

(αR,γS,2S)-N-((3S,4S)-3,4-dihydro-3-hydroxy-2H-1-benzopyran-4-yl)-γ-hydroxy-α-(phenylmethyl)-4-[1-methyl-1-[5-(5-chloro-2-pyridinyl)-2-oxazolyl]ethyl]-2-[[(2,2,2-trifluoroethyl)amino]carbonyl]-1-piperazinepentanamide

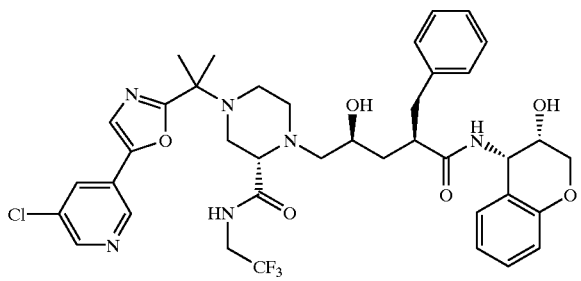

Step A

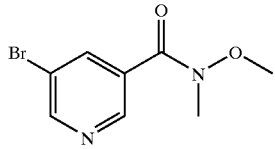

To a solution of 5-bromonicotinic acid (50 g, 247.5 mmol) and 4-methyl morpholine (54.5 mL, 495 mmol) in methylene chloride (500 mL), at −50° C., isobutylchloroformate (32.1 mL, 247.5 mmol) was added. After it was stirred at −20 to −10° C. for 1 hour, N,O-dimethylhydroxylamine hydrochloride (25.4 g, 260 mmol) was added. The reaction solution was slowly warmed to room temperature, at which it was stirred for 6 hours. It was poured into 1 liter of water. The organic layer was washed with water (500 mL) and brine (500 mL), dried over anhydrous sodium sulfate, concentrated, and purified by flash column chromatography on silica gel with hexanes/ethyl acetate=1/1 as eluant to give the title compound as a colorless oil. $^1$H NMR (CDCl$_3$, 400 Hz): δ8.89 (s, 1H), 8.77 (s, 1H), 8.19 (t, J=2.0 Hz, 1 H), 3.59 (s, 3 H). 3.41 (s, 3H).

Step B

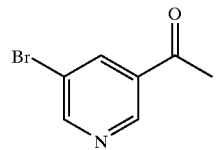

To a solution of the Weinreb intermediate from the previous step (67 g, 275 mmol) in anhydrous THF (500 mL), at 0° C., was added methylmagnesium bromide (1.4M solution, 590 mL, 824 mmol). The reaction solution was stirred at 0° C. for 3 hours and poured into 800 mL of ice-water. Ethyl acetate was used to extract it (3 times, 600 mL each time). The combined organic layers was dried over anhydrous sodium sulfate, concentrated, and purified by flash column chromatography on silica gel with hexanes/ethyl acetate=3/1 as eluant to give the title compound as a white fluffy solid. $^1$H NMR (CDCl$_3$, 400 Hz): δ9.08 (s, 1H), 8.87 (s, 1H), 8.38 (t, J=2.0 Hz, 1 H), 2.66 (s, 3 H).

Step C

A suspension of the bromopyridine from the previous step (40 g, 200 mmol) and copper(I) chloride (100 g, 1 mol) in DMF (500 mL) was stirred at 110° C. for 12 hours to see the starting material was consumed by LCMS. It was concentrated to about 200 mL, and distributed between ethyl acetate (1.5 l) and concentrated ammonium hydroxide (2 l). The aqueous layer was washed with ethyl acetate for 3 times (500 mL each time). The combined organic layers were dried over anhydrous sodium sulfate, concentrated, and purified by flash column chromatography on silica gel with hexanes/ethyl acetate=3/1 as eluant to give the title compound as a white solid. $^1$H NMR (CDCl$_3$, 400 MHz): δ9.05 (s, 1H), 8.77 (s, 1H), 8.22 (t, J=2.0 Hz, 1 H), 2.66 (s, 3 H). LC-MS (M$^+$+1) (EI) 156.1.

Step D

To a suspension of the acetylpyridine obtained as from the previous step (24 g, 154.3 mmol) and hydroxyamine hydrochloride (16.1 g, 231 mmol) in ethyl alcohol (200 mL) was added sodium hydroxide powder (9.3 g, 231 mmol). The reaction mixture was refluxed for 2 hours to see that the starting material was consumed by LCMS. It was filtered. The solid was washed with ethanol (100 mL) and discarded. The combined filtrate and washed was concentrated. The residue was washed with cooled water for several times to give the title compound as a white solid. ¹H NMR (DMSO, 400 MHz): δ8.78 (d, J=1.8 Hz, 1 H), 8.60 (d, J=2.3 Hz, 1 H), 8.07 (t, J=2.1 Hz, 1 H), 2.17 (s, 3 H). LC-MS (M⁺+1) (EI) 171.1.

Step E

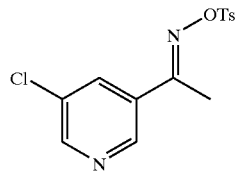

A solution of the oxime form the previous step (25.67 g, 150.5 mmol) and p-toluenesulfonyl chloride (36 g, 188.1 mmol) in pyridine (100 mL) was stirred at room temperature for 48 hours to form a brown precipitate. Ice-cooled water (1 l) was added while stirring. The initially formed brown precipitate dissolved followed by the formation of a white precipitate. It was stirred at 0° C. for 2 hours. The precipitate was collected by filtration and washed with ice-cooled water for 4 times (200 mL each time). It was dried under high vacuum to constant weight to get the titled compound as a pale solid. ¹H NMR (CDCl₃, 400 MHz): δ8.68 (d, J=1.9 Hz, 1 H), 8.63 (d, J=2.3 Hz, 1 H), 7.93 (d, J=8.4 Hz, 2 H), 7.89 (t, J=1.9 Hz, 1 H), 7.39 (d, J=8.0, 2 H), 2.47 (s, 3 H), 2.38 (s, 3 H). LC-MS (M⁺+1) (EI) 432.3.

Step F

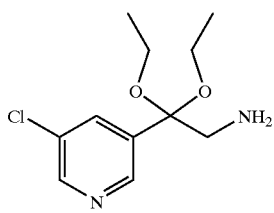

To a solution of potassium ethoxide (12.1 g, 140 mmol) in 80 mL anhydrous ethanol a solution of the tosylamide from the previous step (43.21 g, 133 mmol) in ethanol (1 L) was added at 0° C., dropwise through a dropping funnel. It was slowly warmed to room temperature at which it was stirred for 12 hours to form a white precipitate. It was diluted with 1 liter of anhydrous ether and filtered. The solid was washed with anhydrous ether (100 mL). To the combined filtrate and washes HCl gas was bubbled in for 1 hour to get a cloudy solution. It was concentrated and the residue was distributed between methylene chloride (500 mL) and saturated sodium carbonate (about 500 mL to get pH=12). The organic layer was dried over anhydrous sodium sulfate, concentrated, and purified by flash column chromatography on silica gel with ethyl acetate/methanol=5/1 as eluant to give the title compound as a slightly yellow oil. ¹H NMR (CDCl₃, 400 MHz): δ8.62 (d, J=1.7 Hz, 1H), 8.54 (d, J=2.6 Hz, 1H), 7.86 (t, J=2.0 Hz, 1 H), 3.36–3.54 (m, 4H), 3.04 (s, 2 H), 1.26 (t, J=7.0 Hz, 6 H). LC-MS (M⁺+1) (EI) 198.8.

Step G

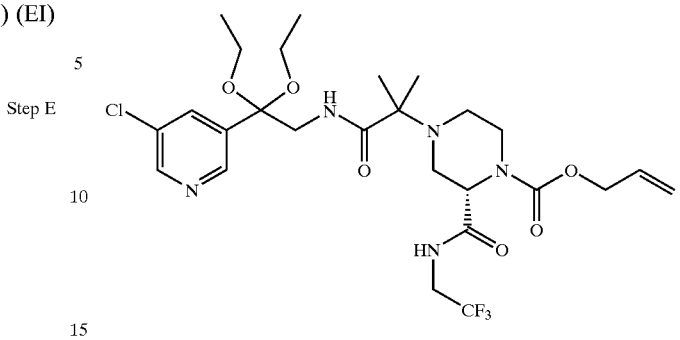

To a solution of the carboxylic acid from Example 66 Step D (1.8 g, 4.72 mmol) in DMF (10 mL) was added O-benzotriazol-1-N,N,N',N'-tetramethyluronium hexafluorophosphate (5.16 g, 13.6 mmol), 1-hydroxybenzotriazol hydrate (1.84 g, 13.6 mmol) and diisopropylethylamine (4.11 mL, 23.6 mmol). It was stirred at room temperature for 30 minutes, and the aminoacetal from the previous step (1.4 g, 5.66 mmol) was added. After stirring at room temperature for 10 hours, the reaction solution was distributed between ethyl acetate (400 mL) and water (400 mL). The organic layer was washed with brine. It was dried over anhydrous sodium sulfate, concentrated and purified by flash column chromatography on silica gel with 1/2 hexanes/ethyl acetate as eluant to give the title compound as a white solid. ¹H NMR (CD₃OD, 400 MHz): δ8.56 (d, J=1.6 Hz, 1 H), 8.48 (d, J=2.3 Hz, 1 H), 7.90 (t, J=2.0 Hz, 1 H), 7.45 (Broad s, 1 H), 5.94 (Broad s, 1 H), 5.16–5.37 (m, 2 H), 4.66 (s, 1 H), 4.60 (d, J=4.5 Hz, 2 H), 4.01–4.11 (m, 1 H), 3.92 (d, J=12.7 Hz, 1 H), 3.76–3.86 (m, 1 H), 3.40–3.67 (m, 3 H), 3.28–3.32 (m, 1 H), 3.18–3.26 (m, 1 H), 2.36–2.42 (m, 2 H), 2.13–2.20 (m 1 H), 1.27 (t, J=7.1 Hz, 2 H), 1.22 (T, J=7.2 Hz, 2 H), 0.98 (s, 3H), 0.93 (s, 3 H). LC-MS (M⁺+1) (EI) 562.3.

Step H

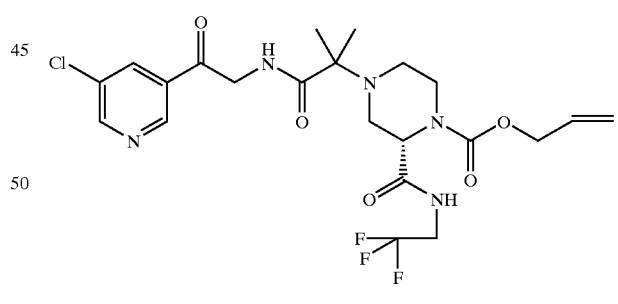

The acetal from the previous step (1.4 g, 2.35 mmol) was dissolved in THF (10 mL) and HCl (6 N, 10 mL) was added. The reaction solution was stirred at 50° C. for 3 hours to see the acetal was consumed. It was diluted with 200 mL of ethyl acetate and 1 N sodium hydroxide solution was added until pH=12. The organic layer was dried over anhydrous sodium sulfate, concentrated and purified by flash column chromatography on silica gel with 2/1 ethyl acetate/hexanes as eluant to give the title compound as a white solid. ¹H NMR (CDCl₃, 400 MHz): δ9.05 (d, J=2.7 Hz, 1 H), 8.78 (d, J=2.3 Hz, 1 H), 8.41 (broad s, 1 H), 8.21 (t, J=2.1 Hz, 1 H), 6.76 (broad s, 1 H), 6.60 (broad s, 1 H), 5.88–6.01 (m, 1 H), 5.28–5.37 (m, 3 H), 4.76–4.88 (m, 2 H), 4.68 (d, J=5.2 Hz, 2 H), 4.53 (d, J=18.2 Hz, 1 H), 4.05–3.27 (m, 3 H), 3.57–3.90 (m, 3 H), 3.25 (t, J=9.3 Hz, 1 H), 2.87 (d, J=11.0 Hz, 1 H), 2.43 (dd, J=3.5, 11.7 Hz, 1 H), 2.33 (dt, J=3.1, 11.7 Hz, 1 H), 1.28 (s, 3 H), 1.26 (s, 3 H).

Step I

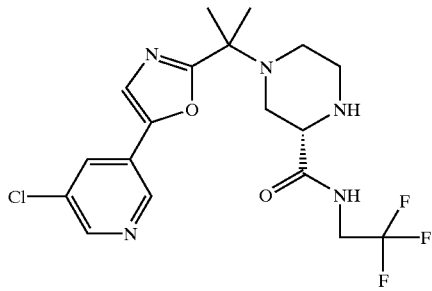

The ketoamide from the previous step (905 mg, 1.7 mmol) was dissolved in 7 mL of fuming sulfuric acid. It was stirred at 55° C. for 15 minutes. After cooled to room temperature it was carefully poured into ice-water (250 mL). While the aqueous solution was stirred, potassium hydroxide (solid) was added slowly until pH=12. It was extracted with ethyl acetate for 3 times (200 mL each time). The combined extractant was dried over anhydrous sodium sulfate, and concentrated to get the title compound as a pale sticky solid. $^1$H NMR (CDCl$_3$, 400 MHz): δ8.77 (d, J=1.7 Hz, 1 H), 8.54 (d, J=2.4 Hz, 1 H), 8.03 (broad s, 1 H), 7.90 (t, J=2.0 Hz, 1 H), 7.39 (s, 2 H), 3.91–4.01 (m, 2 H), 3.51–3.53 (m, 1 H), 2.86–2.99 (m, 3 H), 2.75–2.82 (m, 1 H), 2.52–2.64 (m, 2 H), 1.61 (s, 3 H), 1.60 (s, 3 H). LC-MS (M$^+$+1) (EI) 432.3.

Step J (αR,γS,2S)-N-((3S,4S)-3,4-dihydro-3-hydroxy-2H-1-benzopyran-4-yl)-γ-hydroxy-α-(phenylmethyl)-4-[1-methyl-1-[5-(5-chloro-2-pyridinyl)-2-oxazolyl]ethyl]-2-[[(2,2,2-trifluoroethyl)amino]carbonyl]-1-piperazinepentanamide A solution of the intermediate from the previous step (560 mg, 1.42 mmol) and the epoxide from Example 1 Step P (651 mg, 1.42 mmol) in 2-propanol (15 mL) was refluxed for 36 hours. After the solvent was evaporated the residue was purified by flash column chromatography on silica gel with 10/1 ethyl acetate/methanol as eluant to get a white solid (810 mg) (LC-MS (M$^+$+1) (EI) 825.6). The solid obtained was dissolved in methanol (20 mL) and cooled to 0° C. HCl (1 N in ether, 3.5 mL) was added and the reaction solution was warmed to room temperature at which it was stirred for 18 hours. The solvent was evaporated. The residue was distributed between ethyl acetate (200 mL) and 1 N potassium hydroxide (100 mL). The organic layer was dried over anhydrous sodium sulfate, concentrated and purified by flash column chromatography on silica gel with 10/2 ethyl acetate/methanol as eluant to give the title compound as a white solid. $^1$H NMR (CD$_3$OD, 400 MHz): δ8.84 (t, J=1.9 Hz, 1 H), 8.52 (s, 1H), 8.18–8.19(m, 1 H), 7.69 (d, J=2.0 Hz, 1 H), 7.12–7.25 (m, 5 H), 7.05–7.10 (m, 2 H), 6.80 (t, J=7.2 Hz, 1 H), 6.71 (d, J=7.8 Hz, 1 H), 5.48 (s, 1H), 5.13 (d, J=3.9 Hz, 1 H), 3.90–3.97 (m, 1 H), 3.78–3.87 (m, 1 H), 3.70–3.76 (m, 2 H), 3.08 (dd, J=3.0, 7.1 Hz, 1 H), 2.98–3.04 (m, 2 H), 2.84–2.99 (m, 2 H), 2.70–2.75 (m, 2 H), 2.65 (dd, J=5.0, 11.1 Hz, 1 H), 2.31–2.53 (m, 4 H), 2.0 (t, J=11.9 Hz 1 H), 1.59 (s, 6 H), 1.33–1.40 (m, 1 H). LC-MS (M$^+$+1) (EI) 785.5

EXAMPLE 78

(αR,γS,2S)-N-((3S,4S)-3,4-dihydro-3-hydroxy-2H-1-benzopyran-4-yl)-γ-hydroxy -4-[(3-chloro-1-phenyl-1H-pyrrol-3-yl)methyl]-α-(3-pyridinylmethyl)-2-[[(2,2,2-trifluoroethyl)amino]carbonyl]-1-piperazinepentanamide

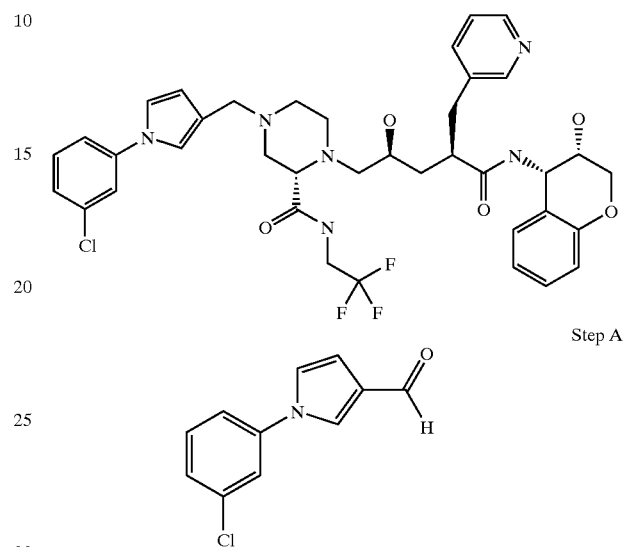

Step A

To a solution of 2,5-dimethoxy-3-tetrahydrofurancarboxaldehyde (230 μL, 1.62 mmol) in acetic acid (2 mL) was added 3-chloroaniline (222 mg, 2.75 mmol). The resulting solution was heated to 90° C. for 1 h, then cooled to ambient temperature and concentrated in vacuo. The residue was purified by flash chromatography (7% hexane in dichloromethane) affording the aldehyde as a clear oil. $^1$H NMR (CDCl$_3$, 400 MHz) 9.87 (s, 1H), 7.67 (d, 1H), 7.45 (m, 2H), 7.38 (m, 2H), 7.10 (d, 1H), 6.82 (d, 1H). HPLC-MS (ES) 206.1 (M+1).

Step B (αR,γS,2S)-N-((3S,4S)-3,4-dihydro-3-hydroxy-2H-1-benzopyran4-yl)-γ-hydroxy-4-[(3-chloro-1-phenyl-1H-pyrrol-3-yl)methyl]-α-(3-pyridinylmethyl)-2-[[(2,2,2-trifluoroethyl)amino]carbonyl]-1-piperazinepentanamide The title compound was obtained following the procedure described in Example 12, Step E, starting with the intermediate prepared in Example 23, Step F (45 mg, 80 μmol) and the aldehyde prepared in Step A (33 mg, 161 μmol). Purification by flash chromatography (5% methanolin dichloromethane) afforded the title compound as a white solid. $^1$H NMR (CDCl$_3$, 400 MHz) 9.26 (s, 1H), 8.36 (s, 1H), 8.32 (s, 1H), 7.55 (d, J=8.0 Hz, 1H), 7.37 (m, 2H), 7.26 (m, 3H), 7.13 (m, 2H), 7.06 (m, 1H), 6.98 (m, 1H), 6.80 (m, 3H), 6.23 (dd, J=1.7 Hz, J=2.7 Hz, 1H), 5.20 (dd, J=3.9 Hz, J=8.2 Hz, 1H), 4.12 (m, 4H), 3.77 (m, 3H), 3.53 (d, J=13 Hz, 2H), 3.51 (m, 7H), 2.96 (m, 4H), 2.70 (m, 4H), 2.45 (dt, J=2.9 Hz, J=10.4 Hz, 2H), 2.33 (m, 1H), 2.04 (s, 1H), 1.88 (t, 1H), 1.48 (t, 1H). HPLC-MS (ES) 756 (M+1).

EXAMPLE 79

(αR,γS,2S)-N-((3S,4S)-3,4-dihydro-3-hydroxy-2H-1-benzopyran-4-yl)-γ-hydroxy-4-[(4-chloro-1-phenyl-1H-pyrrol-3-yl)methyl]-α-(3-pyridinylmethyl)-2-[[(2,2,2-trifluoroethyl)amino]carbonyl]-1-piperazinepentanamide

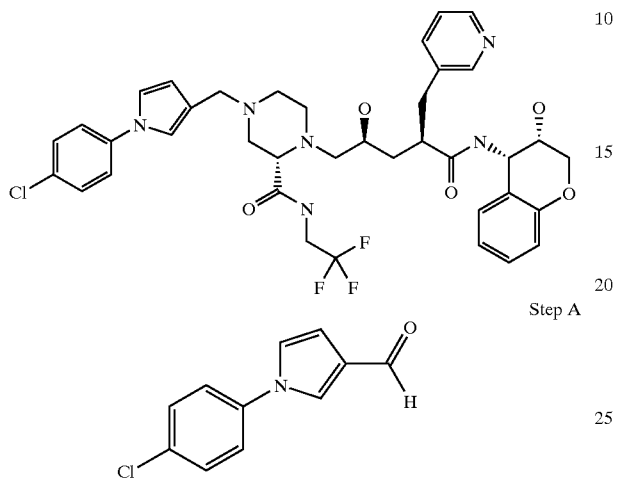

Step A

To a solution of 2,5-dimethoxy-3-tetrahydrofurancarboxaldehyde (230 µL, 1.62 mmol) in acetic acid (2 mL) was added 4-chloroaniline (218 mg, 2.75 mmol). The resulting solution was heated to 90° C. for 1 h, then cooled to ambient temperature and concentrated in vacuo. The residue was purified by flash chromatography (7% hexane in dichloromethane) affording the aldehyde as a clear oil. $^1$H NMR (CDCl$_3$, 400 MHz) 9.88 (s, 1H), 7.65 (d, 1H), 7.49 (d, 2H), 7.39 (d, 2H), 7.06 (d, 1H), 6.83 (d, 1H); HPLC-MS (ES) 206.1 (M+1).

Step B (αR,γS,2S)-N-((3S,4S)-3,4-dihydro-3-hydroxy-2H-1-benzopyran-4-yl) -γ-hydroxy-4-[(4-chloro-1-phenyl-1H-pyrrol-3-yl)methyl]-α-(3-pyridinylmethyl)-2-[[(2,2,2-trifluoroethyl)amino]carbonyl]-1-piperazinepentanamide The title compound was obtained following the procedure described in Example 12, Step E, starting with the intermediate prepared in Example 23, Step F (45 mg, 80 µmol) and the aldehyde prepared in Step A (33 mg, 161 µmol). Purification by flash chromatography (5% methanol in dichloromethane) afforded the title compound as a white solid. $^1$H NMR (CDCl$_3$, 400 MHz) 9.26 (s, 1H), 8.35 (d, J=7.8 Hz, 2H), 7.56 (d, J=7.8 Hz, 1H), 7.41 (d, J=9.0 Hz, 2H), 7.30 (d, J=9.0 Hz, 2H), 7.29 (m, 1H), 7.22 (t, J=4.8 Hz, 1H), 7.11 (d, J=7.6 Hz, 2H), 7.03 (s, 1H), 6.95 (s, 1H), 6.79 (m, 3H), 6.22 (dd, J=1.7 Hz, J=2.9 Hz, 1H), 5.22 (dd, J=5.3 Hz, J=8.2 Hz, 1H), 4.10 (m, 3H), 3.81 (m, 2H), 3.72 (m, 1H), 3.54 (d, J=13.1 Hz, 1H), 3.40 (m, 7H), 2.94 (m, 4H), 2.68 (m, 4H), 2.46 (dt, J=3.2 Hz, J=12.9 Hz, 2H), 2.34 (m, 1H), 2.04 (s, 1H), 1.89 (t, J=11.2 Hz, 1H), 1.49 (m, 1H); HPLC-MS (ES) 755.2 (M+1).

EXAMPLE 80

(αR,γS,2S)-N-((3S,4S)-3,4-dihydro-3-hydroxy-2H-1-benzopyran-4-yl)-γ-hydroxy-4-[1-methyl-1-(1-phenyl-1H-triazoyl-4-yl)ethyl]-α-(3-phenylmethyl)-2-[[(2,2,2-trifluoroethyl)amino]carbonyl]-1-piperazinepentanamide

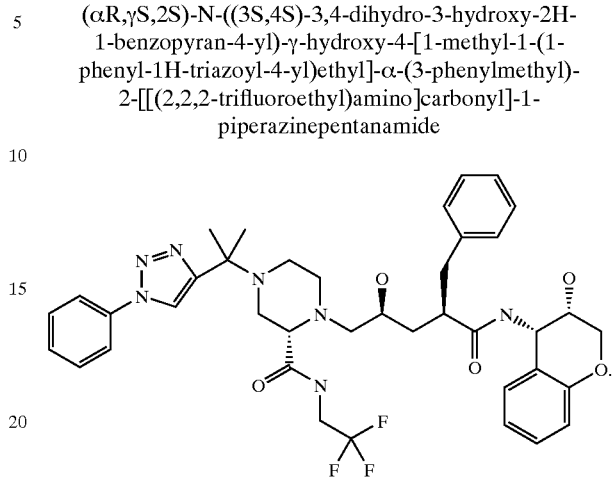

To a solution of the intermediate from Example 39, Step A (126 mg, 0.200 mmol) in 1 mL of toluene was added phenyl azide (24 mg, 0.20 mmol). The resulting mixture was heated to 110° C. for 14 h, then cooled to ambient temperature. Purification of the mixture by flash chromatography (7% methanol in ethyl acetate) afforded the title compound as a white solid. $^1$H NMR (CD$_3$OD, 400 MHz) 8.43 (s, 1H), 7.85 (d, J=8.0 Hz, 2H), 7.57 (t, J=7.2 Hz, 2H), 7.47 (t, J=7.6 Hz, 1H), 7.21 (m, 3H), 7.15 (m, 1H), 7.09 (m, 1H), 6.80 (dt, J=1.2 Hz, J=7.6 Hz, 1H), 6.72 (dd, J=0.8 Hz, J=8.0 Hz, 1H), 5.14 (d, J=4.0 Hz, 1H), 4.08 (m, 3H), 3.74 (m, 3H), 3.30 (m, 1H), 3.09 (dd, J=3.6 Hz, J=6.8 Hz, 1H), 3.02 (m, 2H), 2.81 (d, J=9.2 Hz, 1H), 2.73 (dd, J=6.8 Hz, J=13.2 Hz, 2H), 2.62 (dd, J=7.2 Hz, J=11.6 Hz, 1H, 2.50 (m, 2H), 2.40 (d, J=6.4 Hz, 2H), 2.03 (t, J=11.6 Hz, 1H), 1.39 (m, 1H), 1.23 (t, J=6.8 Hz, 1H); HPLC-MS (ES) 750.4 (M+1).

EXAMPLE 81

(αR,γS,2S)-N-((3S,4S)-3,4-dihydro-3-hydroxy-2H-1-benzopyran-4-yl)-γ-hydroxy-4-[1-methyl-1-(1-phenyl-1H-triazoyl-4-yl)ethyl]-α-(3-pyridinylmethyl)-2-[[(2,2,2-trifluoroethyl)amino]carbonyl]-1-piperazinepentanamide

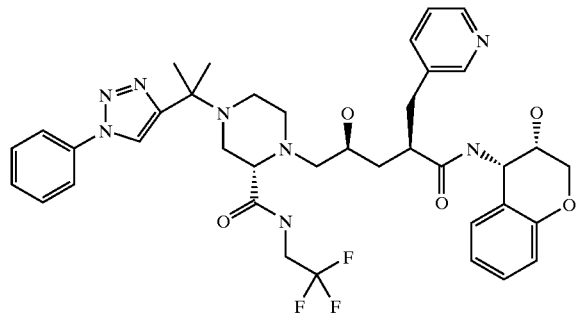

235
-continued

Step A

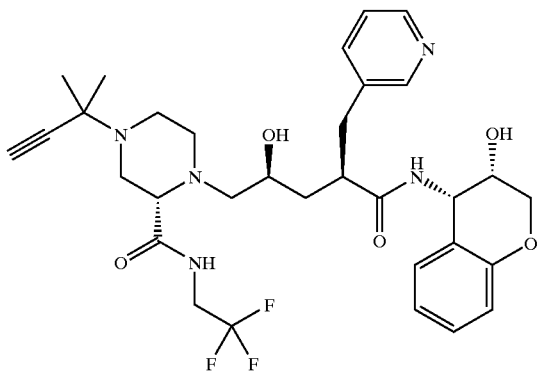

The title compound was made following the procedure described in Example 39, Step A, using the intermediate prepared in Example 23, Step F (265 mg, 0.469 mmol) and 3-methyl-3-chlorobutyne (52.7 μL, 0.469 mmol). Purification by flash chromatography (2% methanol in ethyl acetate) afforded the alkylated compound as a white solid. HPLC-MS (ES) 632.6 (M+1).

Step B (αR,γS,2S)-N-((3S,4S)-3,4-dihydro-3-hydroxy-2H-1-benzopyran-4-yl)-γ-hydroxy-4-[1-methyl-1-(1-phenyl-1H-triazoyl-4-yl)ethyl]-α-(3-pyridinylmethyl)-2-[[(2,2,2-trifluoroethyl)amino]carbonyl]-1-piperazinepentanamide The title compound was prepared by the procedure described in Example 79, Step A, using the intermediate prepared in Step A (126 mg, 0.200 mmol), and phenyl azide (24 mg, 0.20 mmol). Purification by flash chromatography (5% methanol in dichloromethane) afforded the title compound as a white solid. $^1$H NMR (CD$_3$OD, 400 MHz) 8.52 (s, 1H), 8.39 (s, 1H), 8.37 (d, J=4.0 Hz, 1H), 7.95 (d, J=8.8 Hz, 1H), 7.85 (d, J=8.0 Hz, 2H), 7.73 (d, J=7.6 Hz, 1H), 7.51 (t, J=12.8 Hz, 2H), 7.47 (t, J=7.2 Hz, 1H), 7.34 (dd, J=7.6 Hz, J=4.8 Hz, 1H), 7.09 (m, 2H), 6.82 (t, J=7.6 Hz, 1H), 6.72 (d, J=8.0 Hz, 1H), 5.17 (m, 1H), 4.02 (m, 4H), 3.75 (m, 3H), 3.10 (m, 1H), 2.98 (m, 3H), 2.69 (dd, 2H), 2.62 (m, 2H), 2.50 (d, J=5.6 Hz, 2H), 2.03 (t, J=11.6 Hz, 1H), 1.40 (m, 2H); HPLC-MS (ES) 751.4 (M+1).

EXAMPLE 82

(αR,γS,2S)-N-(4S-3,4-dihydro-1H-2,2-dioxobenzothiopyranyl)-γ-hydroxy-α-(phenylmethyl)-4-[[5-(5-pyrimidinyl)-1-furanyl]methyl]-2-[[(2,2,2-trifluoroethyl)amino]carbonyl]-1-piperazinepentanamide

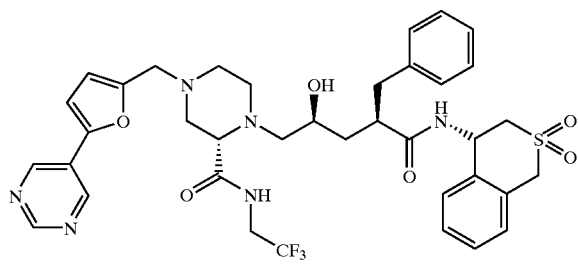

236
-continued

Step A

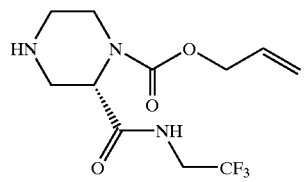

To a solution of the piperazine, prepared as in Example 12 Step A, (338 mg, 0.86 mmol) in dichloromethane (10 mL) was added 10 mL 30% trifluroacetic acid in dichloromethane (10 mL). The reaction mixture was stirred at ambient temperature for 2 hours. The reaction mixture was washed with 1N KOH (20 mL×2), dried over anhydrous sodium sulfate, filtered and concentrated in vacuo to give the title compound as a colorless oil. $^1$H NMR (CDCl$_3$, 400 MHz): 6.9 (bs, 1H), 5.95 (m, 1H), 5.3 (dd, J=11.7, 17.2 Hz, 2 H), 4.68 (d, J=4.9 Hz, 2H), 4.61 (bs, 2 H), 4.0 (m, 2H), 3.79 (m, 1H), 3.56 (d, J=13.1 Hz, 1H), 2.8 (m, 4H).

Step B

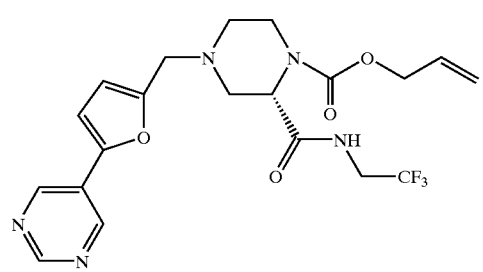

To a solution of the intermediate obtained from Step A (268 mg, 0.91 mmol) in 1,2-dichloroethane (2 mL) was added the aldehyde obtained from Example 16 Step B (158 mg, 0.91 mmol) and sodium triacetoxy borohydride (289 mg, 1.36 mmol). The reaction was stirred at room temperature for 6 hours. The reaction mixture was poured into saturated sodium hydrogen carbonate and extracted with ethyl acetate (4×10 mL). The organic layers were combined, dried over anhydrous sodium sulfate, filtered and concentrated in vacuo to give the title compound. $^1$H NMR (CDCl$_3$, 400 MHz): 9.1 (s, 1H), 8.9 (s, 2H), 6.8 (d, J=3.3 Hz, 1H), 6.4 (d, J=3.3 Hz, 1H), 5.9 (m, 1H), 5.35 (dd, J=7.2 Hz, 1H), 5.3 (dd, J=7.6 Hz7.6 Hz, 1H), 4.9 (bs, 1H), 4.8 (m, 1H), 4.66 (t, J=5.4, 5.5 Hz, 2H), 4.2 (bm, 1H), 3.9 (bm, 2 H), 3.48 (d, J=11.1 Hz, 1H), 3.2 (bs, 1H), 2.9 (bd, 1H), 2.3 (m, 3H).

Step C

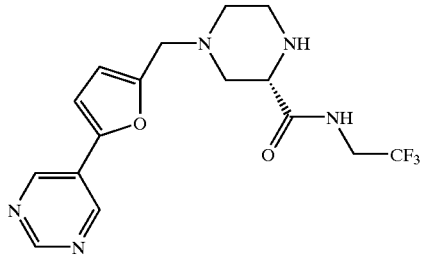

To a solution of the intermediate obtained from Step B (400 mg, 0.88 mmol) in THF was added 1,3-dimethyl barbituric acid (156 mg, 1.0 mmol) and tetrakis triphenyl phosphine palladium (0) (30.5 mg, 0.026 mmol). The resulting mixture was stirred at room temperature for 2 hours. The reaction mixture was diluted with ethyl acetate and extracted with 1 N HCl (4×10 mL). The pH of the aqueous layer was adjusted to 10 with solid sodium carbonate. The aqueous layer was extracted with ethyl acetate (6×10 mL). The organic layers were combined and dried over anhydrous sodium sulfate, filtered and concentrated in vacuo to give the title compound.

Step D

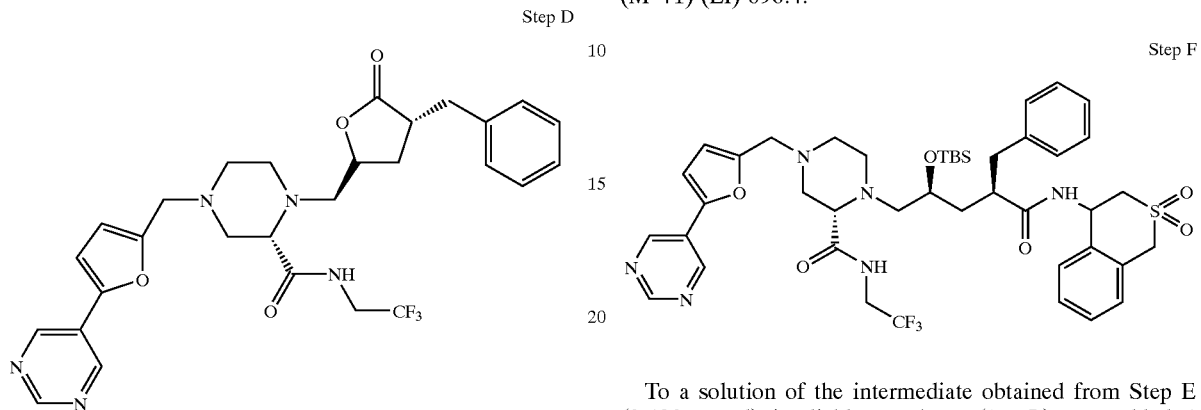

To a solution of the intermediate obtained from Step C (325 mg, 0.88 mmol) in 2-propanol was added the intermediate triflate obtained from Example 35 Step E (297 mg, 0.88 mmol) and diisopropylethylamine (0.153 mL, 0.88 mmol). The reaction was stirred at room temperature for 48 hours. The reaction mixture was concentrated in vacuo and purified by flash chromatography using ethyl acetate to give the title compound as a solid. $^1$H NMR (CDCl$_3$ 400 MHz): 9.1 (s, 1H), 8.9 (s, 2H), 8.1 (bs, 1H), 7.34 (m, 3H), 7.2 (m, 2H), 6.8 (d, J=3.6 Hz, 1H), 6.4 (d, J=3.4 Hz, 1H), 4.4 (m, 1H), 3.6 (m, 3H), 3.25 (t, J=3.7, 5.2 Hz, 1H), 3.19 (dd, J=4.5, 4.3 Hz, 1H), 2.95 (m, 2H), 2.75 (m, 3H), 2.6 (m, 6 H), 1.95 (m, 2H). LC-MS (M$^+$+1) (EI) 558.4

Step E

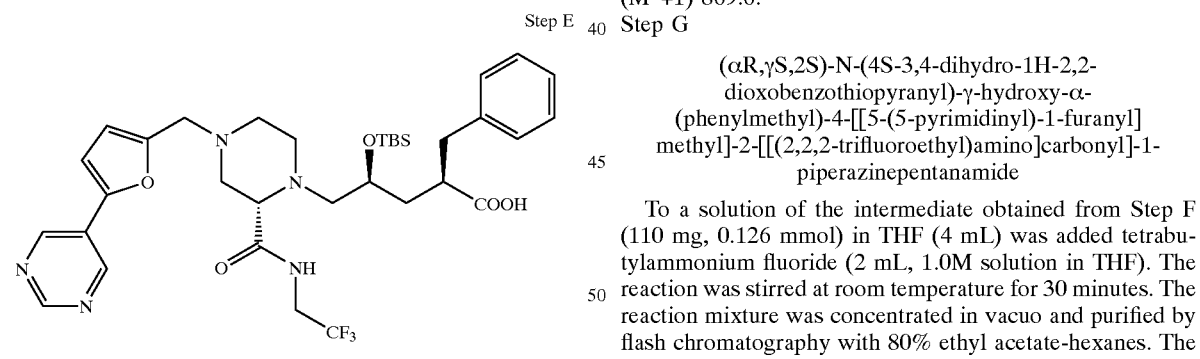

To a solution of the intermediate obtained from Step D (236 mg, 0.42 mmol) in 1,4-dioxane (4 mL) was added 1N LiOH solution (0.465 mL, 0.465 mmol). The reaction was stirred at room temperature for 1 hour. The reaction mixture was then concentrated in vacuo and azeotropically dried with benzene (3×). The yellow solid obtained was dissolved in THF (5 mL) and di-isopropyl ethyl amine (0.228 mL, 1.31 mmol) was added. The reaction mixture was cooled to 0° C. and tert-butyl-dimethyl silyl-trifluromethane sulfonate (0.204 mL, 0.883 mmol) was added. The reaction mixture was slowly warmed to room temperature. After 3 hours the reaction mixture was poured into saturated sodium bicarbonate solution. The resulting mixture was extracted with dichloromethane (3×10 mL). The organic layers were dried over anhydrous sodium sulfate, filtered and concentrated in vacuo. The residue was dissolved in THF (5 mL) and water (5 mL) and stirred vigorously at room temperature for 14 hours. The layers were separated The organic layer was dried over anhydrous sodium sulfate, filtered and concentrated in vacuo to give the title compound. This material was used without further purification in the next step. LC/MS (M$^+$+1) (EI) 690.4.

Step F

To a solution of the intermediate obtained from Step E (0.423 mmol) in dichloromethane (1 mL) was added 4 (R,S)-amino-3,4-dihydro-1H-benzothiopyran (84 mg, 0.423 mmol), 1-hydroxy-7-azabenzotriazole (86 mg, 0.634 mmol) diisopropylethylamine (0.148 mL, 0.846 mmol) and benzotriazole-1-yl-oxy-tris -pyrrolidino-phosphonium hexafluorophosphate (220 mg, 0.423 mmol). The reaction mixture was stirred at room temperature for 3 hours. The reaction mixture was poured into 10% citric acid solution. The resulting biphasic mixture was extracted with dichloromethane (3×10 mL). The organic layers were combined and washed with saturated sodium bicarbonate solution, dried over anhydrous sodium sulfate filtered and concentrated in vacuo. The crude material was purified by flash chromatography with 50% ethyl acetate-hexanes to give the title compound as a 1:1 mixture of diastereomers. LC/MS (M$^+$+1) 869.6.

Step G (αR,γS,2S)-N-(4S-3,4-dihydro-1H-2,2-dioxobenzothiopyranyl)-γ-hydroxy-α-(phenylmethyl)-4-[[5-(5-pyrimidinyl)-1-furanyl] methyl]-2-[[(2,2,2-trifluoroethyl)amino]carbonyl]-1-piperazinepentanamide To a solution of the intermediate obtained from Step F (110 mg, 0.126 mmol) in THF (4 mL) was added tetrabutylammonium fluoride (2 mL, 1.0M solution in THF). The reaction was stirred at room temperature for 30 minutes. The reaction mixture was concentrated in vacuo and purified by flash chromatography with 80% ethyl acetate-hexanes. The title compound was obtained as a 1:1 mixture of diatereomers. The diastereomers were separated by HPLC on a ChiralCel OD column with 25% ethanol-hexanes.

Diastereomer A: HPLC retention time 23.53 min. $^1$H NMR(400 MHz, CDCl$_3$): 9.11 (s, 1H), 8.98 (s, 2H), 8.86 (bs, 1H), 7.17–7.3 (m, 8H), 7.06 (d, J=7.8 Hz, 1H), 6.81 (d, J=3.5 Hz, 1H), 6.74 (d; J=7.4 Hz, 1H), 6.63 (bs, 1H), 6.42 (d, J=2.7 Hz, 1H), 5.63 (m, 1H), 4.34 (d, J=16.4 Hz, 1H), 4.23 (d, J=16.6 Hz, 1H), 4.0 (m, 1H), 3.7 (m, 3H), 3.45 (d, J=4.5 Hz, 2H), 2.98 (m, 4H), 2.85 (m, 2H), 2.7 (m, 4H), 2.5 (m, 2H), 1.86 (dt, J=2.3, 13.6 Hz, 1H), 1.5 (dt, J=3.4, 13.9 Hz).

Diastereomer B: HPLC retention time 33.5 min. $^1$H NMR (400 MHz, CDCl$_3$): 9.13 (s, 1H), 8.98 (s, 2H), 8.83 (bt, J=7.2 Hz, 1H), 7.41 (dd, J=1.3, 8.8 Hz, 1H), 7.19–7.32 (m, 8H), 7.06 (d, J=4.3 Hz, 1H), 6.84 (d, J=9 Hz, 1H), 6.82 (d, J=3.3 Hz, 1H), 6.41 (d, J=3.6 Hz, 1H), 5.8 (m, 1H), 4.32 (d, J=16.8 HZ, 1H), 4.18 (dd, J=3, 16.6 Hz, 1H), 4.03 (m, 1H), 3.7 (m, 3H), 3.56 (t, J=10.4 Hz, 1H), 3.3 (m, 2H), 2.8–3.0 (m, 5H), 2.5–2.7 (m, 5H), 2.4 (m, 2H), 1.85 (dt, J=1.5, 11.1 Hz, 1H), 1.54 (dt, J=3.3, 10.6 Hz, 1H).

EXAMPLE 83

(αR,γS,2S)-N-(4S-3,4-dihydro-1H-2,2-dioxobenzothiopyranyl)-γ-hydroxy-α-(phenylmethyl)-4-[[5-(2-pyridinyl)-2-furanyl]methyl]-2-[[(2,2,2-trifluoroethyl)amino]carbonyl]-1-piperazinepentanamide

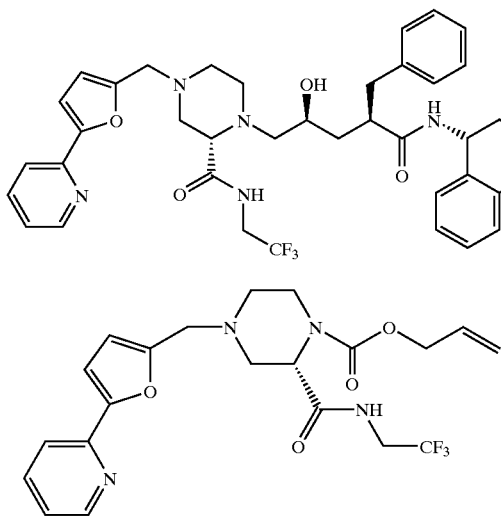

Step A

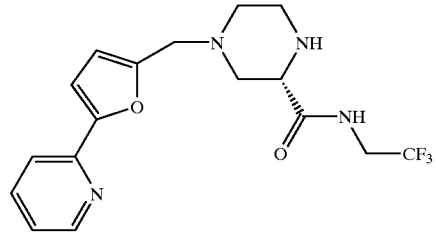

To a solution of the intermediate obtained from Example 12, Step A (310 mg, 1.05 mmol) in 1,2-dichloroethane (2 mL) was added the aldehyde obtained from Example 49 Step B (182 mg, 1.05 mmol) and sodium triacetoxy borohydride (334 mg, 1.51 mmol). The reaction was stirred at room temperature for 6 hours. The reaction mixture was poured into saturated sodium hydrogen carbonate and extracted with ethyl acetate (4×10 mL). The organic layers were combined, dried over anhydrous sodium sulfate, filtered and concentrated in vacuo. The crude material was purified by flash. chromatography with 40% ethyl acetate-hexanes to give the title compound. ¹H-NMR (CDCl₃, 400 MHz): 8.61 (d, J=4.9 Hz, 1H), 7.7 (m, 2H), 7.2 (m, 1H), 7.0 (d, J=3.3 Hz, 1H), 6.4 (d, J=3.3 Hz, 1H), 5.9 (m, 1H), 5.3 (m, 2H), 4.9 (bs, 1H), 4.6 (bm, 2H), 4.1 (m, 1H), 3.95 (m, 2H), 3.8 (d, J=14.1 Hz, 1H), 3.65 (d, J=14.1 Hz, 1H), 3.4 (bs, 1H), 3.2 (bs, 1H), 2.95 (bs, 1H), 2.4 (m, 3H).

Step B

To a solution of the intermediate obtained from Step A (350 mg, 0.77 mmol) in THF(5 mL) was added 1,3-dimethyl barbituric acid (144 mg, 0.92 mmol) and tetrakistriphenylphosphine palladium (0) (44 mg, 0.038 mmol). The resulting mixture was stirred at room temperature for 2 hours. The reaction mixture was diluted with ethyl acetate and extracted with 1N HCl (4×10 mL). The pH of the aqueous layer was adjusted to 10 with solid sodium carbonate. The aqueous layer was extracted with ethyl acetate (6×10 mL). The organic layers were combined and dried over anhydrous sodium sulfate, filtered and concentrated in vacuo to give the title compound LC/MS (M⁺+1) 369.2.

Step C

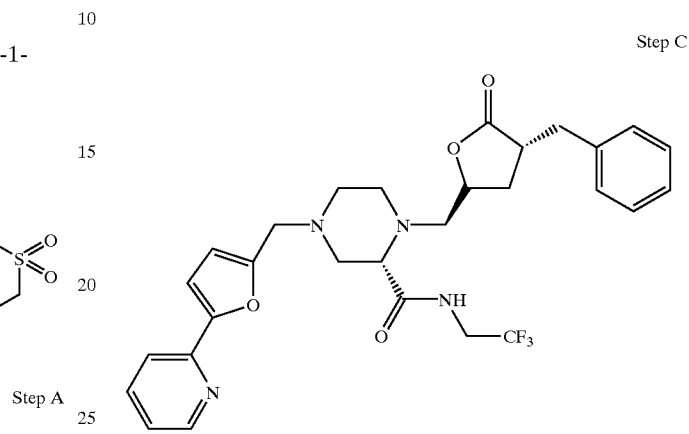

To a solution of the intermediate obtained from Step B (260 mg, 0.7 mmol) in 2-propanol was added the intermediate triflate obtained from Example 35, Step E (237 mg, 0.7 mmol) and di-isopropyl ethyl amine (0.131 mL, 0.75 mmol). The reaction was stirred at room temperature for 16 hours. The reaction mixture was concentrated in vacuo and purified by flash chromatography with ethyl acetate to give the title compound as a light yellow solid. ¹H NMR (CDCl₃, 400 MHz): 8.6 (d, J=4.9 Hz, 1H), 8.4 (bs, 1H), 7.74 (dt, J=1.7, 7.8 Hz, 1H), 7.65 (d, J=8.0 Hz, 1H), 7.3 (m, 3H), 7.2 (m, 3H), 6.99 (d, J=3.3 Hz, 1H), 6.38 (d, J=3.4 Hz, 1H), 4.45 (m, 1H), 4.1 (m, 1H), 3.73 (d, J=5 Hz, 1H), 3.65 (m, 1H), 3.63 (d, J=4.0 Hz, 1H), 3.25 (t, J=3.9 Hz, 1H), 3.18(dd, J=4.5, 13.9 Hz, 1H), 2.9 (m, 2H), 2.68–2.85 (m, 6H), 2.6 (d, J=8.3 Hz, 1H), 2.55 (dd, J=3.1, 14.5 Hz, 1H), 2.05 (m, 2H).

Step D

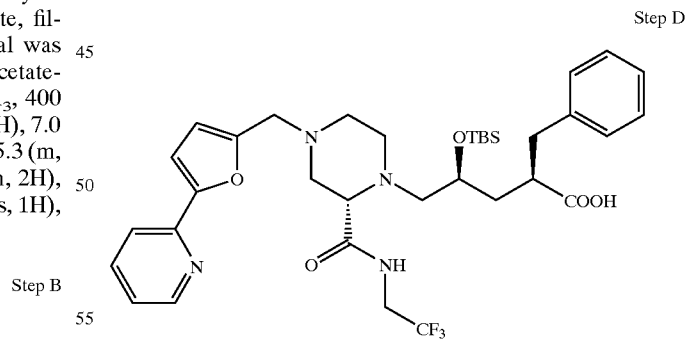

To a solution of the intermediate obtained from step C (270 mg, 0.48 mmol) in 1,4-dioxane-(4 mL) was added 1N LiOH solution (0.53 mL, 0.53 mmol). The reaction was stirred vigorously at room temperature for 16 hours. The reaction mixture was concentrated in vacuo and azeotropically dried with benzene (3×). The off-white solid obtained was dissolved in anhydrous THF (3 mL) and di-isopropyl ethyl amine (0.34 mL, 1.94 mmol) was added. The reaction mixture was cooled to 0° C. and tert-butyldimethylsilyltrifluromethane sulfonate-(0.34 mL, 1.5 mmol) was added. The reaction mixture was slowly warmed to room temperature. After 3 hours the reaction mixture was poured into saturated sodium hydrogen bicarbonate solution. The resulting mixture was extracted with dichloromethane (3×10 mL). The organic layers were dried over anhydrous sodium sulfate and concentrated in vacuo. The residue was dissolved in THF (5 mL) and water (5 mL) and stirred vigorously at room temperature for 14 hours. The layers were separated. The organic layer was dried over anhydrous sodium sulfate, filtered and concentrated in vacuo to give the title compound. This material was used without further purification in the next step.

Step E

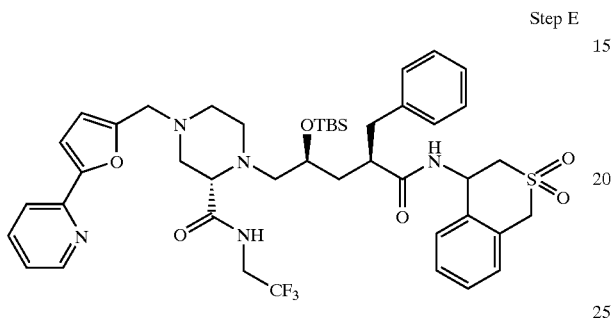

To a solution of the intermediate obtained from step D (0.485 mmol) in dichloromethane (2 mL) was added 4(R, S)-amino-3,4-dihydro-1H-benzothiopyran (95 mg, 0.485 mmol), diisopropylethylamine (0.17 mL, 0.91 mmol) and benzotriazole-1-yl-oxy-tris-pyrrolidino-phosphonium hexafluorophosphate (252 mg, 0.485 mmol). The reaction mixture was stirred at room temperature for 2 hours. The reaction mixture was poured into 10% citric acid solution. The resulting biphasic mixture was extracted with dichloromethane (3×10 mL). The organic layers were combined and washed with saturated sodium bicarbonate solution, dried over anhydrous sodium sulfate filtered and concentrated in vacuo. The crude material was purified by flash chromatography with 50% ethyl acetate-hexanes to give the title compound as a 1:1 mixture of diastereomers. LC/MS (M$^+$+1) 868.4.

Step F (αR,γS,2S)-N-(4S-3,4-dihydro-1H-2,2-dioxobenzothiopyranyl)-γ-hydroxy-α-(phenylmethyl)-4-[[5-(2-pyridinyl)-2-furanyl]methyl]-2-[[(2,2,2-trifluoroethyl)amino]carbonyl]-1-piperazinepentanamide To a solution of the intermediate obtained from step E (252 mg, 0.29 mmol) in THF (2 mL) was added tetrabutylammonium fluoride (0.32 mL, 1.0 M solution in THF). The reaction was stirred at room temperature for 16 hours. The reaction mixture was concentrated in vacuo and purified by flash chromatography with 80% ethyl acetate-hexanes. The title compound was obtained as a 1:1 mixture of diastereomers. The diastereomers were separated by HPLC on a ChiralCel OD column with 25% ethanol-hexanes.

Diastereomer A: HPLC retention time 35.2 min. $^1$H NMR (400 MHz, CDCl$_3$): 9.14 (bt, 6.1 Hz, 1H), 8.61 (dd, J=1.0, 4.9 Hz, 1H), 7.72 (dt, J=1.8, 7.8 Hz, 1H), 7.65 (d, J=8 Hz, 1H), 7.16–7.27 (m, 8H), 7.05 (d, J=7.4 Hz, 1H), 6.99 (d, J=3.1 Hz, 1H), 6.72 (d, J=5.4 Hz, 1H), 6.6 (d, J=8.4 Hz, 1H), 6.39 (d, J=3.3 Hz, 1H), 5.65 (m, 1H), 4.32 (d, J=6.4 Hz, 1H), 4.19 (d, J=6.6 Hz, 1H), 4.1 (m, 1H), 3.73 (d, J=14.1 Hz, 1H), 3.6 (m, 2H), 3.58 (d, J=15.1 Hz, 1H), 3.43 (d, J=4.7 Hz, 2H), 3.35 (bt, J=2.7 Hz, 1H), 3.0 (m, 3H), 2.62–2.85 (m, 5H), 2.59 (dd, J=3.3, 11.7 Hz, 1H), 2.49 (dt, J=3.3, 11.1 Hz, 1H), 2.41 (dd, J=2.5, 13 Hz, 1H), 1.86 (dt, J=2.7, 13.9 Hz, 1H), 1.5 (dt, J=3.5, 10.3 Hz, 1H).

Diastereomer B; HPLC retention time 57.2 min. $^1$H NMR (400 MHz, CDCl$_3$): 9.08 (bt, 5.4 Hz, 1H), 8.61 (d, J=4.1 Hz, 1H), 7.75 (dt, J=1.8, 8.1 Hz, 1H), 7.65 (d, J=8.0 Hz, 1H), 7.41 (d, J=3.6 Hz, 1H), 7.1–7.35 (m, 7H), 7.05 (d, J=9 Hz, 1H), 6.99 (d, J=3.3 Hz, 1H), 6.87 (d, J=9.6 Hz, 1H), 6.39 (d, J=3.4 Hz, 1H), 5.8 (m, 1H), 4.3 (d, J=16.6 Hz, 1H), 4.15 (m, 2H), 3.5–3.7 (m, 5H), 3.25 (m, 3H), 2.8 (m, 5H), 2.6 (m, 5H), 2.4 (m, 2H), 1.85 (dt, J=2.1, 10.7 Hz, 1H), 1.52 (dt, J=3.1, 10.5 Hz).

EXAMPLE 84

(αR,γS,2S)-N-((3S,4S)-3,4-dihydro-3-hydroxy-2H-1-benzopyran-4-yl)-γ-hydroxy-4-[1-methyl-1-[5-(2-methyl-4-pyridinyl)-2-furanyl]ethyl]-α-(phenylmethyl)-2-[[(2,2,2-trifluoroethyl)amino]carbonyl]-1-piperazinepentanamide

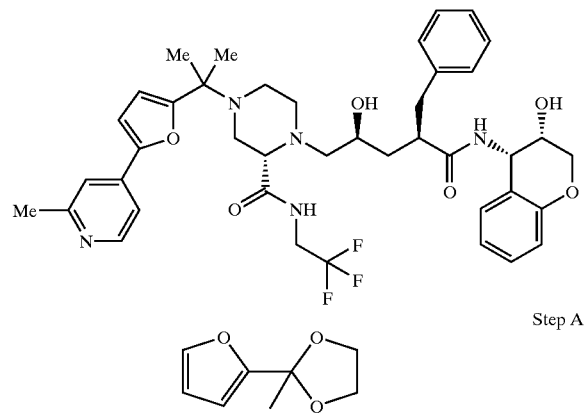

Step A

To a stirred solution of 2-acetylfuran (36.6 g; 332.4 mmol) in benzene (225 mL) was added ethylene glycol (46 mL; 831 mmol) and p-TsOH.H$_2$O (947 mg; 4.99 mmol). The reaction vessel was equipped with a Dean-Stark apparatus and heated to reflux. The next morning, the reaction mixture was poured into Et$_2$O (1.7 L) and washed with saturated NaHCO$_3$ solution, water and brine. The organic layer was dried (Na$_2$SO$_4$), filtered, and concentrated in vacuo. The crude product was purified by vacuum distillation to provide the desired ketal. $^1$H NMR (300 MHz, CDCl$_3$): δ1.73 (s, 3H), 3.97–4.08 (complex m, 4H), 6.32 (m, 1H), 7.38 (m, 2H).

Step B

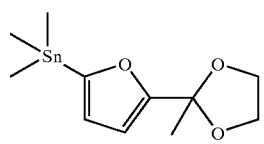

To a stirred solution of the intermediate from Step A (8.73 g; 56.6 mmol) in dry THF (250 mL) cooled to −78° C. was added dropwise tBuLi (41.5 mL; 62.3 mmol). After 15 minutes the solution was warmed to −20° C. and stirred 2 hours, at which time the reaction was cooled to −78° C. A solution of Me$_3$SnCl (13.0 g; 65.1 mmol) in dry THF (15 mL) was added dropwise. The reaction was allowed to warm to ambient temperature after 15 minutes. The reaction was quenched with saturated NaHCO$_3$; the volatiles were removed in vacuo and the residue was poured in Et₂O (1 L); washed with water, and brine; dried (Na₂SO₄), filtered, and concentrated in vacuo to provide the stannane in quantitative yield, which was used without further purification. ¹H-NMR (300 MHz, CDCl₃): δ0.32 (s, 9H), 1.74 (s, 3H), 6.31 (d, J=3.6 Hz, 1H), 6.48 (d, J=4.2 Hz, 1H).

Step C

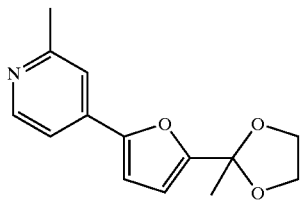

From a stirred solution of the intermediate from Step B above (500 mg; 1.58 mmol), bromopyridine intermediate from Example 51, Step A (326 mg; 1.90 mmol), and Pd(PPh₃)₄ (55 mg; 0.047 mmol) in dry DMF (8 mL), using the procedure from Example 49 Step A the deisred compound was obtained after purification by Biotage column chromatography (40S; 50% EtOAc/hexane). ¹H-NMR (300 MHz, CDCl₃): δ1.80 (s, 3H), 2.58 (s, 3H), 4.04–4.11 (complex m, 4H), 6.44 (d, J=3.4 Hz, 1H), 6.77 (d, J=3.4 Hz, 1H), 7.31 (dd, J=5.2, 1.1 Hz, 1H), 7.39 (s, 1H), 8.47 (d, J=5.2 Hz, 1H).

Step D

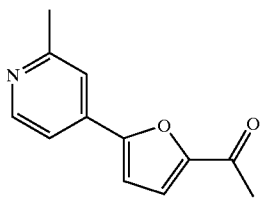

From a stirred solution of intermediate from Step C above (170 mg; 0.69 mmol) and HCl solution (2.76 mL; 2.76 mmol) in THF (3.5 L), following the procedure described in Example 46 Step E, the desired aldehyde was obtained after workup and was used without further purification. ¹H-NMR (300 MHz, CDCl₃): δ2.54 (s, 3H), 2.61 (s, 3H), 6.95 (d, J=3.7 Hz, 1H), 7.26 (d, J=3.6 Hz, 1H), 7.42 (d, J=5.2 Hz, 1H), 7.51 (s, 1H), 8.55 (d, J=5.2 Hz, 1H).

Step E

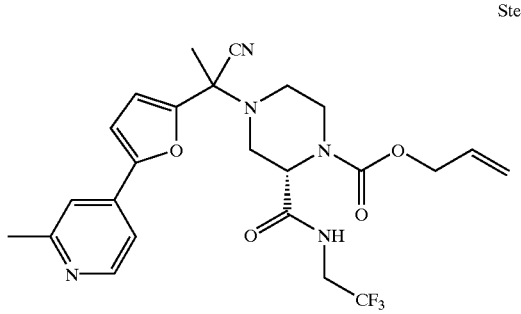

To a stirred solution of intermediate from Step D above (7.1 g; 35.4 mmol) and piperazine intermediate from Example 12 Step A (8.37 g; 28.3 mmol) in AcOH (45 mL) was added TMSCN (19.0 mL; 141.5 mmol). After a slight exotherm, the flask was equipped with a reflux condenser and the reaction was stirred at 60° C. approximately 84hours. The reaction was poured onto icy NH₄OH and extracted 3× EtOAc. The organic extracts were combined, washed with brine, dried (Na₂SO₄), filtered and volatiles removed in vacuo. Flash column chromatography (gradient elution 4% to 5% MeOH/CH₂Cl₂) provided a 2:1 mixture of desired product and starting ketone. Electrospray ionization mass spectrum: m/e 506.6 (MH⁺ calcd for C₂₄H₂₆F₃N₅O₄, 506.2).

Step F

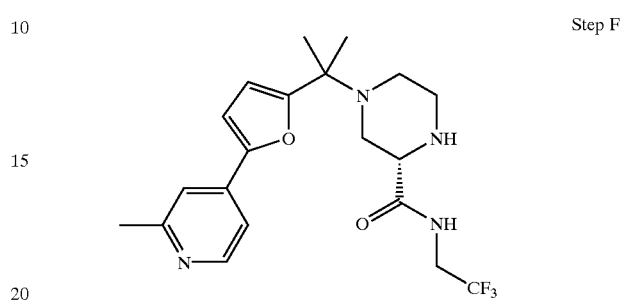

To a solution of the intermediate from Step E above (~20 mmol piperazine) and 1,3-dimethylbarbituric acid (15.6 g; 100 mmol) in dry THF (250 mL) was added Pd(PPh₃)₄ (2.31 g; 2.0 mmol). After 40 minutes the mixture was filtered through celite and the volatiles removed in vacuo. The residue was poured into EtOAc (1.6 L) and washed with 1N HCl (4×125 mL). The acid extracts were combined and brought to basic pH with KOH solution. The aqueous layer was extracted with CHCl₃ (4×300 mL) and the organic layer was dried (Na₂SO₄), filtered, and concentrated in vacuo. Purification by Biotage column chromatography (40M; 97:2:1 EtOAc:MeOH:TEA; in 2 batches) provided 7.65 g of the desired product as a yellow solid. To a vigorously stirred solution of this intermediate (7.22 g; 17.1 mmol) in dry DME (115 mL) at 0° C. was added MeMgBr (122 mL; 171 mmol) over 45 minutes. The reaction mixture was allowed to stir at ambient temperature for 100 minutes. The reaction was quenched at 0° C. with saturated NH₄Cl solution and the aqueous layer washed with EtOAc three times. The organics were combined, washed with brine, dried (Na₂SO₄), filtered, and concentrated in vacuo. Purification by Biotage column chromatography (40M; 93:5:2 EtOAc:MeOH:TEA; in 2 batches) provided the desired product. Electrospray ionization mass spectrum: m/e 411.4 (MH⁺ calcd for C₂₀H₂₅F₃N₄O₂, 411.2).

Step G

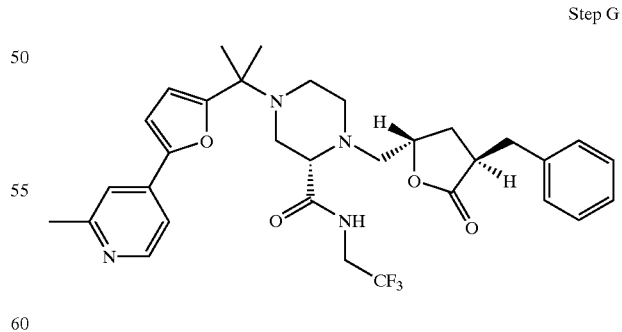

To a stirred solution of intermediate from Step G above (3.40 g; 8.28 mmol) and DIEA (1.52 mL; 8.69 mmol) in dry EPA (60 mL) was added lactone intermediate from Example 35 Step E (2.80 g; 8.28 mmol). After 2 hours, the volatiles were removed in vacuo and the residue poured into EtOAc (500 mL). After washing with saturated NaHCO₃ solution, 50% brine, and brine, drying (Na₂SO₄), filtration, and removal of volatiles in vacuo, purification by Biotage column chromatography (40M; 3% MeOH/CH$_2$Cl$_2$) provided the desired intermediate, which was carried on to Step I.

Step H

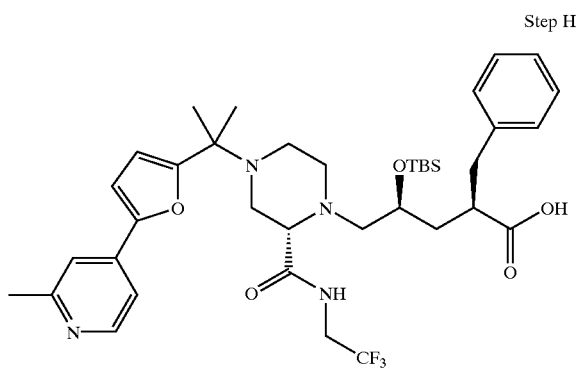

To a stirred solution of intermediate from Step H above (3.9 g; 6.51 mmol) in dry DME (35 mL) at 0° C. was added dropwise aqueous LiOH solution (7.05 mL; 7.16 mmol). After 15 minutes the brown solution was allowed to stir at ambient temperature for 1.5 hours, at which time additional LiOH (0.5 mL; 0.51 mmol) was added. After 30 minutes, the solvents were removed in vacuo at no greater than 35° C. and the residue azeotroped from benzene and MeCN until a foam was obtained. This solid was dissolved in dry EtOAc (65 mL) and dry CH$_2$Cl$_2$ (16 mL) and cooled to 0° C. DIEA (5.1 mL; 29.3 mmol) was added, followed by TBSOTf (5.25 mL; 22.8 mmol) dropwise. The ice bath was removed after 10 minutes, the yellow solution was stirred 20 minutes longer and poured into EtOAc. After washing with H$_2$O, saturated NaHCO$_3$, and brine, drying (Na$_2$SO$_4$), filtration, and removal of solvent in vacuo, purification by flash column chromatography (5% MeOH/CH$_2$Cl$_2$) yielded a mixture of mono- and bis-protected intermediate. This ester/acid mixture was dissolved in THF (145 mL)/H$_2$O (70 mL) and stirred overnight. Solvents were removed in vacuo and the residue azeotroped from benzene and MeCN. The residue was dissolved in Et$_2$O; filtered through silica, washing with EtOAc and MeOH; and the volatiles removed to provide the desired compound, which was carried on to the next step, assuming quantitative yield.

Step I

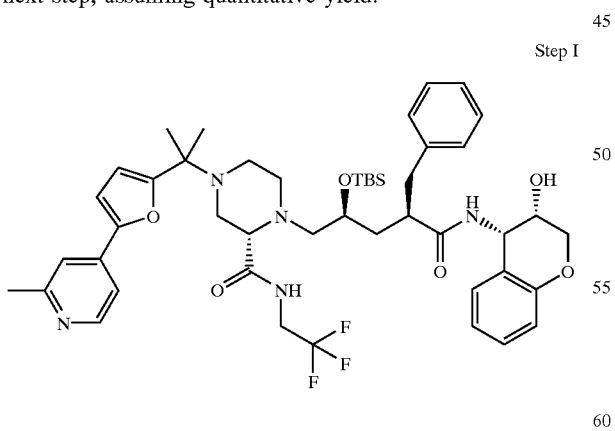

To a stirred solution of intermediate from Step I (~6.5 mmol) in dry NMP (105 mL) cooled to 0° C. was added DIEA (3.40 mL; 19.5 mmol). The following solids were then added sequentially, waiting until complete dissolution of solid occurred before added the next: HOBt (1.98 g; 14.6 mmol); intermediate from Example 12 Step P (1.18 g; 7.15 mmol); and HBTU (3.70 g; 9.75 mmol). The solution was allowed to stir at ambient temperature 45 minutes. The reaction was poured into EtOAc (2 L); washed with dilute NaHCO$_3$ solution, H$_2$O and brine; dried (Na$_2$SO$_4$), filtered, and concentrated in vacuo. Purification by Biotage column chromatography (40M; 60% EtOAc/hexane) provided the desired compound as a pale yellow solid. Electrospray ionization mass spectrum: m/e 878.5 (MH$^+$ calcd for C$_{47}$H$_{62}$F$_3$N$_5$O$_6$Si, 878.4).

Step J (αR,γS,2S)-N-((3S,4S)-3,4-dihydro-3-hydroxy-2H-1-benzopyran-4-yl)-γ-hydroxy-4-[1-methyl-1-[5-(2-methyl-4-pyridinyl)-2-furanyl]ethyl]-α-(phenylmethyl)-2-[[(2,2,2-trifluoroethyl)amino]carbonyl]-1-piperazinepentanamide To a stirred solution of intermediate from Step J above (4.0 g; 4.56 mmol) in dry THF (33 mL) was added TBAF (6.0 mL; 6.0 mmol). After 6 hours at 45–50° C., an additional 5.7 mL (5.7 mmol) TBAF was added to the reaction. Four hours later, the volatiles were removed in vacuo; the residue was poured into EtOAc (450 mL); washed with saturated NaHCO$_3$ solution, alternately with H$_2$O and brine, and finally with brine; dried (Na$_2$SO$_4$), filtered, and concentrated in vacuo. Purification by flash column chromatography (gradient elution 1% to 2% to 3% to 4% MeOH/CH$_2$Cl$_2$) provided the titled compound as a white solid. $^1$H NMR (400 MHz, CDCl$_3$): δ1.36 (m, 1H), 1.52 (s, 6H), 2.02 (m, 1H), 2.32–2.44 (complex m, 3H), 2.49 (m, 1H), 2.53 (s, 3H), 2.62 (m, 1H), 2.69–2.77 (complex m, 2H), 2.84–3.04 (complex m, 4H), 3.08 (dd, J=3.3, 7.4 Hz, 1H), 3.71–3.84 (complex m, 3H), 3.90–4.00 (complex m, 1H), 4.01–4.10 (complex m, 2H), 5.13 (d, J=4.1 Hz, 1H), 6.43 (d, J=3.5 Hz, 1H), 6.72 (dd, J=1.0, 8.2 Hz, 1H), 6.82 (apparent td, J=1.2, 7.5 Hz, 1H), 7.04 (d, J=3.6 Hz, 1H), 7.08 (apparent t, J=7.5 Hz, 2H), 7.13–7.25 (complex m, 5H), 7.45 (dd, J=1.4, 5.3 Hz, 1H), 7.52 (s, 1H), 8.35 (d, J=5.2 Hz, 1H); electrospray ionization mass spectrum: m/e 764.5 (MH$^+$ calcd for C$_{41}$H$_{48}$F$_3$N$_5$O$_6$, 764.4).

EXAMPLE 85

(αR,γS,2S)-N-[(3S,4S)-3,4-dihydro-3-hydroxy-2H-1-benzopyran-4-yl]-γ-hydroxy-4-[1-[5-(5-methoxy-3-pyridinyl)-2-oxazolyl]-1-methylethyl]-α-(phenylmethyl)-2-[[(2,2,2-trifluoroethyl)amino]carbonyl]-1-piperazinepentanamide

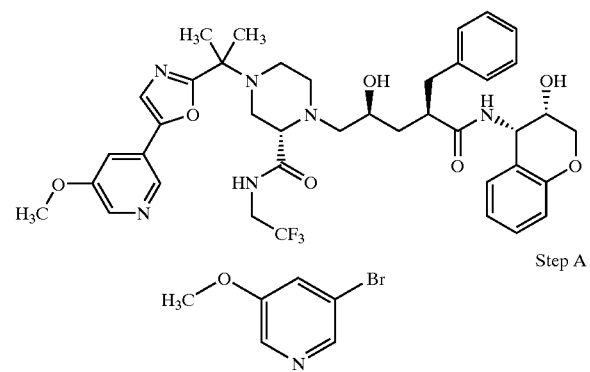

Step A

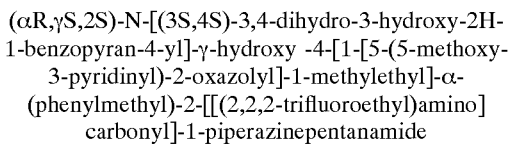

To a suspension of 3,5-dibromopyridine (300 g, 1.27 mol) in DMF (0.5 L) sodium methoxide (25% in methanol, 1.45 L, 6.33 mol) was added. It was refluxed for 6 hours (internal temperature: 91° C.). After it was cooled to room temperature, water (1 L) was added. Methanol was removed under vacuum. The residue was extracted with ethyl acetate (3×1.5 L). The combined organic layer was dried over anhydrous sodium sulfate, concentrated, and purified by flash column chromatography on silica gel with hexanes/ether=1/1 as eluant to get the title compound as a white crystal. $^1$H NMR (CDCl$_3$, 500 Hz): δ8.30 (s, 1 H), 8.25 (d, J=2.3 Hz, 1 H), 7.37–7.38 (m, 1 H), 3.87 (s, 3 H).

Step B

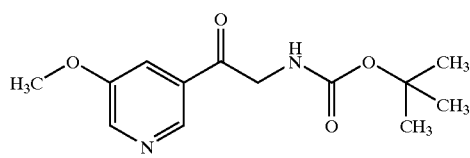

To a solution of the bromopyridine (244 g, 1.30 mol) from the previous step in anhydrous THF (1.5 L) was added isopropyl magnesium chloride (2.0 M in THF, 0.68 L, 1.36 mol) at 0° C. It was warmed to room temperature and stirred for one hour. Then it was cooled to 0° C. and N-(tert-butoxycarbonyl)glycine N'-methoxy-N'-methylamide (141.5 g, 0.65 mol) was added. It was warmed to room temperature and stirred for 10 hours. It was diluted with ethyl acetate (2 L) and washed with water (1.5 L). The organic layer was dried over anhydrous sodium sulfate, concentrated, and purified by flash column chromatography on silica gel with hexanes/ethyl acetate=1/1 as eluant to get the title compound as a pale solid. $^1$H NMR (CDCl$_3$, 500 Hz): δ8.77 (s, 1 H), 8.53 (d, J=2.8 Hz, 1 H), 7.70–7.71 (m, 1 H), 5.49 (broad s, 1 H), 4.48 (d, J=4.1 Hz, 2 H), 3.93 (s, 3 H), 1.49 (s, 9 H).

Step C

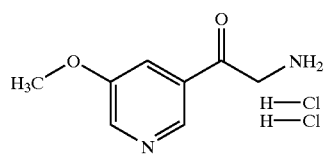

The protected aminoketone from the previous step (110 g, 486 mmol) was treated with a solution of 20% TFA in methylene chloride (300 mL) at room temperature for 8 hours. It was concentrated to get a brown gum, which was treated with hydrogen chloride in ether (1 M, 700 mL) and filtered. The filtrate was discarded. To the solid collected the above mentioned treatment with hydrogen chloride was applied for two more times. It was then dried on high vacuum to constant weight to get a pale fine powder. $^1$H NMR (D$_2$O, 500 Hz): δ8.96 (s, 1 H), 8.73 (d, J=2.5 Hz, 1 H), 8.52~8.53 (m, 1 H), 4.77 (s, 2 H), 4.07 (s, 3 H).

Step D

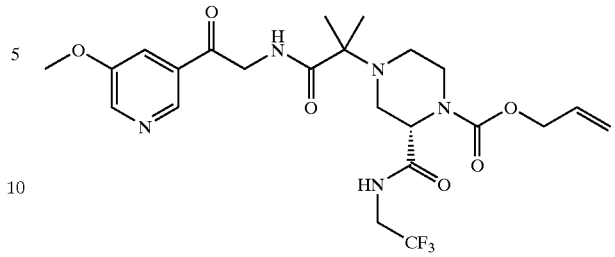

A solution of the carboxylic acid triethylamine salt form Example 66, step D (64.5 g, 169 mmol), PyBop (176 g, 338 m mol), HOAt (46 g, 338 m mol), and N,N-diisopropyl ethylamine (177 mL, 1.01 mol) in DMF (500 mL) was stirred at room temperature for 20 minutes. Then, the hydrochloride from the previous step (40 g, 169 mmol) was added. After stirring at room temperature over night, it was concentrated to a brown slur. Ethyl acetate (1.5 L) was added, and it was washed with water (3×1 L), 1 N potasium hydroxide solution and brine. It was dried over anhydrous sodium sulfate, concentrated, and purified by flash column chromatography on silica gel with hexanes/ethyl acetate=1/1 as eluant to get the title compound as a pale solid. $^1$H NMR (CDCl$_3$, 500 Hz): δ8.80 (s, 1 H), 8.52–8.53 (m, 1 H), 8.37 (broad s, 0.6 H), 7.90 (Broad s, 0.4 H), 7.70–7.71 (m, 1 H), 6.70 (broad s, 1 H), 5.94 (broad s, 1 H), 5.27–5.41 (m, 2 H), 4.87 (broad s, 1 H), 4.82 (s, 1 H), 4.67 (d, J=4.5 Hz, 2 H), 4.57 (d, J=18.3 Hz, 1 H), 4.05–4.14 (m, 2 H), 3.92 (s, 3 H), 3.66 (d, J=11.2 Hz, 1 H), 3.20–3.30 (m, 1 H), 2.90 (d, J=10.8 Hz, 1 H), 2.45 (d, J=9.3 Hz, 1 H), 2.35–2.37 (m, 1 H), 1.28 (s, 6 H).

Step E

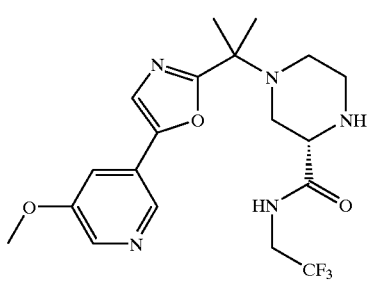

The ketoamide from the previous step (40 g, 75.5 mmol) was treated with fuming sulfuric acid (20% free SO$_3$, 80 mL) at 60° C. for 10 minutes. It was poured into excess ice. Solid potassium hydroxide was added while stirring till pH=12. It was extracted with ethyl acetate (7×0.7 L). The combined organic layer was dried over anhydrous sodium sulfate, concentrated, and purified by flash column chromatography on silica gel with ethyl acetate/methanol=10/1 as eluant to get the title compound as a white solid. $^1$H NMR (CDCl$_3$, 500 Hz): δ8.63 (broad s, 1 H), 8.50 (s, 1 H), 8.28 (s, 1 H), 7.36–7.37 (m, 1 H), 7.34 (s, 1 H), 3,91–4.00 (m, 2 H), 3.94 (s, 3 H), 3.78–3.79 (m, 1 H), 3.02–3.11 (m, 4 H), 2.88~2.91 (m, 1 H), 2.65–2.73 (m, 2 H), 1.60 (s, 3 H), 1.59 (s, 3 H).

Step F

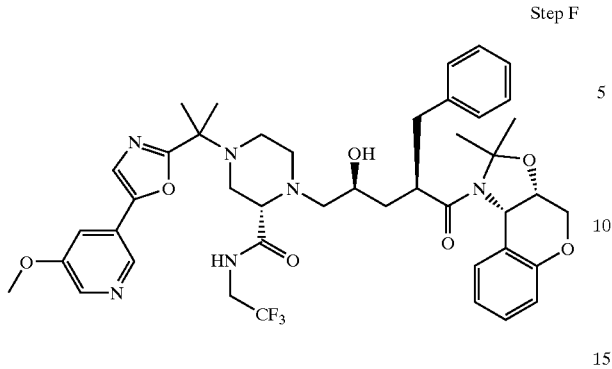

A solution of the oxazole from the previous step (24.5 g, 57.3 mmol) and the epoxide from Example 1, Step P (22.6 g, 57.3 mmol) in isopropanol (200 mL) was refluxed for 10 hours. After the solvent was removed, the residue was purified by flash column chromatography on silica gel with ethyl acetate/methanol=50/1 as eluant to get the title compound as a white solid. $^1$H NMR (CD$_3$OD, 500 Hz): δ8.48 (s, 1 H), 8.23 (d, J=2.3 Hz, 1 H), 7.64–7.65 (m, 1 H), 7.63 (s,1 H), 7.20–7.32 (m, 5 H), 7.01 (t, J=7.5 Hz, 1 H), 6.68 (d, J=8.3 Hz, 1 H), 6.45 (t, J=6.5 Hz, 1 H), 6.35 (d, J=7.7 Hz, 1 H), 5.67 (d, J=3.9 Hz, 1 H), 4.45 (d, J=2.3 Hz, 1 H), 4.32–4.35 (m, 1 H), 4.18 (d, J=3.0 Hz, 1 H), 3.93–4.00 (m, 1 H), 3.95, (s, 3 H), 3.77–3.85 (m,2 H), 3.43–3.48 (m, 1 H), 3.27 (t, J=5.1 Hz, 1 H), 3.03 (d, J=4.4 Hz, 1 H), 2.73–2.83 (m, 2 H), 2.55 (t, J=8.3 Hz, 1 H), 2.34–2.43 (m, 3 H), 1.93–1.98 (m, 1 H), 1.66 (s, 3 H), 1.52 (s, 6 H), 1.14(s, 3 H). LC-MS (M$^+$+1) (EI) 821.5.

Step G (αR,γS,2S)-N-[(3S,4S)-3,4-dihydro-3-hydroxy-2H-1-benzopyran-4-yl]-γ-hydroxy-4-[1-[5-(5-methoxy-3-pyridinyl)-2-oxazolyl]-1-methylethyl]-α-(phenylmethyl)-2-[[(2,2,2-trifluoroethyl)amino]carbonyl]-1-piperazinepentanamide To a solution of the penultimate (33.6 g, 41 mmol) from the previous step in methanol (300 mL) was added hydrogen chloride in ether (1 N, 205 mL, 205 mmol) at 0° C. It was warmed to room temperature and stirred for 10 hours. The reaction was monitored by LC-MS. After the reaction was done, excess of ammonia in methanol was added. The solvents were removed under vacuum. The residue was purified by flash column chromatography on silica gel with ethyl acetate/methanol=50/1 as eluant to get the title compound as a white solid. $^1$H NMR (CD$_3$OD, 500 Hz): δ8.49 (s, 1 H), 8.22 (d, J=1.6Hz, 1 H), 7.66–7.67 (m, 1 H), 7.20–7.25 (m, 4 H), 7.14–7.17 (m, 1 H), 7.06–7.10 (m, 2 H), 6.80 (t, J=7.6 Hz, 1 H), 6.71 (d, J=8.0 Hz, 1 H), 5.13 (d, J=3.8 Hz, 1 H), 4.04–4.06 (m, 2 H), 3.92–3.98 (m, 1 H), 3.94 (s, 3 H), 3.78–3.82 (m, 1 H), 3.72–3.77 (m, 2 H), 3.06–3.10 (m, 1 H), 2.96–3.03 (m, 2 H), 2.88–2.94 (m, 1H), 2.85 (d, J=11.2 Hz, 1 H), 2.70–2.77 (m, 2 H), 2.63–2.67 (m, 1 H), 2.44–2.50 (m, 1 H), 2.34–2.44 (m, 4 H), 2.00–2.04 (m, 1 H), 1.60 (s, 3 H), 1.59 (s, 3 H), 1.35–1.38 (m, 1 H). LC-MS (M$^+$+1) (EI) 781.5.

EXAMPLE 86

(αR,γS,2S)-N-[(3S,4S)-3,4-dihydro-3-hydroxy-2H-1-benzopyran-4-yl]4-[1-[5-(5-methyl-3-pyridinyl)-2-oxazolyl]-1-methylethyl]-γ-hydroxy-α-(phenylmethyl)-2-[[(2,2,2-trifluoroethyl)amino]carbonyl]-1-piperazinepentanamide

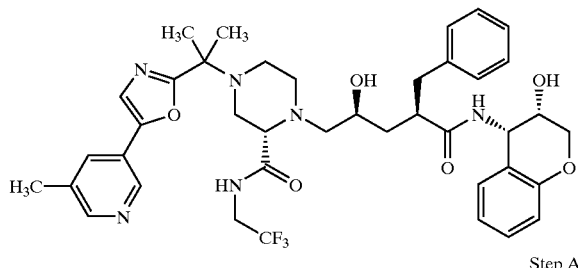

Step A

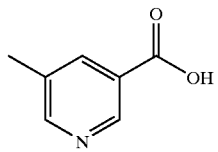

Methyl 5-methylnicotinate (28 g, 185.2 mmol) was dissolved in a mixture of THF (300 mL), methanol (100 mL) and water (100 mL). Lithium hydroxide (13.3 g, 555.7 mmol) was added. It was stirred at room temperature for 2 hours. The excess lithium hydroxide was filtered off. The filtrate was concentrated to get a white solid, which was used in the next step without further purification. $^1$H NMR (CD$_3$OD, 500 Hz): δ8.87 (s, 1 H), 8.47 (s, 2 H), 8.17–8.18 (m, 2 H), 2.38 (s, 3H).

Step B

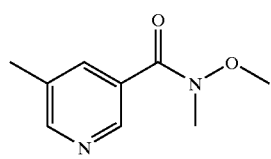

To a suspension of the nicotinic acid from the previous step (185.2 mmol) in methylene chloride (300 mL) was added 4-methyl morpholine (51 mL, 463 mmol). After stirring at room temperature for 10 minutes, it was cooled to −20° C. Then, isobutyl chloroformate (288 mL, 222.3 mmol) was dropped in. It was stirred at −20° C.~−10° C. for one hour. N,O-dimethylhydroxylamine hydrochloride (21.7 g, 185.2 mmol) was added. The reaction solution was warmed to room temperature and stirred for 6 hours. It was washed with water (3×500 mL) and brine, dried over anhydrous sodium sulfate, concentrated, and purified by flash column chromatography on silica gel with hexanes/ethyl acetate=1/1 as eluant to get the title compound as a pale sticky solid. $^1$H NMR (CDCl$_3$, 500 Hz): δ8.76 (d, J=1.4 Hz 1 H), 8.52 (d, J=1.4 Hz, 1 H), 7.82–7.83 (m, 1 H), 3.57 (s, 3 H), 3.40 (s, 3 H), 2.40 (s, 3H).

Step C

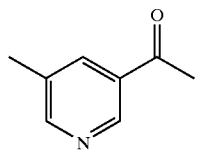

To a solution of the amide from the previous step (14.2 g, 79 mmol) in THF (100 mL) was added methyl magnesium bromide (1.4 M, 280 mL, 395 mmol) at 0° C. After stirring at 0° C. for 4 hours, the reaction solution was poured into ice. Sodium chloride was added to saturation. The aqueous layer was extracted with ethyl acetate (2×200 mL). The combined organic layer was dried over anhydrous sodium sulfate, concentrated, and purified by flash column chromatography on silica gel with hexanes/ethyl acetate=1/1 as eluant to get the title compound as a yellow oil, which was used in the next step directly. LC-MS (M$^+$+1) (EI) 136.3.

Step D

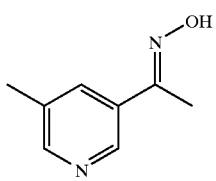

To a solution of the methylketone from the previous step (11.7 g, 86.8 mmol) and hydroxylamine hydrochloride (7.3 g, 104.2 mmol) in ethanol (100 mL) was added sodium hydroxide (5.2 g, 130.2 mmol). After refluxing for 2 hours, it was concentrated. The residue was washed with cooled water and dried on high vacuum over night to get the title compound as a white solid. $^1$H NMR (DMSO, 500 Hz): δ8.62 (s, 1 H), 8.38 (s, 1 H), 7.80(s, 1 H), 2.30 (s, 3 H), 2.15 (s, 3 H).

Step E

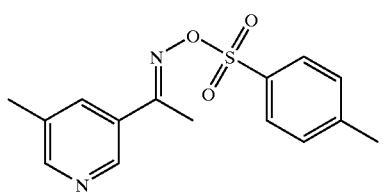

A solution of the oxime from the previous step (6.01 g, 40 mmol) and p-toluenesulfonyl chloride (9.6 g, 50 mmol) in anhydrous pyridine (25 mL) was stirred at room temperature for 24 hours to get some precipitate. Cooled water (1 L) was added to see the dissolving of the original precipitate and the formation of a new precipitate. It was stirred for one hour and filtered. The solid collected was dried under high vacuum to constant weight to get the title compound as a white solid. $^1$H NMR (CDCl$_3$, 500 Hz): δ8.63 (s, 1 H), 8.41 (s, 1 H), 7.95 (d, J=8.0 Hz, 2 H), 7.80–7.81 (m, 1 H), 7.38 (d, J=8.0 Hz, 2 H), 2.47 (s, 3 H), 2.36 (s, 3 H), 2.21 (s, 3 H).

Step F

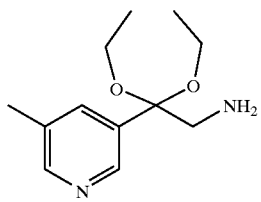

To a solution of the tosylamide from the previous step (4.82 g, 15.8 mmol) in ethanol (40 mL) was added potassium ethoxide (1.41 g, 16.3 mmol) at 0° C. It was slowly warmed to room temperature at which it was stirred for 2 hours. It was then diluted with anhydrous ether (500 mL) and filtered. To the filtrate HCl gas was bubbled in for 30 minutes to get a cloudy mixture. It was concentrated. The residue was distributed between methylene chloride (500 mL) and 1 N potassium hydroxide solution (pH=10). The organic layer was concentrated to get the titled compound as a brown sticky solid. $^1$H NMR (CDCl$_3$, 500 MHz): δ8.55 (d, J=1.8 Hz, 1 H), 8.40 (d, J=1.4 Hz, 1 H), 7.64 (d, J=0.8 Hz, 1H), 3.38–3.53 (m, 4 H), 3.02 (s, 2 H), 1.24 (t, J=7.0 Hz, 6 H).

Step G

A solution of the carboxylic acid from the Example 66, Step D (1.5 g, 3.09 mmol), O-benzoltriazol-1-N,N,N',N'-tetramethyluronium hexafluorophosphate (2.8 g, 7.42 mmol), 1-hydroxybenzotriazol hydrate (1.0 g, 7.42 mmol) and diisipropylethylamine (2.7 mL, 15.45 mmol) in DMF (10 mL) was stirred at room temperature for half hour. The aminoacetal from the previous step (833 mg, 3.71 mmol) was added. After stirring at room temperature for 24 hours, the reaction solution was distributed between ethyl acetate (200 mL) and water (200 mL). The organic layer was washed with water (200 mL) and brine. It was dried over anhydrous sodium sulfate, concentrated and purified by flash column chromatography on silica gel with ethyl acetate as eluant to give the title compound as a white solid. $^1$H NMR (CDCl$_3$, 400 MHz): δ8.69 (d, J=4.0, 1 H), 8.33 (s, 1 H), 7.84 (s, 1 H), 6.63 (t, J=6.1 Hz, 1 H), 5.89–5.99 (m, 1 H), 5.26–5.35 (m, 2 H), 4.65 (d, J=4.8 Hz, 3 H), 4.19 (dd, J=8.0, 13.6 Hz, 1 H), 3.92 (broad s, 2 H), 3.57–3.68 (m, 3 H), 3.27–3.40 (m, 3 H), 2.82 (s, 2 H), 2.79 (broad s, 1 H), 2.49 (d, J=5.6 Hz, 1 H), 2.29 (dd, J=4.0, 8.0 Hz, 1 H), 2.14 (dt, J=3.2, 11.6 Hz, 1 H), 1.18–1.25 (2t, J=7.2 Hz, 6 H), 1.04 (s, 3H), 0.95 (s, 3 H).

Step H

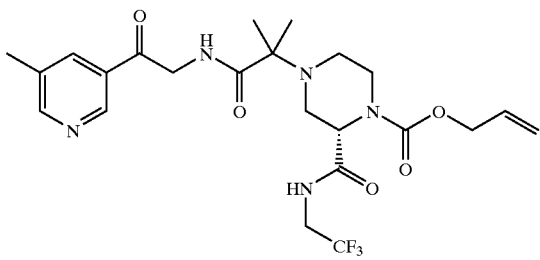

To a solution of the ketal from the previous step (2.1 g, 3.40 mmol) in THF (10 mL) was added hydrochloric acid (6 N, 10 mL). After stirring at 50° C. for 8 hours, the reaction solution was diluted with ethyl acetate (200 mL) and washed with 1 N potassium hydroxide solution. The organic layer was dried over anhydrous sodium sulfate, concentrated and purified by flash column chromatography on silica gel with ethyl acetate as eluant to give the title compound as a white solid. LC-MS (M$^+$+1) (EI) 5.88.4.

Step I

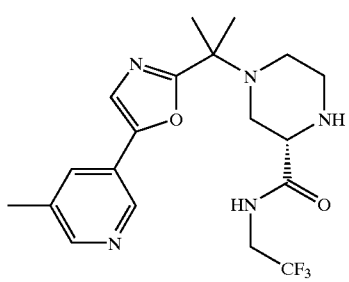

The ketoamide from the previous step (1.0 g, 1.95 mmol) was treated with fuming sulfuric acid (20% free SO$_3$, 4 mL) at 60° C. for 10 minutes. It was poured into excess ice. Solid potassium hydroxide was added while stirring till pH=12. It was extracted with ethyl acetate (5×300 mL). The combined organic layer was dried over anhydrous sodium sulfate, concentrated, and purified by flash column chromatography on silica gel with ethyl acetate/methanol=10/1 as eluant to get the title compound as a white solid. $^1$H NMR (CDCl$_3$, 500 Hz): δ8.71 (d, J=2.0 Hz, 1 H), 8.42 (d, J=1.8 Hz, 1 H), 8.10–8.12 (m, 1 H), 7.71 (broad s, 1 H), 7.33 (s, 1 H), 3,91–4.00 (m, 2 H), 2.51–3.54 (m, 1 H), 2.82–2.99 (m, 3 H), 2.78–2.81 (m, 1 H), 2.53–2.63 (m, 2 H), 2.42 (s, 3 H), 1.61 (s, 3 H), 1.60 (s, 3 H).

Step J

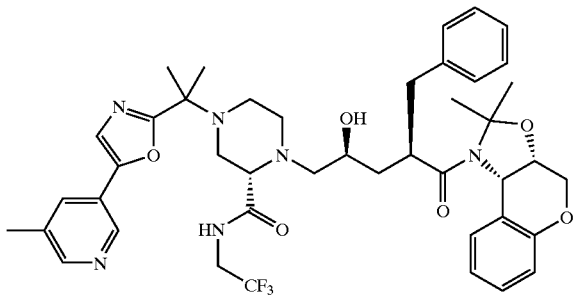

A solution of the oxazole from the previous step (320 mg, 0.78 mmol) and the epoxide from Example 1, Step P (306 mg, 0.78 mmol) in ethanol (10 mL) was refluxed for 2 days. After the solvent was removed, the residue was purified by flash column chromatography on silica gel with ethyl acetate/methanol=20/1 as eluant to get the title compound as a white solid. LC-MS (M$^+$+1) (EI) 805.4

Step K (αR,γS,2S)-N-[(3S,4S)-3,4-dihydro-3-hydroxy-2H-1-benzopyran-4-yl]-4-[1-[5-(5-methyl-3-pyridinyl)-2-oxazolyl]-1-methylethyl]-γ-hydroxy-α-(phenylmethyl)-2-[[(2,2,2-trifluoroethyl)amino]carbonyl]-1-piperazinepentanamide To a solution of the penultimate from the previous step (220 mg, 0.27 mmol) in methanol (10 mL) was added hydrogen chloride in ether (1 N, 1.4 mL, 1.4 mmol) at 0° C. It was warmed to room temperature and stirred for 12 hours. The reaction was monitored by LC-MS. After the reaction was done, excess ammonia in methanol was added. The solvents were removed under vacuum. The residue was purified on preparative TLC (2000 microns, ethyl acetate/methanol=10/1 as eluant) to get the title compound as a white solid. $^1$H NMR (CD$_3$OD, 500 Hz): δ8.70 (d, J=1.8 Hz, 1 H), 8.36 (d, J=1.3 Hz, 1 H), 7.97 (broad s, 1 H), 7.60 (s, 1 H), 7.15–7.25 (m, 5 H), 7.05–7.10 (m, 2 H), 6.80 (t, J=7.6 Hz, 1 H), 6.72 (d, J=8.0 Hz, 1 H), 5.13 (d, J=4.3 Hz, 1 H), 4.02–4.09 (m, 2 H), 3.92 –3.98 (m, 1 H), 3.78–3.82 (m, 1 H), 3.72–3.77 (m, 2 H), 3.06–3.10 (m, 1 H), 2.96–3.03 (m, 2 H), 2.88–2.94 (m, 1H), 2.85 (d, J=11.2 Hz, 1 H), 2.70–2.77 (m, 2 H), 2.63–2.67 (m, 1 H), 2.44–2.50 (m, 1 H), 2.34–2.44 (m, 4 H), 2.42 (s, 3 H), 2.00–2.04(m, 1 H), 1.60 (s, 3 H), 1.59 (s, 3 H) 1.35–1.38 (m, 1 H). LC-MS (M$^+$+1) (EI) 765.4.

EXAMPLE 87

(αR,γS,2S)-N-[(3S,4S)-3,4-dihydro-3-hydroxy-2H-1-benzopyran-4-yl]-4-[1-[5-(5-hydroxy-3-pyridinyl)-2-oxazolyl]-1-methylethyl]-γ-hydroxy-α-(phenylmethyl)-2-[[(2,2,2-trifluoroethyl)amino]carbonyl]-1-piperazinepentanamide

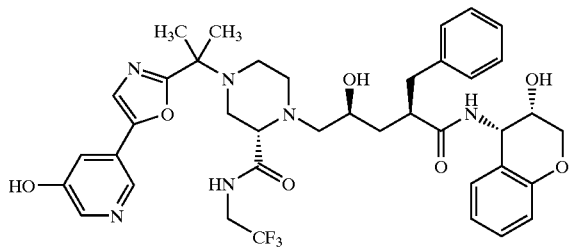

Step A

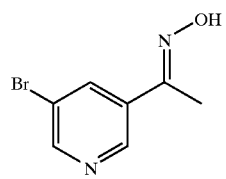

To a solution of the methylketone from Example 77, Step B (35 g, 175 mmol) and hydroxylamine hydrochloride (18.3 g, 263 mmol) in ethanol (200 mL) was added sodium hydroxide (10.5 g, 263 mmol). After refluxing for one hour, it was concentrated. The residue was washed with cooled water. The solid collected was dried under high vacuum over night to get the title compound as a white solid. $^1$H NMR (DMSO, 500 Hz): δ8.78 (d, J=1.9Hz, 1 H), 8.60 (d, J=2.3

Hz, 1 H), 8.26 (t, J=2.1 Hz, 1 H) 2.23 (s, 3 H). LC-MS (M⁺+1) (EI) 215.0, 217.0.

Step B

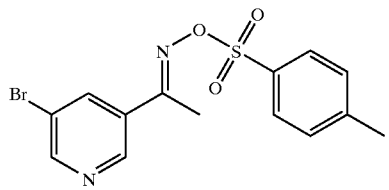

A solution of the oxime from the previous step (46 g, 218 mmol) and p-toluenesulfonyl chloride (52 g, 272.6 mmol) in anhydrous pyridine (100 mL) was stirred at room temperature for 10 hours to get some precipitate. Cooled water (1 L) was added to see the dissolving of the original precipitate and the formation of a new precipitate. It was stirred for one hour and filtered. The solid collected was dried under high vacuum to constant weight to get the title compound as a pale solid. ¹H NMR (CDCl₃, 500 Hz): δ8.74 (d, J=2.3 Hz, 1 H), 8.73 (d, J=18 Hz, 1 H), 8.04–8.05 (m, 1 H), 7.94 (d, J=7.8 Hz, 2 H), 7.38–7.41 (m, 2 H), 2.48 (s, 3 H), 2.38 (s, 3 H).

Step C

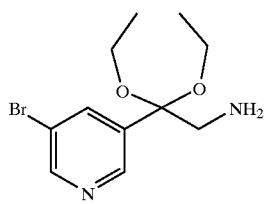

To a solution of the tosylamide from the previous step (64.8 g, 175.5 mmol) in ethanol (200 mL) was added potassium ethoxide (15.6 g, 181 mmol) at 0° C. It was slowly warmed to room temperature at which it was stirred for 10 hour. It was then diluted with anhydrous ether (1 L) and filtered. To the filtrate HCl gas was bubbled in for 30 minutes to get some precipitate. It was filtered. The solid collected was distributed between ethyl acetate (1 L) and 1 N potassium hydroxide solution (ph=10). The organic layer was concentrated to get the titled compound as a colorless oil. ¹H NMR (CDCl₃, 500 MHz): δ8.66 (d, J=1.8 Hz, 1 H), 8.65 (d, J=2.3 Hz, 1 H), 8.01 (d, J=2.1 Hz, 1H), 3.37–3.53 (m, 4 H), 3.03 (s, 2 H), 1.26 (t, J=7.0 Hz, 6 H). LC-MS (M⁺+1) (EI) 243.0.

Step D

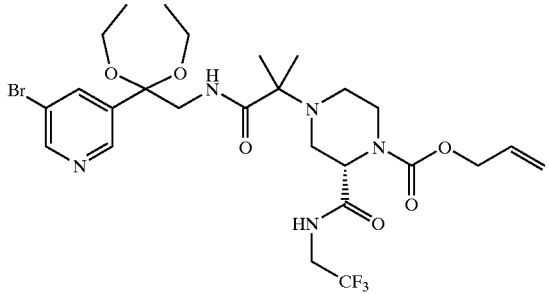

A solution of the carboxylic acid from the Example 66, Step D (6.72 g, 23.2 mmol), O-benzoltriazol-1-N,N,N',N'-tetramethyluronium hexafluorophosphate (17.6 g, 46.45 mmol), 1-hydroxybenzotriazol hydrate (6.28 g, 46.45 mmol) and diisipropylethylamine (16.9 mL, 9.6.8 mmol) in DMF (100 mL) was stirred at room temperature for half hour. The aminoacetal from the previous step (7.38 g, 19.4 mmol) was added. After stirring at room temperature for 3 hours, the reaction solution was distributed between ethyl acetate (1 L) and water (1 L). The organic layer was washed with water (1 L) and brine. It was dried over anhydrous sodium sulfate, concentrated and purified by flash column chromatography on silica gel with ethyl acetate as eluant to give the title compound as a white solid. ¹H NMR (CDCl₃, 400 MHz): 8.69 (s, 1 H), 8.60 (s, 1 H), 8.05 (s, 1 H), 7.70 (Broad s, 1 H), 5.92–5.98 (m, 1 H), 5.28–5.36 (m, 2 H), 4.67 (broad s, 2 H), 4.60 (d, J=4.5 Hz, 2 H), 4.01–4.11 (m, 1 H), 3.92 (d, J=12.7 Hz, 1 H), 3.76–3.86 (m, 1 H), 3.40–3.67 (m, 3 H), 3.28–3.32 (m, 1 H), 3.18–3.26 (m, 1 H), 2.36–2.42 (m, 2 H), 2.13–2.20 (m 1 H), 1.27 (t, J=7.1 Hz, 2 H), 1.22 (T, J=7.2 Hz, 2 H), 0.98 (s, 3H), 0.93 (s, 3 H). LC-MS (M⁺+1) (EI) 652.3.

Step E

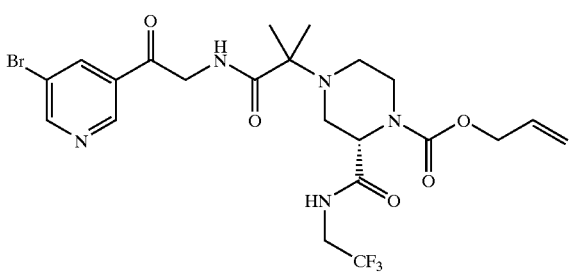

To a solution of the ketal from the previous step (5.1 g, 8.82 mmol) in THF (20 mL) was added hydrochloric acid (6 N, 20 mL). After stirring at 50° C. for 10 hours, the reaction solution was diluted with ethyl acetate (400 mL) and washed with 1 N potassium hydroxide solution. The organic layer was dried over anhydrous sodium sulfate, concentrated and purified by flash column chromatography on silica gel with ethyl acetate as eluant to give the title compound as a white solid. LC-MS (M⁺+1) (EI) 579.0, 580.0.

Step F

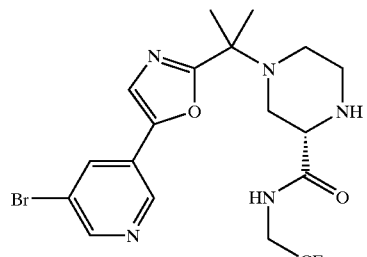

The ketoamide from the previous step (3.5 g, 6.05 mmol) was treated with fuming sulfuric acid (20% free SO₃, 10 mL) at 60° C. for 10 minutes. It was poured into excess ice. Solid potassium hydroxide was added while stirring till pH=12. It was extracted with ethyl acetate (5×200 mL). The combined organic layer was dried over anhydrous sodium sulfate and concentrated to get the title compound as a white solid. ¹H NMR (CDCl₃, 500 Hz): δ8.79 (d, J=1.6 Hz, 1 H), 8.62 (d, J=1.8 Hz, 1 H), 8.06 (broad s, 1 H), 8.03–8.04 (m, 1 H), 7.38 (s, 1 H), 3.91–3.98 (m, 2 H), 2.49–3.52 (m, 1 H), 2.93–2.98 (m, 1 H), 2.87–2.91 (m, 2 H), 2.75–2.79 (m, 1 H), 2.56–2.58 (m, 2 H), 1.59 (s, 3 H), 1.58 (s, 3 H). LC-MS (M⁺+1) (EI) 477.1, 478.1.

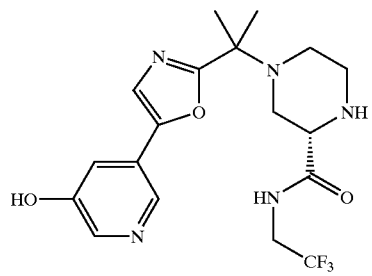

Step G

To a solution the oxazole form the previous step (500 mg, 1.05 mmol) and 18-crown-6 (1.4 g, 5.25 mmol) in DMSO (80 mL) was added potassium superoxide (522 mg, 7.35 mmol). After stirring at room at room temperature for 16 hours, it was distributed between ethyl acetate (400 mL) and water (200 mL). The organic layer was dried over anhydrous sodium sulfate and concentrated to give the title compound as a white solid. LC-MS (M⁺+1) (EI) 579.0, 580.0.

Step H (αR,γS,2S)-N-[(3S,4S)-3,4-dihydro-3-hydroxy-2H-1-benzopyran-4-yl]-4-[1-[5-(5-hydroxy-3-pyridinyl)-2-oxazolyl]-1-methylethyl]-γ-hydroxy-α-(phenylmethyl)-2-[[2,2,2-trifluoroethyl)amino]carbonyl]-1-piperazinepentanamide A solution of the oxazole from the previous step (242 mg, 0.58 mmol) and the epoxide from Example 1, Step P (230 mg, 0.58 mmol) in ethanol (10 mL) was refluxed for 16 hours. After the solvent was removed, the residue was purified by flash column chromatography on silica gel with ethyl acetate/methanol=30/1 as eluant to get a white solid (LC-MS (M⁺+1) (EI) 807.4. The solid obtained was dissolved in methanol (10 mL) and cooled to 0° C. Hydrogen chloride in ether (1 N, 0.74 mL, 0.74 mmol) was added and the reaction solution was warmed to room temperature at which it was stirred for 10 hours. The solvent was removed under vacuum. The residue was distributed between ethyl acetate (100 mL) and potassium hydroxide solution (1 N, 100 mL). The organic layer was dried over anhydrous sodium sulfate, concentrated and purified on preparative TLC (2000 microns, ethyl acetate/methanol 10/1 as eluant) to give the title compound as a white solid. ¹H NMR (CDC₃OD , 500 Hz): δ8.59 (s, 1 H), 8.37 (s, 1 H), 8.07 (s, 1 H), 7.96 (s, 1 H), 7.94 (s, 1 H), 7.16–7.28 (m, 5 H), 7.05–7.15 (m, 2 H), 6.82 (t, J=7.8 Hz, 1 H), 6.72 (d, J=7.8 Hz, 1 H), 5.13 (d, J=4.3 Hz, 1 H), 4.02–4.09 (m, 2 H), 3.92–3.98 (m, 1 H), 3,78–3.82 (m, 1 H), 3.72–3.77 (m, 2 H), 3.06–3.10 (m, 1 H), 2.96–3.03 (m, 2 H), 2.88–2.94 (m, 1H), 2.85 (d, J=11.2 Hz, 1 H), 2.70–2.77 (m, 2 H), 2.63–2.67 (m, 1 H), 2.44–2.50 (m, 1 H), 2.34–2.44 (m, 4 H), 2.42 (s, 3 H), 2.00–2.04 (m, 1 H), 1.60 (s, 3 H), 1.59 (s, 3 H), 1.35–1.38 (m, 1 H). LC-MS (M⁺+1) (EI) 767.5.

EXAMPLE 88

(αR,γS,2S)-4-[1-[5-[5-(difluoromethoxy)-3-pyridinyl]-2-oxazolyl]-1 -methylethyl]-N-[(3S,4S)-3,4-dihydro-3-hydroxy-2H-1-benzopyran-4-yl]-γ-hydroxy-α-(phenylmethyl)-2-[[(2,2,2-trifluoroethyl)amino]carbonyl]-1-piperazinepentanamide

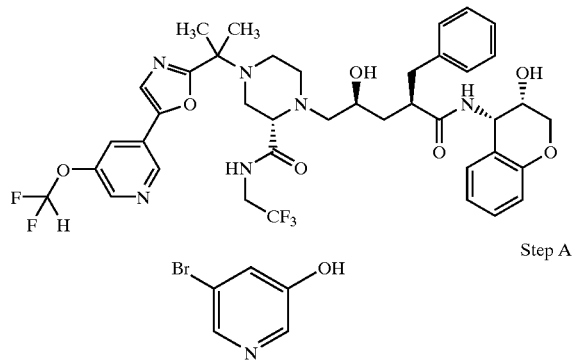

Step A

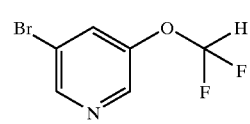

To a solution of furfurylamine (180 g, 1.85 mol) in water (500 mL) and hydrobromic acid (48%, 143 mL) at −20° C. was added bromine dropwise in 6 hours. After the addition, it was stirred at −20~−10° C. for 12 hour. Nitrogen was blew through the reaction mixture for one hour followed by the addition of saturated potassium hydroxide solution till pH=1. It was heated to reflux for 15 minutes and cooled to 80° C. Additional saturated potassiuim hydroxide solution was applied to bring the pH value to about 5.5. It was filtered. The black solid collected was dried under high vacuum and washed with boiling methanol. The methanol washes was concentrated to get the title compound as a brown solid. ¹H NMR (CD₃OD, 500 Hz): δ8.10 (d, J=1.8 Hz, 1 H), 8.07 (d, J=2.5 Hz, 1 H), 7.42–7.43 (m, 1 H). LC-MS (M⁺+1) (EI) 173.0, 175.0.

Step B

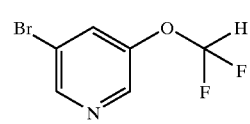

A 3-neck round bottom flask equipped with a stirring bar, a thermometer, a dry ice condenser and a gas inlet was charged with the hydroxylpyridine from the previous step (50 g, 289 mmol), sodium hydroxide (70 g, 1.73 mol), water (250 mL) and 1,4-dioxane (250 mL). Vacuum was applied for 2 minutes. It was heated to 60° C. and vacuum was applied again for 2 minutes. Then, difluorochloromethame was bubbled in for 12 hours. The reaction was monitored by LC-MS. When the start material was converted by about 80%, water (1 L) was added. It was extracted with ethyl acetate (3×1 L). The organic layer was dried over anhydrous sodium sulfate, concentrated and purified by flash column chromatography on silica gel with hexanes/ether=5/1 as eluant to give the title compound as a colorless oil. ¹H NMR (CD₃OD, 500 Hz): δ8.58 (d, J=2.1 Hz, 1 H), 8.44 (s,1 H), 7.69 (d, J=4.6 Hz, 1 H), 6.58 (t, J=72.1 Hz, 1 H). LC-MS (M⁺+1) (EI) 224.0, 226.0.

Step C

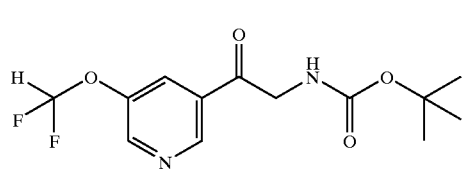

To a solution of bromopyridine from the previous step (4.5 g, 20.2 mmol) in anhydrous THF (30 mL) was added isopropyl magnesium chloride (2.0 M in THF, 26.2 mL, 13.1 mmol) at room temperature. After it was stirred for one hour N-(tert-butoxycarbonyl)glycine N'-methoxy-N'-methylamide (2.2 g, 10.1 mmol) was added. It was stirred at room temperature for 4 hours. Then, it was diluted with ethyl acetate (300 mL) and washed with water (200 mL). The organic layer was dried over anhydrous sodium sulfate, concentrated, and purified by flash column chromatography on silica gel with ethyl acetate as eluant to get the title compound as a white solid. $^1$H NMR (CDCl$_3$, 500 Hz): δ9.05 (d, J=1.6 Hz, 1 H), 8.33 (d, J=2.8 Hz, 1 H), 8.04–8.05 (m, 1 H), 6.65 (t, J=71.9 Hz, 1 H), 4.70 (d, J=4.8 Hz, 2 H), 1.38 (s, 9 H). LC-MS (M$^+$+1) (EI) 303.1.

Step D

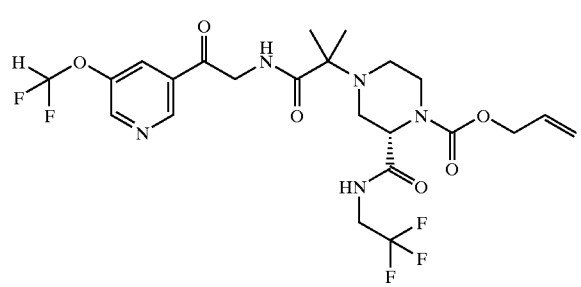

The protected aminoketone from the previous step (2.2 g, 7.28 mmol) was treated with a solution of 20% TFA in methylene chloride (20 mL) at room temperature for 6 hours. It was concentrated to get a brown gum, which was dissolved in DMF (20 mL). The carboxylic acid form Example 66, Step D (2.8 g, 7.28 mmol), PyBop (7.6 g, 14.6 mmol) and HOAt (2.0 g, 14.6 mmol) was added. After it was stirred at room temperature for 20 minutes, N,N-diisopropyl ethylamine (7.6 mL, 43.7 mmol) was added. After stirring at room temperature for 10 hours, it was diluted with methylene chloride (300 mL) and washed with water (150 mL), 1 N potassium hydroxide solution (100 mL) and brine. The organic layer was dried over anhydrous sodium sulfate, concentrated, and purified by flash column chromatography on silica gel with ethyl acetate as eluant to get the title compound as a yellow solid. $^1$H NMR (CDCl$_3$, 500 Hz): δ9.06 (d, J=1.8 Hz, 1 H), 8.71 (d, J=2.3 Hz, 1 H), 8.44 (broad s, 1 H), 8.02–8.03 (m, 1 H), 6.70 (broad s, 1 H), 6.64 (t, J=72.1 Hz, 1 H), 5.94 (broad s, 1 H), 5.27–5.41 (m, 2 H), 4.87 (broad s, 1 H), 4.82 (s, 1 H), 4.67 (d, J=4.5 Hz, 2 H), 4.57 (d, J=18.3 Hz, 1 H), 4.05–4.14 (m, 2 H), 3.66 (d, J=11.2 Hz, 1 H), 3.20–3.30 (m, 1 H), 2.90 (d, J=10.8 Hz, 1 H), 2.45 (d, J=9.3 Hz, 1 H), 2.35–2.37 (m, 1 H), 1.30 (s,3H), 1.28 (s, 3 H). LC-MS (M$^+$+1) (EI) 566.2.

Step E

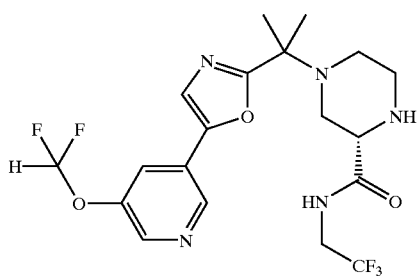

The ketoamide from the previous step (2.1 g, 3.7 mmol) was treated with fuming sulfuric acid (20% free SO$_3$, 10 mL) at 60° C. for 10 minutes. It was poured into excess ice. Solid potassium hydroxide was added while stirring till pH=12. It was extracted with ethyl acetate (5×100 mL). The combined organic layer was dried over anhydrous sodium sulfate and concentrated to get the title compound as a white solid. $^1$H NMR (CDCl$_3$, 500 Hz): δ8.79 (d, J=1.8 Hz, 1 H), 8.47 (d, J=2.5 Hz, 1 H), 8.02–8.03 (m, 1 H), 7.69–7.70 (m, 1 H), 6.65 (t, J=72.3 Hz, 1 H), 3.94–3.99 (m, 2 H), 3.51–3.53 (m, 1 H), 2.96–2.98 (m, 1 H), 2.89–2.93 (m, 2 H), 2.78–2.81 (m, 1 H), 2.57–2.61 (m, 2 H), 1.62 (s, 3 H), 1.61 (s, 3 H). LC-MS (M$^+$+1) (EI) 464.2.

Step F (αR,γS,2S)-4-[1-[5-[5-(difluoromethoxy)-3-pyridinyl]-2-oxazolyl]-1-methylethyl]-N-[(3S,4S)-3,4-dihydro-3-hydroxy-2H-1-benzopyran-4-yl]-γ-hydroxy-α-(phenylmethyl)-2-[[(2,2,2-trifluoroethyl)amino]carbonyl]-1-piperazinepentanamide A solution of the oxazole from the previous step (1.08 g, 2.33 mmol) and the epoxide from Example 1, Step P (916 mg, 2.33 mmol) in ethanol (20 mL) was refluxed for 28 hours. After the solvent was removed, the residue was purified by flash column chromatography on silica gel with ethyl acetate/methanol=30/1 as eluant to get a white solid. (LC-MS (M$^+$+1) (EI) 857.4. The solid obtained was dissolved in methanol (10 mL) and cooled to 0° C. Hydrogen chloride in ether (1 N, 6.8 mL, 6.8 mmol) was added and the reaction solution was warmed to room temperature at which it was stirred for 12 hours. The solvent was removed under vacuum. The residue was distributed between ethyl acetate (100 mL) and potassium hydroxide solution (1 N, 100 mL). The organic layer was dried over anhydrous sodium sulfate, concentrated and purified on preparative HPLC to give the title compound as a white solid. $^1$H NMR (CD$_3$OD, 500 Hz): δ8.79 (d, J=1.6 Hz, 1 H), 8.41 (d, J=2.6 Hz, 1 H), 7.91–7.92 (m, 1 H), 7.69 (s, 1 H), 7.14–7.25 (m, 5 H), 7.03–7.10 (m, 2 H), 6.80 (t, J=7.5 Hz, 1 H), 6.71 (d, J=8.0 Hz, 1 H), 5.13 (d, J=4.0 Hz, 1 H), 4.02–4.09 (m, 2 H), 3.91–3.98 (m, 1 H), 3.78–3.84 (m, 1 H), 3.71–3.76 (m, 2H), 3.07–3.11 (m, 1 H), 2.95–3.04 (m, 2 H), 2.88–2.94 (m, 1H), 2.85 (d, J=11.2 Hz, 1 H), 2.70–2.78 (m, 2 H), 2.63–2.68 (m, 1 H), 2.45–2.49 (m, 1 H), 2.34–2.44 (m, 4 H), 1.98–2.04 (m, 1 H), 1.60 (s, 3 H), 1.59 (s, 3 H), 1.35–1.38 (m, 1 H). LC-MS (M$^+$+1) (EI) 817.4.

EXAMPLE 89

(αR,γS,2S)-4-[1-[5-[5-(difluoromethyl)-3-pyridinyl]-
2-oxazolyl]-1-methylethyl]-N-[(3S,4S)-3,4-dihydro-
3-hydroxy-2H-1-benzopyran-4-yl]-γ-hydroxy-α-
(phenylmethyl)-2-[[(2,2,2-trifluoroethyl)amino]
carbonyl]-1-piperazinepentanamide

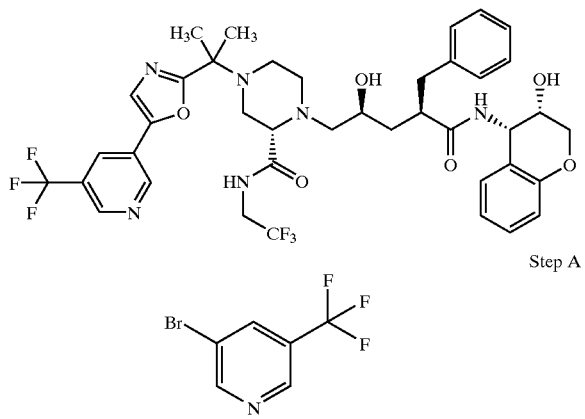

Step A

To a solution of the bromopyridine from Example 59, Step D (1 g, 5.38 mmol) in methylene chloride (10 mL) was added [bis(2-methoxyethyl)amino]sulfur trifluoride (1.5 mL, 8.06 mmol). After stirring at room temperature for two hours, it was washed with potassium hydroxide solution (1 N, 50 mL). The organic layer was dried over anhydrous sodium sulfate, concentrated and purified by flash column chromatography on silica gel with hexanes/ether=2/1 as eluant to give the title compound as a white crystal. $^1$H NMR (CDCl$_3$, 500 Hz): δ8.84 (s, 1 H), 8.71 (s, 1 H), 8.03 (s, 1 H), 7.73 (dt, J=2.1, 53.0 Hz, 1 H). LC-MS (M$^+$+1) (EI) 208.0, 210.0

Step B

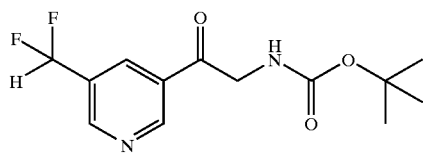

To a solution of bromopyridine from the previous step (1.58 g, 7.63 mmol) in anhydrous THF (20 mL) was added isopropyl magnesium chloride (2.0 M in THF, 4.96 mL, 9.92 mmol) at room temperature. After it was stirred for one hour N-(tert-butoxycarbonyl)glycine N'-methoxy-N'-methylamide (833 mg, 3.82 mmol) was added. It was stirred at room temperature for 10 hours. Then, it was diluted with ethyl acetate (300 mL) and washed with water (200 mL). The organic layer was dried over anhydrous sodium sulfate, concentrated, and purified by flash column chromatography on silica gel with ethyl acetate as eluant to get the title compound as a yellow solid. LC-MS (M$^+$+1) (EI) 287.2.

Step C

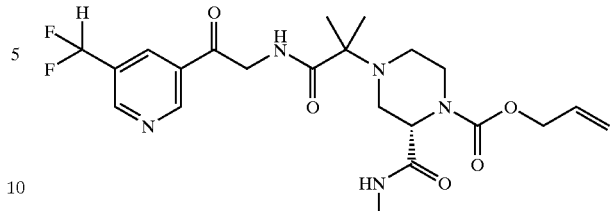

The protected aminoketone from the previous step (1.0 g, 3.49 mmol) was treated with a solution of 20% TFA in methylene chloride (10 mL) at room temperature for 6 hours. After the solvent was removed, the residue was dissolved in DMF (10 mL). The carboxylic acid form Example 66, Step D (1.33 g, 3.49 mmol), PyBop (3.63 g, 6.98 mmol) and HOAt (0.95 g, 6.98 mmol) was added. After it was stirred at room temperature for 20 minutes, N,N-diisopropyl ethylamine (3.65 mL, 21 mmol) was added. It was stirred at room temperature for 10 hours and then, diluted with methylene chloride (200 mL) and washed with water (100 mL), 1 N potassium hydroxide solution (100 mL) and brine. The organic layer was dried over anhydrous sodium sulfate, concentrated, and purified by flash column chromatography on silica gel with ethyl acetate as eluant to get the title compound as a yellow solid. LC-MS (M$^+$+1) (EI) 550.5.

Step D

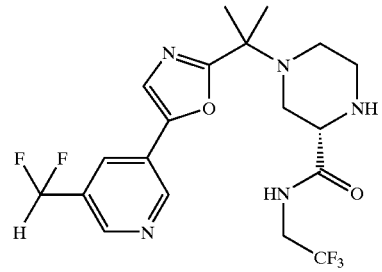

The ketoamide from the previous step (1.1 g, 2.0 mmol) was treated with fuming sulfuric acid (20% free SO$_3$, 3 mL) at 60° C. for 10 minutes. It was poured into excess ice. Solid potassium hydroxide was added while stirring till pH=12. It was extracted with ethyl acetate (5×100 mL). The combined organic layer was dried over anhydrous sodium sulfate and concentrated to get the title compound as a white solid. $^1$H NMR (CDCl$_3$, 500 Hz): δ9.02 (s, 1 H), 8.73 (s, 1 H), 8.05–8.06 (m, 1 H), 8.03–6.04 (m, 1 H), 7.45 (s, 1 H), 6.80 (t, J=56.0 Hz, 1 H), 3.94–3.99 (m, 2 H), 3.51–3.53 (m, 1 H), 2.96–2.98 (m, 1 H), 2.89–2.93 (m, 2 H), 2.78–2.81 (m, 1 H), 2.57–2.61 (m, 2 H), 1.62 (s, 3 H), 1.61 (s, 3 H). LC-MS (M$^+$+1) (EI) 447.2.

Step E (αR,γS,2S)-4-[1-[5-[5-(difluoromethyl)-3-pyridinyl]-
2-oxazolyl]-1-methylethyl]-N-[(3S,4S)-3,4-dihydro-
3-hydroxy-2H-1-benzopyran-4-yl]-γ-hydroxy-α-
(phenylmethyl)-2-[[(2,2,2-trifluoroethyl)amino]
carbonyl-]-1-piperazinepentanamide A solution of the oxazole from the previous step (330 mg, 0.74 mmol) and the epoxide from Example 1, Step P (290 mg, 0.74 mmol) in ethanol (20 mL) was refluxed for 20 hours. After the solvent was removed, the residue was purified by flash column chromatography on silica gel with ethyl acetate/methanol=30/1 as eluant to get a white solid. (LC-MS (M$^+$+1) (EI) 841.4. The solid obtained was dissolved in methanol (10 mL) and cooled to 0° C. Hydrogen chloride in ether (1 N, 2.0 mL, 2.0 mmol) was added and the reaction solution was warmed to room temperature at which it was stirred for 12 hours. The solvent was removed under vacuum. The residue was distributed between ethyl acetate (100 mL) and potassium hydroxide solution (1 N, 100 mL). The organic layer was dried over anhydrous sodium sulfate, concentrated and purified on preparative HPLC to give the title compound as a white solid. $^1$H NMR (CD$_3$OD, 500 Hz): δ9.07 (s, 1 H), 8.72 (s, 1 H), 8.29 (s, 1H), 7.74 (s, 1 H), 7.14–7.25 (m, 5 H), 7.03–7.10 (m, 2 H), 6.80 (t, J=7.5 Hz, 1 H), 6.71 (d, J=8.0 Hz, 1 H), 5.13 (d, J=4.0 Hz, 1 H), 4.02–4.09 (m, 2 H), 3.91–3.98 (m, 1 H), 3.78–3.84 (m, 1 H), 3.71–3.76 (m, 2 H), 3.07–3.11 (m, 1 H), 2.95–3.04 (m, 2 H), 2.88–2.94 (m, 1H), 2.85 (d, J=11.2 Hz, 1 H), 2.70–2.78 (m, 2 H), 2.63–2.68 (m, 1 H), 2.45–2.49 (m, 1 H), 2.34–2.44 (m, 4 H), 1.98–2.04 (m, 1 H), 1.60 (s, 3 H), 1.59 (s, 3 H), 1.35–1.38 (m, 1 H). LC-MS (M$^+$+1) (EI) 801.4

EXAMPLE 90

(αR,γS,2S)-N-[(3S,4S)-3,4-dihydro-3-hydroxy-2H-1-benzopyran-4-yl]-4-[1-[5-(2-fluorophenyl)-2-oxazolyl]-1-methylethyl]-γ-hydroxy-α-(phenylmethyl)-2-[[(2,2,2-trifluoroethyl)amino]carbonyl]-1-piperazine-pentanamide

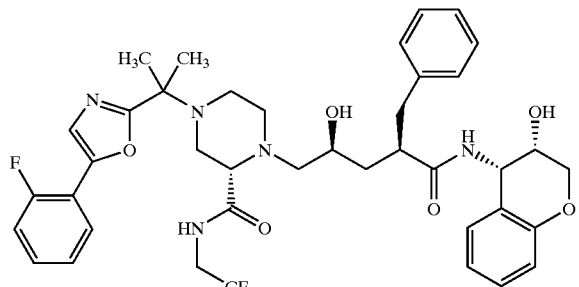

Step A

To a solution of 2'-fluoroacetophenone (40 g, 290 mmol) and hydroxylamine hydrochloride (30.2 g, 434 mmol) in ethanol (200 mL) was added sodium hydroxide (17.4 g, 434 mmol). After refluxing for 12 hour, it was concentrated. The residue was washed with cooled water and dried on high vacuum over night to get the title compound as a white solid. $^1$H NMR (CD$_3$OD, 400 Hz): δ7.44 (dt, J=1.6, 7.5 Hz, 1 H), 7.36–7.40 (m, 1 H), 7.16 (t, J=7.5 Hz, 1 H), 7.12 (dd, J=8.5, 11.2 Hz, 1 H), 2.21 (d, J=2.3 Hz, 3 H). LC-MS (M$^+$+1) (EI) 154.1

Step B

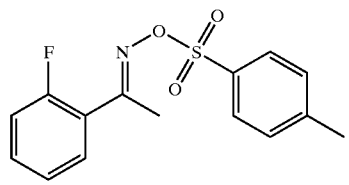

A solution of the oxime from the previous step (42.0 g, 273.4 mmol) and p-toluenesulfonyl chloride (65.2 g, 341.7 mmol) in anhydrous pyridine (100 mL) was stirred at room temperature for one hours to get some precipitate. Cooled water (1 L) was added to see the dissolving of the original precipitate and the formation of a new precipitate. It was stirred for one hour and then filtered, the resulting solid was washed with cooled water and dried under high vacuum to constant weight to get the title compound as a pale solid. $^1$H NMR (CDCl$_3$, 400 Hz): δ7.93 (d, J=7.8 Hz, 2 H), 7.34–7.45 (m, 4 H), 7.15 (dt, J=1.0, 7.6 Hz, 1 H), 7.07–7.12 (m, 1 H), 2.46 (s, 3 H), 2.38 (d, J=1.8 Hz, 3 H).

Step C

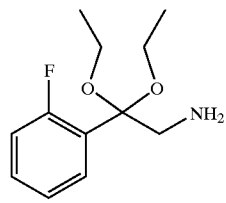

To a solution of the tosylamide from the previous step (63.9 g, 207.9 mmol) in ethanol (100 mL) was added potassium ethoxide (18.8 g, 218.3 mmol) in ethanol (800 mL) at 0° C. It was slowly warmed to room temperature at which it was stirred for one hour to see a precipitate. It was then diluted with anhydrous ether (1 L) and filtered. To the filtrate hydrogen chloride gas was bubbled in for 30 minutes to get some white precipitate. It was concentrated. The residue was distributed between ethyl acetate (1 L) and 1 N potassium hydroxide solution (pH=10). The organic layer was concentrated and vacuum distilled to get the titled compound as a colorless oil. $^1$H NMR (CDCl$_3$, 400 MHz): δ7.73 (dt, J=1.8,7.8 Hz, 1 H), 7.30–7.35 (m, 1 H), 7.16 (dt, J=1.4, 7.8 Hz, 1H), 7.02–7.08 (m, 1 H), 3.37–3.54 (m, 4 H), 3.15 (s, 2 H), 1.25 (t, J=7.0 Hz, 6 H). LC-MS (M$^+$+1) (EI) 182.2, 228.2.

Step D

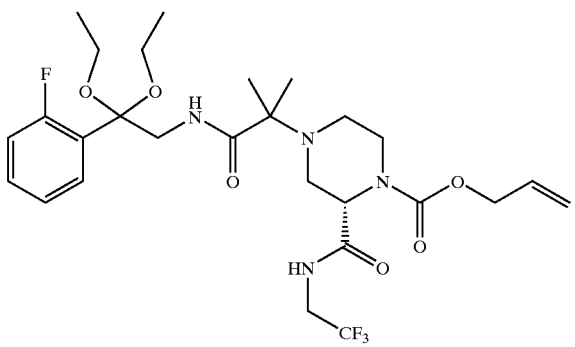

A solution of the carboxylic acid from the Example 66, Step D (1.5 g, 3.09 mmol), O-benzoltriazol-1-N,N,N',N'-tetramethyluronium hexafluorophosphate (2.8 g, 7.42 mmol), 1-hydroxybenzotriazol hydrate (1.0 g, 7.42 mmol) and diisipropylethylamine (2.7 mL, 15.5 mmol) in DMF (10 mL) was stirred at room temperature for half hour. The aminoacetal from the previous step (844 mg, 3.71 mmol) was added. After stirring at room temperature for 10 hours, the reaction solution was distributed between ethyl acetate (500 mL) and water (500 mL). The organic layer was washed with water (500 mL) and brine. It was dried over anhydrous sodium sulfate, concentrated and purified by flash column chromatography on silica gel with hexanes/ethyl acetate=3/1 as eluant to give the title compound as a white solid. $^1$H NMR (CD$_3$OD, 400 MHz): 7.66 (dt, J=1.6, 7.8 Hz, 1 H), 7.31–7.37 (m, 1 H), 7.21 (broad s, 1 H), 7.10–7.14 (m, 1 H), 7.01–7.07 (m, 1 H), 5.28–5.36 (m, 2 H), 4.67 (broad s, 2 H), 4.60 (d, J=4.5 Hz, 2 H), 4.01–4.11 (m, 1 H), 3.92 (d, J=12.7 Hz, 1 H), 3.76–3.86 (m, 1 H), 3.40–3.67 (m, 3 H), 3.28–3.32 (m, 1 H), 3.18–3.26 (m, 1 H), 2.36–2.42 (m, 2 H), 2.13–2.20 (m 1 H), 1.27 (t, J=7.2 Hz, 2 H), 1.18 (T, J=7.2 Hz, 2 H), 0.99 (s, 3H), 0.88 (s, 3 H). LC-MS (M$^+$+1) (EI) 591.2, 544.2.

Step E

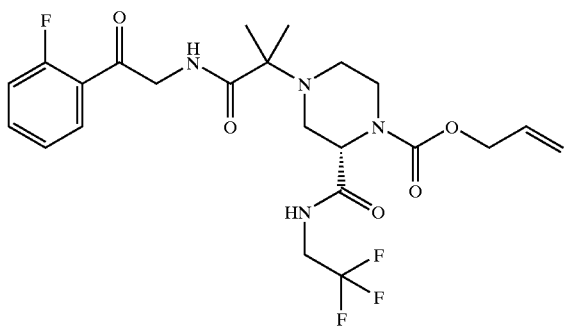

To a solution of the ketal from the previous step (1.4 g, 2.37 mmol) in THF (10 mL) was added hydrochloric acid (6 N, 20 mL). After stirring at 50° C. for 10 hours, the reaction solution was diluted with ethyl acetate (200 mL) and washed with 1 N potassium hydroxide solution. The organic layer was dried over anhydrous sodium sulfate, concentrated and purified by flash column chromatography on silica gel with hexanes/ethyl acetate=1/2 as eluant to give the title compound as a white solid. $^1$H NMR (CDCl$_3$, 400 MHz): 8.42 (broad s, 1 H), 7.93 (dt, J=1.8, 7.6 Hz, 1 H), 7.55–7.61 (m, 1 H), 7.22–7.30 (m, 1 H), 7.15–7.22 (m, 1 H), 6.65 (broad s, 1 H), 5.95 (broad s, 1 H), 5.28–5.36 (m, 2 H), 4.67 (broad s, 2 H), 4.60 (d, J=4.5 Hz, 2 H), 4.01–4.11 (m, 1 H), 3.92 (d, J=12.7 Hz, 1 H), 3.76–3.86 (m, 1 H); 3.40–3.67 (m, 3 H), 3.28–3.32 (m, 1 H), 2.87 (d, J=11.2 Hz, 1 H), 2.44 (dd, J=3.7, 11.8 Hz, 1 H), 2.33 (dt, J=3.3, 11.8 Hz 1 H), 1.29 (s, 3H), 1.26 (s, 3 H). LC-MS (M$^+$+1) (EI) 517.5.

Step F

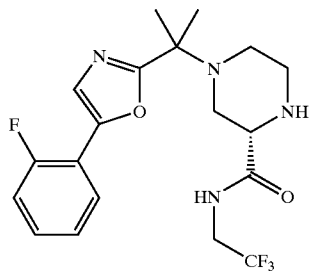

Sulfuric acid (double distilled, 8 mL) was treated with phosphorus pentoxide (651 mg, 2.3 mmol) and added to the ketoamide from the previous step (790 mg, 1.53 mmol). After stirring at 100° C. for 10 minutes the reaction solution was poured into excess ice. Solid potassium hydroxide was added while stirring till pH=12. It was extracted with ethyl acetate (5×200 mL). The combined organic layer was dried over anhydrous sodium sulfate, concentrated and purified by flash column chromatography on silica gel with ethyl acetate/methanol=10/1 as eluant to get the title compound as a white solid. $^1$H NMR (CDCl$_3$, 400 Hz): δ8.19 (broad s, 1 H), 7.73 (dt, J=1.8, 7.6 Hz, 1 H), 7.40 (d, J=3.9 Hz, 1 H), 7.30–7.36 (m, 1 H), 7.15–7.27 (m, 2 H), 3.91–3.98 (m, 2 H), 2.49–3.52 (m, 1 H), 2.93–2.98 (m, 1 H), 2.87–2.91 (m, 2 H), 2.75–2.79 (m, 1 H), 2.56–2.58 (m, 2 H), 1.61 (s, 3 H), 1.60 (s, 3 H). LC-MS (M$^+$+1) (EI) 415.2.

Step G (αR,γS,2S)-N-[(3S,4S)-3,4-dihydro-3-hydroxy-2H-1-benzopyran-4-yl]-4-[1-[5-(2-fluorophenyl)-2-oxazolyl]-1-methylethyl]-γ-hydroxy-α-(phenylmethyl)-2-[[(2,2,2-trifluoroethyl)amino]carbonyl]-1-piperazine-pentanamide A solution of the oxazole from the previous step (330 mg, 0.80 mmol) and the epoxide from Example 1, Step P (344 mg, 0.80 mmol) in ethanol (15 mL) was refluxed for 14 hours. After the solvent was removed, the residue was purified by flash column chromatography on silica gel with hexanes/ethyl acetate=1/2 as eluant to get a pale solid. (LC-MS (M$^+$+1) (EI) 808.4. The solid obtained was dissolved in methanol (10 mL) and cooled to 0° C. Hydrogen chloride in ether (1 N, 1.90 mL, 1.90 mmol) was added and the reaction solution was warmed to room temperature at which it was stirred for 12 hours. The solvent was removed under vacuum. The residue was purified on preparative HPLC to give the title compound as a white solid. $^1$H NMR (CD$_3$OD, 500 Hz): δ7.79 (dt, J=1.6 7.5 Hz, 1 H), 7.36–7.43 (m, 2 H), 7.19–7.32 (m, 6 H), 7.13–7.17 (m, 1H), 7.05–7.11 (m, 2 H), 6.80 (t, J=7.5 Hz, 1 H), 6.71 (d, J=8.0 Hz, 1 H), 5.13 (d, J=4.0 Hz, 1 H), 4.02–4.09 (m, 2 H), 3.91–3.98 (m, 1 H), 3.78–3.84 (m, 1 H), 3.71–3.76 (m, 2 H), 3.07–3.11 (m, 1 H), 2.95–3.04 (m, 2 H), 2.88–2.94 (m, 1H), 2.85 (d, J=11.2 Hz, 1 H), 2.70–2.78 (m, 2 H), 2.63–2.68 (m, 1 H), 2.45–2.49 (m, 1 H), 2.34–2.44 (m, 4 H), 1.98–2.04 (m, 1 H), 1.60 (s, 3 H), 1.59 (s, 3 H), 1.35–1.38 (m, 1 H). LC-MS (M$^+$+1) (EI) 768.4

EXAMPLE 91

(αR,γS,2S)-N-[(3S,4S)-3,4-dihydro-3-hydroxy-2H-1-benzopyran-4-yl]-4-[1-[5-(3-fluorophenyl)-2-oxazolyl]-1-methylethyl]-γ-hydroxy-α-(phenylmethyl)-2-[[(2,2,2-trifluoroethyl)amino]carbonyl]-1-piperazinepentanamide

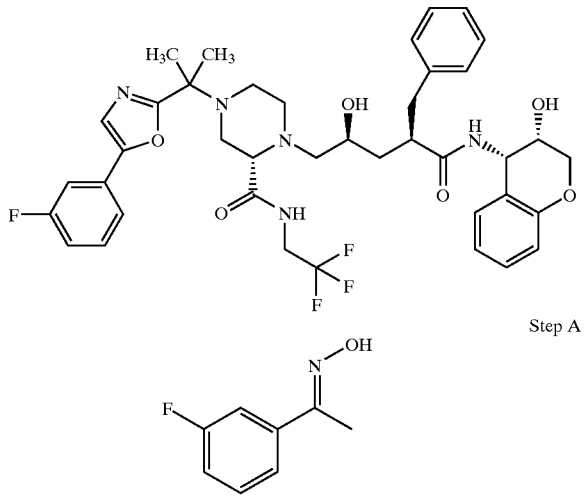

Step A

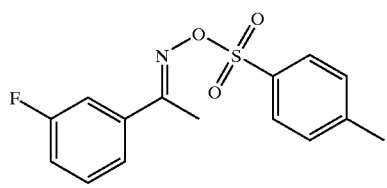

To a solution of 3'-fluoroacetophenone (35 g, 253.4 mmol) and hydroxylamine hydrochloride (26.4 g, 380 mmol) in ethanol (200 mL) was added sodium hydroxide (15.2 g, 380 mmol). After refluxing for 12 hour, it was concentrated. The residue was washed with cooled water and dried on high vacuum over night to get the title compound as a white solid. $^1$H NMR (DMSO, 400 Hz): δ7.44–4.49 (m, 1 H), 7.37–7.44 (m, 2 H), 7.14–7.20 (m, 1 H), 2.12 (s, 3 H). LC-MS (M$^+$+1) (EI) 154.1

Step B

A solution of the oxime from the previous step (38.7 g, 252.6 mmol) and p-toluenesulfonyl chloride (60.2 g, 316 mmol) in anhydrous pyridine (100 mL) was stirred at room temperature for one hours to get some precipitate. Cooled water (1 L) was added to see the dissolving of the original precipitate and the formation of a new precipitate. It was stirred for one hour and then, filtered, washed with cooled water and dried under high vacuum to constant weight to get the title compound as a pale solid. $^1$H NMR (CDCl$_3$, 400 Hz): δ7.94 (d, J=8.4 Hz, 2 H), 7.35–7.40 (m, 4 H), 7.29–7.33 (m, 1 H), 7.13–7.17 (m, 1 H), 2.47 (s, 3 H), 2.35 (d, J=1.8 Hz, 3 H).

Step C

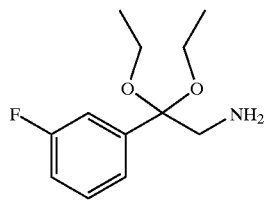

To a solution of the tosylamide from the previous step (66.0 g, 214.8 mmol) in ethanol (100 mL) was added potassium ethoxide (19.4 g, 225.5 mmol) in ethanol (800 mL) at 0° C. It was slowly warmed to room temperature at which it was stirred for one hour to see a precipitate. It was then diluted with anhydrous ether (1 L) and filtered. To the filtrate hydrogen chloride gas was bubbled in for 30 minutes to get some white precipitate. It was concentrated. The residue was distributed between ethyl acetate (1 L) and 1 N potassium hydroxide solution (pH=10). The organic layer was concentrated and vacuum distilled to get the titled compound as a colorless oil. $^1$H NMR (CDCl$_3$, 500 MHz): 7.25–7.38 (m, 3 H), 6.98–7.04 (m, 1 H), 3.36–3.53 (m, 4 H), 3.00 (s, 2 H), 1.24 (t, J=7.0 Hz, 6 H). LC-MS (M$^+$+1) (EI) 182.2, 228.2.

Step D

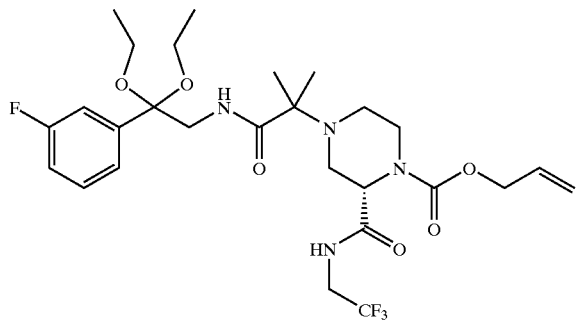

A solution of the carboxylic acid from the Example 66, Step D (1.5 g, 3.09 mmol), O-benzoltriazol-1-N,N,N',N'-tetramethyluronium hexafluorophosphate (2.8 g, 7.42 mmol), 1-hydroxybenzotriazol hydrate (1.0 g, 7.42 mmol) and diisipropylethylamine (2.7 mL, 15.5 mmol) in DMF (10 mL) was stirred at room temperature for half hour. The aminoacetal from the previous step (844 mg, 3.71 mmol) was added. After stirring at room temperature for 10 hours, the reaction solution was distributed between ethyl acetate (500 mL ) and water (500 mL). The organic layer was washed with water (500 mL) and brine. It was dried over anhydrous sodium sulfate, concentrated and purified by flash column chromatography on silica gel with hexanes/ethyl acetate=3/1 as eluant to give the title compound as a white solid. $^1$H NMR (CD$_3$OD, 400 MHz): 7.29–7.38 (m, 2 H), 7.23–7.26 (m, 1 H), 7.19 (broad s, 1 H), 6.99–7.05 (m, 1 H), 5.97 (broad s, 1 H), 5.28–5.36 (m, 2 H), 4.67 (broad s, 2 H), 4.60 (d, J=4.5 Hz, 2 H), 4.01–4.11 (m, 1 H), 3.92 (d, J=12.7 Hz, 1 H), 3.76–3.86 (m, 1 H), 3.40–3.67 (m, 3 H), 3.28–3.32 (m, 1 H), 3.18–3.26 (m, 1 H), 2.34–2.42 (m, 2 H), 2.13–2.20 (m 1 H), 1.27 (t, J=7.2 Hz, 2 H), 1.18 (T, J=7.2 Hz, 2 H), 0.99 (s, 3 H), 0.92 (s, 3 H). LC-MS (M$^+$+1) (EI) 591.2, 544.2.

Step E

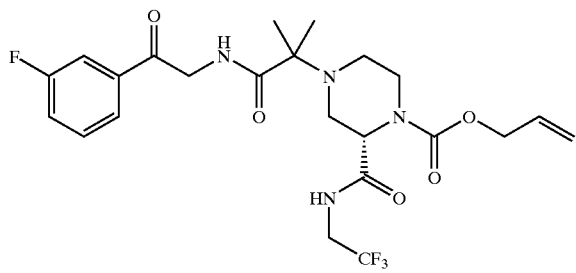

To a solution of the ketal from the previous step (1.5 g, 2.54 mmol) in THF (10 mL) was added hydrochloric acid (6 N, 20 mL). After stirring at 50° C. for 10 hours, the reaction solution was diluted with ethyl acetate (200 mL) and washed with 1 N potassium hydroxide solution. The organic layer was dried over anhydrous sodium sulfate, concentrated and purified by flash column chromatography on silica gel with hexanes/ethyl acetate=1/2 as eluant to give the title compound as a white solid. $^1$H NMR (CDCl$_3$, 400 MHz): 8.24 (broad s, 1 H), 7.73–7.75 (m, 1 H), 7.63–7.67 (m, 1 H), 7.45–7.51 (m, 1 H), 7.28–7.33 (m, 1 H), 6.63 (broad s, 1 H), 5.95 (broad s, 1 H), 5.28–5.37 (m, 2 H), 4.90 (dd, J=7.1, 22.7 Hz, 1 H), 4.82 (broad s, 1 H), 4.69 (d, J=4.9 Hz, 2 H), 4.51 (dd, J=4.0, 8.6 Hz, 1 H), 4.05–4.20 (m, 2 H), 4.01–4.09 (m, 1 H), 3.65 (d, J=11.7 Hz, 1 H), 3.28–3.32 (m, 1 H), 2.86 (d, J=11.3 Hz, 1 H), 2.43 (dd, J=3.9, 11.8 Hz, 1 H), 2.34 (dt, J=3.2, 11.8 Hz 1 H), 1.29 (s, 3H), 1.27 (s, 3 H), LC-MS (M$^+$+1) (EI) 517.5.

Step F

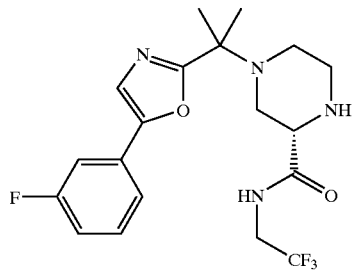

Sulfuric acid (double distilled, 8 mL) was treated with phosphorus pentoxide (730 mg, 2.57 mmol) and added to the ketoamide from the previous step (884 mg, 1.71 mmol). After stirring at 60° C. for 10 minutes the reaction solution was poured into excess ice. Solid potassium hydroxide was added while stirring till pH=12. It was extracted with ethyl acetate (5×200 mL). The combined organic layer was dried over anhydrous sodium sulfate, concentrated and purified by flash column chromatography on silica gel with ethyl acetate/methanol=10/1 as eluant to get the title compound as a white solid. $^1$H NMR (CDCl$_3$, 400 Hz): LC-MS (M$^+$+1) (EI) 415.2.
Step G (αR,γS,2S)-N-[(3S,4S)-3,4-dihydro-3-hydroxy-2H-1-benzopyran-4-yl]-4-[1-[5-(3-fluorophenyl)-2-oxazolyl]-1-methylethyl]-γ-hydroxy-α-(phenylmethyl)-2-[[(2,2,2-trifluoroethyl)amino] carbonyl]-1-piperazinepentanamide A solution of the oxazole from the previous step (501 mg, 1.21 mmol) and the epoxide from Example 1, Step P (522 mg, 1.21 mmol) in ethanol (15 mL) was refluxed for 14 hours. After the solvent was removed, the residue was purified by flash column chromatography on silica gel with hexanes/ethyl acetate=1/2 as eluant to get a pale solid. (LC-MS (M$^+$+1) (EI) 808.4. The solid obtained was dissolved in methanol (10 mL) and cooled to 0° C. Hydrogen chloride in ether (1 N, 5.5 mL, 5.5 mmol) was added and the reaction solution was warmed to room temperature at which it was stirred for 12 hours. The solvent was removed under vacuum. The residue was purified on preparative HPLC to give the title compound as a white solid. $^1$H NMR (CD$_3$OD, 500 Hz): δ7.49–7.53 (m, 2 H), 7.38–7.48 (m, 2 H), 7.19–7.30 (m, 5 H), 7.13–7.17 (m, 1 H), 7.05–7.11 (m, 2 H), 6.80 (t, J=7.5 Hz, 1 H), 6.72 (d, J=8.0 Hz, 1 H), 5.13 (d, J=4.0 Hz, 1 H), 4.02–4.09 (m, 2 H), 3.91–3.98 (m, 1 H), 3.78–3.84 (m, 1 H), 3.71–3.76 (m, 2 H), 3.07–3.11 (m, 1 H), 2.95–3.04 (m, 2 H), 2.88–2.94 (m, 1 H), 2.85 (d, J=11.2 Hz, 1 H), 2.70–2.78 (m, 2 H), 2.63–2.68 (m, I H), 2.45–2.49 (m, 1 H), 2.34–2.44 (m, 4 H), 1.98–2.04 (m, 1 H), 1.60 (s, 3 H), 1.59 (s, 3 H), 1.33–1.39 (m, 1 H). LC-MS (M$^+$+1) (EI) 768.4

EXAMPLE 92

(αR,γS,2S)-N-[(3S,4S)-3,4-dihydro-3-hydroxy-2H-1-benzopyran-4-yl]-4-[1-[5-(4-fluorophenyl)-2-oxazolyl]-1-methylethyl]-γ-hydroxy-α-(phenylmethyl)-2-[[(2,2,2-trifluoroethyl)amino] carbonyl]-1-piperazinepentanamide

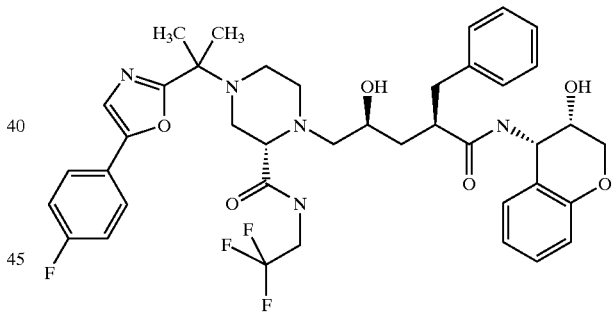

Step A

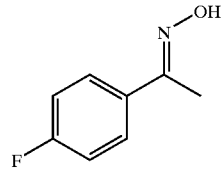

To a solution of 4'-fluoroacetophenone (40 g, 289.6 mmol) and hydroxylamine hydrochloride (24.2 g, 348 mmol) in ethanol (200 mL) was added sodium hydroxide (17.4 g, 434 mmol). After refluxing for 12 hour, it was concentrated. The residue was washed with cooled water and dried on high vacuum over night to get the title compound as a white solid. $^1$H NMR (DMSO,400 Hz): δ7.67(dd, J=5.7, 8.8 Hz, 2 H), 7.19 (t, J=8.8 Hz, 2 H). LC-MS (M$^+$+1) (EI)154.1

Step B

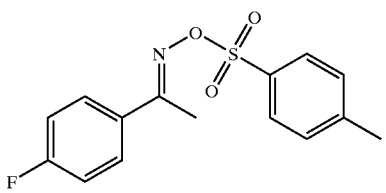

A solution of the oxime from the previous step (42.7 g, 279 mmol) and p-toluenesulfonyl chloride (66.6 g, 349 mmol) in anhydrous pyridine (100 mL) was stirred at room temperature for one hours to get some precipitate. Cooled water (1 L) was added to see the dissolving of the original precipitate and the formation of a new precipitate. It was stirred for one hour and then filtered, and the resulting solid was washed with cooled water and dried under high vacuum to constant weight to get the title compound as a pale solid. $^1$H NMR (CDCl$_3$, 400 Hz): δ7.94 (d, J=8.0 Hz, 2 H), 7.58–7.62 (m, 2 H), 7.37 (d, J=8.0 Hz, 2 H), 7.05–7.11 (m, 2 H), 2.47 (s, 3 H), 2.35 (d, J=1.8 Hz, 3 H).

Step C

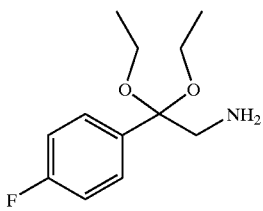

To a solution of the tosylamide from the previous step (71.5 g, 232.7 mmol) in ethanol (100 mL) was added potassium ethoxide (21.1 g, 244.3 mmol) in ethanol (800 mL) at 0° C. It was slowly warmed to room temperature at which it was stirred for one hour to see a precipitate. It was then diluted with anhydrous ether (1 L) and filtered. To the filtrate hydrogen chloride gas was bubbled in for 30 minutes to get some white precipitate. It was concentrated. The residue was distributed between ethyl acetate (1 L) and 1 N potassium hydroxide solution (pH=10). The organic layer was concentrated and vacuum distilled to get the titled compound as a colorless oil. $^1$H NMR (CDCl$_3$, 500 MHz): 7.48–7.53 (m, 2 H), 7.02–7.08 (m, 2 H), 3.35–3.52 (m, 4 H), 2.98 (s, 2 H), 1.23 (t, J=7.0 Hz, 6 H). LC-MS (M$^+$+1) (EI) 182.2, 228.2.

Step D

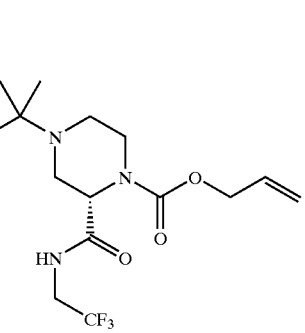

A solution of the carboxylic acid from the Example 66, Step D (1.5 g, 3.09 mmol), O-benzoltriazol-1-N,N,N',N'-tetramethyluronium hexafluorophosphate (2.8 g, 7.42 mmol), 1-hydroxybenzotriazol hydrate (1.0 g, 7.42 mmol) and diisipropylethylamine (2.7 mL, 15.5 mmol) in DMF (10 mL) was stirred at room temperature for half hour. The aminoacetal from the previous step (843 mg, 3.71 mmol) was added. After stirring at room temperature for 10 hours, the reaction solution was distributed between ethyl acetate (500 mL ) and water (500 mL). The organic layer was washed with water (500 mL) and brine. It was dried over anhydrous sodium sulfate, concentrated and purified by flash column chromatography on silica gel with hexanes/ethyl acetate=3/1 as eluant to give the title compound as a white solid. $^1$H NMR (CDCl$_3$, 400 MHz): 7.50–7.55 (m, 2 H), 7.16 (broad s, 1 H), 7.02–7.08 (m, 2 H), 5.97 (broad s, 1H), 5.28–5.36 (m, 2 H), 4.67 (broad s, 2 H), 4.60 (d, J=4.5 Hz, 2 H), 4.01–4.11 (m, 1 H), 3.92 (d, J=12.7 Hz, 1 H), 3.76–3.86 (m, 1 H), 3.40–3.67 (m, 3 H), 3.28–3.32 (m, 1 H), 3.18–3.26 (m, 1 H), 2.36–2.42 (m, 2 H), 2.13–2.20 (m 1 H), 1.27 (t, J=7.2 Hz, 2 H), 1.18 (T, J=7.2 Hz, 2 H), 1.01 (s, 3 H), 0.95 (s, 3 H). LC-MS (M$^+$+1) (EI) 591.2, 544.2.

Step E

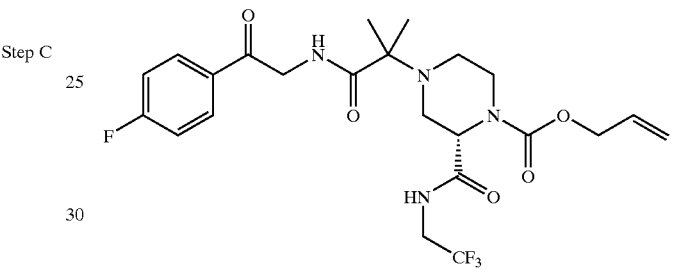

To a solution of the ketal from the previous step (1.5 g, 2.54 mmol) in THF (10 mL) was added hydrochloric acid (6 N, 20 mL). After stirring at 50° C. for 10 hours, the reaction solution was diluted with ethyl acetate (200 mL) and washed with 1 N potassium hydroxide solution. The organic layer was dried over anhydrous sodium sulfate, concentrated and purified by flash column chromatography on silica gel with hexanes/ethyl acetate=1/2 as eluant to give the title compound as a white solid. $^1$H NMR (CDCl$_3$, 400 MHz): 8.21 (broad s, 1 H), 8.00–8.03 (m, 2 H), 7.18 (t, J=8.6 Hz, 2 H), 6.63 (broad s, 1 H), 5.95 (broad s, 1 H), 5.28–5.37 (m, 2 H), 4.90 (dd, J=7.1, 22.7 Hz, 1 H), 4.82 (broad s, 1 H), 4.69 (d, J=4.9 Hz, 2 H), 4.51 (dd, J=4.0, 8.6 Hz, 1 H), 4.05–4.20 (m, 2 H), 4.01–4.09 (m, 1 H), 3.65 (d, J=11.7 Hz, 1 H), 3.28–3.32 (m, 1 H), 2.86 (d, J=11.3 Hz, 1 H), 2.42 (dd, J=3.9, 11.8 Hz, 1 H), 2.34 (dt, J=3.2, 11.8 Hz 1 H), 1.29 (s, 3H), 1.27 (s, 3 H). LC-MS (M$^+$+1) (EI) 517.5.

Step F

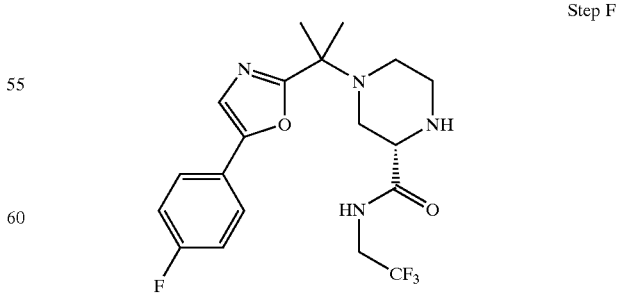

Sulfuric acid (double distilled, 8 mL) was treated with phosphorus pentoxide (573 mg, 2.57 mmol) and added to the ketoamide from the previous step (695 mg, 1.35 mmol).

After stirring at 60° C. for 10 minutes the reaction solution was poured into excess ice. Solid potassium hydroxide was added while stirring till pH=12. It was extracted with ethyl acetate (5×200 mL). The combined organic layer was dried over anhydrous sodium sulfate, concentrated and purified by flash column chromatography on silica gel with ethyl acetate/methanol=10/1 as eluant to get the title compound as a white solid. $^1$H NMR (CDCl$_3$, 400 Hz): LC-MS (M$^+$+1) (EI) 415.2.

Step G (αR,γS,2S)-N-[(3S,4S)-3,4-dihydro-3-hydroxy-2H-1-benzopyran-4-yl]-4-[5-(4-fluorophenyl)-2-oxazolyl]-1-methylethyl]-γ-hydroxy-(phenylmethyl)-2-[[(2,2,2-trifluoroethyl)amino]carbonyl]-1-piperazinepentamide A solution of the oxazole from the previous step (331 mg, 0.80 mmol) and the epoxide from Example 1, Step P (344 mg, 0.80 mmol) in ethanol (15 mL) was refluxed for 14 hours. After the solvent was removed, the residue was purified by flash column chromatography on silica gel with hexanes/ethyl acetate=1/2 as eluant to get a pale solid. (LC-MS (M$^+$+1) (EI) 808.4. The solid obtained was dissolved in methanol (10 mL) and cooled to 0° C. Hydrogen chloride in ether (1 N, 3.5 mL, 3.5 mmol) was added and the reaction solution was warmed to room temperature at which it was stirred for 12 hours. The solvent was removed under vacuum. The residue was purified on preparative HPLC to give the title compound as a white solid. $^1$H NMR (CD$_3$OD, 500 Hz): δ7.70–7.74 (m, 2 H), 7.39 (s, 1 H), 7.13–7.25 (m, 8 H), 7.05–7.11 (m, 2 H), 6.80 (t, J=7.5 Hz, 1 H), 6.72 (d, J=8.0 Hz, 1 H), 5.13 (d, J=4.0 Hz, 1 H), 4.02–4.09 (m, 2 H), 3.91–3.98 (m, 1 H), 3.78–3.84 (m, 1 H), 3.71–3.76 (m, 2 H), 3.07–3.11 (m, 1 H), 2.95–3.04 (m, 2 H), 2.88–2.94 (m, 1H), 2.85 (d, J=11.2 Hz, 1 H), 2.70–2.78 (m, 2 H), 2.63–2.68 (m, 1 H), 2.45–2.49 (m, 1 H), 2.34–2.44 (m, 4 H), 1.98–2.04 (m, 1 H), 1.61 (s, 3 H), 1.60 (s, 3 H), 1.33–1.39 (m, 1 H). LC-MS (M$^+$+1) (EI) 768.4

EXAMPLE 93

(αR,γS,2S)-N-[(3S,4S)-3,4-dihydro-3-hydroxy-2H-1-benzopyran-4-yl]-γ-hydroxy-4-[1-[5-(5-ethoxy-3-pyridinyl)-2-oxazolyl]-1-methylethyl]-α-(phenylmethyl)-2-[[(2,2,2-trifluoroethyl)amino] carbonyl]-1-piperazinepentanamide

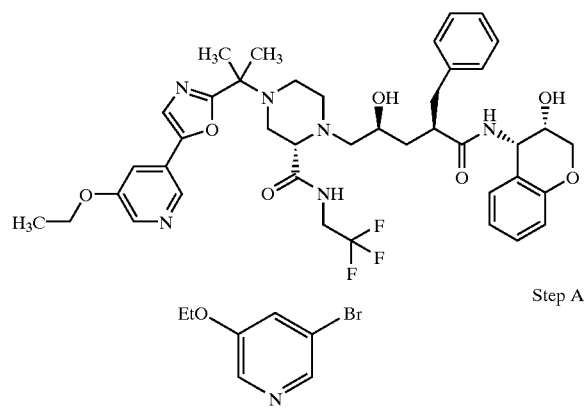

Step A

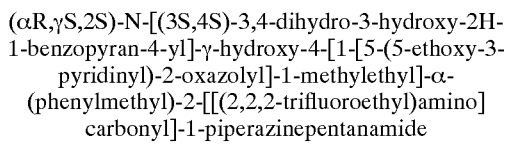

To a stirred solution of 3,5-dibromo pyridine (9.0 g, 38 mmol) in DMF (100 mL) cooled to 0° C. was added a solution of sodium ethoxide in ethanol (21% by wt, 63.31 mL, 190 mmol). The reaction was refluxed at 90° C. for 16 hours. The reaction mixture was cooled to room temperature and quenched by adding water (100 mL). The pH was adjusted to 9 by the addition of concentrated hydrochloric acid. The resulting solution was concentrated in vacuo. The residue was dissolved in water (300 mL) and extracted four times with ethyl acetate. The combined organic layers were dried over anhydrous sodium sulfate filtered and concentrated in vacuo. The crude material was purified by flash chromatography with 1:1 ethyl acetate hexanes to give the desired compound (3.0 g). LC-MS (M$^+$+1)(EI) 202.2.

Step B

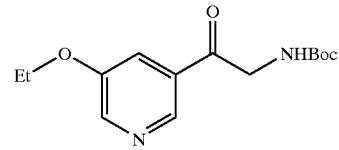

To a stirred solution of the intermediate form step A (3.41 g, 16.87 mmol) in dry THF (5 mL) was added drop wise isopropyl magnesium chloride (11 mL, 21.94 mmol). The reaction mixture was stirred at room temperature for 30 minutes after which time N(tert-Butoxycarbonyl)glycine N'-methoxy-N'-methyl amide (1.84 g, 8.43 mmol) was added as a solid. The reaction was quenched after 3 hours with saturated ammonium chloride. The resulting solution was extracted with ethyl acetate, washed with brine, dried over anhydrous sodium sulfate, filtered and concentrated in vacuo. The residue was purified by flash chromatography with 1:1 ethyl acetate hexanes to give the desired compound (1.88 g) as a white solid. $^1$H NMR (CDCl$_3$,500 MHz): 8.77 (s, 1H), 8.54 (s, 1H), 7.71 (s, 1H), 5.48 (bs, 1H), 4.69 (d, J=4.1 Hz, 2H), 4.18 (q, 2H), 1.51 (s, 9H), 1.48 (t, 3H). LC-MS (M$^+$+1)(EI) 281.1.

Step C

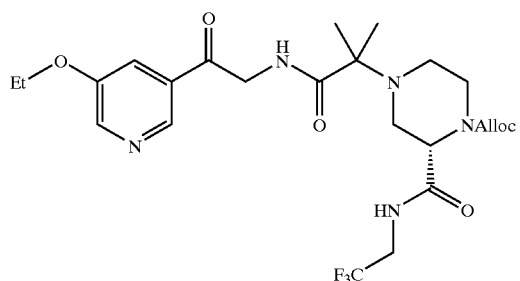

To the intermediate from Step B (257 mg, 0.91 mmol) was added 30% trifluoroacetic acid dichloromethane (10 mL). After 30 minutes the reaction mixture was concentrated in vacuo and the residue azeotropically dried with chloroform (3×). To a stirred solution of the residue in dichloromethane was added the acid from example 66, step D (419 mg, 1.1 mmol), 1-hydroxy-7-azabenzotriazole(150 mg, 1.1 mmol) and Benzotriazole-1-yl-oxy-tris-pyrrolidino-phosphonium hexafluorophosphate (572 mg, 1.1 mmol). N,N-Diisopropyl ethyl amine (951 μL, 5.46 mmol) was added dropwise and the resulting reaction mixture stirred at room temperature for 16 hours. The reaction mixture was diluted with ethyl acetate (10 mL), washed with saturated sodium bicarbonate solution, brine, dried over anhydrous sodium sulfate, filtered and concentrated in vacuo. The residue was purified by flash chromatography with 4:1 ethyl acetate-hexanes to give the desired compound (300 mg) as a white solid. LC-MS (M⁺+1)(EI) 544.2.

Step D

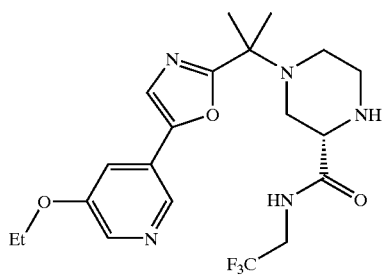

To the intermediate from step C(300 mg, 0.55 mmol) was added fuming sulfuric acid (1 mL). The resulting slurry was heated to 50° C. for 30 minutes. The reaction mixture was cooled to −10° C. and ice-water (5 mL) was added very slowly. The resulting solution was basified with the addition of solid potassium hydroxide until the pH=10. A white solid precipitated out which was filtered and discarded. The filtrate was extracted with ethyl acetate (3×) dried over anhydrous sodium sulfate filtered and concentrated in vacuo. The residue was purified by flash chromatography using 100% ethyl acetate and then 5% 2.0M ammonia/methanol-ethyl acetate to give the desired compound (62 mg) as a white solid. LC-MS (M⁺+1)(EI) 442.2.

Step E

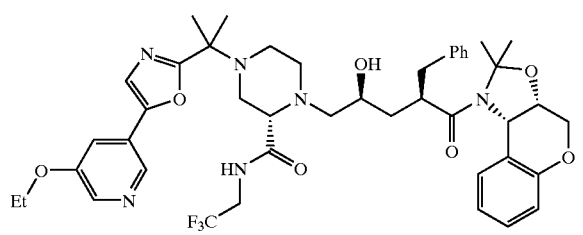

A stirred solution of the intermediate from step D (62 mg, 0.14 mmol) and the intermediate from example 1, step P(55.26 mg, 0.14 mmol) in ethanol (1 mL) was heated to 70° C. for 16 hours. The reaction mixture was concentrated in vacuo and purified by flash chromatography using 5% methanol-ethyl acetate to give the desired product (70 mg) as a yellow solid. $^1$H NMR (CDCl$_3$,500 MHz): 9.26 (bs, 1H), 8.5 (d, J=1.7 Hz, 1H), 8.3 (d, J=2.8 Hz, 1H), 7.3–7.4 (m, 6H), 7.22 (t, J=6.9, 7.1 Hz, 1H), 7.13 (t, J=6.6, 7.1 Hz, 1H), 6.84 (d, J=8.3 Hz, 1H), 6.7 (m, 2H), 5.72 (d, J=4.3 Hz, 1H), 4.46 (dd, J=2.5, 12.8 Hz, 1 H), 4.42 (m, 1H), 4.32 (bs, 1H), 4.2 (m, 4H), 3.8 (m, 1H), 3.7 (m, 1H), 3.4–3.5 (m, 3H), 3.15–3.2 (m, 2H), 2.96 (d, J=10.7 Hz, 1H), 2.9 (m, 2H), 2.3–2.7 (m, 5H), 1.71 (s, 3H), 1.62 (s, 6H), 1.5 (t, 3H), 1.28(s, 3H). LC-MS (M⁺+1)(EI) 835.5.
Step F (α,γS,2S)-N-[(3S,4S)-3,4-dihydro-3-hydroxy-2H-1-benzopyran-4-yl]-γ-hydroxy-4-[1-[5-(5-ethoxy-3-pyridinyl)-2-oxazolyl]-1-methylethyl]-α-(phenylmethyl)-2-[[(2,2,2-trifluoroethyl)amino]carbonyl]-1-piperazinepentanamide To a stirred solution of the intermediate from step E (70 mg, 0.084 mmol) in methanol (3 mL) was added a solution of 1.0 M HCl in ether (1 ml, 1 mmol) and the resulting mixture stirred at room temperature for 3 hours. At the end of this time the reaction mixture was concentrated in vacuo. The residue was dissolved in ethyl acetate (10 mL) and washed with 1N sodium hydroxide solution, dried over anhydrous sodium sulfate filtered and concentrated in vacuo. The residue was purified by flash chromatography with 4% methanol ethyl acetate to give the (42 mg) title compound. $^1$H NMR (CDCl$_3$,500 MHz): 9.25 (bs, 1H), 8.5 (d, J=1.8 Hz, 1H), 8.29(d, J=2.7 Hz, 1H), 7.23–7.4 (m, 7H), 7.13 (t, J=7.1, 8.2 Hz, 1H), 7.09 (d, J=7.8 Hz, 1H), 6.9 (m, 2H), 6.05 (d, J=8.0 Hz, 1H), 5.18 (m, 1H), 4.2 (m, 3H), 4.1 (m, 3H), 3.8 (m, 3H), 3.4(bs, 1H), 3.1 (d, J=11.9 Hz, 1H), 2.9 (m, 3H), 2.65–2.8 (m, 4H), 2.49 (bd, J=11.7 Hz, 2 H), 2.15 (bs, 1H), 1.95 (t, J=11.2 Hz, 1H), 1.63 (s, 6H), 1.51 (t, 3H). LC-MS (M⁺+1)(EI) 795.3.

EXAMPLE 94

(αR,γS,2S)-N-[(3S,4S)-3,4-dihydro-3-hydroxy-2H-1-benzopyran-4-yl]-γ-hydroxy-4-[1-[5-(5-fluoro-3-pyridinyl)-2-oxazolyl]-1-methylethyl]-α-(phenylmethyl)-2-[[(2,2,2-trifluoroethyl)amino]carbonyl]-1-piperazinepentanamide

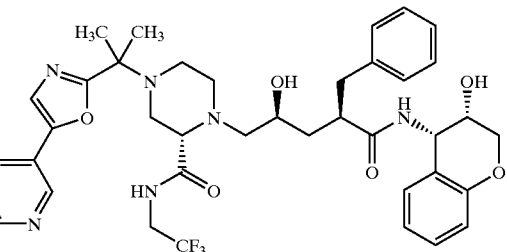

Step A

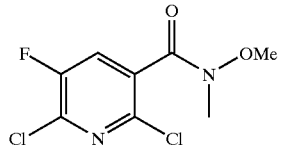

To a stirred solution of 2,6-dichloro-5-fluoro-nicotinic acid (10 g, 47.62 mmol) and N methoxy N-methyl amine (5.57 g, 57.14 mmol) in dichloromethane was added 4-dimethyl amino pyridine (58 mg, 0.47 mmol) N,N-diisopropylethyl amine (16.58 mL, 95.23 mmol) and EDC (9.12 g, 46.62 mmol). The resulting mixture was stirred at room temperature for 16 hours. The reaction mixture was diluted with dichloromethane and washed with 1N HCl and saturated sodium bicarbonate. The organic layer was dried over anhydrous sodium sulfate filtered and concentrated in vacuo. The residue was purified by flash chromatography with 50% ethyl acetate hexanes to give the desired compound (10.58 g)as a colorless oil. $^1$H NMR (CDCl$_3$,500 MHz): 7.54 (d, J=6.9 Hz, 1H), 3.56 (s, 3H), 3.42 (s, 3H). LC-MS (M⁺+1)(EI) 253.2.

Step B

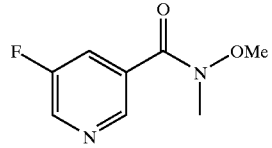

To a stirred solution of the intermediate from step A (10.58 g, 41.81 mmol) in ethanol (150 mL) was added ammonium formate (13.18 g, 209 mmol), formic acid (5 mL) and 10% palladium on carbon (1.0 g). The resulting mixture was heated to 65° C. for 16 hours. The reaction mixture was cooled to room temperature and filtered through a pad of celite. The residue was washed with ethanol (50 mL) and discarded. The filtrate was concentrated in vacuo. The residue was dissolved in ethyl acetate and washed with saturated sodium bicarbonate solution and brine and dried over anhydrous sodium sulfate. The solution was filtered and concentrated in vacuo. The residue was purified by flash chromatography using 40% ethyl acetate hexanes to give the (6.5 g) desired compound. $^1$H NMR (CDCl$_3$,500 MHz): 8.79 (s, 1H), 8.55 (d, J=3.0 Hz, 1H), 7.78 (dd, J=4.4, 8.6 Hz, 1H), 3.57 (s, 3H), 3.4 (s, 3H). LC-MS (M$^+$+1)(EI) 185.3.

Step C

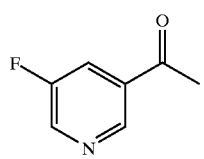

To a stirred solution of the intermediate from step B (4.3 g, 22.8 mmol) in anhydrous THF cooled to −20° C. was added methyl magnesium bromide (48.85 mL, 68.4 mmol, 1.4 M in THF). The reaction was warmed to room temperature and stirred for 2 hours. The reaction mixture was quenched with saturated ammonium chloride solution. The resulting biphasic mixture was extracted with ethyl acetate (3×). The combined organic layers was washed with brine, dried over anhydrous sodium sulfate, filtered and concentrated in vacuo. The residue was purified by flash chromatography with 30% ethyl acetate hexanes to give the desired compound (2.7 g) as colorless oil. $^1$H NMR (CDCl$_3$,500 MHz): 9.01 (s, 1H), 8.68(d, J=2.7 Hz, 1H), 7.96 (d, J=2.7 Hz, 1H), 2.68 (s, 3H). LC-MS (M$^+$+1)(EI) 140.1.

Step D

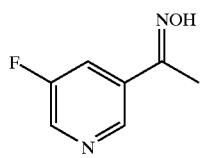

To a stirred solution of the intermediate from step C (5.25 g, 37.73 mmol) in ethanol (50 mL) was added hydroxylamine hydrochloride (2.97 g, 42.79 mmol) and sodium hydroxide (1.71 g, 42.79 mmol). The reaction was refluxed for two hours during which time a white precipitate crashed out. The reaction mixture was cooled to room temperature and filtered. The solid was washed with ethanol (3×100 mL) and discarded. The filtrate was concentrated in vacuo. The residue was dissolved in ethyl acetate and washed with water. The organic layer was dried over anhydrous sodium sulfate, filtered and concentrated in vacuo to give the desired compound (5.7 g) as a white solid. $^1$H NMR (CDCl$_3$,500 MHz):9.0 (bs, 1H), 8.78 (s, 1H), 8.5 (s, 1H), 7.75 (d, J=11.4 Hz, 1H), 2.32 (s, 3H). LC-MS (M$^+$+1)(EI) 155.2.

Step E

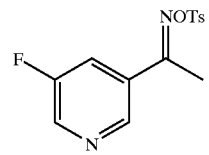

To a solution of the intermediate from step D (5.7 g, 36.97 mmol) in pyridine (20 mL) was added para-toluene sulfonyl chloride (8.81 g, 46.22 mmol) and the resulting mixture was stirred at room temperature for 48 hours. At the end of this time the reaction mixture was diluted with ethyl acetate (300 mL). The organic layer was washed with ice water (3×250 mL), brine, dried over anhydrous sodium sulfate, filtered and concentrated in vacuo. The residue was azeotroped with toluene (5×) to give the desired compound (11.0 g) as a light brown oil. LC-MS (M$^+$+1)(EI) 309.2.

Step F

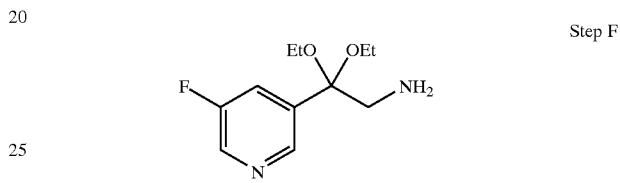

To a stirred solution of the intermediate from step E (11.0 g, 35.67 mmol) in dry ethanol (100 mL) cooled to 0° C. was added dropwise via an addition funnel a solution of potassium ethoxide (3.22 g, 37.45 mmol) in ethanol (200 mL). The reaction mixture was warmed to room temperature and stirred for 18 hours. The reaction mixture was concentrated to half its volume and anhydrous ether(100 mL) was added. A slow stream of hydrogen chloride gas was bubbled for 3 hours. The reaction mixture was concentrated in vacuo and the residue dissolved in ethyl acetate and washed with 1N potassium hydroxide, dried over anhydrous sodium sulfate filtered and concentrated in vacuo. The residue was purified by flash chromatography using 5% 2.0M ammonia/methanol-ethyl acetate to give the desired product (5.0 g) as a brown oil. $^1$H NMR (CDCl$_3$,500 MHz): 8.55 (s, 1H), 8.43 (s, 1H), 7.5(m, 1H), 3.49 (m, 2H), 3.35 (m, 2H), 3.22 (s, 2H), 1.25 (m, 6H). LC-MS (M$^+$+1)(EI) 229.2.

Step G

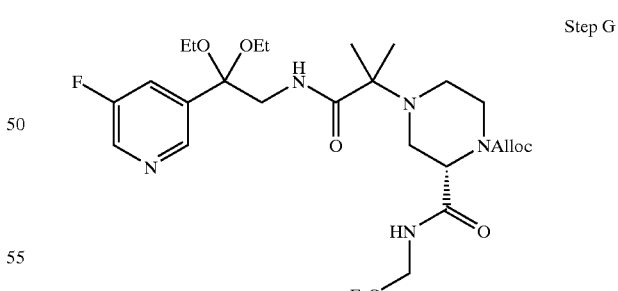

To a stirred solution of the intermediate obtained from step F (2.0 g, 8.76 mmol) in 1:1 DMF/DCM (10 mL) was added the intermediate obtained from example 66 step D (5.06 g, 10.51 mmol), 1-hydroxy-7-azabenzotriazole (1.8 g, 13.14 mmol), N,N-diisopropylethyl amine (2.28 mL, 13.14 mmol) and Benzotriazole-1-yl-oxy-tris-pyrrolidino-phosphonium hexafluorophosphate (5.46 g, 10.51 mmol). The resulting mixture was stirred at room temperature for 16 hours. The reaction mixture was concentrated in vacuo. The residue was dissolved in ethyl acetate (100 mL) and washed with saturated sodium bicarbonate (2x), brine (1x) dried over anhydrous sodium sulfate filtered and concentrated in vacuo. The residue was purified by flash chromatography using 70% ethyl acetate hexanes to give the desired product (4.84 g) as a white solid. $^1$H NMR (CDCl$_3$,500 MHz): 8.58 (s, 1H), 8.37 (s, 1H), 7.58 (d, J=7.8 Hz, 1H), 5.94 (m, 1H), 5.34 (d, J=17.2 Hz, 1H), 5.28 (d, J=10.5 Hz, 1H), 4.65 (bs, 3H), 4.1 (bs, 1H), 4.0 (bs, 2H), 3.6 (m, 3H), 3.4 (m, 3H), 3.29 (d, J=19.2 Hz, 2H), 2.8 (bs, 1H), 2.6 (bd, J=10.3 Hz, 1H), 2.3 (bs, 1H), 2.1 (bs, 1H), 1.2 (m, 6H), 1.06 (s, 3H), 1.01 (s, 3H).). LC-MS (M$^+$=23)(EI) 614.3.

Step H

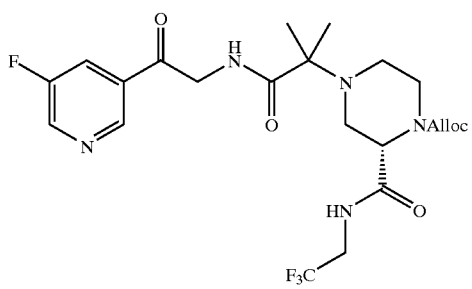

To a stirred solution of the intermediate obtained form step G (4.84 g, 8.18 mmol) in THF (20 mL) was added 6N HCl (20 mL) and the resulting mixture heated to 60° C. for three hours. The reaction mixture was cooled to room temperature and diluted with ethyl acetate (100 mL). A solution of 6N NaOH was added until the pH=12. The resulting biphasic mixture was extracted with ethyl acetate (3x), the organic layer dried over anhydrous sodium sulfate filtered and concentrated in vacuo. The residue was purified by flash chromatography with 70% ethyl acetate hexanes to give the desired product (4.0 g) as a white solid. $^1$H NMR (CDCl$_3$,500 MHz): 8.98 (s, 1H), 8.66 (bs, 1H), 8.34 (bs, 1H), 7.92 (d, J=8.3 Hz, 1H), 6.91 (bs, 1H), 5.91 (bs, 1H), 5.32 (d, J=16.7 Hz, 1H), 5.26 (d, J=10.3 Hz, 1H), 4.85 (m, 2H), 4.62 (bs, 2H), 4.54 (d, J=16.3 Hz, 1H), 4.2 (m, 2H), 3.8 (m, 1H), 3.6 (bs, 1H), 3.2 (bs, 1H), 2.86 (d, J=10.3 Hz, 1H), 2.4 (bs, 1H), 2.25 (t, 1H), 1.24 (s, 6H).). LC-MS (M$^+$+1)(EI) 518.3.

Step I

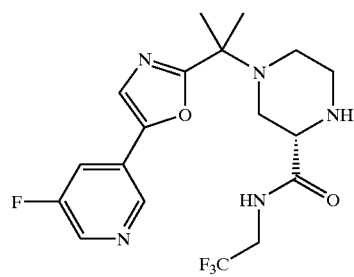

To the intermediate from step H (2.5 g, 4.83 mmol) was added fuming sulfuric acid (4 mL). The resulting slurry was heated to 50° C. for 15 minutes. The reaction mixture was cooled to -10° C. and ice-water (5 mL) was added very slowly. The pH of the solution was adjusted to 10 by the addition of solid potassium hydroxide. A white precipitate crashed out that was filtered and discarded. The filtrate was extracted with ethyl acetate (4x). The organic layer was washed with brine (1x), dried over anhydrous sodium sulfate filtered and concentrated in vacuo. The residue was purified by flash chromatography using 100% ethyl acetate and then 5% 2.0M ammonia/methanol-ethyl acetate to give the desired compound (1.1 g) as a white solid. $^1$H NMR (CDCl$_3$, 500 MHz): 8.72 (s, 1H), 8.44 (d, J=2.7 Hz, 1H), 8.07 (bs, 1H), 7.63 (dt, J=2.0, 2.3, 8.9 Hz, 1H), 7.39 (s, 1H), 4.9 (m, 2H), 3.54 (dd, J=3.2, 5.9 Hz, 1H), 2.9–3.0 (m, 3H), 2.8 (dd, J=5.9, 11.4 Hz, 1H), 2.6 (m, 2H), 1.6 (s, 6H).). LC-MS (M$^+$+1)(EI) 416.3.

Step J

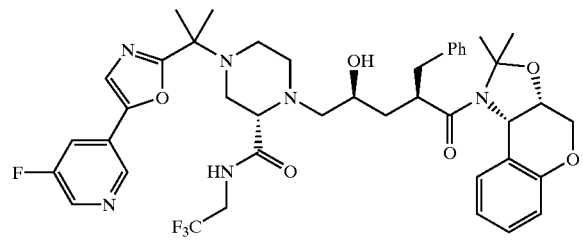

A stirred solution of the intermediate from step I (1.1 g, 2.65 mmol) and the intermediate form example 1, step P(1.04 g, 2.65 mmol) in ethanol (35 mL) was heated to 70° C. for 16 hours. The reaction mixture was concentrated in vacuo and purified by flash chromatography using 100% ethyl acetate and then 5% 2.0M ammonia in methanol-ethyl acetate to give the desired product (1.1 g) as a white solid. $^1$H NMR (CDCl$_3$,500 MHz): 9.19 (bs, 1H), 8.72 (s, 1H), 8.47 (d, J=2.7 Hz, 1H), 7.61 (d, J=9.0 Hz, 1H), 7.42 (s, 1H), 7.27–7.34 (m, 5H), 7.21 (t, J=7.3, 9.0 Hz, 1H), 7.12 (t, J=7.1, 8.0 Hz, 1H), 6.83 (dd, J=3.2, 8.1 Hz, 1H), 6.65 (m, 2H), 5.69 (d, J=4.1 Hz, 1H), 4.4 (d, J=12.8 Hz, 1H), 4.3 (m, 1H), 4.21 (d, J=12.8 Hz, 1H), 4.1 (m, 2H), 3.8 (m, 1H), 3.7 (bt, J=9.4 Hz, 1H), 3.5 (m, 2H), 3.4 (m, 2H), 3.15 (m, 2H), 2.95 (d, J=10.5 Hz, 1H), 2.85 (m, 1H), 2.4–2.7 (m, 4H), 1.7 (s, 3H), 1.61 (s, 6H), 1.27 (s, 3H). LC-MS (M$^+$+1)(EI) 809.3.

Step K (αR,γS,2S)-N-[(3S,4S)-3,4-dihydro-3-hydroxy-2H-1-benzopyran-4-yl]-γ-hydroxy-4-[1-[5-(5-fluoro-3-pyridinyl)-2-oxazolyl]-1-methylethyl]-α-(phenylmethyl)-2-[[(2,2,2-trifluoroethyl)amino]carbonyl]-1-piperazinepentanamide

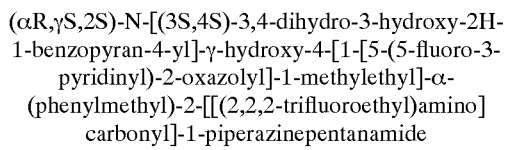

To a solution of the intermediate from step J(1.1 g, 1.35 mmol) in methanol (20 mL) was added a solution of 1.0 M HCl in ether (17.5 ml, 17.5 mmol) and the resulting mixture stirred at room temperature for 4.5 hours. At the end of this time the reaction mixture was concentrated in vacuo. The residue was dissolved in ethyl acetate (100 mL) washed with 1N sodium hydroxide solution, dried over anhydrous sodium sulfate, filtered and concentrated in vacuo. The residue was purified by flash chromatography with 100% ethyl acetate and then 5% 2.0M ammonia/methanol ethyl acetate to give the title compound (880 mg) as a white solid. $^1$H NMR (CDCl$_3$,500 MHz): 9.19 (bs, 1H), 8.73 (s, 1H), 8.47 (d, J=2.3 Hz, 1H), 7.62 (d, J=8.7 Hz, 1H), 7.43 (s, 1H), 7.23–7.33 (m, 5H), 7.12 (t, J=8.0 Hz, 1H), 7.06 (d, J=7.3 Hz, 1H), 6.8 (d, J=7.5 Hz, 1H), 6.03 (d, J=8.0 Hz, 1H), 5.17 (m, 1H), 4.0–4.4 (m, 3H), 3.7–3.9 (m, 3H), 3.5 (bs, 1H), 3.45 (bs, 1H), 3.13 (d, J=11.2 Hz, 1H), 2.9 (m, 3H), 2.7–2.8 (m, 4H), 2.48 (bd, J=11.9 Hz, 2H), 2.19 (d, J=4.5 Hz, 1H), 1.94 (t, J=11.4 Hz, 1H), 1.63 (s, 6H). LC-MS (M$^+$+1)(EI) 769.4.

EXAMPLE 95

(αR,γS,2S)-N-[(3S,4S)-3,4-dihydro-3-hydroxy-2H-1-benzopyran-4-yl)-γ-hydroxy-4-[1-[5-(5-ethyl -3-pyridinyl)-2-oxazolyl]-1-methylethyl]-α-(phenylmethyl)-2-[[(2,2,2-trifluoroethyl)amino]carbonyl]-1-piperazinepentanamide

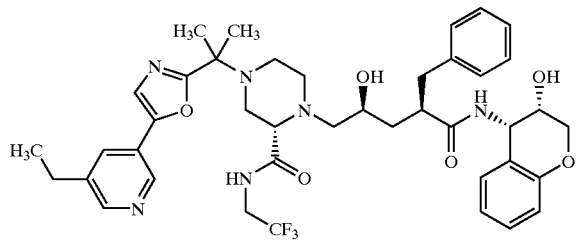

Step A

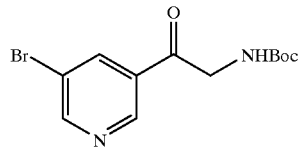

To a solution of 3,5-dibromopyridine (15 g, 63.31 mmol) in dry THF (100 mL) cooled to 0° C. was added drop wise isopropyl magnesium chloride (41 mL, 82.31 mmol). The reaction mixture was stirred at room temperature for 45 minutes after which time N(tert-Butoxycarbonyl)glycine N'-methoxy-N'-methyl amide (6.9 g, 31.65 mmol) was added as a solid. The reaction was quenched after 3 hours with saturated ammonium chloride. The resulting solution was extracted with ethyl acetate, washed with brine, dried over anhydrous sodium sulfate, filtered and concentrated in vacuo. The residue was purified by flash chromatography with 15% ethyl acetate hexanes to give the desired compound (7.0 g) as a white solid. LC-MS (M++1)(EI) 315.3.

Step B

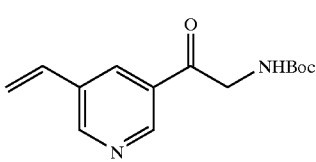

To a solution of the intermediate from step A (5.1 g, 16.18 mmol) in toluene (120 mL) was added tri-n-butyl-vinyl stannane (5.7 mL, 19.41 mmol) and Pd(PPh₃)₄ (935 mg, 0.81 mmol). The resulting mixture was heated to reflux under a N₂ atmosphere. The reaction mixture was cooled to room temperature, a saturated solution of potassium fluoride (120 mL) was added and the resulting biphasic mixture stirred vigorously for 45 minutes. The precipitate was filtered and discarded. The filtrate was extracted with diethyl ether (3×), the organic layer washed with brine, dried over anhydrous sodium sulfate filtered and concentrated in vacuo. The residue was purified-by-flash-chromatography with 35% ethyl acetate hexanes to give the desired compound (3.16 g) as a white solid. ¹H NMR (CDCl₃,500 MHz): 9.05 (s, 1H), 8.84 (s, 1H), 8.26 (s, 1H), 6.81 (dd, J=11, 17.6 Hz, 1H), 5.98 (d, J=17.6 Hz, 1H), 5.55 (d, J=11 Hz, 1H), 4.71 (d, J=3.9 Hz, 2H), 1.5(s, 9H).). LC-MS (M++1)(EI) 263.2.

Step C

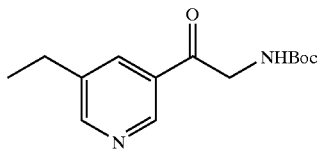

To a solution of the intermediate from step B (2.0 g, 3.81 mmol) in methanol (5 mL) was added 10% Pd/C (350 mg). The resulting solution was stirred at room temperature under hydrogen (1 atmosphere). After 3 hours the reaction was filtered through celite and the filtrate concentrated in vacuo to give the desired (2.0 g) compound. ¹H NMR (CDCl₃,500 MHz): 9.0 (s, 1H), 8.65 (s, 1H), 8.1 (s, 1H), 4.65 (d, 2H), 2.7 (q, 2H), 1.5 (s, 9H), 1.3 (t, 3H).

Step D

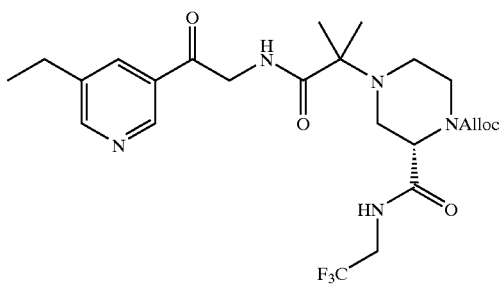

To the intermediate from Step C (1.0 g, 3.78 mmol) was added 30% trifluoroacetic acid dichloromethane (10 mL). After 30 minutes the reaction mixture was concentrated in vacuo and the residue azeotropically dried with toluene (3×) and then chloroform (3×). To a solution of the residue in 1:1DMF/DCM (8 mL) was added the intermediate from example 66, step D(911 mg, 1.89 mmol), 1-hydroxy-7-azabenzotriazole (386 mg; 2.84 mmol) and Benzotriazole-1-yl-oxy-tris-pyrrolidino-phosphonium hexafluorophosphate (985 mg, 1.89 mmol). N,N-Diisopropyl ethyl amine (1.97 mL, 11.34 mmol) was added dropwise and the resulting reaction mixture stirred at room temperature for 16 hours. The reaction mixture was diluted with ethyl acetate (20 mL), washed with saturated sodium bicarbonate solution, brine, dried over anhydrous sodium sulfate, filtered and concentrated in vacuo. The residue was purified by flash chromatography with 4:1 ethyl acetate-hexanes to give the desired compound (650 mg) as an oil. LC-MS (M++1)(EI) 528.2.

Step E

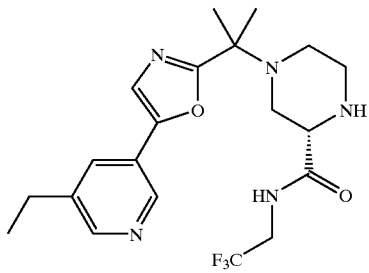

To the intermediate from Step D (300 mg, 0.56 mmol) was added fuming sulfuric acid (1 mL). The resulting slurry was heated to 50° C. for 15 minutes. The reaction mixture was cooled to −10° C. and ice-water (5 mL) was added very slowly. The pH of the resulting solution was adjusted to 10 with addition of solid potassium hydroxide. A white precipitate crashed out that was filtered and discarded. The filtrate was extracted with ethyl acetate (3×). The organic-layer was washed with brine (1×), dried over anhydrous sodium sulfate filtered and concentrated in vacuo. The residue was purified by flash chromatography using 5% 2.0M ammonia/methanol-ethyl acetate to give the desired compound (100 mg) as a white solid. $^1$H NMR (CDCl$_3$, 500 MHz): 8.74 (d, J=2.1 Hz, 1H), 8.45 (d, J=1.8 Hz, 1H), 8.2 (m, 1H), 7.72 (d, J=2.1 Hz, 1H), 7.34 (s, 1H), 3.97 (m, 2H), 3.53 (m, 1H), 2.9 (m, 4H), 2.75 (q, 2H), 2.6 (m, 2H), 1.62 (s, 3H), 1.61 (s, 3H), 1.3 (t, 3H). LC-MS (M$^+$+1)(EI) 426.2.

Step F

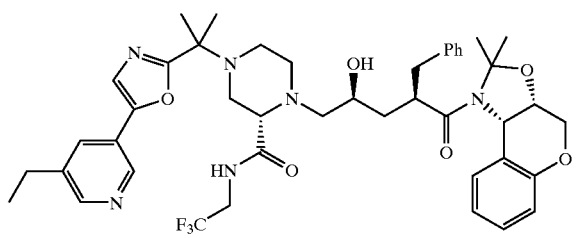

A solution of the intermediate from Step E (100 mg, 0.24 mmol) and the intermediate from Example 1, Step P (93 mg, 0.24 mmol) in ethanol (5 mL) was heated to 70° C. for 16 hours. The reaction mixture was concentrated in vacuo and purified by flash chromatography using 80% ethyl acetate hexanes to give the desired product (100 mg) as a solid. LC-MS (M$^+$+1)(EI) 819.3.

Step G (αR,γS,2S)-N-[(3S,4S)-3,4-dihydro-3-hydroxy-2H-1-benzopyran-4 -yl]-γ-hydroxy-4-[1-[5-(5-ethyl-3-pyridinyl)-2-oxazolyl]-1-methylethyl]-α-(phenylmethyl)-2-[[(2,2,2-trifluoroethyl)amino] carbonyl]-1-piperazinepentanamide To a solution of the intermediate from Step F (100 mg, 0.122 mmol) in methanol (5 mL) was added a solution of 1.0 M HCl in ether (3.22 ml, 3.22 mmol) and the resulting mixture stirred at room temperature for 4 hours. At the end of this time the reaction mixture was concentrated in vacuo. The residue was dissolved in ethyl acetate (10 mL) and washed with 1N sodium hydroxide solution, dried over anhydrous sodium sulfate filtered and concentrated in vacuo. The residue was purified by flash chromatography with 5% methanol ethyl acetate to give the (55 mg) title compound as a white solid. $^1$H NMR (CDCl$_3$, 500 MHz): 9.3 (bs, 1H), 8.72 (d, J=2.1 Hz, 1H), 8.46 (d, J=1.9 Hz, 1H), 7.71 (s, 1H), 7.36 (s, 1H), 7.2–7.4 (m, 5H), 7.12 (d, J=7.8 Hz, 1H), 7.06 (d, J=7.8 Hz, 1H), 6.84 (t, J=7.1 Hz, 1H), 6.77 (d, J=8.0 Hz, 1H), 6.03 (bs, 1H), 5.17 (m, 1H), 4.0–4.2 (m, 4H), 3.8 (m, 3H), 3.15 (bs, 1H), 2.9 (m, 5H), 2.8 (m, 3H), 2.6(q, 2H), 2.55 (bs, 2H), 1.9 (m, 1H), 1.63(s, 6H), 1.57 (m, 1H), 1.33 (t, 3H). LC-MS (M$^+$+1)(EI) 779.4.

EXAMPLE 96

(αR,γS,2S)-N-[(3S,4S)-3,4-dihydro-3-hydroxy-2H-1-benzopyran-4-yl]-γ-hydroxy-4-[1-methyl-1-[5-(5-propyl-3-pyridinyl)-2-oxazolyl]ethyl]-α-(phenylmethyl)-2-[[(2,2,2-trifluoroethyl)amino] carbonyl]-1-piperazinepentanamide

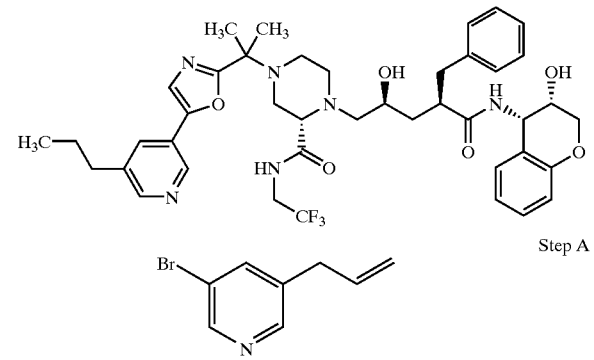

Step A

To a solution of 3,5-dibromopyridine (2.0 g, 8.44 mmol) in THF (4 ml) was added isopropylmagnesium chloride (2M in THF, 5.49 ml, 10.98 mmol). The reaction mixture was stirred at room temperature for 1 h. Cupper cyanide (151 mg, 1.69 mmol) and lithium chloride (143 mg, 3.37 mmol) were added as solid. The reaction was cooled in a water bath and allyl bromide (0.804 ml, 9.29 mmol) was added. After 3 hours stirring at room temperature, the reaction mixture was diluted with methylene chloride, washed with aqueous NH$_4$Cl solution and brine, dried over anhydrous sodium sulfate, filtered and concentrated in vacuo. The crude reaction mixture was purified by flash column chromatography on silica gel with 1:4 ethyl acetate/hexane as the eluant to give the titled compound. $^1$H NMR (CDCl$_3$, 500 MHz): 8.54 (s, 1H), 8.38 (s, 1H), 7.68 (s, 1H), 5.93 (m, 1H), 5.16 (m, 2H), 3.40 (m, 2H).

Step B

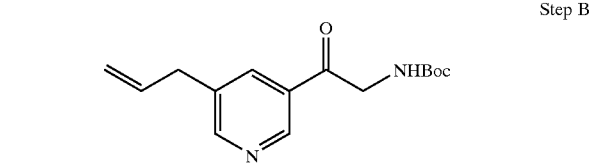

The intermediate prepared in Step A (1.4 g, 7.07 mmol) in THF (3.3 ml) was added isopropylmagnesium chloride (2M in THF, 4.59 ml, 9.19 mmol). The reaction mixture was stirred at room temperature for 1 h. N-(tert-Butoxycarbonyl) glycine-N'-methoxy-N'-methylamide (0.77 g, 3.53 mmol) was added in THF (4 ml). After stirring at room temperature for 3 hours, the reaction mixture was poured into aqueous NH$_4$Cl solution and the product was extracted with methylene chloride. The organic layer was washed with brine, dried over anhydrous sodium sulfate, filtered and concentrated in vacuo. The crude product was purified by flash column chromatography on silica gel with 1:4 ethyl acetate/hexane as the eluant to give the titled compound. $^1$H NMR (CDCl$_3$, 500 MHz): 9.02 (s, 1H), 8.66 (s, 1H), 8.05 (s, 1H), 5.93 (m, 1H), 5.16 (m, 2H), 4.66 (m, 2H), 3.47 (d, J=6.4 Hz, 2H), 2.90 (t, 2H), 1.48 (s, 9H).

Step C

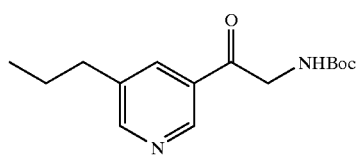

The intermediate prepared in Step B (1.3 g, 4.71 mmol) in MeoH (20 ml) was added 10% palladium on carbon (250 mg). The reaction mixture was stirred under a hydrogen balloon. After half an hour the reaction mixture was filtered through celite and the filtrate was concentrated in vacuo. The crude product was purified by flash column chromatography on silica gel with 3:7 ethyl acetate/hexane as the eluant to give the titled compound. $^1$H NMR (CDCl$_3$, 500 MHz): 8.94 (s, 1H), 8.60 (s, 1H), 8.20 (s, 1H), 4.55 (m, 2H), 2.72 (t, 2H), 1.70 (m, 2H), 1.45 (s, 9H), 0.98 (t, 3H).

Step D

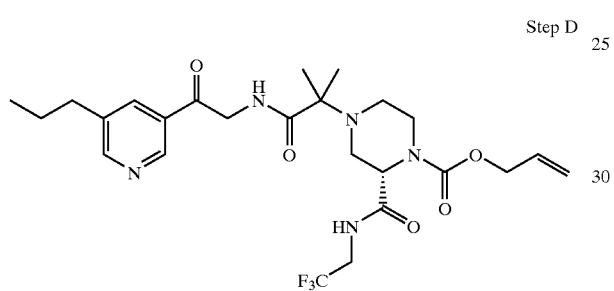

The intermediate prepared in Step C (100 mg, 0.36 mmol) was treated in TFA in methylene chloride (30%, 10 ml) at room temperature for 30 min. Then the reaction mixture was concentrated in vacuo and azeotroped with chloroform three times. The resulting mixture was dissolved in DMF (3 ml) and the intermediate prepared as in Example 66 Step D (114 mg, 0.30 mmol), PyBop (374 mg, 0.72 mmol), HOAt (98 mg, 0.72 mmol), and DIEA (376 µl, 2.16 mmol) were added. The reaction mixture was stirred at room temperature overnight. The crude reaction mixture was poured into water and the product was extracted with ethyl acetate three times. The organic layers were combined, washed with water and brine, dried over anhydrous sodium sulfate, filtered and concentrated in vacuo. The crude product was purified by flash column chromatography on silica gel with ethyl acetate as the eluant to give the titled compound. $^1$H NMR (CDCl$_3$, 500 MHz, mixture of rotamers R1 and R2 2:1 ratio): 9.12 (s, 0.33H, R2), 9.00 (s, 0.67H, R1), 8.64 (s, 0.67H, R1), 8.57 (s, 0.33H, R2), 8.22 (s, 0.33H, R2), 8.03 (s, 0.67H, R1), 5.94 (m, 1H), 5.35–5.26 (m, 1.33H), 4.91–4.52 (m, 3.67H), 4.20–3.20 (m, 6H), 2.88–2.83 (m, 1H), 2.75–2.72 (t, 0.66H, R2), 2.69–2.66 (t, 1.34H, R1), 2.47–2.31 (m, 2H), 1.97–1.94 (m, 1H), 1.78–1.74 (q, 0.66H, R2), 1.7–1.67 (q, 1.34H, R1), 1.27–1.24 (m, 6H), 1.04–1.01 (t, 0.99H, R2), 0.98–0.96 (t, 2.01H, R1).

Step E

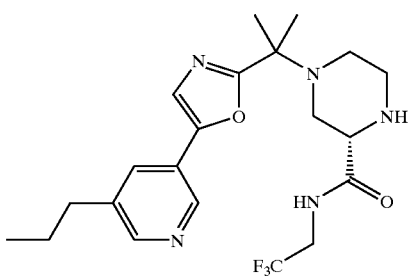

To intermediate prepared in Step D (300 mg, 0.554 mmol) was added fuming sulfuric acid (7 ml). The reaction mixture was stirred at 60° C. for 20 min, and then was slowly poured into ice water with stirring. The mixture was basified with potassium hydroxide to pH 12. The product was extracted with methylene chloride three times. The organic layers were combined, washed with brine, dried over anhydrous sodium sulfate, filtered and concentrated in vacuo. The crude product was purified by flash column chromatography on silica gel with 3:22 ammonia in MeOH (2M)/ethyl acetate as the eluant to give the titled compound. $^1$H NMR (CDCl$_3$, 500 MHz): 8.73 (s, 1H), 8.42 (s, 1H), 7.69 (s, 1H), 7.34 (s, 1H), 3.99–3.92 (m, 2H), 3.52–3.49 (m, 1H), 2.98–2.77 (m, 4H), 2.68–2.65 (t, 2H), 2.60–2.56 (m, 2H), 1.7–1.68 m), 2H), 1.61 (s, 3H), 1.60 (s, 3H), 1.02–0.99(t, 3H).

Step F

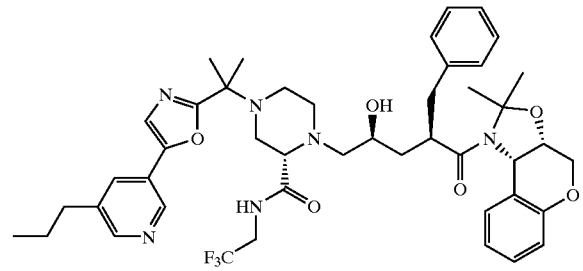

The intermediate prepared in Step E (94 mg, 0.213 mmol) and the epoxide intermediate prepared as in Example 1 Step P (84 mg, 0.213 mmol) in methanol (2 ml) was heated to reflux overnight. The solvent was removed in vacuo. The crude reaction mixture was purified by flash column chromatography on silica gel with ethyl acetate as the eluant to give the titled compound as a white solid. $^1$H NMR (CDCl$_3$, 500 MHz): 9.28 (bs, NH, 1H), 8.73 (s, 1H), 8.45 (s, 1H), 7.69 (s, 1H), 7.37–7.10 (m, 7H), 6.84–6.82 (m, 1H), 6.71–6.67 (m, 2H), 5.71 (d, J=4.60 Hz, 1H), 4.46–4.10 (m, 3H), 3.80–3.70 (m, 2H), 3.54–2.42 (m, 17H), 1.81–1.45 (m, 14H), 1.03–1.00 (t, 3H).

Step G (αR,γS,2S)-N-[(3S,4S)-3,4-dihydro-3-hydroxy-2H-1-benzopyran-4-yl]-γ-hydroxy-4-[1-methyl-1-[5-(5-propyl-3-pyridinyl)-2-oxazolyl]ethyl]-α-(phenylmethyl)-2-[[(2,2,2-trifluoroethyl)amino]carbonyl]-1-piperazinepentanamide To a solution of the intermediate obtained in Step F (65 mg, 0.078 mmol) in methanol (3.4 ml) was added 1 M HCl in ethyl ether (1.3 ml, 1.3 mmol). The reaction mixture was stirred at room temperature. After 5 hours the mixture was neutralized by 2 M ammonia in methanol. The solvent was removed in vacuo and the reaction mixture was diluted with methylene chloride and washed with 1 N NaOH. The aqueous layer was extracted with methylene chloride three times. The organic layers were combined, dried over anhydrous sodium sulfate, filtered and concentrated in vacuo. The crude product was purified by flash column chromatography with 3% 2M ammonia in methanol/ethyl acetate as the eluant. $^1$H NMR (CDCl$_3$, 500 MHz): 9.24 (bs, NH, 1H), 8.71 (s, 1H), 8.43 (s, 2H), 7.69 (s, 1H), 7.36 (s, 1H), 7.32–7.22 (m, 4H), 7.16–7.07 (m, 2H), 6.15 (d, J=8.0 Hz, 1H), 5.18–5.16 (m, 1H), 4.12–3.99 (m, 2H), 3.82–3.74 (m, 3H), 3.36–2.44 (m, 14H), 1.93–1.88 (m, 2H), 1.74–1.69 (m, 2H), 1.63–1.55 (m, 7H), 1.02–0.99 (t, 3H). LC-MS (M$^+$+1) (EI) 793.2.

EXAMPLE 97

(αR,γS,2S)-N-[(3S,4S)-3,4-dihydro-3-hydroxy-2H-1-benzopyran-4-yl]-γ-hydroxy-4-[1-methyl-1-[4-methyl-5-(3-pyridinyl)-2-oxazolyl]ethyl]-α-(phenylmethyl)-2-[[(2,2,2-trifluoroethyl)amino]carbonyl]-1-piperazinepentanamide

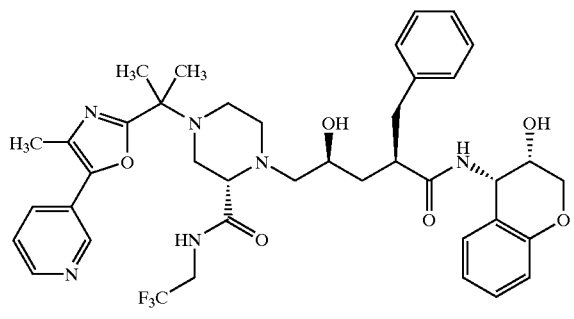

Step A

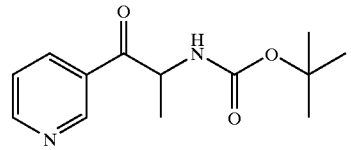

3-Bromopyridine (0.83 ml, 8.61 mmol) in THF (4 ml) was added isopropylmagnesium chloride (2M in THF, 5.6 ml, 11.19 mmol). The reaction mixture was stirred at room temperature for 1 h. N-(tert-Butoxycarbonyl)alanine-N'-methoxy-N'-methylamide (1 g, 4.30 mmol) was added in THF (4 ml). After stirring at room temperature for 3 hours, the reaction mixture was poured into aqueous NH$_4$Cl solution and the product was extracted with methylene chloride. The organic layer was washed with brine, dried over anhydrous sodium sulfate, filtered and concentrated in vacuo. The crude product was purified by flash column chromatography on silica gel with 3:7 ethyl acetate/hexane as the eluant to give the titled compound. $^1$H NMR (CDCl$_3$, 500 MHz): 9.18 (d, J=1.6 Hz, 1H), 8.80–8.78 (m, 1H), 8.26–8.24 (m, 1H), 7.44–7.42 (m, 1H), 5.60 (bs, NH, 1H), 5.25–5.22 (m, 1H), 1.43–1.40 (m, 12H).

Step B

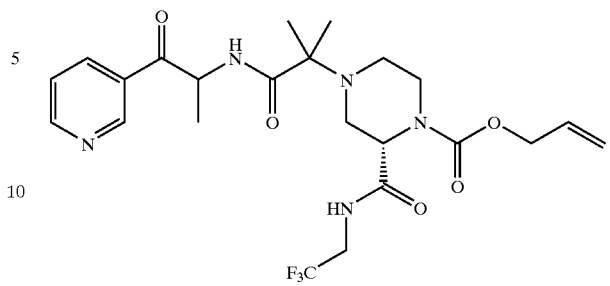

The intermediate prepared in Step A (237 mg, 0.95 mmol) was treated in TFA in methylene chloride (30%, 20 ml) at room temperature for 30 min. Then the reaction mixture was concentrated in vacuo and azeotroped with chloroform three times. To the resulting mixture dissolved in DMF (6 ml) was added the intermediate prepared in Example 66 Step D (300 mg, 0.79 mmol), PyBop (986 mg, 1.90 mmol), HOAt (258 mg, 1.90 mmol), and DIEA (990 μl, 5.69 mmol). The reaction mixture was stirred at room temperature overnight. The crude reaction mixture was poured into water and the product was extracted with ethyl acetate three times. The organic layers were combined, washed with water and brine, dried over anhydrous sodium sulfate, filtered and concentrated in vacuo. The crude product was purified by flash column chromatography on silica gel with 4:1 ethyl acetate/hexane as the eluant to give the titled compound. $^1$H NMR (CDCl$_3$, 500 MHz): 9.18 (d, J=1.6 Hz, 1H), 8.78 (d, J=3.9 Hz, 1H), 8.29–8.27 (m, 1H), 7.45–7.43 (m, 1H), 5.98–5.93 (m, 1H), 5.36–5.28 (m, 3H), 4.74–4.68 (m, 3H), 4.17–4.12 (m, 2H), 3.80–3.40 (m, 2H), 3.18–3.06 (m, 1H), 2.84–2.80 (m, 1H), 2.41–2.28 (m, 2H), 1.51 (d, J=7.1 Hz, 3H), 1.26 (s, 3H), 1.16 (s, 3H).

Step C

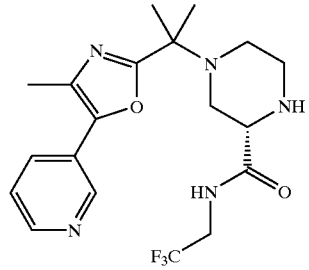

To intermediate prepared in Step B (260 mg, 0.506 mmol) was added fuming sulfuric acid (5 ml). The reaction mixture was stirred at 60° C. for 20 min, and then was slowly poured into ice water with stirring. The mixture was basified with potassium hydroxide to pH 12. The product was extracted with methylene chloride three times. The organic layers were combined, washed with brine, dried over anhydrous sodium sulfate, filtered and concentrated in vacuo to give the titled compound. $^1$H NMR (CDCl$_3$, 500 MHz): 8.87 (d, J=2.0 Hz, 1H), 8.58–8.56 (m, 1H), 8.15 (bs, NH, 1H), 7.89–7.87 (m, 1H), 7.52–7.38 (m, 1H), 4.05–3.84 (m, 2H), 3.56–3.54 (m, 1H), 3.02–2.89 (m, 4H), 2.80–2.76 (m, 1H), 2.65–2.55 (m, 2H) 2.44 (s, 3H), 1.59 (s, 3H), 1.58 (s, 3H).

Step D

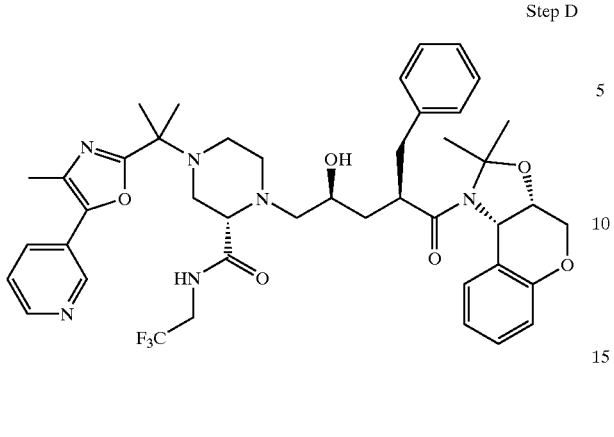

The intermediate prepared in Step C (172 mg, 0.419 mmol) and the epoxide intermediate from Example 1 Step P (165 mg, 0.419 mmol) in methanol (3.5 ml) was heated to reflux overnight. The solvent was removed in vacuo. The crude reaction mixture was purified by flash column chromatography on silica gel with ethyl acetate as the eluant to give the titled compound. $^1$H NMR (CDCl$_3$, 500 MHz): 9.33 (bs, NH, 1H), 8.87 (d, J=2.1 Hz, 1H), 8.61–8.59 (m, 1H), 7.87–7.85 (m, 1H), 7.43–7.40 (m, 1H), 7.35–7.10 (m, 6H), 6.84–6.65 (m, 3H), 5.71 (d, J=4.60 Hz, 1H), 4.46–4.10 (m, 3H), 3.73–2.46 (m, 16H), 2.45 (s, 3H), 1.78–1.57 (m, 10H), 1.28 (s, 3H).

Step E (αR,γS,2S)-N-[(3S,4S)-3,4-dihydro-3-hydroxy-2H-1-benzopyran-4-yl]-γ-hydroxy-4-[1-methyl-1-[4-methyl-5-(3-pyridinyl)-2-oxazolyl]ethyl]-α-(phenylmethyl)-2-[[(2,2,2-trifluoroethyl)amino]carbonyl]-1-piperazinepentanamide To a solution of the intermediate obtained in Step D (176 mg, 0.219 mmol) in methanol (10 ml) was added 1 M HCl in ethyl ether (5 ml, 5 mmol). The reaction mixture was stirred at room temperature. After 6 hours the mixture was neutralized by 2 M ammonia in methanol. The solvent was removed in vacuo and the reaction mixture was diluted with methylene chloride and washed with 1 N NaOH. The aqueous layer was extracted with methylene chloride three times. The organic layers were combined, washed with brine, dried over anhydrous sodium sulfate, filtered and concentrated in vacuo. The crude product was purified by flash column chromatography with 1.5% 2M ammonia in methanol/ethyl acetate as the eluant. $^1$H NMR (CDCl$_3$, 500 MHz): 9.29 (bs, NH, 1H), 8.86 (d, J=2.3 Hz, 1H), 8.59–8.58 (m, 1H), 7.88–7.86 (m, 1H), 7.42–7.40 (m, 1H), 7.32–7.22 (m, 4H), 7.12–7.07 (m, 2H), 6.81–6.78 (m, 2H), 6.16 (d, J=8.2 Hz, 1H), 5.18–5.16 (m, 1H), 4.16–3.99 (m, 3H), 3.82–3.36 (m, 5H), 3.10–2.65 (m, 9H), 2.47–2.44 (m, 4H), 1.93–1.88 (m, 2H), 1.61–1.56 (m, 7H). LC-MS (M$^+$+1) (EI) 765.2.

EXAMPLE 98

(αR,γS,2S)-N-[(3S,4S)-3,4-dihydro-3-hydroxy-2H-1-benzopyran-4-yl]-γ-hydroxy-4-[1-[5-(5-methoxy-3-pyridinyl)-4-methyl-2-oxazolyl]-1-methylethyl]-α-(phenylmethyl)-2-[[(2,2,2-trifluoroethyl)amino]carbonyl]-1-piperazinepentanamide

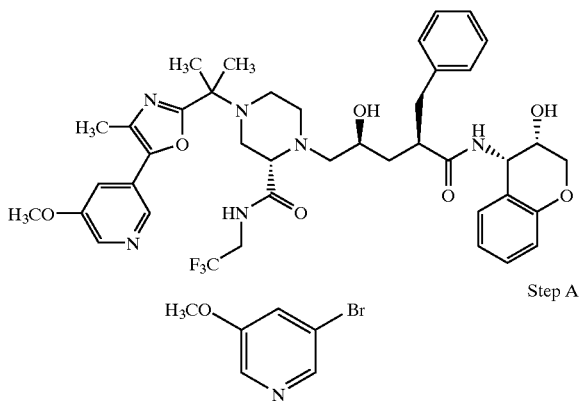

Step A

A solution of 3,5-dibromopyridine (10 g, 42.2 mmol) in DMF (110 ml) was cooled in an ice bath. Sodium methoxide (25% by wt. in MeOH, 48.2 ml, 211.1 mmol) was added. The reaction mixture was heated to 100° C. overnight. The reaction was quenched with water (100 ml). Concentrated HCl was added to pH 9. The mixture was concentrated to dryness in vacuo, then water (250 ml) was added. The product was extracted with ethyl acetate three times. The organic layers were combined, washed with brine, dried over sodium sulfate, filtered and concentrated in vacuo. The crude product was purified by flash column chromatography on silica gel with 30% ethyl acetate/hexane as the eluant to give the titled compound. $^1$H NMR (CDCl$_3$, 500 MHz): 8.29 (s, 1H), 8.25 (s, 1H), 7.37 (s, 1H), 3.86 (s, 3H).

Step B

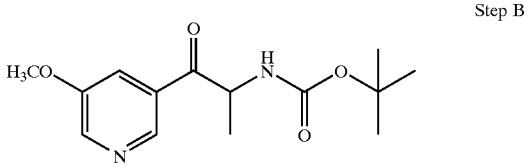

The intermediate prepared in Step A (2.07 g, 11.0 mmol) in THF (4 ml) was added isopropylmagnesium chloride (2M in THF, 6.6 ml, 13.2 mmol). The reaction mixture was stirred at room temperature for 1 h. N-(tert-Butoxycarbonyl)alanine-N'-methoxy-N'-methylamide (1.28 g, 5.50 mmol) was added in THF (15 ml). After stirring at room temperature for 3 hours, the reaction mixture was poured into aqueous NH$_4$Cl solution and the product was extracted with methylene chloride three times. The organic layer was combined, washed with brine, dried over anhydrous sodium sulfate, filtered and concentrated in vacuo. The crude product was purified by flash column chromatography on silica gel with 3:7 ethyl acetate/hexane as the eluant to give the titled compound. $^1$H NMR (CDCl$_3$, 500 MHz): 8.81 (s, 1H), 8.53 (s, 1H), 7.74 (s, 1H), 5.49 (bs, NH, 1H), 5.27–5.24 (m, 1H), 3.98 (s, 3H), 1.47 (s, 9H), 1.45 (d, J=7.3 Hz, 3H).

Step C

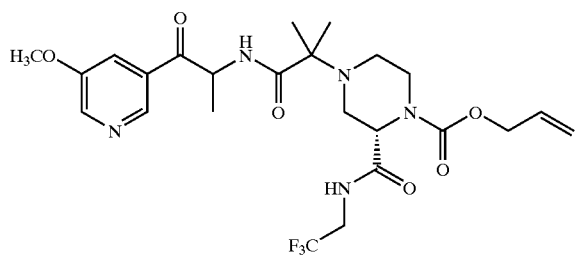

The intermediate prepared in Step B (1.45 g, 5.17 mmol) was treated in TFA in methylene chloride (30%, 100 ml) at room temperature for 30 min. Then the reaction mixture was concentrated in vacuo and azeotroped with chloroform three times. The resulting mixture was dissolved in DMF (10 ml) and to this mixture was added the intermediate prepared in Example 66 Step P (1.97 g, 5.17 mmol), PyBop (5.4 g, 10.3 mmol), HOAt (1.4 g, 10.3 mmol), and DIEA (5.4 ml, 31.0 mmol). The reaction mixture was stirred at room temperature overnight. The crude reaction mixture was poured into water and the product was extracted with ethyl acetate three times. The organic layers were combined, washed with water and brine, dried over anhydrous sodium sulfate, filtered and concentrated in vacuo. The crude product was purified by flash column chromatography on silica gel with ethyl acetate as the eluant to give the titled compound. $^1$H NMR (CDCl$_3$, 500 MHz): 8.80 (s, 1H), 8.49 (s, 1H), 7.70 (s, 1H), 5.98–5.93 (m, 1H), 5.36–5.27 (m, 3H), 4.75–4.68 (m, 3H), 4.18–4.11 (m, 2H), 3.92 (s, 3H), 3.80–3.40 (m, 2H), 3.18–3.06 (m, 1H), 2.85–2.83 (m, 1H), 2.42–2.28 (m, 2H), 1.52 (d, J=7.1 Hz, 3H), 1.27 (s, 3H), 1.17 (s, 3H).

Step D

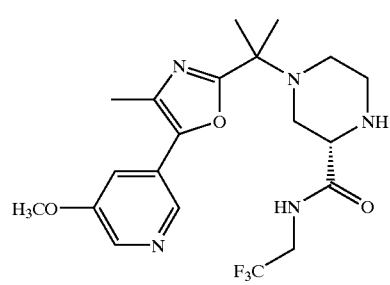

To intermediate prepared in Step C (1.3 g, 2.39 mmol) was added fuming sulfuric acid (10 ml). The reaction mixture was stirred at 60° C. for 20 min, and then was slowly poured into ice water with stirring. The mixture was basified with potassium hydroxide to pH 12. The product was extracted with methylene chloride three times. The organic layers were combined, washed with brine, dried over anhydrous sodium sulfate, filtered and concentrated in vacuo. The crude product was purified by flash column chromatography on silica gel with 4% 2M ammonia in MeOH/methylene chloride as the eluant to give the titled compound. $^1$H NMR (CDCl$_3$, 500 MHz): 8.49 (s, 1H), 8.28 (s, 1H), 8.08 (bs, NH, 1H), 7.37 (s, 1H), 4.06–3.98 (m, 1H), 3.95 (s, 3H), 3.90–3.82 (m, 1H), 3.00–2.87 (m, 3H), 2.78–2.54 (m, 3H), 2.45 (s, 3H), 1.59 (s, 3H), 1.58 (s, 3H).

Step E

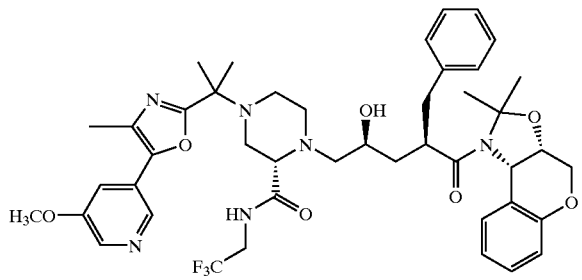

The intermediate prepared in Step D (576 mg, 1.30 mmol) and the epoxide prepared in Example 1 Step P (513 mg, 1.30 mmol) in methanol (10 ml) was heated to reflux overnight. The solvent was removed in vacuo. The crude reaction mixture was purified by flash column chromatography on silica gel with ethyl acetate as the eluant to give the titled compound. $^1$H NMR (CDCl$_3$, 500 MHz): 9.32 (bs, NH, 1H), 8.48 (s, 1H), 8.30 (s, 1H), 7.35–7.10 (m, 7H), 6.84–6.67 (m, 3H), 5.72 (d, J=4.60 Hz, 1H), 4.47–4.13 (m, 3H), 3.95 (s, 3H), 3.72–2.41 (m, 19H), 1.77–1.55 (m, 10H), 1.28 (s, 3H).

Step F (αR,γS,2S)-N-[(3S,4S)-3,4-dihydro-3-hydroxy-2H-1-benzopyran-4-yl]-γ-hydroxy-4-[1-[5-(5-methoxy-3-pyridinyl)-4-methyl-2-oxazolyl]-1-methylethyl]-α-(phenylmethyl)-2-[[(2,2,2-trifluoroethyl)amino]carbonyl]-1-piperazinepentanamide To a solution of the intermediate obtained in Step E (361 mg, 0.432 mmol) in methanol (23 ml) was added 1 M HCl in ethyl ether (11 ml, 11 mmol). The reaction mixture was stirred at room temperature. After 6 hours the mixture was neutralized by 2 M ammonia in methanol. The solvent was removed in vacuo and the reaction mixture was diluted with methylene chloride and washed with 1 N NaOH. The aqueous layer was extracted with methylene chloride three times. The organic layers were combined, washed with brine, dried over anhydrous sodium sulfate, filtered and concentrated in vacuo. The crude product was purified by flash column chromatography with 3% 2M ammonia in methanol/ethyl acetate as the eluant to give the titled the compound. $^1$H NMR (CDCl$_3$, 500 MHz): 9.31 (bs, NH, 1H), 8.48 (s, 1H), 8.30 (s, 1H), 7.35–7.23 (m, 5H), 7.14–7.08 (m, 2H), 6.82–6.79 (m, 2H), 6.08 (d, J=8.0 Hz, 1H), 5.19–5.16 (m, 1H), 4.17–3.99 (m, 3H), 3.95 (s, 3H), 3.82–3.37 (m, 5H), 3.10–2.66 (m, 9H), 2.48–2.45 (m, 4H), 1.91–1.77 (m, 2H), 1.61–1.57 (m, 7H). LC-MS (M$^+$+1) (EI) 795.4.

EXAMPLE 99

(αR,γS,2S)-N-[(3S,4S)-3,4-dihydro-3-hydroxy-2H-1-benzopyran-4-yl]-γ-hydroxy-4-[1-methyl-1-[5-[5-(methylthio)-3-pyridinyl]-2-oxazolyl]ethyl]-α-(phenylmethyl)-2-[[(2,2,2-trifluoroethyl)amino]carbonyl]-1-piperazinepentanamide

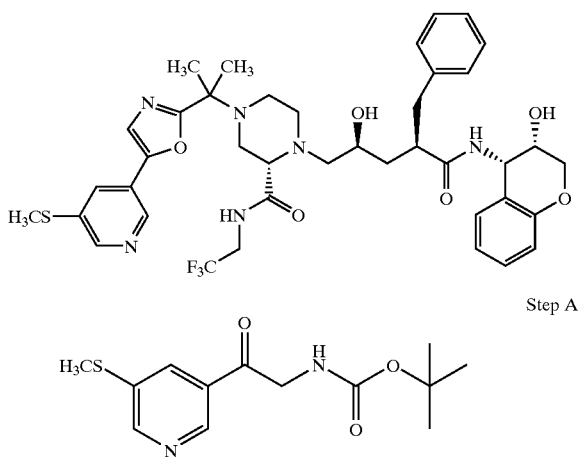

Step A

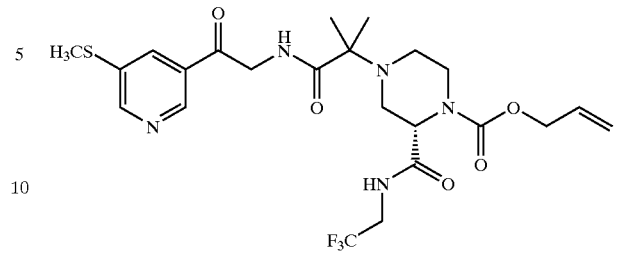

To a solution of 3,5-dibromopyridine (5 g, 21.1 mmol) in THF (10 ml) was added isopropylmagnesium chloride (2M in THF, 13.7 ml, 27.4 mmol). The reaction was stirred at room temperature for 1 h. Methyl disulfide (2.09 ml, 23.2 mmol) was added. After stirring at room temperature overnight, the reaction mixture was poured into aqueous NH$_4$Cl solution and the product was extracted with methylene chloride three times. The organic layer was combined, washed with brine, dried over anhydrous sodium sulfate, filtered and concentrated in vacuo. The crude product was purified by flash column chromatography on silica gel with 1:4 ethyl acetate/hexane as the eluant. The resulting product (1.25 g, 6.16 mmol) in THF (4 ml) was added isopropylmagnesium chloride (2M in THF, 4.0 ml, 8.0 mmol). The reaction mixture was stirred at room temperature for 1 h. N-(tert-Butoxycarbonyl)glycine-N'-methoxy-N'-methylamide (715 mg, 3.08 mmol) was added in THF. After stirring at room temperature overnight, the reaction mixture was poured into aqueous NH$_4$Cl solution and the product was extracted with methylene chloride three times. The organic layer was combined, washed with brine, dried over anhydrous sodium sulfate, filtered and concentrated in vacuo. The crude product was purified by flash column chromatography on silica gel with 3:7 ethyl acetate/hexane as the eluant to give the titled compound. $^1$H NMR (CDCl$_3$, 500 MHz): 8.91 (s, 1H), 8.70 (s, 1H), 8.07 (s, 1H), 5.48 (bs, NH, 1H), 4.68 (d, J=4.6 Hz, 2H), 2.59 (s, 3H), 1.51 (s, 9H).

Step B

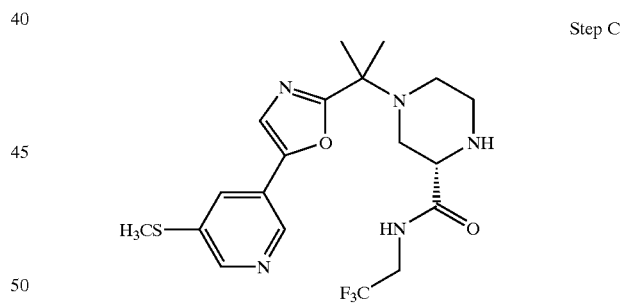

The intermediate prepared in Step A (305 mg, 1.08 mmol) was treated in TFA in Methylene chloride (30%) at room temperature for 30 min. Then the reaction mixture was concentrated in vacuo and azeotroped with chloroform three times. The resulting mixture was dissolved in DMF (4 ml) and to this mixture was added intermediate prepared in Example 66 Step D (412 mg, 1.08 mmol), PyBop (1.12 g, 2.16 mmol), HOAt (294 mg, 2.16 mmol), DIEA (1.13 ml, 6.48 mmol). The reaction mixture was stirred at room temperature overnight. The crude reaction mixture was poured into water and the product was extracted with ethyl acetate three times. The organic layers were combined, washed with water and brine, dried over anhydrous sodium sulfate, filtered and concentrated in vacuo. The crude product was purified by flash column chromatography on silica gel with ethyl acetate as the eluant to give the titled compound. $^1$H NMR (CDCl$_3$, 500 MHz): 8.90 (s, 1H), 8.67 (s, 1H), 8.05 (s, 1H), 6.84 (bs, NH, 1H), 5.98–5.88 (m, 1H), 5.36–5.27 (m, 2H), 4.82–4.50 (m, 5H), 4.16–3.20 (m, 5H), 2.89–2.83 (m, 1H), 2.56 (s, 3H), 2.45–2.33 (m, 2H), 1.27 (m, 6H).

Step C

To intermediate prepared in Step B (270 mg, 0.495 mmol) was added fuming sulfuric acid (5 ml). The reaction mixture was stirred at 60° C. for 20 min, and then was slowly poured into ice water with stirring. The mixture was basified with potassium hydroxide to pH 12. The product was extracted with methylene chloride three times. The organic layers were combined, dried over anhydrous sodium sulfate, filtered and concentrated in vacuo. The crude product was purified by flash column chromatography on silica gel with 5% 2M ammonia in MeOH/ethyl acetate as the eluant to give the titled compound. $^1$H NMR (CDCl$_3$, 500 MHz): 8.65 (s, 1H), 8.45 (s, 1H), 8.09 (bs, NH, 1H), 7.75 (s, 1H), 7.36 (s, 1H), 3.98–3.48 (m, 4H), 2.98–2.72 (m, 4H), 2.59–2.57 (m, 4H), 1.61 (s, 3H), 1.60 (s, 3H).

Step D

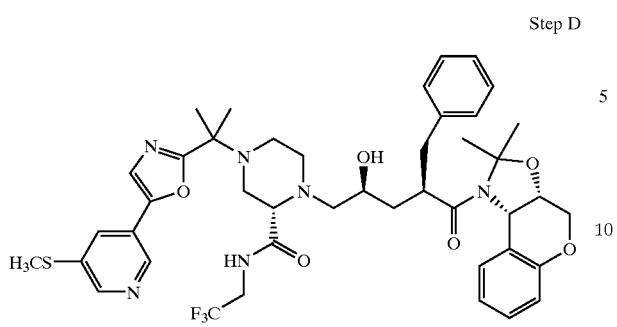

The intermediate prepared in Step C (98 mg, 0.22 mmol) and the epoxide prepared in Example 1 Step P (87 mg, 0.22 mmol) in methanol (2 ml) was heated to reflux overnight. The solvent was removed in vacuo. The crude reaction mixture was purified by flash column chromatography on silica gel with ethyl acetate as the eluant to give the titled compound. $^1$H NMR (CDCl$_3$, 500 MHz): 9.25 (bs, NH, 1H), 8.65 (s, 1H), 8.48 (s, 1H), 7.74 (s, 1H), 7.39 (s, 1H), 7.36–7.10 (m, 6H), 6.84–6.67 (m, 3H), 5.71 (d, J=4.60 Hz, 1H), 4.47–4.11 (m, 3H), 3.82–3.68 (m, 2H), 3.54–2.81 (m, 7H), 2.69–2.42 (m, 9H), 1.80–1.50 (m, 9H), 1.31–1.26 (m, 6H).

Step E (αR,γS,2S)-N-[(3S,4S)-3,4-dihydro-3-hydroxy-2H-1-benzopyran-4-yl]-γ-hydroxy-4-[1-methyl-1-[5-[5-(methylthio)-3-pyridinyl]-2-oxazolyl]ethyl]-α-(phenylmethyl)-2-[[(2,2,2-trifluoroethyl)amino]carbonyl]-1-piperazinepentanamide To a solution of the intermediate obtained in Step D (85 mg, 0.102 mmol) in methanol (5 ml) was added 1 M HCl in ethyl ether (2.5 ml, 2.5 mmol). The reaction mixture was stirred at room temperature. After 6 hours the mixture was neutralized by 2 M ammonia in methanol. The solvent was removed in vacuo and the reaction mixture was diluted with methylene chloride and washed with 1 N NaOH. The aqueous layer was extracted with methylene chloride three times. The organic layers were combined, washed with brine, dried over anhydrous sodium sulfate, filtered and concentrated in vacuo. The crude product was purified by flash column chromatography with 4% 2M ammonia in methanol/ethyl acetate as the eluant to give the titled compound. $^1$H NMR (CDCl$_3$, 500 MHz): 9.21 (bs, NH, 1H), 8.64 (s, 1H), 8.46 (s, 1H), 7.74 (s, 1H), 7.39 (s, 1H), 7.32–7.22 (m, 4H), 7.12–7.07 (m, 2H), 6.80–6.77 (m, 2H), 6.17 (d, J=8.2 Hz, 1H), 5.18–5.16 (m, 1H), 4.16–3.98 (m, 3H), 3.82–3.74 (m, 2H), 3.39–3.36 (m, 1H), 3.10–2.64 (m, 10H), 2.58 (s, 3H), 2.48–2.43 (m, 2H), 1.94–1.88 (m, 2H), 1.63–1.53 (m, 7H). LC-MS (M$^+$+1) (EI) 797.3.

EXAMPLE 100

(αR,γS,2S)-N-[(3S,4S)-3,4-dihydro-3-hydroxy-2H-1-benzopyran-4-yl]-γ-hydroxy-4-[1-[5-(5-dimethylamino-3-pyridinyl)-2-oxazolyl]-1-methylethyl]-α-(phenylmethyl)-2-[[(2,2,2-trifluoroethyl)amino]carbonyl]-1-piperazinepentanamide

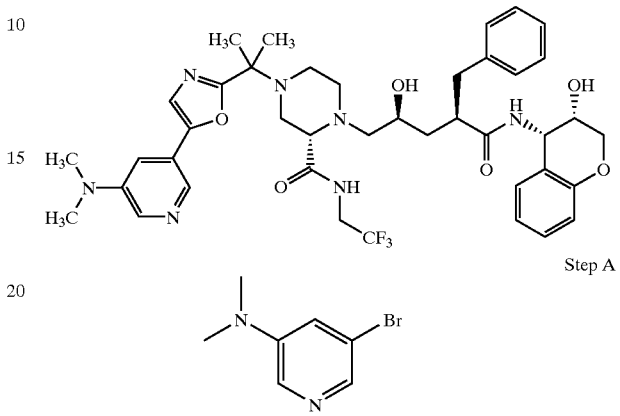

Step A

To a solution of tert-butanol (35.9 mL, 380 mmol) in THF (200 mL) was added sodium amide (59.3 g of a 50% solution in toluene, 760 mmol). The mixture was heated to 50° C. for 2 h. Dimethyamine was added (190 mL of a 2.0 M solution in THE, 380 mmol) and the solution was heated for an additional 2 h at 50° C. A solution of 3,5-dibromopyridine (45.0 g, 190 mmol in 150 mL THF) was added, and the reaction was heated for an additional 2 h at 50° C. The reaction was then cooled to ambient temperature and added slowly to saturated aqueous NaHCO$_3$ (1 L). The mixture was extracted with EtOAc (2×700 mL), and the organic layers were washed with saturated aqueous NaHCO$_3$ (1 L), brine (500 mL), dried (MgSO$_4$), and concentrated in vacuo, affording a 1:1 mixture of 3-bromo-5-dimethylaminopyridine and 3-bromo-4-dimethylaminopyridine. Purification by flash chromatography (5% EtOAc in DCM) afforded the 3-bromo-5-dimethylaminopyridine as a yellow solid. $^1$H NMR (CDCl$_3$, 500 MHz) 8.05 (d, J=2.5 Hz, 1H), 8.02 (d, J=2.0 Hz, 1H), 7.09 (s, 1H), 3.00 (s, 6H).

Step B

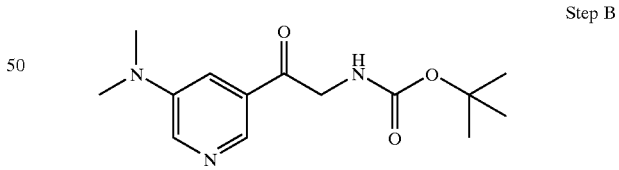

To a solution of the intermediate prepared in Step A (9.35 g, 46.5 mmol) in THF (250 mL) was added iso-propylmagnesium chloride (37.5 mL of a 1.3 M solution in THF, 48.8 mmol). After 1 h at ambient temperature, the reaction was cooled to 0° C., and a solution of N-tert-butylcarboxyglycine-N,O-dimethylhydroxamide (5.07 g, 46.5 mmol) in 50 mL of THF was added, and the solution was warmed to ambient temperature. After 27 h the reaction was cooled to 0° C. and quenched by the addition of saturated aqueous NaHCO$_3$ (500 mL). The organic layer was washed with brine (500 mL), dried (MgSO$_4$), and concentrated in vacuo. Purification by flash chromatography (5% MeOH, 45% EtOAc, 50% hexanes) afforded a 1:1 mixture of the-pyridylketone and 3-dimethylaminopyridine as a brown oil. This mixture was carried on into the next series of reactions.

Step C

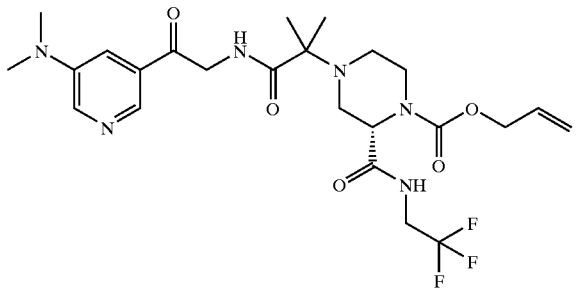

To a solution of the intermediate mixture prepared in Step B (5.65 g) in DCM (100 mL) was added TFA (50 mL). After 1 h at ambient temperature the reaction was concentrated in vacuo. The residue was dissolved in 100 mL DMF. To this solution was added the intermediate from Example 66, Step D (8.68 g, 18 mmol), followed by Pybop (9.36g, 18 mmol), then DIEA (31.3 mL, 180 mmol). The reaction was stirred at ambient temperature for 3 h, then quenched by the addition of saturated aqueous NaHCO$_3$ (200 mL). The mixture was diluted with EtOAc (500 mL) and the organic layer was washed with 0.5 M aqueous NaHCO$_3$ (3×300 mL), brine (300 mL), dried (MgSO$_4$), and concentrated in vacuo. Purification by flash chromatography (5% MeOH, 75% EtOAc, 20% hexanes) afforded the piperazine amide derivative as a yellow solid. $^1$H NMR (CDCl$_3$, 500 MHz) 8.56 (s, 1H), 8.38 (s, 1H), 7.42 (s, 1H), 5.93 (m, 1H), 5.35 (d, 1H), 5.28 (d, 1H), 4.83 m 2H), 4.68 (s, 1H), 4.5 (d, 1H), 4.17 (m, 2H), 3.90 (s, 1H), 3.80 (s, 1H), 3.67 (d, 1H), 3.28 (t, 1H), 3.04 (s, 6H), 2.5 (m, 2H), 2.46 (dd, 1H), 2.38 (dt, 1H), 1.26 (s, 6H). HPLC-MS (ES) 543.2 (M+1).

Step D

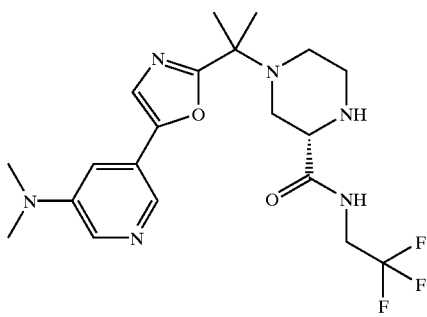

To the intermediate prepared in Step C (5.72 g, 10.55 mmol) was added fuming sulfuric acid (20% oleum, 15 mL). The mixture was heated to 50° C. for 15 minutes, then an additional 10 mL of fuming sulfuric acid was added, and the temperature increased to 70° C. After 30 minutes the reaction was cooled to ambient temperature, and quenched by slow addition of the reaction mixture to saturated aqueous NaHCO$_3$ (1 L). The aqueous layer was saturated with solid NaCl, and extracted with EtOAc (2×200 mL). The organic layer was dried (MgSO$_4$) and concentrated in vacuo, affording the pyridyiloxazole as a yellow solid. HPLC-MS (ES) 441.2 (M+1).

Step E

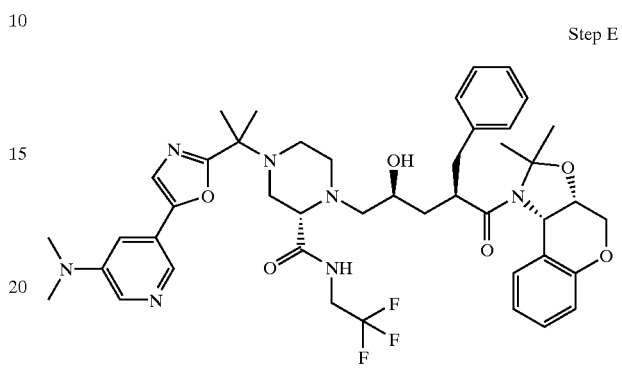

To a solution of the intermediate prepared in Step D (3.77 g, 8.57 mmol) in IPA (20 mL) was added the intermediate from Example 1, Step P (4.04 g, 10.28 mmol). The reaction was heated to reflux for 9 h, then cooled to ambient temperature, and concentrated in vacuo. Purification by flash chromatography (3% MeOH in EtOAc) afforded the coupled product as a yellow solid. HPLC-MS (ES) 834.5 (M+1).

Step F (αR,γS,2S)-N-[(3S,4S)-3,4-dihydro-3-hydroxy-2H-1-benzopyran-4-yl]-γ-hydroxy-4-[1-[5-(5-dimethylamino-3-pyridinyl)-2-oxazolyl]-1-methylethyl]-α-(phenylmethyl)-2-[[(2,2,2-trifluoroethyl)amino]carbonyl]-1-piperazinepentanamide To a solution of the intermediate prepared in Step E (1.62 g, 1.94 mmol) in MeOH (100 mL) was added HCl (50 mL of a 1M solution in Et$_2$O, 50 mmol). After 6 h at ambient temperature, the reaction was quenched by adding it to saturated aqueous NaHCO$_3$ (500 mL). The organic layer was extracted with DCM (2×200 mL). The combined organic layers were dried (Na$_2$SO$_4$) and concentrated in vacuo. The product was purified by flash chromatography (5% MeOH in EtOAc) affording the title compound as a white solid. $^1$H NMR (CDCl$_3$, 500 MHz) 9.31 (s, 1H), 8.26 (d, J=2.0 Hz, 1H), 8.15 (d, J=3.0 Hz, 1H), 7.29 (m, 5H), 7.10 (m, 3H), 6.81 (m, 2H), 5.96 (d, J=0.5 Hz, 1H), 5.18 (dd, J=4.5 Hz, J=0.0 Hz, 1H), 4.09 (m, 2H), 3.83 (m, 1H), 3.76 (m, 1H), 3.39 (s, 1H), 3.12 (m, 1H), 3.12 (d, J=12 Hz, 1H), 3.07 (s, 6H), 2.98 (m, 2H), 2.89 (m, 1H), 2.82 (dd, J=5.0 Hz, J=12.5 Hz, 1H), 2.76 (m, 1H), 2.69 (t, J=13.0 Hz, 2H), 2.48 (dd, J=2.5 Hz, J=13.0 Hz, 2H), 1.89 (t, J=1.5 Hz, 1H) 1.84 (m, 1H), 1.65 (s, 3H), 1.64 (s, 3H), 1.29 (m, 1H). HPLC-MS (ES) 794.2 (M+1).

EXAMPLE 101

(αR,γS,2S)-4-[1-[3-(5-methoxy-3-pyridinyl)-5-isoxazoly]-1-methylethyl]-N-[(3S,4S)-3,4-dihydro-3-hydroxy-2H-1-benzopyran-4-yl]-γ-hydroxy-α-(phenylmethyl)-2-[[(2,2,2-trifluoroethyl)amino]carbonyl]-1-piperazinepentanamide

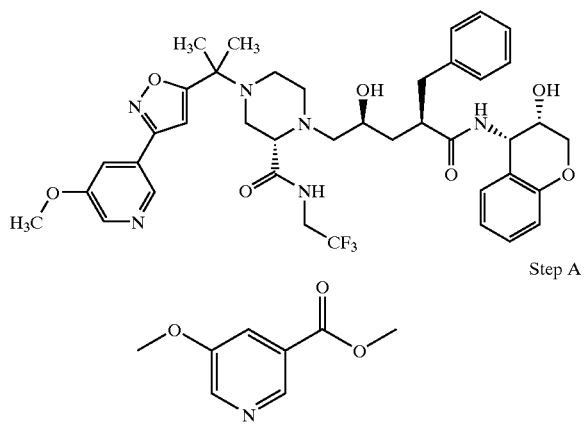

Step A

To a solution of bromonicotinic acid (5.00 g, 24.75 mmol) in DMF (50 mL) was added sodium methoxide (28 mL of a 25% solution in MeOH, 124 mmol), followed by a catalytic amount of CuI (50 mg). The reaction was heated to 100° C. for 72 h, then cooled to 0° C. To the solution was added HCl (29 mL of a 4.0 M solution in dioxane, 116 mmol), followed by triethylamine (17.2 mL, 123 mmol), then Pybop (15.45 g, 29.7 mmol). After 1 h at ambient temperature the reaction was quenched with 0.5 M NaHCO$_3$ (200 mL) and diluted with EtOAc (300 mL). The organic layer was washed with 0.5 M NaHCO$_3$ (3×200 mL), brine (200 mL), dried (MgSO$_4$, and concentrated in vacuo. Purification by flash chromatography (10% MeOH in EtOAc) afforded the methyl ester as a colorless oil. $^1$H NMR (CD$_3$OD, 500 MHz) 8.75 (s, 1H), 8.43 (s, 1H), 7.89 (s, 1H), 4.83 (s, 3H), 3.93 (s, 3H). HPLC-MS (ES) 168.1 (M+1).

Step B

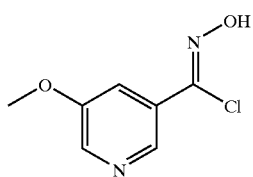

To a solution of the intermediate prepared in Step A (2.56 g, 15.3 mmol) in THF (150 mL) at 0° C. was added lithiumaluminum hydride (46 mL of a 10 M solution in THF). After 30 minutes, the reaction was quenched by the addition of EtOAc (10 mL), followed by the slow addition of saturated aqueous NaHCO$_3$ (500 mL). The mixture was extracted with EtOAc (2×500 mL). The combined organic layers were washed with brine, dried (MgSO$_4$), and concentrated in vauo. The resulting alcohol was dissolved in chloroform (100 mL). To this solution was added celite (5 g), followed by MnO$_2$ (13.0 g, 150 mmol). The mixture was heated to reflux for 30 minutes, then cooled to ambient temperature and filtered thru celite. The liquid was concentrated in vacuo, affording the aldehyde as a yellow oil. This material was dissolved in absolute ethanol (100 mL). To this solution was added pyridine (3.72 mL, 46.0 mmol), followed by hydroxylamine hydrochloride (3.99 g, 57.5 mmol). The reaction was heated to reflux for 1 h, then cooled to ambient temperature and concentrated in vacuo. The residue was dissolved in EtOAc (100 mL) and washed with water (100 mL). The organic layer was dried (MgSO$_4$) and concentrated in vacuo, affording the oxime as a white solid. This material was dissolved in DMF (10 mL) and heated to 50° C. To the mixture was added N-chlorosuccinimide (1.01 g, 7.56 mmol). After 30 minutes at 50° C. the reaction was cooled to ambient temperature and dissolved in EtOAc (200 mL). The solution was washed with water (200 mL), brine, dried (MgSO$_4$), and concentrated in vacuo, affording the chlorooxime as a yellow solid. $^1$H NMR (CD$_3$OD, 500 MHz) 8.60 (s, 1H), 8.35 (s, 1H), 7.78 (s, 1H), 3.97 (s, 3H). HPLC-MS (ES) 187.1 (M+1).

Step C

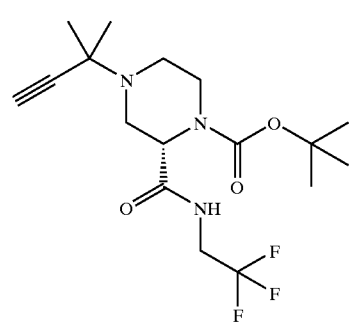

To a solution of the intermediate prepared in Example 37, Step A (44.9 g, 124 mmol) in THF (600 mL) was added thiosalicilic acid (28.8 g, 186 mmol). In a separate flask was prepared a solution of dipalladium(0)tris(dibenzylidineacetone) (5.70 g, 6.22 mmol) and 1,4-bis(diphenylphosphino)butane (7.16 g, 12.45 mmol) in THF (600 mL). The palladium(0) solution was added to the reaction mixture via cannula. After 2 h at ambient temperature the reaction mixture was quenched by the addition of 1% aqueous HCl (500 mL) and diluted with ether (2 L). The organic layer was washed with 1% aqueous HCl (3×500 mL). The combined aqueous layers were brought to pH 8 with saturated aqueous NaHCO$_3$, then extracted with EtOAc (2×600 mL). The combined organic layers were dried (MgSO$_4$) and concentrated in vacuo, affording 27.9 g of a colorless oil. To 8.38 g of this oil (30.2 mmol) in DCM (300 mL) was added triethylamine (6.32 mL, 45.4 mmol), followed by di-tert-butyldicarbonate (7.92 g, 36.3 mmol). After 1 h at ambient temperature, the reaction was quenched by the addition of saturated aqueous NaHCO$_3$ (200 mL). The organic layer was dried (Na$_2$SO$_4$) and concentrated in vacuo. Purification by flash chromatography afforded the Boc-protected piperazine as a colorless oil. $^1$H NMR (CDCl$_3$, 500 MHz) 7.20 (s, 1H), 4.76 (s, 1H), 4.00 (m, 2H), 3.58 (d, 1H), 3.06 (m, 2H), 2.40 (dd, 1H), 2.30 (m, 1H), 1.50 (s, 9H), 1.47 (s, 3H), 1.44 (s, 3H).

Step D

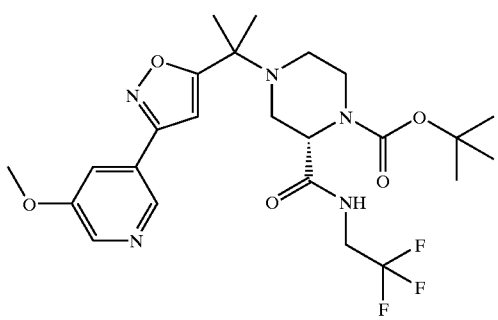

To a solution of the intermediate prepared in Step C (0.380 g, 1.01 mmol) in THF (1.5 mL) was added DIEA (0.875 mL, 5.04 mmol), and the mixture was heated to 55° C. To this solution was added dropwise over 1 h a solution of the intermediate prepared in Step B (0.375 g, 2.01 mmol) in THF (2.5 mL). After completion of the reagent addition, the reaction was stirred at 55° C. for 16 h, then cooled to ambient temperature and quenched by the addition of saturated aqueous NaHCO$_3$ (20 mL). The mixture was diluted with EtOAc (50 mL), and the organic layer was washed with brine (30 mL), and concentrated in vacuo. Purification by flash chromatography afforded the isoxazole as a yellow solid. $^1$H NMR (CDCl$_3$, 500 MHz) 8.60 (s, 1H), 8.41 (s, 1H), 7.69 (s, 1H), 7.00 (s, 1H), 6.49 (s, 1H), 4.71 (s, 1H), 4.09 (m, 2H), 3.60 (d, 1H), 3.04 (s, 1H), 2.95 (d, 1H), 2.31 (dd, 1H), 2.23 (dt, 1H), 1.72 (s, 1H), 1.69 (s, 3H), 1.61 (s, 3H), 1.49 (s, 9H).

Step E

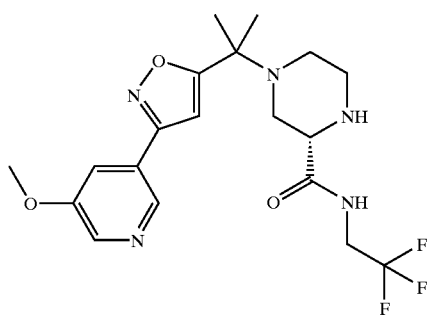

To a solution of the intermediate prepared in Step D (88.3 mg, 0.167 mmol) in DCM (5 mL) was added TFA (2.5 mL). After 2 h at ambient temperature, the reaction was quenched by the addition of saturated aqueous NaHCO$_3$ (10 mL). The organic layer was dried (Na$_2$SO$_4$) and concentrated in vacuo, affording the deprotected piperazine as a colorless oil. HPLC-MS (ES) 428.2 (M+1).

Step F

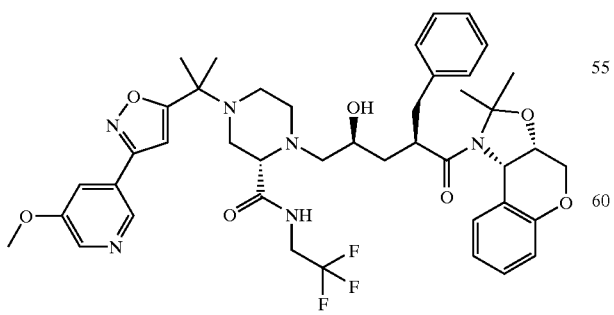

To a solution of the intermediate prepared in Step E (68.0 mg, 0.159 mmol) in IPA (1 mL) was added the epoxide intermediate from Example 1, Step P (93.9 mg, 0.239 mmol). The reaction was heated to reflux for 13 h, then concentrated in vacuo. Purification by flash chromatography afforded the coupled product as a white solid. HPLC-MS (ES) 821.5 (M+1).

Step G (αR,γS,2S)-4-[1-[2-(5-methoxy-3-pyridinyl)-4-isoxazoly]-1-methylethyl]-N-[(3S,4S)-3,4-dihydro-3-hydroxy-2H-1-benzopyran-4-yl]-γ-hydroxy-α-(phenylmethyl)-2-[[(2,2,2-trifluoroethyl)amino]carbonyl]-1-piperazinepentanamide To a solution of the intermediate prepared in Step F (55.6 g, 0.0678 mmol) in MeOH (5 mL) was added HCl (1.5 mL of a 1 M solution in Et$_2$O, 1.5 mmol). After 8 h at ambient temperature, the reaction was quenched by the addition of saturated aqueous NaHCO$_3$ (10 mL), and DCM (30 mL). The organic layer was dried (Na$_2$SO$_4$) and concentrated in vacuo. Purification by flash chromatorgaphy afforded the title compound as a white solid. $^1$H NMR (CDCl$_3$, 500 MHz) 9.12 (s, 1H), 8.58 (d, J=1.0 Hz, 1H), 8.43 (d,J=3.0 Hz, 1H), 7.70 (t, J=2.0 Hz, 1H), 7.30 (m, 4H), 7.13 (t, J=7.5 Hz, 1H), 7.10 (d, J=10.5 Hz, 1H), 6.82 (m, 2H), 6.49 (s, 1H), 6.01 (d, J=8.0 Hz, 1H), 5.18 (dd, J=4.0 Hz, J=8.0 Hz, 1H), 4.23 (m, 1H), 4.06 (d, J=11 Hz, 1H), 4.01 (dd, J=5.0 Hz, J=12.0 Hz, 1H), 3.96 (s, 3H), 3.85 (m, 3H), 3.50 (m, 1H), 3.38 (s, 1H), 3.01 (d, J=12.0 Hz, 1H), 2.90 (m, 3H), 2.82 (dd, J=4.5 Hz, J=12.0 Hz, 1H), 2.72 (m, 3H), 2.49 (dt, J=4.0 Hz, J=15.5 Hz, 2H), 2.20 (s, 1H), 1.93 (t, J=11.0 Hz, 1H), 1.70 (s, 1H), 1.60 (s, 3H), 1.58 (s, 3H). HPLC-MS (ES) 781.4 (M+1).

EXAMPLE 102

(αR,γS,2S)-4-[1-[2-(5-methoxy-3-pyridinyl)-4-thiazolyl]-1-methylethyl]-N-[(3S,4S)-3,4-dihydro-3-hydroxy-2H-1-benzopyran-4-yl -γ-hydroxy-α-(phenylmethyl)-2-[[(2,2,2-trifluoroethyl)amino]carbonyl]-1-piperazinepentanamide

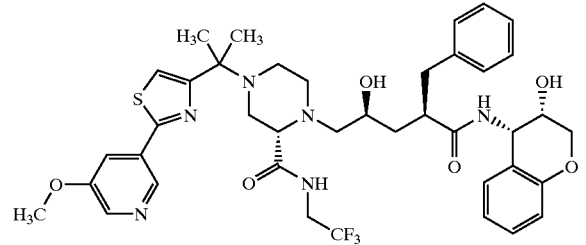

Step A

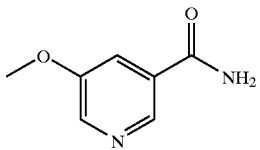

To a solution of 5-bromonicotinic acid (10.0 g, 49.5 mmol) in DMF (80 mL) was added 25% sodium methoxide in MeOH (53.5 mL, 247 mmol) and a catalytic amount of CuI (200 mg). The solution was heated to 100° C. for 19 h, then cooled to ambient temperature. The reaction was concentrated in vacuo, and the residue was suspended in DCM (100 mL). To this mixture was added N-hydroxysuccinimide (6.27 g, 54.4 mmol), followed by EDC (10.44 g, 54.4 mmol). After 4 h at ambient temperature, 30% NH$_4$OH (8.67 mL, 74.25 mmol) was added. After an additional 1 h at ambient temperature, the reaction was concentrated in vacuo. The residue was dissolved in EtOAc (200 mL) and washed with saturated aqueous NaHCO$_3$ (200 mL). The organic layer was dried (MgSO$_4$) and concentrated in vacuo. Purification by flash chromatography afforded the pyridyl amide as a white solid. $^1$H NMR (CD$_3$OD, 500 MHz) 8.63 (s, 1H), 8.38 (s, 1H), 7.80 (s, 1H), 4.82 (s, 3H); HPLC-MS (ES) 153.2 (M+1).

Step B

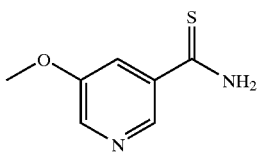

To a suspension of the intermediate prepared in Step A (250 mg, 1.64 mmol) in toluene (15 mL) was added Lawesson's reagent (2.66 g, 6.57 mmol). The mixture was heated to reflux for 3 h, then cooled to ambient temperature and filtered thru celite. The liquid phase was concentrated in vacuo, and purified by flash chromatography (70% EtOAc in hexanes) affording the thioamide as a yellow solid. $^1$H NMR (CDCl$_3$, 500 MHz) 8.58 (s, 1H), 8.37 (s, 1H), 7.80 (s, 1H), 7.64 (s, 1H), 7.32 (s, 1), 3.91 (s, 3H). HPLC-MS (ES) 169.1 (M+1).

Step C

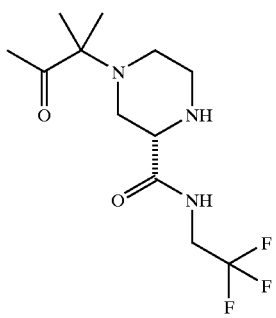

To a solution of the intermediate prepared in Example 37, Step A (44.9 g, 124 mmol) in THF (600 mL) was added thiosalicilic acid (28.8 g, 186 mmol). In a separate flask was prepared a solution of dipalladium(0)tris (dibenzylidineacetone) (5.70 g, 6.22 mmol) and 1,4-bis (diphenylphosphino)butane (7.16 g, 12.45 mmol) in THF (600 mL). The palladium(0) solution was added to the reaction mixture via cannula. After 2 h at ambient temperature the reaction mixture was quenched by the addition of 1% aqueous HCl (500 mL) and diluted with ether (2 L). The organic layer was washed with 1% aqueous HCl (3×500 mL). The combined aqueous layers were brought to pH 8 with saturated aqueous NaHCO$_3$, then extracted with EtOAc (2×600 mL). The combined organic layers were dried (MgSO$_4$) and concentrated in vacuo, affording 27.9 g of a colorless oil. To this oil (19.2 g) in 1M aqueous H$_2$SO$_4$ (300 mL) was added HgO (18.2 g, 83.3 mmol), and the mixture was stirred at ambient temperature. After 1 h, the reaction was quenched by the addition of saturated aqueous NaHCO$_3$ until the solution was pH 8. The solution was further diluted with CH$_3$CN (500 mL), followed by the addition of ethanethiol, which immediately precipitated the mercury salts. The suspension was filtered, and the liquid was extracted with EtOAc (2×1.5 L). The organic layers were washed with saturated aqueous NaHCO$_3$ (500 mL), brine (500 mL), dried (MgSO$_4$), and concentrated in vacuo, affording the methyl ketone as a brown oil. $^1$H NMR (CDCl$_3$, 500 MHz) 7.83 (s, 1H), 4.07 (m, 1H), 3.90 (m, 1H), 3.60 (s, 1H), 2.92 (m, 2H), 2.79 (m, 1H), 2.73 (m, 1H), 2.38 (m, 2H), 2.23 (s, 3H), 1.84 (s, 1H), 1.13 (s, 3H). 1.12 (s, 3H); HPLC-MS (ES) 296.1 (M+1).

Step D

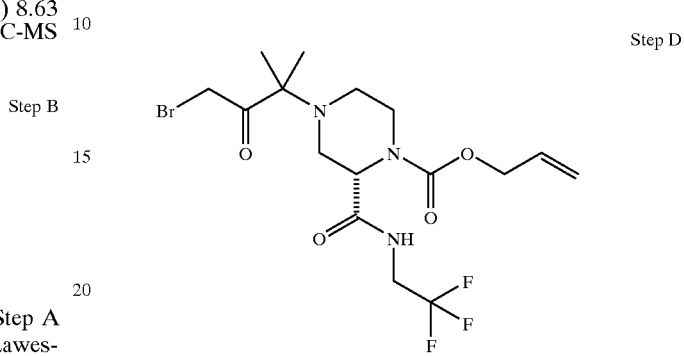

To a solution of the intermediate from Step C (20.5 g, 69.4 mmol) in DCM (500 mL) at −78° C. was added triethylamine (33.8 mL, 243 mmol), followed by trimethylsilyl trifluoromethanesulfonate (33.5 mL, 173 mmol). The reaction was warmed slowly to ambient temperature. After stirring 12 h, solid NaHCO$_3$ was added (15.0 g, 180 mmol), followed by N-bromosuccinimide (27.2 g, 152 mmol). After an additional 1 h at ambient temperature, allyl chloroformate was added (9.57 mL, 90.2 mmol), followed by triethylamine (10 mL, 90.2 mmol). The reaction was stirred for an additional 1 h at ambient temperature, then quenched by the addition of saturated aqueous NaHCO$_3$ (300 mL). The organic layer was dried (Na$_2$SO$_4$), and concentrated in vacuo, yielding a black oil. Purification by flash chromatography (5% EtOAc in DCM) afforded the pure bromoketone as a beige solid. $^1$H NMR (CDCl$_3$, 500 MHz) 6.64 (s, 1H), 5.96 (m, 1H), 5.78 (m, 1H), 5.32 (m, 2H), 4.83 (s, 1H), 4.64 (d, 2H), 4.22 (m, 3H), 3.90 (d, 1H), 3.60 (d, 2H), 3.12 (s, 1H), 2.60 (s, 1H, 2.38 (d, 1H), 2.34 (t, 1H), 1.26 (s, 3H), 1.19 (s, 3H); HPLC-MS (ES) 458.1, 460.1 (1:1 ratio, M−1, M+1).

Step E

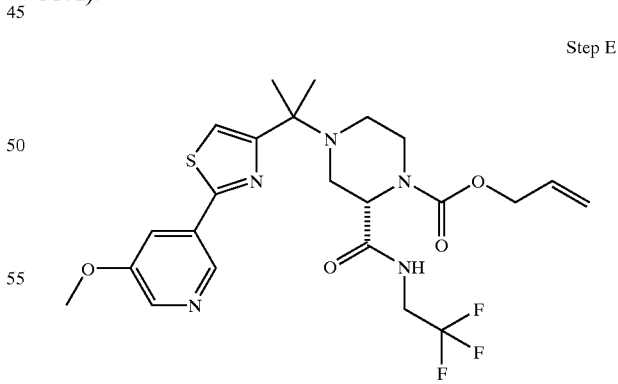

To a solution of the intermediate in Step D (15 mg, 0.330 mmol) in DMF (1 mL) was added the intermediate from Step B (61.0 mg, 0.360 mmol). The solution was heated to 60° C. for 16 h, then cooled to ambient temperature. The reaction was diluted with EtOAc (30 mL) and washed with saturated aqueous NaHCO$_3$ (5 mL) and brine (5 mL), dried (MgSO$_4$), and concentrated in vacuo. The residue was purified by preparative TLC, affording the pure pyridyl thiazoline as a yellow oil. $^1$H NMR (CDCl$_3$, 500 MHz) 8.73 (d, 1H), 8.37 (d, 1H), 7.69 (m, 1H, 7.14 (d, 1H), 5.78 (m, 1H), 5.18 (d, 1H), 5.11 d, 1H), 4.09 (m, 1H), 3.92 (s, 3H), 3.70 (m, 1H), 3.59 (m, 1H), 3.42 (s, 1H), 3.20 (s, 1H), 3.09 (m, 1H), 2.97 (m, 1H), 2.82 (m, 1H), 2.60 (m, 2H), 1.50 (s, 3H), 1.49 (s, 3H). HPLC-MS (ES) 528.2 (M+1).

Step F

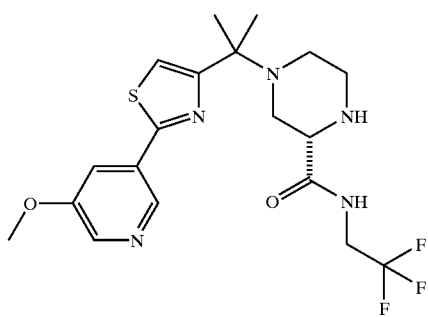

To a solution of the intermediate from Step E (72.0 mg, 0.136 mmol) in THF (0.5 mL) was added thiosalicilic acid (31.0 mg, 0.200 mmol) under N$_2$. In a separate flask was prepared a solution of dipalladium(0)tris (dibenzylidineacetone) (125 mg, 0.136 mmol) and 1,4-bis (diphenylphosphino)butane (156 mg, 0.272 mmol) in THF (0.5 mL). The palladium(0) solution was added to the reaction mixture via cannula. After 2 h at ambient temperature the reaction mixture was quenched by the addition of 1% aqueous HCl (0.5 mL) and diluted with ether (20 mL). The organic layer was washed with 1% aqueous HCl (3×5 mL). The combined aqueous layers were brought to pH 8 with saturated aqueous NaHCO$_3$, then extracted with EtOAc (2×20 mL). The combined organic layers were dried (MgSO$_4$) and concentrated in vacuo, affording the deprotected piperazine as a colorless oil. HPLC-MS (ES) 444.2 (M+1).

Step G

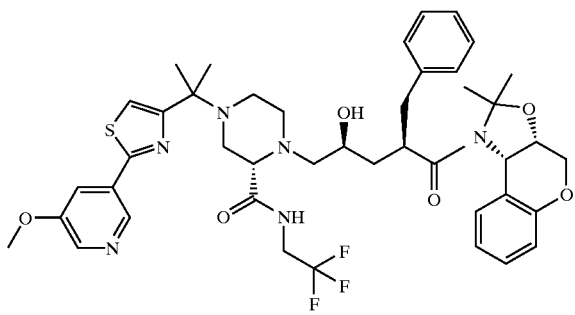

To a solution of the intermediate prepared in Step F (36 mg, 0.081 mmol) in IPA (1 mL) was added the epoxide intermediate from Example 1, Step P (45 mg, 0.12 mmol). The reaction was heated to reflux for 18 h, then concentrated in vacuo. Purification by preparative TLC (EtOAc) afforded the coupled product as a white solid. HPLC-MS (ES) 837.5 (M+1).

Step H (αR,γS,2S)-4-[1-[2-(5-methoxy-3-pyridinyl)-4-thiazolyl]-1-methylethyl]-N-[(3S,4S)-3,4-dihydro-3-hydroxy-2H-1-benzopyran-4-yl]-γ-hydroxy-α-(phenylmethyl)-2-[[(2,2,2-trifluoroethyl)amino]carbonyl]-1-piperazinepentanamide To a solution of the intermediate from Step G (27 mg, 0.032 mmol) in MeOH (3 mL) was added 1 M HCl in Et$_2$O (0.7 mL). After stirring 16 h at ambient temperature, the reaction was quenched by the addition of saturated aqueous NaHCO$_3$ (10 mL). The solution was extracted with EtOAc (30 mL). The organic layer was dried (MgSO$_4$) and concentrated in vacuo. Purification of the residue by preparative TLC (1% MeOH in EtOAc) afforded the title compound as a white solid. $^1$H NMR (CD$_3$OD, 500 MHz) 8.68 (s, 1H), 8.30 (d, J=2.5 Hz, 1H), 7.88 (s, 1H), 7.48 (s, 1H), 7.19 (m, 5H), 7.08 (m, 2H), 6.78 (t, J=7.0 Hz, 1H), 6.71 (d, J=8.0 Hz, 1H), 5.13 (d, J=3.5 Hz, 1H), 4.82 (s, 3H), 4.06 (m, 2H), 3.75 (m, 2H), 3.30 (s, 1H), 3.12 (s, 1H), 3.01 (m, 1H), 2.91 (m, 2H), 2.72 (m, 2H), 2.59 (s, 1H), 2.47 (s, 1H), 2.38 (m, 2H), 2.01 (t, J=13.5 Hz, 1H), 1.56 (s, 6H), 1.39 (m, 2H). HPLC-MS (ES) 797.2 (M+1).

EXAMPLE 103

(αR,γS,2S)-4-[1-[2-(5-chloro-3-pyridinyl)-4-thiazolyl]-1-methylethyl]-N-[(3S,4S)-3,4-dihydro-3-hydroxy-2H-1-benzopyran-4-yl]-γ-hydroxy-α-(phenylmethyl)-2-[[(2,2,2-trifluoroethyl)amino]carbonyl]-1-piperazinepentanamide

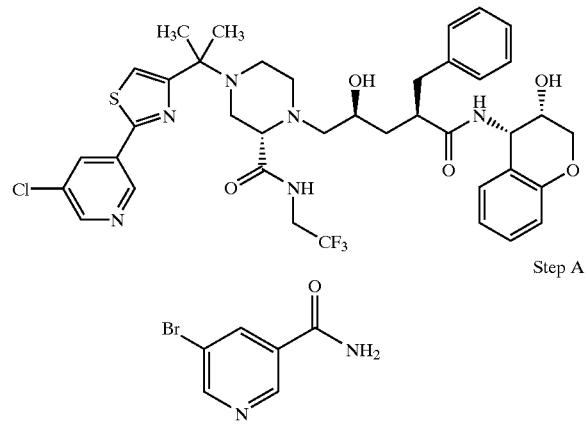

Step A

To a stirred suspension of 5-bromonicotinic acid (15.01 g, 74.3 mmol) in DCM (1 L) was added N-hydroxysuccinamide (8.55 g, 74.3 mmol), followed by a suspension of EDC (14.23 g, 74.2 mmol) in 30 mL DCM. Upon dissolution of the suspension (30 min) the reaction mixture was concentrated in vacuo to a dry solid. This material was dissolved in EtOAc (1 L) and washed with 0.5 N NaHCO$_3$ (2×700 mL) and brine (100 mL). The organic layer was dried (MgSO$_4$) and concentrated in vacuo, affording the succinate ester as a white solid. This material was dissolved in dioxane (600 mL), and treated with 30% aqueous NH$_4$OH (13 mL, 111 mmol), forming a precipitate. The solid was filtered, and washed with dioxane (4×100 mL). The combined liquid phases were concentrated in vacuo, affording the amide as a white solid. $^1$H NMR (CD$_3$OD, 500 MHz) 8.98 (d, J=9.4 Hz, 1H), 8.82 (d, J=9.1 Hz, 1 H), 8.46 (d, J=9.3 Hz, 1H), 4.86 (s, 2H).

Step B

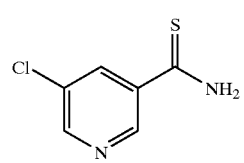

To a solution of the intermediate prepared in Step A (3.50 g, 17.4 mmol) in DMF (40 mL) was added CuCl (8.64 g, 87.2 mmol). The suspension was heated to 100° C. under $N_2$ for 72 h, then cooled to ambient temperature and concentrated to minimum volume in vacuo. To the remaining mixture was added 10% aqueous $NH_4OH$ (200 mL), and this solution was extracted with EtOAc (2×200 mL). The organic layers were washed with water (100 mL), and brine (100 mL), dried ($MgSO_4$), and concentrated. in vacuo, affording 814 mg (30%) of the chlorinated amide as a yellow solid. To this amide (300 mg, 1.92 mmol) in toluene (20 mL) was added Lawesson's reagent (3.10 g, 7.68 mmol). The mixture was heated to reflux for 4 h, then cooled to ambient temperature and filtered thru celite. The liquid phase was concentrated in vacuo, and purified by flash chromatography (40% EtOAc in hexanes) affording the thioamide as a yellow solid. $^1$H NMR ($CD_3OD$, 500 MHz) 8.92 (s, 1H), 8.45 (s, 1H), 8.30 (s, 1H), 3.87 (s, 2H).

(diphenylphosphino)butane (6.8 mg, 0.0016 mmol) in THF (0.5 mL). The palladium(0) solution was added to the reaction mixture via cannula. After 2 h at ambient temperature the reaction mixture was quenched by the addition of 1% aqueous HCl (0.5 mL) and diluted with ether (20 mL). The organic layer was washed with 1% aqueous HCl (3×5 mL). The combined aqueous layers were brought to pH 8 with saturated aqueous $NaHCO_3$, then extracted with EtOAc (2×20 mL). The combined organic layers were dried ($MgSO_4$) and concentrated in vacuo, affording the deprotected piperazine as a colorless oil. HPLC-MS (ES) 448.2 (M+1).

Step E

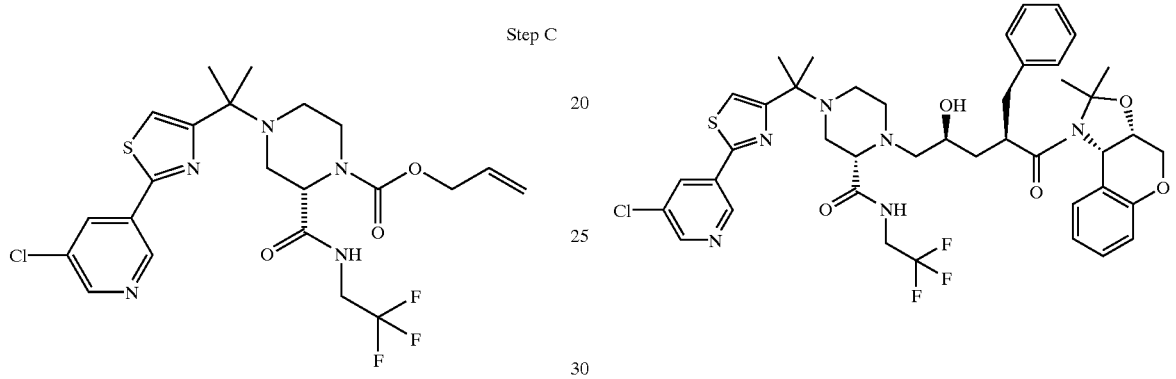

Step C

To a solution of the intermediate from Example 102, Step D (156 mg, 0.342 mmol) in DMF (1 mL) was added the intermediate from Step B (65.9 mg, 0.382 mmol). The solution was heated to 60° C. for 16 h, then cooled to ambient temperature. The reaction was diluted with EtOAc (30 mL) and washed with saturated aqueous $NaHCO_3$ (5 mL) and brine (5 mL), dried ($MgSO_4$), and concentrated in vacuo. The residue was purified by preparative reverse phase HPLC, affording the pure pyridyl thiazoline as a yellow oil. $^1$H NMR ($CDCl_3$, 500 MHz) 9.00 (d, J 1.6 Hz, 1H), 8.63 (d, J=2.3 Hz, 1H), 8.25 (t, J=2.0 Hz, 1H), 5.93 (m, 1H), 5.32 (d, J=17.4 Hz, 1H), 5.23 (d, J=10.6 Hz, 1H), 4.80 (s, 1H), 4.64 (m, 2H), 4.12 (m, 1H), 3.94 (m, 2H), 3.48 (d, J=0.5 Hz, 1H), 3.19 (s, 1H), 3.02 (d, J=10.7 Hz, 1H), 2.48 (s, 1H), 2.38 (s, 1H), 1.60 (s, 3H), 1.58 (s, 3H); HPLC-MS (ES) 532.2 (M+1).

To a solution of the intermediate prepared in Step D (40 mg, 0.089 mmol) in IPA (1 mL) was added the epoxide intermediate from Example 1, Step P (49 mg, 0.12 mmol). The reaction was heated to reflux for 9 h, then concentrated in vacuo. Purification by preparative reversed phase HPLC afforded the coupled product as a white solid. HPLC-MS (ES) 841.4 (M+1).

Step F (αR,γS,2S)-4-[1-[2-(5-chloro-3-pyridinyl)-4-thiazolyl]-1-methylethyl]-N-[(3S,4S)-3,4-dihydro-3-hydroxy-2H-1-benzopyran-4-yl]-γ-hydroxy-α-(phenylmethyl)-2-[[(2,2,2-trifluoroethyl)amino]carbonyl]-1-piperazinepentanamide Step D

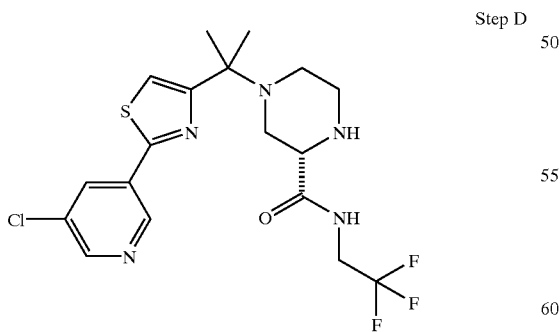

To a solution of the intermediate from Step C (75.0 mg, 0.140 mmol) in THF (0.5 mL) was added thiosalicilic acid (33.9 mg, 0.220 mmol) under $N_2$. In a separate flask was prepared a solution of dipalladium(0)tris (dibenzylidineacetone) (8.1 mg, 0.009 mmol) and 1,4-bis To a solution of the intermediate from Step E (30 mg, 0.036 mmol) in MeOH (3 mL) was added 1M HCl in $Et_2O$ (0.5 mL). After stirring 16 h at ambient temperature, the reaction was quenched by the addition of saturated aqueous $NaHCO_3$ (10 mL). The solution was extracted with EtOAc (30 mL). The organic layer was dried ($MgSO_4$) and concentrated in vacuo. Purification of the residue by chromatotron TLC (3% MeOH in EtOAc) afforded the title compound as a white solid. $^1$H NMR ($CDCl_3$, 500 MHz) 9.60 (s, 1H), 9.00 (s, 1H), 8.66 (s, 1H), 8.25 (s, 1H), 7.26 (m, 5H), 7.10 (m, 4H), 6.80 (s, 2H), 6.12 (m, 1H), 5.17 (s, 2H), 4.06 (m, 3H), 3.82 (m, 2H), 3.61 (m, 2H), 3.36 (m, 1H), 3.07 (d, J=10.5 Hz, 1H), 2.92 (m, 4H), 2.69 (m, 2H), 2.67 (m, 3H), 2.44 (m, 3H), 1.90 (m, 3H), 1.58 (s, 6H), 1.28 (m, 1H); HPLC-MS (ES) 801.3 (M+1).

EXAMPLE 104

(αR,γS,2S)-4-[1-[2-(3-pyridinyl)-4-thiazolyl]-1-methylethyl]-N-[(3S,4S)-3,4-dihydro-3-hydroxy-2H-1-benzopyran-4-yl]-γ-hydroxy-α-(phenylmethyl)-2-[[(2,2,2-trifluoroethyl)amino]carbonyl]-1-piperazinepentanamide

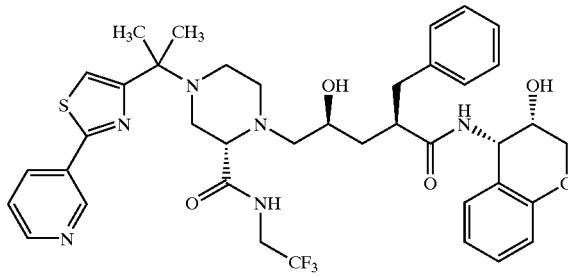

Step A

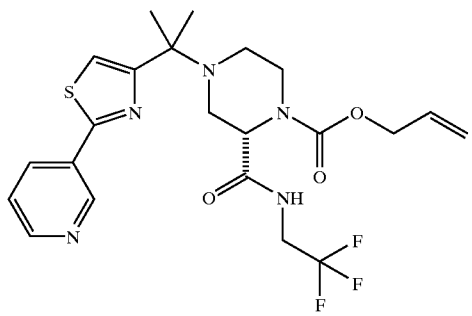

To a solution of the intermediate from Example 102, Step D (200 mg, 0.436 mmol) in DMF (1 mL) was added pyridyl-3-thioamide (85.4 mg, 0.619 mmol). The solution was heated to 60° C. for 16 h, then cooled to ambient temperature. The reaction was diluted with EtOAc (30 mL) and washed with saturated aqueous NaHCO₃ (5 mL) and brine (5 mL), dried (MgSO₄), and concentrated in vacuo. The residue was purified by preparative reverse phase HPLC, affording the pure pyidyl thiazoline as a yellow oil. ¹H NMR (CDCl₃, 500 MHz) 9.17 (s, 1H), 8.70 (s, 1H), 8.23 (d, J=0.1 Hz, 1H), 7.42 (t, J=2.8 Hz, 1H), 7.22 (s, 1H), 5.92 (m, 1H), 5.33 (d, J=17.2 Hz, 1H), 5.22 (dd, J=0.9 Hz, J=9.6 Hz, 1H), 4.77 (s, 1H), 4.63 (t, J=7.3 Hz, 2H), 4.13 (s, 1H), 3.95 (m, 1H), 3.84 (m, 1H), 3.43 (m, 1H), 3.15 (s, 1H), 3.01 (d, J=11.0 Hz, 1H), 2.47 (d, J=11.0 Hz, 1H), 2.35 (m, 1H), 1.58 (s, 3H), 1.56 (s, 3H); 1.28 (m, 1H); HPLC-MS (ES) 498.3 (M+1).

Step B

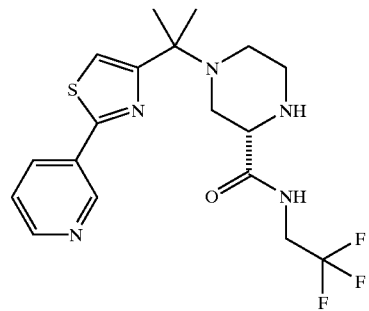

To a solution of the intermediate from Step A (89.0 mg, 0.179 mmol) in THF (0.5 mL) was added thiosalicilic acid (4.9 mg, 0.291 mmol) under N₂. In a separate flask was prepared a solution of dipalladium(0)tris (dibenzylidineacetone) (26.1 mg, 0.029 mmol) and 1,4-bis(diphenylphosphino)butane (21.8 mg, 0.051 mmol) in THF (0.5 mL). The palladium(0) solution was added to the reaction mixture via cannula. After 2 h at ambient temperature the reaction mixture was quenched by the addition of 1% aqueous HCl (0.5 mL) and diluted with ether (20 mL). The organic layer was washed with 1% aqueous HCl (3×5 mL). The combined aqueous layers were brought to pH 8 with saturated aqueous NaHCO₃, then extracted with EtOAc (2×20 mL). The combined organic layers were dried (MgSO₄) and concentrated in vacuo, affording the deprotected piperazine as a colorless oil. HPLC-MS (ES) 414.3 (M+1).

Step C

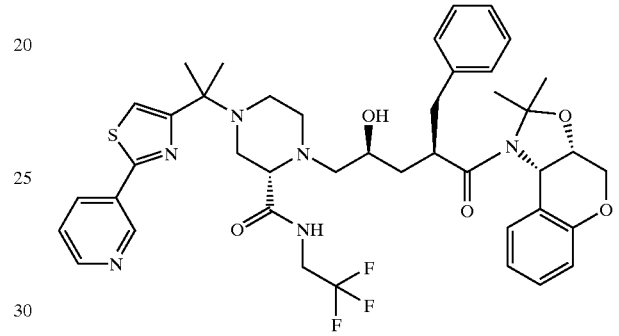

To a solution of the intermediate prepared in Step B (35.5 mg, 0.086 mmol) in IPA (1 mL) was added the epoxide intermediate from Example 1, Step P (67.1 mg, 0.171 mmol). The reaction was heated to reflux for 6 h, then concentrated in vacuo. Purification by preparative reversed phase HPLC afforded the coupled product as a white solid. HPLC-MS (ES) 807.4 (M+1).

Step D (αR,γS,2S)-4-[1-[2-(3-pyridinyl)-4-thiazolyl]-1-methylethyl]-N-[(3S,4S)-3,4-dihydro-3-hydroxy-2H-1-benzopyran-4-yl]-γ-hydroxy-α-(phenylmethyl)-2-[[(2,2,2-trifluoroethyl)amino]carbonyl]-1-piperazinepentanamide To a solution of the intermediate from Step C (21.3 mg, 0.026 mmol) in MeOH (3 mL) was added 1M HCl in Et₂O (0.5 mL). After stirring 16 h at ambient temperature, the reaction was quenched by the addition of saturated aqueous NaHCO₃ (10 mL). The solution was extracted with EtOAc (30 mL). The organic layer was dried (MgSO₄) and concentrated in vacuo. Purification of the residue by chromatotron TLC (2% MeOH in EtOAc) afforded the title compound as a white solid. ¹H NMR (CDCl₃, 500 MHz) 9.68 (s, 1H), 9.14 (d, J=1.8 Hz, 1H), 8.70 (dd, J=1.1 Hz, J=1.3 Hz, 1H), 8.23 (d, J=8.0 Hz, 1H), 7.42 (dd, J=4.8 Hz, J=4.8 Hz, 1H), 7.27 (m, 4H), 7.12 (m, 2H), 6.80 (m, 2H), 6.14 (s, 1H), 5.17 (dd, J=3.9 Hz, J=7.8 Hz, 1H), 4.06 (m, 3H), 3.83 (m, 2H), 3.55 (s, 1H), 3.35 (s, 1H), 3.05 (d, J=11.4 Hz, 1H), 2.94 (m, 3H), 2.80 (dd, J=4.6 Hz, J=12.1 Hz, 2H), 2.67 (m, 2H), 2.43 (d, J=12.8 Hz, 1H), 1.89 (m, 2H), 1.57 (s, 6H), 1.24 (s, 1H); HPLC-MS (ES) 767.4 (M+1).

EXAMPLE 105

(αR,γS,2S)-N-[(3S,4S)-3,4-dihydro-3-hydroxy-2H-1-benzopyran-4-yl]-γ-hydroxy-4-[1-[1-(5-methoxy-3-pyridinyl)-1H-pyrazol-3-yl]-1-methylethyl]-α-(phenylmethyl)-2-[[(2,2,2-trifluoroethyl)amino]carbonyl]-1-piperazinepentanamide

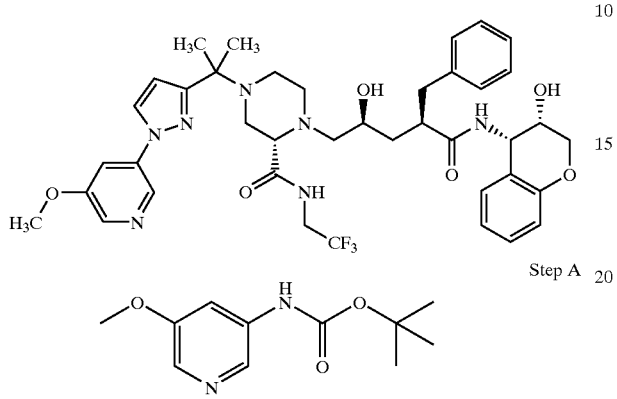

Step A

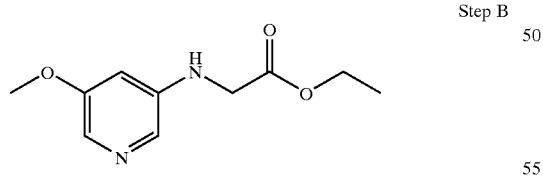

To a solution of 5-bromonicotinic acid (10.0 g, 49.5 mmol) in DMF (80 mL) was added 25% sodium methoxide in MeOH (53.5 mL, 247 mmol) and a catalytic amount of CuI (200 mg). The solution was heated to 100° C. for 19 h, then cooled to ambient temperature. The reaction was concentrated in vacuo, and the residue was suspended in tert-butanol (100 mL). To the mixture was added triethylamine (7.59 mL, 54.4 mmol), followed by diphenylphosphoryl azide (11.7 mL, 54.4 mmol). The resulting mixture was heated to reflux for 2 h, then cooled to ambient temperature and quenched with saturated aqueous NaHCO₃ (200 mL). The mixture was diluted with EtOAc (300 mL) and washed with 10% aqueous NH₄OH (200 mL) and brine (200 mL). The organic layer was dried (MgSO₄) and concentrated in vacuo. Purification by flash chromatography (50% EtOAc in hexanes) afforded the Boc-amine. $^1$H NMR (CDCl₃, 500 MHz) 7.98 (s, 1H), 7.96 (s, 1H), 7.70 (s, 1H), 6.79 (s, 1H), 3.83 (s, 3H), 1.49 (s, H).

Step B

To a solution of the intermediate prepared in Step A (1.70 g, 7.59 mmol) in DCM (16 mL) was added TFA (8 mL). After 1.5 h at ambient temperature the reaction was concentrated in vacuo, and dissolved in DMF (20 mL). This solution was added to a refluxing solution of ethyl glyoxylate (6.2 mL of a 50% solution in toluene). The resulting mixture was cooled to ambient temperature and stirred for 30 minutes. To this solution was added sodium triacetoxyborohydride (6.43 g, 30.4 mmol) and the resulting mixture was stirred for 1 h. The mixture was then diluted with EtOAc (300 mL) and quenched with saturated aqueous NaHCO₃ (200 mL). The organic layer was washed with 0.5 M aqueous NaHCO₃, brine, dried (MgSO₄) and concentrated in vacuo. Purification by flash chromatography afforded the pyridylglycine as a colorless oil. $^1$H NMR (CDCl₃, 500 MHz) 7.72 (s, 1H), 7.68 (s, 1H), 6.40 (s, 1H), 4.45 (s, 1H), 4.23 (q, 2H), 3.86 (s, 2H), 3.79 (s, 3H), 1.28 t, 3H). HPLC-MS (ES) 211.2 (M+1).

Step C

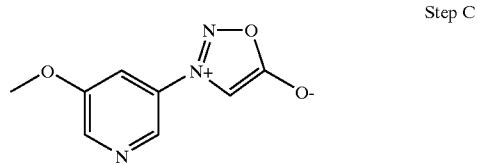

The intermediate prepared in Step B (408 mg, 1.94 mmol) was dissolved in HCl (35% aqueous), and the resulting mixture was heated to 80° C. for 1.5 h. The solution was then cooled to ambient temperature and concentrated in vacuo. The residue was dissolved in water (5 mL) at 0° C., and to this solution was added NaNO₂ (197 mg, 2.13 mmol). After 2.5 h at 0° C. the mixture was concentrated in vacuo, then dissolved in acetic anhydride (20 mL). The resulting mixture was heated to reflux for 45 minutes, then cooled to ambient temperature and concentrated in vacuo. Purification by flash chromatography (35% EtOAc in hexanes) afforded the sydnone as a yellow solid. $^1$H NMR (CDCl₃, 500 MHz) 8.59 (s, 1H), 7.54 (s, 1H), 6.78 (s, 1H), 3.94 (s, 3H). HPLC-MS (ES) 194.1 (M+1).

Step D

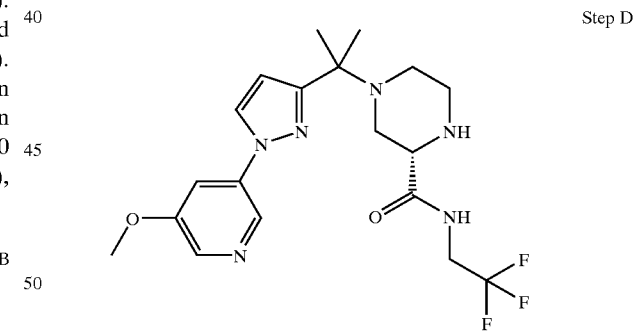

To a solution of the intermediate prepared in Step C (120 mg, 0.620 mmol) in 1,3-dichlorobenzene (2 mL) was added the intermediate prepared in Example 101, Step C (818 mg, 2.25 mmol). The mixture was heated to 135° C. for 36 h, then cooled to ambient temperature and concentrated in vacuo. Purification by flash chromatography (50% EtOAc in hexanes) afforded the pyrazole. This material was dissolved in DCM (0.5 ml) and to this solution was added TFA (Q0.25 mL). After 1 h at ambient temperature the reaction was quenched by the addition of saturated aqueous NaHCO₃ (5 mL) and diluted with DCM (30 mL). The organic layer was dried (Na$_2$SO$_4$) and concentrated in vacuo, affording the deprotected piperazine as a colorless oil. $^1$H NMR (CDCl$_3$, 500 MHz) 8.49 (s, 1H), 8.20 (s, 1H), 8.07 (s, 1H), 7.83 (s, 1H), 7.55 (s, 1H), 6.40 (s, 1H), 3.90 (m, 1H), 3.89 (s, 3H), 3.80 (m, 1H), 3.42 (m, 1H), 0.95 (m, 1H), 2.80 (m, 2H), 2.68 (m, 1H), 2.50 (m, 2H), 1.83 (s, 1H), 1.43 (s, 3H), 1.42 (s, 3H). HPLC-MS (ES) 427.2 (M+1).

Step E

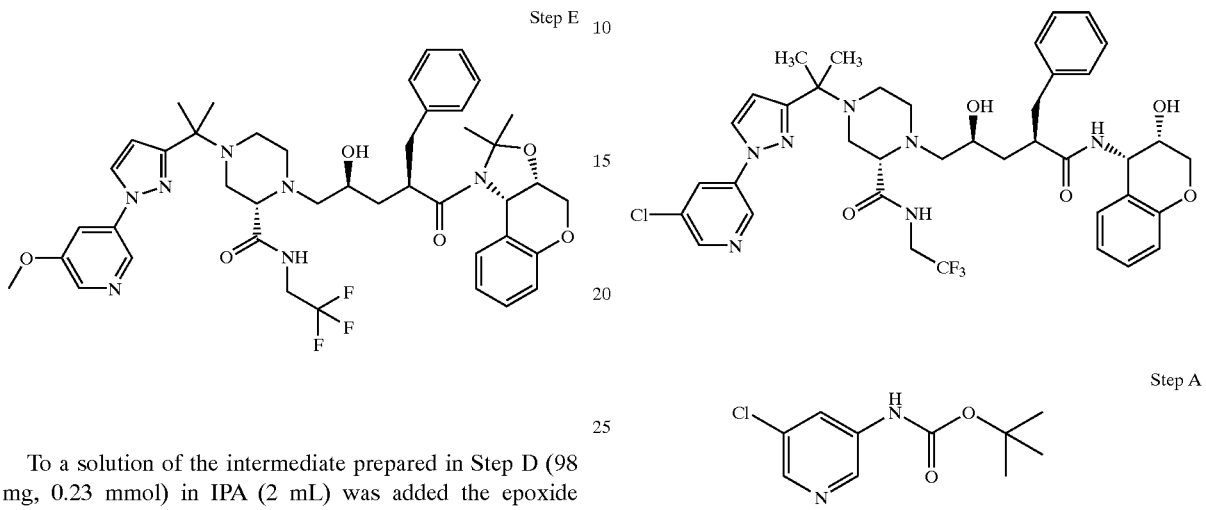

To a solution of the intermediate prepared in Step D (98 mg, 0.23 mmol) in IPA (2 mL) was added the epoxide intermediate prepared-in Example 1, Step P (180 mg, 0.46 mmol). The solution was heated to reflux for 16 h, then cooled to ambient temperature and concentrated in vacuo. Purification by flash chromatography (EtOAc) afforded the coupled product as a white solid. HPLC-MS (ES) 820.5 (M+1).

Step E (αR,γS,2S)-N-[(3S,4S)-3,4-dihydro-3-hydroxy-2H-1-benzopyran-4-yl]-γ-hydroxy-4-[1-[5-(5-methoxy-3-pyridinyl)-1H-pyrazol-3-yl]-1-methylethyl]-α-(phenylmethyl)-2-[[(2,2,2-trifluoroethyl)amino]carbonyl]-1-piperazinepentanamide To a solution of the intermediate prepared in Step F (82.4 mg, 0.100 mmol) in MeOH (3 mL) was added HCl (1.5 mL of a 1.0 M solution in Et$_2$O, 1.5 mmol). After 6 h at ambient temperature the reaction was quenched by the addition of saturated aqueous NaHCO$_3$ (20 mL). The mixture was extracted with DCM (50 mL), and the organic layer was dried (Na$_2$SO$_4$) and concentrated in vacuo. Purification by preparative TLC (1% MeOH in EtOAc) afforded the title compound as a white solid. $^1$H NMR (CD$_3$OD, 500 MHz) 8.59 (d, J=2.0 Hz, 1H), 8.27 (d, J=2.5 Hz, 1H), 8.15 (d, J=2.5 Hz, 1H), 7.77 (t, J=2.5 Hz, 1H), 7.20 (m, 5H) 7.10 (d, J=7.5 Hz, 1H), 7.06 (d, J=7.5 Hz, 1H), 6.80 (t, J=8.0 Hz, 1H), 6.71 (d, J=5.5 Hz, 1H), 0.51 (d, J=2.5 Hz, 1H), 5.14 (d, J=4.0 Hz, 1H), 4.06 (m, 2H), 3.94 (s, 3H), 3.77 (m, 2H), 3.07 (dd, J=4.0 Hz, 1H), 3.01 (m, 1H), 2.95 (m, 3H), 2.81 (d, J=9.0 Hz, 1H) 2.74 (d, J=6.5 Hz, 1H), 2.71 (d, J=6.5 Hz, 1H), 2.68 (m, 2H), 2.53 (m, 1H), 2.43 (m, 1H), 2.37 (d, J=4.0 Hz, 2H), 2.03 (m, 1H), 1.50 (s, 6H), 1.39 (m, 1H). HPLC-MS (ES) 780.5 (M+1).

EXAMPLE 106

(αR,γS,2S)-N-[(3S,4S)-3,4-dihydro-3-hydroxy-2H-1-benzopyran-4-yl]-γ-hydroxy-4-[1-[1-(5-chloro-3-pyridinyl)-1H-pyrazol-3-yl]-1-methylethyl]-α-(phenylmethyl)-2-[[(2,2,2-trifluoroethyl)amino]carbonyl]-1-piperazinepentanamide Step A To a solution of 5-bomonicotinic acid (10 g, 99 mmol) in a 3:1 mixture of benzene/MeOH (200 mL) was added trimethylsilyldiazomethane (74.2 mL of a 2.0 M solution in hexanes, 148 mmol). After 1 h at ambient temperature the reaction was quenched by the addition of acetic acid (5 mL). The reaction was diluted with EtOAc (300 mL) and washed with saturated aqueous NaHCO$_3$ (300 mL), and brine (300 mL). The organic layer was dried (MgSO$_4$) and concentrated in vacuo. The residue was then dissolved in DMF (100 mL), and to this solution was added CuCl (16.9 g, 171 mmol). The mixture was then heated to 100° C. for 24 h. The mixture was cooled to ambient temperature and diluted with EtOAc (1.5 L). The organic layer was washed with 10% aqueous NH$_4$OH (2×80 mL), and brine, dried (MgSO$_4$) and concentrated in vacuo. The material was then dissolved in THF (200 mL) and treated with LiOH (33.4 mL of a 2.0 M solution, 76.8 mmol). After 1 h the reaction was concentrated in vacuo, and the residue was dissolved in THF (50 mL) and brought to pH 7 with HCl (1.0 M in Et$_2$O). This mixture was again concentrated in vacuo, then dissolved in tert-butanol (135 mL). To the mixture was added triethylamine (9.46 mL, 67.9 mmol), followed by diphenylphosphoryl azide (14.6 mL, 67.9 mmol). The resulting mixture was heated to reflux for 2 h, then cooled to ambient temperature and quenched with saturated aqueous NaHCO$_3$ (200 mL). The mixture was diluted with EtOAc (300 mL) and washed with 10% aqueous NH$_4$OH (200 mL) and brine (200 mL). The organic layer was dried (MgSO$_4$) and concentrated in vacuo. Purification by flash chromatography (25% EtOAc in hexanes) afforded the Boc-amine. $^1$H NMR (CDCl$_3$, 500 MHz) 8.28 (s, 1H), 8.22 (s, 1H), 8.16 (s, 1H), 7.30 (s, 1H), 1.51 (s, 9H).

Step B

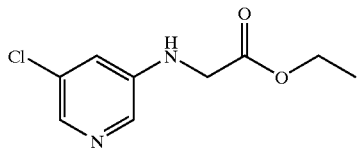

To a solution of the intermediate prepared in Step A (1.70 g, 7.59 mmol) in DCM (16 mL) was added TFA (8 mL). After 1.5 h at ambient temperature the reaction was concentrated in vacuo, and dissolved in DMF (20 mL). This solution was added to a refluxing solution of ethyl glyoxylate (6.2 mL of a 50% solution in toluene). The resulting mixture was cooled to ambient temperature and stirred for 30 minutes. To this solution was added sodium triacetoxyborohydride (6.30 g, 29.7 mmol) and the resulting mixture was stirred for 1 h. The mixture was then diluted with EtOAc (300 mL) and quenched with saturated aqueous $NaHCO_3$ (200 mL). The organic layer was washed with 0.5 M aqueous $NaHCO_3$, brine, dried ($MgSO_4$) and concentrated in vacuo. Purification by flash chromatography afforded the pyridylglycine as a colorless oil. $^1$H NMR ($CDCl_3$, 500 MHz) 7.93 (s, 1H), 7.89 (s, 1H), 6.80 (s, 1H), 4.50 (s, 1H), 4.24 (q, 2H), 3.83 (d, 2H), 1.26 (t, 3H). HPLC-MS (ES) 215.1 (M+1).

Step C

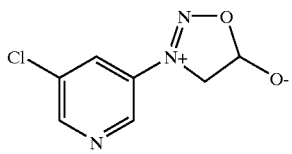

The intermediate prepared in Step B (397 mg, 1.85 mmol) was dissolved in HCl (35% aqueous), and the resulting mixture was heated to 80° C. for 1.5 h. The solution was then cooled to ambient temperature and concentrated in vacuo. The residue was dissolved in water (5 mL) at 0° C., and to this solution was added $NaNO_2$ (140 mg, 2.04 mmol). After 2.5 h at 0° C. the mixture was concentrated in vacuo, then dissolved in acetic anhydride (20 mL). The resulting mixture was heated to reflux for 45 minutes, then cooled to ambient temperature and concentrated in vacuo. Purification by flash chromatography (50% EtOAc in hexanes) afforded the sydnone as a yellow solid. $^1$H NMR ($CDCl_3$, 500 MHz) 8.92 (s, 1H), 8.90 (s, 1H), 8.13 (s, 1H), 6.80 (s, 1H). HPLC-MS (ES) 198.1 (M+1).

Step D

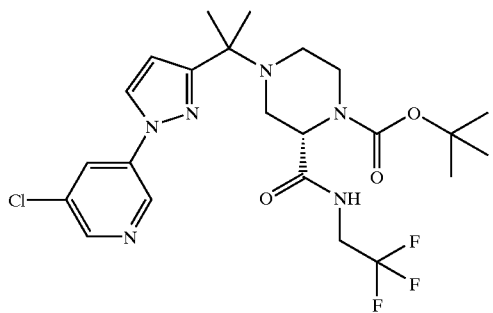

To a solution of the intermediate prepared in Step C (200 mg, 1.00 mmol) in 1,3-dichlorobenzene (2 mL) was added the intermediate prepared in Example 101, Step C (940 mg, 2.51 mmol). The mixture was heated to 135° C. for 24 h, then cooled to ambient temperature and concentrated in vacuo. Purification by flash chromatography (35% EtOAc in hexanes) afforded the pyrazole. $^1$H NMR ($CDCl_3$, 500 MHz) 8.79 (s, 1H), 8.41 (s, 1H), 8.04 (s, 1H), 7.84 s, 1H), 6.40 (s, 1H), 4.60 (s, 1H), 3.90 (m, 3H), 3.41 (d, 1H), 2.97 (s, 1H), 2.80 (s, 1H), 2.32 (dd, 1H), 2.18 (t, 1H), 1.43 (s, 15H). HPLC-MS (ES) 531.2 (M+1).

Step E

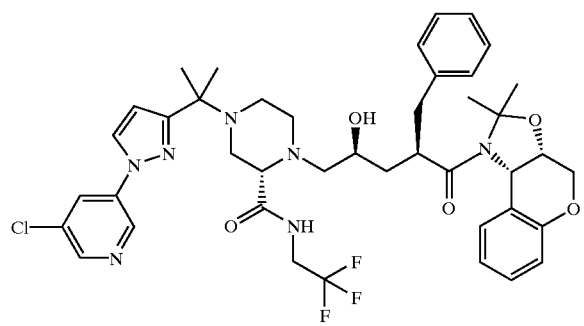

The intermediate from Step D was dissolved in DCM (1 ml) and to this solution was added TFA (0.5 mL). After 1 h at ambient temperature the reaction was quenched by the addition of saturated aqueous $NaHCO_3$ (5 mL) and diluted with DCM (30 mL). The organic layer was dried ($Na_2SO_4$) and concentrated in vacuo, affording the deprotected piperazine as a colorless oil. To a solution of this intermediate (180 mg, 0.41 mmol) in IPA (4 mL) was added the epoxide intermediate prepared in Example 1, Step P (320 mg, 0.82 mmol). The solution was heated to reflux for 16 h, then cooled to ambient temperature and concentrated in vacuo. Purification by flash chromatography (EtOAc) afforded the coupled product as a white solid. HPLC-MS (ES) 824.4 (M+1).

Step F (αR,γS,2S)-N-[(3S,4S)-3,4-dihydro-3-hydroxy-2H-
1-benzopyran-4-yl]-γ-hydroxy-4-[1-[5-(5-chloro-3-
pyridinyl)-1H-pyrazol-3-yl]-1-methylethyl]-α-
(phenylmethyl)-2-[[(2,2,2-trifluoroethyl)amino]
carbonyl]-1-piperazinepentanamide To a solution of the intermediate prepared in Step E (191 mg, 0.230 mmol) in MeOH (3 mL) was added HCl (1.5 mL of a 1.0 M solution in $Et_2O$, 1.5 mmol). After 6 h at ambient temperature the reaction was quenched by the addition of saturated aqueous $NaHCO_3$ (20 mL). The mixture was extracted with DCM (50 mL), and the organic layer was dried ($Na_2SO_4$) and concentrated in vacuo. Purification by preparative TLC (EtOAc) afforded the title compound as a white solid. $^1$H NMR ($CD_3OD$, 500 MHz) 8.95 (d, J=2.5 Hz, 1H), 8.44 (d, J=2.5 Hz, 1H), 8.30 (d, J=2.5 Hz, 1H), 8.29 (s, 1H), 7.17 (m, 7H), 6.80 (t, J=7.5 Hz, 1H) 6.71 (d, J=8.0 Hz, 1H), 6.54 (d, J=2.0 Hz, 1H), 5.14 (d, J=4.5 Hz, 1H), 4.07 (m, 2H), 3.97 (m, 1H), 3.74 (m, 3H), 2.98 (m, 4H), 3.10 (s, 1H) 2.96 (m, 3H), 2.83 (d, 1H), 2.39 (d, J=6.5 Hz, 3H), 2.03 (t, J=12 Hz, 1H), 1.51 (s, 6H), 1.38 (m, 1H). HPLC-MS (ES) 784.4 (M+1).

EXAMPLE 107

(αR,γS,2S)-N-[(3S,4S)-3,4-dihydro-3-hydroxy-2H-1-benzopyran-4-yl]-γ-hydroxy-4-[1-[1-(5-fluoro-3-pyridinyl)-1H-pyrazol-3-yl]-1-methylethyl]-α-(phenylmethyl)-2-[[(2,2,2-trifluoroethyl)amino]carbonyl]-1-piperazinepentanamide

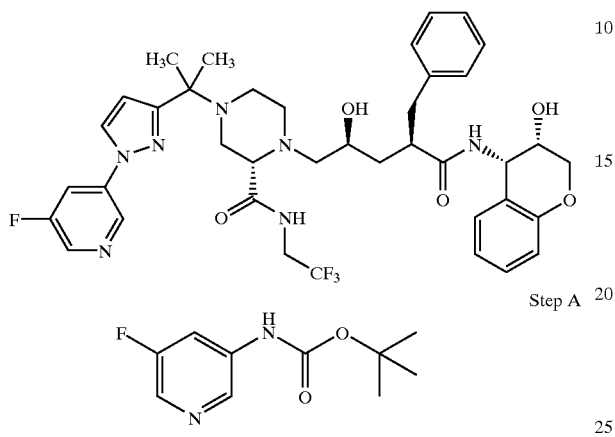

Step A

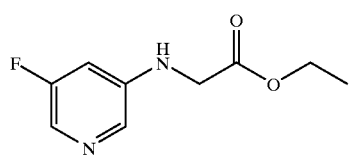

To a solution of 2,6-dichloro-5-fluoro-3-pyridinecarboxylic acid (30.0 g, 143 mmol) in tert-butanol (200 mL) was added triethylamine (21.9 mL, 157 mmol), followed by diphenylphosphoryl azide (33.9 mL, 157 mmol). The resulting mixture was heated to reflux for 2 h, then cooled to ambient temperature and quenched with saturated aqueous NaHCO₃ (200 mL). The mixture was diluted with EtOAc (300 mL) and washed with saturated NaHCO₃ (200 mL) and brine (200 mL). The organic layer was dried (MgSO₄) and concentrated in vacuo. Purification by flash chromatography (3% EtOAc in hexanes) afforded the Boc-amine. This material was dissolved in ethanol (150 mL), and to this solution was added ammonium formate (11.2 g, 177.9 mmol) and formic acid (5 mL), followed by 10% palladium on carbon (1 g). The reaction was heated to reflux for 16 h, then cooled to ambient temperature and filtered thru celite. The liquid was concentrated in vacuo, and the residue dissolved in EtOAc (1 L). The organic layer was washed with saturated aqueous NaHCO₃ (500 mL), brine (500 mL), dried (MgSO₄), and concentrated in vacuo, affording the fluropyridine as a white solid. $^1$H NMR (CDCl₃, 500 MHz) 8.20 (s, 1H), 8.16 (s, 1H), 7.93 (s, 1H), 7.50 (s, 1H), 1.52 (s, 9H).

Step B

To a solution of the intermediate prepared in Step A (5.07 g, 23.9 mmol) in DCM (50 mL) was added TFA (25 mL). After 1.5 h at ambient temperature the reaction was concentrated in vacuo, and dissolved in DMF (28 mL). This solution was added to a refluxing solution of ethyl glyoxy late (19.5 mL of a 50% solution in toluene). The resulting mixture was cooled to ambient temperature and stirred for 30 minutes. To this solution was added sodium triacetoxyborohydride (20.2 g, 95.6 mmol) and the resulting mixture was stirred for 1 h. The mixture was then diluted with EtOAc (300 mL) and quenched with saturated aqueous NaHCO₃ (200 mL). The organic layer was washed with 0.5 M aqueous NaHCO₃, brine, dried (MgSO₄) and concentrated in vacuo. Purification by flash chromatography (35% EtOAc in hexanes) afforded the pyridylglycine as a colorless oil. $^1$H NMR (CDCl₃, 500 MHz) 7.82 (s, 1H), 7.81 (s, 1H), 6.55 (d, 1H), 4.60 (s, 1H), 4.23 (q, 2H), 3.84 (d, 2H), 1.29 (t, 3H). HPLC-MS (ES) 199.2 (M+1).

Step C

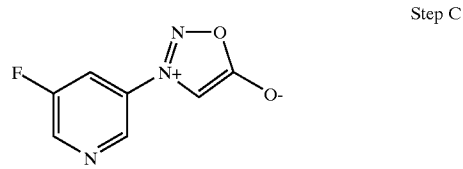

The intermediate prepared in Step B (1.71 g, 8.62 mmol) was dissolved in HCl (8.6 mL of a 35% aqueous solution), and the resulting mixture was heated to 80° C. for 1.5 h. The solution was then cooled to ambient temperature and concentrated in vacuo. The residue was dissolved in water (5 mL) at 0° C., and to this solution was added NaNO₂ (650 mg, 9.48 mmol). After 2.5 h at 0° C. the mixture was concentrated in vacuo, then dissolved in acetic anhydride (30 mL). The resulting mixture was heated to reflux for 45 minutes, then cooled to ambient temperature and concentrated in vacuo. Purification by flash chromatography (50% EtOAc in hexanes) afforded the sydnone as a yellow solid. $^1$H NMR (CDCl₃, 500 MHz) 8.89 (s, 1H), 8.79 (s, 1H), 7.88 (d, 1H), 6.80 (s, H). HPLC-MS (ES) 182.1 (M+1).

Step D

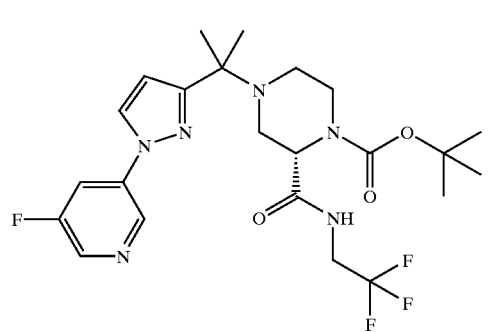

To a solution of the intermediate prepared in Step C (180 mg, 1.00 mmol) in 1,3-dichlorobenzene (2 mL) was added the intermediate prepared in Example 101, Step C (940 mg, 2.51 mmol). The mixture was heated to 135° C. for 24 h, then cooled to ambient temperature and concentrated in vacuo. Purification by flash chromatography (35% EtOAc in hexanes) afforded the pyrazole. $^1$H NMR (CDCl₃, 500 MHz) 8.78 (s, 1H), 8.37 (s, 1H), 7.90 (s, 1H), 7.79 (d, 1H), 7.40 (s, 1H), 6.40 (s, 1H) 4.63 (s, 1H), 3.95 (m, 3H), 3.40 (d, 1H), 3.00 (s, 1H), 2.79 (s, 1H), 2.32 (dd, 1H), 2.17 (t, 1H), 1.44 (s, 6H).

Step E

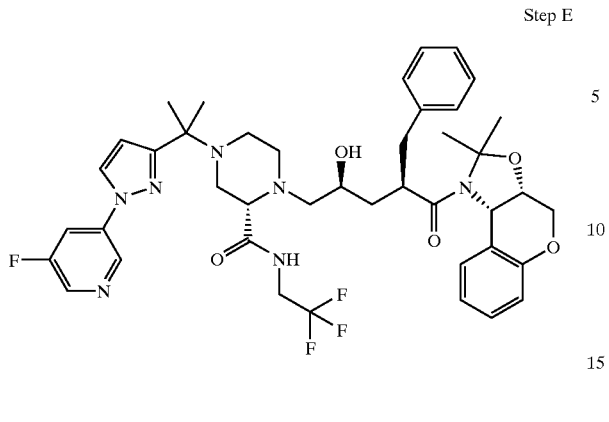

The intermediate from Step D (0.268 g, 0.52 mmol) was dissolved in DCM (1 ml) and to this solution was added TFA (0.5 mL). After 1 h at ambient temperature the reaction was quenched by the addition of saturated aqueous $NaHCO_3$ (5 mL) and diluted with DCM (30 mL). The organic layer was dried ($Na_2SO_4$) and concentrated in vacuo, affording the deprotected piperazine as a colorless oil. To a solution of this intermediate (195 mg, 0.47 mmol) in IPA (4 mL) was added the epoxide intermediate prepared in Example 1, Step P (370 mg, 0.94 mmol). The solution was heated to reflux for 16 h, then cooled to ambient temperature and concentrated in vacuo. Purification by flash chromatography (EtOAc) afforded the coupled product as a white solid.

Step F (αR,γS,2S)-N-[(3S,4S)-3,4-dihydro-3-hydroxy-2H-1-benzopyran-4-yl]-γ-hydroxy-4-[1-[5-(5-fluoro-3-pyridinyl)-1H-pyrazol-3-yl]-1-methylethyl]-α-(phenylmethyl)-2-[[(2,2,2-trifluoroethyl)amino]carbonyl]-1-piperazinepentanamide To a solution of the intermediate prepared in Step E (258 mg, 0.320 mmol) in MeOH (5 mL) was added HCl (5.0 mL of a 1.0 M solution in $Et_2O$, 5.0 mmol). After 6 h at ambient temperature the reaction was quenched by the addition of saturated aqueous $NaHCO_3$ (20 mL). The mixture was extracted with DCM (50 mL), and the organic layer was dried ($Na_2SO_4$) and concentrated in vacuo. Purification by flash chromatography (EtOAc) afforded the title compound as a white solid. $^1$H NMR ($CD_3OD$, 500 MHz) 8.90 d, J=1.5 Hz, 1H), 8.37 (d, J=2.5 Hz, 1H), 8.30 (d, J=2.5 Hz, 1H), 8.07 (dy, J=2.5 Hz, J=9.5 Hz, 1H), 7.20 (m, 5H), 7.09 (m, 2H), 6.80 (t, J=7.5 Hz, 1H), 6.72 (d, J=8.0 Hz, 1H), 6.54 (d, J=3.0 Hz, 1H), 5.14 (d, J=4.0 Hz, 1H), 4.05 (m, 2H), 3.95 (m, 1H), 3.77 (m, 3H), 3.20 (m, 1H), 2.95 (m, 4H), 2.82 (m, 1H), 2.72 (m, 3H), 2.51 (t, J=8.5 Hz, 1H), 2.15 (t, J=8.5 Hz, 1H), 2.38 (d, J=6.5 Hz, 2H), 2.03 (dt, J=4.0 Hz, J=11.5 Hz, 1H), 1.50 (s, 6H), 1.38 (m, 1H). HPLC-MS (ES) 768.4 (M+1).

EXAMPLE 108

(αR,γS,2S)-N-[(3S,4S)-3,4-dihydro-3-hydroxy-2H-1-benzopyran-4-yl]-γ-hydroxy-4-[1-[1-(3-pyridinyl)-1H-pyrazol-3-yl]-1-methylethyl]-α-(phenylmethyl)-2-[[(2,2,2-trifluoroethyl)amino]carbonyl]-1-piperazinepentanamide

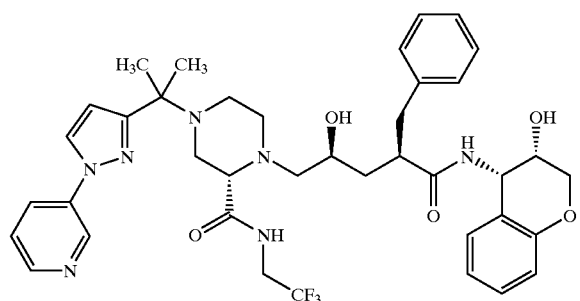

Step A

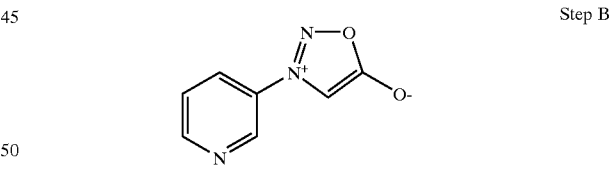

A solution of 3-aminopyridine (940 mg, 10.0 mmol) in DMF (28 mL). was added to a refluxing solution of ethyl glyoxylate (8.17 mL of a 50% solution in toluene, 40.0 mmol). The resulting mixture was cooled to ambient temperature and stirred for 30 minutes. To this solution was added sodium triacetoxyborohydride (8.48 g, 40.0 mmol) and the resulting mixture was stirred for 1 h. The mixture was then diluted with EtOAc (300 mL) and quenched with saturated aqueous $NaHCO_3$ (200 mL). The organic layer was washed with 0.5 M aqueous $NaHCO_3$, brine, dried ($MgSO_4$) and concentrated in vacuo. Purification by flash chromatography (35% EtOAc in hexanes) afforded the pyridylglycine as a colorless oil. $^1$H NMR ($CDCl_3$, 500 MHz) 7.99 (s, 1H), 7.97 (d, 1H), 7.06 (dd, 1H), 6.80 (d, 1H), 4.53 (s, 1H), 4.20 (q, 2H), 3.81 (s, 3H), 1.23 (t, 3H). HPLC-MS (ES) 181.2 (M+1).

Step B

The intermediate prepared in Step A (0.390 g, 2.16 mmol) was dissolved in HCl (3 mL of a 35% aqueous solution), and the resulting mixture was heated to 80° C. for 1.5 h. The solution was then cooled to ambient temperature and concentrated in vacuo. The residue was dissolved in water (5 mL) at 0° C., and to this solution was added $NaNO_2$ (160 mg, 2.38 mmol). After 2.5 h at 0° C. the mixture was concentrated in vacuo, then dissolved in acetic anhydride (8 mL). The resulting mixture was heated to reflux for 45 minutes, then cooled to ambient temperature and concentrated in vacuo. Purification by flash chromatography (EtOAc) afforded the sydnone as a yellow solid. $^1$H NMR ($CDCl_3$, 500 MHz) 9.02 (s, 1H), 8.87 (d, 1H), 8.08 (d, 1H), 7.60 (dd, 1H), 6.80 (s, 1H). HPLC-MS (ES) 166.1 (M+1).

Step C

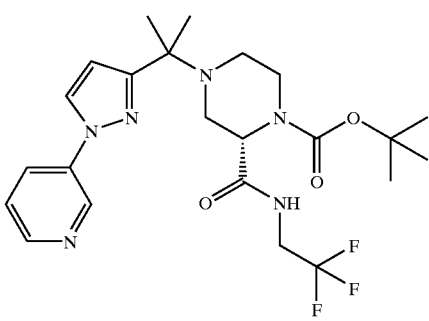

To a solution of the intermediate prepared in Step B (126 mg, 0.76 mmol) in 1,3-dichlorobenzene (2 mL) was added the intermediate prepared in Example 101, Step C (720 mg, 1.90 mmol). The mixture was heated to 135° C. for 24 h, then cooled to ambient temperature and concentrated in vacuo. Purification by flash chromatography (35% EtOAc in hexanes) afforded the pyrazole. ¹H NMR (CDCl₃, 500 MHz) 8.94 (d, 1H), 8.49 (d, 1H), 7.96 (d, 1H), 7.84 (s, 1H), 7.60 (s, 1H), 7.37 (dd, 1H), 6.40 (s, 1H), 4.63 (s, 1H), 3.87 (s, 2H), 3.40 (d, 1H), 2.98 (s, 1H), 2.80 (s, 1H), 2.34 (dd, 1H), 2.16 (t, 1H), 1.49 (s, 12H), 1.47 (s, 3H). HPLC-MS (ES) 497.2 (M+1).

Step D

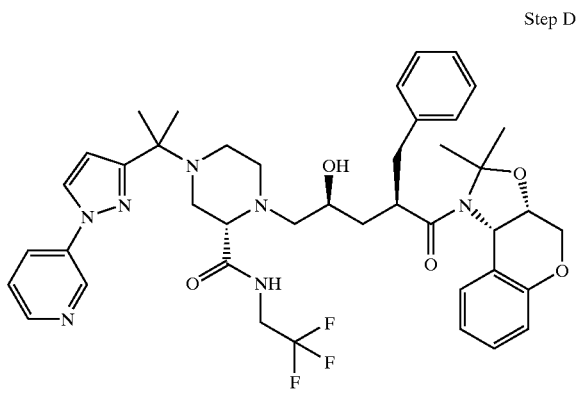

The intermediate from Step C (0.172 g, 0.35 mmol) was dissolved in DCM (1 ml) and to this solution was added TFA (0.5 mL). After 1 h at ambient temperature the reaction was quenched by the addition of saturated aqueous NaHCO₃ (5 mL) and diluted with DCM (30 mL). The organic layer was dried (Na₂SO₄) and concentrated in vacuo, affording the deprotected piperazine as a colorless oil. This intermediate was dissolved in IPA (4 mL) and to this solution was added the epoxide intermediate prepared in Example 1, Step P (340 mg, 0.86 mmol). The solution was heated to reflux for 16 h, then cooled to ambient temperature and concentrated in vacuo. Purification by flash chromatography (EtOAc) afforded the coupled product as a white solid.
Step E (αR,γS,2S)-N-[(3S,4S)-3,4-dihydro-3-hydroxy-2H-1-benzopyran-4-yl]-γ-hydroxy-4-[1-[5-(3-pyridinyl)-1H-pyrazol-3-yl]-1-methylethyl]-α-(phenylmethyl)-2-[[(2,2,2-trifluoroethyl)amino]carbonyl]-1-piperazinepentanamide To a solution of the intermediate prepared in Step D (128 mg, 0.160 mmol) in MeOH (5 mL) was added HCl (5.0 mL of a 1.0 M solution in Et₂O, 5.0 mmol). After 6 h at ambient temperature the reaction was quenched by the addition of saturated aqueous NaHCO₃ (20 mL). The mixture was extracted with DCM (50 mL), and the organic layer was dried (Na₂SO₄) and concentrated in vacuo. Purification by flash chromatography (1% MeOH in EtOAc) afforded the title compound as a white solid. ¹H NMR (CD₃OD, 500 MHz) 9.00 (d, J=2.5 Hz, 1H) 8.44 (dd, J=1.5 Hz, J=5.0 Hz, 1H), 8.25 (d, J=2.5 Hz, 1H), 8.20 (ddd, J=1.5 Hz, J=2.5 Hz, J=4.0 Hz, 1H), 7.51 (dd, J=5.0 Hz, J=8.5 Hz, 1H), 7.23 (m, 5H), 7.08 (m, 2H), 6.80 (dt, J=1.0 Hz, J=7.0 Hz, 1H), 6.71 (d, J=8.0 Hz, 1H), 6.52 (g, J=3.0 Hz, 1H), 5.14 (d, J=4.5 Hz, 1H), 4.08 (m, 2H),3.97 (m, 1H), 3.77 (m, 3H), 3.30 (d, J=6.5 Hz, 1H), 3.08 (dd, 1H), 3.02 (m, 1H), 2.94 (m, 2H), 2.82 (d, J=11.0 Hz, 1H), 2.73 (dd, J=6.5 Hz, J=13 Hz, 1H) 2.69 (m,2H), 2.53 (t, J=8.0 Hz, 1H), 2.42 (t, J=8.5 Hz, 1H), 2.38 (d, J=6.5 Hz, 2H), 2.03 (t, J=13.5 Hz, 1H), 1.51 (s, 6H), 1.38 (m, 1H). HPLC-MS (ES) 750.4 (M+1).

EXAMPLE 109

(αS,γS,2S)-4-[1-[5-phenyl-2-oxazolyl]-1-methylethyl]-N-[(3S,4S)-3,4-dihydro-3-hydroxy-2H-1-benzopyran-4-yl]-α-(furo[2,3-c]pyridin-2-ylmethyl)-γ-hydroxy-2-[[(2,2,2-trifluoroethyl)amino]carbonyl]-1-piperazinepentanamide

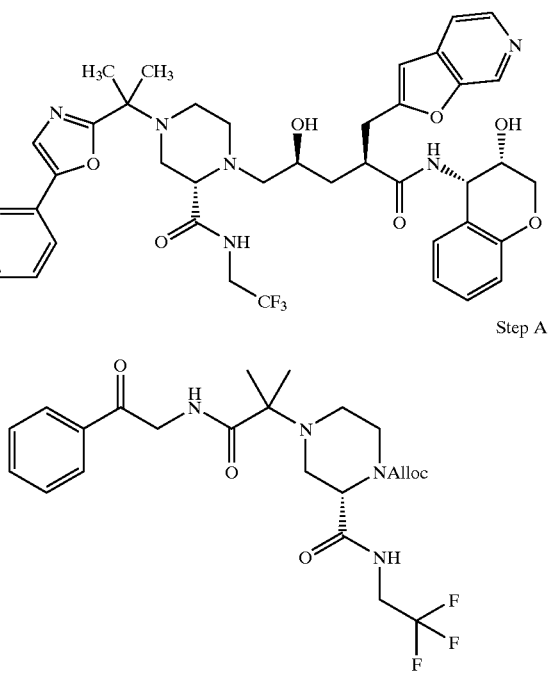

Step A

To a stirred solution of carboxylic acid from Example 66 Step D (332 mg; 0.87 mmol) in dry NMP (12 mL) under nitrogen was added DIEA (0.606 mL; 3.48 mmol). After cooling the solution to 0° C., the following solids were added, allowing one to dissolve before adding the next: HOBt (265 mg; 1.96 mmol), ω-aminoacetophenone hydrochloride (179 mg; 1.04 mmol), and HBTU (495 mg; 1.31 mmol). The reaction was allowed to reach ambient temperature, and the next morning the mixture was poured into EtOAc and washed with saturated NaHCO₃, water, brine, 3×dilute NaHCO₃, and brine. After drying (MgSO₄), filtration, and removal of solvent in vacuo, the residue was purified by flash column chromatography (50% EtOAc/hexane). Residual NMP which remained was removed by dissolution in EtOAc followed by washing with water (2x), brine, drying (MgSO$_4$), filtration, and solvent removal in vacuo as before to provide the desired product; electrospray ionization mass spectrum: m/e 499.3 (MH$^+$ calcd for C$_{23}$H$_{30}$F$_3$N$_4$O$_5$, 499.2).

Step B

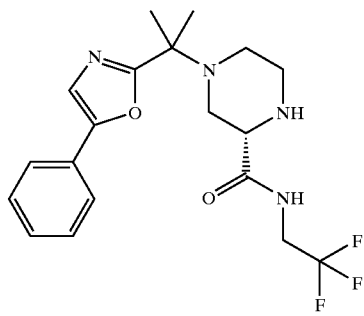

To the amide obtained in Step A (225 mg; 0.45 mmol) was added H$_2$SO$_4$ (5 mL). Partial dissolution occurred. The reaction vessel was purged with nitrogen, P$_2$O$_5$ (192 mg; 0.68 mmol) was added, and the mixture was stirred at 65° C. for 20 minutes. After cooling to 0° C., ice chips were added and the reaction adjusted to pH 9 with the addition of 50% NH$_4$OH, then conc. NH$_4$OH. Extraction with CHCl$_3$ (3x) was followed by drying (Na$_2$SO$_4$), filtration, removal of solvent in vacuo and purification by flash column chromatography (93:5:2 EtOAc:MeOH:TEA) to provide the desired product.

Step C

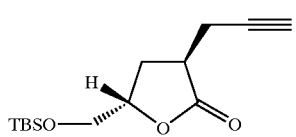

To a stirred solution of DIPA (1.28 mL; 9.74 mmol) in dry THF (26 mL) at 0° C. was added dropwise n-BuLi (3.54 mL; 8.85 mmol). After 15 minutes, the solution was cooled to −78° C. and a solution of (S)-(+)-dihydro-5-(t-butyldimethylsilylhydroxymethyl)-2(3H)-furanone (2.04 g; 8.85 mmol) in dry THF (8 mL) was added dropwise. After an additional 30 minutes, propargyl bromide (1.56 mL; 10.6 mmol) was added dropwise. After 45 minutes the reaction was quenched with 10% citric acid, poured into Et$_2$O, and washed with H$_2$O (2x) and brine, dried (MgSO$_4$), filtered, and solvents removed in vacuo. Purification by Biotage column chromatography (40M; 8% EtOAc/hexane) provided the desired compound.

Step D

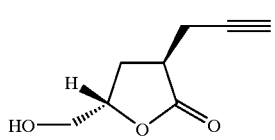

To a stirred solution of the intermediate from Step C above (903 mg; 3.46 mmol) in dry THF (21 mL) was added HF-pyridine complex (1.2 mL). The next morning, the reaction mixture was cooled to 0° C. and adjusted to pH 10 with NH$_4$OH/H$_2$O (2:1). Much solvent was removed in vacuo and the residue was poured into EtOAc and washed with saturated NaHCO$_3$, 2xH$_2$O and brine. Drying (MgSO$_4$), filtration, removal of solvent in vacuo, and purification by Biotage column chromatography (40M; 50% EtOAc/hexane) provided the desired product.

Step E

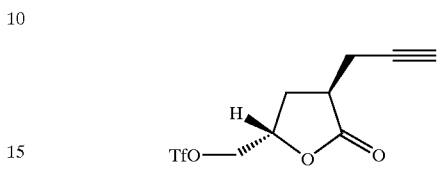

To a stirred solution of intermediate from Step D above (720 mg; 4.67 mmol) in dry CH$_2$Cl$_2$ (19 mL) at 0° C. was added 2,6-lutidine (816 uL; 7.0 mmol) followed dropwise by trifluoromethanesulfonic anhydride (1.02 mL; 6.07 mmol). After 1.75 hours, the reaction mixture was poured into 20 mL ice/brine and stirred 30 minutes. This mixture was poured into CH$_2$Cl$_2$ and washed with 2xH$_2$O and 2xbrine. After drying (MgSO$_4$), filtration, and removal of solvent in vacuo, the residue was purified by Biotage column chromatography (40M; 20% EtOAc/hexane) to provide the desired intermediate. $^1$H NMR (500 MHz, CDCl$_3$): δ2.08 (m, 1H), 2.38–2.44 (complex m, 1H), 2.52–2.59 (complex m, 1H), 2.67 (m, 2H), 2.94–2.98 (complex m, 1H), 4.57 (1/2ABX, J=4.1, 11.2 Hz, 1H), 4.71 (1/2ABX, J=3.0, 11.2 Hz, 1H), 4.89 (m, 1H).

Step F

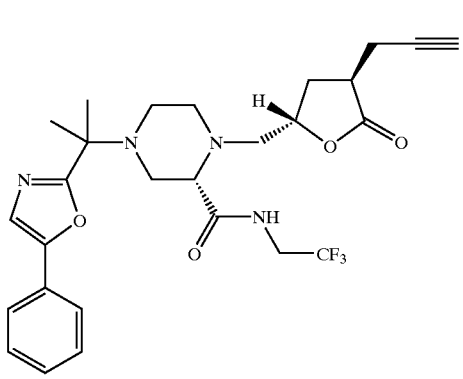

To a stirred solution of piperazine (100 mg; 0.25 mmol) from Step B above and triflate (72 mg; 0.25 mmol) from Step E above in dry iPrOH (1.25 mL) was added DIEA (52 uL; 0.30 mmol). The next morning, the reaction mixture was poured into EtOAc and washed with saturated NaHCO$_3$, water, brine, water, and brine. Drying (MgSO$_4$), filtration, and removal of solvent in vacuo was followed by flash column chromatography (70% EtOAc/hexane) to provide the desired intermediate.

Step G

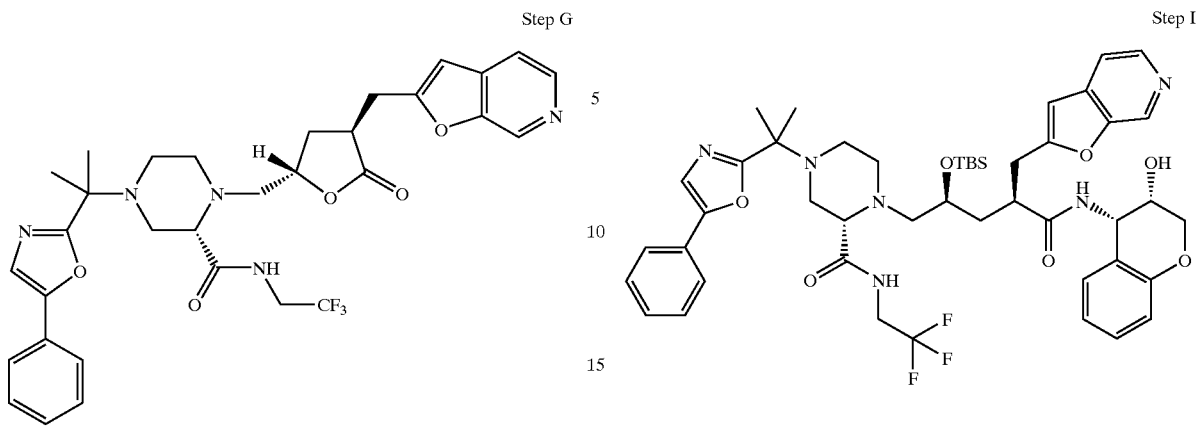

To a solution of acetylene (95 mg; 0.18 mmol) from Step F above and 4-iodo-3-hydroxypyridine (52 mg; 0.23 mmol) in dry pyridine (1.3 mL) was added Cu$_2$O (33 mg; 0.23 mmol). After 35 minutes at 120° C., the mixture was cooled to ambient temperature and filtered through celite, washing with EtOAc. The organics were washed with aqueous Na$_2$SO$_4$, 2×water, brine, dried (Na$_2$SO$_4$), filtered, and the solvents removed in vacuo. Purification by flash column chromatography (gradient elution 3% to 5% MeOH/CH$_2$Cl$_2$) provided the desired intermediate; electrospray ionization mass spectrum: m/e 626.3 (MH$^+$ calcd for C$_{32}$H$_{35}$F$_3$N$_5$O$_5$, 626.3).

Step H

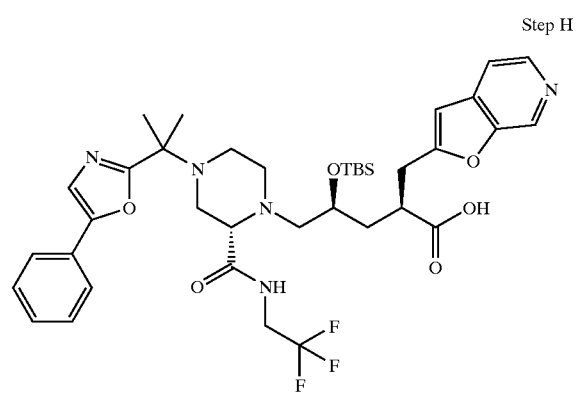

To a solution of the lactone (95 mg; 0. 15 mmol) obtained from Step G above in dry dimethoxyethane (2 mL) cooled to 0° C. under nitrogen was added aqueous LiOH (172 uL; 0.167 mmol). The flask was allowed to warm to ambient temperature and stirred for 3.5 hr. The reaction was azeotroped from MeCN, MeCN/benzene, and benzene, taking care to keep the water bath below 35° C. This salt was further dried under vacuum, then dissolved in dry DMF (3 mL) and imidazole (204 mg; 3.0 mmol) was added. This solution was cooled to 0° C. and TBSCl was added (226 mg; 1.5 mmol). The flask was allowed to warm to ambient temperature and stirred overnight. The next morning the reaction was quenched with pH 7 phosphate buffer and extracted 3×EtOAc. After drying (Na$_2$SO$_4$), filtration, and removal of solvent in vacuo, the residue was dissolved in 3 mL THF/water (2:1). After 1 hr the mixture was azeotroped from MeCN, benzene, and MeCN to provide the carboxylic acid, which was used without further purification; electrospray ionization mass spectrum: m/e 758.4 (MH$^+$ calcd for C$_{38}$H$_{51}$F$_3$N$_5$O$_6$Si, 758.4).

Step I

To a stirred solution of acid (~0.15 mmol) from Step H in dry NMP (2 mL) at 0° C. was added DIEA (78 uL; 0.45 mmol) followed by the following solids, allowing one to dissolve before adding the next: HOBt (46 mg; 0.34 mmol), amino chromanol obtained from Example 1 Step L (30 mg; 0.18 mmol), and HBTU (85 mg; 0.22 mmol). The reaction was allowed to reach ambient temperature and the next morning the mixture was poured into EtOAc and washed with saturated NaHCO$_3$, water, brine, 3×dilute NaHCO$_3$, and brine. After drying (Na$_2$SO$_4$), filtration, and removal of the solvent in vacuo, the residue was purified by flash chromatography (95% EtOAc/hexane) to provide the desired product; electrospray ionization mass spectrum: m/e 905.3 (MH$^+$ calcd for C$_{47}$H$_{60}$F$_3$N$_6$O$_7$Si, 905.4).

Step J (αS,γS,2S)-4-[1-[5-phenyl-2-oxazolyl]-1-methylethyl]-N-[(3S,4S)-3,4-dihydro-3-hydroxy-2H-1-benzopyran-4-yl]-α-(furo[2,3c]pyridin-2-ylmethyl)-γ-hydroxy-2-[[(2,2,2-trifluoroethyl)amino]carbonyl]-1-piperazinepentanamide To a solution of the intermediate (63 mg; 0.07 mmol) from Step I in dry THF (2 mL) was added TBAF (175 uL; 0.175 mmol). The solution was stirred at 55° C. for 2 hours. The reaction mixture was poured into EtOAc and washed with saturated NaHCO$_3$, water, and brine. Drying (Na$_2$SO$_4$), filtration, and removal of the solvent in vacuo followed by purification by MPLC (Lobar column; linear gradient 10% to 90% MeCN/H$_2$O) provided the titled compound after lyophilization from MeCN/water (1:1). $^1$H NMR (500 MHz, CD$_3$OD): δ1.45 (m, 1H), 1.58 (s, 3H), 1.59 (s, 3H), 2.09 (m, 1H), 2.35–2.43 (complex m, 3H), 2.48 (m, 1H), 2.63 (m, 1H), 2.77 (m, 1H), 2.87 (d, J=10.3 Hz, 1H), 2.98–3.01 (complex m, 2H), 3.08 (dd, J=3.2, 7.3 Hz, 1H), 3.20–3.26 (complex m, 2H), 3.75–3.80 (complex m, 2H), 3.88 (m, 1H), 3.91–3.98 (complex m, 1H), 4.02–4.09 (complex m, 2H), 5.22 (d, J=4.1 Hz, 1H), 6.72 (s, 1H), 6.74 (d, J=8.2 Hz, 1H), 6.80 (apparent t, J=7.5 Hz, 1H), 7.08 (apparent t, J=7.7 Hz, 1H), 7.14, (d, J=7.8 Hz, 1H), 7.35 (m, 1H), 7.42 (m, 3H), 7.57 (d, J=5.2 Hz, 1H), 7.68 (d, J=7.4 Hz, 2H), 8.25 (d, J=5.5 Hz, 1H), 8.68 (s, 1 H); electrospray ionization mass spectrum: m/e 791.4 (MH$^+$ calcd for C$_{41}$H$_{46}$F$_3$N$_6$O$_7$, 791.3).

EXAMPLE 110

(αS,γS,2S)-4-[1-[5-(4-chlorophenyl)-2-oxazolyl]-1-methylethyl]-N-[(3S,4S)-3,4-dihydro-3-hydroxy-2H-1-benzopyran-4-yl]-α-(furo[2,3-c]pyridin-2-ylmethyl)-γ-hydroxy-2-[[(2,2,2-trifluoroethyl)amino]carbonyl]-1-piperazinepentanamide

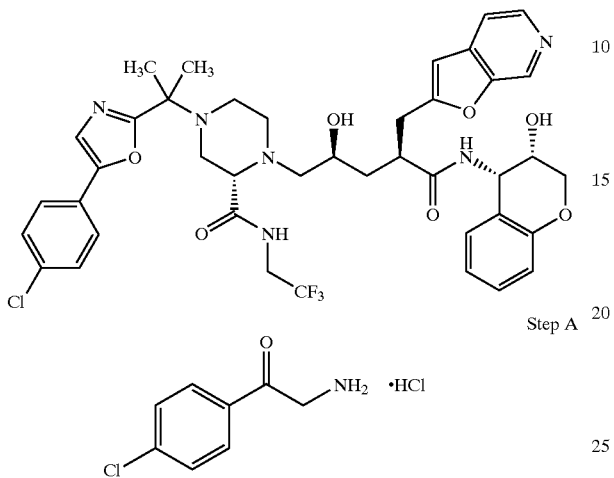

Step A

To a stirring solution of hexamethylenetetramine (12.0 g; 85.7 mmol) in $CH_2Cl_2$ (400 mL) was added portionwise α:-bromo-p-chloroacetophenone (20.0 g; 85.7 mmol). After 30 minutes the precipitate was filtered and then suspended in EtOH (680 mL). Conc. HCl was added (45 mL) and the suspension stirred at 90° C. 1.5 hrs. Dissolution occurred followed by solution turning pale yellow and a new precipitate formed. This solid was filtered, washed with EtOH, and dried under vacuum to provide the desired compound. $^1$H NMR (500 MHz, $CD_3OD$): δ4.60 (s, 2H), 7.61 (d, J=8.7 Hz, 2H), 8.04 (d, J=8.4 Hz, 2H).

Step B

This intermediate was prepared in the same manner as that of Example 109 Step A, employing carboxylic acid from Example 66 Step D (4.96 g; 13 mmol) in dry NMP (75 mL), DIEA (9.06 mL; 52 mmol), HOBt (3.95 g; 29.3 mmol), intermediate from Step A above (3.22 g; 15.6 mmol), and HBTU (7.4 g; 19.5 mmol). The residue resulting after workup was purified by Biotage column chromatography (40M; 45% EtOAc/hexane) to provide the desired product. $^1$H NMR (500 MHz, $CDCl_3$): δ1.28 (s, 3H), 1.30 (s, 3H), 2.35 (apparent td, J=3.0, 11.6 Hz, 1H), 2.45 (apparent dd, J=3.8, 11.8 Hz, 1H), 2.86 (d, J=10.6 Hz, 1H), 3.22–3.33 (broad, 1H), 3.67 (d, J=11.7 Hz, 1H), 3.74–4.30 (broad, 3H), 4.51 (d, J=18.6 Hz, 1H), 4.70 (d, J=4.5 Hz, 2H), 4.83 (s, 1H), 4.89 (1/2ABX, J=6.8, 18.7 Hz, 1H), 5.30 (d, J=10.3 Hz, 1H), 5.36 (d, J=17.1 Hz, 1H), 5.92–6.02 (br s, 1H), 6.60–6.72 (br s, 1H), 7.49 (d, J=8.5 Hz, 2H), 7.93 (d, J=8.5 Hz, 2H), 8.20–8.30 (br s, 1H); electrospray ionization mass spectrum: m/e 533.3 (MH$^+$ calcd for $C_{23}H_{29}ClF_3N_4O_5$, 533.2).

Step C

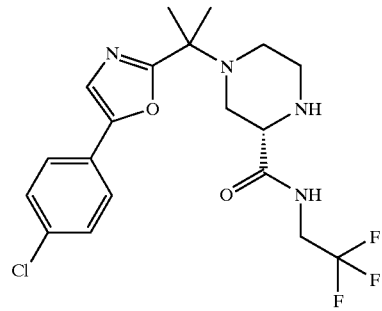

This intermediate was prepared according to the procedure described in Example 109 Step B, employing the compound from Step B above (139 mg; 0.26 mmol), $P_2O_5$ (110 mg; 0.39 mmol), and 2.75 mL $H_2SO_4$. Flash column chromatography (93:5:2 EtOAc:MeOH:TEA) provided the desired compound. $^1$H NMR (500 MHz, $CDCl_3$): δ1.60 (s, 3H), 1.61 (s, 3H), 1.75–1.88 (broad s, 1H), 2.56–2.60 (complex m, 2H), 2.77–2.81 (m, 1H), 2.86–2.98 (complex m, 3H), 3.50–3.52 (m, 1H), 3.93–4.00 (m, 2H), 7.26 (s, 1H), 7.42 (d, J=8.5 Hz, 2H), 7.58 (d, J=8.4 Hz, 2H), 8.10–8.18 (broad s, 1H); electrospray ionization mass spectrum: m/e 431.3 (MH$^+$ calcd for $C_{19}H_{23}ClF_3N_4O_2$, 431.1).

Step D

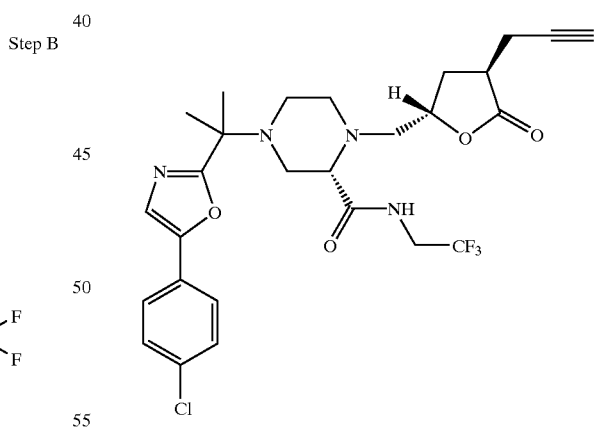

This intermediate was prepared according to the procedure described in Example 109 Step F, employing the compound from Step C above (85 mg; 0.2 mmol), intermediate from Example 109 Step E (58 mg; 0.2 mmol), and DIEA (42 uL; 0.24 mmol) in dry iPrOH (1.0 mL) for 4 hours. Flash column chromatography (70% EtOAc/hexane) provided the desired product. $^1$H NMR (500 MHz; $CDCl_3$): δ1.60 (s, 3H), 1.61 (s, 3H), 2.04 (m, 1H), 2.18–2.24

(complex m, 1H), 2.23–2.36 (complex m, 1H), 2.53–2.66 (complex m, 4H), 2.73 (d, J=8.4 Hz, 2H), 2.82 (s, 2H), 2.87–2.97 (complex m, 3H), 3.29 (m, 1H), 3.66–3.72 (complex m, 1H), 4.15–4.22 (complex m, 1H), 4.69–4.73 (complex m, 1H), 7.27 (s, 1H), 7.44 (d, J=8.5 Hz, 2H), 7.56 (d, J=8.7 Hz, 2H), 8.56–8.63 (br s, 1H); electrospray ionization mass spectrum: m/e 567.3 (MH+ calcd for C$_{27}$H$_{31}$ClF$_3$N$_4$O$_4$, 567.2).

Step E

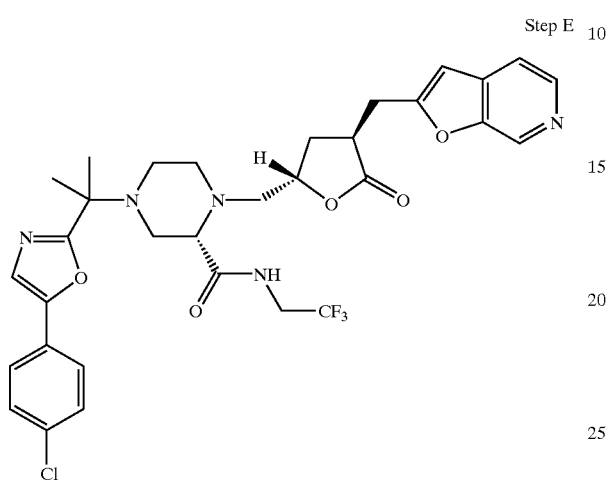

This intermediate was prepared according to the procedure described in Example 109 Step G, employing the compound from Step D above (85 mg; 0.15 mmol), 4-iodo-3-hydroxypyridine (50 mg; 0.23 mmol), and Cu$_2$O (32 mg; 0.23 mmol) in dry pyridine (1.0 mL) for 30 minutes. Following workup, flash column chromatography (gradient elution 3% to 5% MeOH/DCM) provided the desired product. $^1$H NMR (500 MHz, CDCl$_3$): δ1.59 (s, 3H), 1.60 (s, 3H), 2.17–2.21 (complex m, 2H), 2.57–2.61 (complex m, 2H), 2.70–2.86 (complex m, 4H), 2.89–2.97 (complex m, 2H), 3.03 (m, 1H), 3.15–3.20 (complex m, 1H), 3.27 (m, 1H), 3.37 (1/2ABX, J=4.3, 15.3 Hz, 1H), 3.63–3.69 (complex m, 1H), 4.14–4.20 (complex m, 1H), 4.59 (m, 1H), 6.56 (s, 1H), 7.26 (s, 1H), 7.43 (d, J=8.5 Hz, 2H), 7.48 (d, J=5.2 Hz, 1H), 7.55 (d, J=8.4 Hz, 2H), 8.42 (d, J=5.1 Hz, 1H), 8.65 (br s, 1H), 8.81 (s, 1H); electrospray ionization mass spectrum: m/e 660.3 (MH+ calcd for C$_{32}$H$_{34}$ClF$_3$N$_5$O$_5$, 660.2).

Step F

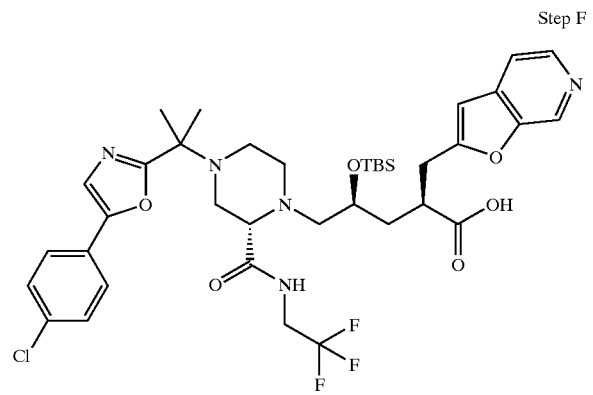

This compound was prepared according to the procedure described in Example 109 Step H, employing the compound from Step E above (53 mg; 0.08 mmol) and aqueous LiOH (86 uL; 0.086 mmol) in dry dimethoxyethane (1.5 mL). Following removal of solvents as before, the lithium salt was treated (as in Example 109 Step H) with imidazole (109 mg; 1.6 mmol) and TBSCl (120 mg; 0.8 mmol) in dry DMF. Upon workup, the product was used without further purification.

Step G

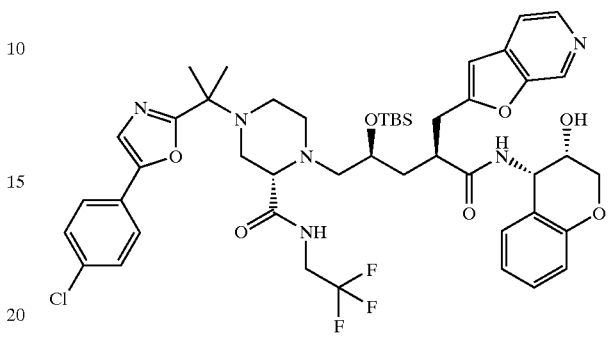

This compound was prepared according to the procedure described in Example 109 Step I, employing the compound from Step F above (~0.08 mmol) in dry NMP (1.2 mL), DIEA (42 uL; 0.24 mmol), HOBt (24 mg; 0.18 mmol), amino chromanol obtained from Example 1 Step L (16 mg; 0.096 mmol), and HBTU (45 mg; 0.12 mmol). Following workup, flash column chromatography (1% MeOH/EA) provided the desired product.

Step H

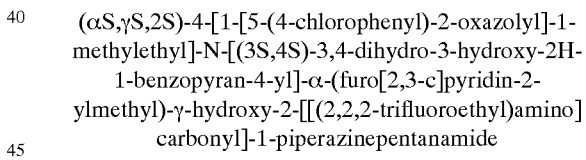

(αS,γS,2S)-4-[1-[5-(4-chlorophenyl)-2-oxazolyl]-1-methylethyl]-N-[(3S,4S)-3,4-dihydro-3-hydroxy-2H-1-benzopyran-4-yl]-α-(furo[2,3-c]pyridin-2-ylmethyl)-γ-hydroxy-2-[[(2,2,2-trifluoroethyl)amino]carbonyl]-1-piperazinepentanamide The titled compound was prepared according to the procedure described in Example 109 Step J, employing the intermediate from Step G above (28 mg; 0.03 mmol) and TBAF (75 uL; 0.075 mmol) in dry THF (1.0 mL). Following workup, flash column chromatography (5% MeOH/CH$_2$Cl$_2$) provided the desired product after lyophilization. $^1$H:NMR (500 M, CD$_3$OD): δ1.44 (m, 1H), 1.57 (s, 3H), 1.58 (s, 3H), 2.09 (m, 1H), 2.35–2.48 (complex m, 4H), 2.61 (m, 1H), 2.75 (m, 1H), 2.87 (d, J=9.6 Hz, 1H), 2.98–3.02 (complex m, 2H), 3.08 (m, 1H), 3.20–3.27 (complex m, 2H), 3.74–3.81 (complex m, 2H), 3.88 (m, 1H), 3.91–3.98 (complex m, 1H), 4.02–4.09 (complex m, 2H), 5.22 (d, J=4.1 Hz, 1H), 6.72 (s, 1H), 6.74 (d, J=8.0 Hz, 1H), 6.80 (apparent t, J=7.6 Hz, 1H), 7.09 (apparent t, J=7.7 Hz, 1H), 7.14, (d, J=7.3 Hz, 1H), 7.44 (m, 3H), 7.57 (d, J=5.2 Hz, 1H), 7.68 (d, J=8.4 Hz, 2H), 8.25 (d, J=5.5 Hz, 1H), 8.68 (s, 1H); electrospray ionization mass spectrum: m/e 825.4 (MH+ calcd for C$_{41}$H$_{45}$ClF$_3$N$_6$O$_7$, 825.3).

EXAMPLE 111

(αS,γS,2S)-4-[1-[5-(4-fluorophenyl)-2-oxazolyl]-1-methylethyl]-N-[(3S,4S)-3,4-dihydro-3-hydroxy-2H-1-benzopyran-4-yl]-α-(furo[2,3-c]pyridin-2-ylmethyl)-γ-hydroxy-2-[[(2,2,2-trifluoroethyl)amino]carbonyl]-1-piperazinepentanamide

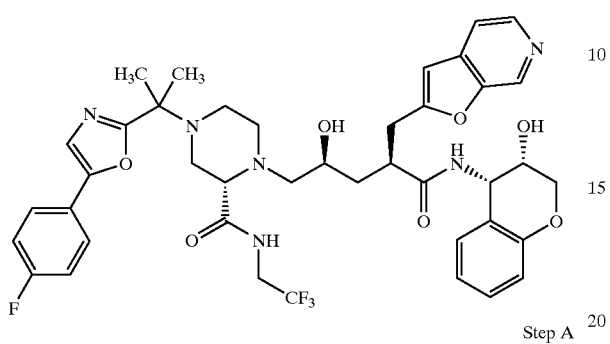

Step A

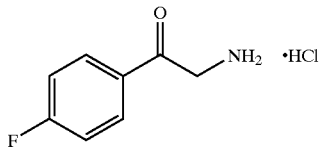

This aminoketone was prepared in the same manner as Example 110 Step A employing hexamethylenetetramine (12.9 g; 92.1 mmol) in $CH_2Cl_2$ (500 mL) and α-bromo-p-fluoroacetophenone (20.0 g; 92.1 mmol). After filtration, the solid was suspended in EtOH (680 mL) and conc. HCl was added (45 mL). The new solid was filtered, washed with EtOH, and dried under vacuum as before to provide the desired compound. $^1$H NMR (500 MHz, $CD_3OD$): δ4.61 (s, 2H), 7.33 (apparent t, J=8.8 Hz, 2H), 8.14 (m, 2H).

Step B

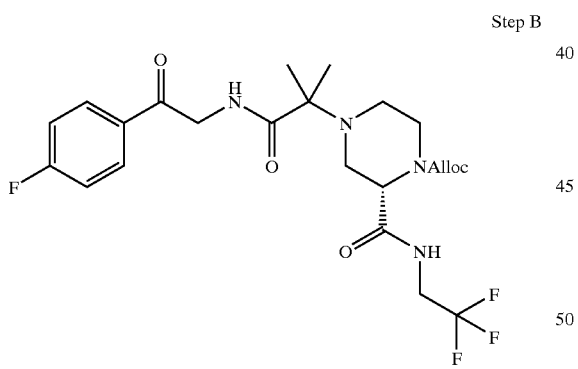

This intermediate was prepared in the same manner as that of Example 109 Step A, employing carboxylic-acid from Example 66 Step,D (12.85 g; 26.6 mmol) in dry NMP (10 mL), DIEA (18.5 mL; 106.4 mmol), HOBt (8.09 g; 59.9 mmol), intermediate from Step A above (6.3 g; 33.25 mmol), and HBTU (15.1 g; 39.9 mmol). The residue resulting after workup was purified by flash column chromatography (gradient elution 45% to 50% to 55% EtOAc/hexane) to provide the desired product. $^1$H NMR (500 MHz, $CDCl_3$): δ1.26 (s, 3H), 1.29 (s, 3H), 2.34 (apparent td, J=3.2, 11.7 Hz, 1H), 2.44 (dd, J=3.9, 11.7 Hz, 1H), 2.85 (d, J=10.9 Hz, 1H), 3.22–3.32 (broad, 1H), 3.66 (d, J=11.9 Hz, 1H), 3.75–4.27 (broad, 3H), 4.50 (apparent dd, J=3.7, 18.8 Hz, 1H), 4.68 (d, J=5.0 Hz, 2H), 4.82 (s, 1H), 4.88 (1/2ABX, J=6.8, 18.7 Hz, 1H), 5.28 (d, J=10.5 Hz, 1H), 5.34 (d, J=16.9 Hz, 1H), 5.90–6.00 (br s, 1H), 6.62–6.72 (br s, 1H), 7.17 (apparent t, J=8.6 Hz, 2H), 8.00 (m, 2H), 8.15–8.25 (br s, 1H); electrospray ionization mass spectrum: m/e 517.3 ($MH^+$ calcd for $C_{23}H_{29}F_4N_4O_5$, 517.2).

Step C

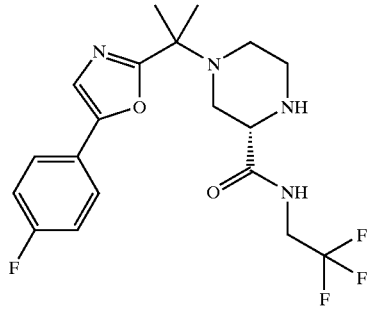

This intermediate was prepared according to the procedure described in Example 109 Step B, employing the compound from Step B above (7.86 g; 15.2 mmol), $P_2O_5$ (6.47 g; 22.8 mmol), and 85 mL $H_2SO_4$. Flash column chromatography (93:5:2 EtOAc:MeOH:TEA) provided the desired compound. $^1$H NMR (500 MHz, $CDCl_3$): δ1.58 (s, 3H), 1.60 (s, 3H), 1.80–1.88 (br s, 1H), 2.55–2.61 (complex m, 2H), 2.76–2.79 (m, 1H), 2.86–2.95 (complex m, 3H), 3.49 (m, 1H), 3.94 (m, 2H), 7.13 (apparent t, J=8.6 Hz, 2H), 7.19 (s, 1H), 7.60 (m, 2H), 8.12–8.18 (br s, 1H); electrospray ionization mass spectrum: m/e 415.3 ($MH^+$ calcd for $C_{19}H_{23}F_4N_4O_2$, 415.2).

Step D:

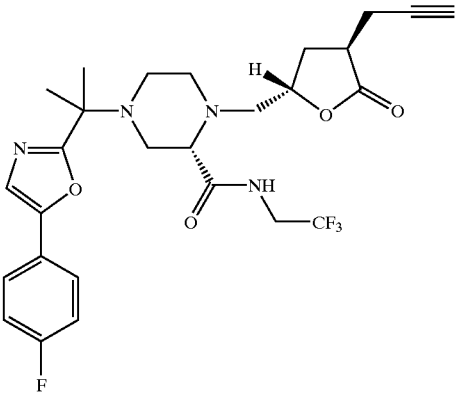

This intermediate was prepared according to the procedure described in Example 109 Step F, employing the compound from Step C above (139 mg; 0.34 mmol), intermediate from Example 109 Step E (96 mg; 0.34 mmol), and DIEA (71 uL; 0.41 mmol) in dry iPrOH (1.7 mL) overnight. Flash column chromatography (70% EtOAc/hexane) provided the desired product. $^1$H NMR (500 MHz, $CDCl_3$): δ1.58 (s, 3H), 1.59 (s, 3H), 2.02 (m, 1H), 2.17–2.22 (complex m, 1H), 2.28–2.34 (complex m, 1H), 2.51–2.64 (complex m, 4H), 2.69–2.73 (m, 2H), 2.81 (m, 2H), 2.85–2.95 (complex m, 3H), 3.279 (m, 1H), 3.63–3.69 (complex m, 1H), 4.15–4.20 (complex m, 1H), 4.67–4.72 (m, 1H), 7.15 (apparent t, J=8.7 Hz, 2H), 7.20 (s, 1H), 7.60 (m, 2H), 8.58–8.65 (br s, 1H).

Step E:

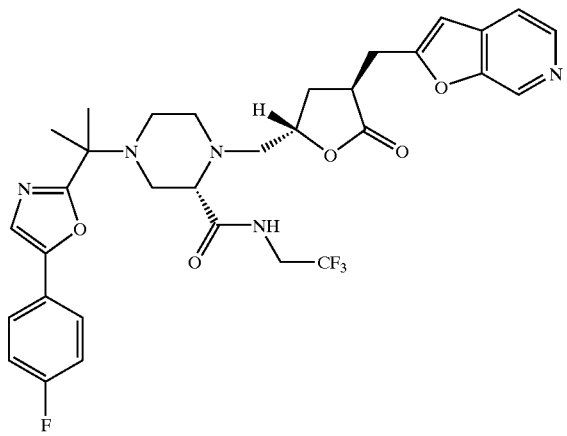

This intermediate was prepared according to the procedure described in Example 109 Step G, employing the compound from Step D above (150 mg; 0.27 mmol), 4-iodo-3-hydroxypyridine (90 mg; 0.41 mmol), and $Cu_2O$ (59 mg; 0.41 mmol) in dry pyridine (2.0 mL) for 30 minutes. Following workup, flash column chromatography (3% $MeOH/CH_2Cl_2$) provided the desired product. $^1H$ NMR (500 MHz, $CDCl_3$): δ1.58 (s, 3H), 1.59 (s, 3H), 2.14–2.22 (complex m, 2H), 2.55–2.60 (complex m, 2H), 2.68–2.96 (complex m, 6H), 3.02 (m, 1H), 3.145–3.20 (complex m, 1H), 3.26 (m, 1H), 3.367 (1/2ABX, J=4.5, 15.3 Hz, 1H), 3.60–3.66 (complex m, 1H), 4.12–4.19 (complex m, 1H), 4.59 (m, 1H), 6.54 (s, 1H), 7.14 (apparent t, J=8.6 Hz, 2H), 7.20 (s, 1H), 7.48 (brs, 1H), 7.58 (m, 2H), 8.38–8.46 (broad s, 1H), 8.63–8.72 (br s, 1H), 8.76–8.90 (br s, 1H); electrospray ionization mass spectrum: m/e 644.2 ($MH^+$ calcd for $C_{32}H_{34}F_4N_5O_5$, 644.2).

Step F:

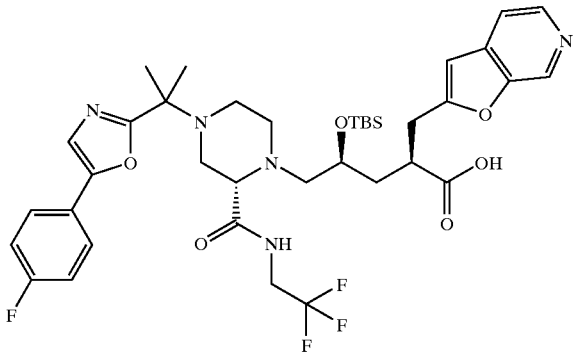

This compound was prepared according to the procedure described in Example 109 Step H, employing the compound from Step E above (68 mg; 0.106 mmol) and aqueous LiOH (14 uL; 0.11 mmol) in dry dimethoxyethane (2 mL). Following removal of solvents as before, the lithium salt was treated (as in Example 109 Step H) with imidazole (144 mg; 2.12 mmol) and TBSCl (160 mg; 1.06 mmol) in dry DMF(2 mL). Upon workup and subsequent hydrolysis in $THF/H_2O$ (1.5mL; 2:1), the product was used without further purification; electrospray ionization mass spectrum: m/e 776.2 ($MH^+$ calcd for $C_{38}H_{50}F_4N_5O_6Si$, 776.3).

Step G:

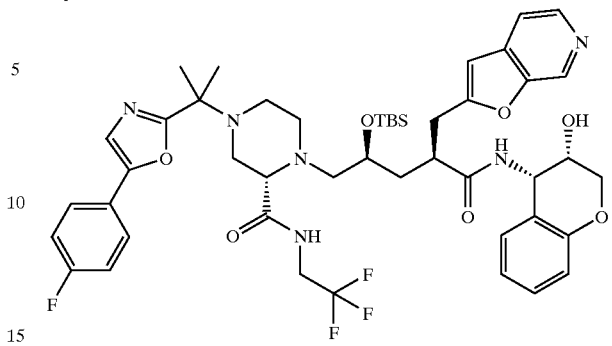

This compound was prepared according to the procedure described in Example 109 Step I, employing the compound from Step F above (~0.106 mmol) in dry NMP (1.5 mL), DIEA (55 uL; 0.32 mmol), HOBt (32 mg; 0.24 mmol), amino chromanol obtained from Example 1 Step L (21 mg; 0.13 mmol), and HBTU (60 mg; 0.16 mmol). Following workup, flash column chromatography (100% EA) provided the desired product. $^1H$ NMR (500 MHz, $CDCl_3$): δ−0.01 (m, 3H), 0.04 (s, 3H), 0.84 (s, 9H), 1.50 (m, 1H), 1.56 (s, 3H), 1.58 (s, 3H), 1.60–1.68 (br s, 1H), 2.27–2.33 (complex m, 2H), 2.57–2.66 (complex m, 4H), 2.75–2.90 (complex m, 4H), 3.00 (m, 1H), 3.04–3.12 (complex m, 1H), 3.18–3.23 (complex m, 2H), 3.66 (m, 1H), 3.86–3.90 (br s, 1H), 3.96 (m, 2H), 4.06–4.14 (complex m, 2H), 5.26 (m, 1H), 6.29 (d, J=8.4 Hz, 1H), 6.53 (s, 1H), 6.82 (d, J=8.0 Hz, 1H), 6.89 (apparent t, J=7.4 Hz, 1H), 7.12–7.20 (complex, 4H), 7.44 (d, J=5.1 Hz, 1H), 7.59 (m, 2H), 8.37 (d, J=5.3 Hz, 1H), 8.43–8.50 (br s, 1H), 8.75 (s, 1H); electrospray ionization mass spectrum: m/e 923.5 ($MH^+$ calcd for $C_{47}H_{59}F_4N_6O_7Si$, 923.4).

Step H (αS,γS,2S)-4-[1-[5-(4-fluorophenyl)-2-oxazolyl]-1-methylethyl]-N-[(3S,4S)-3,4-dihydro-3-hydroxy-2H-1-benzopyran-4-yl]-α-(furo[2,3-c]pyridin-2-ylmethyl)-γ-hydroxy-2-[[(2,2,2-trifluoroethyl)amino] carbonyl]-1-piperazinepentanamide The titled compound was prepared according to the procedure described in Example 109 Step J, employing the intermediate from Step G above (59 mg; 0.064 mmol) and TBAF (160 uL; 0.16 mmol) in dry THF (2.0 mL). Following workup, purification by MPLC (Lobar column; linear gradient 10% to 90% $MeCN/H_2O$) provided the titled compound after lyophilization. $^1H$ NMR (500 MHz, $CD_3OD$): δ1.45 (m, 1H), 1.57 (s, 3H), 1.58 (s, 3H), 2.09 (m, 1H), 2.35–2.43 (complex m, 3H), 2.47 (m, 1H), 2.62 (m, 1H), 2.76 (m, 1H), 2.87 (d, J=9.8 Hz, 1H), 2.98–3.02 (complex m, 2H), 3.08 (dd, J=3.2, 7.3 Hz, 1H), 3.20–3.27 (complex m, 2H), 3.76–3.81 (complex m, 2H), 3.88 (m, 1H), 3.93–4.02 (complex m, 1H), 4.03–4.09 (complex m, 2H), 5.22 (d, J=4.2 Hz, 1H), 6.72 (s, 1H), 6.74 (d, J=8.3 Hz, 1H), 6.80 (apparent t, J=7.9 Hz, 1H), 7.09 (apparent t, J=8.5 Hz, 1H), 7.14, (d, J=7.8 Hz, 1H), 7.18 (apparent t, J=8.8 Hz, 2H), 7.39 (s, 1H), 7.57 (d, J=5.2 Hz, 1H), 7.71 (m, 2H), 8.25 (d, J=5.2 Hz, 1H), 8.68 (s, 1H); electrospray ionization mass spectrum: m/e 809.3 ($MH^+$ calcd for $C_{41}H_{45}F_4N_6O_7$, 809.3).

EXAMPLE 112

(αS,γS,3S)-4-[1-[5-(4-chlorophenyl)-2-oxazolyl]-1-methylethyl]-N-[(3S,4S)-3,4-dihydro-3-hydroxy-2H-1-benzopyran-4-yl]-α-(furo[2,3-c]pyridin-3-ylmethyl)-γ-hydroxy-2-[[(2,2,2-trifluoroethyl)amino]carbonyl]-1-piperazinepentanamide

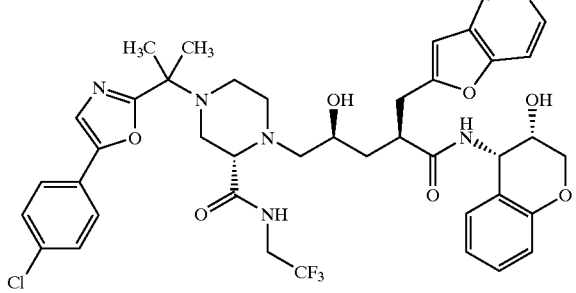

Step A:

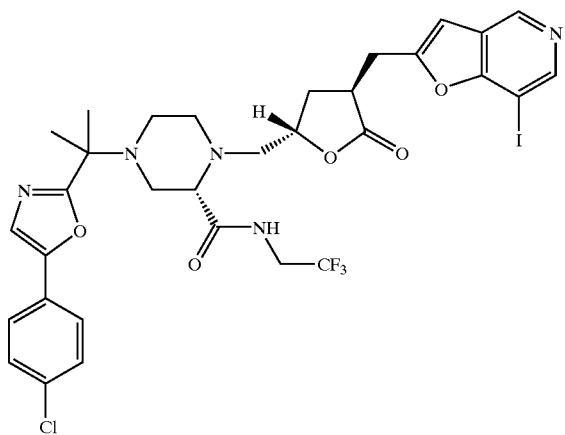

This intermediate was prepared according to the procedure of Example 109 Step G, employing the acetylene from Example 110 Step D (490 mg; 0.86 mmol), 3,5-diiodo-4-hydroxypyridine (330 mg; 0.95 mmol)in dry pyridine (5.75 mL) and $Cu_2O$ (160 mg; 1.12 mmol). After workup, purification by flash column chromatography (gradient elution 75% EtOAc/hexane to 100% EA to 5% MeOH/EtOAc) provided the desired compound. $^1$H NMR (500 MHz, $CDCl_3$): δ1.58 (s, 3H), 1.60 (s, 3H), 2.19–2.28 (complex m, 2H), 2.57–2.62 (complex m, 2H), 2.70–2.79 (complex m, 3H), 2.84–3.04 (complex m, 4H), 3.18–3.21 (complex m, 1H), 3.28 (m, 1H), 3.39 (1/2ABX, J=4.4, 15.4 Hz, 1H), 3.65–3.72 (complex m, 1H), 4.10–4.20 (complex m, 1H), 4.64 (m, 1H), 6.68 (s, 1H), 7.25 (s, 1H), 7.41 (d, J=8.5 Hz, 2H), 7.54 (d, J=8.5 Hz, 2H), 8.71 (m, 3H); electrospray ionization mass spectrum: m/e 786.0 (MH$^+$ calcd for $C_{32}H_{33}ClF_3IN_5O_5$, 786.1).

Step B:

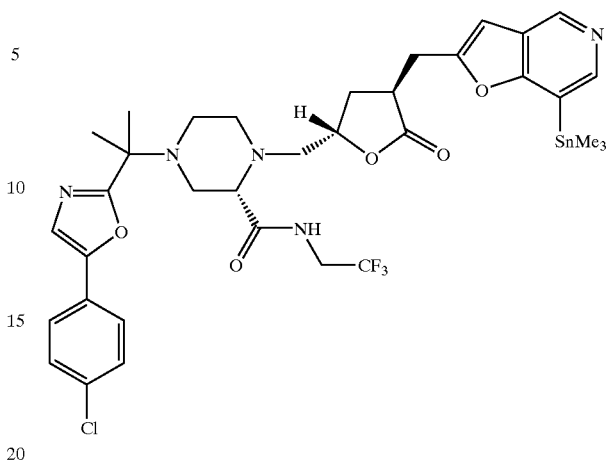

A stirred solution of the iodide obtained in Step A above (183 mg; 0.23 mmol) in dry toluene (1.5 mL) was degassed approximately 10 minutes, after which hexamethylditin (49 ul; 0.26 mmol) was added followed by $PPh_3$ (2 mg; 0.007 mmol) and $Pd(PPh_3)_4$ (13 mg; 0.011 mmol). After 1.25 hours at reflux, the reaction mixture was filtered through Celite, washing with EtOAc. The organics were washed with saturated $NaHCO_3$, water, and brine. Drying ($Na_2SO_4$), filtration, removal of solvent in vacuo and purification by flash column chromatography (4% MeOH/$CH_2Cl_2$) provided the desired compound, which was used without further purification.

Step C:

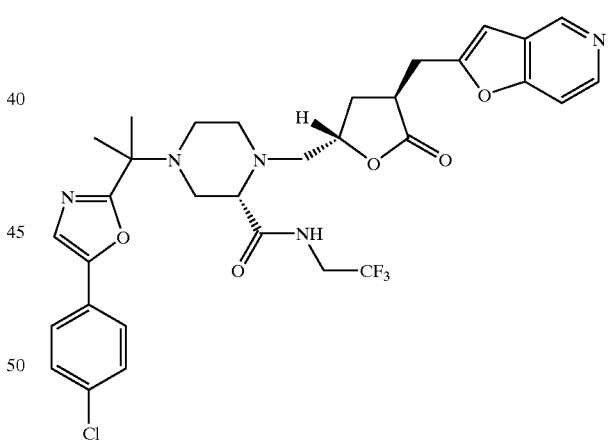

To a stirring solution of stannane from Step B above (104 mg; 0.13 mmol) in dry MeOH (2 mL) was added an anhydrous ethereal solution of HCl (38 uL; 0.38 mmol). After 45 minutes the reaction mixture was diluted with EtOAc and washed with saturated $NaHCO_3$, water and brine. Drying ($Na_2SO_4$), filtration, removal of solvent in vacuo and purification by flash column chromatography (4% MeOH/$CH_2Cl_2$) provided the desired compound. $^1$H NMR (500 MHz, $CDCl_3$): δ1.58 (s, 3H), 1.59 (s, 3H), 2.15–2.19 (complex m, 2H), 2.55–2.61 (complex m, 2H), 2.68–2.84 (complex m, 4H), 2.88–3.02 (complex m, 3H), 3.14 (m, 1H), 3.26 (m, 1H), 3.34 (1/2ABX, J=4.5, 15.3 Hz, 1H), 3.62–3.68

(complex m, 1H), 4.13–4.19 (complex m, 1H), 4.58 (m, 1H), 6.58 (s, 1H), 7.25 (s, 1H), 7.38 (d, J=5.0 Hz, 1H), 7.42 (d, J=8.5 Hz, 2H), 7.54 (d, J=8.5 Hz, 2H), 8.45 (br s, 1H), 8.63 (br s, 1H), 8.86 (br s, 1H); electrospray ionization mass spectrum: m/e 660.2 (MH$^+$ calcd for $C_{32}H_{34}ClF_3N_5O_5$, 660.2).

Step D

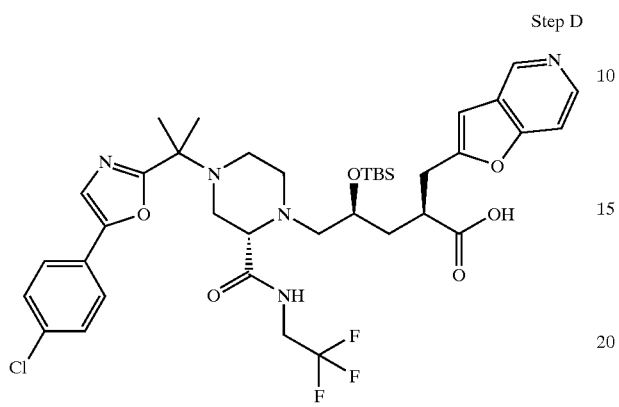

This compound was prepared according to the procedure described in Example 109 Step H, employing the compound from Step C above (58 mg; 0.088 mmol) and aqueous LiOH (100 uL; 0.097 mmol) in dry dimethoxyethane (1.5 mL). Following removal of solvents as before, the lithium salt was treated (as in Example 109 Step H) with imidazole (120 mg; 1.76 mmol) and TBSCl (133 mg; 0.88 mmol) in dry DMF (1.5 mL). Upon workup, the product was purified by flash column chromatography (gradient elution 5% to 10% MeOH/CH$_2$Cl$_2$); electrospray ionization mass spectrum: m/e 792.1 (MH$^+$ calcd for $C_{38}H_{50}ClF_3N_5O_6Si$, 792.3).

Step E

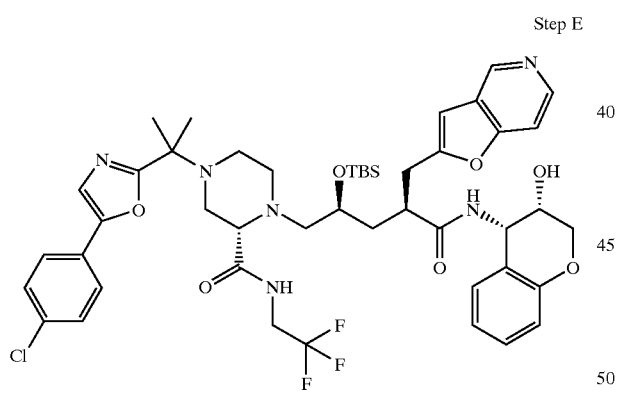

This compound was prepared according to the procedure described in Example 109 Step I, employing the compound from Step D above (~0.088 mmol) in dry NMP (1.3 mL), DIEA (46 uL; 0.26 mmol), HOBt (27 mg; 0.20 mmol), amino chromanol obtained from Example 1 Step L (18 mg; 0.11 mmol), and HBTU (50 mg; 0.13 mmol). Following workup, flash column chromatography(1.5% MeOH/EA) provided the desired product. Residual NMP which remained was removed by dissolution in EtOAc followed by washing with water (2×), brine, drying (MgSO$_4$), filtration, and solvent removal in vacuo as before to provide the desired product which was used without further purification; electrospray ionization mass spectrum: m/e 939.4 (MH$^+$ calcd for $C_{47}H_{59}ClF_3N_6O_7Si$, 939.4).

Step F (αS,γS,2S)-4-[1-[5-(4-chlorophenyl)-2-oxazolyl]-1-methylethyl]-N-[(3S,4S)-3,4-dihydro-3-hydroxy-2H-1-benzopyran-4-yl]-α-(furo[2,3-c]pyridin-3-ylmethyl)-γ-hydroxy-2-[[(2,2,2-trifluoroethyl)amino] carbonyl]-1-piperazinepentanamide This compound was prepared according to the procedure described in Example 109 Step J, employing the intermediate from Step E above (47 mg; 0.05 mmol) and TBAF (125 uL; 0.125 mmol) in dry THF (1.0 mL). Following workup, purification by MPLC (Lobar column; linear gradient 10% to 90% MeCN/H$_2$O) provided the titled compound after lyophilization. $^1$H NMR (500 MHz, CD$_3$OD): δ1.44 (m, 1H), 1.57 (s, 3H), 1.58 (s, 3H), 2.08 (m, 1H), 2.35–2.49 (complex m, 4H), 2.62 (m, 1H), 2.75 (m, 1H), 2.87 (d, J=9.9 Hz, 1H), 2.95–3.02 (complex m, 2H), 3.08 (dd, J=3.0, 7.3 Hz, 1H), 3.17–3.25 (complex m, 2H), 3.74–3.81 (complex m, 2H), 3.88 (m, 1H), 3.93–4.09 (complex m, 3H), 5.22 (d, J=4.1 Hz, 1H), 6.74 (m, 2H), 6.80 (apparent t, J=7.5 Hz, 1H), 7.09 (apparent t, J=7.7 Hz, 1H), 7.14, (d, J=7.8 Hz, 1H), 7.45 (m, 3H), 7.50 (d, J=5.7 Hz, 1H), 7.68 (d, J=8.5 Hz, 2H), 8.32 (d, J=5.7 Hz, 1H), 8.74 (s, 1H); electrospray ionization mass spectrum: m/e 825.1 (MH$^+$ calcd for $C_{41}H_{45}ClF_3N_6O_7$, 825.3).

EXAMPLE 113

(αS,γS,2S)-4-[1-[5-(4-fluorophenyl)-2-oxazolyl]-1-methylethyl]-N-[(3S,4S)-3,4-dihydro-3-hydroxy-2H-1-benzopyran-4-yl]-α-(furo[2,3-c]pyridin-3-ylmethyl)-γ-hydroxy-2-[[(2,2,2-trifluoroethyl)amino] carbonyl]-1-piperazinepentanamide

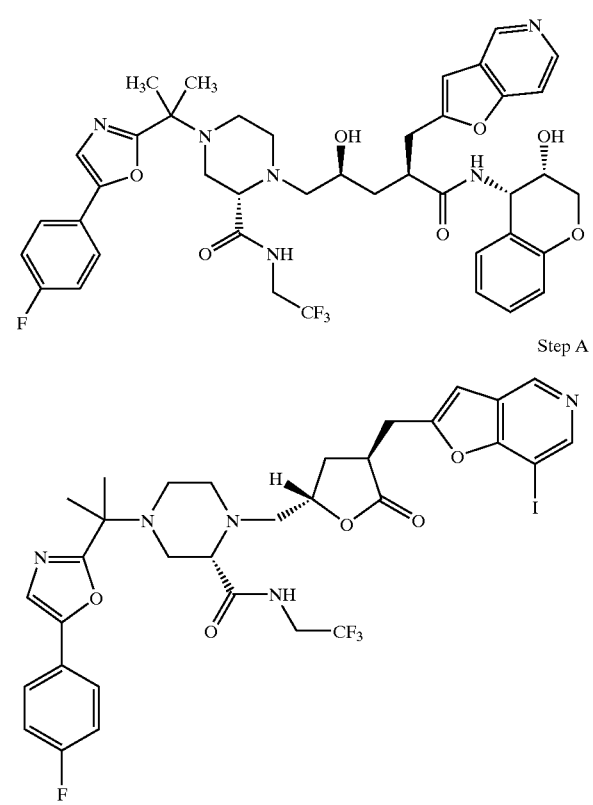

Step A

This intermediate was prepared according to the procedure of Example 109 Step G, employing the acetylene from Example 110 Step D (225 mg; 0.41 mmol), 3,5-diiodo-4- hydroxypyridine (156 mg; 0.45 mmol) in dry pyridine (2.75 mL) and $Cu_2O$ (76 mg; 0.53 mmol). After workup, purification by flash column chromatography (gradient elution 75% EtOAc/hexane to 100% EA to 5% MeOH/EtOAc) provided the desired compound. $^1H$ NMR (500 MHz, $CDCl_3$): δ1.58 (s, 3H), 1.60 (s, 3H), 2.19–2.28 (complex m, 2H), 2.56–2.62 (complex m, 2H), 2.72–2.79 (complex m, 3H), 2.84–2.92 (complex m, 2H), 2.95–3.04 (complex m, 2H), 3.18–3.21 (complex m, 1H), 3.28 (m, 1H), 3.39 (1/2ABX, J=4.5, 15.4 Hz, 1H), 3.62–3.68 (complex m, 1H), 4.12–4.19 (complex m, 1H), 4.64 (m, 1H), 6.68 (s, 1H), 7.14 (apparent t, J=8.6 Hz, 2H), 7.20 (s, 1H), 7.59 (m, 2H), 8.72 (m, 3H); electrospray ionization mass spectrum: m/e 770.1 ($MH^+$ calcd for $C_{32}H_{33}F_4IN_5O_5$, 770.1).

Step B

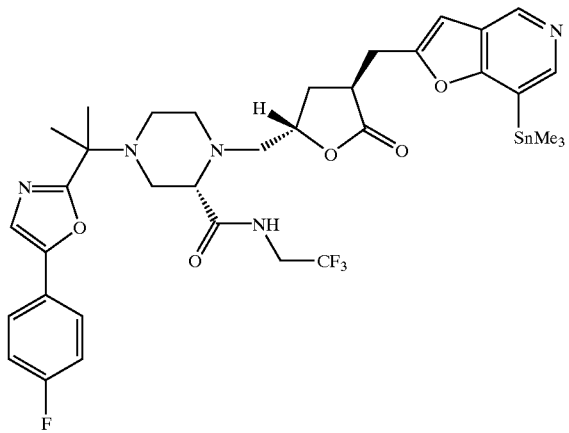

The stannane was prepared according to the procedure set forth in Example 112 Step B, employing the iodide obtained in Step A above (270 mg; 0.35 mmol) in dry toluene (2.3 mL), hexamethylditin (75 ul; 0.39 mmol), $PPh_3$ (3 mg; 0.011 mmol), and $Pd(PPh_3)_4$ (20 mg; 0.018 mmol) for 2.5 hours. After workup, purification by flash column chromatography (4% $MeOH/CH_2Cl_2$) provided the desired compound. $^1H$ NMR (500 MHz, $CDCl_3$): δ0.44 (s, 9H), 1.57 (s, 3H), 1.59 (s, 3H), 2.12–2.20 (complex m, 2H), 2.53–2.59 (complex m, 2H), 2.67–2.84 (complex m, 4H), 2.87–2.94 (complex m, 2H), 3.01 (1/2ABX, J=8.9, 15.1 Hz, 1H), 3.08–3.14 (complex m, 1H), 3.25 (m, 1H), 3.33 (1/2ABX, J=4.3, 15.3 Hz, 1H), 3.60–3.66 (complex m, 1H), 4.10–4.19 (complex m, 1H), 4.55 (m, 1H), 6.54 (s, 1H), 7.14 (apparent t, J=8.6 Hz, 2H), 7.20 (s, 1H), 7.59 (m, 2H), 8.41 (s, 1H) 8.65 (br s, 1H), 8.80 (s, 1H).

Step C

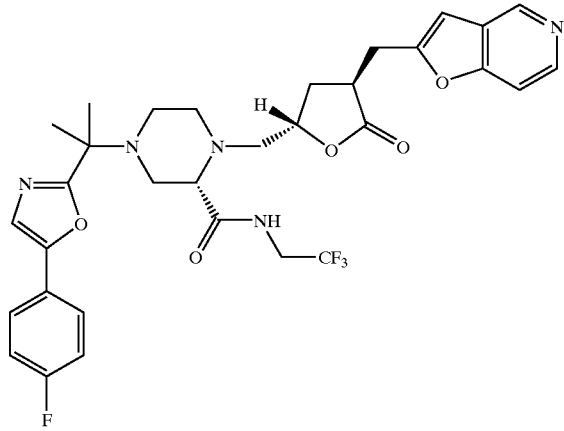

This intermediate was prepared according to the procedure described in Example 112 Step C, employing stannane from Step B above (200 mg; 0.25 mmol) and ethereal HCl (750 uL; 0.75 mmol) in dry MeOH (4 mL). Following workup, purification by flash column chromatography (gradient elution 4% to 5% $MeOH/CH_2Cl_2$) provided the desired compound. $^1H$ NMR (500 MHz, $CDCl_3$): δ1.58 (s, 3H), 1.59 (s, 3H), 2.15–2.19 (complex m, 2H), 2.55–2.60 (complex m, 2H), 2.68–2.85 (complex m, 4H), 2.87–3.02 (complex m, 3H), 3.12–3.17 (complex m, 1H), 3.26 (m, 1H), 3.34 (1/2ABX, J=4.6, 15.4 Hz, 1H), 3.58–3.68 (complex m, 1H), 4.12–4.19 (complex m, 1H), 4.57 (m, 1H), 6.57 (s, 1H), 7.15 (apparent t, J=8.7 Hz, 2H), 7.20 (s, 1H), 7.38 (d, J=5.7 Hz, 1H), 7.59 (m, 2H), 8.48 (d, J=5.3 Hz, 1H), 8.66 (br s, 1H), 8.86 (s, 1H); electrospray ionization mass spectrum: m/e 644.2 ($MH^+$ calcd for $C_{32}H_{34}F_4N_5O_5$, 644.2).

Step D

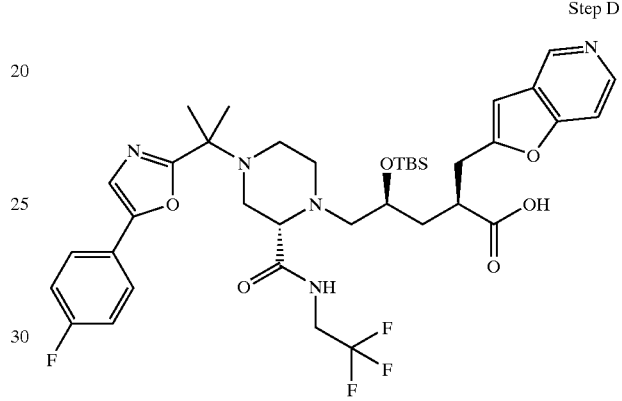

This compound was prepared according to the procedure described in Example 109 Step H, employing the compound from Step C above (130 mg; 0.20 mmol) and aqueous LiOH (220 uL; 0.21 mmol) in dry dimethoxyethane (2 mL). Following removal of solvents as before, the lithium salt was treated (as in Example 109 Step H) with imidazole (272 mg; 4.0 mmol) and TBSCl (301 mg; 2.0 mmol) in dry DMF (2 mL). Upon workup and hydrolysis in THF/H2O (6 mL; 2:1), the product was purified by flash column chromatography (gradient elution 7% to 9% $MeOH/CH_2Cl_2$); m/e 776.3 ($MH^+$ calcd for $C_{38}H_{50}F_4N_5O_6Si$, 776.3).

Step E

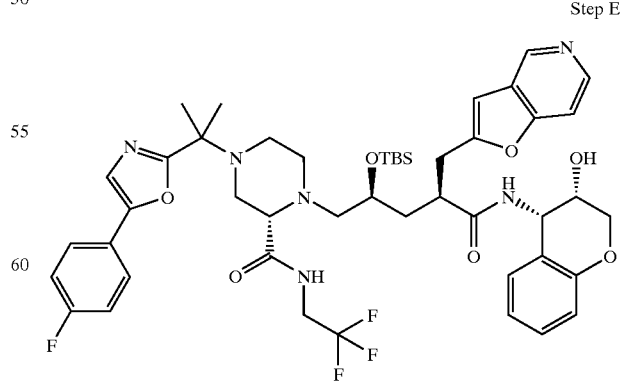

This compound was prepared according to the procedure described in Example 109 Step I, employing the compound from Step D above (~0.20 mmol) in dry NMP (1.0 mL), DIEA (104 uL; 0.60 mmol), HOBt (61 mg; 0.45 mmol), amino chromanol obtained from Example 1 Step L (40 mg; 0.24 mmol), and HBTU (114 mg; 0.30 mmol). Following workup, flash column chromatography (gradient elution 1% to 2% MeOH/EA) provided the desired product.

Step F (αS,γS,2S)-4-[1-[5-(4-fluorophenyl)-2-oxazolyl]-1-methylethyl]-N-[(3S,4S)-3,4-dihydro-3-hydroxy-2H-1-benzopyran-4-yl]-α-(furo[2,3-c]pyridin-3-ylmethyl)-γ-hydroxy-2-[[(2,2,2-trifluoroethyl)amino]carbonyl]-1-piperazinepentanamide The titled compound was prepared according to the procedure described in Example 109 Step J, employing the intermediate from Step E above (170 mg; 0.18 mmol) and TBAF (405 uL; 0.405 mmol) in dry THF (3.0 mL). Following workup, purification by flash column chromatography (gradient elution 5% to 6% MeOH/CH$_2$Cl$_2$) provided the titled compound after lyophilization. $^1$H NMR (500 MHz, CD$_3$OD): δ1.45 (m, 1H), 1.57 (s, 3H), 1.58 (s, 3H), 2.09 (m, 1H), 2.35–2.49 (complex m, 4H), 2.62 (m, 1H), 2.76 (m, 1H), 2.87 (d, J=11.2 Hz, 1H), 2.95–3.01 (complex m, 2H), 3.08 (m, 1H), 3.17–3.24 (complex m, 2H), 3.74–3.81 (complex m, 2H), 3.89 (m, 1H), 3.93–4.00 (complex m, 1H), 4.02–4.10 (complex m, 2H), 5.22 (d, J=4.2 Hz, 1H), 6.74 (m, 2H), 6.80 (apparent t, J=7.6 Hz, 1H), 7.09 (apparent t, J=7.7 Hz, 1H), 7.17, (m, 3H), 7.39 (s, 1H), 7.50 (d, J=5.7 Hz, 1H), 7.71 (m, 2H), 8.32 (d, J=5.9 Hz, 1H), 8.74 (s, 1H); electrospray ionization mass spectrum: m/e 809.2 (MH$^+$ calcd for C$_{41}$H$_{45}$F$_4$N$_6$O$_7$, 809.3).

EXAMPLE 114

(αS,γS,2S)-N-[(3S,4S)-3,4-dihydro-3-hydroxy-2H-1-benzopyran-4-yl]-4-[1-[5-(4-fluorophenyl)-2-oxazolyl]-1-methylethyl]-α-(furo[2,3-d]pyrimidin-6-ylmethyl)-γ-hydroxy-2-[[(2,2,2-trifluoroethyl)amino]carbonyl]-1-piperazinepentanamide

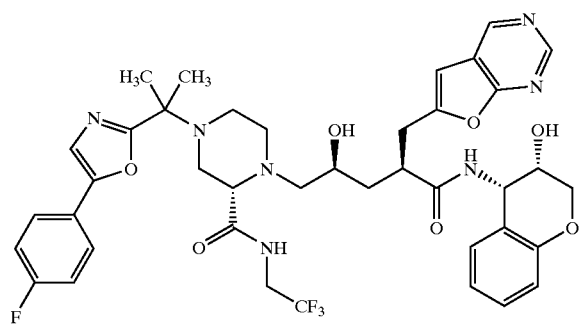

-continued

Step A

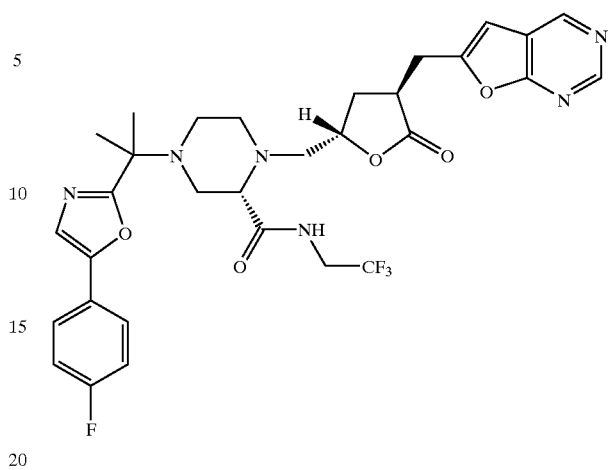

To a stirred solution of the acetylene from Example 111 Step D (411 mg; 0.75 mmol) and 5-iodo-pyrimidin-4-ol (199 mg; 0.89 mmol) in anhydrous DMF (7 mL) under nitrogen was added Cl$_2$Pd(PPh$_3$)$_2$ (5 mol %; 26 mg), CuI (10 mol %; 14 mg) and TEA (0.260 mL; 1.5 mmol). The reaction was heated to 50°–60° C. for 3 hours. After cooling, EtOAc and water were added followed by filtration through celite. The organic layer was washed with water, NaHCO$_3$ solution and brine. Drying (MgSO$_4$), filtration, concentration of the solvent in vacuo and purification by flash column chromatography (5% MeOH/DCM) provided the desired product. $^1$H NMR (500 MHz, CDCl$_3$): δ1.58 (s, 3H), 1.60 (s, 3H), 2.19–2.28 (complex m, 2H), 2.56–2.62 (complex m, 2H), 2.71–2.78 (complex m, 3H), 2.84–3.04 (complex m, 4H), 3.16–3.23 (complex m, 1H), 3.28 (m, 1H), 3.39 (1/2ABX, J=4.6, 15.3 Hz, 1H), 3.62–3.71 (complex m, 1H), 4.11–4.21 (complex m, 1H), 4.65 (m, 1H), 6.61 (s, 1H), 7.15 (apparent t, J=8.6 Hz, 2H), 7.21 (s, 1H), 7.60 (m, 2H), 8.57 (broad s, 1H); 8.95 (s, 1H); 8.96 (s, 1H); electrospray ionization mass spectrum: m/e 645.2 (MH$^+$ calcd for C$_{31}$H$_{33}$F$_4$N$_6$O$_5$, 645.2).

Step B

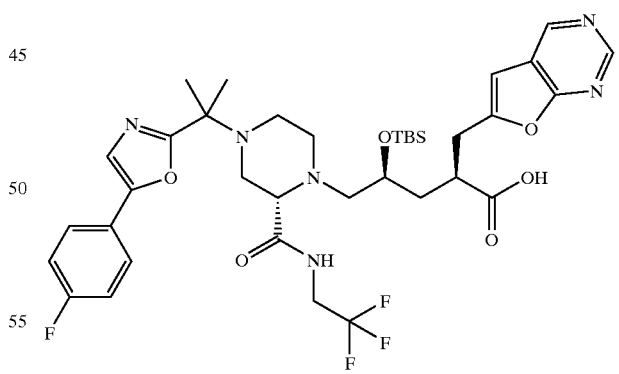

This compound was prepared according to the procedure described in Example 109 Step H, employing the compound from Step A above (226 mg; 0.35 mmol) and aqueous LiOH (397 uL; 0.385 mmol) in dimethoxyethane (4 mL). Following removal of solvents as before, the lithium salt was treated (as in Example 109 Step H) with imidazole (476 mg; 7.0 mmol) and TBSCl (527 mg; 3.5 mmol) in dry DMF (4 mL). Upon workup and hydrolysis in THF/H$_2$O (2:1), the product was purified by flash column chromatography (gradient elution 5% to 10% MeOH/CH$_2$Cl$_2$) to provide the desired carboxylic acid: electrospray ionization mass spectrum: m/e 777.4 (MH$^+$ calcd for C$_{37}$H$_{49}$F$_4$N$_6$O$_6$Si, 777.3).

Step C

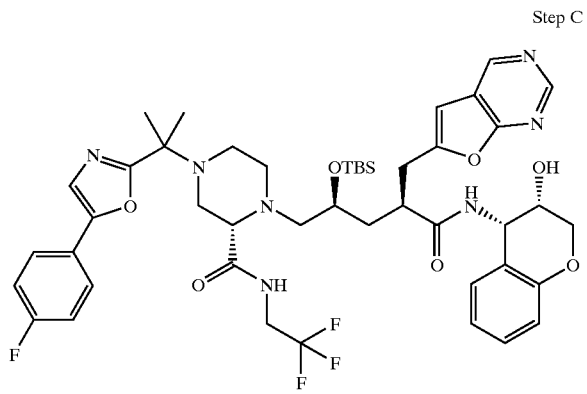

This compound was prepared according to the procedure described in Example 109 Step I, employing the compound from Step B above (0.23 mmol) in dry NMP (3.0 mL), DIEA (118 uL; 0.70 mmol), HOBt (71 mg; 0.52 mmol), amino chromanol obtained from Example 1 Step L (54 mg; 0.32 mmol), and HBTU (133 mg; 0.35 mmol). Following workup, flash column chromatography (5% MeOH/DCM) provided the desired product electrospray ionization mass spectrum: m/e 924.5 (MH$^+$ calcd for C$_{37}$H$_{49}$F$_4$N$_6$O$_6$Si, 924.4).

Step D (αS,γS,2)-N-[(3S,4S)-3,4-dihydro-3-hydroxy-2H-1-benzopyran-4-yl]-4-[1-[5-(4-fluorophenyl)-2-oxazolyl]-1-methylethyl]-α-(furo[2,3-d]pyrimidin-6-ylmethyl)-γ-hydroxy-2-[[(2,2,2-trifluoroethyl)amino]carbonyl]-1-piperazinepentanamide The titled compound was prepared according to the procedure described in Example 109 Step J, employing the intermediate from Step C above (170 mg; 0.18 mmol) and TBAF (405 uL; 0.405 mmol) in dry THF (3.0 mL). Following workup, purification by flash column chromatography (5% MeOH/CH$_2$Cl$_2$) provided the titled compound after lyophilization. $^1$H NMR (500 MHz, CD$_3$OD): δ1.45 (m, 1H), 1.58 (s, 3H), 1.59 (s, 3H), 2.10 (m, 1H), 2.35–2.44 (complex m, 3H), 2.47 (m, 1H), 2.62 (m, 1H), 2.78 (m, 1H), 2.87 (d, J=9.8 Hz, 1H), 2.95–3.02 (complex m, 2H), 3.07 (dd, J=3.2, 7.3 Hz, 1H), 3.18–3.29 (complex m, 2H), 3.75–3.82 (complex m, 2H), 3.92 (m, 1H), 3.93–4.09 (complex m, 3H), 5.22 (d, J=4.4 Hz, 1H), 6.74 (d, J=8.3 Hz, 2H), 6.78 (s, 1H), 6.81 (apparent t, J=7.6 Hz, 1H), 7.09 (apparent t, J=7.7 Hz, 1H), 7.14–7.20, (complex m, 3H), 7.32 (s, 1H), 7.39 (s, 1H), 7.72 (m, 2H), 8.80 (s, 1H), 8.92 (s, 1H); electrospray ionization mass spectrum: m/e 810.3 (MH$^+$ calcd for C$_{40}$H$_{44}$F$_4$N$_7$O$_7$, 810.3).

EXAMPLE 115
Preparation of Enzymes

Synthetic oligonucleotide cassettes of 444 base pairs were designed according to the wild-type sequence of pET-3b-HIVPR. Point mutations were incorporated into the DNA with a bias toward optimal codon usage in *E. Coli* to yield amino acid mutations listed in Table 2 below. The oligonucleotides were annealed and ligated into pUC-18 or pUC-19 by Midland Certified Reagent Company. The primary sequence was verified before subcloning into a pET-3b expression vector via Nde I and Bpul 102 I sites and reconfirmed by automated double-stranded DNA sequencing. Clones carrying the mutant DNA were transformed and expressed as previously. described in Schock et al., *J. Biol. Chem.* 1996, 271: 31957–31963 and Chen et al., *J. Biol. Chem.* 1995, 270: 21433–21436. The cells were lysed in 50 mM Tris-HCl pH 8.0, 1 mM EDTA, 0.1% NP40, 10 mM MgCl$_2$, and 100μg/mL DNase I using a microfluidizer processor (Microfluidics International Corp., Newton, Mass.). The mutant protease was extracted, refolded, and purified over affinity columns as previously described in Schock et al., *J. Biol. Chem.* 1991, 271: 31957–31963. Protein concentrations were determined by amino acid analysis and purity was confirmed by SDS gel electrophoresis.

EXAMPLE 116
Assay for Inhibition of Microbial Expressed HIV Protease

Inhibition studies of the reaction of the protease (which was expressed in *Eschericia coli*) with a peptide substrate [Val-Ser-Gln-Asn-(betanapthyl)Ala-Pro-Ile-Val, 0.5 mg/mL at the time the reaction is initiated] were in 50 mM Na acetate, pH 5.5, 0.1% bovine serum albumin, 3.75% DMSO at 30° C. for 1 hour. Various concentrations of inhibitor in 2 mL DMSO were added to 50 μL of the peptide solution in buffer. The reaction is initiated by the addition of 28 μL of 14.3 picomolar (wild type, K-60, Q-60) and 28.6 pM (V-18) protease in a solution of 50mM Na acetate pH 5.5 and 0.1% bovine serum albumin. The reaction was quenched with 120 μL of 10% phosphoric acid. Products of the reaction were separated by HPLC (VYDAC wide pore 5 cm C-18 reverse phase, acetonitrile gradient, 0.1% phosphoric acid). The extent of inhibition of the reaction was determined from the peak heights of the products. HPLC of the products, independently synthesized, proved quantitation standards and confirmation of the product composition. The compounds of the invention prepared in Examples 1–114 exhibited IC$_{50}$ values ranging from about 0.05 to about 1 nM against the wild-type enzyme. The indinavir IC$_{50}$ value against the wild type enzyme is 0.6 nM (average). The compounds of the invention prepared in Examples 1–114 exhibited IC$_{50}$ values in the range of about 0.02 to about 5 nM against the mutant enzymes Q-60, K-60, and V-18. These IC$_{50}$ values range from about 4-fold to greater than about 100-fold more potent than the values of of 20 to 50 nM obtained for indinavir against these same mutant enzymes.

EXAMPLE 117
Preparation of Viral Constructs

Mutant viruses were constructed using gapped-duplex oligonucleotide mutagenesis of a subclone of plasmid pWT-6 as described in Colonno et al., *Proc. Nat'l Acad. Sci.* 1988, 85: 5449–5453. Infectious mutant proviral clones were constructed by subcloning the 833-b.p. ApaI-Sse83871 fragment containing the mutagenized protease gene into the corresponding sites of plasmid pNL4-3 (see *J. Virol.* 1986, 59: 284–291). After transfection of the mutant proviral clone into HeLa cells and growth of viral stocks in cocultivated H9 human T-lymphoid cells, the complete sequence of the viral protease gene from the mutant viral population was verified as described in *Nature* 1995, 374: 569–571. The amino acid changes from wild type sequence for three of these viral constructs are shown in Table 2.

TABLE 2

Wild-type and Mutant HIV-1 Protease Sequences

| Wild-type | L10 | K20 | L24 | M36 | S37 | R41 | M46 | I54 | R57 | Q58 | I62 | L63 | I64 | A71 | G73 | V77 | V82 | I84 | L90 | I93 |
|---|---|---|---|---|---|---|---|---|---|---|---|---|---|---|---|---|---|---|---|---|
| Q-60 | I | | | | | | K | I | V | | V | P | | V | | I | A | | M | L |
| K-60 | I | | | | | | | I | V | E | | P | V | | | I | F | | M | L |
| V-18 | I | | I | D | | | | I | | K | | P | | V | S | | | V | M | L |

See Condra et al., J. Virol. 1996, 70: 8270–8276 and Olsen et al., J. Biol. Chem. 1999, 274: 23699–23701 for further details.

EXAMPLE 118
Cell Spread Assay

Inhibition of the spread of HIV in cell culture was measured according to Nunberg et al., J. Virol. 1991, 65: 4887. In this assay, MT-4 T-lymphoid cells were infected with HIV-1 (wild-type, unless otherwise indicated) by using a predetermined inoculum, and cultures were incubated for 24 h. At this time, $\leq 1\%$ of the cells were positive by indirect immunofluorescence. Cells were then extensively washed and distributed into 96-well culture dishes. Serial twofold dilutions of inhibitor were added to the wells, and cultures were continued for 3 additional days. At 4 days postinfection, 100% of the cells in control cultures were infected. HIV-1 p24 accumulation was directly correlated with virus spread. The cell culture inhibitory concentration was defined as the inhibitor concentration in nanomoles/liter which reduced the spread of infection by at least 95%, or $CIC_{95}$. The compounds of the invention prepared in Examples 1–114 exhibited $CIC_{95}$ values in the range of from less than about 8 to about 50 nM against the wild-type viral construct. The $CIC_{95}$ of indinavir against the wild-type viral construct is from 50 to 100 nM. The compounds of the invention prepared in Examples 1–114 exhibited $CIC_{95}$ values in the range of about 8 to about 125 nM against the viral constructs Q60, K-60, and V-18. These $CIC_{95}$ values range from about 4-fold to more than about 100-fold more potent than the values of greater than 1000 nM obtained for indinavir against these same viral constructs.

EXAMPLE 119
Inhibition of Virus Spread

A. Preparation of HIV-infected MT-4 Cell Suspension

MT cells are infected at Day 0 at a concentration of 250,000 per ml with a 1:1000 dilution of HIV-1 strain IIIb stock (final 125 pg p24/ml; sufficient to yield $\leq 1\%$ infected cells on day 1 and 25–100% on day 4). Cells are infected and grown in the following medium: RPMI 1640 (Whittaker BioProducts), 10% inactivated fetal bovine serum, 4 mM glutamine (Gibco Labs) and 1:100 Penicillin-Streptomycin (Gibco Labs).

The mixture is incubated overnight at 37° C. in 5% $CO_2$ atmosphere.

B. Treatment with Inhibitors

A matrix of nanomolar range concentrations of the pairwise combinations is prepared. At Day 1, aliquots of 125 ml of inhibitors are added to equal volumes of HIV-infected MT-4 cells (50,000 per well) in a 96-well microtiter cell culture plate. Incubation is continued for 3 days at 37° C. in 5% $CO_2$ atmosphere.

C. Measurement of Virus Spread

Using a multichannel pipettor, the settled cells are resuspended and 125 ml harvested into a separate microtiter plate. The supernatant is assayed for HIV p24 antigen.

The concentration of HIV p24 antigen is measured by an enzyme immunoassay, described as follows. Aliquots of p24 antigen to be measured are added to microwells coated with a monoclonal antibody specific for HIV core antigen. The microwells are washed at this point, and at other appropriate steps that follow. Biotinylated HIV-specific antibody is then added, followed by conjugated streptavidin-horseradish peroxidase. A color reaction occurs from the added hydrogen peroxide and tetramethylbenzidine substrate. Color intensity is proportional to the concentration of HIV p24 antigen.

Calculation of Degree of Synergy

When there is synergy, pairwise combinations of inhibitors are found to exhibit markedly enhanced inhibition of virus spread, in comparison to each inhibitor alone, or in comparison to merely additive inhibition of each inhibitor.

The data is processed as follows: fractional inhibitory concentration ratios(FIC) are calculated according to Elion, et al., J. Biol. Chem. 1954, 208: 477. The minimum sum of FICs, which is the maximum synergy, is determined for various pairwise combinations. The smaller the number, the greater the synergy.

EXAMPLE 120

Preparation of 4-(tert-butyloxycarbonyl)-2(S)-((2,2,2-trifluoroethyl)aminocarbonyl)piperazine Step One: Preparation of the pyrazine amide

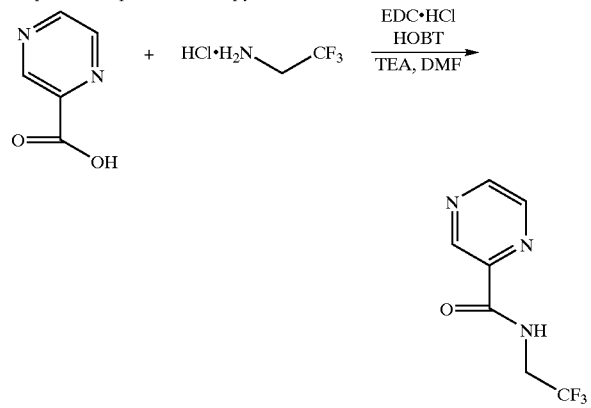

Pyrazine 2-carboxylic acid (1204 g) was suspended in DMF (4.8 L, 4 mL/g acid). 2,2,2-trifluoroethylamine.HCl (TFEA.HCl) (1200 g), 1-hydroxybenzotriazole (HOBT) (60 g) and triethylamine (TEA) (1410 mL) were then added sequentially (exotherm upon addition of TEA, flask cooled with ice bath and temperature kept below 35° C.). The reaction was cooled to 15° C. and 1-(3-dimethylaminopropyl)-3-ethylcarbodiimide.HCl (EDC.HCl) (1940 g) was added portionwise over 15–30 min. The reaction temperature was kept below 35° C. When the reaction appeared complete (approx. two hours, <5% pyrazine 2-carboxylic acid by LC assay), the reaction mixture (yellow/white slurry) was diluted with 10% $K_2CO_3$ in water (24 L, 20 mL/g acid) and the reaction slurry was kept below 35° C. The slurry was cooled to 10° C., aged for two hours and filtered (mother liquor assay=3–4 mg/mL). The wet cake was washed with deionized water (12 L, 10 mL/g acid) and dried under vacuum (22" Hg) at 40° C. with a nitrogen purge. Theoretical yield of 1816 g . Actual yield 1533 g (84%). $^1$H NMR: (CD$_3$CN, 400 MHz): δ9.29(d, J=1.5 Hz, 1H), 8.82 (d, J=2.5 Hz, 1H), 8.63 (dd, J=2.6,1.4 Hz, 1H), 8.40 (bs, 1H), 4.14 (dq, J=9.4, 6.8 Hz, 2H).

HPLC Assay conditions: Waters Xterra RP8 column, elution with acetonitrile and 5 mM K phosphate adjusted to pH=8, detection at 220 nm.

Step Two: Preparation of the piperazine amide

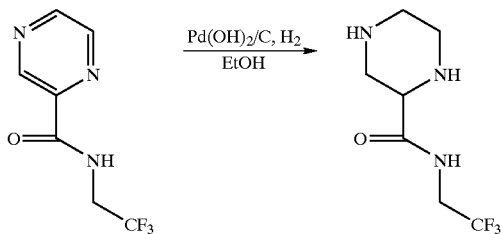

Pyrazine amide (60.2 g 0.268 mol, not corrected for water content) was suspended in absolute ethanol (550 mL) in a 1.0 L autoclave hydrogenation vessel and cooled to 15° C. Wet 20% Pd(OH)$_2$/C 11.0 g (20 wt %, 50 wt % wet) was added and reaction was purged with N$_2$ three times. H$_2$ (5 psig) was introduced with stirring and the temperature maintained at 15° C. for 60 minutes. The temperature was then increased to 60° C. and the hydrogen pressure increased to 40 psig and the reaction mixture stirred for 18 additional hours. The reaction was considered complete when conversion is >99% by LC assay. The reaction mixture was filtered through Solka-Floc and the catalyst solids were washed with ethanol 2×110 m L. Assay of the combined filtrate and washes gave 53.5 g of racemic piperazine amide (Yield= 86%) 1H NMR (CD3CN, 400 MHz): δ7.58 (bs, 1H), 3.90 (dq, J=9.5,6.7 Hz, 2H), 3.24(dd, J=7.9, 5.5 Hz, 1H), 2.96 (dd, J=12.1, 3.6 Hz, 1H), 2.84–2.78 (m, 1H), 2.77–2.67 (m, 3H), 2.66–2.56 (m, 1H), 1.90 (s, 2 H).

HPLC Assay conditions: YMC Basic column, elution with acetonitrile and 0.1% aqueous H$_3$PO$_4$, detection at 210 nm.

Step Three: Resolution of the piperazine amide

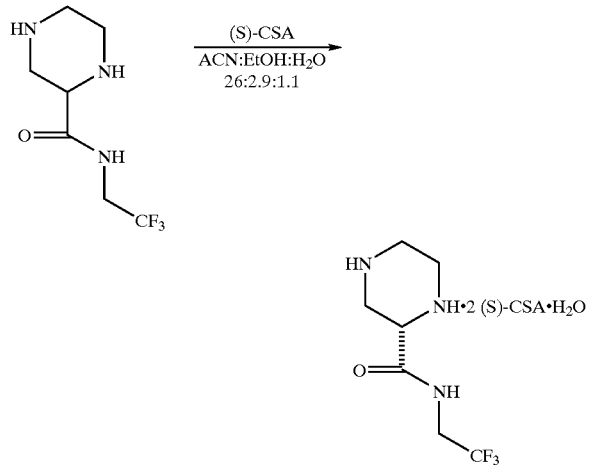

The pip amide ethanol filtrate (116.37 g containing 10.3 g of racemic pip amide by LC assay) was concentrated in vacuo to a final volume of 40.2 mL (3.9 mL per gram of pip amide) and the slurry is diluted with 82.4 mL (8 mL per gram pip amide) of acetonitrile (ACN) and stirred until homogenous. Separately (S)-camphorsulfonic acid ((S)-CSA) (19.26 g, MW=232.30, 1.7 eq) was dissolved in 185 mL of ACN (18 mL per gram of pip amide). The water content of the two solutions was then determined by Karl Fisher titration. The CSA solution was added to the pip amide solution giving a small exotherm to approx. 31–32° C. Water (11.02 mL, 1.118 mL per gram of pip amide minus the total water content of the two solutions) was then added, such that the acetonitrile:ethanol:water ratio was 26:2.9:1.1 (v/v/v). Solids began to form after 15–30 min. The solution/slurry was heated to 72° C. to completely dissolve all solids. The yellow solution was recooled to 62° C. and seeded with a slurry of 10.3 mg of pip amide salt in 1 mL of acetonitrile. After a two hour age at 62° C. the slurry was allowed to cool to room temperature overnight (crystallization was complete when loss to mother liquors was <21 mg pip amide/mL by LC assay. The slurry was filtered then washed with 2×30 mL of ACN:EtOH:H$_2$O [(26:2.9:1.1), (v:v:v)] solution. The wet cake (~13 g, white solid) was dried at 40° C. in a vacuum oven (24 in Hg, nitrogen sweep) to give 11.16 g of product (yield=33%). Assay method (Pip Amide) as above. Chiral assay gives an enantiomeric excess (ee) of 98.0%. 1H NMR (CD$_3$OD, 400 MHz): d4.84(bs, 5H), 4.64 (dd, J=12.0, 3.6 Hz, 1H), 4.13–3.94 (m, 3H), 3.77 (m, 2H), 3.66 (m, 1H), 3.54–3.43 (m, 2H), 3.28(d, J=14.7 Hz, 2H), 2.82 (d, 14.7 Hz, 2H), 2.55 (m, 2H), 2.36 (m, 2H), 2.12–1.998 (m, 4H), 1.92 (d, J=18.4 Hz, 2H), 1.72 (m, 2H), 1.45 (m, 2H), 1.09 (s, 6H), 0.87 (s, 6H).

Enantiomeric excess determined by chiral HPLC of the mono BOC piperazine amide. HPLC assay conditions: Chiral AGP column, elution with acetonitrile and 10 mM Kphospate, pH=6.5, detection at 210 nm.

Step Four: Upgrade of ee of (S)-piperazine amide bis (S)-CSA salt

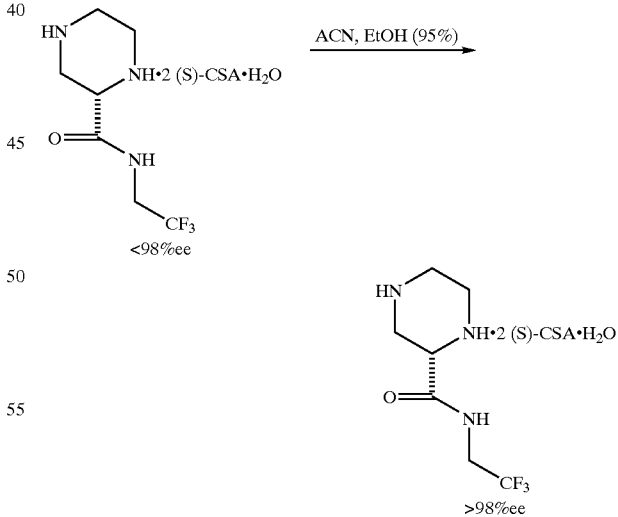

To a 12 L flask was charged (S)-pip amide salt (412.87 g) having an ee of less than 98%, 7.43 L of ACN and 825 mL of 190 proof EtOH. The slurry was heated to 75° C., aged for 1 hr at 75° C. (during heating the slurry thickened considerably), then allowed to cool to 25° C. overnight. The slurry was filtered and washed with EtOH (190 proof):ACN (10:90) (2×800 mL, 2 mL/g). The white solid was dried in a vacuum oven at 24 in Hg, 40° C. with a nitrogen sweep to give 400 g of product with an ee of 99%. Assays (normal and chiral) were performed as described above in the prior steps.

Step Five: Procedure for (S)-Mono BOC piperazine amide: BOC Protection

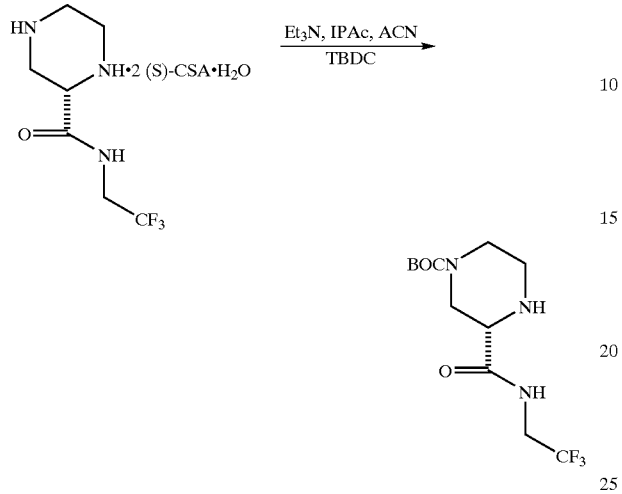

Bis(S)-CSA piperazine amide salt (20 g) was suspended in a mixture of 113 mL of isopropyl acetate (IPAc) and 57 mL of acetonitrile. Triethylamine (8.26 mL, 2 eq) was added and the mixture stirred until homogenous. A solution of di t-butyl dicarbonate (TBCD) (6.46 g, 1.0 eq) in a mixture of 20 mL isopropyl acetate and 10 mL of acetonitrile (ACN) was then added over 10 minutes. After aging for two hours the solution was assayed as necessary by LC (Pip Amide Assay, see above) until the reaction was complete (i.e., less than 5% starting material). When the reaction was complete, 100 mL of water and 135 mL of isopropyl acetate were added, the resulting layers were separated and the organic layer was concentrated to 28 mL. The residue was then diluted with 28 mL of isopropyl alcohol and reconcentrated to 28 mL. This was repeated two additional times. The yield of BOC pip amide was 87% with a mono:bis BOC ratio of 95:5, as determined by HPLC. $^1$H NMR (CDCl$_3$, 400 MHz): δ=7.39 (app t, J=6.3 Hz, 1H), 3.96 (dd, J=3.5, 13.4 Hz, 1H), 3.88 (m, 2H), 3.67 (d, J=11.5 Hz, 1H), 3.39 (dd, J=3.8, 8.6 Hz, 1H), 3.13 (dd, J=8.6, 13.3 Hz, 1H), 3.02 (br, 1H), 2.91 (m, 1H), 277 (m, 1H) 1.43 (s, 9H). $^{13}$C NMR (CDCl$_3$,) δ=171.43, 154.41, 123.89 (q, J=78.5 Hz), 80.16, 57.65, 43.63, 45.6 (br), 44.0 (br), 40.20 (q, J=34.7 Hz), 28.19.

HPLC Assay conditions: YMC Basic column, elution with acetonitrile and 0.1% aqueous H$_3$PO$_4$, detection at 210 nm.

While the foregoing specification teaches the principles of the present invention, with examples provided for the purpose of illustration, the practice of the invention encompasses all of the usual variations, adaptions and/or modifications that come within the scope of the following claims.

What is claimed is:
1. A compound of formula:

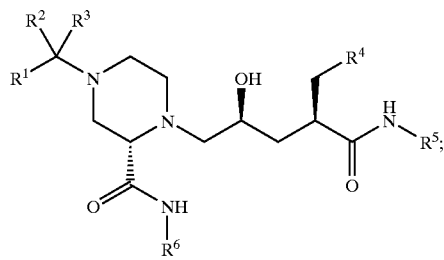

wherein
   $R^1$ is aryl, substituted aryl, heteroaryl, or substituted heteroaryl; wherein aryl is phenyl or naphthyl and heteroaryl is (i) a 5- or 6-membered aromatic ring consisting of carbon atoms and from 1 to 3 heteroatoms selected from N, S, and O or (ii) an 8- to 10-membered bicyclic ring system consisting of carbon atoms and from 1 to 3 heteroatoms selected from N, S, and O, wherein at least one of the rings in the bicyclic system is an aromatic ring; wherein
   (i) each of the substituents on substituted aryl is independently
      (a) halogen,
      (b) cyano,
      (c) hydroxy,
      (d) $C_1$–$C_6$ alkyl,
      (e) $C_2$–$C_6$ alkenyl,
      (f) $C_2$–$C_6$ alkynyl,
      (g) fluorinated $C_1$–$C_6$ alkyl,
      (h) $C_1$–$C_6$ alkoxy,
      (i) fluorinated $C_1$–$C_6$ alkoxy,
      (j) S—($C_1$–$C_6$ alkyl),
      (k) heterocycle, or
      (l) heterocycle substituted with one or more substituents independently selected from halogen, cyano, hydroxy, $C_1$–$C_6$ alkyl, $C_2$–$C_6$ alkenyl, $C_2$–$C_6$ alkynyl, fluorinated $C_1$–$C_6$ alkyl, $C_1$–$C_6$ alkoxy, fluorinated $C_1$–$C_6$ alkoxy, S—($C_1$–$C_6$ alkyl), and $NR^aR^b$;
   (ii) each of the substituents on substituted heteroaryl is independently
      (a) halogen,
      (b) cyano,
      (c) hydroxy,
      (d) $NR^aR^b$,
      (e) $C_1$–$C_6$ alkyl,
      (f) $C_2$–$C_6$ alkenyl,
      (g) $C_2$–$C_6$ alkynyl,
      (h) fluorinated $C_1$–$C_6$ alkyl,
      (i) $C_1$–$C_6$ alkoxy,
      (j) fluorinated $C_1$–$C_6$ alkoxy,
      (k) S—($C_1$–$C_6$ alkyl),
      (l) phenyl,
      (m) phenyl substituted with one or more substituents independently selected from halogen, cyano, hydroxy, $C_1$–$C_6$ alkyl, $C_2$–$C_6$ alkenyl, $C_2$–$C_6$ alkynyl, fluorinated $C_1$–$C_6$ alkyl, $C_1$–$C_6$ alkoxy, fluorinated $C_1$–$C_6$ alkoxy, and S—($C_1$–$C_6$ alkyl),
      (n) heterocycle, or
      (o) heterocycle substituted with one or more substituents independently selected from halogen, cyano, hydroxy, $C_1$–$C_6$ alkyl, $C_2$–$C_6$ alkenyl, $C_2$–$C_6$ alkynyl, fluorinated $C_1$–$C_6$ alkyl, $C_1$–$C_6$ alkoxy, fluorinated $C_1$–$C_6$ alkoxy, S—($C_1$–$C_6$ alkyl), NR$^a$R$^b$, and a 5- or 6-member heteroaromatic ring consisting of carbon atoms and from 1 to 3 heteroatoms selected from N, O and S;

wherein heterocycle in (i)(k), (i)(l), (ii)(n), or (ii)(o) is independently a 5- or 6-membered unsaturated monocyclic ring consisting of carbon atoms and from 1 to 3 heteroatoms selected from N, O, and S;

R$^2$ and R$^3$ are each independently hydrogen or C$_1$–C$_4$ alkyl; or R$^2$ and R$^3$ together with the carbon to which they are attached form C$_3$–C$_6$ cycloalkyl;

R$^4$ is C$_1$–C$_6$ alkyl, C$_3$–C$_6$ cycloalkyl, aryl, substituted aryl, heteroaryl, or substituted heteroaryl; wherein aryl is phenyl or naphthyl, and heteroaryl is selected from pyridyl, pyrazinyl, pyrimidinyl, thiophenyl, thiazolyl, pyridofuranyl, pyrimidofuranyl, pyridothienyl, pyridazothienyl, pyridooxazolyl, pyridazooxazolyl, pyrimidooxazolyl, pyridothiazolyl, and pyridazothiazolyl; and wherein each of the substituents on substituted aryl is independently halogen, cyano, hydroxy, C$_1$–C$_6$ alkyl, C$_2$–C$_6$ alkenyl, C$_2$–C$_6$ alkynyl, fluorinated C$_1$–C$_6$ alkyl, or C$_1$–C$_6$ alkoxy; and each of the substituents on substituted heteroaryl is independently halogen, cyano, hydroxy, C$_1$–C$_6$ alkyl, C$_2$–C$_6$ alkenyl, C$_2$–C$_6$ alkynyl, fluorinated C$_1$–C$_6$ alkyl, C$_1$–C$_6$ alkoxy, or aryl;

R$^5$ is carbocyclic, substituted carbocyclic, heterocyclic or substituted heterocyclic, wherein carbocyclic is cyclopentyl, indanyl, or tetralin, and heterocyclic is chroman, thiochroman, or dioxoisothiochroman; wherein each of the substituents on substituted carbocyclic or substituted heterocyclic is independently halogen, hydroxy, C$_1$–C$_6$ alkyl, fluorinated C$_1$–C$_6$ alkyl, or C$_1$–C$_6$ alkoxy;

R$^6$ is fluorinated C$_1$–C$_6$ alkyl; and

R$^a$ and R$^b$ are each independently hydrogen or C$_1$–C$_4$ alkyl; or R$^a$ and R$^b$ together with the nitrogen to which they are attached form C$_3$–C$_6$ azacycloalkyl;

or a pharmaceutically acceptable salt thereof.

2. A compound according to claim 1, wherein

R$^1$ is aryl, substituted aryl, heteroaryl, or substituted heteroaryl; wherein aryl is phenyl or naphthyl and heteroaryl is (i) a 5- or 6-membered aromatic ring consisting of carbon atoms and from 1 to 3 heteroatoms selected from N, S, and O or (ii) an 8- to 10-membered bicyclic ring system consisting of carbon atoms and from 1 to 3 heteroatoms selected from N, S, and O, wherein at least one of the rings in the bicyclic system is an aromatic ring; and wherein (i) each of the substituents on substituted aryl is independently
  (a) halogen,
  (b) cyano,
  (c) hydroxy,
  (d) C$_1$–C$_6$ alkyl,
  (e) C$_2$–C$_6$ alkenyl,
  (f) C$_2$–C$_6$ alkynyl,
  (g) fluorinated C$_1$–C$_6$ alkyl,
  (h) C$_1$–C$_6$ alkoxy,
  (i) heterocycle, or
  (j) heterocycle substituted with one or more substituents independently selected from halogen, cyano, hydroxy, C$_1$–C$_6$ alkyl, C$_2$–C$_6$ alkenyl, C$_2$–C$_6$ alkynyl, fluorinated C$_1$–C$_6$ alkyl, C$_1$–C$_6$ alkoxy, and NR$^a$R$^b$;

(ii) each of the substituents on substituted heteroaryl is independently
  (a) halogen,
  (b) cyano,
  (c) hydroxy,
  (d) NR$^a$R$^b$,
  (e) C$_1$–C$_6$ alkyl,
  (f) C$_2$–C$_6$ alkenyl,
  (g) C$_2$–C$_6$ alkynyl,
  (h) fluorinated C$_1$–C$_6$ alkyl,
  (i) C$_1$–C$_6$ alkoxy,
  (j) phenyl,
  (k) phenyl substituted with one or more substituents independently selected from halogen, cyano, hydroxy, C$_1$–C$_6$ alkyl, C$_2$–C$_6$ alkenyl, C$_2$–C$_6$ alkynyl, fluorinated C$_1$–C$_6$ alkyl, and C$_1$–C$_6$ alkoxy,
  (l) heterocycle, or
  (m) heterocycle substituted with one or more substituents independently selected from halogen, cyano, hydroxy, C$_1$–C$_6$ alkyl, C$_2$–C$_6$ alkenyl, C$_2$–C$_6$ alkynyl, fluorinated C$_1$–C$_6$ alkyl, C$_1$–C$_6$ alkoxy, and NR$^a$R$^b$;

wherein heterocycle in (i)(i), (i)(j), (ii)(l), or (ii)(m) is independently a 5- or 6-membered unsaturated monocyclic ring consisting of carbon atoms and from 1 to 3 heteroatoms selected from N, O, and S;

or a pharmaceutically acceptable salt thereof.

3. The compound according to claim 1, wherein

R$^4$ is C$_1$–C$_6$ alkyl, C$_3$–C$_6$ cycloalkyl, phenyl, substituted phenyl, heteroaryl, or substituted heteroaryl, wherein heteroaryl is selected from pyridyl, pyrazinyl, pyrimidinyl, thiophenyl, thiazolyl, pyridofuranyl, pyrimidofuranyl, pyridothienyl, pyridazothienyl, pyridooxazolyl, pyridazooxazolyl, pyrimidooxazolyl, pyridothiazolyl, and pyridazothiazolyl; and wherein each of the substituents on substituted phenyl or substituted heteroaryl is independently halogen, cyano, hydroxy, C$_1$–C$_6$ alkyl, fluorinated C$_1$–C$_6$ alkyl, or C$_1$–C$_6$ alkoxy;

or a pharmaceutically acceptable salt thereof.

4. The compound according to claim 3, wherein

R$^4$ is

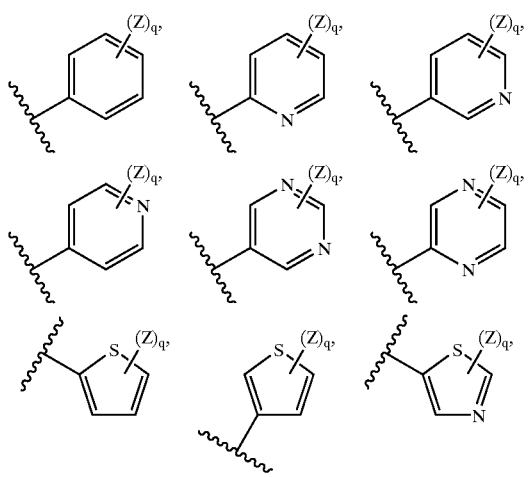

-continued

[structures: cyclopropyl; isopropyl; furo-pyridine with (Z)q; thieno-pyridazine (Z)q'; thieno-pyridine (Z)q'; furo-pyridine (Z)q'; furo-pyridine (Z)q'; furo-pyridine (Z)q'; furo-pyrimidine (Z)q'; furo-pyridine (Z)q'; oxazolo-pyridine (Z)q'; oxazolo-pyridazine (Z)q'; oxazolo-pyrimidine (Z)q'; thiazolo-pyridazine (Z)q; or thiazolo-pyridine (Z)q']

each Z is independently hydrogen, halogen, cyano, $C_1$–$C_6$ alkyl, or $C_1$–$C_6$ alkoxy; and q is an integer from 0 to 2;

or a pharmaceutically acceptable salt thereof.

5. The compound according to claim 1, wherein $R^5$ is

[structures: chroman with OH and A, (Y)p; indanol with $R^c$, $R^d$, (Y)p; isothiochroman-SO2; cyclopentanol with $R^c$]

wherein

A is $CR^cR^d$, O, or S;

each Y is independently hydrogen, halogen, $C_1$–$C_6$ alkyl, fluorinated $C_1$–$C_6$ alkyl, or $C_1$–$C_6$ alkoxy;

$R^c$ and $R^d$ are each independently hydrogen or $C_1$–$C_4$ alkyl, or $R^c$ and $R^d$ together with the carbon to which they are attached from $C_3$–$C_6$ cycloalkyl;

$R^e$ is hydrogen, $C_1$–$C_4$ alkyl, fluorinated $C_1$–$C_4$ alkyl, or phenyl; and p is an integer from 0 to 2;

or a pharmaceutically acceptable salt thereof.

6. The compound according to claim 5, wherein $R^5$ is

[structure: chroman-3-ol with (Y)p]

or a pharmaceutically acceptable salt thereof.

7. The compound according to claim 1, wherein $R^6$ is

[structures: —CH2F; —CHF2; —CF3; —CH2CF3; —CF2CF3; —C(CH3)2CF3; —C(CH3)2CH2F; —C(CH3)(CH2F)CH2F; —C(CH2F)2CH2F]

or a pharmaceutically acceptable salt thereof.

8. The compound according to claim 7, wherein $R^6$ is

[structure: —CH2CF3]

or a pharmaceutically acceptable salt thereof.

9. The compound according to claim 1, wherein
$R^1$ is phenyl, substituted phenyl, heteroaryl, or substituted heteroaryl, wherein heteroaryl is pyridyl, methylenedioxyphenyl, furanyl, benzofuranyl, benzothiofuranyl, benzoxazolyl, benzothiazolyl, azabenzothiazolyl, azabenzoxazolyl, azabenzofuranyl, azabenzothiofuranyl, oxazolyl, thiazolyl, isoxazolyl, triazolyl, thiadiazolyl, oxadiazolyl, indazolyl, pyrrolyl, pyrazolyl, thiophenyl, or thienothiophenyl; and wherein
  (i) each of the substituents on substituted phenyl is independently
    (a) halogen,
    (b) cyano,
    (c) hydroxy,
    (d) $C_1$–$C_4$ alkyl,
    (e) fluorinated $C_1$–$C_4$ alkyl,
    (f) $C_1$–$C_4$ alkoxy,
    (g) fluorinated $C_1$–$C_4$ alkoxy,
    (h) S—($C_1$–$C_4$ alkyl),
    (i) heterocycle which is a 5- or 6-membered unsaturated monocyclic ring consisting of carbon atoms and from 1 to 3 heteroatoms selected from N, O and S, or (j) substituted heterocycle which is a 5- or 6-membered unsaturated monocyclic ring as defined in (i) substituted with one or more substituents independently selected from halogen, cyano, hydroxy, $C_1$–$C_4$ alkyl fluorinated $C_1$–$C_4$ alkyl, $C_1$–$C_4$ alkoxy, fluorinated $C_1$–$C_4$ alkoxy, S—($C_1$–$C_4$ alkyl) and $NR^aR^b$; and (ii) each of the substituents on substituted heteroaryl is independently
(a) halogen,
(b) cyano,
(c) hydroxy,
(d) $NR^aR^b$, if and only if the heteroaryl is pyridyl,
(e) $C_1$–$C_4$ alkyl,
(f) fluorinated $C_1$–$C_4$ alkyl,
(g) $C_1$–$C_4$ alkoxy,
(h) fluorinated $C_1$–$C_4$ alkoxy,
(i) S—($C_1$–$C_4$ alkyl),
(j) phenyl,
(k) phenyl substituted with one or more substituents independently selected from halogen, cyano, hydroxy, $C_1$–$C_4$ alkyl, fluorinated $C_1$–$C_4$ alkyl, $C_1$–$C_4$ alkoxy, fluorinated $C_1$–$C_4$ alkoxy, and S—($C_1$–$C_4$ alkyl),
(l) heterocycle which is a 5- or 6-membered unsaturated monocyclic ring consisting of carbon atoms and from 1 to 3 heteroatoms selected from N, O and S;
(m) substituted heterocycle which is a 5- or 6-membered unsaturated monocyclic ring as defined in (l) substituted with one or more substituents independently selected from halogen, cyano, hydroxy, $C_1$–$C_4$ alkyl, fluorinated $C_1$–$C_4$ alkyl, $C_1$–$C_4$ alkoxy, fluorinated $C_1$–$C_4$ alkoxy, S—($C_1$–$C_4$ alkyl), $NR^aR^b$, thiazolyl, oxazolyl, imidazolyl, pyrazolyl, triazolyl, pyrrolyl, furanyl, thienyl, isoxazolyl, and isothiazolyl;

or a pharmaceutically acceptable salt thereof.

10. The compound according to claim 9, wherein heterocycle in (i)(i) and in (ii)(l) are each independently

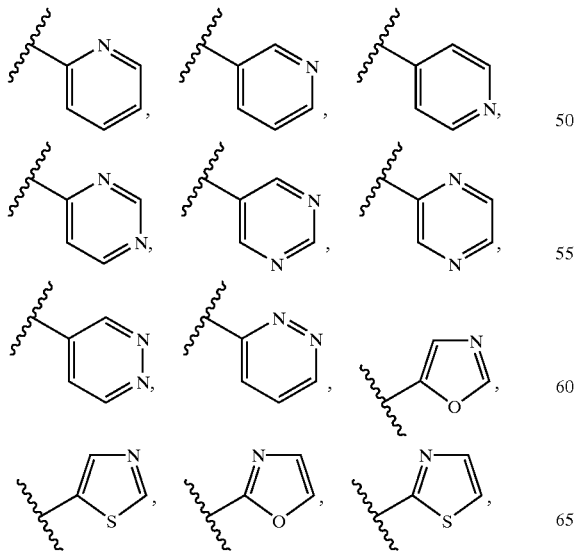

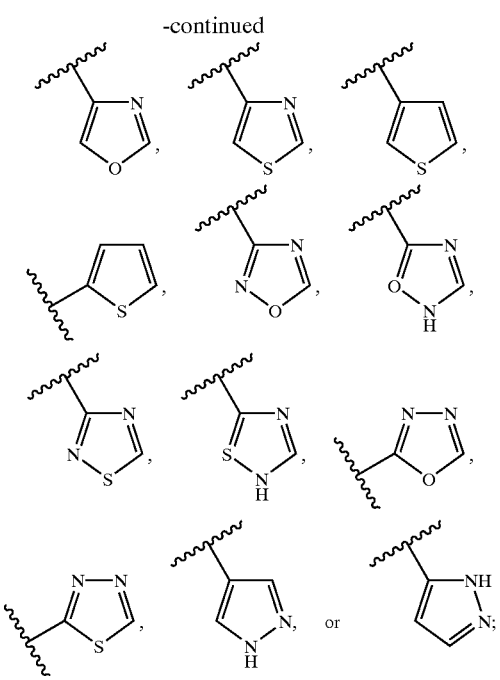

and wherein substituted heterocycle in (i)(j) is heterocycle as defined above with one or more substituents independently selected from halogen, cyano, $C_1$–$C_4$ alkyl, fluorinated $C_1$–$C_4$ alkyl, $C_1$–$C_4$ alkoxy, fluorinated $C_1$–$C_4$ alkoxy, and S—($C_1$–$C_4$ alkyl); and substituted heterocycle in (ii)(m) is heterocycle as defined above with one or more substituents independently selected from halogen, hydroxy, cyano, $C_1$–$C_4$ alkyl, fluorinated $C_1$–$C_4$ alkyl, $C_1$–$C_4$ alkoxy, fluorinated $C_1$–$C_4$ alkoxy, S—($C_1$–$C_4$ alkyl), $NR^aR^b$, thiazolyl, oxazolyl, imidazolyl, pyrazolyl, triazolyl, pyrrolyl, isoxazolyl, and isothiazolyl; or is

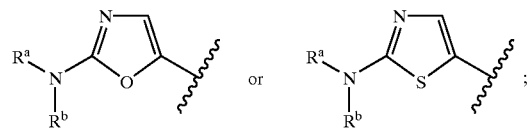

or a pharmaceutically acceptable salt thereof.

11. The compound according to claim 1, wherein $R^1$ is

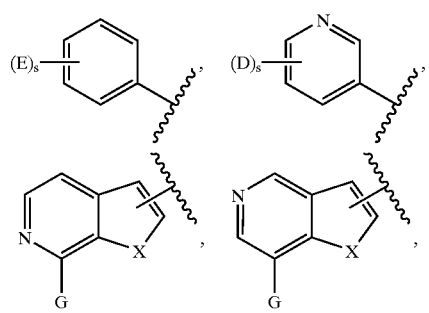

-continued

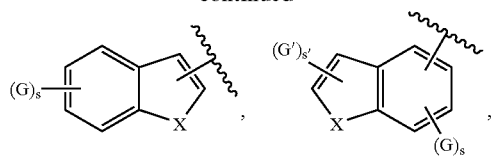

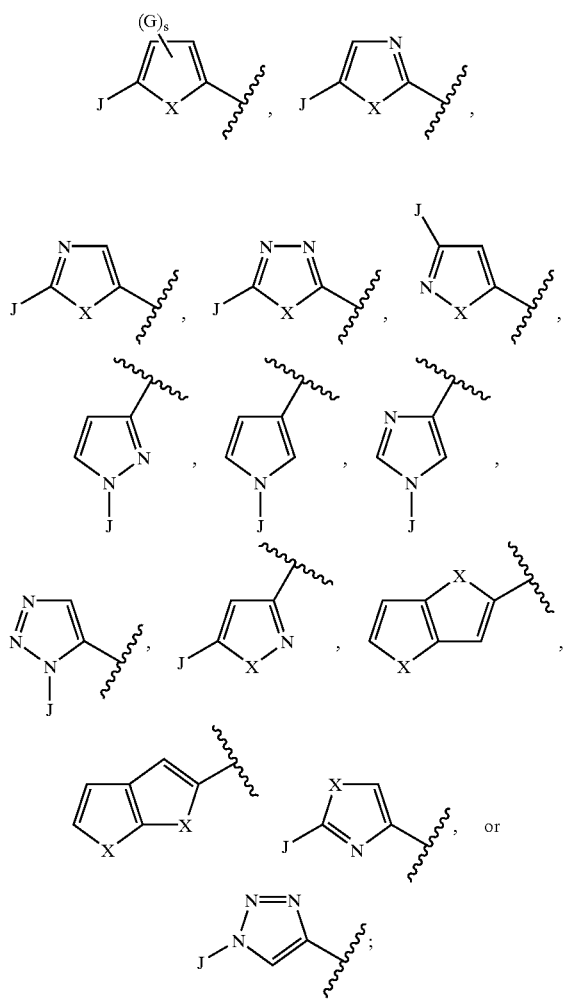

each D is independently hydrogen, halogen, cyano, hydroxy, $NR^aR^b$, $C_1$–$C_4$ alkyl, $C_1$–$C_4$ alkoxy, fluorinated $C_1$–$C_4$ alkoxy, S—($C_1$–$C_4$ alkyl), phenyl, substituted phenyl, heterocycle, or substituted heterocycle; wherein substituted phenyl is phenyl with one or more subsituents independently selected from halogen, hydroxy, $C_1$–$C_4$ alkyl, and $C_1$–$C_4$ alkoxy; and wherein substituted heterocycle is heterocycle with one or more substituents independently selected from halogen, hydroxy, $C_1$–$C_4$ alkyl, $C_1$–$C_4$ alkoxy, fluorinated $C_1$–$C_4$ alkoxy, and S—($C_1$–$C_4$ alkyl);

each E is independently hydrogen, halogen, cyano, hydroxy, $C_1$–$C_4$ alkyl, $C_1$–$C_4$ alkoxy, heterocycle, or substituted heterocycle;

G and G' are each independently selected from hydrogen, halogen, cyano, hydroxy, $C_1$–$C_4$ alkyl, fluorinated $C_1$–$C_4$ alkyl, and $C_1$–$C_4$ alkoxy;

J is

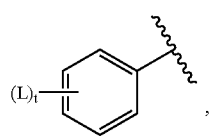

heterocycle, or substituted heterocycle;

each L is independently hydrogen, halogen, cyano, hydroxy, $C_1$–$C_4$ alkyl, fluorinated $C_1$–$C_4$ alkyl, or $C_1$–$C_4$ alkoxy;

X is O or S;

heterocycle in each of D, E and J is independently

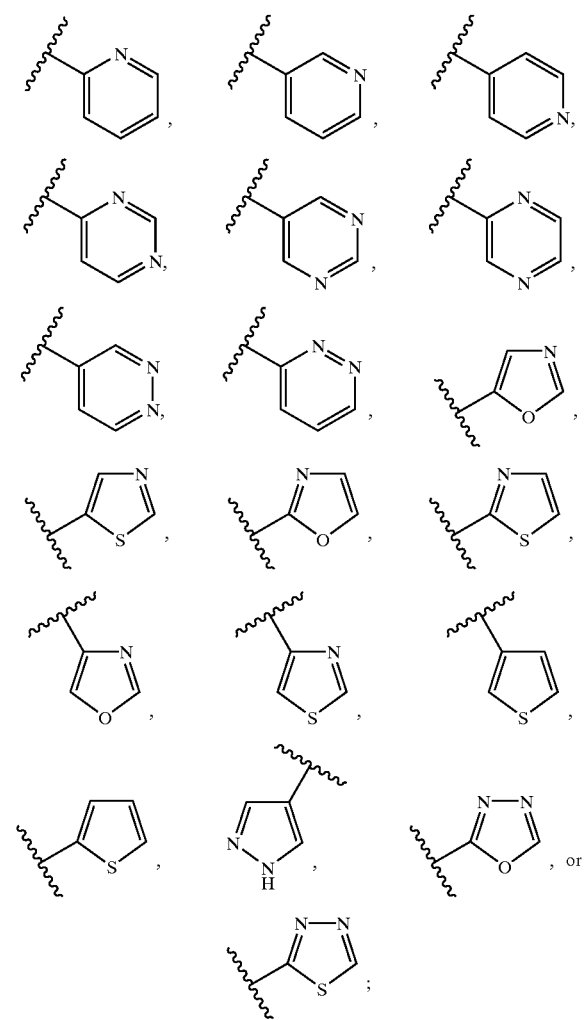

substituted heterocycle in each of E and J is independently heterocycle as defined above with one or more substituents independently selected from halogen, hydroxy, cyano, $C_1$–$C_4$ alkyl, fluorinated $C_1$–$C_4$ alkyl, $C_1$–$C_4$ alkoxy, fluorinated $C_1$–$C_4$ alkoxy, S—($C_1$–$C_4$ alkyl), $NR^aR^b$, thiazolyl, oxazolyl, imidazolyl, pyrazolyl, triazolyl, pyrrolyl, isoxazolyl, and isothiazolyl; or is

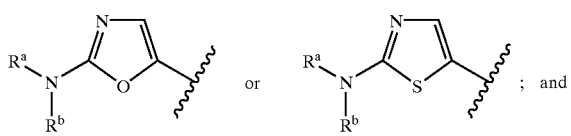

s, s', and t are each independently integers from 0 to 2;

or a pharmaceutically acceptable salt thereof.

12. The compound according to claim 11, wherein $R^6$ is

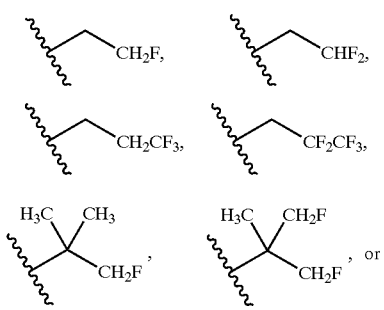

or a pharmaceutically acceptable salt thereof.

13. The compound according to claim 12, wherein $R^4$ is

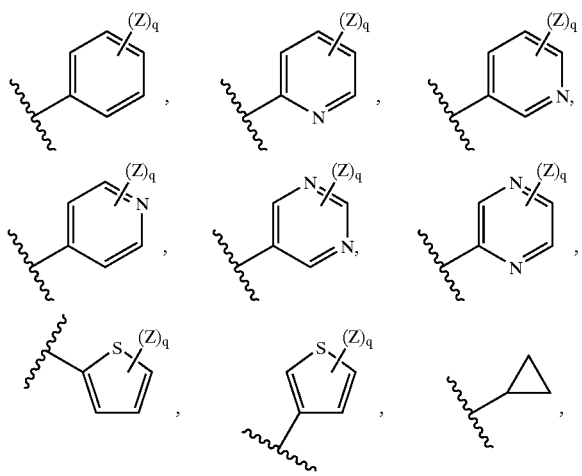

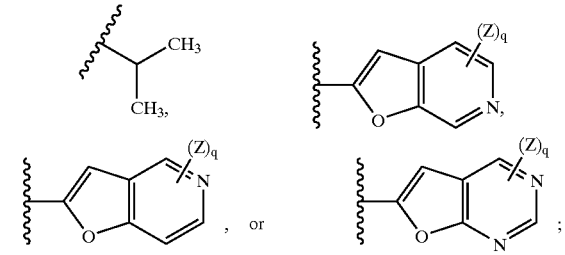

each Z is independently hydrogen, halogen, cyano, $C_1$–$C_6$ alkyl, or $C_1$–$C_6$ alkoxy; and q is an integer from 0 to 2;

or a pharmaceutically acceptable salt thereof.

14. The compound according to claim 13, wherein $R^1$ is

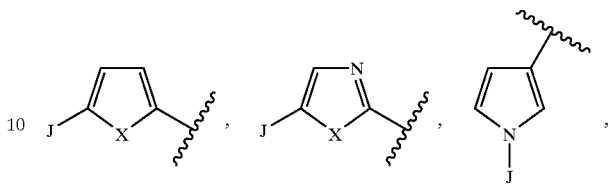

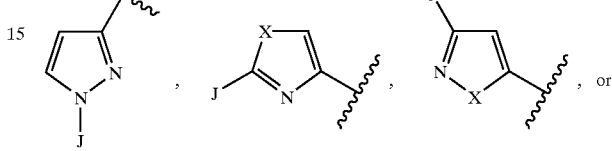

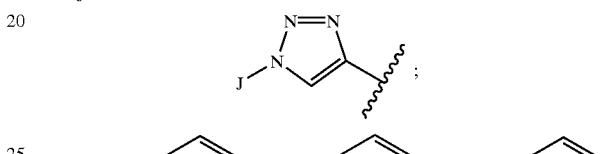

$R^4$ is

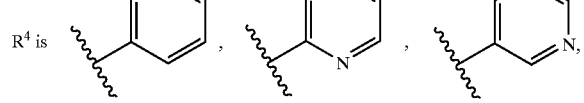

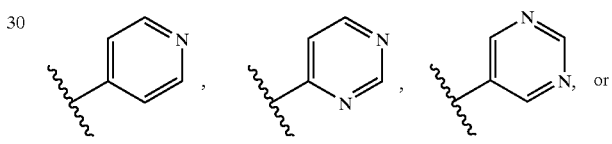

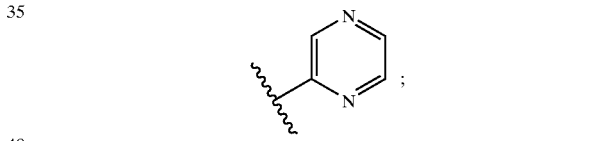

$R^5$ is

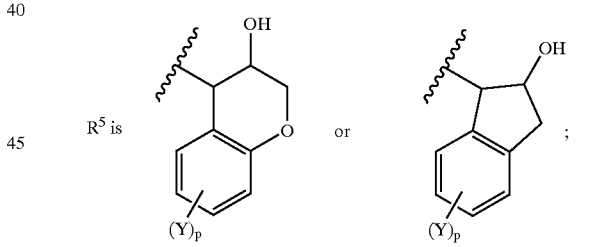

$R^6$ is

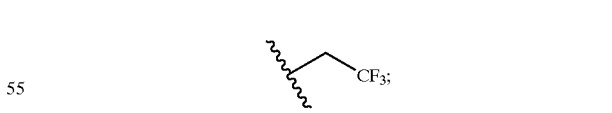

J is

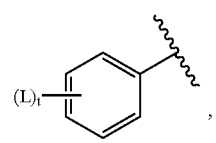

heterocycle, or substituted heterocycle; heterocycle is

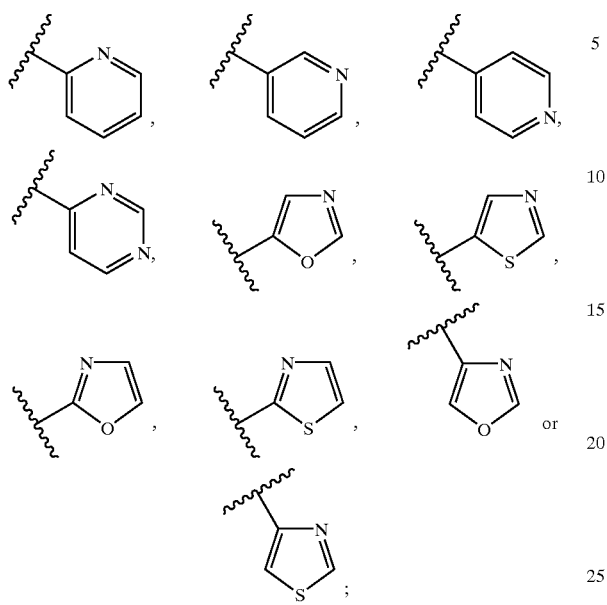

substituted heterocycle is heterocycle as defined above having one or more substituents independently selected from halogen, $C_1$–$C_4$ alkoxy, $C_1$–$C_4$ alkyl, fluorinated $C_1$–$C_4$ alkoxy, fluorinated $C_1$–$C_4$ alkyl, —S—$CH_3$, —N($CH_3$)$_2$, thiazolyl, and oxazolyl;

X is O or S;

each Y is independently hydrogen, halogen, $C_1$–$C_6$ alkyl, fluorinated $C_1$–$C_6$ alkyl, or $C_4$–$C_4$ alkoxy; and p is an integer from 0 to 2;

or a pharmaceutically acceptable salt thereof.

15. The compound according to claim 14, wherein $R^2$ and $R^3$ are each independently hydrogen or methyl;

each L is independently hydrogen, chlorine, or fluorine;

each Y is independently hydrogen, chlorine, or fluorine; and each of the substituents on substituted heterocycle is independently chlorine, fluorine, methoxy, ethoxy, —$OCF_3$, —$OCHF_2$, methyl, ethyl, n-propyl, —S—$CH_3$, —N($CH_3$)$_2$, and thiazolyl;

or a pharmaceutically acceptable salt thereof.

16. The compound according to claim 14, wherein $R^1$ is

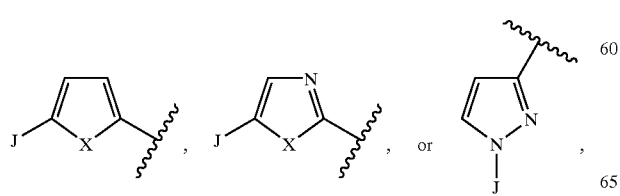

$R^4$ is

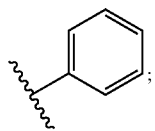

$R^5$ is

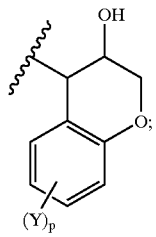

$R^6$ is

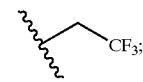

J is

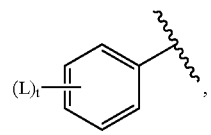

heterocycle, or substituted heterocycle; heterocycle is

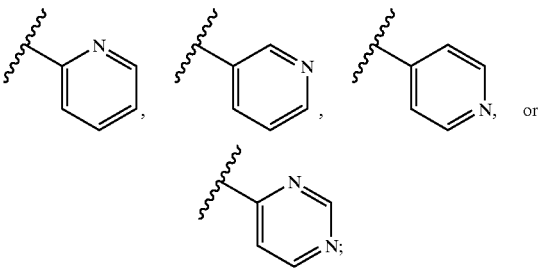

substituted heterocycle is heterocycle as defined above having one or more substituents independently selected from halogen, $C_1$–$C_4$ alkoxy, $C_1$–$C_4$ alkyl, fluorinated $C_1$–$C_4$ alkoxy, fluorinated $C_1$–$C_4$ alkyl, —S—$CH_3$, —N($CH_3$)$_2$, thiazolyl, and oxazolyl;

X is O or S;

each Y is independently hydrogen, halogen, $C_1$–$C_6$ alkyl, fluorinated $C_1$–$C_6$ alkyl, or $C_1$–$C_4$ alkoxy; and p is an integer from 0 to 2;

or a pharmaceutically acceptable salt thereof.

17. The compound according to claim 16, wherein $R^2$ and $R^3$ are each independently hydrogen or methyl;

each L is independently hydrogen, chlorine, or fluorine;

each Y is independently hydrogen, chlorine, or fluorine; and each of the substituents on substituted heterocycle is independently chlorine, fluorine, methoxy, ethoxy, —OCF$_3$, —OCHF$_2$, methyl, ethyl, n-propyl, —S—CH$_3$, —N(CH$_3$)$_2$, and thiazolyl;

or a pharmaceutically acceptable salt thereof.

18. The compound according to claim 1, wherein the compound is selected from the group consisting of (αR,γS,2S)-N-((3S,4S)-3,4-dihydro-3-hydroxy-2H-1-benzopyran-4-yl)-4-(1-furo[3,2-c]pyridin-2-yl-1-methylethyl)-γ-hydroxy-α-(phenylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-2-[[(2-fluoroethyl)amino]carbonyl]-4-(1-furo[3,2-c]pyridin-2-yl-1-methylethyl)-γ-hydroxy-α-(phenylmethyl)-1-piperazinepentanamide;

(αR,γS,2S)-N-((3S,4S)-3,4-dihydro-3-hydroxy-2H-1-benzofuran-4-yl)-2-[[[2-fluoro-1,1-bis(fluoromethyl)ethyl]amino]carbonyl]-4-(1-furo[3,2-c]pyridin-2-yl-1-methylethyl)-γ-hydroxy-α-(phenylmethyl)-1-piperazinepentanamide;

(αR,γS,2S)-2-[[[1,1-bis(fluoromethyl)ethyl]amino]carbonyl]-N-((3S,4S)-3,4-dihydro-3-hydroxy-2H-1-benzopyran-4-yl)-4-(1-furo[3,2-c]pyridin-2-yl-1-methylethyl)-γ-hydroxy-α-(phenylmethyl)-1-piperazinepentanamide;

(αR,γS,2S)-N-((3S,4S)-3,4-dihydro-3-hydroxy-2H-1-benzopyran-4-yl)-4-(1-furo[3,2,-c]pyridin-2-yl-1-methylethyl)-γ-hydroxy-α-(phenylmethyl)-2-[[(3,3,3-trifluoropropyl)amino]carbonyl]-1-piperazinepentanamide;

(αR,γS,2S)-N-((3S,4S)-3,4-dihydro-3-hydroxy-2H-1-benzopyran-4-yl)-4-(1-furo[3,2-c]pyridin-2-yl-1-methylethyl)-γ-hydroxy-2-[[(2,2,3,3,3-pentafluoropropyl)-amino]carbonyl]-α-(phenylmethyl)-1-piperazinepentanamide;

(αR,γS,2S)-N-((3S,4S)-3,4-dihydro-3-hydroxy-2H-1-benzopyran-4-yl)-2-[[(2-fluoro-1,1-dimethylethyl)amino]carbonyl]-4-(1-furo[3,2-c]pyridin-2-yl-1-methylethyl)-γ-hydroxy-α-(phenylmethyl)-1-piperazinepentanamide;

(αR,γS,2S)-N-((1S,2R)-1,2-dihydro-2-hydroxy-1H-inden-1-yl)-4-(1-furo[3,2-c]pyridin-2-yl-1-methylethyl)-γ-hydroxy-α-(phenylmethyl)-2-[[(2,2,2-trifluoroethyl)amino]carbonyl]-1-piperazinepentanamide;

(αR,γS,2S)-N-((1S,2R)-1,2-dihydro-2-hydroxy-1H-inden-1-yl)-2-[[(2-fluoroethyl)amino]carbonyl]-4-[1-furo[3,2-c]pyridin-2-yl-1-methylethyl]-γ-hydroxy-α-(phenylmethyl)-1-piperazinepentanamide;

(αR,γS,2S)-N-((1S,2R)-1,2-dihydro-2-hydroxy-1H-inden-1-yl)-4-(1-furo[3,2-c]pyridin-2-yl-1-methylethyl)-γ-hydroxy-α-(phenylmethyl)-2-[[(3,3,3-trifluoropropyl)amino]carbonyl]-1-piperazinepentanamide;

(αR,γS,2S)-N-((1S,2R)-1,2-dihydro-2-hydroxy-1H-inden-1-yl)-4-(1-furo[3,2-c]pyridin-2-yl-1-methylethyl)-γ-hydroxy-2-[[(2,2,3,3,3-pentafluoropropyl)amino]-carbonyl]-α-(phenylmethyl)-1-piperazinepentanamide;

(αR,γS,2S)-4-(2-benzofuranylmethyl)-N-((3S,4S)-3,4-dihydro-3-hydroxy-2H-1-benzopyran-4-yl)-γ-hydroxy-α-(phenylmethyl)-2-[[(2,2,2-trifluoroethyl)amino]-carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[5-(3-pyridinyl)-1-furanyl]methyl]-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-(3-pyridinylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[5-(3-pyridinyl)-1-furanyl]methyl]-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[5-(5-pyrimidinyl)-1-furanyl]methyl]-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[(3-methyl-7-methoxy-4-benzofuranyl)methyl]α-(3-phenylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[(7-methoxy-2-benzofuranyl)methyl]-α-(phenylmethyl)-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[(1-phenyl-1H-pyrrol-3-yl)methyl]-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[(1-phenyl-1H-imidazol-4-yl)methyl]-α-(phenylmethyl)-2-[[(2,2,2-trifluoroethyl)-amino]carbonyl]-1-piperazinepentanamide;

(αR,γS,2S)-4-(2-benzofuranylmethyl)-N-((1S,2R)-1,2-dihydro-2-hydroxy-1H-inden-1-yl)-γ-hydroxy-α-(phenylmethyl)-2-[[(2,2,2-trifluoroethyl)amino]carbonyl]-1-piperazinepentanamide;

(αR,γS,2S)-N-((1S,2R)-1,2-dihydro-2-hydroxy-1H-inden-1-yl)-γ-hydroxy-α-(phenylmethyl)-4-(3-pyridinylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[(5-phenyl-2-furanyl)methyl]-α-(3-pyridinylmethyl)-2-[[(2,2,2-trifluoroethyl)-amino]carbonyl]-1-piperazinepentanamide;

(αR,γS,2S)-4-(2-benzopyranylmethyl)-N-((3S,4S)-3,4-dihydro-3-hydroxy-2H-1-benzopyran-4-yl)-γ-hydroxy-α-(3-pyridinylmethyl)-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(3-pyridinylmethyl)-4-(thieno[2,3-b]thien-2-ylmethyl)-2-[[(2,2,2-trifluoroethyl)-amino]carbonyl]-1-piperazinepentanamide;

(αR,γS,2S)-4-[(2,6-difluorophenyl)methyl]-N-((3S,4S)-3,4-dihydro-3-hydroxy-2H-1-benzopyran-4-yl)-γ-hydroxy-α-(3-pyridinylmethyl)-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(3-pyridinylmethyl)-4-(thieno[3,2-b]thien-2-ylmethyl)-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[(7-methoxy-2-benzofuranyl methyl]-α-(3-pyridinylmethyl)-2-[[(2,2,2-trifluoroethyl)amino]carbonyl]-1-piperazinepentanamide;

(αR,γS,2S)-N-(3S,4S)-3,4-dihydro-3-hydroxy-2H-1-benzopyran-4-yl)-γ-hydroxy-α-(3-pyridinylmethyl)-4-[[5-(3-thienyl)-2-furanyl]methyl]-2-[[(2,2,2-trifluoroethyl)-amino]carbonyl]-1-piperazinepentanamide;

(αR,γS,2S)-N-(3S,4S)-3,4-dihydro-3-hydroxy-2H-1-benzopyran-4-yl)-γ-hydroxy-4-[(1-phenyl-1H-pyrrol- 3yl)methyl]-α-(3-pyrinylmethyl)-2-[[(2,2,2-trifluoroethyl)-amino]carbonyl]-1-piperazinepentanamide;

(αR,γS,2S)-N-(3S,4S)-3,4-dihydro-3-hydroxy-2H-1-benzopyran-4-yl)-γ-hydroxy-4-(1-phenyl-1H-imidazol-4yl)methyl]-α-(3-pyrinylmethyl)-2-[[(2,2,2-trifluoroethyl)-amino]carbonyl]-1-piperazinepentanamide;

(αR,γS,2S)-N-(3S,4S)-3,4-dihydro-3-hydroxy-2H-1-benzopyran-4-yl)-γ-hydroxy-4-[[5-(5-methyl-2-thienyl)-2-furanyl]methyl]-α-(3-pyrinylmethyl)-2-[[(2,2,2-trifluoroethyl)-amino]carbonyl]-1-piperazinepentanamide;

(αR,γS,2S)-N-(3S,4S)-3,4-dihydro-3-hydroxy-2H-1-benzopyran-4-yl)-γ-hydroxy-4-[(5-phenyl-2-furanyl)methyl]-α-(4-pyrinylmethyl)-2-[[2,2,2-trifluoroethyl)-amino]carbonyl]-1-piperazinepentanamide;

(αR,γS,2S)4-(2-benzofuranylmethyl)-N-(3S,4S)-3,4-dihydro-3-hydroxy-2H-1-benzopyran-4-yl)-γ-hydroxy-α-(4-pyrinylmethyl)-2-[[(2,2,2-trifluoroethyl-amino]carbonyl]-1-piperazinepentanamide;

(αR,γS,2S)-N-(3S,4S)-3,4-dihydro-3-hydroxy-2H-1-benzopyran-4-yl)-γ-hydroxy-4-[1-methyl-1-[5-(4-pyridinyl)-2-furanyl]ethyl]-α-(phenylmethyl)-2-[[(2,2,2-trifluoroethyl)-amino]carbonyl]-1-piperazinepentanamide;

(αR,γS,2S)-N-(3S,4S)-3,4-dihydro-3-hydroxy-2H-1-benzopyran-4-yl)-γ-hydroxy-α-(phenylmethyl)-4-[1-[5-(4-pyridinyl)-1-furanyl]ethyl]-2-[[(2,2,2-trifluoroethyl)-amino]carbonyl]-1-piperazinepentanamide;

(αR,γS,2S)-N-(3S,4S)-3,4-dihydro-3-hydroxy-2H-1-benzopyran-4-yl)-γ-hydroxy-α-(phenylmethyl)-4-[1-[5-(4-pyridinyl)-1-furanyl]ethyl]-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[1-methyl-1-(1-phenyl-1H-pyrazol-3-yl)ethyl]-α-(3-pyridinylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[1-methyl-1-(3-phenyl-5-isoxazolyl)ethyl]-α-(3-pyridinylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[1-methyl-1-(3-phenyl-5-isoxazolyl)ethyl]]-α-(phenylmethyl)-2-[[(2,2,2-trifluoroethyl)amino]carbonyl]-1-piperazinepentanamide;

(αR,γS,2S)-4-[(7-chlorobenzofuran-2-yl)methyl]-N-((3S,4S)-3,4-dihydro-3-hydroxy-2H-1-benzopyran-4-yl)-γ-hydroxy-α-(3-pyridinylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-4-(1-furo[3,2c]pyridin-2yl-1methylethyl)-γ-hydroxy-α-(phenylmethyl)-2-[[(2,2,-difluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[5-(2-thiazolyl)-3-pyridinyl]methyl]2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[[5-(2-oxazolyl)-3-pyridinyl]methyl)-α-(phenylmethyl)-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[5-(4-thiazolyl)-3-pyridinyl]methyl]-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[5-(2-thiazolyl)-2-furanyl]methyl]-2-[[(2,2,2-trifluoroethyl)-amino]carbonyl]-1-piperazinepentanamide;

(αR,γS,2S)-4-[[5-(5-chloro-3-pyridinyl)-2-furanyl]methyl]-N-((3S,4S)-3,4-dihydro-3-hydroxy-2H-1-benzopyran-4-yl)-γ-hydroxy-α-(phenylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[(5-phenyl-2-furanyl)methyl]-α-(phenylmethyl)-2-[[(2,2,2-trifluoroethyl)amino]-carbonyl]-1-piperazinepentanamide;

(αR,γS,2S)-4-[(4-chloro-5-phenyl-2-furanyl)methyl]-N-((3S,4S)-3,4-dihydro-3-hydroxy-2H-1-benzopyran-4-yl)-γ-hydroxy-α-(phenylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[5-(2-pyridinyl)-2-furanyl]methyl]-2-[[(2,2,2-trifluoroethyl)-amino]carbonyl]-1-piperazinepentanamide;

(αR,γS,2S)4-[[5-(5-chloro-2-pyridinyl)-2-furanyl]methyl]-N-((3S,4S)-3,4-dihydro-3-hydroxy-2H-1-benzopyran4-yl)-γ-hydroxy-α-(phenylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[[5-(2-methyl-4-pyridinyl)-2-furanyl]methyl]-α-(phenylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-4-[[5-(2-ethyl-4-pyridinyl)-2-furanyl]methyl]-α-hydroxy-γ-(phenylmethyl)-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[[5-(5-oxazolyl)-2-furanyl]methyl]-α-(phenylmethyl)-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[1-(4-pyridinyl)-1H-pyrrol-3-yl]methyl]-2-[[(2,2,2trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[1-(3-pyridinyl)-1H-pyrrol-3-yl]methyl ]-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[5-(4-pyridazinyl)-2-furanyl]methyl]-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[1-methyl-1-[3-methyl-5-(4-pyridinyl)-2-furanyl]ethyl]-α-(phenylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[5-(2-pyrazinyl)-2-furanyl]methyl]-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[[5-(1-methyl-1H-pyrazol-4-yl)-3-pyridinyl]methyl]-α-(phenylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[5-(2-thienyl)-3-pyridinyl]methyl]-2-[[(2,2,2-trifluoroethyl)amino]-carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[5-(3-thienyl)-3-pyridinyl]methyl]-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[5-(4-pyrimidinyl)-2-furanyl]methyl]-2-[[(2,2,2-trifluoroethyl)amino]carbonyl]-1-piperazinepentanamide;

(αR,γS,2S)-4-[(7-chlorofuro[3,2-c]pyridin-2-yl)methyl]-N-((3S,4S)-3,4-dihydro-3-hydroxy-2H-1-benzopyran-4-yl)-γ-hydroxy-α-(phenylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[5-(3-pyridinyl)-2-oxazolyl]methyl]-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[5-(2-pyridinyl)-2-oxazolyl]methyl]-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[1-methyl-1-[5-(2-pyridinyl)-2-oxazolyl]ethyl]-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[1-methyl-1-[5-(3-pyridinyl)-2-oxazolyl]ethyl]-α-(phenylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[(5-phenyl-2-furanyl)methyl]-α-(5-pyrimidinylmethyl)-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[(5-phenyl-2-furanyl)methyl]-α-(2-pyrazinylmethyl)-2-[[(2,2,2-trifluoroethyl)amino]carbonyl]-1-piperazinepentanamide;

(αS,γS,2S)-N-((3S,4S)-3,4-dihydro-3-hydroxy-2H-1-benzopyran-4-yl)-γ-hydroxy-4-[[5-(2-pyridinyl)-2-furanyl]methyl]-α-(2-thienylmethyl)-2-[[(2,2,2-trifluoroethyl)-amino]carbonyl]-1-piperazinepentanamide;

(αS,γS,2S)-N-((3S,4S)-3,4-dihydro-3-hydroxy-2H-1-benzopyran-4-yl)-γ-hydroxy-4-[[5(5-pyrimidinyl)-2-furanyl]methyl]-α-(5-thienylmethyl)-2-[[(2,2,2-trifluoroethyl)amino]carbonyl]-1-piperazinepentanamide;

(αS,γS,2S)-N-((3S,4S)-3,4-dihydro-3-hydroxy-2H-1-benzopyran-4-yl)-γ-hydroxy-4-[[5-(2-pyridinyl)-2-furanyl]methyl]-α-(3-thienylmethyl)-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[(5-phenyl-2-furanyl)methyl]-α-(2-pyridinylmethyl)-2-[[(2,2,2-trifluoroethyl)amino]-carbonyl]-1-piperazinepentanamide;

(αR,γS,2S)-N-((1S,2R)-1,2-dihydro-2-hydroxy-1H-inden-1-yl)-γ-hydroxy-α-(phenylmethyl)-4-[[5-(2-pyridinyl)-2-furanyl]methyl]-2-[[(2,2,2-trifluoroethyl)-amino]carbonyl]-1-piperazinepentanamide;

(αR,γS,2S)-4-[[5-(5-chloro-2-pyridinyl)-2-furanyl]methyl]-N-((1S,2R)-1,2-dihydro-2-hydroxy-1H-inden-1-yl)-γ-hydroxy-α-(phenylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[1-methyl-1-[5-(5-chloro-3-pyridinyl)-2-oxazolyl]ethyl]-α-(phenylmethyl)-2-[[(2,2,2 trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[1-methyl-1-[5-(5-chloro-2-pyridinyl)-2-oxazolyl]ethyl]-2-[[2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[(3-chloro-1-phenyl-1H-pyrrol-3-yl)methyl]-α-(3-pyridinylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[(4-chloro-1-phenyl-1H-pyrrol-3-yl)methyl]-α-(3-pyridinylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[1-methyl-1-(1-phenyl-1H-triazoyl-4-yl)ethyl]-α-(3-phenylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[1-methyl-1-(1-phenyl-1H-triazoyl-4-yl)ethyl]-α-(3-pyridinylmethyl)-2-[[(2,2,2-trifluoroethyl)amino]carbonyl]-1-piperazinepentanamide;

(αR,γS,2S)-N-(4S-3,4-dihydro-1H-2,2-dioxobenzothiopyranyl)-γ-hydroxy-α-(phenylmethyl)-4-[[5-(5-pyrimidinyl)-1-furanyl]methyl]-2-[[(2,2,2-trifluoroethyl)amino]carbonyl]-1-piperazinepentanamide;

(αR,γS,2S)-N-(4S-3,4-dihydro-1H-2,2-dioxobenzothiopyranyl)-γ-hydroxy-α-(phenylmethyl)-4-[[5-(2-pyridinyl)-2-furanyl]methyl]-2-[[(2,2,2-trifluoroethyl)-amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[1-methyl-1-[5-(2-methyl-4-pyridinyl)-2-furanyl]ethyl]-α-(phenylmethyl)-2-[[(2,2,2-trifluoroethyl)amino]carbonyl]-1-piperazinepentanamide;

and pharmaceutically acceptable salts thereof.

19. The compound according to claim 1, wherein the compound is selected from the group consisting of (αR,γS,2S)-N-[(3S,4S)-3,4-dihydro-3-hydroxy-2H-1-benzopyran-4-yl]-γ-hydroxy-4-[1-[5-(5-methoxy-3-pyridinyl)-2-oxazolyl]-1-methylethyl]-α-(phenylmethyl)-2-[[(2,2,2-trifluoroethyl)amino]carbonyl]-1-piperazinepentanamide;

(αR,γS,2S)-N-[(3S,4S)-3,4-dihydro-3-hydroxy-2H-1-benzopyran-4-yl]-4-[1-[5-(5-methyl-3-pyridinyl)-2-oxazolyl]-1-methylethyl]-γ-hydroxy-α-(phenylmethyl)-2-[[(2,2,2-trifluoroethyl)amino]carbonyl]-1-piperazinepentanamide;

(αR,γS,2S)-N-[(3S,4S)-3,4-dihydro-3-hydroxy-2H-1-benzopyran-4-yl]-4-[1-[5-(5-hydroxy-3-pyridinyl)-2-oxazolyl]-1-methylethyl]-γ-hydroxy-α-(phenylmethyl)-2-[[(2,2,2-trifluoroethyl)amino]carbonyl]-1-piperazinepentanamide;

(αR,γS,2S)-4-[1-[5-[5-(difluoromethoxy)-3-pyridinyl]-2-oxazolyl]-1-methylethyl]-N-[(3S,4S)-3,4-dihydro-3-hydroxy-2H-1-benzopyran-4-yl]-γ-hydroxy-α-(phenylmethyl)-2-[[(2,2,2-trifluoroethyl)amino]carbonyl]-1-piperazinepentanamide;

(αR,γS,2S)-4-[1-[5-[5-(difluoromethyl)-3-pyridinyl]-2-oxazolyl]-1-methylethyl]-N-[(3S,4S)-3,4-dihydro-3- hydroxy-2H-1-benzopyran-4-yl]-γ-hydroxy-α-
(phenylmethyl)-2-[[(2,2,2-trifluoroethyl)amino]
carbonyl]-1-piperazinepentanamide;

(αR,γS,2S)-N-[(3S,4S)-3,4-dihydro-3-hydroxy-2H-1-
benzopyran-4-yl]-4-[1-[5-(2-fluorophenyl)-2-oxazolyl]-
1-methylethyl]-γ-hydroxy-α-(phenylmethyl)-2-[[(2,2,2-
trifluoroethyl)amino]carbonyl]-1-piperazinepentanamide;

(αR,γS,2S)-N-[(3S,4S)-3,4-dihydro-3-hydroxy-2H-1-
benzopyran-4-yl]-4-[1-[5-(3-fluorophenyl)-2-oxazolyl]-
1-methylethyl]-γ-hydroxy-α-(phenylmethyl)-2-[[(2,2,2-
trifluoroethyl)amino]carbonyl]-1-piperazinepentanamide;

(αR,γS,2S)-N-[(3S,4S)-3,4-dihydro-3-hydroxy-2H-1-
benzopyran-4-yl]-4-[1-[5-(4-fluorophenyl)-2-oxazolyl]-
1-methylethyl]-γ-hydroxy-α-(phenylmethyl)-2-[[(2,2,2-
trifluoroethyl)amino]carbonyl]-1-piperazinepentanamide;

(αR,γS,2S)-N-[(3S,4S)-3,4-dihydro-3-hydroxy-2H-1-
benzopyran-4-yl]-γ-hydroxy-4-[1-[5-(5-ethoxy-3-
pyridinyl)-2-oxazolyl]-1-methylethyl]-α-
(phenylmethyl)-2-[[(2,2,2-trifluoroethyl)amino]
carbonyl]-1-piperazinepentanamide;

(αR,γS,2S)-N-[(3S,4S)-3,4-dihydro-3-hydroxy-2H-1-
benzopyran-4-yl]-γ-hydroxy-4-[1-[5-(5-fluoro-3-
pyridinyl)-2-oxazolyl]-1-methylethyl]-α-
(phenylmethyl)-2-[[(2,2,2-trifluoroethyl)amino]
carbonyl]-1-piperazinepentanamide;

(αR,γS,2S)-N-[(3S,4S)-3,4-dihydro-3-hydroxy-2H-1-
benzopyran-4-yl]-γ-hydroxy-4-[1-[5-(5-ethyl-3-
pyridinyl)-2-oxazolyl]-1-methylethyl]-α-
(phenylmethyl)-2-[[(2,2,2-trifluoroethyl)amino]
carbonyl]-1-piperazinepentanamide;

(αR,γS,2S)-N-[(3S,4S)-3,4-dihydro-3-hydroxy-2H-1-
benzopyran-4-yl]-γ-hydroxy-4-[1-methyl-1-[5-(5-propyl-
3-pyridinyl)-2-oxazolyl]ethyl]-α-(phenylmethyl)-2-[[(2,
2,2-trifluoroethyl)amino]carbonyl]-1-
piperazinepentanamide;

(αR,γS,2S)-N-[(3S,4S)-3,4-dihydro-3-hydroxy-2H-1-
benzopyran-4-yl]-γ-hydroxy-4-[1methyl-1-[4-methyl-5-
(3-pyridinyl)-2-oxazolyl]ethyl]-α-(phenylmethyl)-2-[[(2,
2,2-trifluoroethyl)amino]carbonyl]-1-
piperazinepentanamide;

(αR,γS,2S)-N-[(3S,4S)-3,4-dihydro-3-hydroxy-2H-1-
benzopyran-4-yl]-γ-hydroxy-4-[1-[5-(5-methoxy-3-
pyridinyl)-4-methyl-2-oxazolyl]-1-methylethyl]-α-
(phenylmethyl)-2-[[(2,2,2-trifluoroethyl)amino]
carbonyl]-1-piperazinepentanamide;

(αR,γS,2S)-N-[(3S,4S)-3,4-dihydro-3-hydroxy-2H-1-
benzopyran-4-yl]-γ-hydroxy-4-[1-methyl-1-[5-[5-
(methylthio)-3-pyridinyl]-2-oxazolyl]ethyl]-α-
(phenylmethyl)-2-[[(2,2,2-trifluoroethyl)amino]
carbonyl]-1-piperazinepentanamide;

(αR,γS,2S)-N-[(3S,4S)-3,4-dihydro-3-hydroxy-2H-1-
benzopyran-4-yl]-γ-hydroxy-4-[1-[5-(5-dimethylamino-
3-pyridinyl)-2-oxazolyl]-1-methylethyl]-α-
(phenylmethyl)-2-[[(2,2,2-trifluoroethyl)amino]
carbonyl]-1-piperazinepentanamide;

(αR,γS,2S)-4-[1-[3-(5-methoxy-3-pyridinyl)-5-isoxazolyl]-
1-methylethyl]-N-[(3S,4S)-3,4-dihydro-3-hydroxy-2H-1-
benzopyran-4-yl]-γ-hydroxy-α-(phenylmethyl)-2-[[(2,2,
2-trifluoroethyl)amino]carbonyl]-1-
piperazinepentanamide;

(αR,γS,2S)-4-[1-[2-(5-methoxy-3-pyridinyl)-4-thiazolyl]-1-
methylethyl]-N-[(3S,4S)-3,4-dihydro-3-hydroxy-2H-1-
benzopyran-4-yl]-γ-hydroxy-α-(phenylmethyl)-2-[[(2,2,
2-trifluoroethyl)amino]carbonyl]-1-
piperazinepentanamide;

(αR,γS,2S)-4-[1-[2-(5-chloro-3-pyridinyl)-4-thiazolyl]-1-
methylethyl]-N-[(3S,4S)-3,4-dihydro-3-hydroxy-2H-1-
benzopyran-4-yl]-γ-hydroxy-α-(phenylmethyl)-2-[[(2,2,
2-trifluoroethyl)amino]carbonyl]-1-
piperazinepentanamide;

(αR,γS,2S)-4-[1-[2-(3-pyridinyl)-4-thiazolyl]-1-
methylethyl]-N-[(3S,4S)-3,4-dihydro-3-hydroxy-2H-1-
benzopyran-4-yl]-γ-hydroxy-α-(phenylmethyl)-2-[[(2,2,
2-trifluoroethyl)amino]carbonyl]-1-
piperazinepentanamide;

(αR,γS,2S)-N-[(3S,4S)-3,4-dihydro-3-hydroxy-2H-1-
benzopyran-4-yl]-γ-hydroxy-4-[1-[1-(5-methoxy-3-
pyridinyl)-1H-pyrazol-3-yl]-1-methylethyl]-α-
(phenylmethyl)-2-[[(2,2,2-trifluoroethyl)amino]
carbonyl]-1-piperazinepentanamide;

(αS,γS2S)-N-[(3S,4S)-3,4-dihydro-3-hydroxy-2H-1-
benzopyran-4-yl]-γ- hydroxy-4-[1-[1-(5-chloro-3-
pyridinyl)-1H-pyrazol-3-yl]-1-methylethyl]-α-
(phenylmethyl)-2-[[(2,2,2-trifluoroethyl)amino]
carbonyl]-1-piperazinepentanamide;

(αS,γS,2S)-N-[(3S,4S)-3,4-dihydro-3-hydroxy-2H-1-
benzopyran-4-yl]-γ-hydroxy-4-[1-[1-(5-fluoro-3-
pyridinyl)-1H-pyrazol-3-yl]-1-methylethyl]-α-
(phenylmethyl)-2-[[(2,2,2-trifluoroethyl)amino]
carbonyl]-1-piperazinepentanamide;

(αR,γS,2S)-N-[(3S,4S)-3,4-dihydro-3-hydroxy-2H-1-
benzopyran-4-yl]-γ-hydroxy-4-[1-[1-(3-pyridinyl)-1H-
pyrazol-3-yl]-1-methylethyl]-α-(phenylmethyl)-2-[[(2,2,
2-trifluoroethyl)amino]carbonyl]-1-
piperazinepentanamide;

(αS,γS,2S)-4-[1-[5-phenyl-2-oxazolyl]-1-methylethyl]-N-
[(3S,4S)-3,4-dihydro-3-hydroxy-2H-1-benzopyran-4-yl]-
α-(furo[2,3-c]pyridin-2-ylmethyl)-γ-hydroxy-2-[[(2,2,2-
trifluoroethyl)amino]carbonyl]-1-piperazinepentanamide;

(αS,γS,2S)-4-[1-[5-(4-chlorophenyl)-2-oxazolyl]-1-
methylethyl]-N-[(3S,4S)-3,4-dihydro-3-hydroxy-2H-1-
benzopyran-4-yl]-α-(furo[2,3-c]pyridin-2-ylmethyl)-γ-
hydroxy-2-[[(2,2,2-trifluoroethyl)amino]carbonyl]-1-
piperazinepentanamide;

(αS,γS,2S)-4-[1-[5-(4-fluorophenyl)-2-oxazolyl]-1-
methylethyl]-N-[(3S,4S)-3,4-dihydro-3-hydroxy-2H-1-
benzopyran-4-yl]-α-(furo[2,3-c]pyridin-2-ylmethyl)-γ-
hydroxy-2-[[(2,2,2-trifluoroethyl)amino]carbonyl]-1-
piperazinepentanamide;

(αS,γS,2S)-4-[1-[5-(4-chlorophenyl)-2-oxazolyl]-1-
methylethyl]-N-[(3S,4S)-3,4-dihydro-3-hydroxy-2H-1-
benzopyran-4-yl]-α-(furo[2,3-c]pyridin-3-ylmethyl)-γ-
hydroxy-2-[[(2,2,2-trifluoroethyl)amino]carbonyl]-1-
piperazinepentanamide;

(αS,γS,2S)-4-[1-[5-(4-fluorophenyl)-2-oxazolyl]-1-
methylethyl]-N-[(3S,4S)-3,4-dihydro-3-hydroxy-2H-1-
benzopyran-4-yl]-α-(furo[2,3-c]pyridin-3-ylmethyl)-γ-
hydroxy-2-[[(2,2,2-trifluoroethyl)amino]carbonyl]-1-
piperazinepentanamide;

(αS,γS,2S)-N-[(3S,4S)-3,4-dihydro-3-hydroxy-2H-1-
benzopyran-4-yl]-4-[1-[5-(4-fluorophenyl)-2-oxazolyl]-
1-methylethyl]-α-(furo[2,3-d]pyrimidin-6-ylmethyl)-γ-
hydroxy-2-[[(2,2,2-trifluoroethyl)amino]carbonyl]-1-
piperazinepentanamide;

and pharmaceutically acceptable salts thereof.

20. The compound according to claim 1, wherein the compound is selected from the group consisting of (αR,γS,2S)-N-((3S,4S)-3,4-dihydro-3-hydroxy-2H-1-
benzopyran-4-yl)-4-(1-furo[3,2-c]pyridin-2-yl-1-
methylethyl)-γ-hydroxy-α-(phenylmethyl)-2-[[(2,2,2-
trifluoroethyl)amino]carbonyl]-1-piperazinepentanamide;

(αS,γS,2S)-N-((3S,4S)-3,4-dihydro-3-hydroxy-2H-1-
benzopyran-4-yl)-γ-hydroxy-4-[(5-phenyl-2-furanyl)

methyl]-α-(4-pyridinylmethyl)-2-[[(2,2,2-trifluoroethyl)amino]-carbonyl]-1-piperazinepentanamide;

(αS,γS,2S)-N-((3S,4S)-3,4-dihydro-3-hydroxy-2H-1-benzopyran-4-yl)-γ-hydroxy-4-[1-methyl-1(1-phenyl-1H-pyrazol-3-yl)ethyl]-α-(3-pyridinylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-α-(phenylmethyl)-4-[[5-(2-pyridinyl)-2-furanyl]methyl]-2-[[(2,2,2-trifluoroethyl)-amino]carbonyl]-1-piperazinepentanamide;

(αR,γS,2S)-4-[[5-(5-chloro-2-pyridinyl)-2-furanyl]methyl]-N-((3S,4S)-3,4-dihydro-3hydroxy-2H-1-benzopyran-4-yl)-γ-hydroxy-α-(phenylmethyl)-2-[[(2,2,2-trifluoroethyl)amino]carbonyl]-1-piperazinepentanamide;

(αR,γS,2S)-N-((3S,4S)-3,4-dihydro-3-hydroxy-2H-1-benzopyran-4-yl)-γ-hydroxy-4-[1-methyl-1-[5-(3-pyridinyl)-2-oxazolyl]ethyl]-α-(phenylmethyl)-2-[[(2,2,2-trifluoroethyl)amino]carbonyl]-1-piperazinepentanamide;

(αR,γS,2S)-N-[(3S,4S)-3,4-dihydro-3-hydroxy-2H-1-benzopyran-4-yl]-γ-hydroxy-4-[1-[5-(5-methoxy-3-pyridinyl)-2-oxazolyl]-1-methylethyl]-α-(phenylmethyl)-2-[[(2,2,2-trifluoroethyl)amino]carbonyl]-1-piperazinepentanamide;

(αR,γS,2S)-N-[(3S,4S)-3,4-dihydro-3-hydroxy-2H-1-benzopyran-4-yl]-γ-hydroxy-4-[1-[5-(5-fluoro-3-pyridinyl)-2-oxazolyl]-1-methylethyl]-α-(phenylmethyl)-2-[[(2,2,2trifluoroethyl)amino]carbonyl]-1-piperazinepentanamide;

(αR,γS,2S)-N-[(3S,4S)-3,4-dihydro-3-hydroxy-2H-1-benzopyran-4-yl]-γ-hydroxy-4-[1-[1-(5-fluoro-3-pyridinyl)-1H-pyrazol-3-yl]-1-methylethyl]-α-(phenylmethyl)-2-[[(2,2,2-trifluoroethyl)amino]carbonyl]-1-piperazinepentanamide;

(αS,γS,2S)-4-[1-[5-(4-chlorophenyl)-2-oxazolyl]-1-methylethyl]-N-[(3S,4S)-3,4-dihydro-3hydroxy-2H-1-benzopyran-4-yl]-α-(furo[2,3-c]pyridin-2-ylmethyl)-γ-hydroxy-2-[[(2,2,2-trifluoroethyl)amino]carbonyl]-1-piperazinepentanamide;

(αS,γS,2S)-4-[1-[5-(4-fluorophenyl)-2-oxazolyl]-1-methylethyl]-N-[(3S,4S)-3,4-dihydro-3-hydroxy-2H-1-benzopyran-4-yl]-α-(furo[2,3-c]pyridin-2-ylmethyl)-γ-hydroxy-2-[[(2,2,2-trifluoroethyl)amino]carbonyl]-1-piperazinepentanamide;

(αS,γS,2S)-4-[1-[5-(4-chlorophenyl)-2-oxazolyl]-1-methylethyl]-N-[(3S,4S)-3,4-dihydro-3-hydroxy-2H-1-benzopyran-4-yl]-α-(furo[2,3-c]pyridin-3-ylmethyl)-γ-hydroxy-2-[[(2,2,2-trifluoroethyl)amino]carbonyl]-1-piperazinepentanamide;

(αS,γS,2S)-4-[1-[5-(4-fluorophenyl)-2-oxazolyl]-1-methylethyl]-N-[(3S,4S)-3,4-dihydro-3-hydroxy-2H-1-benzopyran-4-yl]-α-(furo[2,3-c]pyridin-3-ylmethyl)-γ-hydroxy-2-[[(2,2,2-trifluoroethyl)amino]carbonyl]-1-piperazinepentanamide;

(αS,γS,2S)-N-[(3S,4S)-3,4-dihydro-3-hydroxy-2H-1-benzopyran-4-yl]-4-[1-[5-(4-fluorophenyl)-2-oxazolyl]-1-methylethyl]-α-(furo[2,3-d]pyrimidin-6-ylmethyl)-γ-hydroxy-2-[[(2,2,2-trifluoroethyl)amino]carbonyl]-1-piperazinepentanamide;

and pharmaceutically acceptable salts thereof.

21. A pharmaceutical composition comprising a therapeutically effective amount of a compound according to claim 1 and a pharmaceutically acceptable carrier.

22. A pharmaceutical composition made by combining a therapeutically effective amount of a compound according to claim 1 and a pharmaceutically acceptable carrier.

23. A method of inhibiting HIV protease in a subject in need thereof which comprises administering to the subject a therapeutically effective amount of the compound according to claim 1.

24. A method of treating infection by HIV in a subject in need thereof which comprises administering to the subject a therapeutically effective amount of the compound according to claim 1.

25. A method of treating AIDS in a subject in need thereof which comprises administering to the subject a therapeutically effective amount of the compound according to claim 1.

26. A method of inhibiting HIV protease in a subject in need thereof which comprises administering to the subject a therapeutically effective amount of the composition according to claim 21.

27. A method of treating infection by HIV in a subject in need thereof which comprises administering to the subject a therapeutically effective amount of the composition according to claim 21.

28. A method of treating AIDS in a subject in need thereof which comprises administering to the subject a therapeutically effective amount of the composition according to claim 21.

* * * * *